United States Patent
Gray et al.

(10) Patent No.: US 10,906,889 B2
(45) Date of Patent: Feb. 2, 2021

(54) POLYCYCLIC INHIBITORS OF CYCLIN-DEPENDENT KINASE 7 (CDK7)

(71) Applicant: Dana-Farber Cancer Institute, Inc., Boston, MA (US)

(72) Inventors: Nathanael Gray, Boston, MA (US); Tinghu Zhang, Brookline, MA (US); Stephane Ciblat, Montreal (CA); Melissa Leblanc, Laval (CA); Jason J. Marineau, Franklin, MA (US); Joel Moore, Lexington, MA (US); Kevin Sprott, Needham, MA (US); M. Arshad Siddiqui, Newton, MA (US); Anzhelika Kabro, Montreal (CA); Tom Miller, Wakefield, MA (US); Stephanie Roy, Lachine (CA); Darby Schmidt, Arlington, MA (US); Dana K. Winter, Rigaud (CA); Michael Bradley, Allston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/051,896

(22) Filed: Aug. 1, 2018

(65) Prior Publication Data
US 2019/0031642 A1    Jan. 31, 2019

Related U.S. Application Data

(62) Division of application No. 15/030,245, filed as application No. PCT/US2014/061232 on Oct. 17, 2014, now Pat. No. 10,047,070.

(60) Provisional application No. 61/893,005, filed on Oct. 18, 2013.

(51) Int. Cl.
| | |
|---|---|
| *C07D 403/04* | (2006.01) |
| *C07D 401/04* | (2006.01) |
| *C07D 413/04* | (2006.01) |
| *C07D 417/04* | (2006.01) |
| *C07D 471/04* | (2006.01) |
| *C07F 7/08* | (2006.01) |

(52) U.S. Cl.
CPC ......... *C07D 403/04* (2013.01); *C07D 401/04* (2013.01); *C07D 413/04* (2013.01); *C07D 417/04* (2013.01); *C07D 471/04* (2013.01); *C07F 7/0812* (2013.01)

(58) Field of Classification Search
CPC .. C07D 403/04; C07D 401/04; C07D 413/04; C07D 417/04; C07D 471/04; C07F 7/0812
See application file for complete search history.

(56) References Cited

U.S. PATENT DOCUMENTS

| | | | |
|---|---|---|---|
| 4,231,938 A | 11/1980 | Monaghan et al. | |
| 4,270,537 A | 6/1981 | Romaine et al. | |
| 4,596,556 A | 6/1986 | Morrow et al. | |

(Continued)

FOREIGN PATENT DOCUMENTS

| | | |
|---|---|---|
| CA | 2486101 A1 | 11/2003 |
| CA | 2503646 A1 | 5/2004 |

(Continued)

OTHER PUBLICATIONS

International Search Report and Written Opinion from corresponding International Application No. PCT/US2014/061232 dated Dec. 23, 2014.

(Continued)

*Primary Examiner* — Jeffrey S Lundgren
*Assistant Examiner* — Ibrahim D Bori
(74) *Attorney, Agent, or Firm* — Wolf, Greenfield & Sacks, P.C.

(57) ABSTRACT

The present invention provides novel compounds of Formula (I), and pharmaceutically acceptable salts, solvates, hydrates, polymorphs, co-crystals, tautomers, stereoisomers, isotopically labeled derivatives, prodrugs, and compositions thereof. Also provided are methods and kits involving the inventive compounds or compositions for treating or preventing proliferative diseases (e.g., cancers (e.g., leukemia, lymphoma, melanoma, multiple myeloma, breast cancer, Ewing's sarcoma, osteosarcoma, brain cancer, neuroblastoma, lung cancer), benign neoplasms, angiogenesis, inflammatory diseases, autoinflammatory diseases, and autoimmune diseases) in a subject. Treatment of a subject with a proliferative disease using a compound or composition of the invention may inhibit the aberrant activity of a kinase, such as a cyclin-dependent kinase (CDK) (e.g., cyclin-dependent kinase 7 (CDK7), cyclin-dependent kinase 12 (CDK12), or cyclin-dependent kinase 13 (CDK13)), and therefore, induce cellular apoptosis and/or inhibit transcription in the subject.

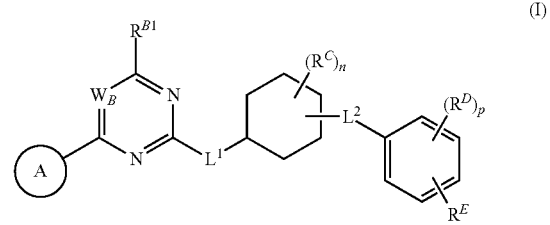

32 Claims, 9 Drawing Sheets

(56) References Cited

U.S. PATENT DOCUMENTS

| | | |
|---|---|---|
| 4,782,084 A | 11/1988 | Vyas et al. |
| 4,790,824 A | 12/1988 | Morrow et al. |
| 4,885,314 A | 12/1989 | Vyas et al. |
| 4,886,499 A | 12/1989 | Cirelli et al. |
| 4,940,460 A | 7/1990 | Casey et al. |
| 4,941,880 A | 7/1990 | Burns et al. |
| 5,015,235 A | 5/1991 | Crossman et al. |
| 5,064,413 A | 11/1991 | McKinnon et al. |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby et al. |
| 5,334,144 A | 8/1994 | Alchas et al. |
| 5,339,163 A | 8/1994 | Homma et al. |
| 5,383,851 A | 1/1995 | McKinnon et al. |
| 5,417,662 A | 5/1995 | Hjertman et al. |
| 5,420,245 A | 5/1995 | Brown et al. |
| 5,466,220 A | 11/1995 | Brenneman et al. |
| 5,480,381 A | 1/1996 | Weston et al. |
| 5,484,596 A | 1/1996 | Hanna et al. |
| 5,503,627 A | 4/1996 | McKinnon et al. |
| 5,510,510 A | 4/1996 | Patel et al. |
| 5,520,639 A | 5/1996 | Peterson et al. |
| 5,523,430 A | 6/1996 | Patel et al. |
| 5,527,288 A | 6/1996 | Gross et al. |
| 5,532,359 A | 7/1996 | Marsters et al. |
| 5,569,189 A | 10/1996 | Parsons et al. |
| 5,571,792 A | 11/1996 | Bolton et al. |
| 5,589,485 A | 12/1996 | Hocolowski et al. |
| 5,599,302 A | 2/1997 | Lilley et al. |
| 5,602,098 A | 2/1997 | Sebti et al. |
| 5,643,958 A | 7/1997 | Iwasawa et al. |
| 5,649,912 A | 7/1997 | Peterson et al. |
| 5,661,152 A | 8/1997 | Bishop et al. |
| 5,704,911 A | 1/1998 | Parsons et al. |
| 5,750,567 A | 5/1998 | Baudoin et al. |
| 5,856,439 A | 1/1999 | Clerc et al. |
| 5,889,053 A | 3/1999 | Baudoin et al. |
| 5,893,397 A | 4/1999 | Peterson et al. |
| 5,925,641 A | 7/1999 | Kanda et al. |
| 5,936,097 A | 8/1999 | Commercon et al. |
| 5,993,412 A | 11/1999 | Deily et al. |
| 6,069,134 A | 5/2000 | Roth et al. |
| 6,214,852 B1 | 4/2001 | Kim et al. |
| 6,921,763 B2 | 7/2005 | Hirst et al. |
| 6,939,874 B2 | 9/2005 | Harmange et al. |
| 7,115,617 B2 | 10/2006 | Buchanan et al. |
| 7,312,225 B2 | 12/2007 | Luecking et al. |
| 7,884,117 B2 | 2/2011 | Zhang et al. |
| 7,928,140 B2 | 4/2011 | Booker et al. |
| 8,273,765 B2 | 9/2012 | Fancelli et al. |
| 8,394,818 B2 | 3/2013 | Gray et al. |
| 8,765,747 B2 | 7/2014 | Choi et al. |
| 8,889,706 B2 | 11/2014 | Gray et al. |
| 8,987,275 B2 | 3/2015 | Gray et al. |
| 9,180,127 B2 | 11/2015 | Gray et al. |
| 9,358,231 B2 | 6/2016 | Gray et al. |
| 9,382,239 B2 | 7/2016 | Gray et al. |
| 9,505,784 B2 | 11/2016 | Choi et al. |
| 9,670,165 B2 | 6/2017 | Cohen et al. |
| 9,758,522 B2 | 9/2017 | Gray et al. |
| 9,814,709 B2 | 11/2017 | Liu et al. |
| 9,862,688 B2 | 1/2018 | Gray et al. |
| 9,879,003 B2 | 1/2018 | Gray et al. |
| 10,000,483 B2 | 6/2018 | Gray et al. |
| 10,017,477 B2 | 7/2018 | Gray et al. |
| 10,047,070 B2 | 8/2018 | Gray et al. |
| 10,112,927 B2 | 10/2018 | Gray et al. |
| 10,144,730 B2 | 12/2018 | Gray et al. |
| 10,550,121 B2 | 2/2020 | Gray et al. |
| 2003/0139416 A1 | 7/2003 | Buchanan et al. |
| 2004/0106634 A1 | 6/2004 | Satoh et al. |
| 2004/0126359 A1 | 7/2004 | Lamb et al. |
| 2004/0209878 A1 | 10/2004 | Guzi et al. |
| 2005/0026914 A1 | 2/2005 | Buchanan et al. |
| 2005/0197338 A1 | 9/2005 | Huang et al. |
| 2005/0250837 A1 | 11/2005 | D'Mello et al. |
| 2006/0106083 A1 | 5/2006 | Martina et al. |
| 2006/0189627 A1 | 8/2006 | Laird et al. |
| 2007/0060546 A1 | 3/2007 | Ruat et al. |
| 2007/0093537 A1 | 4/2007 | Hynes et al. |
| 2007/0185171 A1 | 8/2007 | Germain et al. |
| 2007/0225286 A1 | 9/2007 | Ren et al. |
| 2007/0275963 A1 | 11/2007 | Guzi et al. |
| 2007/0281907 A1 | 12/2007 | Watkins |
| 2008/0039629 A1 | 2/2008 | Ramesh et al. |
| 2008/0090849 A1 | 4/2008 | Bordon-Pallier et al. |
| 2008/0103167 A1 | 5/2008 | Bebernitz et al. |
| 2008/0214501 A1 | 9/2008 | Pan et al. |
| 2008/0249079 A1 | 10/2008 | Chen et al. |
| 2008/0300267 A1 | 12/2008 | Okram et al. |
| 2009/0054392 A1 | 2/2009 | Pelletier et al. |
| 2009/0054405 A1 | 2/2009 | Booker et al. |
| 2009/0082346 A1 | 3/2009 | Brasca et al. |
| 2009/0105250 A1 | 4/2009 | Sim et al. |
| 2009/0156582 A1 | 6/2009 | Tsukamoto et al. |
| 2010/0056524 A1 | 3/2010 | Mciver et al. |
| 2010/0197688 A1 | 8/2010 | Nantermet et al. |
| 2010/0254905 A1 | 10/2010 | Honigberg et al. |
| 2011/0086858 A1 | 4/2011 | Wang et al. |
| 2011/0098280 A1 | 4/2011 | Garcia-Echeverria et al. |
| 2011/0178070 A1 | 7/2011 | Gong et al. |
| 2011/0207711 A1 | 8/2011 | Katz et al. |
| 2011/0212053 A1 | 9/2011 | Qian et al. |
| 2012/0088766 A1 | 4/2012 | Choi et al. |
| 2012/0094999 A1 | 4/2012 | Gray et al. |
| 2012/0165309 A1 | 6/2012 | Takahashi et al. |
| 2012/0196865 A1 | 8/2012 | Ruat et al. |
| 2012/0202809 A1 | 8/2012 | Li et al. |
| 2012/0277248 A1 | 11/2012 | Caruso et al. |
| 2012/0329771 A1 | 12/2012 | Treu et al. |
| 2013/0040949 A1 | 2/2013 | Gray et al. |
| 2013/0184264 A1 | 7/2013 | Bradner et al. |
| 2013/0184287 A1 | 7/2013 | Gray et al. |
| 2014/0187772 A1 | 7/2014 | Bebbington et al. |
| 2014/0303112 A1 | 10/2014 | Chen et al. |
| 2014/0309249 A1 | 10/2014 | Gray et al. |
| 2015/0094315 A1 | 4/2015 | Choi et al. |
| 2015/0157629 A1 | 6/2015 | Gray et al. |
| 2015/0166532 A1 | 6/2015 | Gray et al. |
| 2015/0246913 A1 | 9/2015 | Gray et al. |
| 2015/0274728 A1 | 10/2015 | Gray et al. |
| 2016/0046636 A1 | 2/2016 | Gray et al. |
| 2016/0122323 A1 | 5/2016 | Gray et al. |
| 2016/0264551 A1 | 9/2016 | Ciblat et al. |
| 2016/0264554 A1 | 9/2016 | Gray et al. |
| 2016/0368910 A1 | 12/2016 | Gray et al. |
| 2017/0044111 A1 | 2/2017 | Gray et al. |
| 2017/0044112 A1 | 2/2017 | Gray et al. |
| 2018/0093990 A1 | 4/2018 | Gray et al. |
| 2018/0169097 A1 | 6/2018 | Hammerman et al. |
| 2018/0319801 A1 | 11/2018 | Gray et al. |
| 2018/0362483 A1 | 12/2018 | Gray et al. |
| 2019/0015411 A9 | 1/2019 | Hammerman et al. |
| 2019/0055248 A1 | 2/2019 | Gray et al. |
| 2019/0241541 A1 | 8/2019 | Ciblat et al. |
| 2019/0248778 A1 | 8/2019 | Gray et al. |
| 2019/0315747 A9 | 10/2019 | Gray et al. |
| 2020/0017475 A9 | 1/2020 | Gray et al. |
| 2020/0024271 A9 | 1/2020 | Gray et al. |

FOREIGN PATENT DOCUMENTS

| | | |
|---|---|---|
| CA | 2526430 A1 | 12/2004 |
| CA | 2550128 A1 | 6/2005 |
| CA | 2563212 A1 | 10/2005 |
| CN | 1701073 | 11/2005 |
| CN | 1735614 | 2/2006 |
| CN | 100482665 | 5/2006 |
| CN | 1784410 | 6/2006 |
| EP | 0604181 A1 | 12/1993 |
| EP | 0618221 A2 | 3/1994 |
| EP | 0675112 A1 | 3/1995 |
| EP | 0696593 A2 | 8/1995 |

(56) References Cited

FOREIGN PATENT DOCUMENTS

| | | |
|---|---|---|
| EP | 1 935 890 A1 | 6/2008 |
| EP | 2 311 842 A2 | 4/2011 |
| GB | 796524 A | 6/1958 |
| JP | H11-514336 | 12/1999 |
| JP | 2000-515550 | 11/2000 |
| JP | 2002-537300 | 11/2002 |
| JP | 2003-503481 A | 1/2003 |
| JP | 2004-505977 | 2/2004 |
| JP | 2004-516326 | 6/2004 |
| JP | 2004-517075 | 6/2004 |
| JP | 2004-529140 A | 9/2004 |
| JP | 2005-501860 A | 1/2005 |
| JP | 2005-505535 A | 2/2005 |
| JP | 2005-530711 A | 10/2005 |
| JP | 2005-534635 A | 11/2005 |
| JP | 2005-538100 A | 12/2005 |
| JP | 2006-502163 | 1/2006 |
| JP | 2006-502184 | 1/2006 |
| JP | 2006-514026 | 4/2006 |
| JP | 2006-521394 A | 9/2006 |
| JP | 2007-500226 A | 1/2007 |
| JP | 2007-500725 A | 1/2007 |
| JP | 2007-522220 | 8/2007 |
| JP | 2008-500320 A | 1/2008 |
| JP | 2008-501669 A | 1/2008 |
| JP | 2008-502610 A | 1/2008 |
| JP | 2009-510110 A | 3/2009 |
| JP | 2009-511483 | 3/2009 |
| JP | 2009-520805 | 5/2009 |
| JP | 2009-538304 | 11/2009 |
| JP | 2010-505905 | 2/2010 |
| JP | 2010-511655 A | 4/2010 |
| JP | 2010-518069 | 5/2010 |
| JP | 2010-521487 A | 6/2010 |
| JP | 2010-523643 | 7/2010 |
| JP | 2010-529140 | 8/2010 |
| JP | 2011-516533 A | 5/2011 |
| JP | 2012-530071 A | 11/2012 |
| JP | 2016-533379 A | 10/2016 |
| JP | 2017-504651 A | 2/2017 |
| MX | 2016-009974 A | 10/2016 |
| MX | 2016-009975 A | 10/2016 |
| MX | 2016-009976 A | 11/2016 |
| WO | WO 84/02131 A1 | 6/1984 |
| WO | WO 94/19357 A1 | 9/1994 |
| WO | WO 95/08542 A1 | 3/1995 |
| WO | WO 95/10514 A1 | 4/1995 |
| WO | WO 95/10515 A1 | 4/1995 |
| WO | WO 95/10516 A1 | 4/1995 |
| WO | WO 95/11917 A1 | 5/1995 |
| WO | WO 95/12572 A1 | 5/1995 |
| WO | WO 95/12612 A1 | 5/1995 |
| WO | WO 95/25086 A1 | 9/1995 |
| WO | WO 95/34535 A1 | 12/1995 |
| WO | WO 96/00736 A1 | 1/1996 |
| WO | WO 96/05168 A1 | 2/1996 |
| WO | WO 96/05169 A1 | 2/1996 |
| WO | WO 96/05529 A1 | 2/1996 |
| WO | WO 96/06138 A1 | 2/1996 |
| WO | WO 96/06193 A1 | 2/1996 |
| WO | WO 96/16443 A1 | 5/1996 |
| WO | WO 96/17861 A1 | 6/1996 |
| WO | WO 96/21456 A1 | 7/1996 |
| WO | WO 96/21701 A2 | 7/1996 |
| WO | WO 96/22278 A1 | 7/1996 |
| WO | WO 96/24611 A1 | 8/1996 |
| WO | WO 96/24612 A1 | 8/1996 |
| WO | WO 96/30017 A1 | 10/1996 |
| WO | WO 96/30018 A1 | 10/1996 |
| WO | WO 96/30343 A1 | 10/1996 |
| WO | WO 96/30362 A1 | 10/1996 |
| WO | WO 96/30363 A1 | 10/1996 |
| WO | WO 96/31111 A1 | 10/1996 |
| WO | WO 96/31477 A1 | 10/1996 |
| WO | WO 96/31478 A1 | 10/1996 |
| WO | WO 96/31501 A1 | 10/1996 |
| WO | WO 96/33159 A1 | 10/1996 |
| WO | WO 96/34850 A1 | 11/1996 |
| WO | WO 96/34851 A1 | 11/1996 |
| WO | WO 97/00252 A1 | 1/1997 |
| WO | WO 97/03047 A1 | 1/1997 |
| WO | WO 97/03050 A1 | 1/1997 |
| WO | WO 97/04785 A1 | 2/1997 |
| WO | WO 97/17070 A1 | 5/1997 |
| WO | WO 97/18813 A1 | 5/1997 |
| WO | WO 97/21701 A1 | 6/1997 |
| WO | WO 97/23478 A1 | 7/1997 |
| WO | WO 97/26246 A1 | 7/1997 |
| WO | WO 97/30053 A1 | 8/1997 |
| WO | WO 97/38665 A2 | 10/1997 |
| WO | WO 97/44350 A1 | 11/1997 |
| WO | WO 98/02436 A1 | 1/1998 |
| WO | WO 98/28980 A1 | 7/1998 |
| WO | WO 98/29119 A1 | 7/1998 |
| WO | WO 2000/050032 A1 | 8/2000 |
| WO | WO 2001/002369 A2 | 1/2001 |
| WO | WO 2001/019829 A2 | 3/2001 |
| WO | WO 2002/076986 A1 | 10/2002 |
| WO | WO 2002/079197 A1 | 10/2002 |
| WO | WO 2002/080926 A1 | 10/2002 |
| WO | WO 2002/083653 A1 | 10/2002 |
| WO | WO 2002/096905 A1 | 12/2002 |
| WO | WO 2002/102800 A1 | 12/2002 |
| WO | WO 2003/018021 A1 | 3/2003 |
| WO | WO 2003/018022 A1 | 3/2003 |
| WO | WO 2003/026664 A1 | 4/2003 |
| WO | WO 2003/051847 A1 | 6/2003 |
| WO | WO 2003/078403 A2 | 9/2003 |
| WO | WO 2003/097610 A1 | 11/2003 |
| WO | WO 2004/005283 A1 | 1/2004 |
| WO | WO 2004/009601 A1 | 1/2004 |
| WO | WO 2004/010995 A1 | 2/2004 |
| WO | WO 2004/022561 A1 | 3/2004 |
| WO | WO 2004/026229 A2 | 4/2004 |
| WO | WO 2004/039796 A1 | 5/2004 |
| WO | WO 2004/046118 A2 | 6/2004 |
| WO | WO 2004/074283 A1 | 9/2004 |
| WO | WO 2004/076458 A1 | 9/2004 |
| WO | WO 2004/078757 A2 | 9/2004 |
| WO | WO 2004/081013 A1 | 9/2004 |
| WO | WO 2004/087699 A2 | 10/2004 |
| WO | WO 2004/087707 A1 | 10/2004 |
| WO | WO 2004/100868 A1 | 11/2004 |
| WO | WO 2004/113303 A1 | 12/2004 |
| WO | WO 2004/113304 A1 | 12/2004 |
| WO | WO 2005/011597 A2 | 2/2005 |
| WO | WO 2005/012256 A1 | 2/2005 |
| WO | WO 2005/058891 A1 | 6/2005 |
| WO | WO 2005/097790 A1 | 10/2005 |
| WO | WO 2005/108397 A1 | 11/2005 |
| WO | WO 2005/116025 A2 | 12/2005 |
| WO | WO 2006/003276 A1 | 1/2006 |
| WO | WO 2006/024834 A1 | 3/2006 |
| WO | WO 2006/031806 A2 | 3/2006 |
| WO | WO 2006/034341 A2 | 3/2006 |
| WO | WO 2006/040568 A1 | 4/2006 |
| WO | WO 2006/124731 A2 | 11/2006 |
| WO | WO 2007/002325 A1 | 1/2007 |
| WO | WO 2007/002433 A1 | 1/2007 |
| WO | WO 2007/024680 A1 | 3/2007 |
| WO | WO 2007/035428 A1 | 3/2007 |
| WO | WO 2007/042786 A1 | 4/2007 |
| WO | WO 2007/044420 A1 | 4/2007 |
| WO | WO 2007/048070 A2 | 4/2007 |
| WO | WO 2007/075869 A2 | 7/2007 |
| WO | 2007129195 A2 | 11/2007 |
| WO | WO 2007/129195 A2 | 11/2007 |
| WO | WO-2007129195 A2 * | 11/2007 ........... C07D 401/04 |
| WO | WO 2007/138277 A1 | 12/2007 |
| WO | WO 2008/049856 A1 | 5/2008 |
| WO | WO 2008/063888 A2 | 5/2008 |
| WO | WO 2008/068171 A1 | 6/2008 |
| WO | WO 2008/074749 A1 | 6/2008 |
| WO | WO 2008/080015 A2 | 7/2008 |

(56) References Cited

FOREIGN PATENT DOCUMENTS

| WO | WO 2008/112913 A1 | 9/2008 |
|---|---|---|
| WO | WO 2008/124393 A1 | 10/2008 |
| WO | WO 2008/144253 A1 | 11/2008 |
| WO | WO 2008/151183 A1 | 12/2008 |
| WO | WO 2008/151304 A1 | 12/2008 |
| WO | WO 2009/017822 A2 | 2/2009 |
| WO | WO 2009/028655 A1 | 3/2009 |
| WO | WO 2009/032694 A1 | 3/2009 |
| WO | WO 2009/145360 A1 | 12/2009 |
| WO | WO 2009/152027 A1 | 12/2009 |
| WO | WO 2009/155017 A2 | 12/2009 |
| WO | WO 2010/008847 A2 | 1/2010 |
| WO | WO 2010/044885 A2 | 4/2010 |
| WO | WO 2010/051781 A1 | 5/2010 |
| WO | WO 2010/125799 A1 | 11/2010 |
| WO | WO 2010/144909 A1 | 12/2010 |
| WO | WO 2011/079231 A1 | 6/2011 |
| WO | WO 2011/115725 A2 | 9/2011 |
| WO | WO 2013/014162 A1 | 1/2013 |
| WO | WO 2013/040436 A2 | 3/2013 |
| WO | 2013074986 A1 | 5/2013 |
| WO | WO 2013/074986 A1 | 5/2013 |
| WO | WO 2013/136070 A1 | 9/2013 |
| WO | WO 2013/154778 A1 | 10/2013 |
| WO | 2014063068 A1 | 4/2014 |
| WO | WO 2014/063061 A1 | 4/2014 |
| WO | WO 2014/063068 A1 | 4/2014 |
| WO | WO 2015/013635 A2 | 1/2015 |
| WO | 2015058140 A1 | 4/2015 |
| WO | WO 2015/058126 A1 | 4/2015 |
| WO | WO 2015/058140 A1 | 4/2015 |
| WO | WO 2015/117087 A1 | 8/2015 |
| WO | WO 2015/154022 A1 | 10/2015 |
| WO | WO 2015/154038 A1 | 10/2015 |
| WO | WO 2015/164604 A1 | 10/2015 |
| WO | WO 2015/164614 A1 | 10/2015 |
| WO | WO 2016/014542 A1 | 1/2016 |
| WO | WO 2016/014551 A1 | 1/2016 |
| WO | WO 2016/023014 A2 | 2/2016 |
| WO | WO 2016/058544 A1 | 4/2016 |
| WO | WO 2016/105528 A2 | 6/2016 |
| WO | WO 2016/142855 A2 | 9/2016 |
| WO | WO 2016/201370 A1 | 12/2016 |
| WO | WO 2017/037576 A1 | 3/2017 |

OTHER PUBLICATIONS

Extended European Search Report for EP 19168422.4, dated Aug. 13, 2019.
Extended European Search Report for EP 16808476.2, dated Jun. 14, 2019.
International Search Report and Written Opinion for PCT/US2012/065618, dated Mar. 19, 2013.
International Preliminary Report on Patentability for PCT/US2012/065618, dated May 30, 2014.
International Search Report and Written Opinion for PCT/US2013/065708, dated Feb. 4, 2014.
International Preliminary Report on Patentability for PCT/US2013/065708, dated Apr. 30, 2015.
International Search Report and Written Opinion for PCT/US2013/065689, dated Mar. 4, 2014.
International Preliminary Report on Patentability for PCT/US2013/065689, dated Apr. 30, 2015.
International Search Report and Written Opinion for PCT/US2013/065698, dated Feb. 20, 2014.
International Preliminary Report on Patentability for PCT/US2013/065698, dated Apr. 30, 2015.
International Search Report and Written Opinion for PCT/US2014/061232, dated Dec. 23, 2014.
International Search Report and Written Opinion for PCT/US2015/027312, dated Jul. 10, 2015.
International Preliminary Report on Patentability for PCT/US2015/027312, dated Nov. 3, 2016.
International Search Report and Written Opinion for PCT/US2015/027294, dated Jul. 10, 2015.
Extended European Search Report for EP 10786967.9, dated Oct. 23, 2012.
International Search Report and Written Opinion for PCT/US2010/038518, dated Aug. 6, 2010.
International Preliminary Report on Patentability for PCT/US2010/038518, dated Dec. 22, 2011.
Extended European Search Report for EP 10844280.7, dated Apr. 17, 2013.
Extended European Search Report for EP 15160591.2, dated Nov. 2, 2015.
International Search Report and Written Opinion for PCT/US2010/062310, dated Oct. 4, 2011.
International Preliminary Report on Patentability for PCT/US2010/062310, dated Jul. 12, 2012.
International Search Report and Written Opinion for PCT/US2015/000297, dated Mar. 4, 2016.
International Preliminary Report on Patentability PCT/US2015/000297, dated Jul. 6, 2017.
International Search Report and Written Opinion for PCT/US2016/037086, dated Sep. 2, 2016.
International Preliminary Report on Patentability for PCT/US/2016/037086, dated Dec. 21, 2017.
Extended European Search Report for EP 15773870.7, dated Oct. 17, 2018.
Invitation to Pay Additional Fees for PCT/US2016/024345, dated Aug. 9, 2016.
International Search Report and Written Opinion for PCT/US2016/024345, dated Oct. 6, 2016.
International Preliminary Report on Patentability for PCT/US2016/024345, dated Oct. 12, 2017.
Extended European Search Report for EP 16845194.6, dated Mar. 1, 2019.
Invitation to Pay Additional Fees for PCT/US2016/051118, dated Dec. 1, 2016.
International Search Report and Written Opinion for PCT/US2016/051118, dated Mar. 13, 2017.
International Preliminary Report on Patentability for PCT/US2016/051118, dated Mar. 22, 2018.
International Preliminary Report on Patentability for PCT/US2011/025423, dated Nov. 29, 2012.
International Search Report and Written Opinion from PCT/US2011/025423, dated Nov. 5, 2012.
Invitation to Pay Additional Fees for PCT/US2011/025423, dated May 31, 2011.
Akhtar et al., TFIIH kinase places bivalent marks on the carboxy-terminal domain of RNA polymerase II. Mol Cell. May 15, 2009;34(3):387-93. doi: 10.1016/j.molcel.2009.04.016.
Bai et al., Design, synthesis and anticancer activity of 1-acyl-3-amino-1,4,5,6-tetrahydropyrrolo[3,4-c]pyrazole derivatives. Bioorg Med Chem Lett. Nov. 15, 2012;22(22):6947-51. Suppl. Info, 46 pages. doi: 10.1016/j.bmcl.2012.08.117. Epub Sep. 8, 2012.
Bajrami et al., Genome-wide profiling of genetic synthetic lethality identifies CDK12 as a novel determinant of PARP1/2 inhibitor sensitivity. Cancer Res. Jan. 1, 2014;74(1):287-97. doi: 10.1158/0008-5472.CAN-13-2541. Epub Nov. 15, 2013.
Bartkowiak et al., CDK12 is a transcription elongation-associated CTD kinase, the metazoan ortholog of yeast Ctk1. Genes Dev. Oct. 15, 2010;24(20):2303-16. doi: 10.1101/gad.1968210.
Beeler et al., Role of the JNK-interacting protein 1/islet brain 1 in cell degeneration in Alzheimer disease and diabetes. Brain Res Bull. Oct. 28, 2009;80(4-5):274-81. doi: 10.1016/j.brainresbull.2009.07.006. Epub Jul. 16, 2009.
Bell et al., Integrated genomic analyses of ovarian carcinoma. Nature. Jun. 29, 2011;474(7353):609-15. doi: 10.1038/nature10166.
Ben-Av et al., Induction of vascular endothelial growth factor expression in synovial fibroblasts by prostaglandin E and interleukin-1: a potential mechanism for inflammatory angiogenesis. FEBS Letters 1995;372:83-7.

(56) References Cited

OTHER PUBLICATIONS

Benezra et al., In vivo angiogenic activity of interleukins. Archives of Opthamology 1990;108:573.
Blachly et al., Emerging drug profile: cyclin-dependent kinase inhibitors. Leuk Lymphoma. Oct. 2013;54(10):2133-43. doi: 10.3109/10428194.2013.783911. Epub Jul. 29, 2013. Author manuscript.
Blazek et al., The Cyclin K/Cdk12 complex maintains genomic stability via regulation of expression of DNA damage response genes. Genes Dev. Oct. 15, 2011;25(20):2158-72. doi: 10.1101/gad.16962311.
Blazek et al., The cyclin K/Cdk12 complex: an emerging new player in the maintenance of genome stability. Cell Cycle. Mar. 15, 2012;11(6):1049-50. doi: 10.4161/cc.11.6.19678. Epub Mar. 15, 2012.
Bloom et al., The requirement for Phr1 in CNS axon tract formation reveals the corticostriatal boundary as a choice point for cortical axons. Genes Dev. Oct. 15, 2007;21(20):2593-606. Epub Sep. 27, 2007.
Bogoyevitch et al., c-Jun N-terminal kinase (JNK) signaling: recent advances and challenges. Biochim Biophys Acta. Mar. 2010;1804(3):463-75. doi: 10.1016/j.bbapap.2009.11.002. Epub Nov. 10, 2009.
Bosken et al., The structure and substrate specificity of human Cdk12/Cyclin K. Nat Commun. Mar. 24, 2014;5:3505. doi: 10.1038/ncomms4505.
Brasca et al., 6-Substituted pyrrolo[3,4-c]pyrazoles: an improved class of CDK2 inhibitors. ChemMedChem. Jun. 2007;2(6):841-52.
Brower et al., Tumor Angiogenesis: New drugs on the block. Nature Biotechnology 1999;17:963-8.
Brunton et al., eds., Chemotherapy of Neoplastic Diseases. In Goodman & Gilman's The Pharmacological Basis of Therapeutics. 2008; 11th edition:853-908.
Cai et al., Discovery of orally active pyrrolopyridine- and aminopyridine-based Met kinase inhibitors. Bioorg Med Chem Lett. Jun. 1, 2008;18(11):3224-9. doi: 10.1016/j.bmcl.2008.04.047. Epub Apr. 25, 2008.
Cappuzzo et al., Increased MET gene copy number negatively affects survival of surgically resected non-small-cell lung cancer patients. J Clin Oncol. Apr. 1, 2009;27(10):1667-74. doi: 10.1200/JCO.2008.19.1635. Epub Mar. 2, 2009.
Carvajal et al., KIT as a therapeutic target in metastatic melanoma. JAMA. Jun. 8, 2011;305(22):2327-34. doi: 10.1001/jama.2011.746.
CAS Registry No. 1334419-59-8, STN Entry Date Dec. 30, 2013.
CAS Registry No. 769961-59-3, STN Entry Date Oct. 27, 2004.
CAS Registry No. 916173-61-0, STN Entry Date Dec. 21, 2006.
CAS Registry No. 769961-42-4, STN Entry Date Oct. 27, 2004.
Castillo et al., suzuki reaction on pyridinium N-haloheteroarylaminides: regioselective synthesis of 3,5-disubstituted 2-aminopyrazines. Available Online 2007 Nov. 22, 2008; 64(7);1351-1370.
Chakraborty et al., Developmental expression of the cyclooxygenase-1 and cyclo-oxygenase-2 genes in the peri-implantation mouse uterus and their differential regulation by the blastocyst and ovarian steroids. Journal of Molecular Endocrinology 1996;16:107-122.
Chen et al., Antiapoptotic and trophic effects of dominant-negative forms of dual leucine zipper kinase in dopamine neurons of the substantia nigra in vivo. J Neurosci. Jan. 16, 2008;28(3):672-80. doi: 10.1523/JNEUROSCI.2132-07.2008.
Chen et al., Cdk12 and Cdk13 regulate axonal elongation through a common signaling pathway that modulates Cdk5 expression. Exp Neurol. Nov. 2014;261:10-21. doi: 10.1016/j.expneurol.2014.06.024. Epub Jul. 3, 2014.
Chène, Challenges in design of biochemical assays for the identification of small molecules to target multiple conformations of protein kinases. Drug Discov Today. Jun. 2008;13(11-12):522-9. doi: 10.1016/j.drudis.2008.03.023. Epub May 5, 2008.
Chiarugi et al., Cox-2, iNOS and p53 as play-makers of tumor angiogenesis. International Journal of Molecular Medicine 1998;2:715-9.

Choi et al., Development of 'DFG-out' inhibitors of gatekeeper mutant kinases. Bioorg Med Chem Lett. Aug. 15, 2012;22(16):5297-302. doi: 10.1016/j.bmcl.2012.06.036. Epub Jun. 23, 2012.
Choi et al., Discovery and structural analysis of Eph receptor tyrosine kinase inhibitors. Bioorg Med Chem Lett. Aug. 1, 2009;19(15):4467-70. doi: 10.1016/j.bmcl.2009.05.029. Epub May 13, 2009. Supplementary Materials.
Chong et al., Positive and negative regulation of Raf kinase activity and function by phosphorylation EMBO J. Jul. 16, 2001;20(14):3716-27.
Christensen et al., Targeting transcriptional addictions in small cell lung cancer with a covalent CDK7 inhibitor. Cancer Cell. Dec. 8, 2014;26(6):909-22.
Christian et al., Flavopiridol in chronic lymphocytic leukemia: a concise review. Clin Lymphoma Myeloma. 2009;9 Suppl 3:S179-85. doi: 10.3816/CLM.2009.s.009.
Database Registry [Online] Retrieved from STN, Dec. 4, 2011, search date: Oct. 7, 2019; RN 1350102-23-6, 1349782-05-3, 1349471-31-3, 1349357-86-3, 1349106-33-7, 1348397-56-7, 1348192-23-3, 1348088-42-5.
Davies et al., Mutations of the BRAF gene in human cancer Nature. Jun. 27, 2002;417(6892):949-54. Epub Jun. 9, 2002.
Davis et al., Comprehensive analysis of kinase inhibitor selectivity. Nat Biotechnol. Oct. 30, 2011;29(11):1046-51. doi: 10.1038/nbt.1990.
Dent et al. Synergistic combinations of signaling pathway inhibitors: mechanisms for improved cancer therapy. Drug Resist Updat. Jun. 2009;12(3):65-73. doi: 10.1016/j.drup.2009.03.001.
Desai et al., Effects of phosphorylation by CAK on cyclin binding by CDC2 and CDK2. Mol Cell Biol. Jan. 1995;15(1):345-50.
Diaz-Flores et al., Intense vascular sprouting from rat femoral vein induced by prostaglandins E1 and E2. Anatomical Record 1994;238:68-76.
Downward, Targeting RAS signalling pathways in cancer therapy Nat Rev Cancer. Jan. 2003;3(1):11-22.
Drapkin et al., Human cyclin-dependent kinase-activating kinase exists in three distinct complexes. Proc Natl Acad Sci U S A. Jun. 25, 1996;93(13):6488-93.
Ercan et al., Reactivation of ERK signaling causes resistance to EGFR kinase inhibitors. Cancer Discov. Oct. 2012;2(10):934-47.
Even et al., CDC2L5, a Cdk-like kinase with RS domain, interacts with the ASF/SF2-associated protein p32 and affects splicing in vivo. J Cell Biochem. Oct. 15, 2006;99(3):890-904.
Fan et al., Dual leucine zipper-bearing kinase (DLK) activates p46SAPK and p38mapk but not ERK2. J Biol Chem. Oct. 4, 1996;271(40):24788-93.
Fancelli et al., Potent and selective Aurora inhibitors identified by the expansion of a novel scaffold for protein kinase inhibition. J Med Chem. Apr. 21, 2005;48(8):3080-4.
Fernandes et al., JNK2 and JNK3 are major regulators of axonal injury-induced retinal ganglion cell death. Neurobiol Dis. May 2012;46(2):393-401. doi: 10.1016/j.nbd.2012.02.003. Epub Feb. 14, 2012.
Fernandez et al., Neovascularization produced by angiotensin I.Journal of Laboratory and Clinical Medicine 1985;105(2):141-5.
Filippakopoulos et al., Selective inhibition of BET bromodomains. Nature. Dec. 23, 2010;468(7327):1067-73.
Finn et al., Dasatinib, an orally active small molecule inhibitor of both the src and abl kinases, selectively inhibits growth of basal-type/"triple-negative" breast cancer cell lines growing in vitro. Breast Cancer Res Treat. Nov. 2007;105(3):319-26. Epub Feb. 1, 2007.
Fiskus et al., BET protein antagonist JQ1 is synergistically lethal with FLT3 tyrosine kinase inhibitor (TKI) and overcomes resistance to FLT3-TKI in AML cells expressing FLT-ITD. Mol Cancer Ther. Oct. 2014; 13(10): 2315-2327. Published online Jul. 22, 2014. doi: 10.1158/1535-7163.MCT-14-0258.
Fizazi, The role of Src in prostate cancer. Ann Oncol. Nov. 2007;18(11):1765-73. Epub Apr. 10, 2007.
Fleming et al., Synergistic inhibition of ErbB signaling by combined treatment with seliciclib and ErbB-targeting agents. Clin Cancer Res. Jul. 1, 2008;14(13):4326-35. doi: 10.1158/1078-0432.CCR-07-4633.

(56) References Cited

OTHER PUBLICATIONS

Fraser et al., Dasatinib inhibits the secretion of TNF-alpha following TLR stimulation in vitro and in vivo. Exp Hematol. Dec. 2009;37(12):1435-44. doi: 10.1016/j.exphem.2009.09.007. Epub Sep. 26, 2009.
Fry et al., Specific inhibition of cyclin-dependent kinase 4/6 by PD 0332991 and associated antitumor activity in human tumor xenografts. Mol Cancer Ther. Nov. 2004;3(11):1427-38.
Garnett et al., Guilty as charged: B-RAF is a human oncogene Cancer Cell. Oct. 2004;6(4):313-9.
GenBank Accession No. M80629. Lapidot-Lifson et al., Dec. 31, 1994. 2 pages.
GenBank Accession No. NP_001790. Yang et al., Oct. 6, 2016. 4 pages.
Girotti et al., No longer an untreatable disease: How targeted and immunotherapies have changed the management of melanoma patients. Mol Oncol. Sep. 2014; 8(6): 1140-1158. Published online Aug. 15, 2014. doi: 10.1016/j.molonc.2014.07.027.
Glover-Cutter et al., TFIIH-associated Cdk7 kinase functions in phosphorylation of C-terminal domain Ser7 residues, promoter-proximal pausing, and termination by RNA polymerase II. Mol Cell Biol. Oct. 2009;29(20):5455-64. doi: 10.1128/MCB.00637-09. Epub Aug. 10, 2009.
Gojo et al., The cyclin-dependent kinase inhibitor flavopiridol induces apoptosis in multiple myeloma cells through transcriptional repression and down-regulation of Mcl-1. Clin Cancer Res. Nov. 2002;8(11):3527-38.
Gu et al., Effect of novel CAAX peptidomimetic farnesyltransferase inhibitor on angiogenesis in vitro and in vivo. European Journal of Cancer 1999;35(9):1394-1401.
Harada et al., Expression and regulation of vascular endothelial growth factor in osteoblasts. Clinical Orthopedics 1995;313:76-80.
Hart et al., SB1518, a novel macrocyclic pyrimidine-based JAK2 inhibitor for the treatment of myeloid and lymphoid malignancies. Leukemia. Nov. 2011;25(11):1751-9. doi: 10.1038/leu.2011.148. Epub Jun. 21, 2011.
Hirai et al., The c-Jun N-terminal kinase activator dual leucine zipper kinase regulates axon growth and neuronal migration in the developing cerebral cortex. J Neurosci. Nov. 15, 2006;26(46):11992-2002.
Hla et al., Human cyclooxygenase-2 cDNA. Proceedings of the National Academy of Sciences 1992;89(16):7384-8.
Hur et al., Clinical stage EGFR inhibitors irreversibly alkylate Bmx kinase. Bioorg Med Chem Lett. Nov. 15, 2008;18(22):5916-9. doi: 10.1016/j.bmcl.2008.07.062. Epub Jul. 18, 2008.
Iorns et al., CRK7 modifies the MAPK pathway and influences the response to endocrine therapy. Carcinogenesis. Oct. 2009;30(10):1696-701. doi: 10.1093/carcin/bgp187. Epub Aug. 3, 2009.
Itoh et al., Impaired regenerative response of primary sensory neurons in ZPK/DLK gene-trap mice. Biochem Biophys Res Commun. May 29, 2009;383(2):258-62. doi: 10.1016/j.bbrc.2009.04.009. Epub Apr. 7, 2009.
Janne et al., Factors underlying sensitivity of cancers to small-molecule kinase inhibitors. Nat Rev Drug Discov. Sep. 2009;8(9):709-23. doi: 10.1038/nrd2871. Epub Jul. 24, 2009.
Joh et al., Ginsenoside Rb1 and its metabolite compound K inhibit IRAK-1 activation—the key step of inflammation. Biochem Pharmacol. Aug. 1, 2011;82(3):278-86. doi: 10.1016/j.bcp.2011.05.003. Epub May 12, 2011.
Joshi et al., Ovarian cancer-associated mutations disable catalytic activity of CDK12, a kinase that promotes homologous recombination repair and resistance to cisplatin and poly(ADP-ribose) polymerase inhibitors. J Biol Chem. Mar. 28, 2014;289(13):9247-53. doi: 10.1074/jbc.M114.551143. Epub Feb. 19, 2014.
Jouve et al., Oxidative cyclization of n-methyl- and n-benzoylpyridylthioureas. Preparation of new thiazolo[4,5-b] and [5,4-b]pyridine derivatives. J Heterocyclic Chemistry. 2003;40(2):261-68.
Kaldis et al., Analysis of CAK activities from human cells. Eur J Biochem. Jul. 2000;267(13):4213-21.
Kantarjian et al., Dasatinib versus imatinib in newly diagnosed chronic-phase chronic myeloid leukemia. N Engl J Med. Jun. 17, 2010;362(24):2260-70.
Katt et al., Dissemination from a Solid Tumor: Examining the Multiple Parallel Pathways. Trends Cancer. Jan. 2018;4(1):20-37. doi: 10.1016/j.trecan.2017.12.002. Epub Jan. 10, 2018. Author manuscript.
Kauraniemi et al., New amplified and highly expressed genes discovered in the ERBB2 amplicon in breast cancer by cDNA microarrays. Cancer Res. Nov. 15, 2001;61(22):8235-40.
Kim et al., Discovery of pyrrolopyridine-pyridone based inhibitors of Met kinase: synthesis, X-ray crystallographic analysis, and biological activities. J Med Chem. Sep. 11, 2008;51(17):5330-41. doi: 10.1021/jm800476q. Epub Aug. 9, 2008.
Kim et al., Inhibition of vascular endothelial growth factor-induced angiogenesis suppresses tumour growth in vivo. Nature 1993;362:841.
King et al., Demonstration of a genetic therapeutic index for tumors expressing oncogenic BRAF by the kinase inhibitor SB-590885. Cancer Res. Dec. 1, 2006;66(23):11100-5.
Ko et al., CrkRS: a novel conserved Cdc2-related protein kinase that colocalises with SC35 speckles. J Cell Sci. Jul. 2001;114(Pt 14):2591-603.
Koivunen et al., EML4-ALK fusion gene and efficacy of an ALK kinase inhibitor in lung cancer. Clin Cancer Res. Jul. 1, 2008;14(13):4275-83. doi: 10.1158/1078-0432.CCR-08-0168.
Konig et al., The novel cyclin-dependent kinase inhibitor flavopiridol downregulates Bcl-2 and induces growth arrest and apoptosis in chronic B-cell leukemia lines. Blood. Dec. 1, 1997;90(11):4307-12.
Kwiatkowski et al., Targeting transcription regulation in cancer with a covalent CDK7 inhibitor. Nature. Jul. 31, 2014;511(7511):616-20.
Kwong et al., Targeted therapy for melanoma: rational combinatorial approaches. Oncogene. Jan. 2, 20104;33(1):1-9. doi: 10.1038/onc.2013.34. Epub Feb. 18, 2013.
Larochelle et al., Requirements for Cdk7 in the assembly of Cdk1/cyclin B and activation of Cdk2 revealed by chemical genetics in human cells. Mol Cell. Mar. 23, 2007;25(6):839-50.
Lavis et al., Bright ideas for chemical biology. ACS Chem Biol. Mar. 20, 2008;3(3):142-55. doi: 10.1021/cb700248m.
Lee et al., BRAF mutations in non-Hodgkin's lymphoma. Br J Cancer. Nov. 17, 2003;89(10):1958-60.
Li et al., Identification of novel pyrrolopyrazoles as protein kinase C β II inhibitors. Bioorg Med Chem Lett. Jan. 1, 2011;21(1):584-7. doi: 10.1016/j.bmcl.2010.10.032. Epub Oct. 13, 2010.
Lin et al., Phase II study of flavopiridol in relapsed chronic lymphocytic leukemia demonstrating high response rates in genetically high-risk disease. J Clin Oncol. Dec. 10, 2009;27(35):6012-8.
Liu et al., Discovery and optimization of potent and selective benzonaphthyridinone analogs as small molecule mTOR inhibitors with improved mouse microsome stability. Bioorg Med Chem Lett. Jul. 1, 2011;21(13):4036-40. doi: 10.1016/j.bmcl.2011.04.129. Epub May 7, 2011.
Liu et al., Discovery of 1-(4-(4-propionylpiperazin-l-yl)-3-(trifluoromethypphenyl)-9-(quinolin-3-yl)benzo[h][1,6]naphthyridin-2(1H)-one as a highly potent, selective mammalian target of rapamycin (mTOR) inhibitor for the treatment of cancer. J Med Chem. Oct. 14, 2010;53(19):7146-55. doi: 10.1021/jm101144f.
Liu et al., Salt-inducible kinase is involved in the regulation of corticotropin-releasing hormone transcription in hypothalamic neurons in rats. Endocrinology. Jan. 2012;153(1):223-33. doi: 10.1210/en.2011-1404. Epub Nov. 22, 2011.
Liu et al., Two cyclin-dependent kinases promote RNA polymerase II transcription and formation of the scaffold complex. Mol Cell Biol. Feb. 2004;24(4):1721-35.
Llambi et al., Apoptosis and oncogenesis: give and take in the BCL-2 family. Curr Opin Genet Dev. Feb. 2011;21(1):12-20. doi: 10.1016/j.gde.2010.12.001. Epub Jan. 13, 2011.
Lorenzo et al., Expression of proto-oncogene c-kit in high risk prostate cancer. Eur J Surg Oncol. Nov. 2004;30(9):987-92.
Lyne et al., Identification of amidoheteroaryls as potent inhibitors of mutant (V600E) B-Raf kinase with in vivo activity. Bioorg Med Chem Lett. Feb. 1, 2009;19(3):1026-9. doi: 10.1016/j.bmcl.2008.10.053. Epub Oct. 15, 2008.

(56) References Cited

OTHER PUBLICATIONS

Majima et al., Significant Roles of Inducible Cyclooxygenase (COX)-2 in Angiogenesis in Rat Sponge Implants. Japanese Journal of Pharmacology 1997;75;105-14.
Mallinson et al., Macrocycles in new drug discovery. Future Med Chem. Jul. 2012;4(11):1409-38. doi: 10.4155/fmc.12.93.
Marelli et al., Tumor targeting via integrin ligands. Front. Oncol., Aug. 30, 2013. https://doi.org/10.3389/fonc.2013.00222.
Marques et al., A new subfamily of high molecular mass CDC2-related kinases with PITAI/VRE motifs. Biochem Biophys Res Commun. Dec. 29, 2000;279(3):832-7.
Matsuyama et al., Activation of Discoidin Domain Receptor 1 Isoform b with Collagen Up-Regulates Chemokine Production in Human Macrophages: Role of p38 Mitogen-Activated Protein Kinase and NF-κB. J Immunol Feb. 15, 2004, 172 (4) 2332-2340; DOI: https://doi.org/10.4049/jimmunol.172.4.2332.
McAuley et al., CARMA3 Is a Critical Mediator of G Protein-Coupled Receptor and Receptor Tyrosine Kinase-Driven Solid Tumor Pathogenesis. Front Immunol. Aug. 15, 2018;9:1887. doi: 10.3389/fimmu.2018.01887. eCollection 2018.
Neklesa et al., Small-molecule hydrophobic tagging-induced degradation of HaloTag fusion proteins. Nat Chem Biol. Jul. 3, 2011;7(8):538-43. doi: 10.1038/nchembio.597.
Obenauf et al., Therapy-induced tumour secretomes promote resistance and tumour progression. Nature. Apr. 16, 2015;520(7547):368-72. doi: 10.1038/nature14336. Epub Mar. 25, 2015.
Ochiana et al., The human Aurora kinase inhibitor danusertib is a lead compound for anti-trypanosomal drug discovery via target repurposing. Eur J Med Chem. Apr. 2013;62:777-84. doi: 10.1016/j.ejmech.2012.07.038. Epub Jul. 31, 2012.
Odingo et al., Synthesis and evaluation of the 2,4-diaminoquinazoline series as anti-tubercular agents. Bioorg Med Chem. Dec. 15, 2014;22(24):6965-79. doi: 10.1016/j.bmc.2014.10.007. Epub Oct. 22, 2014.
Orzaez et al., Intrinsic caspase-8 activation mediates sensitization of erlotinib-resistant tumor cells to erlotinib/cell-cycle inhibitors combination treatment. Cell Death Dis. Oct. 25, 2012;3:e415. doi: 10.1038/cddis.2012.155.
Ou et al., Activity of crizotinib (PF02341066), a dual mesenchymal-epithelial transition (MET) and anaplastic lymphoma kinase (ALK) inhibitor, in a non-small cell lung cancer patient with de novo MET amplification. J Thorac Oncol. May 2011;6(5):942-6. doi: 10.1097/JTO.0b013e31821528d3.
Patel et al., Discovery of dual leucine zipper kinase (DLK, MAP3K12) inhibitors with activity in neurodegeneration models. J Med Chem. Jan. 8, 2015;58(1):401-18. doi: 10.1021/jm5013984. Epub Oct. 23, 2014.
Peifer et al., Small-molecule inhibitors of PDK1. ChemMedChem. Dec. 2008;3(12):1810-38. doi: 10.1002/cmdc.200800195.
Pevarello et al., 3-Amino-1,4,5,6-tetrahydropyrrolo[3,4-c]pyrazoles: A new class of CDK2 inhibitors. Bioorg Med Chem Lett. Feb. 15, 2006;16(4):1084-90.
Powell et al., Regulation of immune responses by mTOR. Annu Rev Immunol. 2012;30:39-68. doi:10.1146/annurev-immunol-020711-075024. Epub Nov. 29, 2011.
Powers et al., Discovery and initial SAR of inhibitors of interleukin-1 receptor-associated kinase-4. Bioorg Med Chem Lett. Jun. 1, 2006;16(11):2842-5. Epub Mar. 24, 2006.
PubChem—CID-68365059. Available at https://pubchem.ncbi.nlm.nih.gov/compound/68365059. Accessed Jun. 17, 2016.
Roberts et al., Antiangiogenic and antitumor activity of a selective PDGFR tyrosine kinase inhibitor, CP-673,451. Cancer Res. Feb. 1, 2005;65(3):957-66.
Robinson et al., Discovery of the hemifumarate and (alpha-L-alanyloxy)methyl ether as prod rugs of an anti rheumatic oxindole: prod rugs for the enolic OH group. J. Med. Chem. 1996;39:10-8.
Rubin et al., KIT activation is a ubiquitous feature of gastrointestinal stromal tumors. Cancer Res. Nov. 15, 2001;61(22):8118-21.
Sánchez-Martínez et al., Cyclin dependent kinase (CDK) inhibitors as anticancer drugs. Bioorg Med Chem Lett. Sep. 1, 2015;25(17):3420-35. doi: 10.1016/j.bmcl.2015.05.100. Epub Jun. 6, 2015.
Schroeder et al., Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), a selective and orally efficacious inhibitor of the Met kinase superfamily. J Med Chem. Mar. 12, 2009;52(5):1251-4. doi: 10.1021/jm801586s.
Seed et al., The Inhibition of colon-26 Adenocarcinoma Development and Angiogenesis by Topical Diclofenac in 2.5% Hyaluronan. Cancer Research 1997;57:1625-9.
Sengupta et al., DLK induces developmental neuronal degeneration via selective regulation of proapoptotic JNK activity. Journal of Cell Biology 2011;194(5):751-764. DOI https://doi.org/10.1083/jcb.201103153.
Serizawa et al., Association of Cdk-activating kinase subunits with transcription factor TFIIH. Nature. Mar. 16, 1995;374(6519):280-2.
Sharma et al., A chromatin-mediated reversible drug-tolerant state in cancer cell subpopulations. Cell. Apr. 2, 2010;141(1):69-80.
Shiekhattar et al., Cdk-activating kinase complex is a component of human transcription factor TFIIH. Nature. Mar. 16, 1995;374(6519):283-7.
Shin et al., Dual leucine zipper kinase is required for retrograde injury signaling and axonal regeneration. Neuron. Jun. 21, 2012;74(6):1015-22. doi: 10.1016/j.neuron.2012.04.028.
Sidow et al., Concepts in solid tumor evolution. Trends Genet. Apr. 2015;31(4):208-14. doi: 10.1016/j.tig.2015.02.001. Epub Feb. 27, 2015. Author manuscript.
Smith et al., Recent advances in the research and development of RAF kinase inhibitors. Curr. Top Med. Chem. 2006; 6(11):1071-89.
Smith et al., The effect of the nature of the amine leaving group on the nature of the E2 transition state for the reaction of 1-phenylethylammonium ions sodium ethoxide in ethanol. Can J Chem. Mar. 28, 1989;67:1457-67.
Srivastava et al., Augmentation of therapeutic responses in melanoma by inhibition of IRAK-1,-4. Cancer Res. Dec. 1, 2012;72(23):6209-16. doi: 10.1158/0008-5472.CAN-12-0337. Epub Oct. 4, 2012.
Stuhlmiller et al., Inhibition of Lapatinib-Induced Kinome Reprogramming in ERBB2-Positive Breast Cancer by Targeting BET Family Bromodomains. Cell Rep. Apr. 21, 2015;11(3):390-404.
Takemori et al., Inactivation of HDAC5 by SIK1 in AICAR-treated C2C12 myoblasts. Endocr J. 2009;56(1):121-30. Epub Oct. 22, 2008.
Terai et al., Activation of the FGF2-FGFR1 autocrine pathway: a novel mechanism of acquired resistance to gefitinib in NSCLC. Mol Cancer Res. Jul. 2013;11(7):759-67.
Tian et al., mTOR Signaling in Cancer and mTOR Inhibitors in Solid Tumor Targeting Therapy. Int J Mol Sci. Feb. 11, 2019;20(3). pii: E755. doi: 10.3390/ijms20030755.
Tsai et al., Discovery of a selective inhibitor of oncogenic B-Raf kinase with potent antimelanoma activity. Proc Natl Acad Sci U S A. Feb. 26, 2008;105(8):3041-6. doi: 10.1073/pnas.0711741105. Epub Feb. 19, 2008.
Tsujii et al., Cyclooxygenase regulates angiogenesis induced by colon cancer cells. Cell. May 29, 1998;93(5):705-16.
Uniprot No. Q9NYV4. Last modified Mar. 15, 2017. 14 pages.
Vora et al., CDK 4/6 inhibitors sensitize PIK3CA Mutant Breast Cancer to PI3K inhibitors. Cancer Cell. Jul. 14, 2014;26(1):136-149. Published online Jul. 4, 2014. doi: 10.1016/j.ccr.2014.05.020.
Wang et al., IRAK-4 inhibitors for inflammation. Curr Top Med Chem. 2009;9(8):724-37.
Wang et al., Ligand-associated ERBB2/3 activation confers acquired resistance to FGFR inhibition in FGFR3-dependent cancer cells. Oncogene. Apr. 23, 2015;34(17):2167-77. doi: 10.1038/onc.2014.161. Epub Jun. 9, 2014.
Wang et al., Pharmacophore and structure-activity relationships of integrase inhibition within a dual inhibitor scaffold of HIV reverse transcriptase and integrase. Bioorg Med Chem. Jun. 15, 2010;18(12):4202-11. doi: 10.1016/j.bmc.2010.05.004. Epub May 7, 2010.
Wellbrock et al., The RAF proteins take centre stage Nat Rev Mol Cell Biol. Nov. 2004;5(11):875-85.

(56) References Cited

OTHER PUBLICATIONS

Wietek et al., IRAK-4: a new drug target in inflammation, sepsis, and autoimmunity. Mol Interv. Jul. 2002;2(4):212-5.
Williamson et al., Structure-guided design of pyrazolo[1,5-a]pyrimidines as inhibitors of human cyclin-dependent kinase 2. Bioorg Med Chem Lett. Feb. 15, 2005;15(4):863-7.
Wu et al., FDA-approved small-molecule kinase inhibitors. Trends Pharmacol Sci. Jul. 2015;36(7):422-39. doi: 10.1016/j.tips.2015.04.005. Epub May 12, 2015.
Xin et al., Peroxisome proliferator-activated receptor gamma ligands are potent inhibitors of angiogenesis in vitro and in vivo. Journal of Biological Chemistry 1996;274(13):9116-21.
Yalpani, Cholesterol Lowering Drugs. Chemistry and Industry Feb. 1996;3:85-89.
Yasuda et al., The stem cell factor/c-kit receptor pathway enhances proliferation and invasion of pancreatic cancer cells. Mol Cancer. Oct. 18, 2006;5:46.
Zambon et al., Small molecule inhibitors of BRAF in clinical trials. Bioorg Med Chem Lett. Jan. 15, 2012;22(2):789-92. doi: 10.1016/j.bmcl.2011.11.060. Epub Dec. 3, 2011.
Zang et al., Genetic and structural variation in the gastric cancer kinome revealed through targeted deep sequencing. Cancer Res. Jan. 1, 2011;71(1):29-39. doi: 10.1158/0008-5472.CAN-10-1749. Epub Nov. 19, 2010.
Zebisch et al., Back to the roots: the remarkable RAF oncogene story Cell Mol Life Sci. Jun. 2006;63(11):1314-30.
Zhang et al., Discovery of potent and selective covalent inhibitors of JNK. Chem Biol. Jan. 27, 2012;19(1):140-54. doi: 10.1016/j.chembiol.2011.11.010.
Zhang et al., Etk/Bmx transactivates vascular endothelial growth factor 2 and recruits phosphatidylinositol 3-kinase to mediate the tumor necrosis factor-induced angiogenic pathway. J Biol Chem. Dec. 19, 2003;278(51):51267-76. Epub Oct. 7, 2003.
Zhou et al., Novel mutant-selective EGFR kinase inhibitors against EGFR T790M. Nature. Dec. 24, 2009;462(7276):1070-4.
Ziche et al., Role of prostaglandin E1 and copper in angiogenesis. Journal of the National Cancer Institute 1982;69(2):475.
Zompi et al., Animal models of dengue virus infection. Viruses. Jan. 2012;4(1):62-82. doi: 10.3390/v4010062. Epub Jan. 9, 2012.
U.S. Appl. No. 16/179,833, filed Nov. 2, 2018, Gray et al.
U.S. Appl. No. 16/780,268, filed Feb. 3, 2020, Gray et al.
PCT/US2011/025423, May 31, 2011, Invitation to Pay Additional Fees.
PCT/US2011/025423, Nov. 5, 2012, International Search Report and Written Opinion.
PCT/US2011/025423, Nov. 29, 2012, International Preliminary Report on Patentability.
PCT/US2016/037086, Sep. 2, 2016, International Search Report and Written Opinion.
PCT/US2016/024345, Oct. 6, 2016, International Search Report and Written Opinion.
PCT/US2015/027312, Nov. 3, 2016, International Preliminary Report on Patentability.
PCT/US2015/027294, Nov. 3, 2016, International Preliminary Report on Patentability.
PCT/US2016/051118, Dec. 1, 2016, Invitation to Pay Additional Fees.
PCT/US2016/051118, Mar. 13, 2017, International Search Report and Written Opinion.
PCT/US2015/000297, Jul. 6, 2017, International Preliminary Report on Patentability.
PCT/US2016/024345, Oct. 12, 2017, International Preliminary Report on Patentability.
PCT/US2016/037086, Dec. 21, 2017, International Preliminary Report on Patentability.
PCT/US2010/038518, Aug. 6, 2010, International Search Report and Written Opinion.
PCT/US2010/062310, Oct. 4, 2011, International Search Report and Written Opinion.
PCT/US2010/038518, Dec. 22, 2011, International Preliminary Report on Patentability.
PCT/US2010/062310, Jul. 12, 2012, International Preliminary Report on Patentability.
EP 10786967.9, Oct. 23, 2012, Extended European Search Report.
PCT/US2012/065618, Mar. 19, 2013, International Search Report and Written Opinion.
EP 10844280.7, Apr. 17, 2013, Extended European Search Report.
PCT/US2013/065708, Feb. 4, 2014, International Search Report and Written Opinion.
PCT/US2013/065698, Feb. 20, 2014, International Search Report and Written Opinion.
PCT/US2013/065689, Mar. 4, 2014, International Search Report and Written Opinion.
PCT/US2012/065618, May 30, 2014, International Preliminary Report on Patentability.
PCT/US2014/061232, Dec. 23, 2014, International Search Report and Written Opinion.
PCT/US2013/065708, Apr. 30, 2015, International Preliminary Report on Patentability.
PCT/US2013/065689, Apr. 30, 2015, International Preliminary Report on Patentability.
PCT/US2013/065698, Apr. 30, 2015, International Preliminary Report on Patentability.
PCT/US2015/027312, Jul. 10, 2015, International Search Report and Written Opinion.
PCT/US2015/027294, Jul. 10, 2015, International Search Report and Written Opinion.
EP 15160591.2, Jul. 14, 2015, Partial European Search Report.
EP 15160591.2, Nov. 2, 2015, Partial European Search Report.
PCT/US2015/000297, Mar. 4, 2016, International Search Report and Written Opinion.
PCT/US2016/024345, Aug. 9, 2016, Invitation to Pay Additional Fees.
PCT/US2016/051118, Mar. 22, 2018, International Preliminary Report on Patentability.
EP 16773870.7, Jul. 12, 2018, Partial Supplementary European Search Report.
EP 16773870.7, Oct. 17, 2018, Extended European Search Report.
EP16845194.6, Mar. 1, 2019, Extended European Search Report.
EP 16808476.2, Mar. 7, 2019, Partial Supplementary European Search Report.
EP 16808476.2, Jun. 14, 2019, Extended European Search Report.
EP 19168422.4, Aug. 13, 2019, Extended European Search Report.

\* cited by examiner

*FIG. 1A*

| Patent Compound No. | Structure |
|---|---|
| 100 | 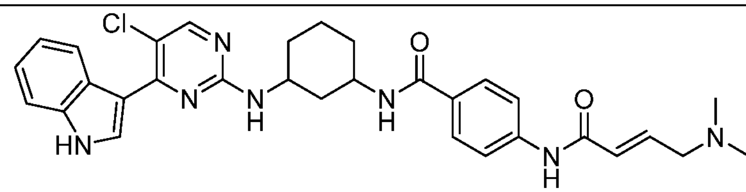 |
| 101 | 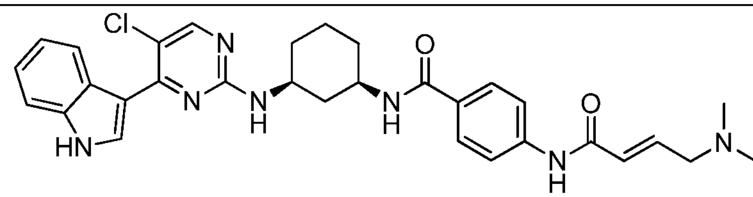 |
| 102 | 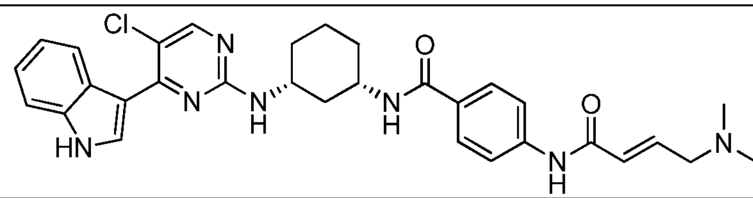 |
| 103 | 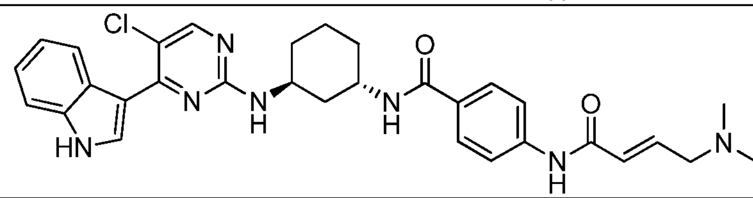 |
| 104 | 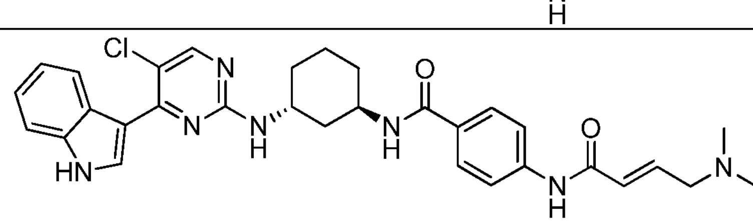 |
| 105 | 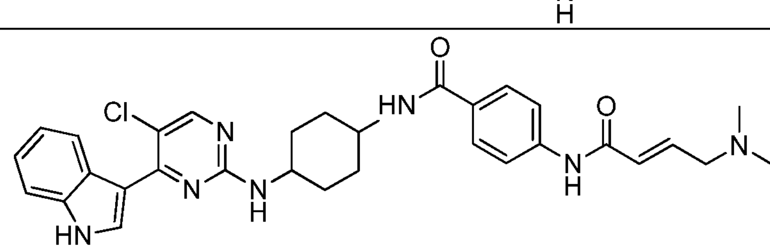 |
| 106 | 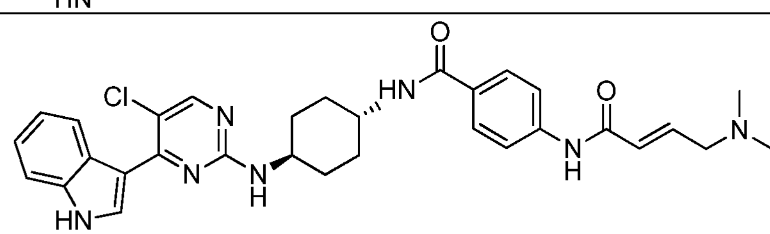 |

FIG. 1B

| Patent Compound No. | Structure |
|---|---|
| 108 | 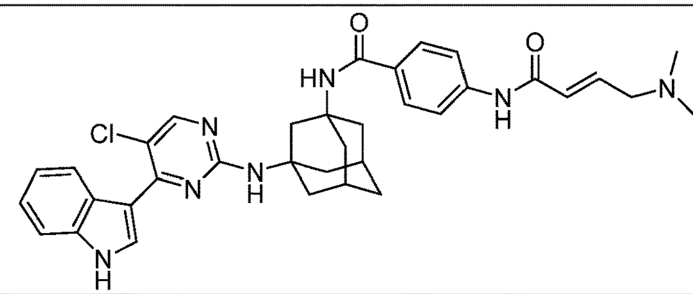 |
| 109 | 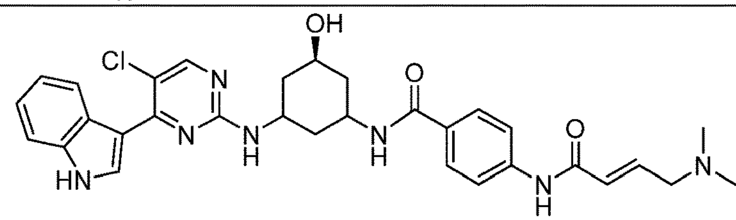 |
| 110 | 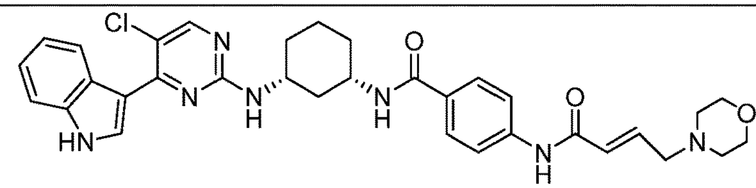 |
| 111 | 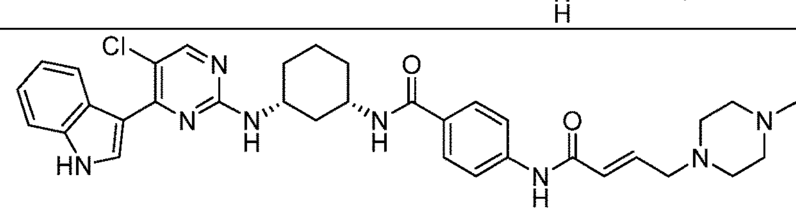 |
| 112 | 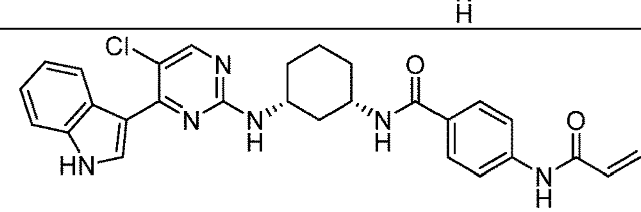 |
| 113 | 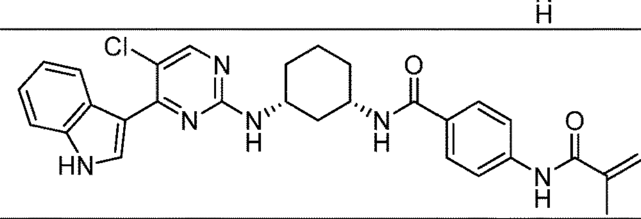 |
| 114 | 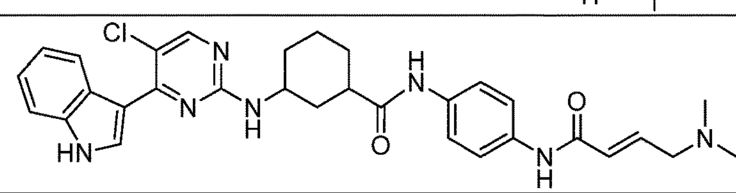 |
| 115 | 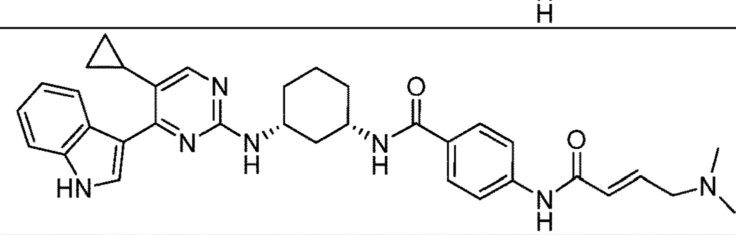 |

*FIG. 1C*

| Patent Compound No. | Structure |
|---|---|
| 116 | 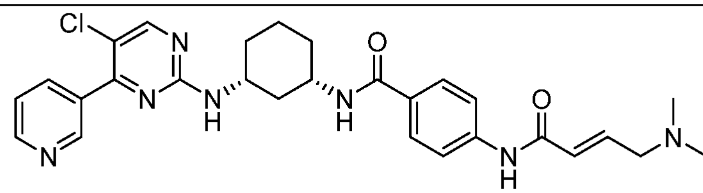 |
| 117 | 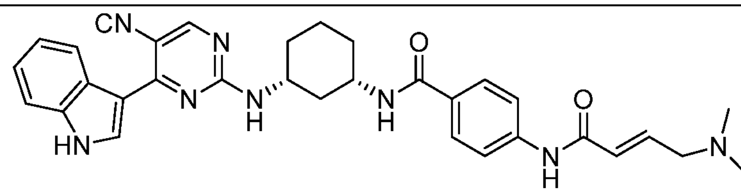 |
| 118 | 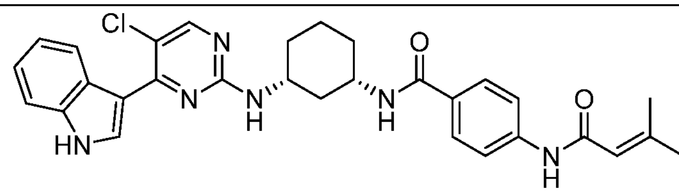 |
| 119 | 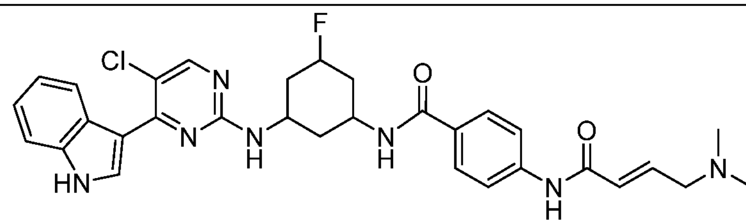 |
| 120 | 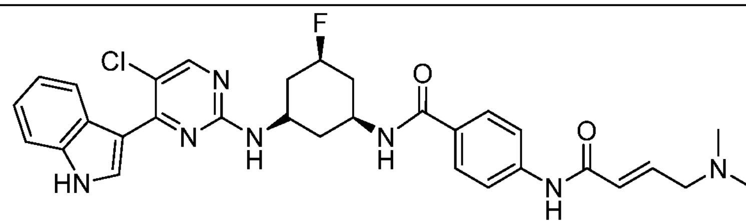 |
| 121 | 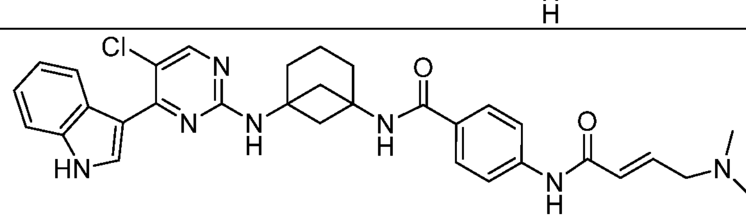 |
| 122 | 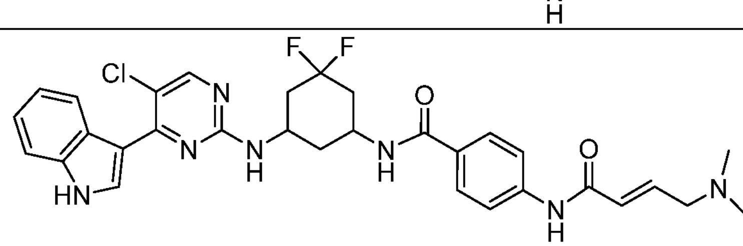 |
| 123 | 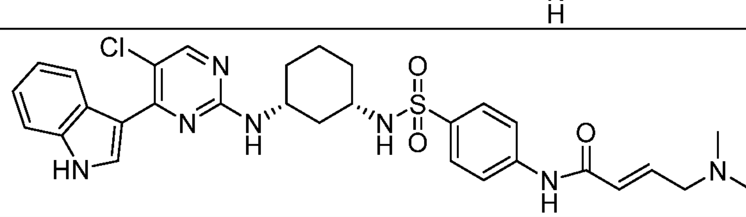 |

| Patent Compound No. | Structure |
|---|---|
| 124 | 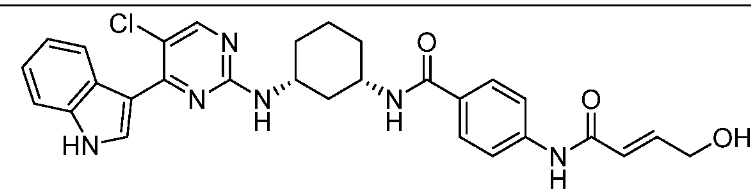 |
| 125 | 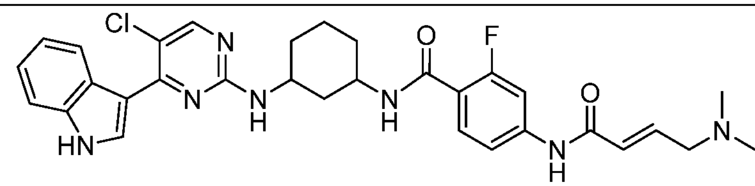 |
| 126 | 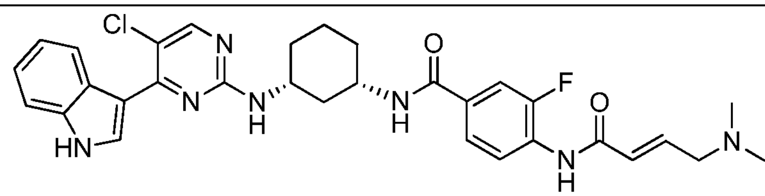 |
| 127 | 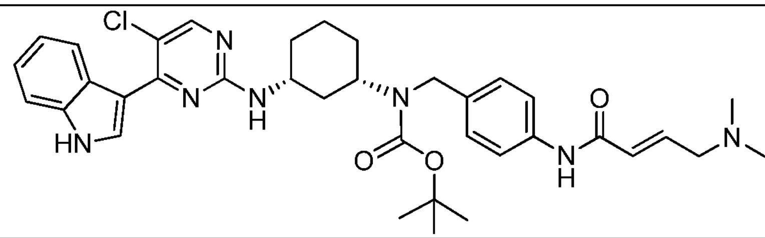 |
| 128 | 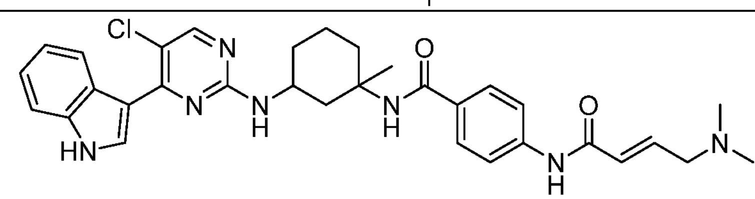 |
| 129 | 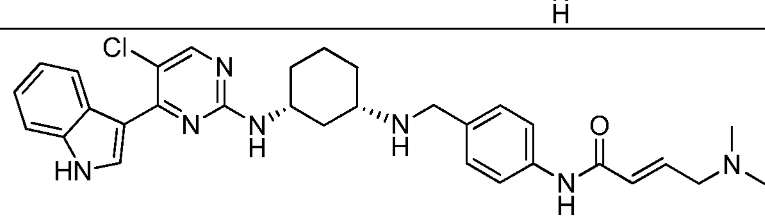 |
| 130 | 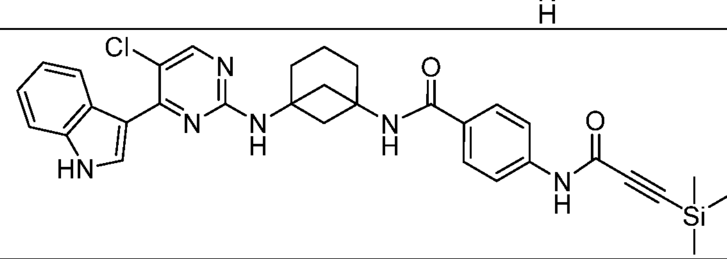 |
| 131 | 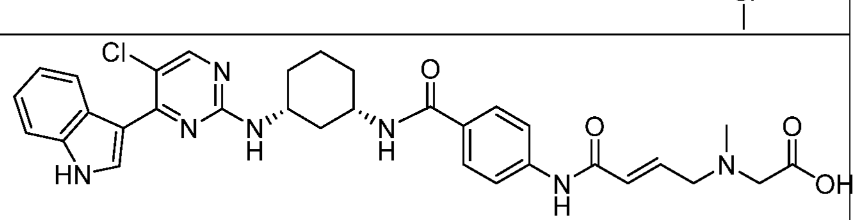 |

FIG. 1E

| Patent Compound No. | Structure |
|---|---|
| 132 | 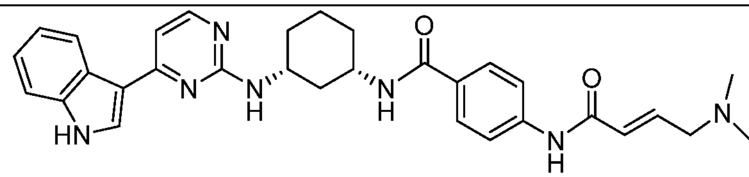 |
| 133 | 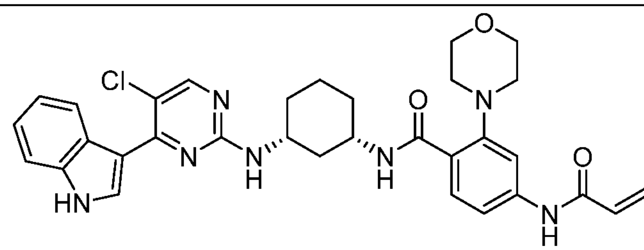 |
| 135 | 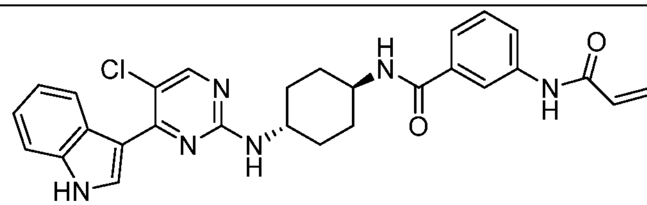 |
| 136 | 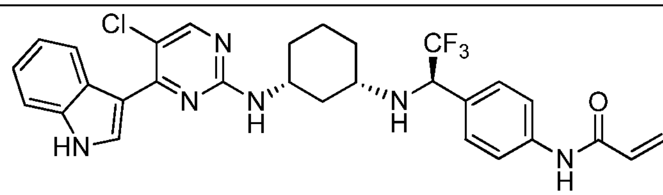 |
| 137 | 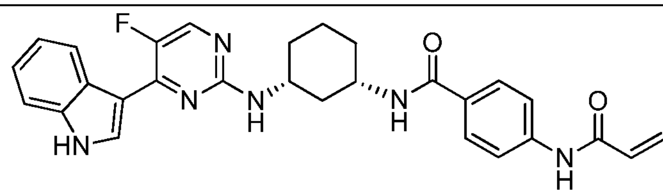 |
| 138 | 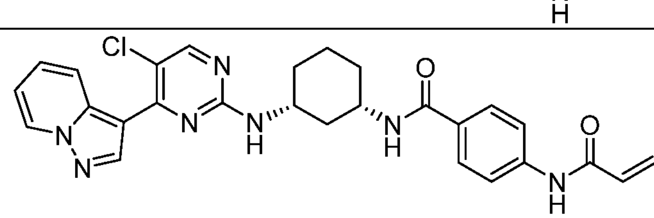 |
| 139 | 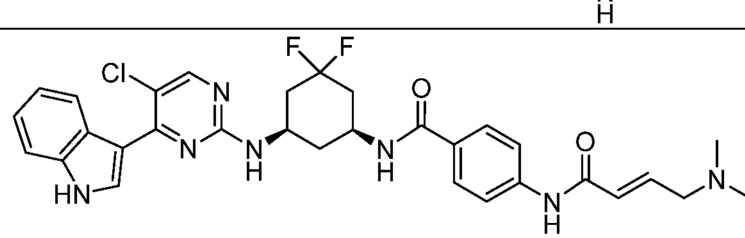 |
| 140 | 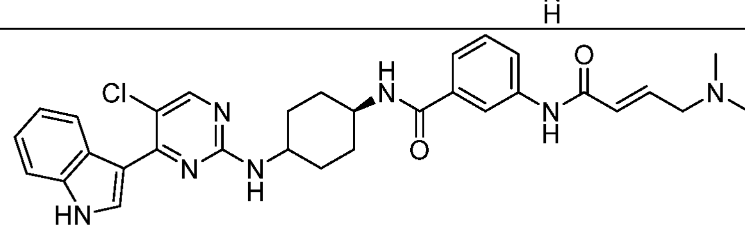 |

FIG. 1F

| Patent Compound No. | Structure |
|---|---|
| 141 | 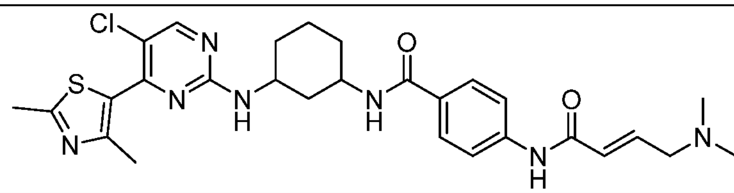 |
| 142 | 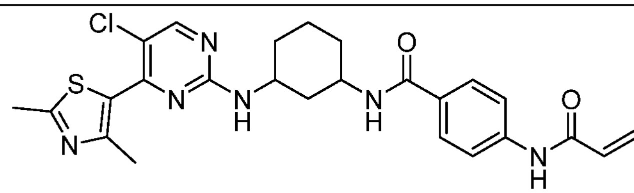 |
| 143 | 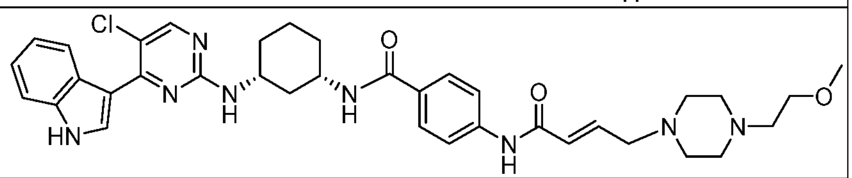 |
| 144 | 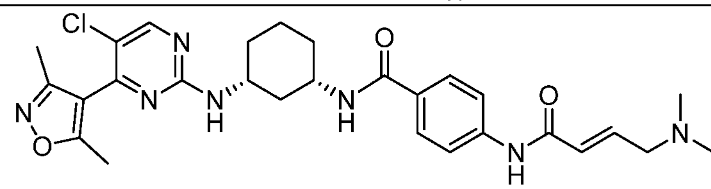 |
| 145 | 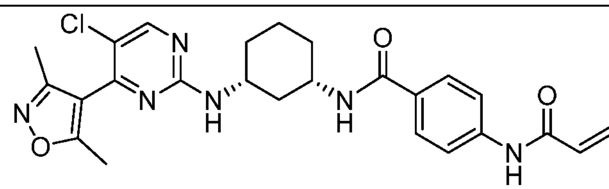 |
| 146 | 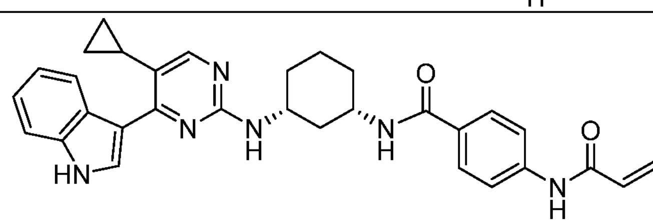 |
| 147 | 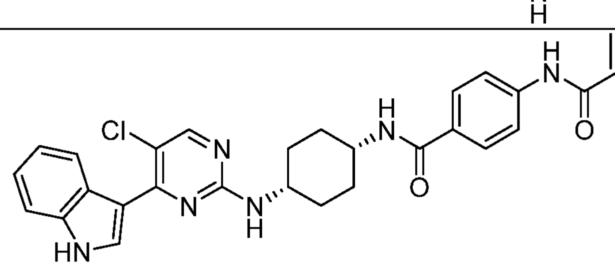 |
| 148 | 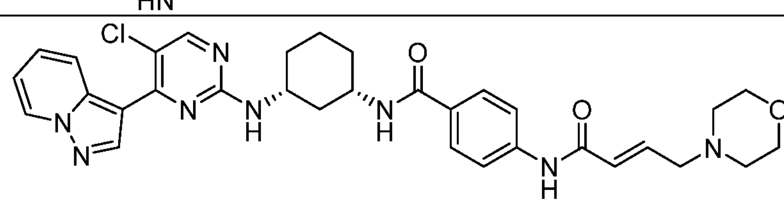 |

| Patent Compound No. | Structure |
|---|---|
| 149 | 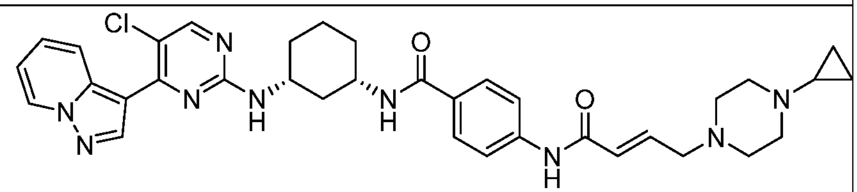 |
| 150 | 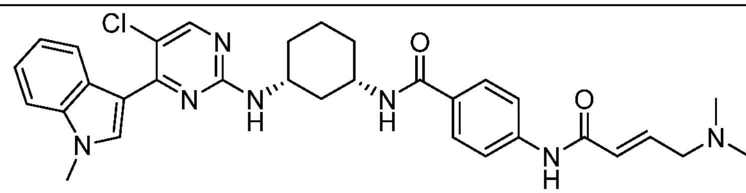 |
| 151 | 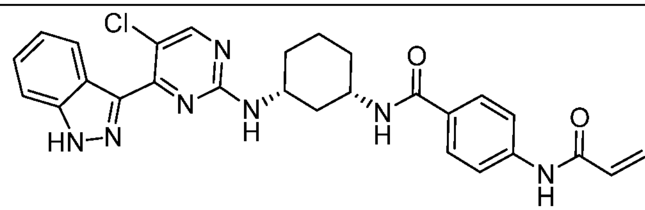 |
| 152 | 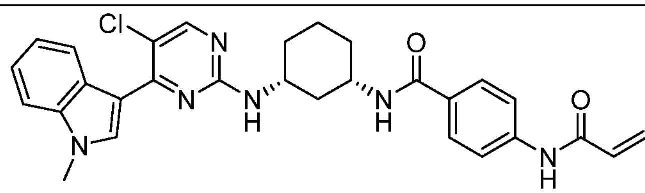 |
| 153 | 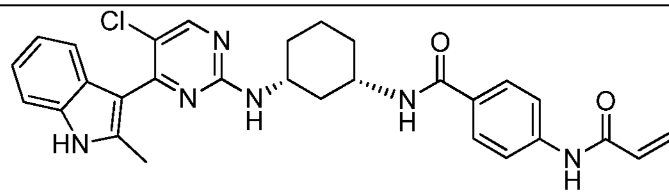 |
| 154 | 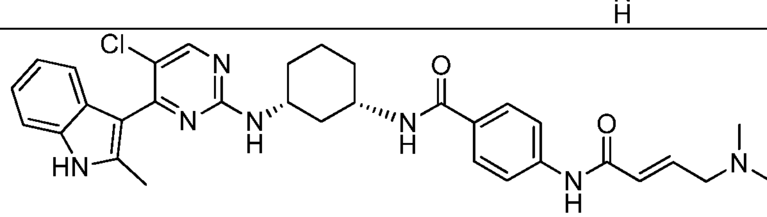 |
| 155 | 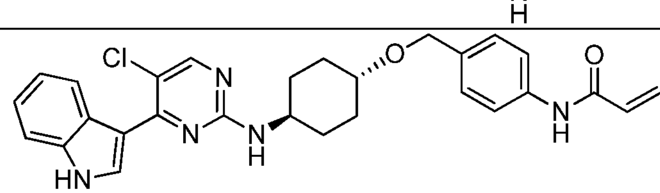 |
| 156 | 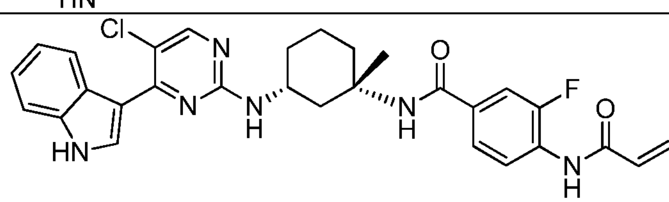 |

| Patent Compound No. | Structure |
|---|---|
| 157 | 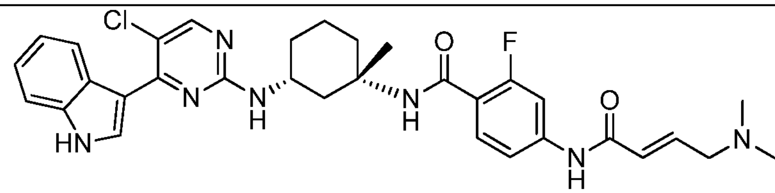 |
| 158 | 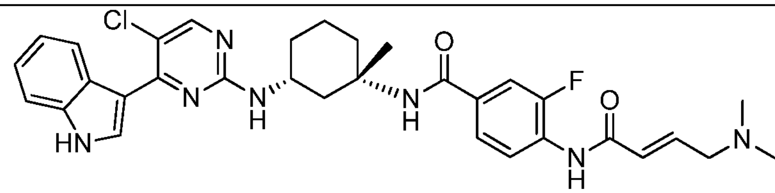 |
| 159 | 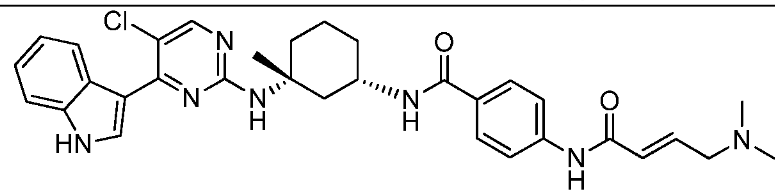 |
| 160 | 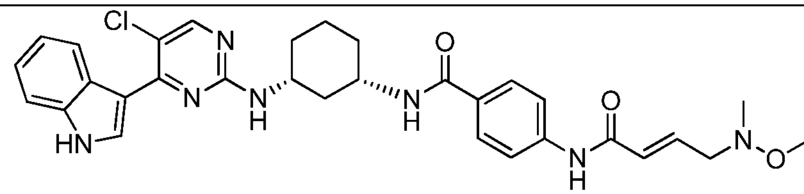 |
| 161 | 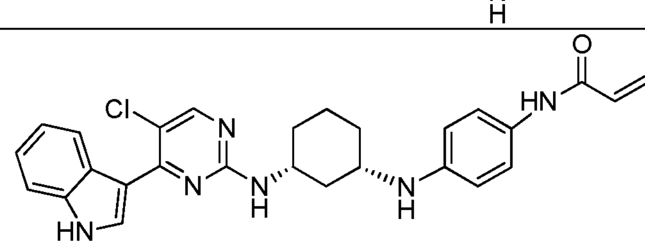 |
| 162 | 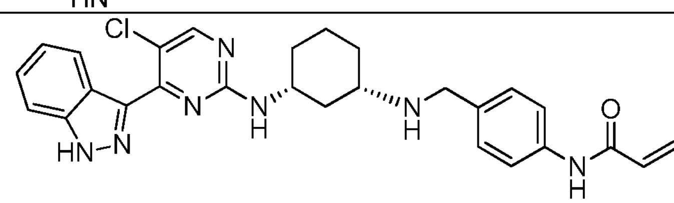 |
| 164 | 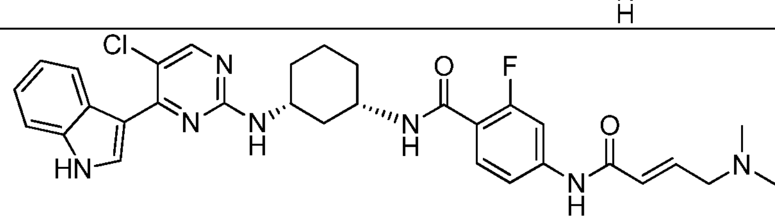 |
| 173 | 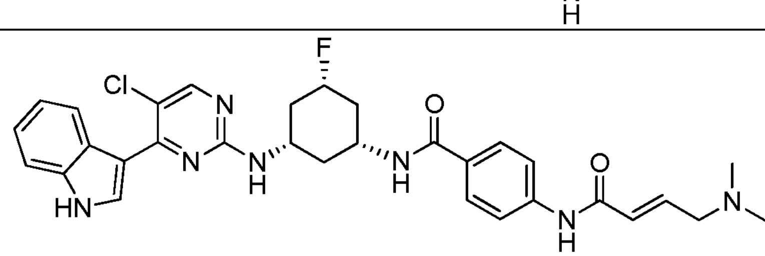 |

*FIG. 1I*

| Patent Compound No. | Structure |
|---|---|
| 174 | 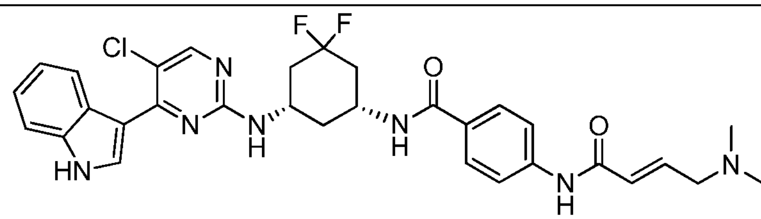 |
| 175 | 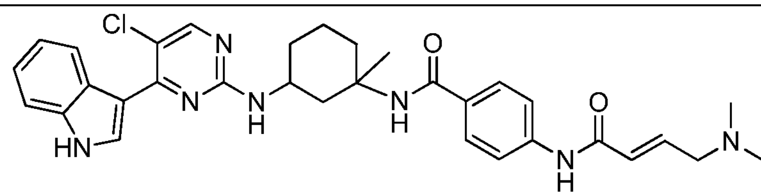 |
| 176 | 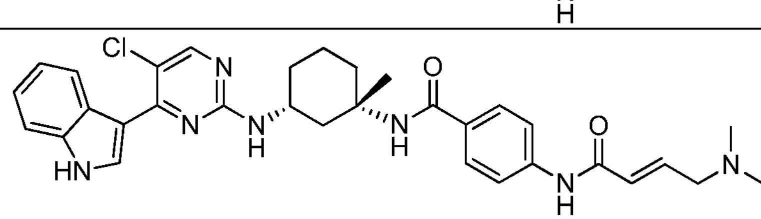 |
| 177 | 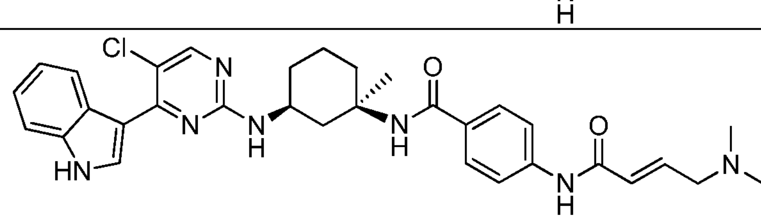 |
| 178 | 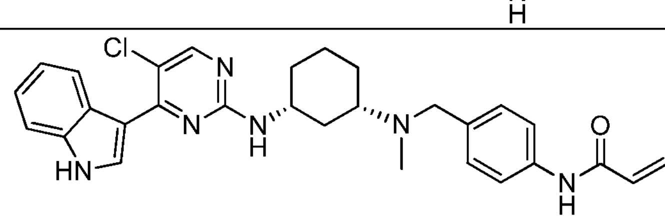 |

POLYCYCLIC INHIBITORS OF CYCLIN-DEPENDENT KINASE 7 (CDK7)

RELATED APPLICATIONS

The present application is a Divisional Application of U.S. application Ser. No. 15/030,245, filed Apr. 18, 2016, which is a U.S. National Stage Application under 35 U.S.C. § 371 of International Application No. PCT/US2014/061232, filed Oct. 17, 2014, which claims priority under 35 U.S.C. § 119(e) to U.S. Provisional Application 61/893,005, filed Oct. 18, 2013. The entire contents of each of the foregoing applications are incorporated herein by reference.

GOVERNMENT SUPPORT

This invention was made with government support under grant number HG006097, HG005693, CA006516, CA148164, CA130876, and CA156732 awarded by The National Institutes of Health. The government has certain rights in the invention.

BACKGROUND OF THE INVENTION

The members of the cyclin-dependent kinase (CDK) family play critical regulatory roles in proliferation. There are currently 20 known mammalian CDKs. While CDK7-13 have been linked to transcription, only CDK1, 2, 4, and 6 show demonstrable association with the cell cycle. Unique among the mammalian CDKs, CDK7 has consolidated kinase activities, regulating both the cell cycle and transcription. In the cytosol, CDK7 exists as a heterotrimeric complex and is believed to function as a CDK1/2-activating kinase (CAK), whereby phosphorylation of conserved residues in CDK1/2 by CDK7 is required for full catalytic CDK activity and cell cycle progression (Desai et al., "Effects of phosphorylation by CAK on cyclin binding by CDC2 and CDK2." *Mol. Cell Biol.* 15, 345-350 (1995); Kaldis et al., "Analysis of CAK activities from human cells." *Eur. J. Biochem.* 267, 4213-4221 (2000); Larochelle et al., "Requirements for CDK7 in the assembly of CDK1/cyclin B and activation of CDK2 revealed by chemical genetics in human cells." *Mol. Cell* 25, 839-850 (2007)). In the nucleus, CDK7 forms the kinase core of the RNA polymerase (RNAP) II general transcription factor complex and is charged with phosphorylating the C-terminal domain (CTD) of RNAP II, a requisite step in gene transcriptional initiation (Serizawa. et al., "Association of CDK-activating kinase subunits with transcription factor TFIIH." *Nature* 374, 280-282 (1995); Shiekhattar et al., "CDK-activating kinase complex is a component of human transcription factor TFIIH." *Nature* 374, 283-287 (1995); Drapkin et al., "Human cyclin-dependent kinase-activating kinase exists in three distinct complexes." *Proc. Natl. Acad. Sci. U.S.A.* 93, 6488-6493 (1996); Liu. et al., "Two cyclin-dependent kinases promote RNA polymerase II transcription and formation of the scaffold complex." *Mol. Cell Biol.* 24, 1721-1735 (2004); Akhtar et al., "TFIIH kinase places bivalent marks on the carboxy-terminal domain of RNA polymerase II." *Mol. Cell* 34, 387-393 (2009); Glover-Cutter et al., "TFIIH-associated CDK7 kinase functions in phosphorylation of C-terminal domain Ser7 residues, promoter-proximal pausing, and termination by RNA polymerase II." *Mol. Cell Biol.* 29, 5455-5464 (2009)). Together, the two functions of CDK7, i.e., CAK and CTD phosphorylation, support critical facets of cellular proliferation, cell cycling, and transcription.

Disruption of RNAP II CTD phosphorylation has been shown to preferentially effect proteins with short half-lives, including those of the anti-apoptotic BCL-2 family (Konig et al., "The novel cyclin-dependent kinase inhibitor flavopiridol downregulates Bcl-2 and induces growth arrest and apoptosis in chronic B-cell leukemia lines." *Blood* 1, 4307-4312 (1997); Gojo et al., "The cyclin-dependent kinase inhibitor flavopiridol induces apoptosis in multiple myeloma cells through transcriptional repression and down-regulation of Mcl-1." *Clin. Cancer Res.* 8, 3527-3538 (2002)). Cancer cells have demonstrated ability to circumvent pro-cell death signaling through upregulation of BCL-2 family members (Llambi et al., "Apoptosis and oncogenesis: give and take in the BCL-2 family." *Curr. Opin. Genet. Dev.* 21, 12-20 (2011)). Therefore, inhibition of human CDK7 kinase activity is likely to result in anti-proliferative activity, and pharmacological inhibition could be used to treat proliferative disorders, including cancer. Indeed, flavopiridol, a non-selective pan-CDK inhibitor that targets CTD kinases, has demonstrated efficacy for the treatment of chronic lymphocytic leukemia (CLL), but suffers from a poor toxicity profile (Lin et al., "Phase II study of flavopiridol in relapsed chronic lymphocytic leukemia demonstrating high response rates in genetically high-risk disease." *J. Clin. Oncol.* 27, 6012-6018 (2009); Christian et al., "Flavopiridol in chronic lymphocytic leukemia: a concise review." Clin. Lymphoma Myeloma 9 Suppl. 3, S179-S185 (2009)). A selective CDK7 inhibitor may hold promise as a therapeutic agent for the treatment of CLL and other cancers.

BRIEF DESCRIPTION OF THE DRAWINGS

FIGS. 1A-1I are a table of exemplary compounds of Formula (I).

SUMMARY OF THE INVENTION

Figure 1D:
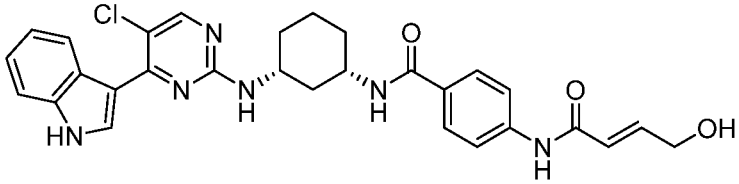
Figure 1D:
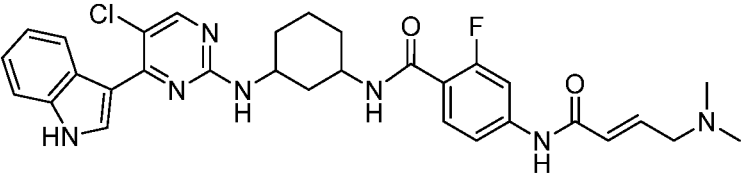
Figure 1D:
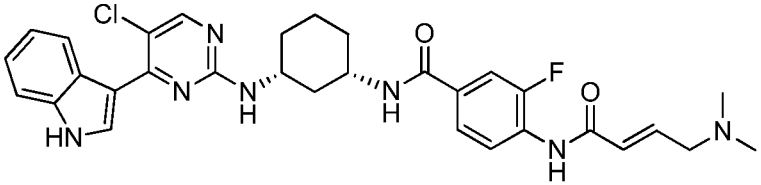
Figure 1D:
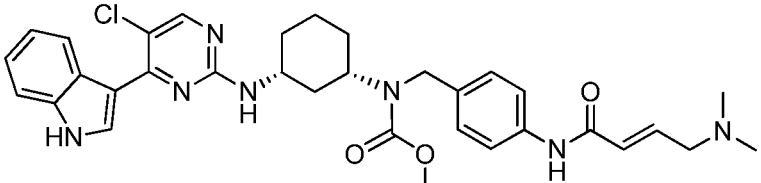
Figure 1D:
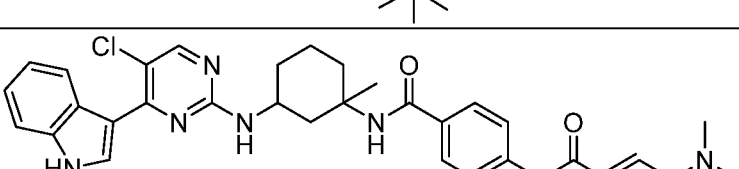
Figure 1D:
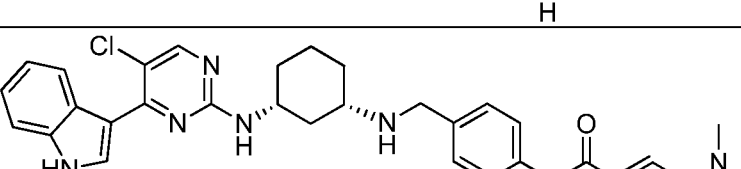
Figure 1D:
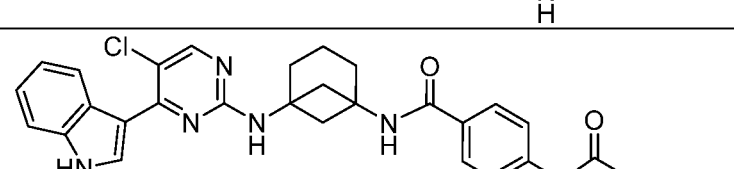
Figure 1D:
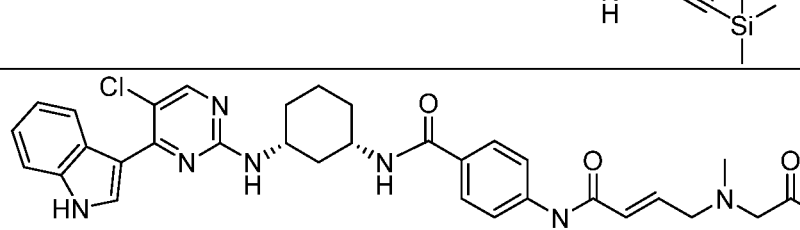

Cyclin dependent kinases (CDKs) (e.g., cyclin-dependent kinase 7 (CDK7), cyclin-dependent kinase 12 (CDK12), and cyclin-dependent kinase 13 (CDK13)) are key regulators of the cell cycle. Their successive activation and inactivation drives the cycle forward. The activity of CDKs is regulated by multiple mechanisms such as positive and negative phosphorylation, binding of regulatory proteins like cyclins, and CDK inhibitors. Most CDKs require the phosphorylation of a threonine residue located in the T-loop to achieve full kinase activity. This threonine residue is conserved in all CDKs that function in cell cycle regulation. The enzyme responsible for this phosphorylation is therefore termed CDK-activating-kinase or CAK. CAK complexes have been found to be composed of CDK7, cyclin H, and MAT1. The CAK complex containing CDK7 appears to constitute the major CAK activity in the cell. Besides its CAK function, CDK7 also plays a role in transcription and possibly in DNA repair. The trimeric CAK complex CDK7/cyclin H/MAT1 is also a component of TFIIH, the general transcription/DNA repair factor IIH. As a TFIIH subunit, CDK7 phosphorylates the carboxy-terminal-domain (CTD) of the largest subunit of RNAP II. This suggests that the CDK7 enzyme complexes are involved in multiple functions in the cell, e.g., cell cycle control, apoptosis, transcription regulation, and DNA repair.

The present invention provides compounds of Formula (I), and pharmaceutically acceptable salts, solvates, hydrates, polymorphs, co-crystals, tautomers, stereoisomers, isotopically labeled derivatives, prodrugs, and compositions thereof. The compounds of Formula (I), and pharmaceutically acceptable salts, solvates, hydrates, polymorphs, co-crystals, tautomers, stereoisomers, isotopically labeled derivatives, prodrugs, and compositions thereof, may inhibit the activity of a kinase. In certain embodiments, the kinase is a CDK. In certain embodiments, the kinase is CDK7, CDK12, and/or CDK13. In certain embodiments, the compound of Formula (I) is selective for CDK7 compared to other kinases. The present invention further provides methods of using the inventive compounds, and pharmaceutically acceptable salts, solvates, hydrates, polymorphs, co-crystals, tautomers, stereoisomers, isotopically labeled derivatives, prodrugs, and compositions thereof, to study the inhibition of a kinase (e.g., CDK7) and as therapeutics for the prevention and/or treatment of diseases associated with overexpression and/or aberrant activity of a kinase (e.g., CDK7). In certain embodiments, the inventive compounds are used for the prevention and/or treatment of proliferative diseases (e.g., cancers (e.g., leukemia, lymphoma, melanoma, multiple myeloma, breast cancer, Ewing's sarcoma, osteosarcoma, brain cancer, neuroblastoma, lung cancer), benign neoplasms, angiogenesis, inflammatory diseases, autoinflammatory diseases, and autoimmune diseases) in a subject.

The compounds of Formula (I) may selectively inhibit the activity of a CDK. In some embodiments, the compounds of Formula (I) may selectively inhibit the activity of CDK7, CDK12, and/or CDK13. In certain embodiments, the compounds of Formula (I) may selectively inhibit the activity of CDK7 compared to other kinases. Since the discovery of selective inhibitors of CDK7 has been hampered by the high sequence and structural similarities of the kinase domain of CDK family members, the development of selective inhibitors of the transcriptional cyclin-dependent kinases (tCDKs) will allow dissection of their individual contributions to the regulation of transcription and evaluation of their therapeutic potential. Without wishing to be bound by any particular theory, the inventive compounds' selectivity for CDK7 may be due to the compounds' ability to covalently modify the cysteine (Cys312) residue of CDK7, the Cys312 residue being largely unique among the CDKs and other kinases.

In one aspect, the present invention provides compounds of Formula (I):

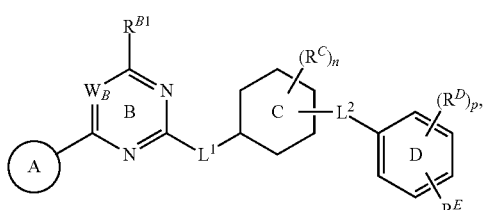

and pharmaceutically acceptable salts, solvates, hydrates, polymorphs, co-crystals, tautomers, stereoisomers, isotopically labeled derivatives, and prodrugs thereof, wherein Ring A, $L^1$, $L^2$, $W_B$, $R^{B1}$, $R^{B2}$, $R^C$, $R^D$, $R^E$, n, and p are as defined herein.

In certain embodiments, a compound of Formula (I) is of the formula:

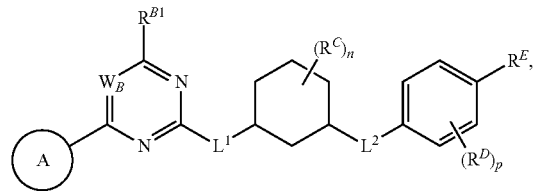

or a pharmaceutically acceptable salt, solvate, hydrate, polymorph, co-crystal, tautomer, stereoisomer, isotopically labeled derivative, or prodrug thereof.

In certain embodiments, a compound of Formula (I) is the formula:

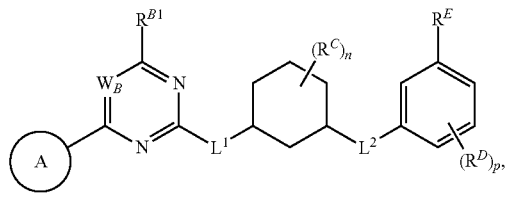

or a pharmaceutically acceptable salt, solvate, hydrate, polymorph, co-crystal, tautomer, stereoisomer, isotopically labeled derivative, or prodrug thereof.

In certain embodiments, a compound of Formula (I) is of the formula:

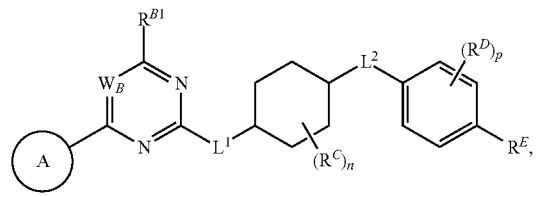

or a pharmaceutically acceptable salt, solvate, hydrate, polymorph, co-crystal, tautomer, stereoisomer, isotopically labeled derivative, or prodrug thereof.

In certain embodiments, a compound of Formula (I) is of the formula:

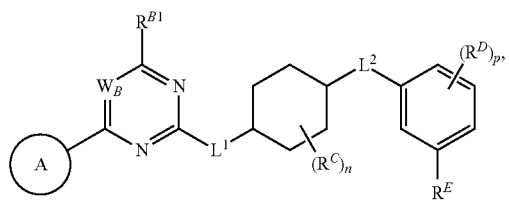

or a pharmaceutically acceptable salt, solvate, hydrate, polymorph, co-crystal, tautomer, stereoisomer, isotopically labeled derivative, or prodrug thereof.

Figure 1G:
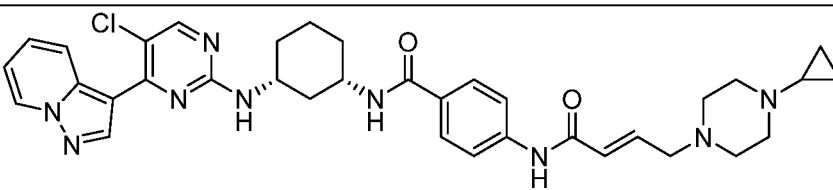
Figure 1G:
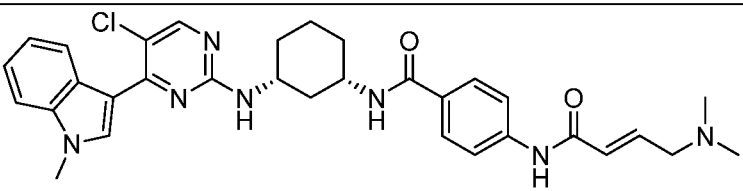
Figure 1G:
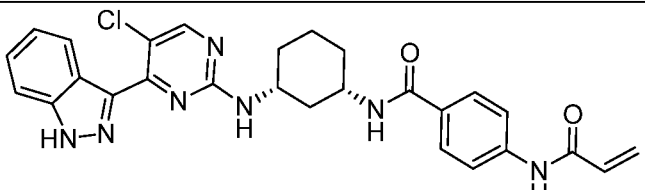
Figure 1G:
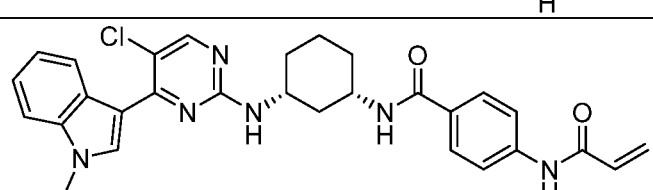
Figure 1G:
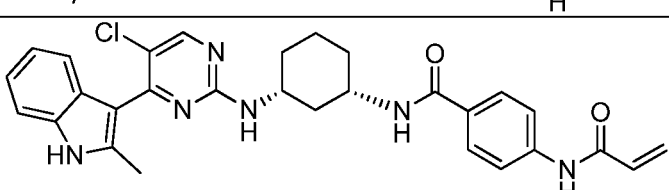
Figure 1G:
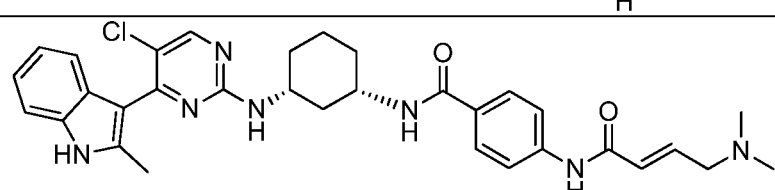
Figure 1G:
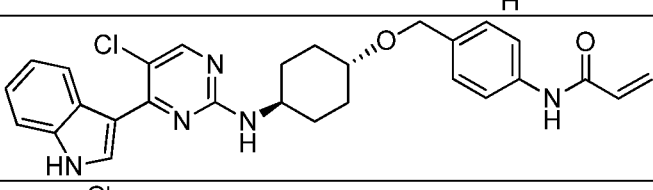
Figure 1G:
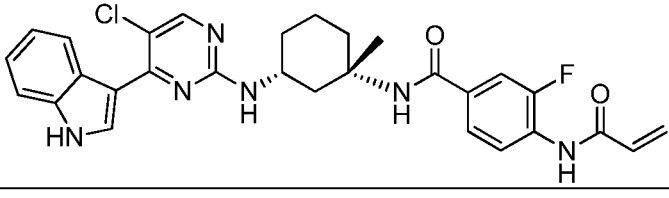
Figure 1H:
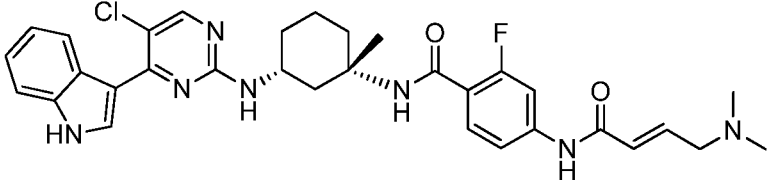
Figure 1H:
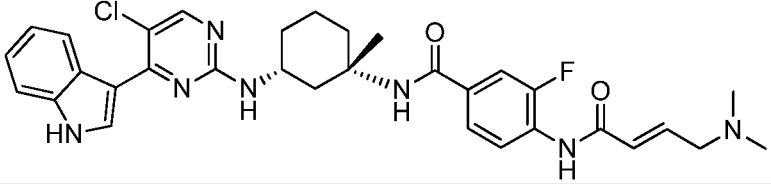
Figure 1H:
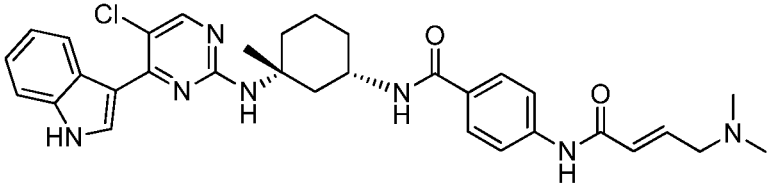
Figure 1H:
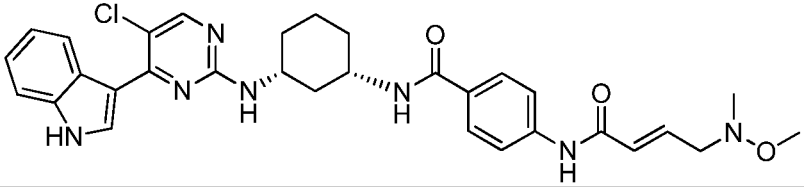
Figure 1H:
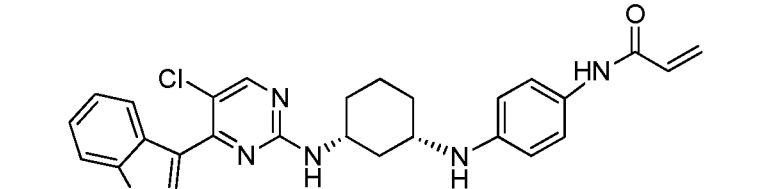
Figure 1H:
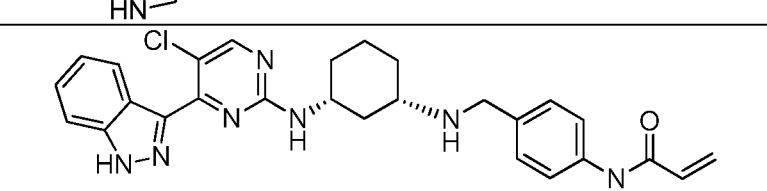
Figure 1H:
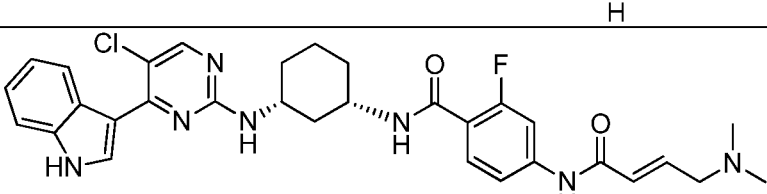
Figure 1H:
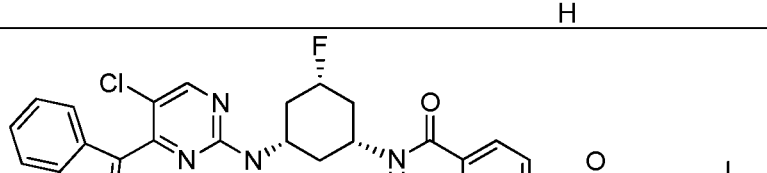

Exemplary compounds of Formula (I) include, but are not limited to, those compounds depicted in FIGS. 1A-1I, and any pharmaceutically acceptable salts, solvates, hydrates, polymorphs, co-crystals, tautomers, stereoisomers, isotopically labeled derivatives, and prodrugs thereof.

In certain embodiments, the compound of Formula (I) is of the formula:

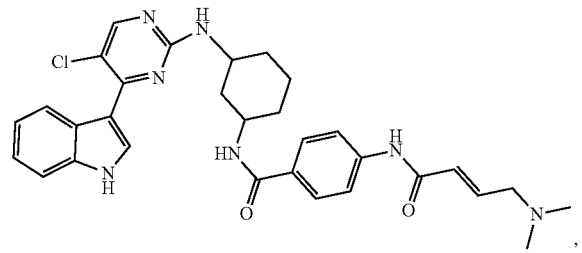

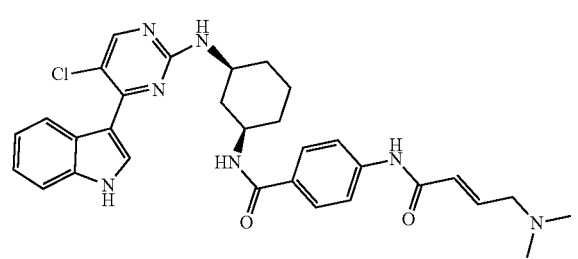

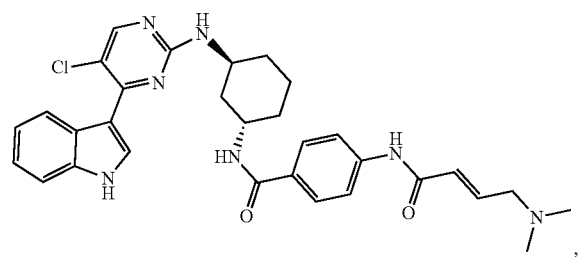

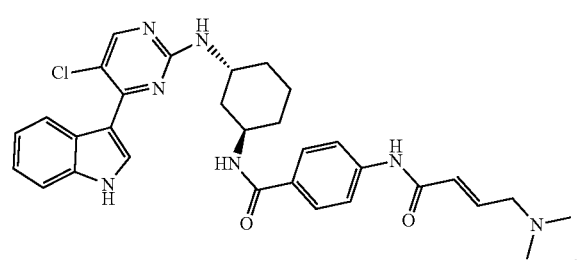

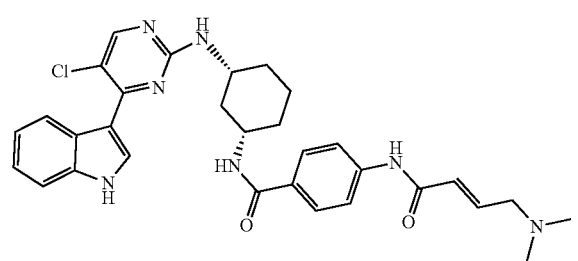

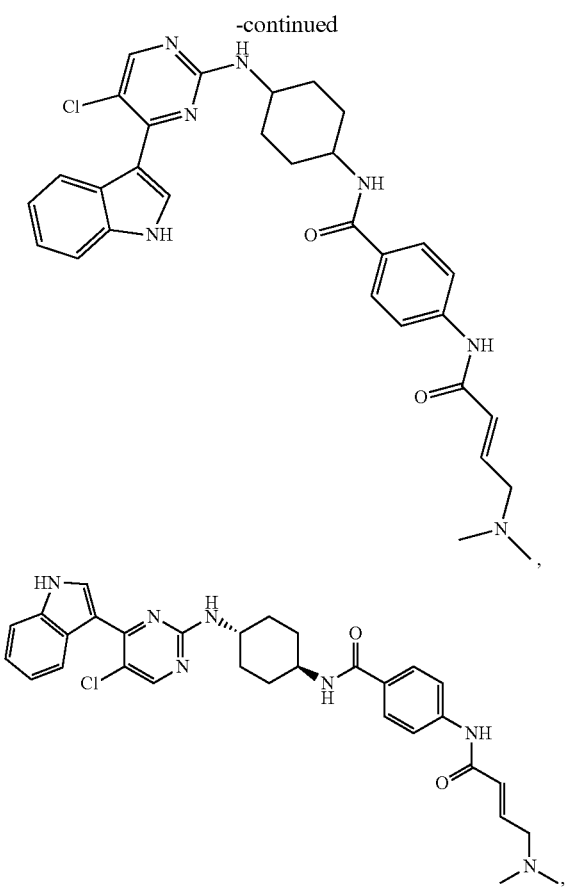

or a pharmaceutically acceptable salt, solvate, hydrate, polymorph, co-crystal, tautomer, stereoisomer, isotopically labeled derivative, or prodrug thereof.

In another aspect, the present invention provides pharmaceutical compositions comprising a compound of Formula (I), or a pharmaceutically acceptable salt, solvate, hydrate, polymorph, co-crystal, tautomer, stereoisomer, isotopically labeled derivative, or prodrug thereof, and optionally a pharmaceutically acceptable excipient. In certain embodiments, the pharmaceutical compositions described herein include a therapeutically effective amount of a compound of Formula (I), or a pharmaceutically acceptable salt, solvate, hydrate, polymorph, co-crystal, tautomer, stereoisomer, isotopically labeled derivative, or prodrug thereof. The pharmaceutical composition may be useful for treating and/or preventing a proliferative disease (e.g., cancer) or an infectious disease.

In another aspect, the present invention provides methods for treating and/or preventing proliferative diseases. Exemplary proliferative diseases include cancer (e.g., leukemia, lymphoma, melanoma, multiple myeloma, breast cancer, Ewing's sarcoma, osteosarcoma, brain cancer, neuroblastoma, lung cancer), benign neoplasm, angiogenesis, inflammatory diseases, autoinflammatory diseases, and autoimmune diseases. In other embodiments, the present invention provides methods for treating and/or preventing an infectious disease (e.g., a viral infection).

In still another aspect, the present invention provides methods of down-regulating the expression of a kinase (e.g., CDK (e.g., CDK7)) in a biological sample or subject. In certain embodiments, the method involves the specific down-regulation of the expression of CDK7.

Another aspect of the invention relates to methods of inhibiting the activity of a kinase (e.g., CDK (e.g., CDK7)) in a biological sample or subject. In certain embodiments, the method involves the selective inhibition of CDK7.

Also provided by the present invention are methods of inhibiting transcription in a biological sample or subject. The transcription of genes affected by the activity of CDK7 may be inhibited by the compounds of the invention.

The present invention also provides methods of inhibiting cell growth in a biological sample or subject.

In still another aspect, the present invention provides methods of inducing apoptosis of a cell in a biological sample or a subject.

Another aspect of the invention relates to methods of screening a library of compounds (e.g., compounds of Formula (I)) to identify one or more compounds useful in the treatment of a proliferative disease (e.g., cancer (e.g., leukemia, lymphoma, melanoma, multiple myeloma, breast cancer, Ewing's sarcoma, osteosarcoma, brain cancer, neuroblastoma, lung cancer), benign neoplasm, angiogenesis, inflammatory diseases, autoinflammatory diseases, and autoimmune diseases) or an infectious disease (e.g., viral infection) in a subject, in inhibiting a kinase (e.g., CDK, such as CDK7), in inhibiting cell growth, in inducing apoptosis of a cell, and/or in inhibiting transcription.

In yet another aspect, the present invention provides compounds of Formula (I), and pharmaceutically acceptable salts, solvates, hydrates, polymorphs, co-crystals, tautomers, stereoisomers, isotopically labeled derivatives, prodrugs, and compositions thereof, for use in the treatment of a proliferative disease in a subject.

In yet another aspect, the present invention provides compounds of Formula (I), and pharmaceutically acceptable salts, solvates, hydrates, polymorphs, co-crystals, tautomers, stereoisomers, isotopically labeled derivatives, prodrugs, and compositions thereof, for use in the treatment or prevention of an infectious disease in a subject. In certain embodiments, the infectious disease is a viral infection.

Another aspect of the present invention relates to kits comprising a container with a compound of Formula (I), or a pharmaceutically acceptable salt, solvate, hydrate, polymorph, co-crystal, tautomer, stereoisomer, isotopically labeled derivative, or prodrug thereof, or a pharmaceutical composition thereof. The kits of the invention may include a single dose or multiple doses of a compound of Formula (I), or a pharmaceutically acceptable salt, solvate, hydrate, polymorph, co-crystal, tautomer, stereoisomer, isotopically labeled derivative, or prodrug thereof, or a pharmaceutical composition thereof. The provided kits may be useful for the treatment and/or prevention of a proliferative disease (e.g., cancer (e.g., leukemia, lymphoma, melanoma, multiple myeloma, breast cancer, Ewing's sarcoma, osteosarcoma, brain cancer, neuroblastoma, lung cancer), benign neoplasm, angiogenesis, inflammatory diseases, autoinflammatory diseases, and autoimmune diseases) or an infectious disease in a subject. In certain embodiments, the kits described herein further include instructions for administering the compound of Formula (I), or the pharmaceutically acceptable salt, solvate, hydrate, polymorph, co-crystal, tautomer, stereoisomer, isotopically labeled derivative, or prodrug thereof, or the pharmaceutical composition thereof.

The details of one or more embodiments of the invention are set forth herein. Other features, objects, and advantages of the invention will be apparent from the Detailed Description, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Hydrocarbon chain" refers to a substituted or unsubstituted divalent alkyl, alkenyl, or alkynyl group. A hydrocarbon chain includes at least one chain, each node ("carbon unit") of which including at least one carbon atom, between the two radicals of the hydrocarbon chain. For example, hydrocarbon chain —$C^AH(C^BH_2C^CH_3)$— includes only one carbon unit $C^A$. The term "$C_x$ hydrocarbon chain," wherein x is a positive integer, refers to a hydrocarbon chain that includes x number of carbon unit(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

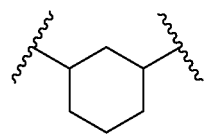 [SMILES: *C1CCCC(*)C1]

is a $C_3$ hydrocarbon chain. When a range of values is used, e.g., a $C_{1-6}$ hydrocarbon chain, the meaning of the range is as described herein. A hydrocarbon chain may be saturated (e.g., —$(CH_2)_4$—). A hydrocarbon chain may also be unsaturated and include one or more C=C and/or C≡C bonds anywhere in the hydrocarbon chain. For instance, —CH=CH—(CH₂)₂—, —CH₂—C≡C—CH₂—, and —C≡C—CH=CH— are all examples of a unsubstituted and unsaturated hydrocarbon chain. In certain embodiments, the hydrocarbon chain is unsubstituted (e.g., —(CH₂)₄—). In certain embodiments, the hydrocarbon chain is substituted (e.g., —CH(C₂H₅)— and —CF₂—). Any two substituents on the hydrocarbon chain may be joined to form an optionally substituted carbocyclyl, optionally substituted heterocyclyl, optionally substituted aryl, or optionally substituted heteroaryl ring. For instance,

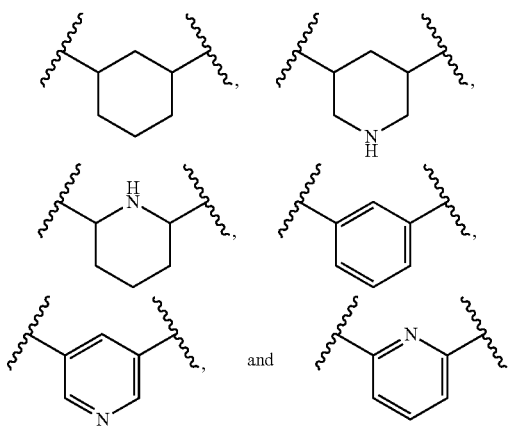

and are all examples of a hydrocarbon chain. In contrast, in certain embodiments

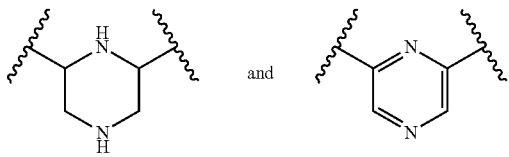 [SMILES: *C1CNCC(*)N1 ; *c1cncc(*)n1]

are not within the scope of the hydrocarbon chains described herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —CH₃). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-4}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 p electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 p electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups are further referred to using the suffix -ene, e.g., alkylene, alkenylene, alkynylene, carbocyclylene, heterocyclylene, arylene, and heteroarylene.

The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3{}^+X^-$, —$NH(C_{1-6}$ alkyl$)_2{}^+X^-$, —$NH_2(C_{1-6}$ alkyl$)^+X^-$, —$NH_3{}^+X^-$, —$N(OC_{1-6}$ alkyl$)_2(C_{1-6}$ alkyl), —$N(OH)(C_{1-6}$ alkyl), —NH (OH), —SH, —$SC_{1-6}$ alkyl, —$SS(C_{1-6}$ alkyl), —C(=O) ($C_{1-6}$ alkyl), —$CO_2H$, —$CO_2(C_{1-6}$ alkyl), —OC(=O)($C_{1-6}$ alkyl), —$OCO_2(C_{1-6}$ alkyl), —C(=O)$NH_2$, —C(=O)N ($C_{1-6}$ alkyl$)_2$, —OC(=O)NH($C_{1-6}$ alkyl), —NHC(=O) ($C_{1-6}$ alkyl), —N($C_{1-6}$ alkyl)C(=O)($C_{1-6}$ alkyl), —$NHCO_2$ ($C_{1-6}$ alkyl), —NHC(=O)N($C_{1-6}$ alkyl$)_2$, —NHC(=O)NH ($C_{1-6}$ alkyl), —NHC(=O)$NH_2$, —C(=NH)O($C_{1-6}$ alkyl), —OC(=NH)($C_{1-6}$ alkyl), —OC(=NH)$OC_{1-6}$ alkyl, —C(=NH)N($C_{1-6}$ alkyl$)_2$, —C(=NH)NH($C_{1-6}$ alkyl), —C(=NH)$NH_2$, —OC(=NH)N($C_{1-6}$ alkyl$)_2$, —OC(NH) NH($C_{1-6}$ alkyl), —OC(NH)$NH_2$, —NHC(NH)N($C_{1-6}$ alkyl$)_2$, —NHC(=NH)$NH_2$, —$NHSO_2(C_{1-6}$ alkyl), —$SO_2N(C_{1-6}$ alkyl$)_2$, —$SO_2NH(C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —$Si(C_{1-6}$ alkyl$)_3$, —$OSi(C_{1-6}$ alkyl$)_3$-C (=S)N($C_{1-6}$ alkyl$)_2$, C(=S)NH($C_{1-6}$ alkyl), C(=S)$NH_2$, —C(=O)S($C_{1-6}$ alkyl), —C(=S)$SC_{1-6}$ alkyl, —SC(=S) $SC_{1-6}$ alkyl, —P(=O)$_2(C_{1-6}$ alkyl), —P(=O)($C_{1-6}$ alkyl$)_2$, —OP(=O)($C_{1-6}$ alkyl$)_2$, —OP(=O)($OC_{1-6}$ alkyl$)_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X is a counterion.

A "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $F^-$), $NO_3{}^-$, $ClO_4{}^-$, $OH^-$, $H_2PO_4{}^-$, $HSO_4{}^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —$CO_2R^{aa}$, —C(=O)N ($R^{bb})_2$, —C(=$NR^{bb}$)$R^{aa}$, —C(=$NR^{bb}$)$OR^{aa}$, —C(=$NR^{bb}$) N($R^{bb})_2$, —C(=O)$NR^{bb}SO_2R^{aa}$, —C(=S)N($R^{bb})_2$, —C(=O)$SR^{aa}$, or —C(=S)$SR^{aa}$, wherein $R^{aa}$ and $R^{bb}$ are as defined herein.

"Alkoxy" or "alkoxyl" refers to a radical of the formula: —O-alkyl.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —$OR^{aa}$, —N($R^{cc})_2$, —CN, —C(=O)$R^{aa}$, —C(=O)N ($R^{cc})_2$, —$CO_2R^{aa}$, —$SO_2R^{aa}$, —C(=$NR^{bb}$)$R^{aa}$, —C(=$NR^{cc}$)$OR^{aa}$, —C(=$NR^{cc}$)N($R^{cc})_2$, —$SO_2N(R^{cc})_2$, —$SO_2R^{cc}$, —$SO_2OR^{cc}$, —$SOR^{aa}$, —C(=S)N($R^{cc})_2$, —C(=O)$SR^{cc}$, —C(=S)$SR^{cc}$, —P(=O)$_2R^{aa}$, —P(=O) ($R^{aa})_2$, —P(=O)$_2N(R^{cc})_2$, —P(=O)(N$R^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{1-4}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —$OR^{aa}$, —N($R^{cc})_2$, —C(=O)$R^{aa}$, —C(=O)N($R^{cc})_2$, —$CO_2R^{aa}$, —$SO_2R^{aa}$, —C(=$NR^{cc}$)$R^{aa}$, —C(=NR)$OR^{aa}$, —C(=$NR^{cc}$)N($R^{cc})_2$, —$SO_2N(R^{cc})_2$, —$SO_2R^{cc}$, —$SO_2OR^{cc}$, —$SOR^{aa}$, —C(=S) N($R^{cc})_2$, —C(=O)$SR^{cc}$, —C(=S)$SR^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)$OR^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10, 10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., $-S(=O)_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"- dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is an sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

The term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

These and other exemplary substituents are described in more detail in the Detailed Description, FIGURES, Examples, and Claims. The invention is not intended to be limited in any manner by the above exemplary listing of substituents.

Other Definitions

The following definitions are more general terms used throughout the present application:

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R.xH_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates ($R.0.5H_2O$)), and polyhydrates (x is a number greater than 1, e.g., dihydrates ($R.2H_2O$) and hexahydrates ($R.6H_2O$)).

The term "tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds of Formula (I), which have cleavable groups and become by solvolysis or under physiological conditions the compounds of Formula (I) which are pharmaceutically active in vivo. Such examples include, but are not limited to, ester derivatives and the like. Other derivatives of the compounds of this invention have activity in both their acid and acid derivative forms, but in the acid sensitive form often offers advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy) alkyl esters or ((alkoxycarbonyl)oxy)alkylesters. $C_1$ to $C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of Formula (I) may be preferred.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

The terms "administer," "administering," or "administration," refers to implanting, absorbing, ingesting, injecting, inhaling, or otherwise introducing an inventive compound, or a pharmaceutical composition thereof.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The terms "condition," "disease," and "disorder" are used interchangeably.

An "effective amount" of a compound of Formula (I) refers to an amount sufficient to elicit the desired biological response, i.e., treating the condition. As will be appreciated by those of ordinary skill in this art, the effective amount of a compound of Formula (I) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor.

A "therapeutically effective amount" of a compound of Formula (I) is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound of Formula (I) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, autoinflammatory diseases, and autoimmune diseases.

The terms "neoplasm" and "tumor" are used interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angio-immunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrinetumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and the growth of new blood vessels. Normal angiogenesis occurs in the healthy body of a subject for healing wounds and for restoring blood flow to tissues after injury. The healthy body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal or pathological angiogenesis refers to angiogenesis greater than that in a normal body, especially angiogenesis in an adult not related to normal angiogenesis (e.g., menstruation or wound healing). Abnormal angiogenesis can provide new blood vessels that feed diseased tissues and/or destroy normal tissues, and in the case of cancer, the new vessels can allow tumor cells to escape into the circulation and lodge in other organs (tumor metastases). In certain embodiments, the angiogenesis is pathological angiogenesis.

An "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or noninfectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, antiphospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme arthritis, Guillain-Barré syndrome, Hashimoto's thyroiditis, and cardiomyopathy.

The term "autoinflammatory disease" refers to a category of diseases that are similar but different from autoimmune diseases. Autoinflammatory and autoimmune diseases share common characteristics in that both groups of disorders result from the immune system attacking a subject's own tissues and result in increased inflammation. In autoinflammatory diseases, a subject's innate immune system causes inflammation for unknown reasons. The innate immune system reacts even though it has never encountered autoantibodies or antigens in the subject. Autoinflammatory disorders are characterized by intense episodes of inflammation that result in such symptoms as fever, rash, or joint swelling. These diseases also carry the risk of amyloidosis, a potentially fatal buildup of a blood protein in vital organs. Autoinflammatory diseases include, but are not limited to, familial Mediterranean fever (FMF), neonatal onset multisystem inflammatory disease (NOMID), tumor necrosis factor (TNF) receptor-associated periodic syndrome (TRAPS), deficiency of the interleukin-1 receptor antagonist (DIRA), and Behçet's disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

A "protein" or "peptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, or synthetic, or any combination of these.

The term "kinase" refers to any enzyme that catalyzes the addition of phosphate groups to an amino acid residue of a protein. For example, a serine kinase catalyzes the addition of a phosphate group to serine residue in a protein. In certain embodiments, the kinase is a protein kinase. Examples of kinases include, but are not limited to, a CMGC kinase (e.g., a cyclin-dependent kinase (CDK, e.g., CDK1, CDK2, CDK2, CDK4, CDK5, CDK7, CDK8, CDK9, CDK10, CDK11, CDK12, CDK13, CDK14, CDK16, CDK20), a mitogen-activated protein kinase (MAPK, e.g., MAPK1, MAPK3, MAPK4, MAPK6, MAPK7, MAPK8, MAPK9, MAPK10, MAPK11, MAPK12, MAPK13, MAPK14, MAPK15), a glycogen synthase kinase 3 (GSK3, e.g., GSK3α, GSK3β), or a CDC-like kinase (CLK, e.g., CLK1, CLK2, CLK3, CLK4)), an AGC kinase (e.g., protein kinase A (PKA), protein kinase C (PKC), protein kinase G (PKG)), a $Ca^{2+}$/calmodulin-dependent protein kinase (CaM kinase, e.g., a specialized CaM kinase, a multifunctional CaM kinase), a casein kinase 1 (CK1, e.g., CK1alpha, CK1beta 1, CK1gamma 1, CK1gamma 2, CK1gamma 3, CK1delta, CK1epsilon), a STE kinase (e.g., a homolog of yeast Sterile 7, Sterile 11, or Sterile 20 kinase), a tyrosine kinase (TK, e.g., a receptor tyrosine kinase (RTK), a non-receptor tyrosine kinase (nRTK)), and a tyrosine-kinase-like kinase (TKL, e.g., a mixed lineage kinase (MLK), RAF, a serine threonine kinase receptor (STKR), a leucine rich repeat kinase (LRRK), a LIM domain kinase (LIMK), a testis expressed serine kinase (TESK), an IL1 receptor associated kinase (IRAK), a receptor interacting protein kinase (RIPK)).

The term "CDK" refers to a cyclin-dependent kinase. A CDK binds a cyclin (e.g., Cyclin H), which is a regulatory protein. CDKs phosphorylate their substrates at serines and threonines. The consensus sequence for the phosphorylation site in the amino acid sequence of a CDK substrate is [S/T*]PX[K/R], where S/T* is the phosphorylated serine or threonine, P is proline, X is any amino acid, K is lysine, and R is arginine. CDKs include CDK1, CDK2, CDK2, CDK4, CDK5, CDK7, CDK8, CDK9, CDK10, CDK11, CDK12, CDK14, CDK16, and CDK20. CDK7 is a CDK wherein the substrate is Cyclin H, MAT1 (e.g., MNAT1), or Cyclin H and MAT1.

DETAILED DESCRIPTION OF CERTAIN EMBODIMENTS OF THE INVENTION

The present invention provides compounds, which inhibit the activity of a kinase, for the prevention and/or treatment of a proliferative disease of a subject. In certain embodiments, the inventive compounds inhibit the activity of cyclin-dependent kinase (CDK). In certain embodiments, the inventive compounds inhibit the activity of cyclin-dependent kinase 7 (CDK7). The present invention further provides methods of using the compounds described herein, e.g., as biological probes to study the inhibition of the activity of a kinase (e.g., CDK (e.g., CDK7)), and as therapeutics, e.g., in the prevention and/or treatment of diseases associated with the overexpression and/or aberrant activity of the kinase (e.g., CDK (e.g., CDK7)). In certain embodiments, the diseases are proliferative diseases. The proliferative diseases include, but are not limited to, cancer (e.g., leukemia, melanoma, multiple myeloma), benign neoplasm, angiogenesis, inflammatory diseases, autoinflammatory diseases, and autoimmune diseases. In certain embodiments, the cancer is associated with the overexpression and/or aberrant activity of a kinase (e.g., CDK (e.g., CDK7)).

Compounds

In one aspect of the present invention, provided are compounds of Formula (I):

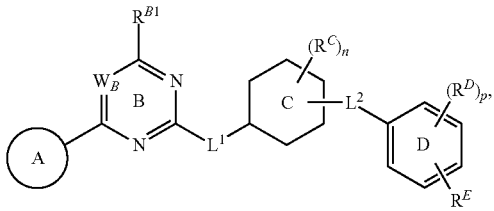

and pharmaceutically acceptable salts, solvates, hydrates, polymorphs, co-crystals, tautomers, stereoisomers, isotopically labeled derivatives, and prodrugs thereof, wherein:

Ring A is an optionally substituted heteroaryl ring of any one of the Formulae (i-1)-(i-6):

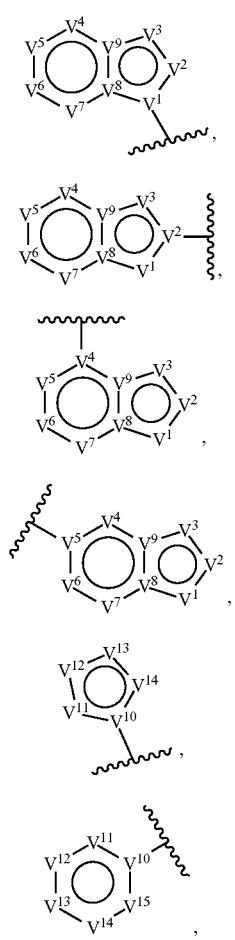

wherein:
each instance of $V^1$, $V^2$, $V^3$, $V^4$, $V^5$, $V^6$, $V^7$, $V^8$, $V^9$, $V^{10}$, $V^{11}$, $V^{12}$, $V^{13}$, $V^{14}$, and $V^{15}$ is independently O, S, N, $NR^{A1}$, C, or $CR^{A2}$;
each instance of $R^{A1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group;

each instance of $R^{A2}$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{A2a}$, —$N(R^{A2a})_2$, and —$SR^{A2a}$, wherein each occurrence of $R^{A2a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{A2a}$ groups are joined to form an optionally substituted heterocyclic ring; and optionally any two of $R^{A1}$, $R^{A2}$, and $R^{A2a}$ groups are joined to form an optionally substituted carbocyclic, optionally substituted heterocyclic, optionally substituted aryl, or optionally substituted heteroaryl ring;

$R^{B1}$ is selected from the group consisting of hydrogen, halogen, optionally substituted acyl, optionally substituted alkyl, optionally substituted alkenyl, optionally substituted alkynyl, optionally substituted carbocyclyl, optionally substituted aryl, optionally substituted heteroaryl, —CN, —$OR^{B1a}$, —$N(R^{B1a})_2$, and —$SR^{B1a}$, wherein each occurrence of $R^{B1a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or $R^{B1}$ and $R^{B2}$ are joined to form an optionally substituted carbocyclic, optionally substituted heterocyclic, optionally substituted aryl, or optionally substituted heteroaryl ring;

$W_B$ is N or $CR^{B2}$, wherein $R^{B2}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{B2a}$, —$N(R^{B2a})_2$, and —$SR^{B2a}$, or $R^{B2}$ and $R^{B1}$ are joined to form an optionally substituted carbocyclic, optionally substituted heterocyclic, optionally substituted aryl, or optionally substituted heteroaryl ring, wherein each occurrence of $R^{B2a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{B2a}$ groups are joined to form an optionally substituted heterocyclic ring;

$L^1$ is a bond or an optionally substituted $C_{1-4}$ hydrocarbon chain, optionally wherein one or more carbon units of the optionally substituted $C_{1-4}$ hydrocarbon chain are independently replaced with —O—, —S—, —NR$^{L1}$—, —S(=O)—, or —S(=O)$_2$—, wherein R$^{L1}$ is hydrogen, substituted or unsubstituted $C_{1-4}$ alkyl, or a nitrogen protecting group, and optionally wherein two substituents on the optionally substituted $C_{1-4}$ hydrocarbon chain are taken together to form an optionally substituted carbocyclic or optionally substituted heterocyclic ring;

$L^2$ is a bond or an optionally substituted $C_{1-4}$ hydrocarbon chain, optionally wherein one or more carbon units of the optionally substituted $C_{1-4}$ hydrocarbon chain are independently replaced with —O—, —S—, —NR$^{L2}$—, —S(=O)—, or —S(=O)$_2$—, wherein R$^{L2}$ is hydrogen, substituted or unsubstituted $C_1$ alkyl, or a nitrogen protecting group, and optionally wherein two substituents on the optionally substituted $C_{1-4}$ hydrocarbon chain are taken together to form an optionally substituted carbocyclic or optionally substituted heterocyclic ring;

each instance of R$^C$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, =O, —CN, —OR$^{C1}$, —N(R$^{C1}$)$_2$, and —SR$^{C1}$; or two R$^C$ groups are taken together to form an optionally substituted, heterocyclic, carbocyclic, aryl, or heteroaryl ring, wherein two substituents on the substituted heterocyclic ring or substituted carbocyclic ring, or one substituent on the substituted heterocyclic ring or substituted carbocyclic ring and a third R$^C$ group, are taken together to form another optionally substituted heterocyclic ring or optionally substituted carbocyclic ring; wherein each occurrence of R$^{C1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two R$^{C1}$ groups are joined to form an optionally substituted heterocyclic ring;

n is 0, 1, 2, 3, 4, 5, 6, 7, 8, 9, or 10;

each instance of R$^D$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —OR$^{D1}$, —N(R$^{D1}$)$_2$, and —SR$^{D1}$, wherein each occurrence of R$^{D1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two R$^{D1}$ groups are joined to form an optionally substituted heterocyclic ring;

p is 0, 1, 2, 3, or 4;

R$^E$ is of any one of the Formulae (ii-1)-(ii-20):

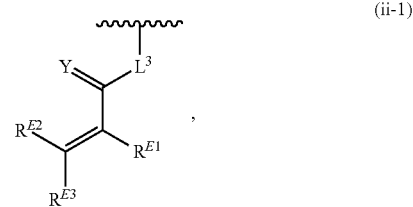
(ii-1)

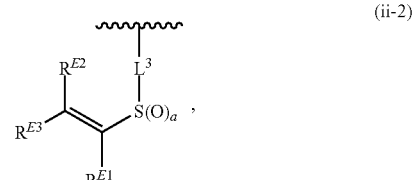
(ii-2)

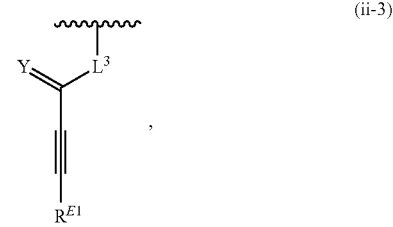
(ii-3)

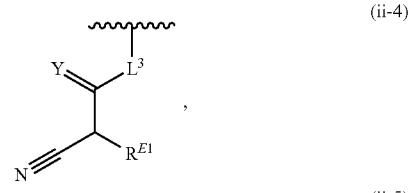
(ii-4)

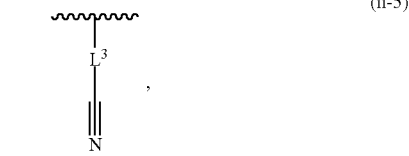
(ii-5)

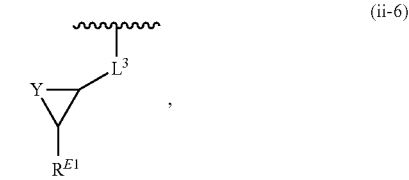
(ii-6)

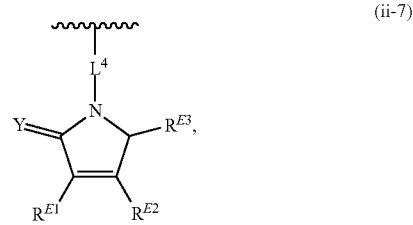
(ii-7)

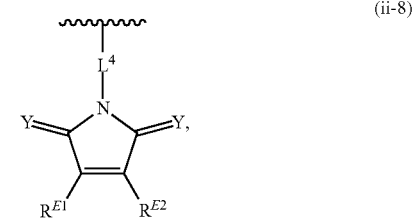
(ii-8)

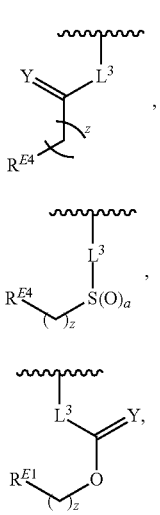

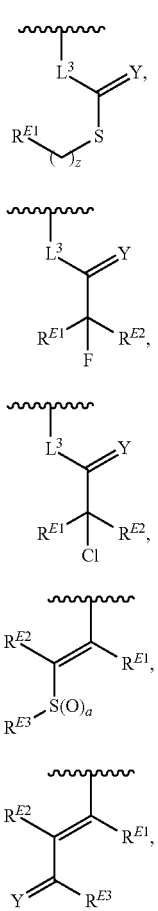

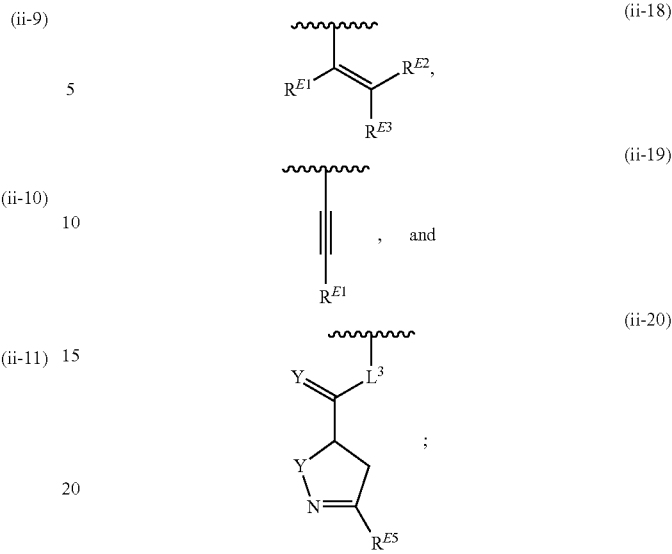

L³ is a bond, —O—, —S—, —NR$^{L3a}$—, or an optionally substituted C$_{1-4}$ hydrocarbon chain, optionally wherein one or more carbon units of the hydrocarbon chain are independently replaced with —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_{2O}$—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted C$_{1-6}$ alkyl, or a nitrogen protecting group, and wherein each occurrence of R$^{L3b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{L3b}$ groups are joined to form an optionally substituted carbocyclic or optionally substituted heterocyclic ring;

L⁴ is a bond or an optionally substituted C$_{1-4}$ hydrocarbon chain;

R$^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E1a}$, —CH$_2$N(R$^{E1a}$)$_2$, —CH$_2$SR$^{E1a}$, —OR$^{E1a}$, —N(R$^{E1a}$)$_2$, —Si(R$^{E1a}$)$_3$, and —SR$^{E1a}$, wherein each occurrence of R$^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E1a}$ groups are joined to form an optionally substituted heterocyclic ring;

R$^{E2}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E2a}$, —CH$_2$N(R$^{E2a}$)$_2$, —CH$_2$SR$^{E2a}$, —OR$^{E2a}$, —N(R$^{E2a}$)$_2$, and —SR$^{E2a}$, wherein each occurrence of R$^{E2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E2a}$ groups are joined to form an optionally substituted heterocyclic ring;

R$^{E3}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E3a}$, —CH$_2$N(R$^{E3a}$)$_2$, —CH$_2$SR$^{E3a}$, —OR$^{E3a}$, —N(R$^{E3a}$)$_2$, and —SR$^{E3a}$, wherein each occurrence of R$^{E3a}$ is independently selected from the group consisting of hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, and optionally substituted heteroaryl, or two R$^{E3a}$ groups are joined to form an optionally substituted heterocyclic ring;

optionally R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

R$^{E5}$ is halogen;

Y is O, S, or NR$^{E6}$, wherein R$^{E6}$ is hydrogen, substituted or unsubstituted C$_{1-6}$ alkyl, or a nitrogen protecting group;

a is 1 or 2; and z is 0, 1, 2, 3, 4, 5, or 6.

Compounds of Formula (I) include Ring A attached to Ring B. Ring A may be an optionally substituted bicyclic heteroaryl ring. In certain embodiments, Ring A is an optionally substituted monocyclic heteroaryl ring fused with an optionally substituted monocyclic aryl ring. In certain embodiments, Ring A is an optionally substituted monocyclic heteroaryl ring fused with another optionally substituted monocyclic heteroaryl ring. Ring A may be an optionally substituted 6,5-membered heteroaryl ring or an optionally substituted 5,6-membered heteroaryl ring. In certain embodiments, Ring A is an optionally substituted monocyclic 5-membered heteroaryl ring fused with an optionally substituted monocyclic 6-membered aryl ring. In certain embodiments, Ring A is an optionally substituted monocyclic 5-membered heteroaryl ring fused with an optionally substituted monocyclic 6-membered heteroaryl ring. The point of attachment of Ring A to Ring B may be at any atom of Ring A, as valency permits. In certain embodiments, Ring A is of Formula (i-1):

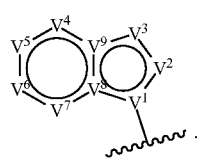

(i-1)

In certain embodiments, Ring A is of Formula (i-2):

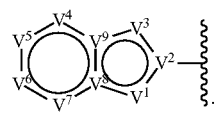

(i-2)

In certain embodiments, Ring A is of Formula (i-3):

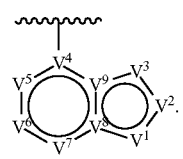

(i-3)

In certain embodiments, Ring A is of Formula (i-4):

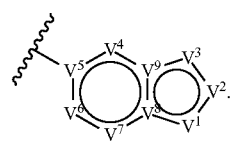

(i-4)

In compounds of Formula (I), V$^1$, V$^2$, V$^3$, V$^4$, V$^5$, V$^6$, V$^7$, V$^8$, and V$^9$ of Ring A may each independently be O, S, N, NR$^{A1}$, C, or CR$^{A2}$, as valency permits. In certain embodiments, V$^1$ is O, S, N or NR$^{A1}$. In certain embodiments, V$^L$ is N or NR$^{A1}$. In certain embodiments, Ring A is of the formula:

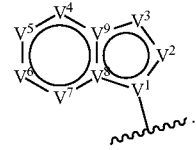

In certain embodiments, Ring A is of the formula:

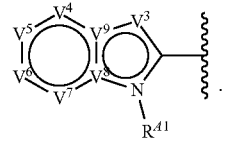

In certain embodiments, Ring A is of the formula:

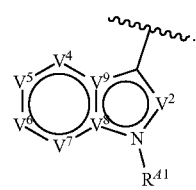

In certain embodiments, Ring A is of the formula:

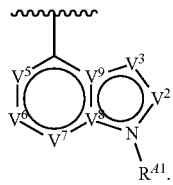

In certain embodiments, Ring A is of the formula:

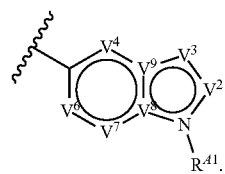

In certain embodiments, Ring A is of the formula:

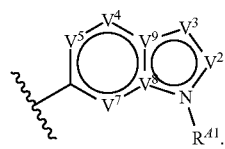

In certain embodiments, Ring A is of the formula:

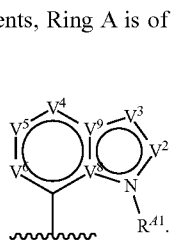

In certain embodiments, only one of $V^1$, $V^2$, $V^3$, $V^4$, $V^5$, $V^6$, $V^7$, $V^8$, and $V^9$ is selected from the group consisting of O, S, N, and $NR^{A1}$. In certain embodiments, only one of $V^1$, $V^2$, $V^3$, $V^4$, $V^5$, $V^6$, $V^7$, $V^8$, and $V^9$ is selected from the group consisting of N and $NR^{A1}$. In certain embodiments, $V^1$ is N or $NR^{A1}$; $V^2$, $V^3$, $V^4$, $V^5$, $V^6$, $V^7$, $V^8$, and $V^9$ are each independently C or $CR^{A2}$; and therefore, Ring A is an optionally substituted indole ring. In certain embodiments, Ring A is of Formula (iii-1):

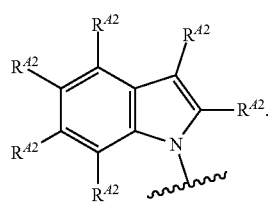
(iii-1)

In certain embodiments, Ring A is of Formula (iii-2):

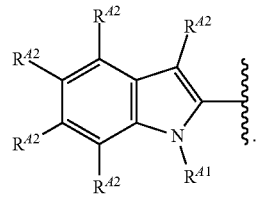
(iii-2)

In certain embodiments, Ring A is of Formula (iii-3):

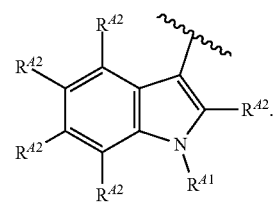
(iii-3)

In certain embodiments, Ring A is of the formula:

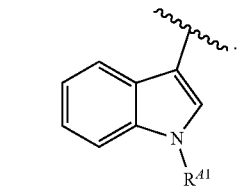

In certain embodiments, Ring A is of the formula:

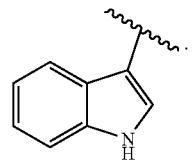 [SMILES: *c1c[nH]c2ccccc12]

In certain embodiments, Ring A is of Formula (iii-4):

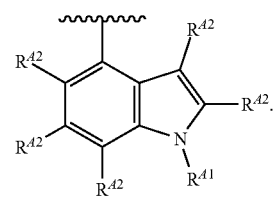
(iii-4)

In certain embodiments, Ring A is of Formula (iii-5):

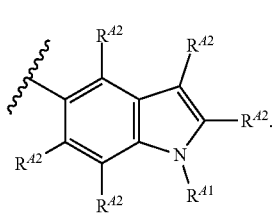
(iii-5)

In certain embodiments, Ring A is of Formula (iii-6):

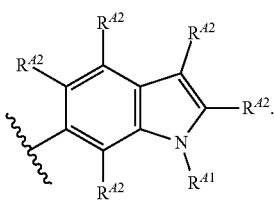
(iii-6)

In certain embodiments, Ring A is of Formula (iii-7):

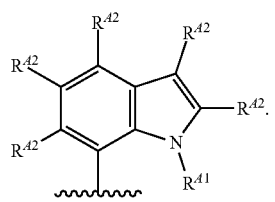
(iii-7)

In certain embodiments, only two of $V^1$, $V^2$, $V^3$, $V^4$, $V^5$, $V^6$, $V^7$, $V^8$, and $V^9$ are each independently selected from the group consisting of O, S, N, and $NR^{A1}$. In certain embodiments, only two of $V^1$, $V^2$, $V^3$, $V^4$, $V^5$, $V^6$, $V^7$, $V^8$, and $V^9$ are each independently selected from the group consisting of N and $NR^{A1}$. In certain embodiments, $V^1$ is N or $NR^{A1}$; and only one of $V^2$, $V^3$, $V^4$, $V^5$, $V^6$, $V^7$, $V^8$, and $V^9$ is N or $NR^{A1}$. In certain embodiments, $V^1$ and $V^2$ are each independently N or $NR^{A1}$; $V^3$, $V^4$, $V^5$, $V^6$, $V^7$, $V^8$, and $V^9$ are each independently C or $CR^{A2}$; and therefore, Ring A is an optionally substituted indazole ring. In certain embodiments, Ring A is of the formula:

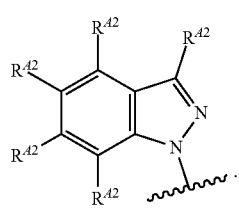

In certain embodiments, Ring A is of the formula:

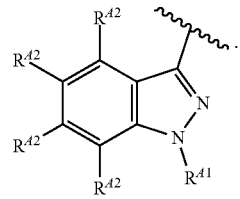

In certain embodiments, Ring A is of the formula:

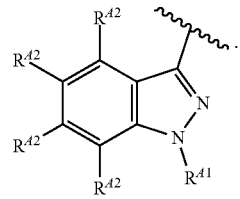

In certain embodiments, Ring A is of the formula:

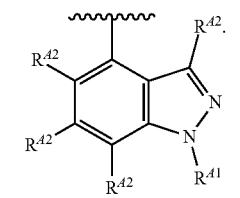

In certain embodiments, Ring A is of the formula:

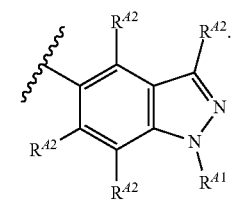

In certain embodiments, Ring A is of the formula:

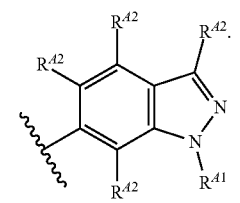

In certain embodiments, Ring A is of the formula:

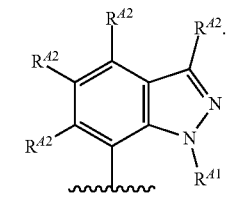

In certain embodiments, $V^1$ and $V^3$ are each independently N or $NR^{A1}$; $V^2$, $V^4$, $V^5$, $V^6$, $V^7$, $V^8$, and $V^9$ are each independently C or $CR^{A2}$; and therefore, Ring A is an optionally substituted benzimidazole ring. In certain embodiments, Ring A is of Formula (iv-1):

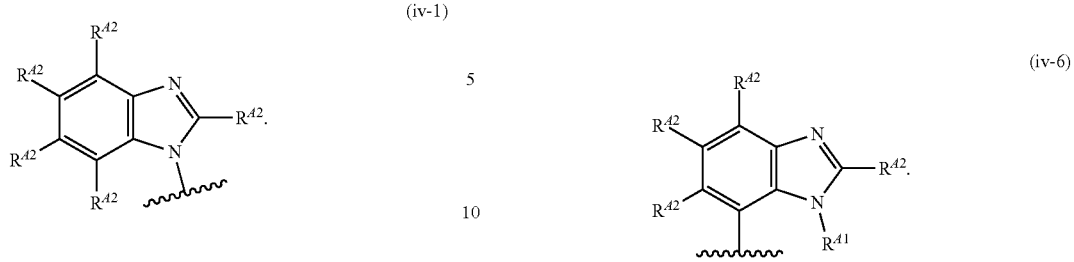

(iv-1)

In certain embodiments, Ring A is of Formula (iv-2):

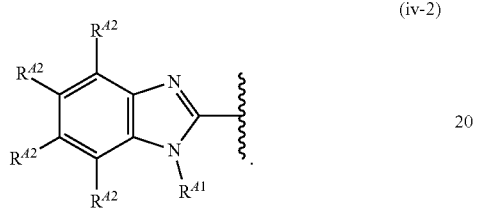

(iv-2)

In certain embodiments, Ring A is of Formula (iv-3):

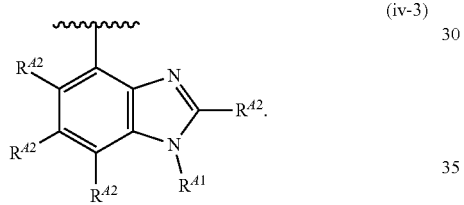

(iv-3)

In certain embodiments, Ring A is of Formula (iv-4):

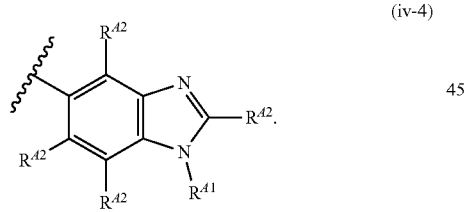

(iv-4)

In certain embodiments, Ring A is of Formula (iv-5):

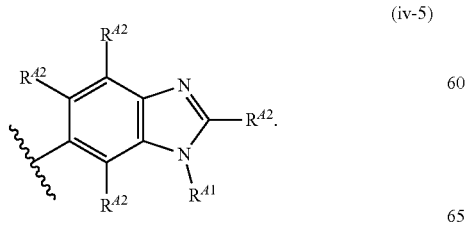

(iv-5)

In certain embodiments, Ring A is of Formula (iv-6):

(iv-6)

In certain embodiments, $V^1$ and $V^4$ are each independently N or $NR^{A1}$; $V^2$, $V^3$, $V^5$, $V^6$, $V^7$, $V^8$, and $V^9$ are each independently C or $CR^{A2}$; and therefore, Ring A is an optionally substituted 4-azaindazole ring. In certain embodiments, Ring A is of the formula:

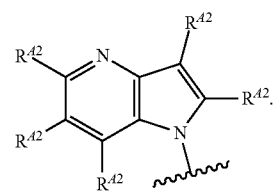

In certain embodiments, Ring A is of the formula:

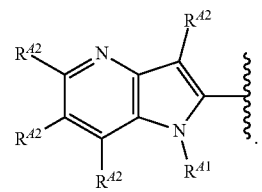

In certain embodiments, Ring A is of the formula:

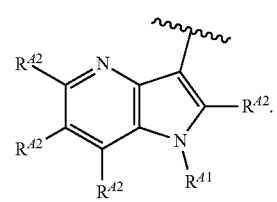

In certain embodiments, Ring A is of the formula:

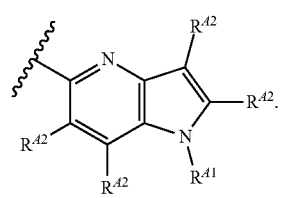

In certain embodiments, Ring A is of the formula:

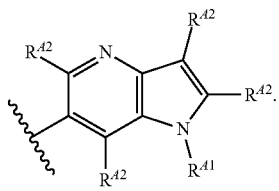

In certain embodiments, Ring A is of the formula:

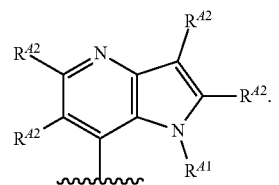

In certain embodiments, $V^L$ and $V^5$ are each independently N or $NR^{A1}$; $V^2$, $V^3$, $V^4$, $V^6$, $V^7$, $V^8$, and $V^9$ are each independently C or $CR^{A2}$; and therefore, Ring A is an optionally substituted 5-azaindazole ring. In certain embodiments, Ring A is of the formula:

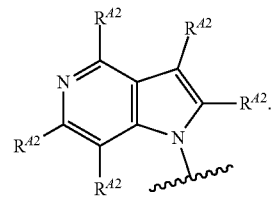

In certain embodiments, Ring A is of the formula:

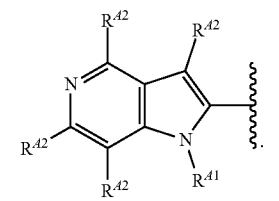

In certain embodiments, Ring A is of the formula:

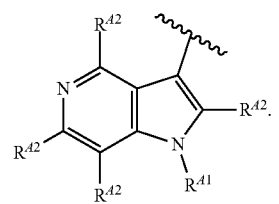

In certain embodiments, Ring A is of the formula:

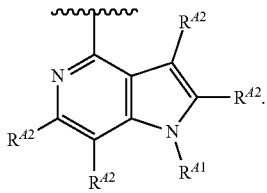

In certain embodiments, Ring A is of the formula:

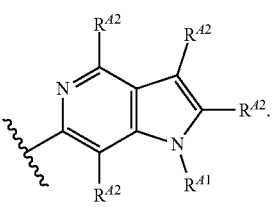

In certain embodiments, Ring A is of the formula:

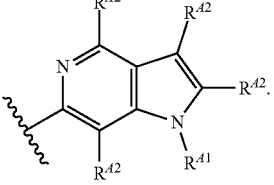

In certain embodiments, Ring A is of the formula:

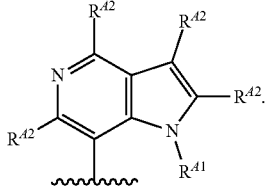

In certain embodiments, $V^L$ and $V^6$ are each independently N or $NR^{A1}$; $V^2$, $V^3$, $V^4$, $V^5$, $V^7$, $V^8$, and $V^9$ are each independently C or $CR^{A2}$; and therefore, Ring A is an optionally substituted 6-azaindole ring. In certain embodiments, Ring A is of the formula:

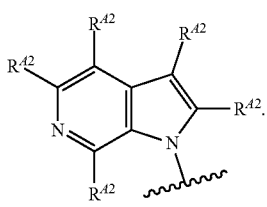

In certain embodiments, Ring A is of the formula:

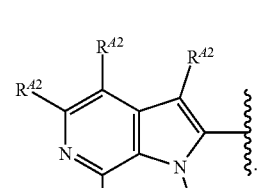

In certain embodiments, Ring A is of the formula:

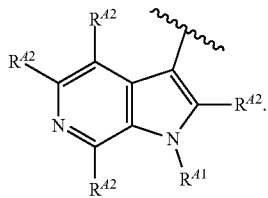

In certain embodiments, Ring A is of the formula:

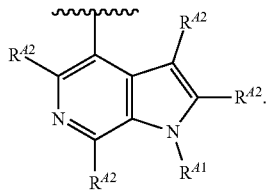

In certain embodiments, Ring A is of the formula:

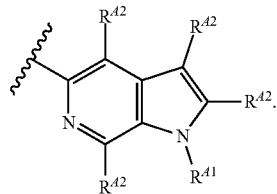

In certain embodiments, Ring A is of the formula:

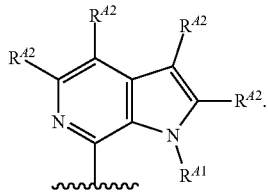

In certain embodiments, $V^1$ and $V^7$ are each independently N or $NR^{A1}$; $V^2$, $V^3$, $V^4$, $V^5$, $V^6$, $V^8$, and $V^9$ are each independently C or $CR^{A2}$; and therefore, Ring A is an optionally substituted 7-azaindole ring. In certain embodiments, Ring A is of Formula (v-1):

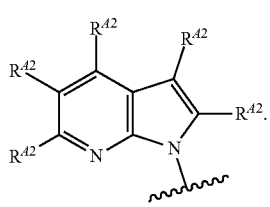

(v-1)

In certain embodiments, Ring A is of Formula (v-2):

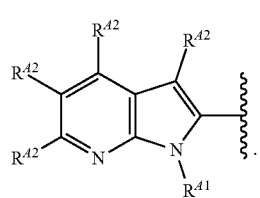

(v-2)

In certain embodiments, Ring A is of Formula (v-3):

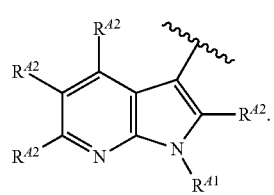

(v-3)

In certain embodiments, Ring A is of Formula (v-4):

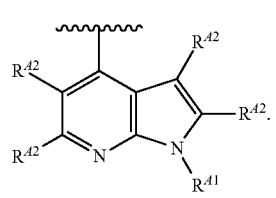

(v-4)

In certain embodiments, Ring A is of Formula (v-5):

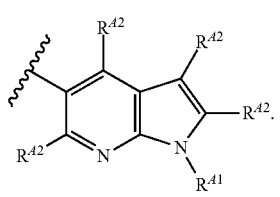

(v-5)

In certain embodiments, Ring A is of Formula (v-6):

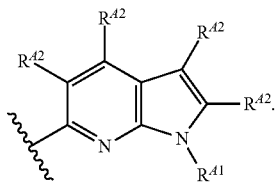

(v-6)

In certain embodiments, $V^L$ and $V^8$ are each independently N or $NR^{A1}$, $V^2$, $V^3$, $V^4$, $V^5$, $V^6$, $V^7$, and $V^9$ are each independently C or $CR^{A2}$; and therefore, Ring A is an optionally substituted 8-azaindole ring. In certain embodiments, Ring A is of Formula (vi-1):

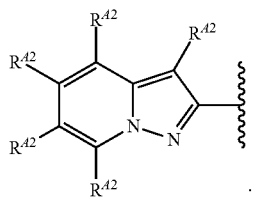
(vi-1)

In certain embodiments, Ring A is of Formula (vi-2):

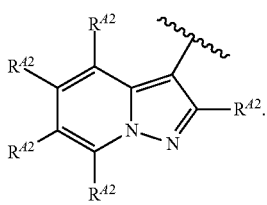
(vi-2)

In certain embodiments, Ring A is of Formula (vi-3):

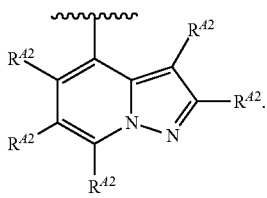
(vi-3)

In certain embodiments, Ring A is of Formula (vi-4):

(vi-4)

In certain embodiments, Ring A is of Formula (vi-5):

(vi-5)

In certain embodiments, Ring A is of Formula (vi-6):

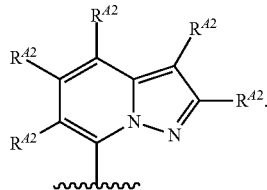
(vi-6)

In certain embodiments, $V^L$ and $V^9$ are each independently N or $NR^{A1}$; $V^2$, $V^3$, $V^4$, $V^5$, $V^6$, $V^7$, and $V^8$ are each independently C or $CR^{A2}$; and therefore, Ring A is an optionally substituted 9-azaindole ring. In certain embodiments, Ring A is of the formula:

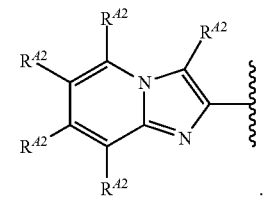

In certain embodiments, Ring A is of the formula:

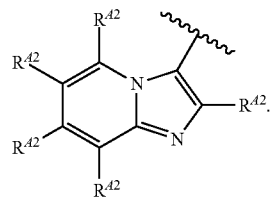

In certain embodiments, Ring A is of the formula:

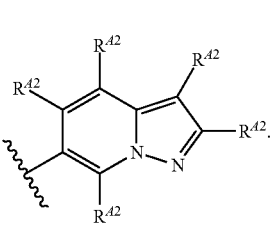

In certain embodiments, Ring A is of the formula:

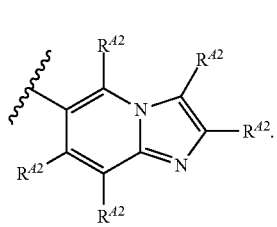

In certain embodiments, Ring A is of the formula:

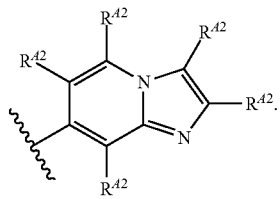

In certain embodiments, Ring A is of the formula:

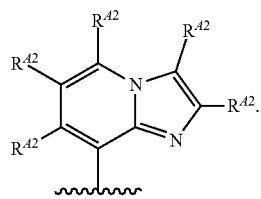

In certain embodiments, only three of $V^1$, $V^2$, $V^3$, $V^4$, $V^5$, $V^6$, $V^7$, $V^8$, and $V^9$ are each independently selected from the group consisting of O, S, N, and $NR^{41}$. In certain embodiments, only three of $V^1$, $V^2$, $V^3$, $V^4$, $V^5$, $V^6$, $V^7$, $V^8$, and $V^9$ are each independently selected from the group consisting of N and $NR^{41}$. In certain embodiments, $V^1$ is N or $NR^{41}$; and only two of $V^2$, $V^3$, $V^4$, $V^5$, $V^6$, $V^7$, $V^8$, and $V^9$ are each independently N or $NR^{41}$.

In compounds of Formula (I), Ring A may also be an optionally substituted 5-membered heteroaryl ring. In certain embodiments, Ring A is of Formula (i-5):

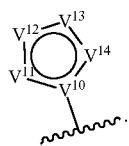

(i-5)

In compounds of Formula (I), $V^{10}$, $V^{11}$, $V^{12}$, $V^{13}$, and $V^4$ of Ring A may each independently be O, S, N, $NR^{41}$, C, or $CR^{42}$, as valency permits. In certain embodiments, only one of $V^{10}$, $V^{11}$, $V^{12}$, $V^{13}$, and $V^{14}$ is selected from the group consisting of O, S, N, and $NR^{41}$. In certain embodiments, Ring A is of the formula:

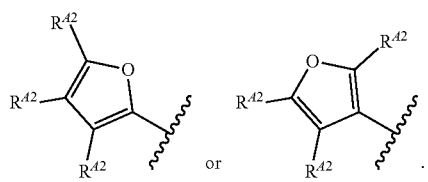

In certain embodiments, Ring A is of the formula:

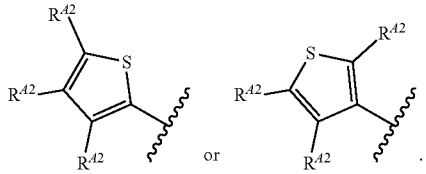

In certain embodiments, Ring A is of the formula:

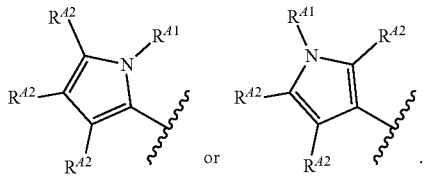

In certain embodiments, only two of $V^{10}$, $V^{11}$, $V^{12}$, $V^{13}$, and $V^{14}$ are each independently selected from the group consisting of O, S, N, and $NR^{41}$. In certain embodiments, Ring A is of the formula:

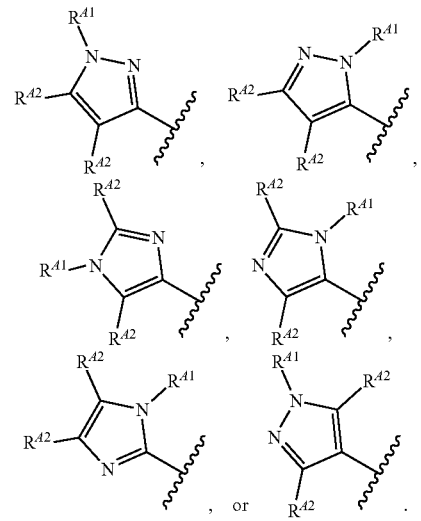

In certain embodiments, Ring A is of the formula:

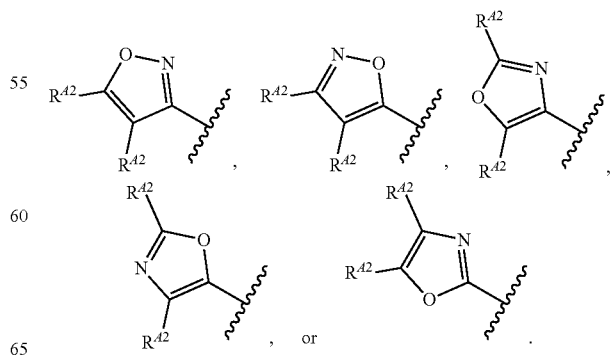

In certain embodiments, Ring A is of the formula:

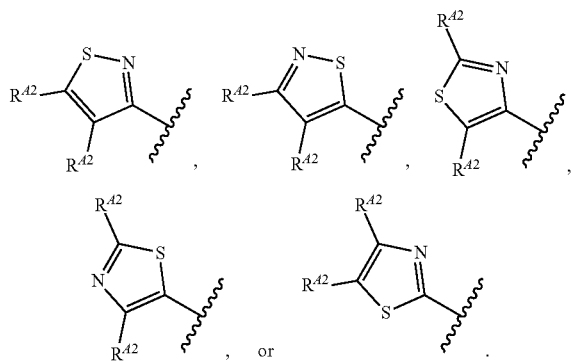

In certain embodiments, Ring A is of Formula (vii):

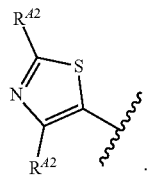

(vii)

In certain embodiments, Ring A is of the formula:

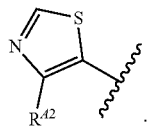

In certain embodiments, Ring A is of the formula:

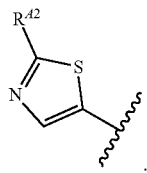

In certain embodiments, Ring A is of the formula:

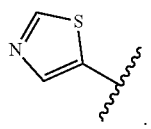 [SMILES: *c1cncs1]

In certain embodiments, only three of $V^{10}$, $V^{11}$, $V^{12}$, $V^{13}$, and $V^{14}$ are each independently selected from the group consisting of O, S, N, and $NR^{41}$. In certain embodiments, Ring A is of the formula:

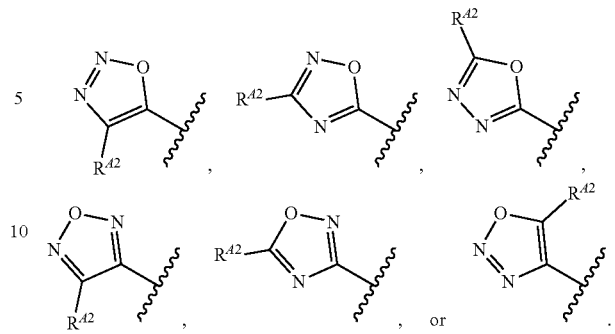

In certain embodiments, Ring A is of the formula:

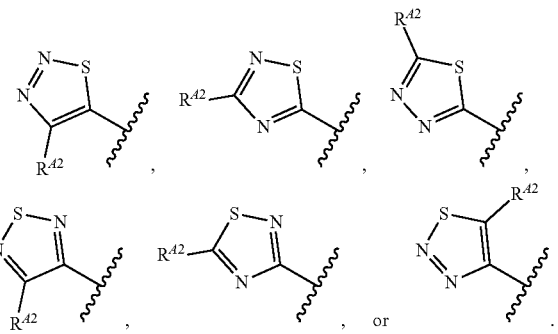

In certain embodiments, Ring A is of the formula:

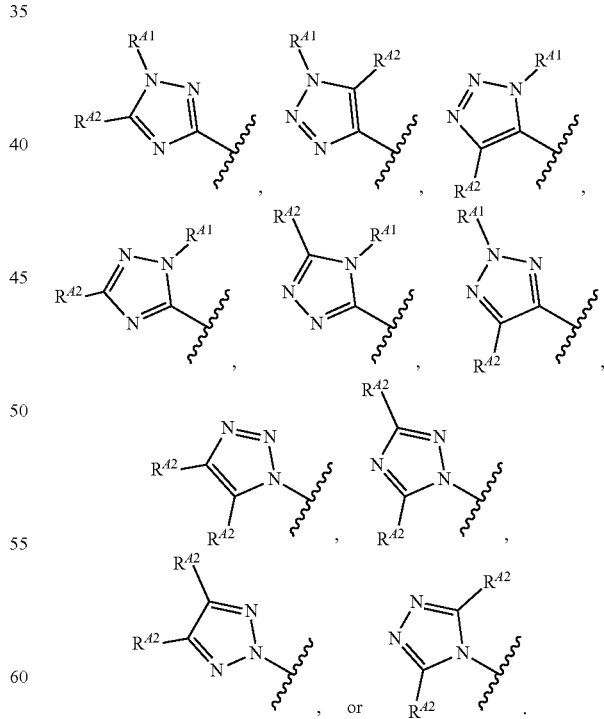

In certain embodiments, only four of $V^{10}$, $V^{11}$, $V^{12}$, $V^{13}$, and $V^{14}$ are each independently selected from the group consisting of N and $NR^{41}$. In certain embodiments, Ring A is of the formula:

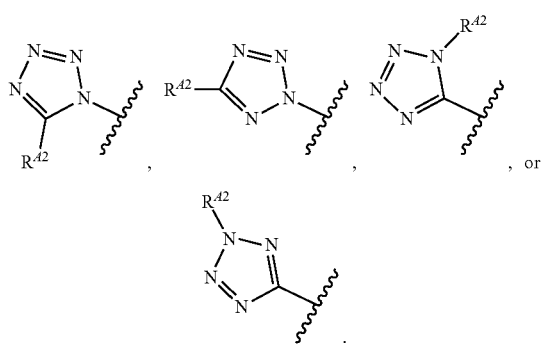

, or

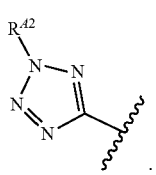

.

In compounds of Formula (I), Ring A may also be an optionally substituted 6-membered heteroaryl ring. In certain embodiments, Ring A is of Formula (i-6):

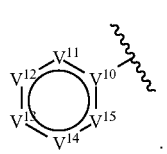

(i-6)

In compounds of Formula (I) $V^{10}$, $V^{11}$, $V^{12}$, $V^{13}$, $V^{14}$, and $V^{15}$ of Ring A may each independently be N, C, or $CR^{A2}$, as valency permits. In certain embodiments, only one of $V^{10}$, $V^{11}$, $V^{12}$, $V^{13}$, $V^{14}$, and $V^{15}$ is N. In certain embodiments, Ring A is of the formula:

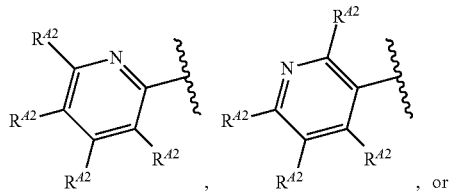

In certain embodiments, only two of $V^{10}$, $V^{11}$, $V^{12}$, $V^{13}$, $V^{14}$, and $V^{15}$ are N. In certain embodiments, Ring A is of the formula:

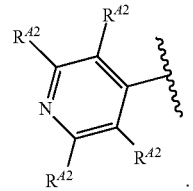

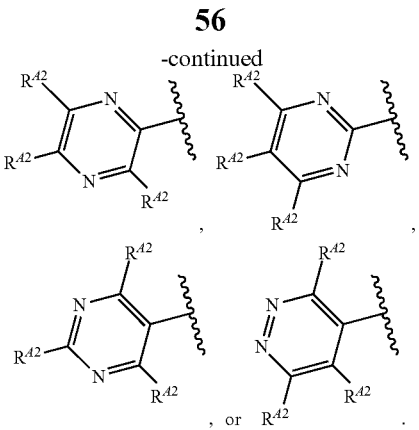

In certain embodiments, only three of $V^{10}$, $V^{11}$, $V^{12}$, $V^{13}$, $V^{14}$, and $V^{15}$ are N. In certain embodiments, Ring A is of the formula:

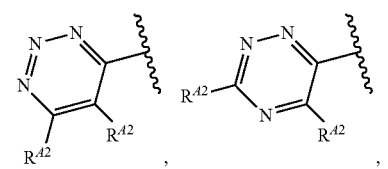

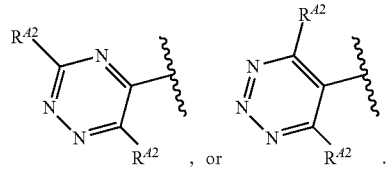

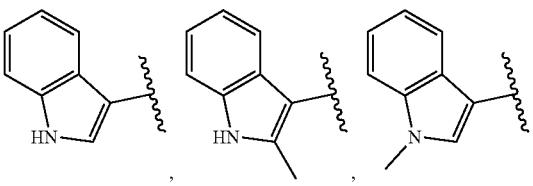

In certain embodiments, Ring A is of Formula (i-1), (i-5), or (i-6). In certain embodiments, Ring A is of the formula:

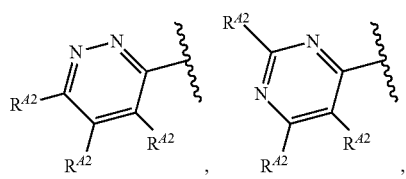

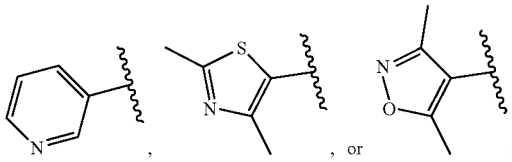

In compounds of Formula (I), Ring A may be substituted with one or more $R^{A1}$ groups when the $R^{A1}$ group is attached to a nitrogen atom. In certain embodiments, at least one instance of $R^{A1}$ is H (hydrogen). In certain embodiments, at least one instance of $R^{A1}$ is halogen. In certain embodiments, at least one instance of $R^{A1}$ is F (fluorine). In certain embodiments, at least one instance of $R^{A1}$ is Cl (chlorine). In certain embodiments, at least one instance of $R^{A1}$ is Br (bromine). In certain embodiments, at least one instance of $R^{A1}$ is I (iodine). In certain embodiments, at least one instance of $R^{A1}$ is substituted acyl. In certain embodiments, at least one instance of $R^{A1}$ is unsubstituted acyl. In certain embodiments, at least one instance of $R^{A1}$ is acetyl. In certain embodiments, at least one instance of $R^{A1}$ is substituted acetyl. In certain embodiments, at least one instance of $R^{A1}$ is substituted alkyl. In certain embodiments, at least one instance of $R^{A1}$ is unsubstituted alkyl. In certain embodiments, at least one instance of $R^{A1}$ is $C_{1-6}$ alkyl. In certain embodiments, at least one instance of $R^{A1}$ is methyl. In certain embodiments, at least one instance of $R^{A1}$ is ethyl. In certain embodiments, at least one instance of $R^{A1}$ is propyl. In certain embodiments, at least one instance of $R^{A1}$ is butyl. In certain embodiments, at least one instance of $R^{A1}$ is substituted alkenyl. In certain embodiments, at least one instance of $R^{A1}$ is unsubstituted alkenyl. In certain embodiments, at least one instance of $R^{A1}$ is vinyl. In certain embodiments, at least one instance of $R^{A1}$ is substituted alkynyl. In certain embodiments, at least one instance of $R^{A1}$ is unsubstituted alkynyl. In certain embodiments, at least one instance of $R^{A1}$ is ethynyl. In certain embodiments, at least one instance of $R^{A1}$ is substituted carbocyclyl. In certain embodiments, at least one instance of $R^{A1}$ is unsubstituted carbocyclyl. In certain embodiments, at least one instance of $R^{A1}$ is substituted heterocyclyl. In certain embodiments, at least one instance of $R^{A1}$ is unsubstituted heterocyclyl. In certain embodiments, at least one instance of $R^{A1}$ is substituted aryl. In certain embodiments, at least one instance of $R^{A1}$ is unsubstituted aryl. In certain embodiments, at least one instance of $R^{A1}$ is substituted phenyl. In certain embodiments, at least one instance of $R^{A1}$ is unsubstituted phenyl. In certain embodiments, at least one instance of $R^{A1}$ is substituted heteroaryl. In certain embodiments, at least one instance of $R^{A1}$ is unsubstituted heteroaryl. In certain embodiments, at least one instance of $R^{A1}$ is substituted pyridyl. In certain embodiments, at least one instance of $R^{A1}$ is unsubstituted pyridyl. In certain embodiments, at least one instance of $R^{A1}$ is a nitrogen protecting group. In certain embodiments, at least one instance of $R^{A1}$ is Bn, BOC, Cbz, Fmoc, trifluoroacetyl, triphenylmethyl, acetyl, or Ts.

In certain embodiments, at least one $R^{A1}$ is hydrogen, $C_{1-6}$ alkyl, or a nitrogen protecting group. In certain embodiments, all instances of $R^{A1}$ are each independently hydrogen, $C_{1-6}$ alkyl, or a nitrogen protecting group. In certain embodiments, all instances of $R^{A1}$ are hydrogen.

In compounds of Formula (I), Ring A may be substituted with one or more $R^{A2}$ groups when the $R^{A2}$ group is attached to a carbon atom. In certain embodiments, at least one $R^{A2}$ is H. In certain embodiments, at least one $R^{A2}$ is halogen. In certain embodiments, at least one $R^{A2}$ is F. In certain embodiments, at least one $R^{A2}$ is Cl. In certain embodiments, at least one $R^{A2}$ is Br. In certain embodiments, at least one $R^{A2}$ is I (iodine). In certain embodiments, at least one $R^{A2}$ is substituted acyl. In certain embodiments, at least one $R^{A2}$ is unsubstituted acyl. In certain embodiments, at least one $R^{A2}$ is acetyl. In certain embodiments, at least one $R^{A2}$ is substituted acetyl. In certain embodiments, at least one $R^{A2}$ is substituted alkyl. In certain embodiments, at least one $R^{A2}$ is unsubstituted alkyl. In certain embodiments, at least one $R^{A2}$ is $C_{1-6}$ alkyl. In certain embodiments, at least one $R^{A2}$ is methyl. In certain embodiments, at least one $R^{A2}$ is ethyl. In certain embodiments, at least one $R^{A2}$ is propyl. In certain embodiments, at least one $R^{A2}$ is butyl. In certain embodiments, at least one $R^{A2}$ is substituted alkenyl. In certain embodiments, at least one $R^{A2}$ is unsubstituted alkenyl. In certain embodiments, at least one $R^{A2}$ is vinyl. In certain embodiments, at least one $R^{A2}$ is substituted alkynyl. In certain embodiments, at least one $R^{A2}$ is unsubstituted alkynyl. In certain embodiments, at least one $R^{A2}$ is ethynyl. In certain embodiments, at least one $R^{A2}$ is substituted carbocyclyl. In certain embodiments, at least one $R^{A2}$ is unsubstituted carbocyclyl. In certain embodiments, at least one $R^{A2}$ is substituted heterocyclyl. In certain embodiments, at least one $R^{A2}$ is unsubstituted heterocyclyl. In certain embodiments, at least one $R^{A2}$ is substituted aryl. In certain embodiments, at least one $R^{A2}$ is unsubstituted aryl. In certain embodiments, at least one $R^{A2}$ is substituted phenyl. In certain embodiments, at least one $R^{A2}$ is unsubstituted phenyl. In certain embodiments, at least one $R^{A2}$ is substituted heteroaryl. In certain embodiments, at least one $R^{A2}$ is unsubstituted heteroaryl. In certain embodiments, at least one $R^{A2}$ is substituted pyridyl. In certain embodiments, at least one $R^{A2}$ is unsubstituted pyridyl. In certain embodiments, at least one $R^{A2}$ is $-OR^{A2a}$. In certain embodiments, at least one $R^{A2}$ is $-N(R^{A2a})_2$. In certain embodiments, at least one $R^{A2}$ is $-SR^{A2a}$.

In certain embodiments, two $R^{A2}$ groups are each independently halogen, optionally substituted alkyl, or optionally substituted aryl; and all other instances of $R^{A2}$ are hydrogen. In certain embodiments, two $R^{A2}$ groups are each independently halogen or optionally substituted alkyl; and all other instances of $R^{A2}$ are hydrogen. In certain embodiments, two $R^{A2}$ groups are halogen; and all other instances of $R^{A2}$ are hydrogen. In certain embodiments, two $R^{A2}$ groups are optionally substituted alkyl; and all other instances of $R^{A2}$ are hydrogen. In certain embodiments, two $R^{A2}$ groups are $C_{1-6}$ alkyl; and all other instances of $R^{A2}$ are hydrogen. In certain embodiments, two $R^{A2}$ groups are methyl; and all other instances of $R^{A2}$ are hydrogen. In certain embodiments, two $R^{A2}$ groups are ethyl; and all other instances of $R^{A2}$ are hydrogen. In certain embodiments, two $R^{A2}$ groups are propyl; and all other instances of $R^{A2}$ are hydrogen. In certain embodiments, two $R^{A2}$ groups are butyl; and all other instances of $R^{A2}$ are hydrogen. In certain embodiments, two $R^{A2}$ groups are optionally substituted aryl; and all other instances of $R^{A2}$ are hydrogen. In certain embodiments, two $R^{A2}$ groups are optionally substituted phenyl; and all other instances of $R^{A2}$ are hydrogen.

In certain embodiments, one $R^{A2}$ groups is halogen, optionally substituted alkyl, or optionally substituted aryl; and all other instances of $R^{A2}$ are hydrogen. In certain embodiments, one $R^{A2}$ is halogen or optionally substituted alkyl; and all other instances of $R^{A2}$ are hydrogen. In certain embodiments, one $R^{A2}$ is halogen; and all other instances of $R^{A2}$ are hydrogen. In certain embodiments, one $R^{A2}$ is optionally substituted alkyl; and all other instances of $R^{A2}$ are hydrogen. In certain embodiments, one $R^{A2}$ is $C_{1-6}$ alkyl; and all other instances of $R^{A2}$ are hydrogen. In certain embodiments, one $R^{A2}$ is methyl; and all other instances of $R^{A2}$ are hydrogen. In certain embodiments, one $R^{A2}$ is ethyl; and all other instances of $R^{A2}$ are hydrogen. In certain embodiments, one $R^{A2}$ is propyl; and all other instances of $R^{A2}$ are hydrogen. In certain embodiments, one $R^{A2}$ is butyl; and all other instances of $R^{A2}$ are hydrogen. In certain embodiments, one $R^{A2}$ is optionally substituted aryl; and all other instances of $R^{A2}$ are hydrogen. In certain embodiments, one $R^{A2}$ is optionally substituted phenyl; and all other instances of $R^{A2}$ are hydrogen.

In certain embodiments, all instances of $R^{A2}$ are hydrogen.

In certain embodiments, when $R^{A2}$ is —$OR^{A2a}$, —$N(R^{A2a})_2$, or —$SR^{A2a}$, at least one $R^{A2a}$ is H. In certain embodiments, at least one $R^{A2a}$ is halogen. In certain embodiments, at least one $R^{A2a}$ is F. In certain embodiments, at least one $R^{A2a}$ is Cl. In certain embodiments, at least one $R^{A2a}$ is Br. In certain embodiments, at least one $R^{A2a}$ is I (iodine). In certain embodiments, at least one $R^{A2a}$ is substituted acyl. In certain embodiments, at least one $R^{A2a}$ is unsubstituted acyl. In certain embodiments, at least one $R^{A2a}$ is acetyl. In certain embodiments, at least one $R^{A2a}$ is substituted acetyl. In certain embodiments, at least one $R^{A2a}$ is substituted alkyl. In certain embodiments, at least one $R^{A2a}$ is unsubstituted alkyl. In certain embodiments, at least one $R^{A2a}$ is $C_{1-6}$ alkyl. In certain embodiments, at least one $R^{A2a}$ is methyl. In certain embodiments, at least one $R^{A2a}$ is ethyl. In certain embodiments, at least one $R^{A2a}$ is propyl. In certain embodiments, at least one $R^{A2a}$ is butyl. In certain embodiments, at least one $R^{A2a}$ is substituted alkenyl. In certain embodiments, at least one $R^{A2a}$ is unsubstituted alkenyl. In certain embodiments, at least one $R^{A2a}$ is vinyl. In certain embodiments, at least one $R^{A2a}$ is substituted alkynyl. In certain embodiments, at least one $R^{A2a}$ is unsubstituted alkynyl. In certain embodiments, at least one $R^{A2a}$ is ethynyl. In certain embodiments, at least one $R^{A2a}$ is substituted carbocyclyl. In certain embodiments, at least one $R^{A2a}$ is unsubstituted carbocyclyl. In certain embodiments, at least one $R^{A2a}$ is substituted heterocyclyl. In certain embodiments, at least one $R^{A2a}$ is unsubstituted heterocyclyl. In certain embodiments, at least one $R^{A2a}$ is substituted aryl. In certain embodiments, at least one $R^{A2a}$ is unsubstituted aryl. In certain embodiments, at least one $R^{A2a}$ is substituted phenyl. In certain embodiments, at least one $R^{A2a}$ is unsubstituted phenyl. In certain embodiments, at least one $R^{A2a}$ is substituted heteroaryl. In certain embodiments, at least one $R^{A2a}$ is unsubstituted heteroaryl. In certain embodiments, at least one $R^{A2a}$ is substituted pyridyl. In certain embodiments, at least one $R^{A2a}$ is unsubstituted pyridyl. In certain embodiments, at least one $R^{A2a}$ is a nitrogen protecting group when attached to a nitrogen atom. In certain embodiments, at least one $R^{A2a}$ is Bn, BOC, Cbz, Fmoc, trifluoroacetyl, triphenylmethyl, acetyl, or Ts when attached to a nitrogen atom. In certain embodiments, at least one $R^{A2a}$ is an oxygen protecting group when attached to an oxygen atom. In certain embodiments, at least one $R^{A2a}$ is silyl, TBDPS, TBDMS, TIPS, TES, TMS, MOM, THP, t-Bu, Bn, allcetyacetyl, pivaloyl, or benzoyl when attached to an oxygen atom. In certain embodiments, at least one $R^{A2a}$ is a sulfur protecting group when attached to a sulfur atom. In certain embodiments, at least one $R^{A2a}$ is acetamidomethyl, t-Bu, 3-nitro-2-pyridine sulfenyl, 2-pyridine-sulfenyl, or triphenylmethyl when attached to a sulfur atom. In certain embodiments, two $R^{A2a}$ groups are joined to form a substituted heterocyclic ring. In certain embodiments, two $R^{A2a}$ groups are joined to form an unsubstituted heterocyclic ring.

In compounds of Formula (I), any two of $R^{A1}$, $R^{A2}$, and $R^{A2a}$ groups may be joined to form an optionally substituted carbocyclic, optionally substituted heterocyclic, optionally substituted aryl, or optionally substituted heteroaryl ring. In certain embodiments, one instance of $R^{A1}$ and one instance of $R^{A2}$ are joined to form a substituted carbocyclic ring. In certain embodiments, one instance of $R^{A1}$ and one instance of $R^{A2}$ are joined to form an unsubstituted carbocyclic ring. In certain embodiments, one instance of $R^{A1}$ and one instance of $R^{A2}$ are joined to form a substituted heterocyclic ring. In certain embodiments, one instance of $R^{A1}$ and one instance of $R^{A2}$ are joined to form an unsubstituted heterocyclic ring. In certain embodiments, one instance of $R^{A1}$ and one instance of $R^{A2}$ are joined to form a substituted aryl ring. In certain embodiments, one instance of $R^{A1}$ and one instance of $R^{A2}$ are joined to form an unsubstituted aryl ring. In certain embodiments, one instance of $R^{A1}$ and one instance of $R^{A2}$ are joined to form a substituted heteroaryl ring. In certain embodiments, one instance of $R^{A1}$ and one instance of $R^{A2}$ are joined to form an unsubstituted heteroaryl ring. In certain embodiments, one instance of $R^{A1}$ and one instance of $R^{A2a}$ are joined to form a substituted carbocyclic ring. In certain embodiments, one instance of $R^{A1}$ and one instance of $R^{A2a}$ are joined to form an unsubstituted carbocyclic ring. In certain embodiments, one instance of $R^{A1}$ and one instance of $R^{A2a}$ are joined to form a substituted heterocyclic ring. In certain embodiments, one instance of $R^{A1}$ and one instance of $R^{A2a}$ are joined to form an unsubstituted heterocyclic ring. In certain embodiments, one instance of $R^{A1}$ and one instance of $R^{A2a}$ are joined to form a substituted aryl ring. In certain embodiments, one instance of $R^{A1}$ and one instance of $R^{A2a}$ are joined to form an unsubstituted aryl ring. In certain embodiments, one instance of $R^{A1}$ and one instance of $R^{A2a}$ are joined to form a substituted heteroaryl ring. In certain embodiments, one instance of $R^{A1}$ and one instance of $R^{A2a}$ are joined to form an unsubstituted heteroaryl ring. In certain embodiments, one instance of $R^{A2a}$ and one instance of $R^{A2}$ are joined to form a substituted carbocyclic ring. In certain embodiments, one instance of $R^{A2a}$ and one instance of $R^{A2}$ are joined to form an unsubstituted carbocyclic ring. In certain embodiments, one instance of $R^{A2a}$ and one instance of $R^{A2}$ are joined to form a substituted heterocyclic ring. In certain embodiments, one instance of $R^{A2a}$ and one instance of $R^{A2}$ are joined to form an unsubstituted heterocyclic ring. In certain embodiments, one instance of $R^{A2a}$ and one instance of $R^{A2}$ are joined to form a substituted aryl ring. In certain embodiments, one instance of $R^{A2a}$ and one instance of $R^{A2}$ are joined to form an unsubstituted aryl ring. In certain embodiments, one instance of $R^{A2a}$ and one instance of $R^{A2}$ are joined to form a substituted heteroaryl ring. In certain embodiments, one instance of $R^{A2a}$ and one instance of $R^{A2}$ are joined to form an unsubstituted heteroaryl ring.

Compounds of Formula (I) include a substituted or unsubstituted heteroaryl ring of the formula:

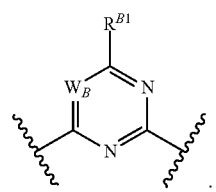

In certain embodiments, $W_B$ is N. In certain embodiments, $W_B$ is $CR^{B2}$; and thus Ring B is of the formula:

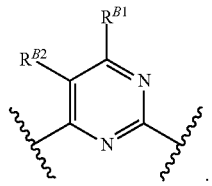

In certain embodiments, Ring B is of the formula:

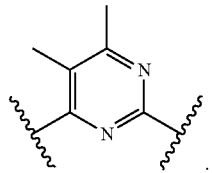 [SMILES: *c1nc(*)c(C)c(C)n1]

In certain embodiments, Ring B is of the formula:

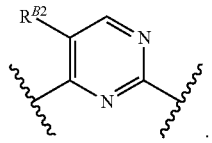

In certain embodiments, Ring B is of the formula:

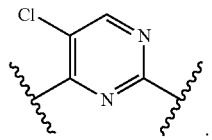

In certain embodiments, Ring B is of the formula:

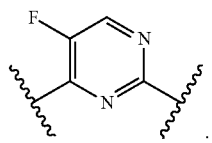 [SMILES: *c1ncc(F)c(*)n1]

In certain embodiments, Ring B is of the formula:

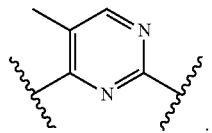 [SMILES: *c1ncc(C)c(*)n1]

In certain embodiments, Ring B is of the formula:

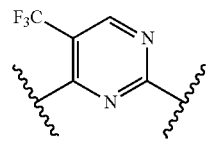

In certain embodiments, Ring B is of the formula:

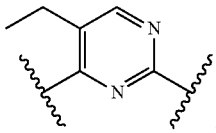

In certain embodiments, Ring B is of the formula:

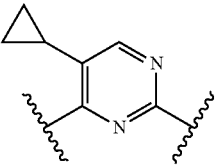

In certain embodiments, Ring B is of the formula:

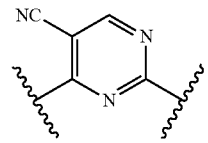

In certain embodiments, Ring B is of the formula:

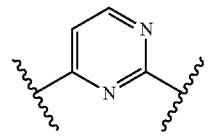

In compounds of Formula (I), Ring B includes a substituent $R^{B1}$. In certain embodiments, $R^{B1}$ is H. In certain embodiments, $R^{B1}$ is halogen. In certain embodiments, $R^{B1}$ is F. In certain embodiments, $R^{B1}$ is Cl. In certain embodiments, $R^{B1}$ is Br. In certain embodiments, $R^{B1}$ is I (iodine). In certain embodiments, $R^{B1}$ is substituted acyl. In certain embodiments, $R^{B1}$ is unsubstituted acyl. In certain embodiments, $R^{B1}$ is acetyl. In certain embodiments, $R^{B1}$ is substituted acetyl. In certain embodiments, $R^{B1}$ is substituted alkyl. In certain embodiments, RB is unsubstituted alkyl. In certain embodiments, RB is $C_{1-6}$ alkyl. In certain embodiments, $R^{B1}$ is methyl. In certain embodiments, $R^{B1}$ is ethyl. In certain embodiments, $R^{B1}$ is propyl. In certain embodiments, $R^{B1}$ is butyl. In certain embodiments, $R^{B1}$ is substituted alkenyl. In certain embodiments, $R^{B1}$ is unsubstituted alkenyl. In certain embodiments, $R^{B1}$ is vinyl. In certain embodiments, $R^{B1}$ is substituted alkynyl. In certain embodiments, $R^{B1}$ is unsubstituted alkynyl. In certain embodiments, $R^{B1}$ is ethynyl. In certain embodiments, $R^{B1}$ is substituted carbocyclyl. In certain embodiments, $R^{B1}$ is unsubstituted carbocyclyl. In certain embodiments, $R^{B1}$ is substituted aryl. In certain embodiments, $R^{B1}$ is unsubstituted aryl. In certain embodiments, $R^{B1}$ is substituted phenyl. In certain embodiments, $R^{B1}$ is unsubstituted phenyl. In certain embodiments, $R^{B1}$ is substituted heteroaryl. In certain embodiments, $R^{B1}$ is unsubstituted heteroaryl. In certain embodiments, $R^{B1}$ is substituted pyridyl. In certain embodiments, $R^{B1}$ is unsubstituted pyridyl. In certain embodiments, $R^{B1}$ is —CN. In certain embodiments, $R^{B1}$ is —OR$^{B1a}$. In certain embodiments, $R^{B1}$ is —N(R$^{B1a}$)$_2$. In certain embodiments, $R^{B1}$ is —SR$^{B1a}$ In certain embodiments, $R^{B1}$ is hydrogen, halogen, substituted or unsubstituted $C_{1-6}$ alkyl, —CN, —OR$^{B1a}$, or —N(R$^{B1a}$)$_2$. In certain embodiments, $R^{B1}$ is hydrogen, halogen, —CN, —OR$^{B1a}$, —N(R$^{B1a}$)$_2$, unsubstituted $C_{1-6}$ alkyl, or $C_{1-6}$ alkyl substituted with one or more halogen, wherein each instance of $R^{B1a}$ is independently hydrogen, unsubstituted $C_{1-6}$ alkyl, or $C_{1-6}$ alkyl substituted with one or more halogen.

In certain embodiments, when $R^{B1}$ is —OR$^{B1a}$, —N(R$^{B1a}$)$_2$, or —SR$^{B1a}$, $R^{B1a}$ is H. In certain embodiments, $R^{B1a}$ is halogen. In certain embodiments, $R^{B1a}$ is F. In certain embodiments, $R^{B1a}$ is Cl. In certain embodiments, $R^{B1a}$ is Br. In certain embodiments, $R^{B1a}$ is I (iodine). In certain embodiments, $R^{B1a}$ is substituted acyl. In certain embodiments, $R^{B1a}$ is unsubstituted acyl. In certain embodiments, $R^{B1a}$ is acetyl. In certain embodiments, $R^{B1a}$ is substituted acetyl. In certain embodiments, $R^{B1a}$ is substituted alkyl. In certain embodiments, $R^{B1a}$ is unsubstituted alkyl. In certain embodiments, $R^{B1a}$ is $C_{1-6}$ alkyl. In certain embodiments, $R^{B1a}$ is methyl. In certain embodiments, $R^{B1a}$ is ethyl. In certain embodiments, $R^{B1a}$ is propyl. In certain embodiments, $R^{B1a}$ is butyl. In certain embodiments, $R^{B1a}$ is substituted alkenyl. In certain embodiments, $R^{B1a}$ is unsubstituted alkenyl. In certain embodiments, $R^{B1a}$ is vinyl. In certain embodiments, $R^{B1a}$ is substituted alkynyl. In certain embodiments, $R^{B1a}$ is unsubstituted alkynyl. In certain embodiments, $R^{B1a}$ is ethynyl. In certain embodiments, $R^{B1a}$ is substituted carbocyclyl. In certain embodiments, $R^{B1a}$ is unsubstituted carbocyclyl. In certain embodiments, $R^{B1a}$ is substituted heterocyclyl. In certain embodiments, $R^{B1a}$ is unsubstituted heterocyclyl. In certain embodiments, $R^{B1a}$ is substituted aryl. In certain embodiments, $R^{B1a}$ is unsubstituted aryl. In certain embodiments, $R^{B1a}$ is substituted phenyl. In certain embodiments, $R^{B1a}$ is unsubstituted phenyl. In certain embodiments, $R^{B1a}$ is substituted heteroaryl. In certain embodiments, $R^{B1a}$ is unsubstituted heteroaryl. In certain embodiments, $R^{B1a}$ is substituted pyridyl. In certain embodiments, $R^{B1a}$ is unsubstituted pyridyl. In certain embodiments, $R^{B1a}$ is a nitrogen protecting group when attached to a nitrogen atom. In certain embodiments, $R^{B1a}$ is Bn, BOC, Cbz, Fmoc, trifluoroacetyl, triphenylmethyl, acetyl, or Ts when attached to a nitrogen atom. In certain embodiments, $R^{B1a}$ is an oxygen protecting group when attached to an oxygen atom. In certain embodiments, $R^{B1a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{B1a}$ is a sulfur protecting group when attached to a sulfur atom. In certain embodiments, $R^{B1a}$ is acetamidomethyl, t-Bu, 3-nitro-2-pyridine sulfenyl, 2-pyridine-sulfenyl, or triphenylmethyl when attached to a sulfur atom.

In compounds of Formula (I), when $W_B$ is CR$^{B2}$, Ring B also includes a substituent $R^{B2}$. In certain embodiments, $R^{B2}$ is H. In certain embodiments, $R^{B2}$ is selected from the group consisting of halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —OR$^{B2a}$, —N(R$^{B2a}$)$_2$, and —SR$^{B2a}$. In certain embodiments, $R^{B2}$ is halogen. In certain embodiments, $R^{B2}$ is F. In certain embodiments, $R^{B2}$ is Cl. In certain embodiments, $R^{B2}$ is Br. In certain embodiments, $R^{B2}$ is I (iodine). In certain embodiments, $R^{B2}$ is substituted acyl. In certain embodiments, $R^{B2}$ is unsubstituted acyl. In certain embodiments, $R^{B2}$ is acetyl. In certain embodiments, $R^{B2}$ is substituted acetyl. In certain embodiments, $R^{B2}$ is substituted alkyl. In certain embodiments, $R^{B2}$ is unsubstituted alkyl. In certain embodiments, $R^{B2}$ is $C_{1-6}$ alkyl. In certain embodiments, $R^{B2}$ is partially fluorinated $C_{1-6}$ alkyl. In certain embodiments, $R^{B2}$ is perfluorinated $C_{1-6}$ alkyl. In certain embodiments, $R^{B2}$ is methyl. In certain embodiments, $R^{B2}$ is —CH$_2$F. In certain embodiments, $R^{B2}$ is —CHF$_2$. In certain embodiments, $R^{B2}$ is —CF$_3$. In certain embodiments, $R^{B2}$ is ethyl. In certain embodiments, $R^{B2}$ is —C$_2$F$_5$. In certain embodiments, $R^{B2}$ is propyl. In certain embodiments, $R^{B2}$ is butyl. In certain embodiments, $R^{B2}$ is substituted alkenyl. In certain embodiments, $R^{B2}$ is unsubstituted alkenyl. In certain embodiments, $R^{B2}$ is vinyl. In certain embodiments, $R^{B2}$ is substituted alkynyl. In certain embodiments, $R^{B2}$ is unsubstituted alkynyl. In certain embodiments, $R^{B2}$ is ethynyl. In certain embodiments, $R^{B2}$ is substituted carbocyclyl. In certain embodiments, $R^{B2}$ is unsubstituted carbocyclyl. In certain embodiments, $R^{B2}$ is cyclopropyl. In certain embodiments, $R^{B2}$ is cyclobutyl. In certain embodiments, $R^{B2}$ is cyclopentyl. In certain embodiments, $R^{B2}$ is cyclohexyl. In certain embodiments, $R^{B2}$ is cycloheptyl. In certain embodiments, $R^{B2}$ is substituted heterocyclyl. In certain embodiments, $R^{B2}$ is unsubstituted heterocyclyl. In certain embodiments, $R^{B2}$ is substituted aryl. In certain embodiments, $R^{B2}$ is unsubstituted aryl. In certain embodiments, $R^{B2}$ is substituted phenyl. In certain embodiments, $R^{B2}$ is unsubstituted phenyl. In certain embodiments, $R^{B2}$ is substituted heteroaryl. In certain embodiments, $R^{B2}$ is unsubstituted heteroaryl. In certain embodiments, $R^{B2}$ is substituted pyridyl. In certain embodiments, $R^{B2}$ is unsubstituted pyridyl. In certain embodiments, $R^{B2}$ is —CN. In certain embodiments, $R^{B2}$ is —OR$^{B2a}$. In certain embodiments, $R^{B2}$ is —N(R$^{B2a}$)$_2$. In certain embodiments, $R^{B2}$ is —SR$^{B2a}$. In certain embodiments, $R^{B2}$ is hydrogen, halogen, substituted or unsubstituted $C_{1-6}$ alkyl, —CN, —OR$^{B2a}$, or —N(R$^{B2a}$)$_2$. In certain embodiments, $R^{B2}$ is hydrogen, halogen, —CN, —OR$^{B2a}$, —N(R$^{B2a}$)$_2$, unsubstituted $C_{1-6}$ alkyl, or $C_{1-6}$ alkyl substituted with one or more halogen, wherein each instance of $R^{B2a}$ is independently hydrogen, unsubstituted $C_{1-6}$ alkyl, or $C_{1-6}$ alkyl substituted with one or more halogen. In certain embodiments, $R^{B2}$ is hydrogen, halogen, substituted or unsubstituted $C_{1-6}$ alkyl, substituted or unsubstituted carbocyclyl, —CN, —OR$^{B2a}$, or —N(R$^{B2a}$)$_2$. In certain embodiments, $R^{B2}$ is hydrogen, halogen, —CN, —OR$^{B2a}$, —N(R$^{B2a}$)$_2$, unsubstituted $C_{1-6}$ alkyl, $C_{1-6}$ alkyl substituted with one or more halogen, or unsubstituted carbocyclyl, wherein each instance of $R^{B2a}$ is independently hydrogen, unsubstituted $C_{1-6}$ alkyl, or $C_{1-6}$ alkyl substituted with one or more halogen. $R^{B2}$ is hydrogen, halogen, substituted or unsubstituted $C_{1-6}$ alkyl, unsubstituted 3- to 6-membered monocyclic carbocyclyl consisting of 0, 1, or 2 double bonds in the carbocyclic ring system, or —CN. In certain embodiments, $R^{B2}$ is hydrogen, chloro, fluoro, —CH$_3$, —C$_2$H$_5$, cyclopropyl, —CF$_3$, or —CN.

In certain embodiments, when $R^{B2}$ is —OR$^{B2a}$, —N(R$^{B2a}$)$_2$, or —SR$^{B2a}$, $R^{B2a}$ is H. In certain embodiments, $R^{B2a}$ is halogen. In certain embodiments, $R^{B2a}$ is F. In certain embodiments, $R^{B2a}$ is Cl. In certain embodiments, $R^{B2a}$ is Br. In certain embodiments, $R^{B2a}$ is I (iodine). In certain embodiments, $R^{B2a}$ is substituted acyl. In certain embodiments, $R^{B2a}$ is unsubstituted acyl. In certain embodiments, $R^{B2a}$ is acetyl. In certain embodiments, $R^{B2a}$ is substituted acetyl. In certain embodiments, $R^{B2a}$ is substituted alkyl. In certain embodiments, $R^{B2a}$ is unsubstituted alkyl. In certain embodiments, $R^{B2a}$ is $C_{1-6}$ alkyl. In certain embodiments, $R^{B2a}$ is methyl. In certain embodiments, $R^{B2a}$ is ethyl. In certain embodiments, $R^{B2a}$ is propyl. In certain embodiments, $R^{B2a}$ is butyl. In certain embodiments, $R^{B2a}$ is substituted alkenyl. In certain embodiments, $R^{B2a}$ is unsubstituted alkenyl. In certain embodiments, $R^{B2a}$ is vinyl. In certain embodiments, $R^{B2a}$ is substituted alkynyl. In certain embodiments, $R^{B2a}$ is unsubstituted alkynyl. In certain embodiments, $R^{B2a}$ is ethynyl. In certain embodiments, $R^{B2a}$ is substituted carbocyclyl. In certain embodiments, $R^{B2a}$ is unsubstituted carbocyclyl. In certain embodiments, $R^{B2a}$ is substituted heterocyclyl. In certain embodiments, $R^{B2a}$ is unsubstituted heterocyclyl. In certain embodiments, $R^{B2a}$ is substituted aryl. In certain embodiments, $R^{B2a}$ is unsubstituted aryl. In certain embodiments, $R^{B2a}$ is substituted phenyl. In certain embodiments, $R^{B2a}$ is unsubstituted phenyl. In certain embodiments, $R^{B2a}$ is substituted heteroaryl. In certain embodiments, $R^{B2a}$ is unsubstituted heteroaryl. In certain embodiments, $R^{B2a}$ is substituted pyridyl. In certain embodiments, $R^{B2a}$ is unsubstituted pyridyl. In certain embodiments, $R^{B2a}$ is a nitrogen protecting group when attached to a nitrogen atom. In certain embodiments, $R^{B2a}$ is Bn, BOC, Cbz, Fmoc, trifluoroacetyl, triphenylmethyl, acetyl, or Ts when attached to a nitrogen atom. In certain embodiments, $R^{B2a}$ is an oxygen protecting group when attached to an oxygen atom. In certain embodiments, $R^{B2a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{B2a}$ is a sulfur protecting group when attached to a sulfur atom. In certain embodiments, $R^{B2a}$ is acetamidomethyl, t-Bu, 3-nitro-2-pyridine sulfenyl, 2-pyridine-sulfenyl, or triphenylmethyl when attached to a sulfur atom. In certain embodiments, two $R^{B2a}$ groups are joined to form a substituted heterocyclic ring. In certain embodiments, two $R^{B2a}$ groups are joined to form an unsubstituted heterocyclic ring.

In compounds of Formula (I), $R^{B1}$ and $R^{B2}$ groups may be joined to form a ring fused to Ring B. In certain embodiments, $R^{B1}$ and $R^{B2}$ are joined to form a substituted carbocyclic ring. In certain embodiments, $R^{B1}$ and $R^{B2}$ are joined to form an unsubstituted carbocyclic ring. In certain embodiments, $R^{B1}$ and $R^{B2}$ are joined to form a substituted heterocyclic ring. In certain embodiments, $R^{B1}$ and $R^{B2}$ are joined to form an unsubstituted heterocyclic ring. In certain embodiments, $R^{B1}$ and $R^{B2}$ are joined to form a substituted aryl ring. In certain embodiments, $R^{B1}$ and $R^{B2}$ are joined to form an unsubstituted aryl ring. In certain embodiments, $R^{B1}$ and $R^{B2}$ are joined to form a substituted phenyl ring. In certain embodiments, $R^{B1}$ and $R^{B2}$ are joined to form an unsubstituted phenyl ring. In certain embodiments, $R^{B1}$ and $R^{B2}$ are joined to form a substituted heteroaryl ring. In certain embodiments, $R^{B1}$ and $R^{B2}$ are joined to form an unsubstituted heteroaryl ring. In certain embodiments, $R^{B1}$ and $R^{B2}$ are joined to form a substituted pyridyl ring. In certain embodiments, $R^{B1}$ and $R^{B2}$ are joined to form an unsubstituted pyridyl ring.

In certain embodiments, Ring B is of the formula:

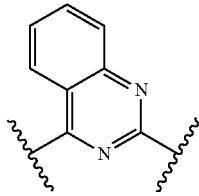

In certain embodiments, Ring B is of the formula:

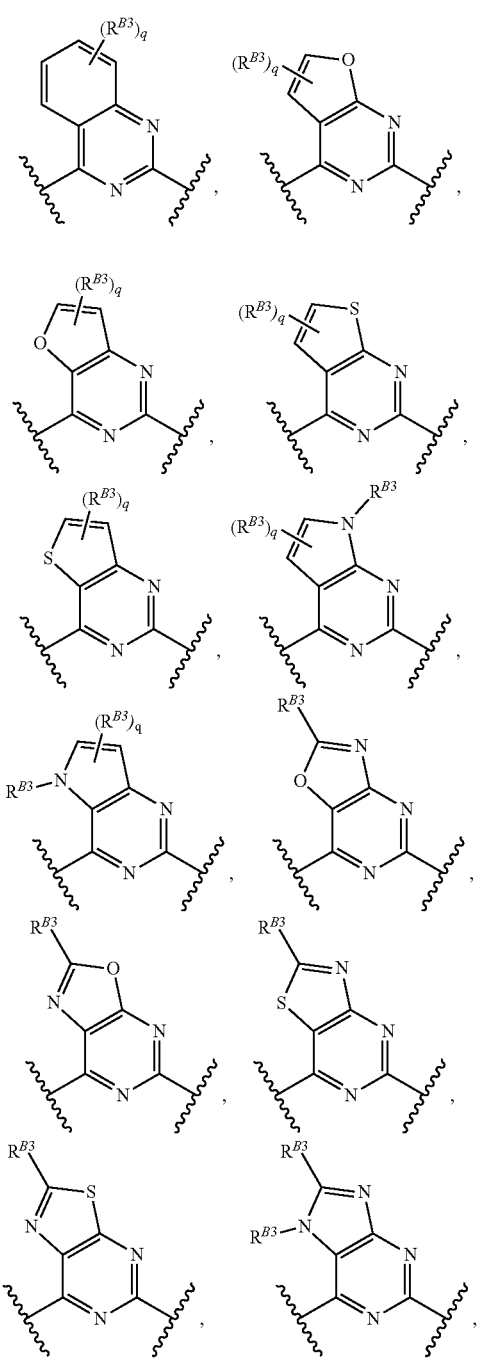

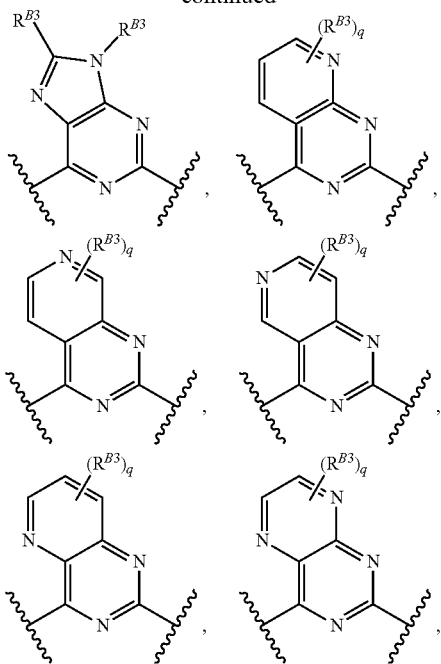

wherein
each instance of $R^{B3}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —OR$^{B3a}$, —N(R$^{B3a}$)$_2$, and —SR$^{B3a}$, wherein each occurrence of R$^{B3a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two R$^{B3a}$ groups are joined to form an optionally substituted heterocyclic ring; and q is 0, 1, 2, or 3.

In certain embodiments, at least one instance of R$^{B3}$ is H. In certain embodiments, at least one instance of R$^{B3}$ is halogen. In certain embodiments, at least one instance of R$^{B3}$ is F. In certain embodiments, at least one instance of R$^{B3}$ is Cl. In certain embodiments, at least one instance of R$^{B3}$ is Br. In certain embodiments, at least one instance of R$^{B3}$ is I (iodine). In certain embodiments, at least one instance of R$^{B3}$ is substituted acyl. In certain embodiments, at least one instance of R$^{B3}$ is unsubstituted acyl. In certain embodiments, at least one instance of R$^{B3}$ is acetyl. In certain embodiments, at least one instance of R$^{B3}$ is substituted acetyl. In certain embodiments, at least one instance of R$^{B3}$ is substituted alkyl. In certain embodiments, at least one instance of R$^{B3}$ is unsubstituted alkyl. In certain embodiments, at least one instance of R$^{B3}$ is C$_{1-6}$ alkyl. In certain embodiments, at least one instance of R$^{B3}$ is methyl. In certain embodiments, at least one instance of R$^{B3}$ is ethyl. In certain embodiments, at least one instance of R$^{B3}$ is propyl. In certain embodiments, at least one instance of R$^{B3}$ is butyl. In certain embodiments, at least one instance of R$^{B3}$ is substituted alkenyl. In certain embodiments, at least one instance of R$^{B3}$ is unsubstituted alkenyl. In certain embodiments, at least one instance of R$^{B3}$ is vinyl. In certain embodiments, at least one instance of R$^{B3}$ is substituted alkynyl. In certain embodiments, at least one instance of R$^{B3}$ is unsubstituted alkynyl. In certain embodiments, at least one instance of R$^{B3}$ is ethynyl. In certain embodiments, at least one instance of R$^{B3}$ is substituted carbocyclyl. In certain embodiments, at least one instance of R$^{B3}$ is unsubstituted carbocyclyl. In certain embodiments, at least one instance of R$^{B3}$ is substituted heterocyclyl. In certain embodiments, at least one instance of R$^{B3}$ is unsubstituted heterocyclyl. In certain embodiments, at least one instance of R$^{B3}$ is substituted aryl. In certain embodiments, at least one instance of R$^{B3}$ is unsubstituted aryl. In certain embodiments, at least one instance of R$^{B3}$ is substituted phenyl. In certain embodiments, at least one instance of R$^{B3}$ is unsubstituted phenyl. In certain embodiments, at least one instance of R$^{B3}$ is substituted heteroaryl. In certain embodiments, at least one instance of R$^{B3}$ is unsubstituted heteroaryl. In certain embodiments, at least one instance of R$^{B3}$ is substituted pyridyl. In certain embodiments, at least one instance of R$^{B3}$ is unsubstituted pyridyl. In certain embodiments, at least one instance of R$^{B3}$ is —CN. In certain embodiments, at least one instance of R$^{B3}$ is —OR$^{B3a}$. In certain embodiments, at least one instance of R$^{B3}$ is —N(R$^{B3a}$)$_2$. In certain embodiments, at least one instance of R$^{B3}$ is —SR$^{B3a}$.

In certain embodiments, when R$^{B3}$ is —OR$^{B3a}$, —N(R$^{B3a}$)$_2$, or —SR$^{B3a}$, R$^{B3a}$ is H. In certain embodiments, R$^{B3a}$ is halogen. In certain embodiments, R$^{B3a}$ is F. In certain embodiments, R$^{B3a}$ is Cl. In certain embodiments, R$^{B3a}$ is Br. In certain embodiments, R$^{B3a}$ is I (iodine). In certain embodiments, R$^{B3a}$ is substituted acyl. In certain embodiments, R$^{B3a}$ is unsubstituted acyl. In certain embodiments, R$^{B3a}$ is acetyl. In certain embodiments, R$^{B3a}$ is substituted acetyl. In certain embodiments, R$^{B3a}$ is substituted alkyl. In certain embodiments, R$^{B3a}$ is unsubstituted alkyl. In certain embodiments, R$^{B3a}$ is C$_{1-6}$ alkyl. In certain embodiments, R$^{B3a}$ is methyl. In certain embodiments, R$^{B3a}$ is ethyl. In certain embodiments, R$^{B3a}$ is propyl. In certain embodiments, R$^{B3a}$ is butyl. In certain embodiments, R$^{B3a}$ is substituted alkenyl. In certain embodiments, R$^{B3a}$ is unsubstituted alkenyl. In certain embodiments, R$^{B3a}$ is vinyl. In certain embodiments, R$^{B3a}$ is substituted alkynyl. In certain embodiments, R$^{B3a}$ is unsubstituted alkynyl. In certain embodiments, R$^{B3a}$ is ethynyl. In certain embodiments, R$^{B3a}$ is substituted carbocyclyl. In certain embodiments, R$^{B3a}$ is unsubstituted carbocyclyl. In certain embodiments, R$^{B3a}$ is substituted heterocyclyl. In certain embodiments, R$^{B3a}$ is unsubstituted heterocyclyl. In certain embodiments, R$^{B3a}$ is substituted aryl. In certain embodiments, R$^{B3a}$ is unsubstituted aryl. In certain embodiments, R$^{B3a}$ is substituted phenyl. In certain embodiments, R$^{B3a}$ is unsubstituted phenyl. In certain embodiments, R$^{B3a}$ is substituted heteroaryl. In certain embodiments, R$^{B3a}$ is unsubstituted heteroaryl. In certain embodiments, R$^{B3a}$ is substituted pyridyl. In certain embodiments, R$^{B3a}$ is unsubstituted pyridyl. In certain embodiments, R$^{B3a}$ is a nitrogen protecting group when attached to a nitrogen atom. In certain embodiments, R$^{B3a}$ is Bn, BOC, Cbz, Fmoc, trifluoroacetyl, triphenylmethyl, acetyl, acetyl, or Ts when attached to a nitrogen atom. In certain embodiments, R$^{B3a}$ is an oxygen protecting group when attached to an oxygen atom. In certain embodiments, R$^{B3a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, R$^{B3a}$ is a sulfur protecting group when attached to a sulfur atom.

In certain embodiments, $R^{B3a}$ is acetamidomethyl, t-Bu, 3-nitro-2-pyridine sulfenyl, 2-pyridine-sulfenyl, or triphenylmethyl when attached to a sulfur atom. In certain embodiments, two $R^{B3a}$ groups are joined to form a substituted heterocyclic ring. In certain embodiments, two $R^{B3a}$ groups are joined to form an unsubstituted heterocyclic ring.

In certain embodiments, q is 0. In certain embodiments, q is 1. In certain embodiments, q is 2. In certain embodiments, q is 3.

In compounds of Formula (I), $L^1$ is a divalent linker moiety connecting Ring B and Ring C. $L^1$ may be an optionally substituted $C_{1-4}$ hydrocarbon chain, optionally wherein one or more carbon units of the hydrocarbon chain is replaced with —O—, —S—, —NR$^{L1}$—, —S(=O)—, or —S(=O)$_2$—. In certain embodiments, $L^1$ is an optionally substituted $C_{1-2}$ hydrocarbon chain, optionally wherein one or two carbon units of the hydrocarbon chain is replaced with —O—, —S—, —NR$^{L1}$—, —S(=O)—, or —S(=O)$_2$—. In certain embodiments, $L^1$ is an optionally substituted $C_1$ hydrocarbon chain, optionally wherein the carbon unit of the hydrocarbon chain is replaced with —O—, —S—, —NR$^{L1}$—, —S(=O)—, or —S(=O)$_2$—. In certain embodiments, $L^1$ is —O—, —S—, —NR$^{L1}$—, —NR$^{L1}$C(R$^{L1a}$)$_2$—, —C(R$^{L1a}$)$_2$—NR$^{L1}$—, or —C(R$^{L1a}$)$_2$—, wherein: each instance of $R^{L1}$ is independently hydrogen or unsubstituted $C_{1-6}$ alkyl; and each instance of $R^{L1a}$ is independently hydrogen, halogen, substituted or unsubstituted $C_{1-6}$ alkyl, —CN, —OR$^{L1b}$, or —N(R$^{L1b}$)$_2$, wherein each instance of $R^{L1b}$ is independently hydrogen or substituted or unsubstituted $C_{1-6}$ alkyl. In certain embodiments, each instance of $R^{L1a}$ is independently hydrogen, halogen, —CN, —OR$^{L1b}$, —N(R$^{L1b}$)$_2$, unsubstituted $C_{1-6}$ alkyl, or $C_{1-6}$ alkyl substituted with one or more halogen, wherein each instance of $R^{L1b}$ is independently hydrogen, unsubstituted $C_{1-6}$ alkyl, or $C_{1-6}$ alkyl substituted with one or more halogen. In certain embodiments, $L^1$ is —O—. In certain embodiments, $L^1$ is —S—. In certain embodiments, $L^1$ is —NR$^{L1}$—. In certain embodiments, $L^1$ is —CH$_2$—. In certain embodiments, $L^1$ is of the formula: —C(=O)NR$^{L1}$— or —NR$^{L1}$C(=O)—. In certain embodiments, $L^1$ is of the formula: —C(=O)NH— or —NH(=O)—. In certain embodiments, $L^1$ is an optionally substituted $C_3$ hydrocarbon chain, optionally wherein one or more carbon units of the hydrocarbon chain is replaced with —O—, —S—, —NR$^{L1}$—, —S(=O)—, or —S(=O)$_2$—. In certain embodiments, $L^1$ is an optionally substituted $C_4$ hydrocarbon chain, optionally wherein one or more carbon units of the hydrocarbon chain is replaced with —O—, —S—, —NR$^{L1}$—, —S(=O)—, or —S(=O)$_2$—. In certain embodiments, at least one carbon unit of the $C_{1-4}$ hydrocarbon chain is substituted with one or more substituents independently selected from the group consisting of halogen, unsubstituted $C_{1-6}$ alkyl, $C_{1-6}$ alkyl substituted with at least one instance of halogen, and oxo (=O). In certain embodiments, two substituents on the optionally substituted $C_{1-4}$ hydrocarbon chain are taken together to form an unsubstituted carbocyclic ring. In certain embodiments, two substituents on the optionally substituted $C_{1-4}$ hydrocarbon chain are taken together to form a substituted carbocyclic ring. In certain embodiments, two substituents on the optionally substituted $C_{1-4}$ hydrocarbon chain are taken together to form an unsubstituted heterocyclic ring. In certain embodiments, two substituents on the optionally substituted $C_{1-4}$ hydrocarbon chain are taken together to form a substituted heterocyclic ring.

In certain embodiments, $R^{L1}$ is H. In certain embodiments, $R^{L1}$ is substituted alkyl. In certain embodiments, $R^{L1}$ is unsubstituted alkyl. In certain embodiments, $R^{L1}$ is substituted $C_{1-6}$ alkyl. In certain embodiments, $R^{L1}$ is unsubstituted $C_{1-6}$ alkyl. In certain embodiments, $R^{L1}$ is methyl. In certain embodiments, $R^{L1}$ is ethyl. In certain embodiments, $R^{L1}$ is propyl. In certain embodiments, $R^{L1}$ is butyl. In certain embodiments, $R^{L1}$ is a nitrogen protecting group. In certain embodiments, $R^{L1}$ is Bn, BOC, Cbz, Fmoc, trifluoroacetyl, triphenylmethyl, acetyl, or Ts.

In compounds of Formula (I), $L^2$ is a divalent linker moiety connecting Ring B and Ring C. $L^2$ may be an optionally substituted $C_{1-4}$ hydrocarbon chain, optionally wherein one or more carbon units of the hydrocarbon chain is replaced with —O—, —S—, —NR$^{L2}$—, —S(=O)—, or —S(=O)$_2$—. In certain embodiments, $L^2$ is an optionally substituted $C_{1-2}$ hydrocarbon chain, optionally wherein one or two carbon units of the hydrocarbon chain is replaced with —O—, —S—, —NR$^{L2}$—, —S(=O)—, or —S(=O)$_2$—. In certain embodiments, $L^2$ is —NR$^{L2}$C(=O)—, —C(=O)NR$^{L2}$—, —NR$^{L2}$—, —S(=O)$_2$—, —S(=O)$_2$NR$^{L2}$—, —NR$^{L2}$(C$_{1-2}$ alkylene)-, or —(C$_{1-2}$ alkylene)NR$^{L2}$—, wherein the $C_{1-2}$ alkylene is optionally substituted with 1 to 4 substituents independently selected from the group consisting of halogen, =O, —CN, —OR$^{L2}$, —N(R$^{L2}$)$_2$, —C(=O)N(R$^{L2}$)$_2$, —C(=O)OR$^{L2}$, or substituted or unsubstituted $C_{1-6}$ alkyl, wherein each instance of $R^{L2}$ is independently hydrogen or substituted or unsubstituted $C_{1-6}$ alkyl. In certain embodiments, the $C_{1-2}$ alkylene is optionally substituted with 1 to 4 substituents independently selected from the group consisting of halogen, =O, —CN, —OR$^{L2}$, —N(R$^{L2}$)$_2$, —C(=O)N(R$^{L2}$)$_2$, —C(=O)OR$^{L2}$, unsubstituted $C_{1-6}$ alkyl, or $C_{1-6}$ alkyl substituted with one or more substituents independently selected from the group consisting of halogen, —CN, —OR$^{L2a}$, or —N(R$^{L2a}$)$_2$, wherein each instance of $R^{L2}$ and $R^{L2a}$ is independently hydrogen, unsubstituted $C_{1-6}$ alkyl, or $C_{1-6}$ alkyl substituted with one or more halogen. In certain embodiments, $L^2$ is —NR$^{L2}$C(=O)—, —C(=O)NR$^{L2}$—, —NR$^{L2}$S(=O)$_2$—, —S(=O)$_2$NR$^{L2}$—, —NR$^{L2}$(C$_{1-2}$ alkylene)-(e.g., —NR$^{L2}$—CH$_2$— (e.g., —NH—CH$_2$—, —NMe-CH$_2$—, or —N(Boc)-CH$_2$—) or —NR$^{L2}$—CH(substituted or unsubstituted $C_{1-6}$ alkyl)-(e.g., —NH—CH(CF$_3$)—), —(C$_{1-2}$ alkylene)NR$^{L2}$— (e.g., —CH$_2$—NR$^{L2}$— (e.g., —CH$_2$—NH—, —CH$_2$—NMe-, or —CH$_2$—N(Boc)-) or —CH(substituted or unsubstituted $C_{1-6}$ alkyl)-NR$^{L2}$— (e.g., —CH(CF$_3$)—NH—), —NR$^{L2}$— (e.g., —NH—), —O(C$_{1-2}$ alkylene)-(e.g., —O—CH$_2$—), or —(C$_{1-2}$ alkylene)O— (e.g., —CH$_2$—O—), wherein the $C_{1-2}$ alkylene is optionally substituted with 1 to 4 substituents independently selected from the group consisting of halogen, =O, —CN, —OR$^{L2}$, —N(R$^{L2}$)$_2$, —C(=O)N(R$^{L2}$)$_2$, —C(=O)OR$^{L2}$, or substituted or unsubstituted $C_{1-6}$ alkyl, wherein each instance of $R^{L2}$ is independently hydrogen, substituted or unsubstituted $C_{1-6}$ alkyl, or a nitrogen protecting group (e.g., Bn, BOC, Cbz, Fmoc, trifluoroacetyl, triphenylmethyl, acetyl, or Ts). In certain embodiments, $L^2$ is —NHC(=O)—, —C(=O)NH—, —NHS(=O)$_2$—, —N(C(O)OC(CH$_3$)$_3$)—, —N(Boc)-CH$_2$—, —NH—, —NHCH$_2$—, —NMeCH$_2$—, —OCH$_2$—, or —NHCH(CF$_3$)—. In certain embodiments, $L^2$ is an optionally substituted $C_1$ hydrocarbon chain, optionally wherein the carbon unit of the hydrocarbon chain is replaced with —O—, —S—, —NR$^{L2}$—, —S(=O)—, or —S(=O)$_2$—. In certain embodiments, $L^2$ is —O—, —S—, —NR$^{L2}$—, —NR$^{L2}$—C(R$^{L2a}$)$_2$—, —C(R$^{L2a}$)$_2$—NR$^{L2}$—, or —C(R$^{L2a}$)$_2$—, wherein: each instance of $R^{L2}$ is independently hydrogen or unsubstituted $C_{1-6}$ alkyl; and each instance of $R^{L2a}$ is independently hydrogen, halogen, substituted or unsubstituted $C_{1-6}$ alkyl, —CN, —OR$^{L2b}$, or —N(R$^{L2b}$)$_2$, wherein each instance of $R^{L2b}$ is independently hydrogen or substituted or unsubstituted $C_{1-6}$ alkyl. In certain embodiments, each instance of $R^{L2a}$ is independently hydrogen, halogen, —CN, —OR$^{L2b}$, —N(R$^{L2b}$)$_2$, unsubstituted $C_{1-6}$ alkyl, or $C_{1-6}$ alkyl substituted with one or more halogen, wherein each instance of $R^{L2b}$ is independently hydrogen, unsubstituted $C_{1-6}$ alkyl, or $C_{1-6}$ alkyl substituted with one or more halogen. In certain embodiments, $L^2$ is —O—. In certain embodiments, $L^2$ is —S—. In certain embodiments, $L^2$ is —NR$^{L2}$— (e.g., —NH— or —N(Me)-). In certain embodiments, $L^2$ is —CH$_2$—. In certain embodiments, $L^2$ is of the formula: —C(=O)NR$^{L2}$— or —NR$^{L2}$C(=O)—. In certain embodiments, $L^2$ is of the formula: —C(=O)NH— or —NH(=O)—. In certain embodiments, $L^2$ is an optionally substituted $C_3$ hydrocarbon chain, optionally wherein one or more carbon units of the hydrocarbon chain is replaced with —O—, —S—, —NR—, —S(=O)—, or —S(=O)$_2$—. In certain embodiments, $L^2$ is an optionally substituted $C_4$ hydrocarbon chain, optionally wherein one or more carbon units of the hydrocarbon chain is replaced with —O—, —S—, —NR$^{L2}$—, —S(=O)—, or —S(=O)$_2$—. In certain embodiments, at least one carbon unit of the $C_{1-4}$ hydrocarbon chain is substituted with one or more substituents independently selected from the group consisting of halogen, unsubstituted $C_{1-6}$ alkyl, $C_{1-6}$ alkyl substituted with at least one instance of halogen, and oxo (=O). In certain embodiments, two substituents on the optionally substituted $C_{1-4}$ hydrocarbon chain are taken together to form an unsubstituted carbocyclic ring. In certain embodiments, two substituents on the optionally substituted $C_{1-4}$ hydrocarbon chain are taken together to form a substituted carbocyclic ring. In certain embodiments, two substituents on the optionally substituted $C_{1-4}$ hydrocarbon chain are taken together to form an unsubstituted heterocyclic ring. In certain embodiments, two substituents on the optionally substituted $C_{1-4}$ hydrocarbon chain are taken together to form a substituted heterocyclic ring.

In certain embodiments, $R^{L2}$ is H. In certain embodiments, $R^{L2}$ is substituted alkyl. In certain embodiments, $R^{L2}$ is unsubstituted alkyl. In certain embodiments, $R^{L2}$ is substituted $C_{1-6}$ alkyl. In certain embodiments, $R^{L2}$ is unsubstituted $C_{1-6}$ alkyl. In certain embodiments, $R^{L2}$ is methyl. In certain embodiments, $R^{L2}$ is ethyl. In certain embodiments, $R^{L2}$ is propyl. In certain embodiments, $R^{L2}$ is butyl. In certain embodiments, $R^{L2}$ is a nitrogen protecting group. In certain embodiments, $R^{L2}$ is Bn, BOC, Cbz, Fmoc, trifluoroacetyl, triphenylmethyl, acetyl, or Ts.

In compounds of Formula (I), Ring C is an optionally substituted cyclohexylene moiety. In certain embodiments, Ring C is an optionally substituted trans-cyclohexylene moiety. In certain embodiments, Ring C is an optionally substituted cis-cyclohexylene moiety. In certain embodiments, Ring C is an optionally substituted 1,2-cyclohexylene moiety. In certain embodiments, Ring C is an optionally substituted 1,3-cyclohexylene moiety. In certain embodiments, Ring C is an optionally substituted 1,4-cyclohexylene moiety. In certain embodiments, Ring C is of the formula:

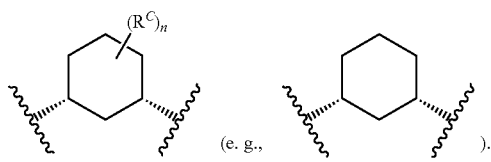
(e.g., ).

In certain embodiments, Ring C is of the formula:

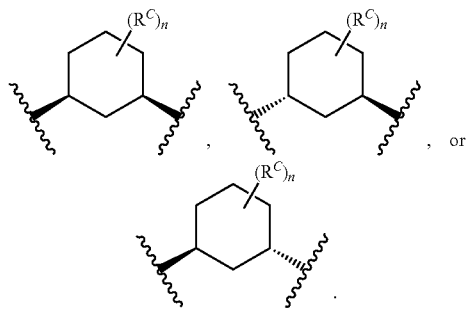

In certain embodiments, Ring C is of the formula:

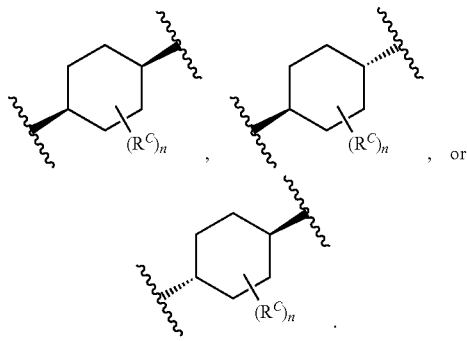

In certain embodiments, Ring C is of the formula:

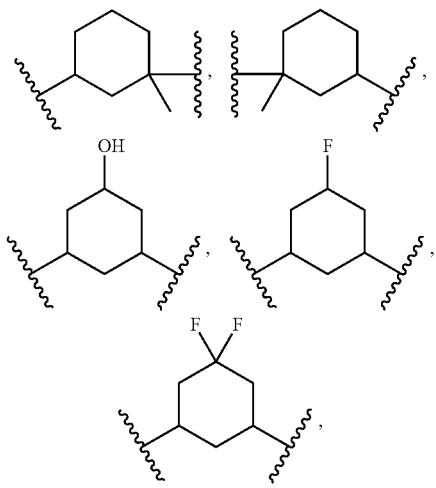

or a stereoisomeric form thereof. Ring C may be unsubstituted or may be substituted with one or more $R^C$ groups. In certain embodiments, at least one $R^C$ is H. In certain embodiments, at least one $R^C$ is halogen. In certain embodiments, at least one $R^C$ is F. In certain embodiments, at least one $R^C$ is Cl. In certain embodiments, at least one $R^C$ is Br. In certain embodiments, at least one $R^C$ is I (iodine). In certain embodiments, at least one $R^C$ is substituted acyl. In certain embodiments, at least one $R^C$ is unsubstituted acyl. In certain embodiments, at least one $R^C$ is acetyl. In certain embodiments, at least one $R^C$ is substituted acetyl. In certain embodiments, at least one $R^C$ is substituted alkyl. In certain embodiments, at least one $R^C$ is unsubstituted alkyl. In certain embodiments, at least one $R^C$ is $C_{1-6}$ alkyl. In certain embodiments, at least one $R^C$ is methyl. In certain embodiments, at least one $R^C$ is ethyl. In certain embodiments, at least one $R^C$ is propyl. In certain embodiments, at least one $R^C$ is butyl. In certain embodiments, at least one $R^C$ is substituted alkenyl. In certain embodiments, at least one $R^C$ is unsubstituted alkenyl. In certain embodiments, at least one $R^C$ is vinyl. In certain embodiments, at least one $R^C$ is substituted alkynyl. In certain embodiments, at least one $R^C$ is unsubstituted alkynyl. In certain embodiments, at least one $R^C$ is ethynyl. In certain embodiments, at least one $R^C$ is substituted carbocyclyl. In certain embodiments, at least one $R^C$ is unsubstituted carbocyclyl. In certain embodiments, at least one $R^C$ is substituted heterocyclyl. In certain embodiments, at least one $R^C$ is unsubstituted heterocyclyl. In certain embodiments, at least one $R^C$ is substituted aryl. In certain embodiments, at least one $R^C$ is unsubstituted aryl. In certain embodiments, at least one $R^C$ is substituted phenyl. In certain embodiments, at least one $R^C$ is unsubstituted phenyl. In certain embodiments, at least one $R^C$ is substituted heteroaryl. In certain embodiments, at least one $R^C$ is unsubstituted heteroaryl. In certain embodiments, at least one $R^C$ is substituted pyridyl. In certain embodiments, at least one $R^C$ is unsubstituted pyridyl. In certain embodiments, at least one $R^C$ is =O. In certain embodiments, at least one $R^C$ is —CN. In certain embodiments, at least one $R^C$ is —$OR^{C1}$. In certain embodiments, at least one $R^C$ is —$N(R^{C1})_2$. In certain embodiments, at least one $R^C$ is —$SR^{C1}$. In certain embodiments, each instance of $R^C$ is independently halogen, =O, —CN, —$OR^{C1}$, —$N(R^{C1})_2$, —C(=O)$N(R^{C1})_2$, —C(=O)$OR^{C1}$, or substituted or unsubstituted $C_{1-6}$ alkyl, wherein each instance of $R^{C1}$ is independently hydrogen or substituted or unsubstituted $C_{1-6}$ alkyl. In certain embodiments, each instance of $R^C$ is independently halogen, =O, —CN, —$OR^{C1}$, —$N(R^{C1})_2$, —C(=O)$N(R^{C1})_2$, —C(=O)$OR^{C1}$, unsubstituted $C_{1-6}$ alkyl, or $C_{1-6}$ alkyl substituted with one or more substituents independently selected from the group consisting of halogen, —CN, —$OR^{C1a}$, or —$N(R^{C1a})_2$, wherein each instance of $R^{C1}$ and $R^{C1a}$ is independently hydrogen, unsubstituted $C_{1-6}$ alkyl, or $C_{1-6}$ alkyl substituted with one or more halogen.

In certain embodiments, two instances of $R^C$ are joined to form a optionally substituted carbocyclic ring. In certain embodiments, two instances of $R^C$ are joined to form a optionally substituted heterocyclic ring. In certain embodiments, two instances of $R^C$ are joined to form a optionally substituted aryl ring (e.g., phenyl ring). In certain embodiments, two instances of $R^C$ are joined to form a optionally substituted heteroaryl ring. In certain embodiments, when two $R^C$ groups are taken together to form an optionally substituted, heterocyclic or carbocyclic ring, two substituents on the substituted heterocyclic ring or substituted carbocyclic ring, or one substituent on the substituted heterocyclic ring or substituted carbocyclic ring and a third $R^C$ group, are taken together to form another optionally substituted heterocyclic ring or optionally substituted carbocyclic ring. In certain embodiments, Ring C and all instances of $R^C$ are taken together to form an unsubstituted 7- to 10-membered bicyclic carbocyclic ring consisting of 0, 1, or 2 double bonds in the carbocyclic ring system. In certain embodiments, Ring C and all instances of $R^C$ are taken together to form unsubstituted bicyclo[3.1.1]heptanyl (e.g.,

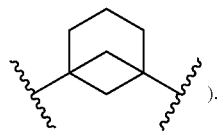 [SMILES: *C12CCCC(*)(C1)C2]).

In certain embodiments, Ring C and all instances of $R^C$ are taken together to form an unsubstituted 8- to 14-membered tricyclic carbocyclic ring consisting of 0, 1, 2, 3, or 4 double bonds in the carbocyclic ring system. In certain embodiments, Ring C and all instances of $R^C$ are taken together to form unsubstituted adamantyl (e.g.,

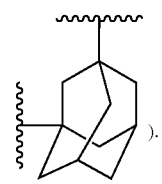).

In certain embodiments, each instance of $R^C$ is independently halogen, =O, —CN, —$OR^{C1}$, —$N(R^{C1})_2$, —C(=O)$N(R^{C1})_2$, —C(=O)$OR^{C1}$, or substituted or unsubstituted $C_{1-6}$ alkyl, wherein each instance of $R^{C1}$ is independently hydrogen or substituted or unsubstituted $C_{1-6}$ alkyl, or two $R^C$ groups are taken together to form an optionally substituted heterocyclic ring or optionally substituted carbocyclic ring, wherein two substituents on the substituted heterocyclic ring or substituted carbocyclic ring, or one substituent on the substituted heterocyclic ring or substituted carbocyclic ring and a third $R^C$ group, are taken together to form another optionally substituted heterocyclic ring or optionally substituted carbocyclic ring. In certain embodiments, each instance of $R^C$ is independently halogen, —$OR^{C1}$, or unsubstituted $C_{1-6}$ alkyl, wherein each instance of $R^{C1}$ is independently hydrogen or substituted or unsubstituted $C_{1-6}$ alkyl, or two $R^C$ groups are taken together to form an optionally substituted heterocyclic ring or optionally substituted carbocyclic ring, wherein two substituents on the substituted heterocyclic ring or substituted carbocyclic ring, or one substituent on the substituted heterocyclic ring or substituted carbocyclic ring and a third $R^C$ group, are taken together to form another optionally substituted heterocyclic ring or optionally substituted carbocyclic ring. In certain embodiments, each instance of $R^C$ is independently fluoro or —OH, or Ring C and all instances of $R^C$ are taken together to form:

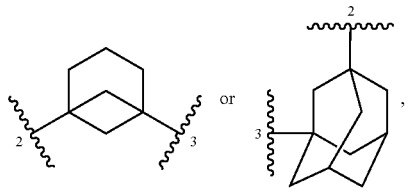 [SMILES: *C12CCCC(*)(C1)C2 ; *C12CC3CC(C1)CC(*)(C3)C2]

wherein the carbon atom labeled with "2" attaches to $L^1$ and the carbon atom labeled with "3" attaches to $L^2$.

In certain embodiments, when $R^C$ is —$OR^{C1}$, —$N(R^{C1})_2$, or —$SR^{C1}$, at least one $R^{C1}$ is H. In certain embodiments, at least one $R^{C1}$ is halogen. In certain embodiments, at least one $R^{C1}$ is F. In certain embodiments, at least one $R^{C1}$ is Cl.

In certain embodiments, at least one $R^{C1}$ is Br. In certain embodiments, at least one $R^{C1}$ is I (iodine). In certain embodiments, at least one $R^{C1}$ is substituted acyl. In certain embodiments, at least one $R^{C1}$ is unsubstituted acyl. In certain embodiments, at least one $R^{C1}$ is acetyl. In certain embodiments, at least one $R^{C1}$ is substituted acetyl. In certain embodiments, at least one $R^{C1}$ is substituted alkyl. In certain embodiments, at least one $R^{C1}$ is unsubstituted alkyl. In certain embodiments, at least one $R^{C1}$ is $C_{1-6}$ alkyl. In certain embodiments, at least one $R^{C1}$ is methyl. In certain embodiments, at least one $R^{C1}$ is ethyl. In certain embodiments, at least one $R^{C1}$ is propyl. In certain embodiments, at least one $R^{C1}$ is butyl. In certain embodiments, at least one $R^{C1}$ is substituted alkenyl. In certain embodiments, at least one $R^{C1}$ is unsubstituted alkenyl. In certain embodiments, at least one $R^{C1}$ is vinyl. In certain embodiments, at least one $R^{C1}$ is substituted alkynyl. In certain embodiments, at least one $R^{C1}$ is unsubstituted alkynyl. In certain embodiments, at least one $R^{C1}$ is ethynyl. In certain embodiments, at least one $R^{C1}$ is substituted carbocyclyl. In certain embodiments, at least one $R^{C1}$ is unsubstituted carbocyclyl. In certain embodiments, at least one $R^{C1}$ is substituted heterocyclyl. In certain embodiments, at least one $R^{C1}$ is unsubstituted heterocyclyl. In certain embodiments, at least one $R^{C1}$ is substituted aryl. In certain embodiments, at least one $R^{C1}$ is unsubstituted aryl. In certain embodiments, at least one $R^{C1}$ is substituted phenyl. In certain embodiments, at least one $R^{C1}$ is unsubstituted phenyl. In certain embodiments, at least one $R^{C1}$ is substituted heteroaryl. In certain embodiments, at least one $R^{C1}$ is unsubstituted heteroaryl. In certain embodiments, at least one $R^{C1}$ is substituted pyridyl. In certain embodiments, at least one $R^{C1}$ is unsubstituted pyridyl. In certain embodiments, at least one $R^{C1}$ is a nitrogen protecting group when attached to a nitrogen atom. In certain embodiments, at least one $R^{C1}$ is Bn, BOC, Cbz, Fmoc, trifluoroacetyl, triphenylmethyl, acetyl, or Ts when attached to a nitrogen atom. In certain embodiments, at least one $R^{C1}$ is an oxygen protecting group when attached to an oxygen atom. In certain embodiments, at least one $R^{C1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, at least one $R^{C1}$ is a sulfur protecting group when attached to a sulfur atom. In certain embodiments, at least one $R^{C1}$ is acetamidomethyl, t-Bu, 3-nitro-2-pyridine sulfenyl, 2-pyridine-sulfenyl, or triphenylmethyl when attached to a sulfur atom. In certain embodiments, two $R^{C1}$ groups are joined to form a substituted heterocyclic ring. In certain embodiments, two $R^{C1}$ groups are joined to form an unsubstituted heterocyclic ring.

Ring C may be unsubstituted or substituted with one or more $R^C$ groups. In certain embodiments, Ring C is unsubstituted, and thus n is 0. In certain embodiments, n is 1. In certain embodiments, n is 2. In certain embodiments, n is 3. In certain embodiments, n is 4. In certain embodiments, n is 5. In certain embodiments, n is 6. In certain embodiments, n is 7. In certain embodiments, n is 8. In certain embodiments, n is 9. In certain embodiments, n is 10.

In compounds of Formula (I), Ring D is a substituted phenyl ring. Ring D is substituted with $R^E$ and may also be substituted with one or more $R^D$ groups. In certain embodiments, at least one $R^D$ is H. In certain embodiments, at least one $R^D$ is halogen. In certain embodiments, at least one $R^D$ is F. In certain embodiments, at least one $R^D$ is Cl. In certain embodiments, at least one $R^D$ is Br. In certain embodiments, at least one $R^D$ is I (iodine). In certain embodiments, at least one $R^D$ is substituted acyl. In certain embodiments, at least one $R^D$ is unsubstituted acyl. In certain embodiments, at least one $R^D$ is acetyl. In certain embodiments, at least one $R^D$ is substituted acetyl. In certain embodiments, at least one $R^D$ is substituted alkyl. In certain embodiments, at least one $R^D$ is unsubstituted alkyl. In certain embodiments, at least one $R^D$ is $C_{1-6}$ alkyl. In certain embodiments, at least one $R^D$ is methyl. In certain embodiments, at least one $R^D$ is ethyl. In certain embodiments, at least one $R^D$ is propyl. In certain embodiments, at least one $R^D$ is butyl. In certain embodiments, at least one $R^D$ is substituted alkenyl. In certain embodiments, at least one $R^D$ is unsubstituted alkenyl. In certain embodiments, at least one $R^D$ is vinyl. In certain embodiments, at least one $R^D$ is substituted alkynyl. In certain embodiments, at least one $R^D$ is unsubstituted alkynyl. In certain embodiments, at least one $R^D$ is ethynyl. In certain embodiments, at least one $R^D$ is substituted carbocyclyl. In certain embodiments, at least one $R^D$ is unsubstituted carbocyclyl. In certain embodiments, at least one $R^D$ is substituted heterocyclyl. In certain embodiments, at least one $R^D$ is unsubstituted heterocyclyl. In certain embodiments, at least one instance of $R^D$ is substituted or unsubstituted, 5- to 6-membered monocyclic heterocyclyl consisting of 0, 1, or 2 double bonds in the heterocyclic ring system, wherein 1, 2, or 3 atoms in the heterocyclic ring system are independently nitrogen, oxygen, or sulfur. In certain embodiments, at least one instance of $R^D$ is morpholinyl (e.g.,

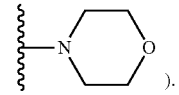 [SMILES: *N1CCOCC1]

).

In certain embodiments, each instance of $R^D$ is independently fluoro or morpholinyl. In certain embodiments, at least one $R^D$ is substituted aryl. In certain embodiments, at least one $R^D$ is unsubstituted aryl. In certain embodiments, at least one $R^D$ is substituted phenyl. In certain embodiments, at least one $R^D$ is unsubstituted phenyl. In certain embodiments, at least one $R^D$ is substituted heteroaryl. In certain embodiments, at least one $R^D$ is unsubstituted heteroaryl. In certain embodiments, at least one $R^D$ is substituted pyridyl. In certain embodiments, at least one $R^D$ is unsubstituted pyridyl. In certain embodiments, at least one $R^D$ is —CN. In certain embodiments, at least one $R^D$ is —$OR^D$. In certain embodiments, at least one $R^D$ is —$N(R^{D1})_2$. In certain embodiments, at least one $R^D$ is —$SR^{D1}$. In certain embodiments, each instance of $R^D$ is independently halogen, —CN, —$OR^{C1}$, —$N(R^{C1})_2$, —C(=O)N($R^{C1})_2$, —C(=O)O$R^{C1}$, substituted or unsubstituted $C_{1-6}$ alkyl, or substituted or unsubstituted heterocyclyl, wherein each instance of $R^{C1}$ is independently hydrogen or substituted or unsubstituted $C_{1-6}$ alkyl. In certain embodiments, each instance of $R^D$ is independently halogen or substituted or unsubstituted heterocyclyl.

In certain embodiments, when $R^D$ is —$OR^{D1}$, —$N(R^{D1})_2$, or —$SR^{D1}$, at least one $R^{D1}$ is H. In certain embodiments, at least one $R^{D1}$ is substituted acyl. In certain embodiments, at least one $R^{D1}$ is unsubstituted acyl. In certain embodiments, at least one $R^{D1}$ is acetyl. In certain embodiments, at least one $R^{D1}$ is substituted acetyl. In certain embodiments, at least one $R^{D1}$ is substituted alkyl. In certain embodiments, at least one $R^{D1}$ is unsubstituted alkyl. In certain embodiments, at least one $R^{D1}$ is $C_{1-6}$ alkyl. In certain embodiments, at least one $R^{D1}$ is methyl. In certain embodiments, at least one $R^{D1}$ is ethyl. In certain embodiments, at least one $R^{D1}$ is propyl. In certain embodiments, at least one $R^{D1}$ is butyl. In certain embodiments, at least one $R^{D1}$ is substituted alkenyl. In certain embodiments, at least one $R^{D1}$ is unsubstituted alkenyl. In certain embodiments, at least one $R^{D1}$ is vinyl. In certain embodiments, at least one $R^{D1}$ is substituted alkynyl. In certain embodiments, at least one $R^{D1}$ is unsubstituted alkynyl. In certain embodiments, at least one $R^{D1}$ is ethynyl. In certain embodiments, at least one $R^{D1}$ is substituted carbocyclyl. In certain embodiments, at least one $R^{D1}$ is unsubstituted carbocyclyl. In certain embodiments, at least one $R^{D1}$ is substituted heterocyclyl. In certain embodiments, at least one $R^{D1}$ is unsubstituted heterocyclyl. In certain embodiments, at least one $R^{D1}$ is substituted aryl. In certain embodiments, at least one $R^{D1}$ is unsubstituted aryl. In certain embodiments, at least one $R^{D1}$ is substituted phenyl. In certain embodiments, at least one $R^{D1}$ is unsubstituted phenyl. In certain embodiments, at least one $R^{D1}$ is substituted heteroaryl. In certain embodiments, at least one $R^{D1}$ is unsubstituted heteroaryl. In certain embodiments, at least one $R^{D1}$ is substituted pyridyl. In certain embodiments, at least one $R^{D1}$ is unsubstituted pyridyl. In certain embodiments, at least one $R^{D1}$ is a nitrogen protecting group when attached to a nitrogen atom. In certain embodiments, at least one $R^{D1}$ is Bn, BOC, Cbz, Fmoc, trifluoroacetyl, triphenylmethyl, acetyl, or Ts when attached to a nitrogen atom. In certain embodiments, $R^{D1}$ is an oxygen protecting group when attached to an oxygen atom. In certain embodiments, $R^{D1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D1}$ is a sulfur protecting group when attached to a sulfur atom. In certain embodiments, $R^{D1}$ is acetamidomethyl, t-Bu, 3-nitro-2-pyridine sulfenyl, 2-pyridine-sulfenyl, or triphenylmethyl when attached to a sulfur atom. In certain embodiments, two $R^D$ groups are joined to form a substituted heterocyclic ring. In certain embodiments, two $R^{D1}$ groups are joined to form an unsubstituted heterocyclic ring.

Ring D may be unsubstituted or substituted with one or more $R^D$ groups. In certain embodiments, Ring D is unsubstituted, and thus p is 0. In certain embodiments, p is 1. In certain embodiments, p is 2. In certain embodiments, p is 3. In certain embodiments, p is 4.

In certain embodiments, $R^D$ is halogen; and p is 1. In certain embodiments, $R^D$ is F; and p is 1. In certain embodiments, $R^D$ is Cl; and p is 1. In certain embodiments, $R^D$ is Br; and p is 1. In certain embodiments, $R^D$ is I (iodine); and p is 1. In certain embodiments, $R^D$ is substituted alkyl; and p is 1. In certain embodiments, $R^D$ is unsubstituted alkyl; and p is 1. In certain embodiments, $R^D$ is $C_{1-6}$ alkyl; and p is 1. In certain embodiments, $R^D$ is methyl; and p is 1. In certain embodiments, $R^D$ is ethyl, propyl, or butyl; and p is 1. In certain embodiments, each instance of $R^D$ is independently halogen or optionally substituted alkyl; and p is 2. In certain embodiments, each instance of $R^D$ is independently halogen or $C_{1-6}$ alkyl; and p is 2.

In compounds of Formula (I), Ring D also includes a substituent $R^E$. In certain embodiments, $R^E$ comprises a Michael acceptor moiety. This Michael acceptor moiety may react with a cysteine residue of a kinase (e.g., CDK (e.g., CDK7)) to allow covalent attachment of the compound to the kinase. In certain embodiments, the covalent attachment is irreversible. In other embodiments, the covalent attachment is reversible.

In certain embodiments, $R^E$ is of Formula (ii-1):

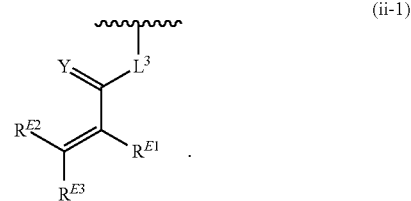

In certain embodiments, $R^E$ is of Formula (ii-2):

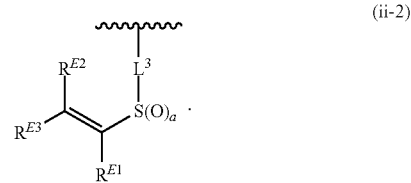

In certain embodiments, $R^E$ is of Formula (ii-3):

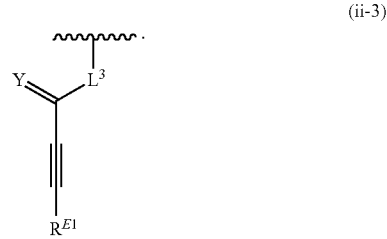

In certain embodiments, $R^E$ is of Formula (ii-4):

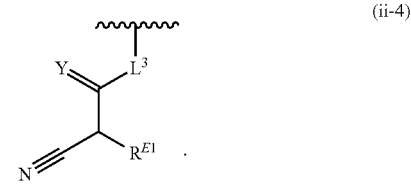

In certain embodiments, $R^E$ is of Formula (ii-5):

In certain embodiments, $R^E$ is of Formula (ii-6):

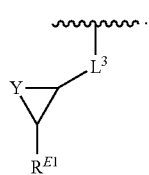

(ii-6)

In certain embodiments, $R^E$ is of Formula (ii-7):

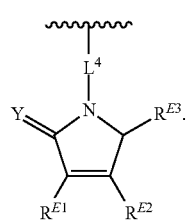

(ii-7)

In certain embodiments, $R^E$ is of Formula (ii-8):

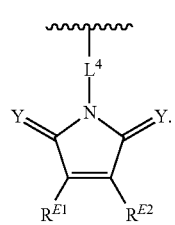

(ii-8)

In certain embodiments, $R^E$ is of Formula (ii-9):

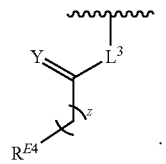

(ii-9)

In certain embodiments, $R^E$ is of Formula (ii-10):

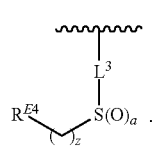

(ii-10)

In certain embodiments, $R^E$ is of Formula (ii-11):

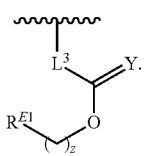

(ii-11)

In certain embodiments, $R^E$ is of Formula (ii-12):

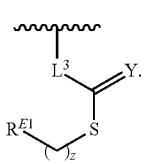

(ii-12)

In certain embodiments, $R^E$ is of Formula (ii-13):

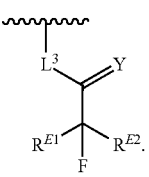

(ii-13)

In certain embodiments, $R^E$ is of Formula (ii-14):

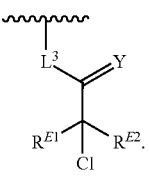

(ii-14)

In certain embodiments, $R^E$ is of Formula (ii-15):

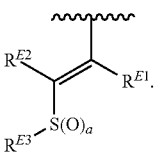

(ii-15)

In certain embodiments, $R^E$ is of Formula (ii-16):

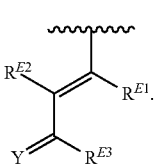

(ii-16)

In certain embodiments, $R^E$ is of Formula (ii-17):

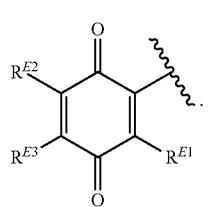
(ii-17)

In certain embodiments, $R^E$ is of Formula (ii-18):

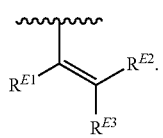
(ii-18)

In certain embodiments, $R^E$ is of Formula (ii-19):

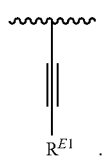
(ii-19)

In certain embodiments, $R^E$ is of Formula (ii-20):

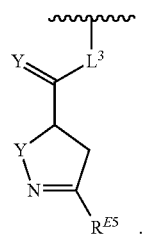
(ii-20)

In certain embodiments, $R^E$ is of Formula (ii-1) or (ii-3).

In certain embodiment, $R^E$ and $L^2$ are para or meta to each other. In certain embodiments, $R^E$ and $L^2$ are meta to each other. In certain embodiments, Ring D is of the formula:

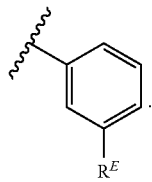

In certain embodiments, Ring D is of the formula:

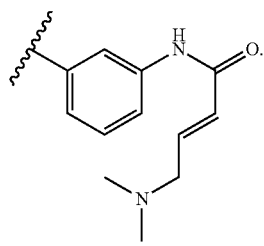 [SMILES: *c1cccc(NC(=O)/C=C/CN(C)C)c1]

In certain embodiments, Ring D is of the formula:

In certain embodiments, Ring D is of the formula:

In certain embodiments, Ring D is of the formula:

In certain embodiments, Ring D is of the formula:

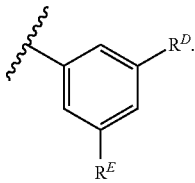

In certain embodiments, Ring D is of the formula:

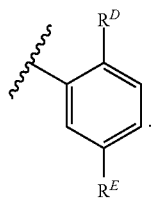

In certain embodiments, Ring D is of the formula:

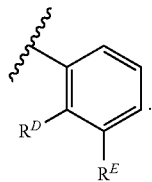

In certain embodiments, $R^E$ and $L^2$ are para to each other.
In certain embodiments, Ring D is of the formula:

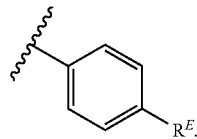

In certain embodiments, Ring D is of the formula:

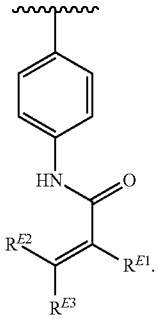

In certain embodiments, Ring D is of the formula:

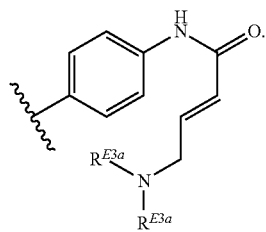

In certain embodiments, Ring D is of the formula:

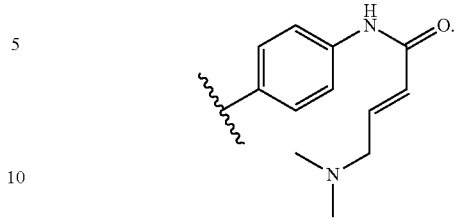

In certain embodiments, Ring D is of the formula:

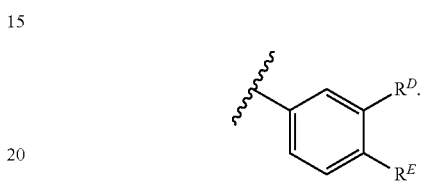

In certain embodiments, Ring D is of the formula:

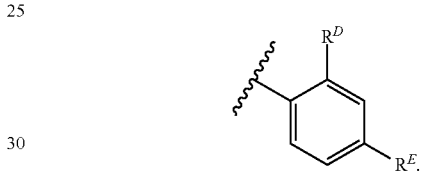

In compounds of Formula (I), $L^3$ is a divalent linker moiety. $L^3$ may contain 0-4 carbon or hetero atoms in the backbone of $L^3$. $L^3$ may be saturated or unsaturated. $L^3$ may be substituted or unsubstituted. $L^3$ may be branched or unbranched. In certain embodiments, $L^3$ is a bond. In certain embodiments, $L^3$ is —O—. In certain embodiments, $L^3$ is —S—. In certain embodiments, $L^3$ is —NR$^{L3a}$—. In certain embodiments, $L^3$ is —NH—. In certain embodiments, $L^3$ is a substituted $C_{1-4}$ hydrocarbon chain. In certain embodiments, $L^3$ is an unsubstituted $C_{1-4}$ hydrocarbon chain. In certain embodiments, $L^3$ is —C($R^{L3b}$)$_2$—. In certain embodiments, $L^3$ is —CHR$^{L3b}$—. In certain embodiments, $L^3$ is —CH$_2$—. In certain embodiments, $L^3$ is a substituted $C_2$ hydrocarbon chain. In certain embodiments, $L^3$ is an unsubstituted $C_2$ hydrocarbon chain. In certain embodiments, $L^3$ is —C($R^{L3b}$)$_2$C($R^{L3b}$)$_2$—. In certain embodiments, $L^3$ is —CH$_2$CH$_2$—. In certain embodiments, $L^3$ is trans-CR$^{L3b}$=CR$^{L3b}$—. In certain embodiments, $L^3$ is trans-CH=CH—. In certain embodiments, $L^3$ is cis-CR$^{L3b}$=CR$^{L3b}$—. In certain embodiments, $L^3$ is cis-CH=CH—. In certain embodiments, $L^3$ is —C≡C—. In certain embodiments, $L^3$ is a substituted $C_3$ hydrocarbon chain. In certain embodiments, $L^3$ is an unsubstituted $C_3$ hydrocarbon chain. In certain embodiments, $L^3$ is —(CH$_2$)$_3$—. In certain embodiments, $L^3$ is —CH=CH—CH$_2$—, wherein CH=CH is trans or cis. In certain embodiments, $L^3$ is —CH$_2$—CH=CH—, wherein CH=CH is trans or cis. In certain embodiments, $L^3$ is —C≡C—CH$_2$—. In certain embodiments, $L^3$ is —CH$_2$—C≡C—. In certain embodiments, $L^3$ is a substituted $C_4$ hydrocarbon chain. In certain embodiments, $L^3$ is an unsubstituted $C_4$ hydrocarbon chain. In certain embodiments, $L^3$ is —(CH$_2$)$_4$—. In certain embodiments, $L^3$ is —CH=CH—CH=CH—, wherein each instance of CH=CH is independently trans or cis. In certain embodiments, $L^3$ is —CH=CH—C≡C—, wherein CH=CH is trans or cis. In certain embodiments, $L^3$ is —C≡C—CH=CH—, wherein CH=CH is trans or cis. In certain embodiments, $L^3$ is —C≡C—C≡C—. In certain embodiments, $L^3$ is an optionally substituted C1A hydrocarbon chain, wherein one or more carbon units of the hydrocarbon chain is replaced with —O—, —S—, —NR$^{L3a}$—, —NR$^{L3a}$C(=)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)$_2$O—, —OS(=O)$_2$—, —S(=O)$_2$NR$^{L3a}$—, or —NR$^{L3a}$S(=O)$_2$—.

In certain embodiments, $R^{L3a}$ is H. In certain embodiments, $R^{L3a}$ is substituted alkyl. In certain embodiments, $R^{L3a}$ is unsubstituted alkyl. In certain embodiments, $R^{L3}$ is $C_{1-6}$ alkyl. In certain embodiments, $R^{L3a}$ is methyl. In certain embodiments, $R^{L3a}$ is ethyl. In certain embodiments, $R^{L3}$ is propyl. In certain embodiments, $R^{L3}$ is butyl. In certain embodiments, $R^{L3a}$ is a nitrogen protecting group. In certain embodiments, $R^{L3a}$ is Bn, BOC, Cbz, Fmoc, trifluoroacetyl, triphenylmethyl, acetyl, or Ts.

In certain embodiments, at least one $R^{L3b}$ is H. In certain embodiments, at least one $R^{L3b}$ is halogen. In certain embodiments, at least one $R^{L3b}$ is F. In certain embodiments, at least one $R^{L3b}$ is Cl. In certain embodiments, at least one $R^{L3b}$ is Br. In certain embodiments, at least one $R^{L3b}$ is I (iodine). In certain embodiments, at least one $R^{L3b}$ is substituted alkyl. In certain embodiments, at least one $R^{L3b}$ is unsubstituted alkyl. In certain embodiments, at least one $R^{L3b}$ is $C_{1-6}$ alkyl. In certain embodiments, at least one $R^{L3b}$ is methyl. In certain embodiments, at least one $R^{L3b}$ is ethyl. In certain embodiments, at least one $R^{L3b}$ is propyl. In certain embodiments, at least one $R^{L3b}$ is butyl. In certain embodiments, at least one $R^{L3b}$ is substituted alkenyl. In certain embodiments, at least one $R^{L3b}$ is unsubstituted alkenyl. In certain embodiments, at least one $R^{L3b}$ is vinyl. In certain embodiments, at least one $R^{L3b}$ is substituted alkynyl. In certain embodiments, at least one $R^{L3b}$ is unsubstituted alkynyl. In certain embodiments, at least one $R^{L3b}$ is ethynyl. In certain embodiments, at least one $R^{L3b}$ is substituted carbocyclyl. In certain embodiments, at least one $R^{L3b}$ is unsubstituted carbocyclyl. In certain embodiments, at least one $R^{L3b}$ is substituted heterocyclyl. In certain embodiments, at least one $R^{L3b}$ is unsubstituted heterocyclyl. In certain embodiments, at least one $R^{L3b}$ is substituted aryl. In certain embodiments, at least one $R^{L3b}$ is unsubstituted aryl. In certain embodiments, at least one $R^{L3b}$ is substituted phenyl. In certain embodiments, at least one $R^{L3b}$ is unsubstituted phenyl. In certain embodiments, at least one $R^{L3b}$ is substituted heteroaryl. In certain embodiments, at least one $R^{L3b}$ is unsubstituted heteroaryl. In certain embodiments, at least one $R^{L3b}$ is substituted pyridyl. In certain embodiments, at least one $R^{L3b}$ is unsubstituted pyridyl. In certain embodiments, two $R^{L3b}$ groups are joined to form a substituted carbocyclic ring. In certain embodiments, two $R^{L3b}$ groups are joined to form an unsubstituted carbocyclic ring. In certain embodiments, two $R^{L3b}$ groups are joined to form a substituted heterocyclic ring. In certain embodiments, two $R^{L3b}$ groups are joined to form an unsubstituted heterocyclic ring.

In compounds of Formula (I), $L^4$ is a divalent linker moiety. $L^4$ may contain 0-4 carbon or hetero atoms in the backbone of $L^4$. $L^4$ may be saturated or unsaturated. $L^4$ may be substituted or unsubstituted. $L^4$ may be branched or unbranched. In certain embodiments, $L^4$ is a bond. In certain embodiments, $L^4$ is a substituted $C_{1-4}$ hydrocarbon chain. In certain embodiments, $L^4$ is an unsubstituted $C_{1-4}$ hydrocarbon chain. In certain embodiments, $L^4$ is —C(R$^{L4b}$)$_2$—. In certain embodiments, $L^4$ is —CHR$^{L4b}$—. In certain embodiments, $L^4$ is —CH$_2$—. In certain embodiments, $L^4$ is a substituted $C_2$ hydrocarbon chain. In certain embodiments, $L^4$ is a unsubstituted $C_2$ hydrocarbon chain. In certain embodiments, $L^4$ is —C(R$^{L4b}$)$_2$C(R$^{L4b}$)$_2$—. In certain embodiments, $L^4$ is —CH$_2$CH$_2$—. In certain embodiments, $L^4$ is trans-CR$^{L4b}$=CR$^{L4b}$—. In certain embodiments, $L^4$ is trans-CH=CH—. In certain embodiments, $L^4$ is cis-CR$^{L4b}$=CR$^{L4b}$—. In certain embodiments, $L^4$ is cis-CH=CH—. In certain embodiments, $L^4$ is —C≡C—. In certain embodiments, $L^4$ is a substituted $C_3$ hydrocarbon chain. In certain embodiments, $L^4$ is an unsubstituted $C_3$ hydrocarbon chain. In certain embodiments, $L^4$ is —(CH$_2$)$_3$—. In certain embodiments, $L^4$ is —CH=CH—CH$_2$—, wherein CH=CH is trans or cis. In certain embodiments, $L^4$ is —CH$_2$—CH=CH—, wherein CH=CH is trans or cis. In certain embodiments, $L^4$ is —C≡C—CH$_2$—. In certain embodiments, $L^4$ is —CH$_2$—C≡C—. In certain embodiments, $L^4$ is a substituted $C_4$ hydrocarbon chain. In certain embodiments, $L^4$ is an unsubstituted $C_4$ hydrocarbon chain. In certain embodiments, $L^4$ is —(CH$_2$)$_4$—. In certain embodiments, $L^4$ is —CH=CH—CH=CH—, wherein each instance of CH=CH is independently trans or cis. In certain embodiments, $L^4$ is —CH=CH—C≡C—, wherein CH=CH is trans or cis. In certain embodiments, $L^4$ is —C≡C—CH=CH—, wherein CH=CH is trans or cis. In certain embodiments, $L^4$ is —C≡C—C≡C—.

In compounds of Formula (I), $R^E$ may include a substituent $R^{E1}$. In certain embodiments, $R^{E1}$ is H. In certain embodiments, $R^{E1}$ is halogen. In certain embodiments, $R^{E1}$ is F. In certain embodiments, $R^{E1}$ is Cl. In certain embodiments, $R^{E1}$ is Br. In certain embodiments, $R^{E1}$ is I (iodine). In certain embodiments, $R^{E1}$ is substituted acyl. In certain embodiments, $R^{E1}$ is unsubstituted acyl. In certain embodiments, $R^{E1}$ is acetyl. In certain embodiments, $R^{E1}$ is substituted acetyl. In certain embodiments, $R^{E1}$ is substituted alkyl. In certain embodiments, $R^E$ is unsubstituted alkyl. In certain embodiments, $R^{E1}$ is $C_{1-6}$ alkyl. In certain embodiments, $R^{E1}$ is methyl. In certain embodiments, $R^{E1}$ is ethyl. In certain embodiments, $R^{E1}$ is propyl. In certain embodiments, $R^{E1}$ is butyl. In certain embodiments, $R^{E1}$ is substituted alkenyl. In certain embodiments, $R^{E1}$ is unsubstituted alkenyl. In certain embodiments, $R^{E1}$ is vinyl. In certain embodiments, $R^{E1}$ is substituted alkynyl. In certain embodiments, $R^{E1}$ is unsubstituted alkynyl. In certain embodiments, $R^{E1}$ is ethynyl. In certain embodiments, $R^{E1}$ is substituted carbocyclyl. In certain embodiments, $R^{E1}$ is unsubstituted carbocyclyl. In certain embodiments, $R^{E1}$ is substituted heterocyclyl. In certain embodiments, $R^{E1}$ is unsubstituted heterocyclyl. In certain embodiments, $R^{E1}$ is substituted aryl. In certain embodiments, $R^{E1}$ is unsubstituted aryl. In certain embodiments, $R^{E1}$ is substituted phenyl. In certain embodiments, $R^{E1}$ is unsubstituted phenyl. In certain embodiments, $R^{E1}$ is substituted heteroaryl. In certain embodiments, $R^{E1}$ is unsubstituted heteroaryl. In certain embodiments, $R^{E1}$ is substituted pyridyl. In certain embodiments, $R^{E1}$ is unsubstituted pyridyl. In certain embodiments, $R^{E1}$ is —CN. In certain embodiments, $R^{E1}$ is —OR$^{E1a}$. In certain embodiments, $R^{E1}$ is —N(R$^{E1a}$)$_2$. In certain embodiments, $R^{E1}$ is —SR$^{E1a}$. In certain embodiments, $R^{E1}$ is —CH$_2$OR$^{E1a}$. In certain embodiments, $R^{E1}$ is —CH$_2$N(R$^{E1a}$)$_2$. In certain embodiments, $R^{E1}$ is —CH$_2$SR$^{E1a}$.

In certain embodiments, when $R^{E1}$ is —OR$^{E1a}$, —N(R$^{E1a}$)$_2$, —SR$^{E1a}$, —CH$_2$OR$^{E1a}$, —CH$_2$N(R$^{E1a}$)$_2$, or —CH$_2$SR$^{E1a}$, $R^{E1a}$ is H. In certain embodiments, $R^{E1}$ is —Si(R$^{E1a}$)$_3$, optionally wherein each instance of $R^{E1a}$ is independently unsubstituted $C_{1-6}$ alkyl or unsubstituted phenyl. In certain embodiments, $R^{E1}$ is —Si(Me)$_3$). In certain embodiments, $R^{E1a}$ is substituted acyl. In certain embodiments, $R^{E1a}$ is unsubstituted acyl. In certain embodiments, $R^{E1a}$ is acetyl. In certain embodiments, $R^{E1a}$ is substituted acetyl. In certain embodiments, $R^{E1a}$ is substituted alkyl. In certain embodiments, $R^{E1a}$ is unsubstituted alkyl. In certain embodiments, $R^{E1a}$ is $C_{1-6}$ alkyl. In certain embodiments, $R^{E1a}$ is methyl. In certain embodiments, $R^{E1a}$ is ethyl. In certain embodiments, $R^{E1a}$ is propyl. In certain embodiments, $R^{E1a}$ is butyl. In certain embodiments, $R^{E1a}$ is substituted alkenyl. In certain embodiments, $R^{E1a}$ is unsubstituted alkenyl. In certain embodiments, $R^{E1a}$ is vinyl. In certain embodiments, $R^{E1a}$ is substituted alkynyl. In certain embodiments, $R^{E1a}$ is unsubstituted alkynyl. In certain embodiments, $R^{E1a}$ is ethynyl. In certain embodiments, $R^{E1a}$ is substituted carbocyclyl. In certain embodiments, $R^{E1a}$ is unsubstituted carbocyclyl. In certain embodiments, $R^{E1a}$ is substituted heterocyclyl. In certain embodiments, $R^{E1a}$ is unsubstituted heterocyclyl. In certain embodiments, $R^{E1a}$ is substituted aryl. In certain embodiments, $R^{E1a}$ is unsubstituted aryl. In certain embodiments, $R^{E1a}$ is substituted phenyl. In certain embodiments, $R^{E1a}$ is unsubstituted phenyl. In certain embodiments, $R^{E1a}$ is substituted heteroaryl. In certain embodiments, $R^{E1a}$ is unsubstituted heteroaryl. In certain embodiments, $R^{E1a}$ is substituted pyridyl. In certain embodiments, $R^{E1a}$ is unsubstituted pyridyl. In certain embodiments, $R^{E1a}$ is a nitrogen protecting group when attached to a nitrogen atom. In certain embodiments, $R^{E1a}$ is Bn, BOC, Cbz, Fmoc, trifluoroacetyl, triphenylmethyl, acetyl, or Ts when attached to a nitrogen atom. In certain embodiments, $R^{E1a}$ is an oxygen protecting group when attached to an oxygen atom. In certain embodiments, $R^{E1a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{E1a}$ is a sulfur protecting group when attached to a sulfur atom. In certain embodiments, $R^{E1}a$ is acetamidomethyl, t-Bu, 3-nitro-2-pyridine sulfenyl, 2-pyridine-sulfenyl, or triphenylmethyl when attached to a sulfur atom. In certain embodiments, two $R^{E1a}$ groups are joined to form a substituted heterocyclic ring. In certain embodiments, two $R^{E1a}$ groups are joined to form an unsubstituted heterocyclic ring.

In compounds of Formula (I), $R^E$ may include a substituent $R^{E2}$. In certain embodiments, $R^{E2}$ is H. In certain embodiments, $R^{E2}$ is halogen. In certain embodiments, $R^{E2}$ is F. In certain embodiments, $R^{E2}$ is Cl. In certain embodiments, $R^{E2}$ is Br. In certain embodiments, $R^{E2}$ is I (iodine). In certain embodiments, $R^{E2}$ is substituted acyl. In certain embodiments, $R^{E2}$ is unsubstituted acyl. In certain embodiments, $R^{E2}$ is acetyl. In certain embodiments, $R^{E2}$ is substituted acetyl. In certain embodiments, $R^{E2}$ is substituted alkyl. In certain embodiments, $R^{E2}$ is unsubstituted alkyl. In certain embodiments, $R^{E2}$ is $C_{1-6}$ alkyl. In certain embodiments, $R^{E2}$ is methyl. In certain embodiments, $R^{E2}$ is ethyl. In certain embodiments, $R^{E2}$ is propyl. In certain embodiments, $R^{E2}$ is butyl. In certain embodiments, $R^{E2}$ is substituted alkenyl. In certain embodiments, $R^{E2}$ is unsubstituted alkenyl. In certain embodiments, $R^{E2}$ is vinyl. In certain embodiments, $R^{E2}$ is substituted alkynyl. In certain embodiments, $R^{E2}$ is unsubstituted alkynyl. In certain embodiments, $R^{E2}$ is ethynyl. In certain embodiments, $R^{E2}$ is substituted carbocyclyl. In certain embodiments, $R^{E2}$ is unsubstituted carbocyclyl. In certain embodiments, $R^{E2}$ is substituted heterocyclyl. In certain embodiments, $R^{E2}$ is unsubstituted heterocyclyl. In certain embodiments, $R^{E2}$ is substituted aryl. In certain embodiments, $R^{E2}$ is unsubstituted aryl. In certain embodiments, $R^{E2}$ is substituted phenyl. In certain embodiments, $R^{E2}$ is unsubstituted phenyl. In certain embodiments, $R^{E2}$ is substituted heteroaryl. In certain embodiments, $R^{E2}$ is unsubstituted heteroaryl. In certain embodiments, $R^{E2}$ is substituted pyridyl. In certain embodiments, $R^{E2}$ is unsubstituted pyridyl. In certain embodiments, $R^{E2}$ is —CN. In certain embodiments, $R^{E2}$ is —$OR^{E2a}$. In certain embodiments, $R^{E2}$ is —$N(R^{E2a})_2$. In certain embodiments, $R^{E2}$ is —$SR^{E2a}$. In certain embodiments, $R^{E2}$ is —$CH_2OR^{E2a}$. In certain embodiments, $R^{E2}$ is —$CH_2N(R^{E2a})_2$. In certain embodiments, $R^{E2}$ is —$CH_2SR^{E2a}$.

In certain embodiments, when $R^{E2}$ is —$OR^{E2a}$, —$N(R^{E2a})_2$, —$SR^{E2a}$, —$CH_2OR^{E2a}$, —$CH_2N(R^{E2a})_2$, or —$CH_2SR^{E2a}$, $R^{E2a}$ is H. In certain embodiments, $R^{E2a}$ is substituted acyl. In certain embodiments, $R^{E2a}$ is unsubstituted acyl. In certain embodiments, $R^{E2a}$ is acetyl. In certain embodiments, $R^{E2a}$ is substituted acetyl. In certain embodiments, $R^{E2a}$ is substituted alkyl. In certain embodiments, $R^{E2a}$ is unsubstituted alkyl. In certain embodiments, $R^{E2a}$ is $C_{1-6}$ alkyl. In certain embodiments, $R^{E2a}$ is methyl. In certain embodiments, $R^{E2a}$ is ethyl. In certain embodiments, $R^{E2a}$ is propyl. In certain embodiments, $R^{E2a}$ is butyl. In certain embodiments, $R^{E2a}$ is substituted alkenyl. In certain embodiments, $R^{E2a}$ is unsubstituted alkenyl. In certain embodiments, $R^{E2a}$ is vinyl. In certain embodiments, $R^{E2a}$ is substituted alkynyl. In certain embodiments, $R^{E2a}$ is unsubstituted alkynyl. In certain embodiments, $R^{E2a}$ is ethynyl. In certain embodiments, $R^{E2a}$ is substituted carbocyclyl. In certain embodiments, $R^{E2a}$ is unsubstituted carbocyclyl. In certain embodiments, $R^{E2a}$ is substituted heterocyclyl. In certain embodiments, $R^{E2a}$ is unsubstituted heterocyclyl. In certain embodiments, $R^{E2a}$ is substituted aryl. In certain embodiments, $R^{E2a}$ is unsubstituted aryl. In certain embodiments, $R^{E2a}$ is substituted phenyl. In certain embodiments, $R^{E2a}$ is unsubstituted phenyl. In certain embodiments, $R^{E2a}$ is substituted heteroaryl. In certain embodiments, $R^{E2a}$ is unsubstituted heteroaryl. In certain embodiments, $R^{E2a}$ is substituted pyridyl. In certain embodiments, $R^{E2a}$ is unsubstituted pyridyl. In certain embodiments, $R^{E2a}$ is a nitrogen protecting group when attached to a nitrogen atom. In certain embodiments, $R^{E2a}$ is Bn, BOC, Cbz, Fmoc, trifluoroacetyl, triphenylmethyl, acetyl, or Ts when attached to a nitrogen atom. In certain embodiments, $R^{E2a}$ is an oxygen protecting group when attached to an oxygen atom. In certain embodiments, $R^{E2a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{E2a}$ is a sulfur protecting group when attached to a sulfur atom. In certain embodiments, $R^{E2a}$ is acetamidomethyl, t-Bu, 3-nitro-2-pyridine sulfenyl, 2-pyridine-sulfenyl, or triphenylmethyl when attached to a sulfur atom. In certain embodiments, two $R^{E2a}$ groups are joined to form a substituted heterocyclic ring. In certain embodiments, two $R^{E2a}$ groups are joined to form an unsubstituted heterocyclic ring.

In compounds of Formula (I), $R^E$ may include a substituent $R^{E3}$. In certain embodiments, $R^{E3}$ is H. In certain embodiments, $R^{E3}$ is halogen. In certain embodiments, $R^{E3}$ is F. In certain embodiments, $R^{E3}$ is Cl. In certain embodiments, $R^{E3}$ is Br. In certain embodiments, $R^{E3}$ is I (iodine). In certain embodiments, $R^{E3}$ is substituted acyl. In certain embodiments, $R^{E3}$ is unsubstituted acyl. In certain embodiments, $R^{E3}$ is acetyl. In certain embodiments, $R^{E3}$ is substituted acetyl. In certain embodiments, $R^{E3}$ is substituted alkyl. In certain embodiments, $R^{E3}$ is unsubstituted alkyl. In certain embodiments, $R^{E3}$ is $C_{1-6}$ alkyl. In certain embodiments, $R^{E3}$ is methyl. In certain embodiments, $R^{E3}$ is ethyl. In certain embodiments, $R^{E3}$ is propyl. In certain embodiments, $R^{E3}$ is butyl. In certain embodiments, $R^{E3}$ is substituted alkenyl. In certain embodiments, $R^{E3}$ is unsubstituted alkenyl. In certain embodiments, $R^{E3}$ is vinyl. In certain embodiments, $R^{E3}$ is substituted alkynyl. In certain embodiments, $R^{E3}$ is unsubstituted alkynyl. In certain embodiments, $R^{E3}$ is ethynyl. In certain embodiments, $R^{E3}$ is substituted carbocyclyl. In certain embodiments, $R^{E3}$ is unsubstituted carbocyclyl. In certain embodiments, $R^{E3}$ is substituted heterocyclyl. In certain embodiments, $R^{E3}$ is unsubstituted heterocyclyl. In certain embodiments, $R^{E3}$ is substituted aryl. In certain embodiments, $R^{E3}$ is unsubstituted aryl. In certain embodiments, $R^{E3}$ is substituted phenyl. In certain embodiments, $R^{E3}$ is unsubstituted phenyl. In certain embodiments, $R^E$ is substituted heteroaryl. In certain embodiments, $R^{E3}$ is unsubstituted heteroaryl. In certain embodiments, $R^{E3}$ is substituted pyridyl. In certain embodiments, $R^{E3}$ is unsubstituted pyridyl. In certain embodiments, $R^{E3}$ is —CN. In certain embodiments, $R^{E3}$ is —$OR^{E3a}$. In certain embodiments, $R^{E3}$ is —$N(R^{E3a})_2$. In certain embodiments, $R^{E3}$ is —$SR^{E3a}$. In certain embodiments, $R^{E3}$ is —$CH_2OR^{E3a}$. In certain embodiments, $R^E$ is —$CH_2N(R^{E3a})_2$. In certain embodiments, $R^{E3}$ is —$CH_2SR^{E3a}$.

In certain embodiments, when $R^{E3}$ is —$OR^{E3a}$, —$N(R^{E3a})_2$, —$SR^{E3a}$, —$CH_2OR^{E3a}$, —$CH_2N(R^{E3a})_2$, or —$CH_2SR^{E3a}$, $R^{E3a}$ is H. In certain embodiments, $R^{E3a}$ is substituted acyl. In certain embodiments, $R^{E3a}$ is unsubstituted acyl. In certain embodiments, $R^{E3a}$ is acetyl. In certain embodiments, $R^{E3a}$ is substituted acetyl. In certain embodiments, $R^{E3a}$ is substituted alkyl. In certain embodiments, $R^{E3a}$ is unsubstituted alkyl. In certain embodiments, $R^{E3a}$ is $C_{1-6}$ alkyl. In certain embodiments, $R^{E3a}$ is methyl. In certain embodiments, $R^{E3a}$ is ethyl. In certain embodiments, $R^{E3a}$ is propyl. In certain embodiments, $R^{E3a}$ is butyl. In certain embodiments, $R^{E3a}$ is substituted alkenyl. In certain embodiments, $R^{E3a}$ is unsubstituted alkenyl. In certain embodiments, $R^{E3a}$ is vinyl. In certain embodiments, $R^{E3a}$ is substituted alkynyl. In certain embodiments, $R^{E3a}$ is unsubstituted alkynyl. In certain embodiments, $R^{E3a}$ is ethynyl. In certain embodiments, $R^{E3a}$ is substituted carbocyclyl. In certain embodiments, $R^{E3a}$ is unsubstituted carbocyclyl. In certain embodiments, $R^{E3a}$ is substituted heterocyclyl. In certain embodiments, $R^{E3a}$ is unsubstituted heterocyclyl. In certain embodiments, $R^{E3a}$ is substituted aryl. In certain embodiments, $R^{E3a}$ is unsubstituted aryl. In certain embodiments, $R^{E3a}$ is substituted phenyl. In certain embodiments, $R^{E3a}$ is unsubstituted phenyl. In certain embodiments, $R^{E3a}$ is substituted heteroaryl. In certain embodiments, $R^{E3a}$ is unsubstituted heteroaryl. In certain embodiments, $R^{E3a}$ is substituted pyridyl. In certain embodiments, $R^{E3a}$ is unsubstituted pyridyl. In certain embodiments, $R^{E3a}$ is a nitrogen protecting group when attached to a nitrogen atom. In certain embodiments, $R^{E3a}$ is Bn, BOC, Cbz, Fmoc, trifluoroacetyl, triphenylmethyl, acetyl, or Ts when attached to a nitrogen atom. In certain embodiments, $R^{E3a}$ is an oxygen protecting group when attached to an oxygen atom. In certain embodiments, $R^{E3a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{E3a}$ is a sulfur protecting group when attached to a sulfur atom. In certain embodiments, $R^{E3a}$ is acetamidomethyl, t-Bu, 3-nitro-2-pyridine sulfenyl, 2-pyridine-sulfenyl, or triphenylmethyl when attached to a sulfur atom. In certain embodiments, two $R^{E3a}$ groups are joined to form a substituted heterocyclic ring. In certain embodiments, two $R^{E3a}$ groups are joined to form an unsubstituted heterocyclic ring.

In compounds of Formula (I), $R^{E1}$ and $R^{E3}$, or $R^{E2}$ and $R^{E3}$, or $R^{E1}$ and $R^{E2}$ may be joined to form an optionally substituted carbocyclic or optionally substituted heterocyclic ring. In certain embodiments, $R^{E1}$ and $R^{E3}$ are joined to form an optionally substituted carbocyclic ring. In certain embodiments, $R^{E1}$ and $R^{E3}$ are joined to form an optionally substituted heterocyclic ring. In certain embodiments, $R^{E2}$ and $R^{E3}$ are joined to form an optionally substituted carbocyclic ring. In certain embodiments, $R^{E2}$ and $R^{E3}$ are joined to form an optionally substituted heterocyclic ring. In certain embodiments, $R^E$ and $R^{E2}$ are joined to form an optionally substituted carbocyclic ring. In certain embodiments, $R^{E1}$ and $R^{E2}$ are joined to form an optionally substituted heterocyclic ring.

In compounds of Formula (I), $R^E$ may include a substituent $R^{E4}$. In certain embodiments, $R^{E4}$ is a leaving group. In certain embodiments, $R^{E4}$ is halogen. In certain embodiments, $R^{E4}$ is F. In certain embodiments, $R^{E4}$ is Cl. In certain embodiments, $R^{E4}$ is Br. In certain embodiments, $R^{E4}$ is I (iodine). In certain embodiments, $R^{E4}$ is —$OS(=O)_wR^{E4a}$. In certain embodiments, w is 1. In certain embodiments, w is 2. In certain embodiments, $R^{E4}$ is —OMs. In certain embodiments, $R^{E4}$ is —OTf. In certain embodiments, $R^{E4}$ is —OTs. In certain embodiments, $R^{E4}$ is —OBs. In certain embodiments, $R^{E4}$ is 2-nitrobenzenesulfonyloxy. In certain embodiments, $R^{E4}$ is —$OR^{E4a}$. In certain embodiments, $R^{E4}$ is —OMe. In certain embodiments, $R^{E4}$ is —$OCF_3$. In certain embodiments, $R^{E4}$ is —OPh. In certain embodiments, $R^{E4}$ is —$OC(=O)R^{E4a}$. In certain embodiments, $R^{E4}$ is —OC(=O)Me. In certain embodiments, $R^{E4}$ is —$OC(=O)CF_3$. In certain embodiments, $R^{E4}$ is —OC(=O)Ph. In certain embodiments, $R^{E4}$ is —OC(=O)Cl. In certain embodiments, $R^{E4}$ is —$OC(=O)OR^{E4a}$. In certain embodiments, $R^{E4}$ is —OC(=O)OMe. In certain embodiments, $R^{E4}$ is —OC(=O)O(t-Bu).

In certain embodiments, $R^{E4a}$ is substituted alkyl. In certain embodiments, $R^{E4a}$ is unsubstituted alkyl. In certain embodiments, $R^{E4a}$ is $C_{1-6}$ alkyl. In certain embodiments, $R^{E4a}$ is methyl. In certain embodiments, $R^{E4a}$ is ethyl. In certain embodiments, $R^{E4a}$ is propyl. In certain embodiments, $R^{E4a}$ is butyl. In certain embodiments, $R^{E4a}$ is substituted alkenyl. In certain embodiments, $R^{E4a}$ is unsubstituted alkenyl. In certain embodiments, $R^{E4a}$ is vinyl. In certain embodiments, $R^{E4a}$ is substituted alkynyl. In certain embodiments, $R^{E4a}$ is unsubstituted alkynyl. In certain embodiments, $R^{E4a}$ is ethynyl. In certain embodiments, $R^{E4a}$ is substituted carbocyclyl. In certain embodiments, $R^{E4a}$ is unsubstituted carbocyclyl. In certain embodiments, $R^{E4a}$ is substituted heterocyclyl. In certain embodiments, $R^{E4a}$ is unsubstituted heterocyclyl. In certain embodiments, $R^{E4a}$ is substituted aryl. In certain embodiments, $R^{E4a}$ is unsubstituted aryl. In certain embodiments, $R^{E4a}$ is substituted phenyl. In certain embodiments, $R^{E4a}$ is unsubstituted phenyl. In certain embodiments, $R^{E4a}$ is substituted heteroaryl. In certain embodiments, $R^{E4a}$ is unsubstituted heteroaryl. In certain embodiments, $R^{E4a}$ is substituted pyridyl. In certain embodiments, $R^{E4a}$ is unsubstituted pyridyl.

In compounds of Formula (I), $R^E$ may include a Y group. In certain embodiments, Y is =O. In certain embodiments, Y is —O—. In certain embodiments, Y is =S. In certain embodiments, Y is —S—. In certain embodiments, Y is =$NR^{E6}$. In certain embodiments, Y is —$NR^{E6}$—. In certain embodiments, Y is =NH. In certain embodiments, Y is —NH—. In certain embodiments, $R^{E6}$ is H. In certain embodiments, $R^{E6}$ is substituted or unsubstituted $C_{1-6}$ alkyl (e.g., —$CH_3$). In certain embodiments, $R^{E6}$ is a nitrogen protecting group (e.g., Bn, BOC, Cbz, Fmoc, trifluoroacetyl, triphenylmethyl, acetyl, or Ts).

In compounds of Formula (I), $R^E$ may include a substituent $R^{E5}$, which is halogen. In certain embodiments, $R^{E5}$ is F, Cl, Br, or I (iodine).

In certain embodiments, a is 1. In certain embodiments, a is 2.

In certain embodiments, z is 0. In certain embodiments, z is 1. In certain embodiments, z is 2. In certain embodiments, z is 3. In certain embodiments, z is 4. In certain embodiments, z is 5. In certain embodiments, z is 6.

In certain embodiments, $R^E$ is of Formula (ii-1); and $R^{E1}$ is hydrogen. In certain embodiments, $R^E$ is of Formula (ii-1); and $R^{E2}$ is hydrogen. In certain embodiments, $R^E$ is of Formula (ii-1); and $R^{E3}$ is hydrogen. In certain embodiments, $R^E$ is of Formula (ii-1); and $R^{E2}$ and $R^{E3}$ are each hydrogen. In certain embodiments, $R^E$ is of Formula (ii-1); and $R^{E1}$, $R^{E2}$ and $R^{E3}$ are each hydrogen. In certain embodiments, $R^E$ is of Formula (ii-1); and $R^{E1}$ is —$CH_2N(R^{E1a})$. In certain embodiments, $R^E$ is of Formula (ii-1); $R^{E1}$ is —$CH_2N(R^{E1a})$; and $R^{E1a}$ is $C_{1-6}$ alkyl. In certain embodiments, $R^E$ is of Formula (ii-1); $R^{E1}$ is —$CH_2N(R^{E1a})$; and $R^{E1a}$ is methyl. In certain embodiments, $R^E$ is of Formula (ii-1); and $R^{E2}$ is —$CH_2N(R^{E2a})$. In certain embodiments, $R^E$ is of Formula (ii-1); $R^{E2}$ is —$CH_2N(R^{E2a})$; and $R^{E2a}$ is $C_{1-6}$ alkyl. In certain embodiments, $R^E$ is of Formula (ii-1); $R^{E2}$ is —$CH_2N(R^{E2a})$; and $R^{E2a}$ is methyl. In certain embodiments, $R^E$ is of Formula (ii-1); and $R^{E3}$ is —$CH_2N(R^{E3a})$. In certain embodiments, $R^E$ is of Formula (ii-1); $R^{E3}$ is —$CH_2N(R^{E3a})$; and $R^{E3a}$ is $C_{1-6}$ alkyl. In certain embodiments, $R^E$ is of Formula (ii-1); $R^{E3}$ is —$CH_2N(R^{E3a})$; and $R^{E3a}$ is methyl. In certain embodiments, $R^E$ is of Formula (ii-1); and Y is =O. In certain embodiments, $R^E$ is of Formula (ii-1); and $L^3$ is —$NR^{L3a}$—. In certain embodiments, $R^E$ is of Formula (ii-1); and $L^3$ is —NH—. In certain embodiments, $R^E$ is of the formula:

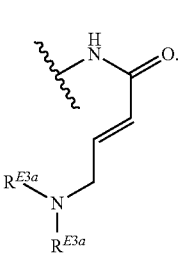

In certain embodiments, $R^E$ is of the formula:

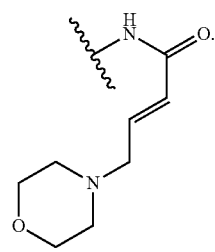

In certain embodiments, $R^E$ is of the formula:

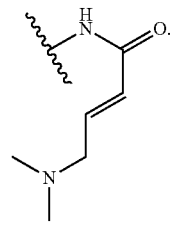 [SMILES: *NC(=O)/C=C/CN(C)C]

n certain embodiments, $R^E$ is of the formula:

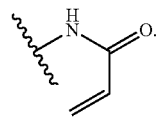

In certain embodiments, $R^E$ is of the formula:

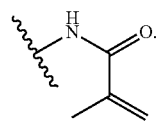

In certain embodiments, $R^E$ is of the formula:

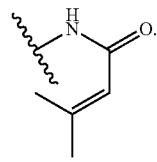 [SMILES: *NC(=O)C=C(C)C]

In certain embodiments, $R^E$ is of the formula:

In certain embodiments, $R^E$ is f the formula:

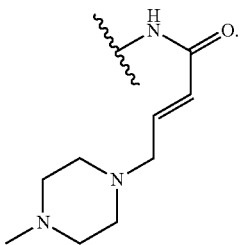 [SMILES: *NC(=O)/C=C/CN1CCN(C)CC1]

In certain embodiments, $R^E$ is of the formula:

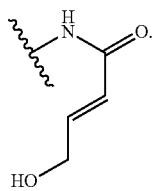 [SMILES: *NC(=O)/C=C/CO]

In certain embodiments, $R^E$ is of the formula:

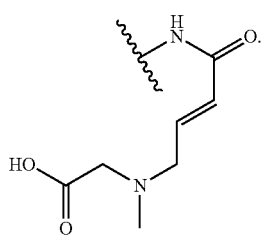 [SMILES: *NC(=O)/C=C/CN(C)CC(=O)O]

In certain embodiments, $R^E$ is of the formula:

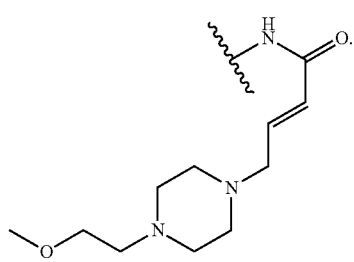 [SMILES: *NC(=O)/C=C/CN1CCN(CCOC)CC1]

In certain embodiments, $R^E$ is of the formula:

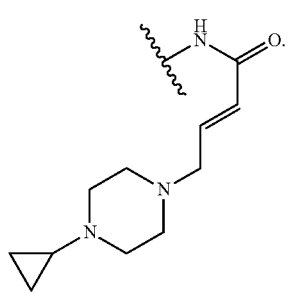 [SMILES: *NC(=O)/C=C/CN1CCN(C2CC2)CC1]

In certain embodiments, $R^E$ is of the formula:

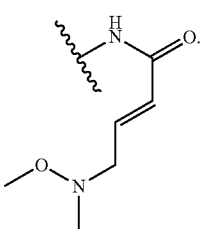 [SMILES: *NC(=O)/C=C/CN(C)OC]

In certain embodiments, $R^E$ is of the formula:

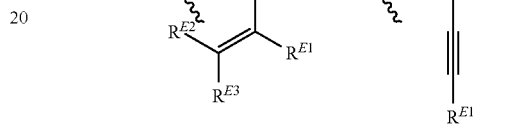

In certain embodiments, $R^E$ is of the formula:

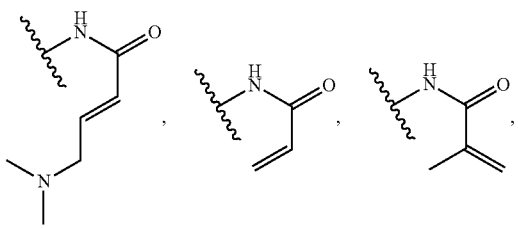

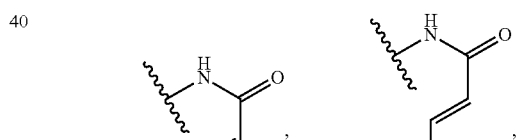

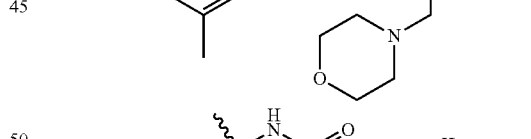

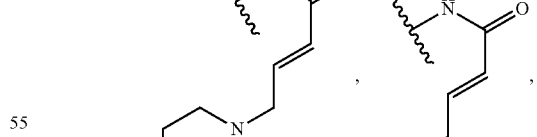

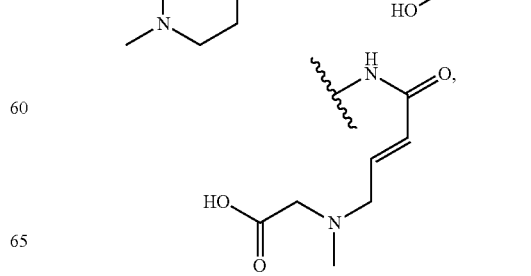

-continued

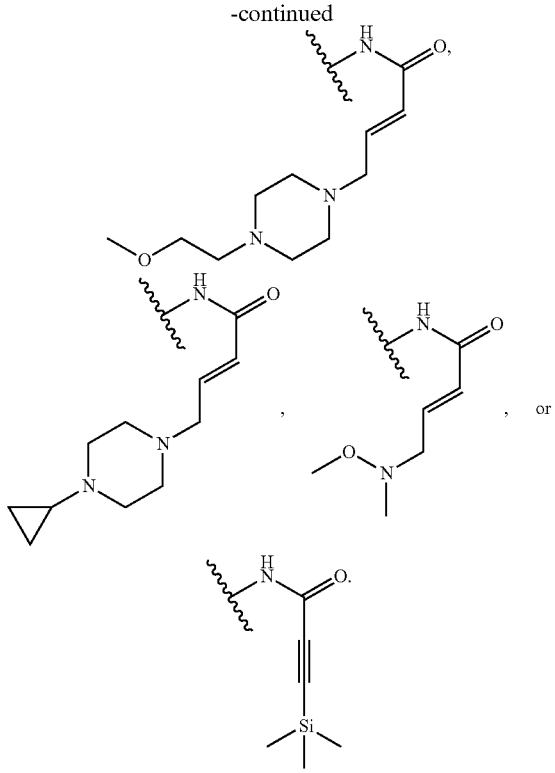

In certain embodiments, $R^E$ is of Formula (ii-3); and $R^{E1}$ is hydrogen. In certain embodiments, $R^E$ is of Formula (ii-3); and $R^{E1}$ is —CH$_2$N($R^{E1a}$). In certain embodiments, $R^E$ is of Formula (ii-3); and $R^{E1}$ is —Si($R^{E1a}$)$_3$ (e.g., —Si(Me)$_3$). In certain embodiments, $R^E$ is of Formula (ii-3); $R^{E1}$ is —CH$_2$N($R^{E1a}$); and $R^{E1a}$ is C$_{1-6}$ alkyl. In certain embodiments, $R^E$ is of Formula (ii-3); $R^{E1}$ is —H$_2$N($R^{E1a}$); and $R^{E1a}$ is methyl. In certain embodiments, $R^E$ is of Formula (ii-3); and Y is =O. In certain embodiments, $R^E$ is of Formula (ii-3); and $L^3$ is —NR$^{L3a}$—. In certain embodiments, $R^E$ is of Formula (ii-3); and $L^3$ is —NH—.

In certain embodiments, $R^E$ is of the formula:

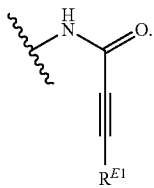

In certain embodiments, $R^E$ is of the formula:

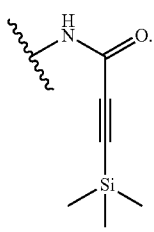 [SMILES: *NC(=O)C#C[Si](C)(C)C]

In certain embodiments, $R^E$ is not of the formula:

(ii-5)

In certain embodiments, the compound of Formula (I) is of Formula (Ia):

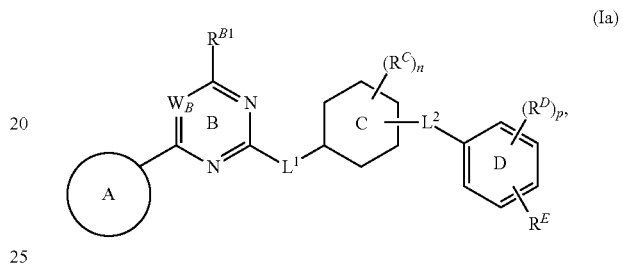

(Ia)

or a pharmaceutically acceptable salt, solvate, hydrate, polymorph, co-crystal, tautomer, stereoisomer, isotopically labeled derivative, or prodrug thereof, wherein:

Ring A is substituted or unsubstituted, 5- to 6-membered, monocyclic heteroaryl, or substituted or unsubstituted, 9- to 10-membered, bicyclic heteroaryl, wherein 1, 2, or 3 atoms in the heteroaryl ring system are independently oxygen, nitrogen, or sulfur;

$W_B$ is CR$^{B2}$, wherein $R^{B2}$ is halogen, substituted or unsubstituted carbocyclyl, or —CN;

$R^{B1}$ is hydrogen;

$L^1$ is —NR$^{L1}$—, wherein $R^{L1}$ is hydrogen or unsubstituted C$_{1-6}$ alkyl;

each instance of $R^C$ is independently halogen, —OR$^{C1}$, or substituted or unsubstituted C$_{1-6}$ alkyl, wherein each instance of $R^{C1}$ is independently hydrogen or substituted or unsubstituted C$_{1-6}$ alkyl, or two $R^C$ are taken together to form an optionally substituted heterocyclic ring or optionally substituted carbocyclic ring;

$L^2$ is —NR$^{L2}$C(=O)—, —C(=O)NR$^{L2}$—, —NR$^{L2}$(substituted or unsubstituted C$_{1-2}$ alkylene)-, or —NR$^{L2}$—, wherein each instance of $R^{L2}$ is independently hydrogen or substituted or unsubstituted C$_{1-6}$ alkyl;

each instance of $R^D$ is independently halogen;

$R^E$ is of the formula:

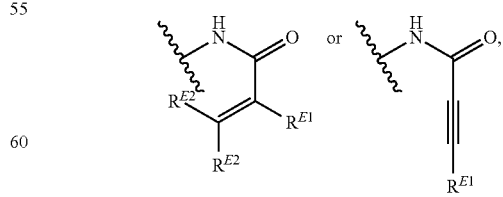

wherein $R^{E1}$, $R^{E2}$, and $R^{E3}$ are as described herein;
n is 0, 1, or 2; and
p is 0 or 1.

In certain embodiments, in Formula (Ia):
Ring A is of the formula:

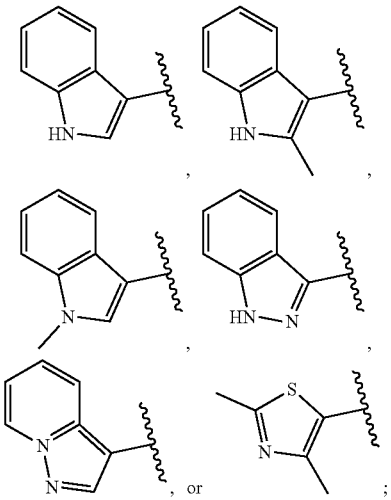

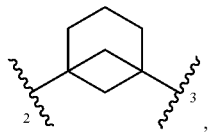

wherein the carbon atom labeled with "2" attaches to $L^1$ and the carbon atom labeled with "3" attaches to $L^2$. In certain embodiments, in Formula (Ia), n is 0, 1, or 2. In certain embodiments, in Formula (Ia), $L^2$ is —NHC(=O)—, —C(=O)NH—, —NH(C_{1-2} alkylene)-, or —NH—. In certain embodiments, in Formula (Ia), each instance of $R^D$ is independently fluoro. In certain embodiments, in Formula (Ia), p is 0 or 1. In certain embodiments, in Formula (Ia), $R^E$ is of the formula:

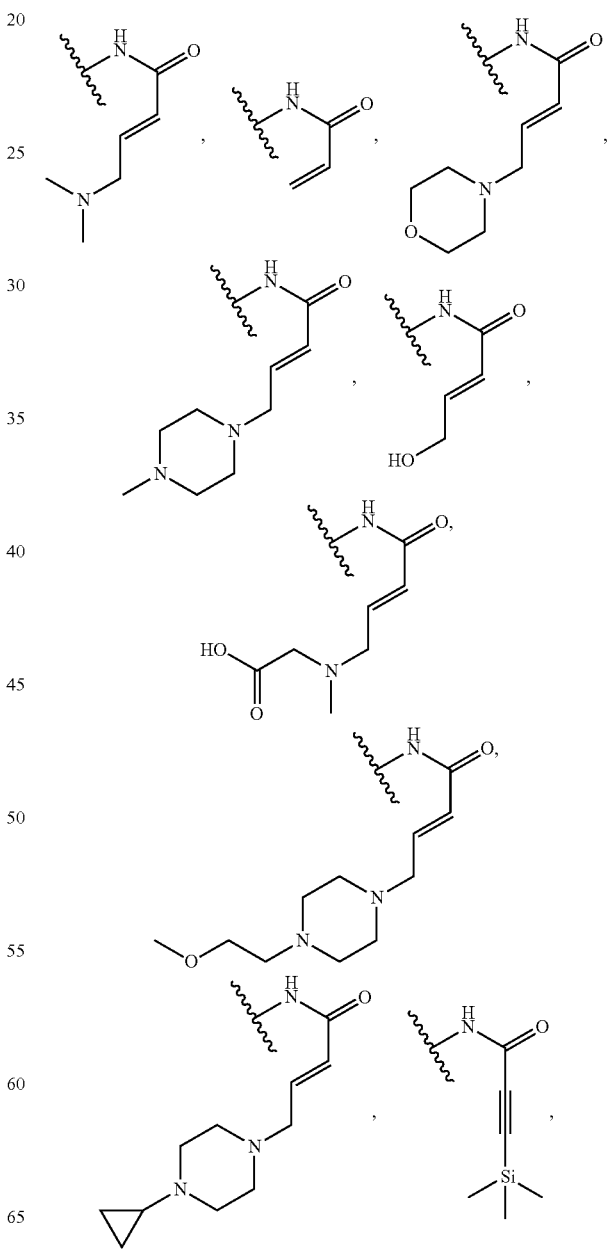

$W_B$ is $CR^{B2}$, wherein $R^{B2}$ is halogen, substituted or unsubstituted, 3- to 6-membered, monocyclic carbocyclyl consisting of 0, 1, or 2 double bonds in the carbocyclic ring system, or —CN;

$R^{B1}$ is hydrogen;

$L^1$ is —$NR^{L1}$—, wherein $R^{L1}$ is hydrogen or unsubstituted $C_{1-6}$ alkyl;

each instance of $R^C$ is independently halogen, —$OR^{C1}$, or substituted or unsubstituted $C_{1-6}$ alkyl, wherein each instance of $R^{C1}$ is independently hydrogen or substituted or unsubstituted $C_{1-6}$ alkyl, or two $R^C$ are taken together to form an optionally substituted carbocyclic ring;

$L^2$ is —$NR^{L2}C(=O)$—, —$C(=O)NR^{L2}$—, —$NR^{L2}$(substituted or unsubstituted $C_{1-2}$ alkylene)-, or —$NR^{L2}$—, wherein each instance of $R^{L2}$ is independently hydrogen or substituted or unsubstituted $C_{1-6}$ alkyl;

each instance of $R^D$ is independently halogen;

$R^E$ is of the formula:

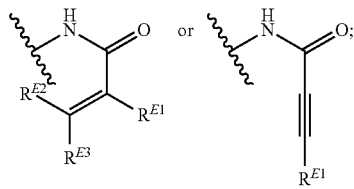

each instance of $R^{E1}$ is independently hydrogen, substituted or unsubstituted $C_{1-6}$ alkyl, or —$Si(R^{E1a})_3$, wherein each instance of $R^{E1a}$ is independently substituted or unsubstituted $C_{1-6}$ alkyl or substituted or unsubstituted phenyl;

$R^{E2}$ is hydrogen or substituted or unsubstituted $C_{1-6}$ alkyl;

$R^{E3}$ is hydrogen or substituted or unsubstituted $C_{1-6}$ alkyl;

n is 0, 1, or 2; and p is 0 or 1.

In certain embodiments, in Formula (Ia), $W_B$ is $CR^{B2}$ and $R^{B2}$ is chloro, cyclopropyl, or —CN. In certain embodiments, in Formula (Ia), $L^1$ is —NH—. In certain embodiments, in Formula (Ia), each instance of $R^C$ is independently fluoro, —OH, or —$CH_3$, or Ring C and all instances of $R^C$ are taken together to form

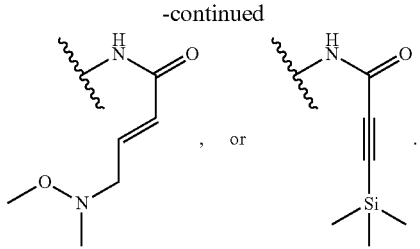

, or

In certain embodiments, the compound of Formula (I) is of the formula:

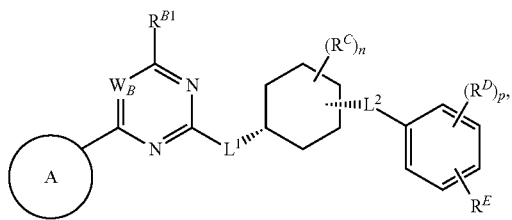

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

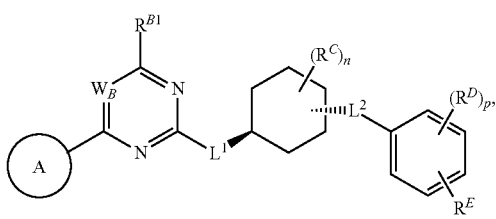

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

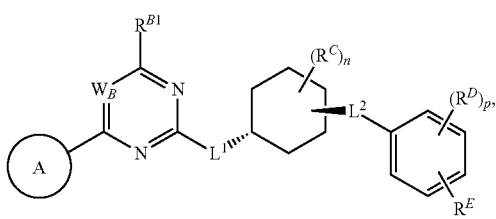

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

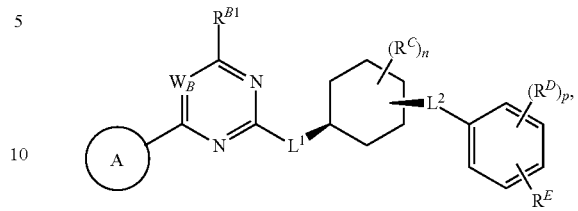

or a pharmaceutically acceptable salt, solvate, hydrate, polymorph, co-crystal, tautomer, stereoisomer, isotopically labeled derivative, or prodrug thereof.

In certain embodiments, a compound of Formula (I) is of the formula:

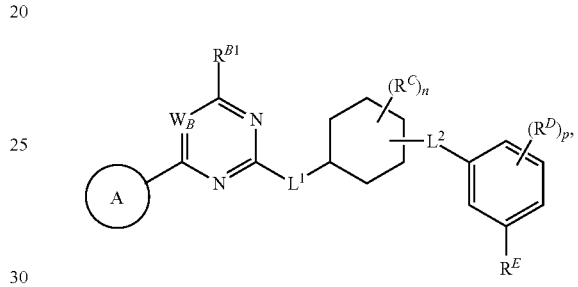

or a pharmaceutically acceptable salt, solvate, hydrate, polymorph, co-crystal, tautomer, stereoisomer, isotopically labeled derivative, or prodrug thereof.

In certain embodiments, a compound of Formula (I) is the formula:

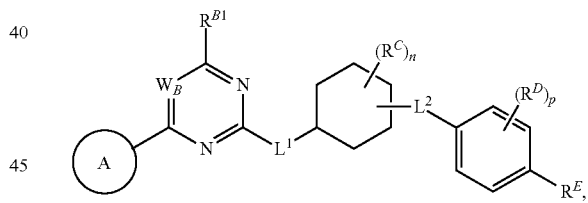

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

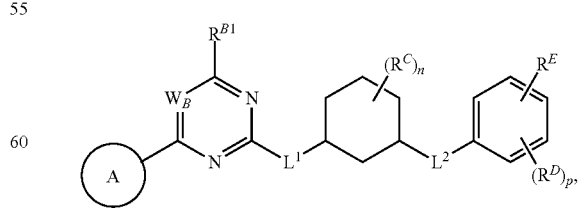

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

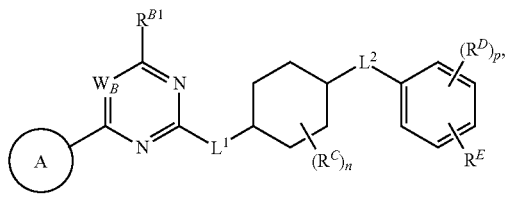

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

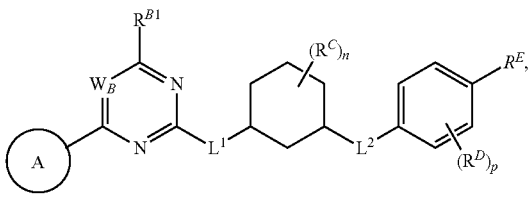

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

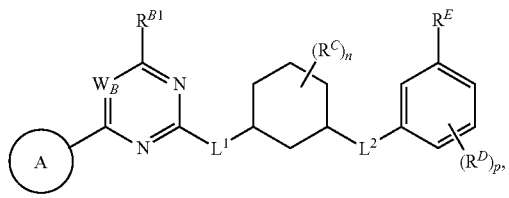

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

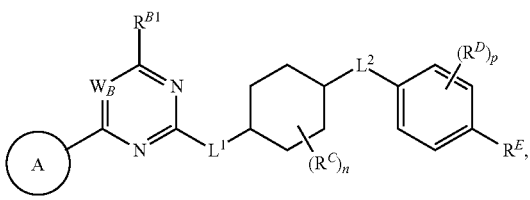

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

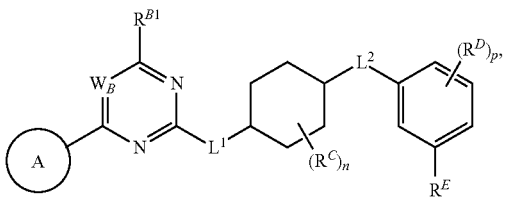

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

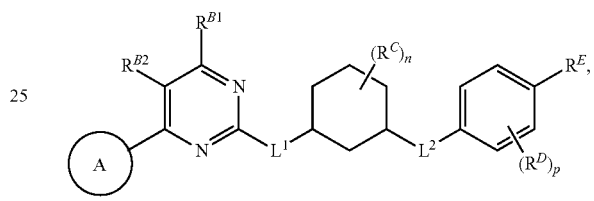

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

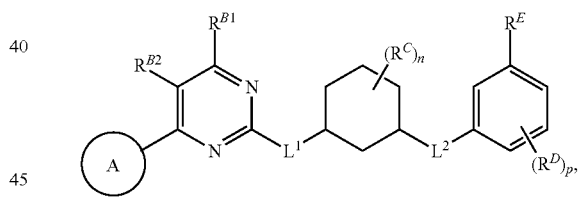

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

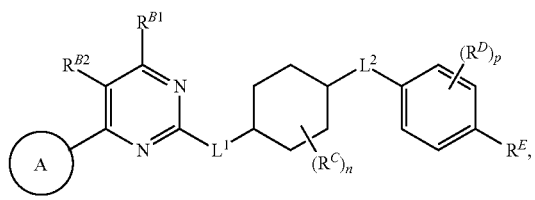

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

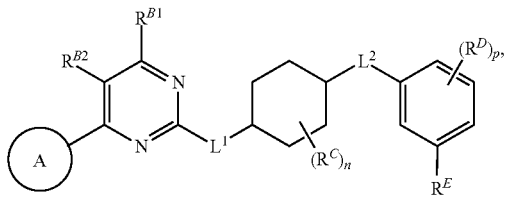

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

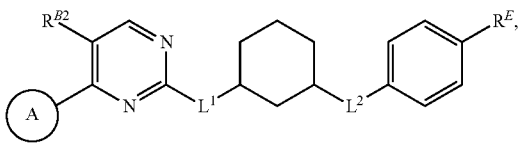

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

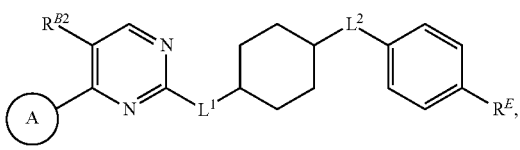

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

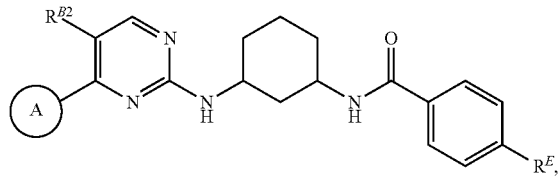

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

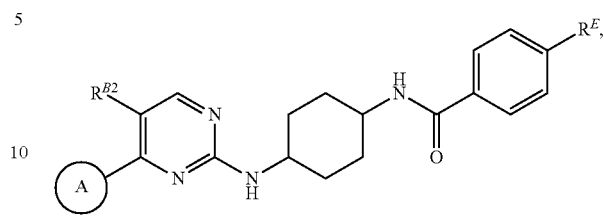

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:


or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

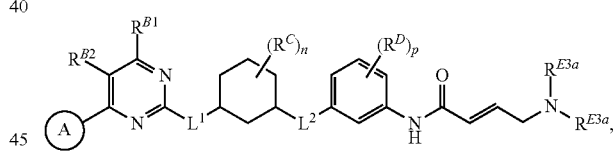

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

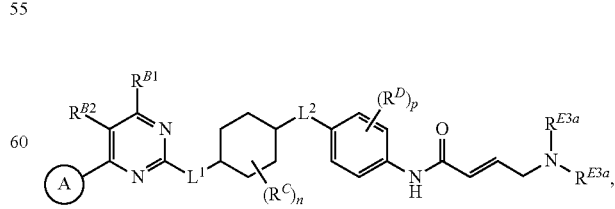

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

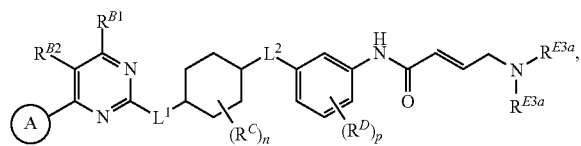

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

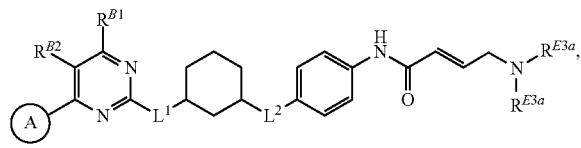

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

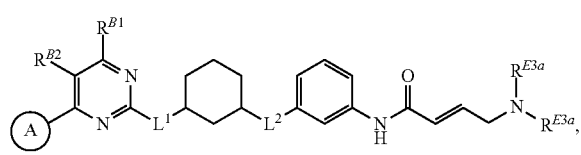

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

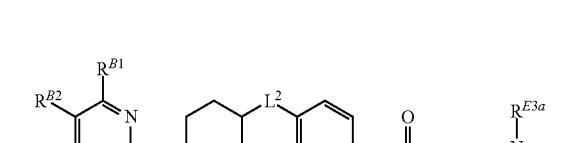

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

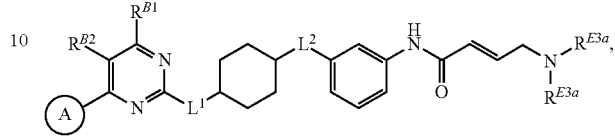

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

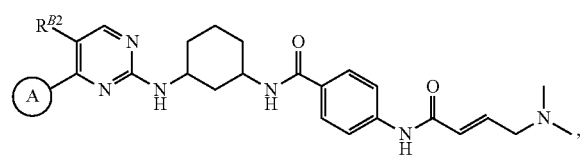

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

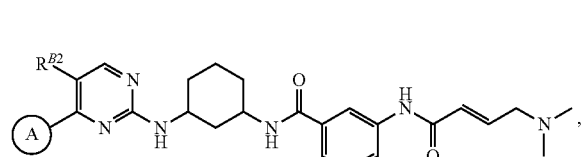

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

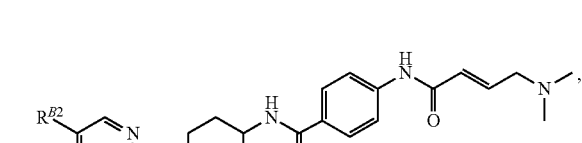

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

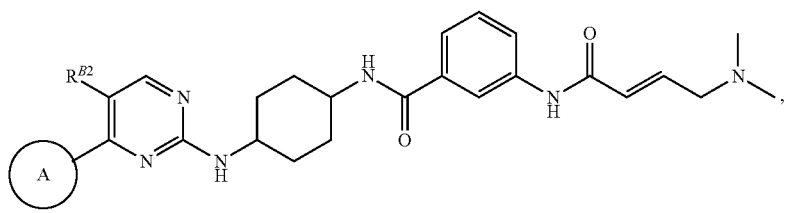

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

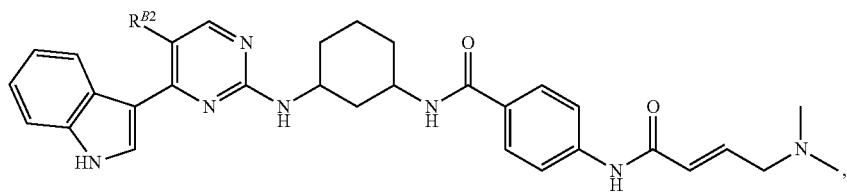

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

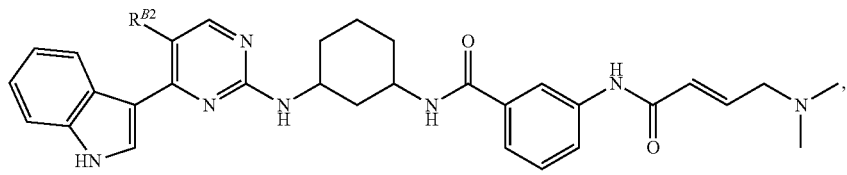

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

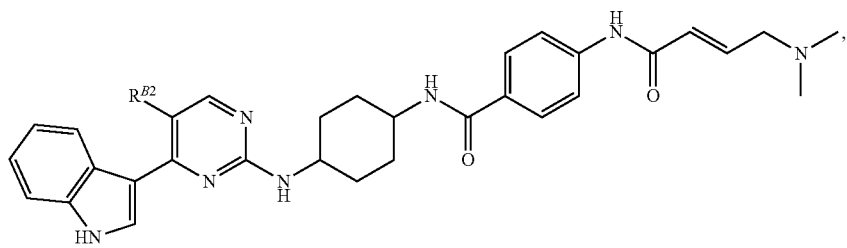

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

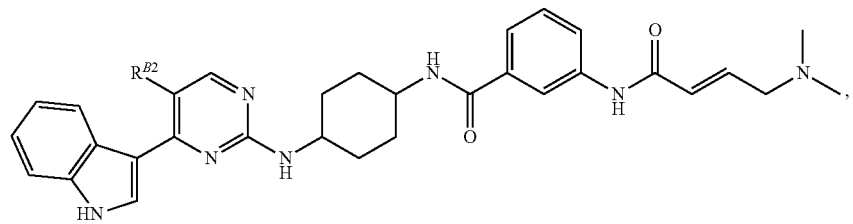

or a pharmaceutically acceptable salt, solvate, hydrate, polymorph, co-crystal, tautomer, stereoisomer, isotopically labeled derivative, or prodrug thereof.

In certain embodiments, the compound of Formula (I) is a compound depicted in FIGS. 1A-1I, or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

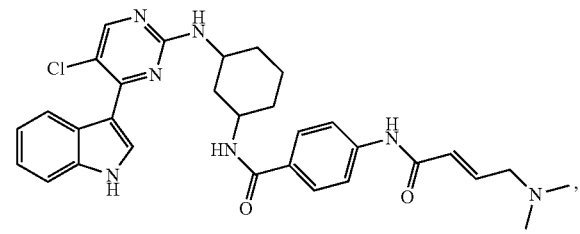 [SMILES: CN(C)C/C=C/C(=O)Nc1ccc(C(=O)NC2CCCC(Nc3ncc(Cl)c(-c4c[nH]c5ccccc45)n3)C2)cc1]

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

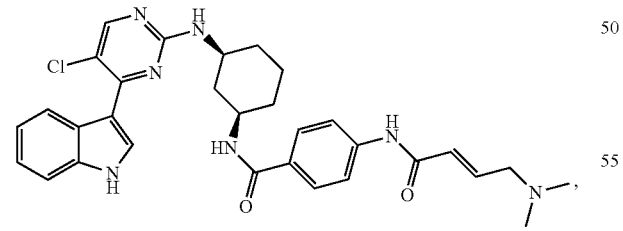

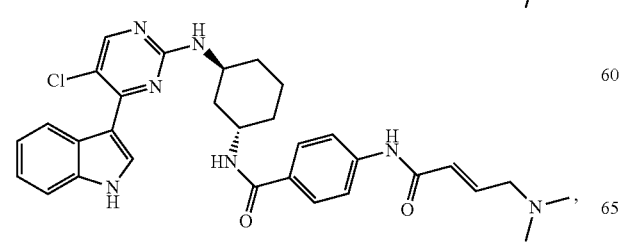

-continued

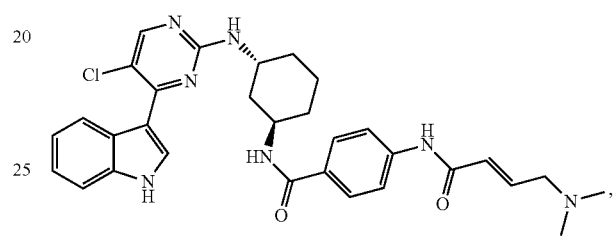

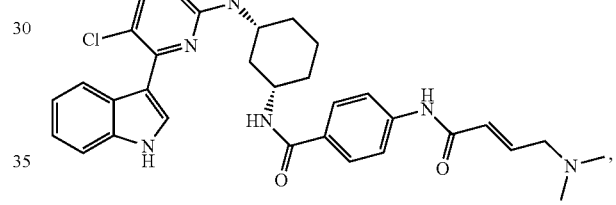

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

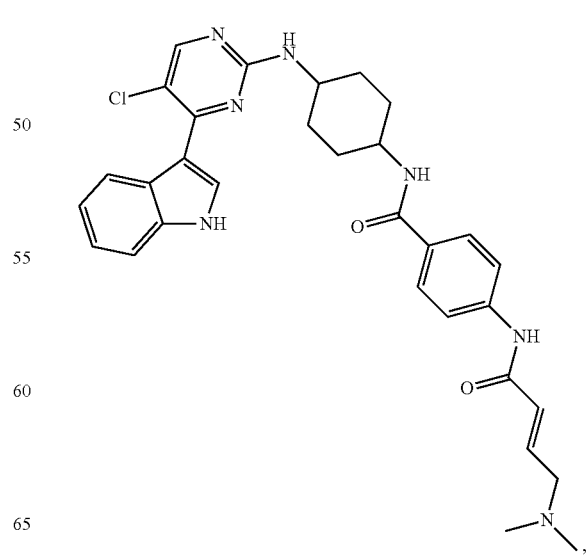

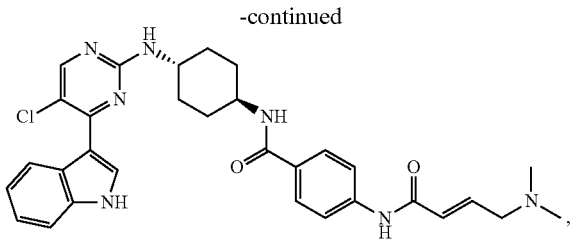

or a pharmaceutically acceptable salt, solvate, hydrate, polymorph, co-crystal, tautomer, stereoisomer, isotopically labeled derivative, or prodrug thereof.

In certain embodiments, the compound of Formula (I) is any one of Compounds 100-178 (e.g., Compound 102), or a pharmaceutically acceptable salt, solvate, hydrate, polymorph, co-crystal, tautomer, stereoisomer, isotopically labeled derivative, or prodrug thereof. In certain embodiments, the compound of Formula (I) is any one of Compounds 100-178 (e.g., Compound 102), or a pharmaceutically acceptable salt thereof.

In certain embodiments, a compound of Formula (I) is substantially pure. In certain embodiments, a compound of Formula (I) is a substantially pure stereoisomer. In certain embodiments, the compounds of the present invention are compounds of Formula (I), and pharmaceutically acceptable salts, solvates, hydrates, polymorphs, co-crystals, tautomers, stereoisomers, isotopically labeled derivatives, and prodrugs thereof. In certain embodiments, the compounds of the present invention are compounds of Formula (I), and pharmaceutically acceptable salts and stereoisomers thereof. In certain embodiments, the compounds of the present invention are compounds of Formula (I), and pharmaceutically acceptable salts thereof. In certain embodiments, the compounds of the present invention are a stereoisomeric mixture of compounds of Formula (I), and pharmaceutically acceptable salts thereof. In certain embodiments, the compounds of the present invention are a racemic stereoisomeric mixture of compounds of Formula (I), and pharmaceutically acceptable salts thereof.

The compounds of the present invention may bear multiple binding motifs for binding to a CDK (e.g., CDK7, CDK12, and/or CDK13), specifically, CDK7. Ring A of the inventive compounds may be accommodated by a hydrophobic pocket in the ATP-binding site of the CDK (e.g., CDK7). Functionalities on Rings A and B may bind to residues of the CDK (e.g., CDK7). For example, Ring A may form a hydrogen bond with Asp155 of the CDK (e.g., CDK7). Functional groups of $R^E$ may form one or more hydrogen bonds with the CDK (e.g., CDK7). Moreover, the Michael acceptor moiety of $R^E$ may react with a cysteine residue (e.g., Cys312) of the CDK (e.g., CDK7) to allow covalent attachment of the compound to the CDK (e.g., CDK7).

The compounds of the present invention are thought to be kinase inhibitors. In certain embodiments, the inventive compounds are CDK inhibitors. In certain embodiments, the inventive compounds are CDK7 inhibitors. In certain embodiments, the inventive compounds are selective CDK inhibitors (e.g., being more active in inhibiting a CDK than a non-CDK kinase). In certain embodiments, the inventive compounds are selective CDK7 inhibitors (e.g., being more active in inhibiting CDK7 than a non-CDK7 kinase). In certain embodiments, the inventive compounds are selective CDK12 inhibitors. In certain embodiments, the inventive compounds are selective CDK13 inhibitors.

The selectivity of an inventive compound for a first kinase (e.g., CDK7) over a second kinase (e.g., a non-CDK7 kinase) may be measured by the quotient of the $IC_{50}$ (half maximal inhibitory concentration) value of the inventive compound in inhibiting the activity of the second kinase over the $IC_{50}$ value of the inventive compound in inhibiting the activity of the first kinase. The selectivity of an inventive compound for a first kinase over a second kinase may also be measured by the quotient of the $K_d$ (dissociation constant) value of an adduct (covalent or non-covalent) of the inventive compound and the second kinase over the $K_d$ value of an adduct of the inventive compound and the first kinase. In certain embodiments, the selectivity is at least about 1-fold, at least about 2-fold, at least about 5-fold, at least about 10-fold, at least about 30-fold, at least about 100-fold, at least about 300-fold, at least about 1,000-fold, at least about 3,000-fold, at least about 10,000-fold, at least about 30,000-fold, or at least about 100,000-fold. In certain embodiments, $IC_{50}$ values are measured by a functional antagonist assay. In certain embodiments, $IC_{50}$ values are measured by a competition binding assay. In certain embodiments, $IC_{50}$ values are measured by a method described herein. In certain embodiments, $K_d$ values are measured by a nuclear magnetic resonance method (e.g., a linearization method and a curve fitting method). In certain embodiments, $K_d$ values are measured by a mass spectrometry method (e.g., a one-ligand one-binding-site ESI-MS method).

Pharmaceutical Compositions, Kits, and Administration

The present invention provides pharmaceutical compositions comprising a compound of Formula (I), e.g., a compound of Formula (I), or a pharmaceutically acceptable salt, solvate, hydrate, polymorph, co-crystal, tautomer, stereoisomer, isotopically labeled derivative, or prodrug thereof, as described herein, and optionally a pharmaceutically acceptable excipient. In certain embodiments, the pharmaceutical composition of the invention comprises a compound of Formula (I), or a pharmaceutically acceptable salt thereof, and optionally a pharmaceutically acceptable excipient. In certain embodiments, the compound of Formula (I), or a pharmaceutically acceptable salt, solvate, hydrate, polymorph, co-crystal, tautomer, stereoisomer, isotopically labeled derivative, or prodrug thereof, is provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound of Formula (I) (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the compound in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil-in-water and/or water-in-oil emulsions such as creams, ointments, and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets, and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of Formula (I) may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, immunosuppressant agents, and a pain-relieving agent. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The inventive kits may be useful for preventing and/or treating a proliferative disease (e.g., cancer (e.g., leukemia, lymphoma, melanoma, multiple myeloma, breast cancer, Ewing's sarcoma, osteosarcoma, brain cancer, neuroblastoma, lung cancer), benign neoplasm, angiogenesis, inflammatory disease, autoinflammatory disease, or autoimmune disease). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided are kits including a first container comprising a compound described herein, or a pharmaceutically acceptable salt, solvate, hydrate, polymorph, co-crystal, tautomer, stereoisomer, isotopically labeled derivative, and prodrug thereof, or a pharmaceutical composition thereof. In certain embodiments, the kit of the invention includes a first container comprising a compound described herein, or a pharmaceutically acceptable salt thereof, or a pharmaceutical composition thereof. In certain embodiments, the kits are useful in preventing and/or treating a proliferative disease in a subject. In certain embodiments, the kits further include instructions for administering the compound, or a pharmaceutically acceptable salt, solvate, hydrate, polymorph, co-crystal, tautomer, stereoisomer, isotopically labeled derivative, and prodrug thereof, or a pharmaceutical composition thereof, to a subject to prevent and/or treat a proliferative disease.

Methods of Treatment and Uses

The present invention also provides methods for the treatment or prevention of a proliferative disease (e.g., cancer, benign neoplasm, angiogenesis, inflammatory disease, autoinflammatory disease, or autoimmune disease) or an infectious disease (e.g., a viral disease) in a subject.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

The proliferative disease to be treated or prevented using the compounds of Formula (I) may be associated with overexpression of a kinase, such as cyclin-dependent kinase (CDK). The process of eukaryotic cell division may be broadly divided into a series of sequential phases termed G1, S, G2, and M. Correct progression through the various phases of the cell cycle has been shown to be critically dependent upon the spatial and temporal regulation of a family of proteins known as cyclin dependent kinases (CDKs) and a diverse set of their cognate protein partners termed cyclins. CDKs are CDC2 (also known as CDK1) homologous serine-threonine kinase proteins that are able to utilize ATP as a substrate in the phosphorylation of diverse polypeptides in a sequence-dependent context. Cyclins are a family of proteins characterized by a homology region, containing approximately 100 amino acids, termed the "cyclin box" which is used in binding to, and defining selectivity for, specific CDK partner proteins.

Modulation of the expression levels, degradation rates, and activation levels of various CDKs and cyclins throughout the cell cycle leads to the cyclical formation of a series of CDK/cyclin complexes, in which the CDKs are enzymatically active. The formation of these complexes controls passage through discrete cell cycle checkpoints and thereby enables the process of cell division to continue. Failure to satisfy the prerequisite biochemical criteria at a given cell cycle checkpoint, i.e., failure to form a required CDK/cyclin complex, can lead to cell cycle arrest and/or cellular apoptosis. Aberrant cellular proliferation can often be attributed to loss of correct cell cycle control. Inhibition of CDK enzymatic activity therefore provides a means by which abnormally dividing cells can have their division arrested and/or be killed. The diversity of CDKs, and CDK complexes, and their critical roles in mediating the cell cycle, provides a broad spectrum of potential therapeutic targets selected on the basis of a defined biochemical rationale.

CDK7, a member of the CDK family, was originally isolated as the catalytic subunit of the trimeric CDK-activating kinase (CAK) complex. This complex, consisting of CDK7, cyclin H, and MAT1, is responsible for activation of the mitotic promoting factor in vitro. The discovery that CDK7 was also a component of the basal transcription repair factor IIH (TFIIH) implicated a dual role for CDK7 in transcription as part of TFIIH and in the control of the cell cycle as the trimeric CAK complex. TFIIH is a multisubunit protein complex identified as a factor required for RNA polymerase II (RNAP II)-catalyzed transcription, and subsequently this complex was found to play a key role in nucleotide excision repair. CDK7 is a component of at least three complexes, i.e., the trimeric CAK complex, the quaternary complex with the XPD (or ERCC2, a protein involved in transcription-coupled nucleotide excision repair), and the nine-subunit TFIIH complex. The two functions of CDK7 in CAK and CTD phosphorylation support critical facets of cellular proliferation, cell cycling, and transcription. Overexpression of CDK7 may inhibit apoptosis, promote transcription and cell proliferation, and/or disrupt DNA repair, and therefore, cause proliferative diseases. In certain embodiments, the proliferative disease to be treated or prevented using the compounds of Formula (I) may be associated with overexpression of a CDK (e.g., CDK7). The compounds of Formula (I), or pharmaceutically acceptable salts, solvates, hydrates, polymorphs, co-crystals, tautomers, stereoisomers, isotopically labeled derivatives, and prodrugs thereof, or pharmaceutical compositions thereof, may down-regulate the expression of a CDK (e.g., CDK7).

A proliferative disease may be associated with aberrant activity of a CDK (e.g., CDK7). Aberrant activity of a CDK (e.g., CDK7) may be an elevated and/or an inappropriate activity of the CDK. Deregulation of cell cycle progression is a characteristic of a proliferative disease, and a majority of proliferative diseases have abnormalities in some component of CDK (e.g., CDK7) activity, frequently through elevated and/or inappropriate CDK activation. Inhibition of the catalytic activity of CDK7 would be expected to inhibit cell cycle progression by blocking the phosphorylation of cell cycle CDKs, and would additionally inhibit transcription of effectors of cell division. In certain embodiments, CDK7 is not overexpressed, and the activity of CDK7 is elevated and/or inappropriate. In certain other embodiments, CDK7 is overexpressed, and the activity of CDK7 is elevated and/or inappropriate. The compounds of Formula (I), and pharmaceutically acceptable salts, solvates, hydrates, polymorphs, co-crystals, tautomers, stereoisomers, isotopically labeled derivatives, prodrugs, and compositions thereof, may inhibit the activity of CDK7 and be useful in treating and/or preventing proliferative diseases.

In other embodiments, the proliferative disease to be treated or prevented using the compounds of Formula (I) will typically be associated with aberrant activity of CDK12. Aberrant activity of CDK12 may be an elevated and/or an inappropriate (e.g., abnormal) activity of CDK12. In certain embodiments, CDK12 is not overexpressed, and the activity of CDK12 is elevated and/or inappropriate. In certain other embodiments, CDK12 is overexpressed, and the activity of CDK12 is elevated and/or inappropriate. The compounds of Formula (I), and pharmaceutically acceptable salts, solvates, hydrates, tautomers, stereoisomers, isotopically labeled derivatives, and compositions thereof, may inhibit the activity of CDK12 and be useful in treating and/or preventing proliferative diseases.

In other embodiments, the proliferative disease to be treated or prevented using the compounds of Formula (I) will typically be associated with aberrant activity of CDK13. Aberrant activity of CDK13 may be an elevated and/or an inappropriate (e.g., abnormal) activity of CDK13. In certain embodiments, CDK13 is not overexpressed, and the activity of CDK13 is elevated and/or inappropriate. In certain other embodiments, CDK13 is overexpressed, and the activity of CDK13 is elevated and/or inappropriate. The compounds of Formula (I), and pharmaceutically acceptable salts, solvates, hydrates, tautomers, stereoisomers, isotopically labeled derivatives, and compositions thereof, may inhibit the activity of CDK13 and be useful in treating and/or preventing proliferative diseases.

A proliferative disease may also be associated with inhibition of apoptosis of a cell in a biological sample or subject. All types of biological samples described herein or known in the art are contemplated as being within the scope of the invention. Apoptosis is the process of programmed cell death. Inhibition of apoptosis may result in uncontrolled cell proliferation and, therefore, may cause proliferative diseases. The cell cycle CDKs (CDK1, 2, 4, and 6) are activated by phosphorylation by CDK7/cyclin H (also called CAK). Inhibition of CDK7 would therefore result in cell-cycle arrest at multiple points in the cell cycle due to failure to activate the cell cycle CDKs. CDK 7 activates transcription by phosphorylating the CTD of RNAP II. Inhibition of CTD phosphorylation has been shown to inhibit transcription and reduce expression of short lived proteins, including those involved in apoptosis regulation. It is appreciated in the art that stalling of RNA polymerase may activate p53 (also known as protein 53 or tumor protein 53, a tumor suppressor protein that is encoded in humans by the TP53 gene), leading to apoptosis. Thus, inhibition of the activity of CDK7 are expected to cause cytotoxicity by inducing apoptosis. The compounds of Formula (I), and pharmaceutically acceptable salts, solvates, hydrates, polymorphs, co-crystals, tautomers, stereoisomers, isotopically labeled derivatives, prodrugs, and compositions thereof, may induce apoptosis, and therefore, be useful in treating and/or preventing proliferative diseases.

In certain embodiments, the proliferative disease to be treated or prevented using the compounds of Formula (I) is cancer. All types of cancers disclosed herein or known in the art are contemplated as being within the scope of the invention. In certain embodiments, the proliferative disease is a cancer associated with dependence on BCL-2 anti-apoptotic proteins (e.g., MCL-1 and/or XIAP). In certain embodiments, the proliferative disease is a cancer associated with overexpression of MYC (a gene that codes for a transcription factor). In certain embodiments, the proliferative disease is a hematological malignancy. In certain embodiments, the proliferative disease is a blood cancer. In certain embodiments, the proliferative disease is a hematological malignancy. In certain embodiments, the proliferative disease is leukemia. In certain embodiments, the proliferative disease is chronic lymphocytic leukemia (CLL). In certain embodiments, the proliferative disease is acute lymphoblastic leukemia (ALL). In certain embodiments, the proliferative disease is T-cell acute lymphoblastic leukemia (T-ALL). In certain embodiments, the proliferative disease is chronic myelogenous leukemia (CML). In certain embodiments, the proliferative disease is acute myelogenous leukemia (AML). In certain embodiments, the proliferative disease is acute monocytic leukemia (AMoL). In certain embodiments, the proliferative disease is lymphoma. In certain embodiments, the proliferative disease is a Hodgkin's lymphoma. In certain embodiments, the proliferative disease is a non-Hodgkin's lymphoma. In certain embodiments, the proliferative disease is multiple myeloma. In certain embodiments, the proliferative disease is melanoma. In certain embodiments, the proliferative disease is breast cancer. In certain embodiments, the proliferative disease is triple-negative breast cancer (TNBC). In certain embodiments, the proliferative disease is a bone cancer. In certain embodiments, the proliferative disease is osteosarcoma. In certain embodiments, the proliferative disease is Ewing's sarcoma. In some embodiments, the proliferative disease is a brain cancer. In some embodiments, the proliferative disease is neuroblastoma. In some embodiments, the proliferative disease is a lung cancer. In some embodiments, the proliferative disease is small cell lung cancer (SCLC). In some embodiments, the proliferative disease is non-small cell lung cancer. In some embodiments, the proliferative disease is a benign neoplasm. All types of benign neoplasms disclosed herein or known in the art are contemplated as being within the scope of the invention. In some embodiments, the proliferative disease is associated with angiogenesis. All types of angiogenesis disclosed herein or known in the art are contemplated as being within the scope of the invention. In certain embodiments, the proliferative disease is an inflammatory disease. All types of inflammatory diseases disclosed herein or known in the art are contemplated as being within the scope of the invention. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

In certain embodiments, the infectious disease to be treated or prevented using the compounds of Formula (I) is a viral disease. Such viral infections are described in U.S. Provisional Patent Application Ser. No. 61/622,828, filed Apr. 11, 2012, and international PCT application, PCT/US2013/032488, filed Mar. 15, 2013, each of which is incorporated herein in its entirety by reference.

The cell described herein may be an abnormal cell. The cell may be in vitro or in vivo. In certain embodiments, the cell is a proliferative cell. In certain embodiments, the cell is a blood cell. In certain embodiments, the cell is a lymphocyte. In certain embodiments, the cell is a B-cell. In certain embodiments, the cell is a T-cell. In certain embodiments, the cell is a cancer cell. In certain embodiments, the cell is a leukemia cell. In certain embodiments, the cell is a CLL cell. In certain embodiments, the cell is a melanoma cell. In certain embodiments, the cell is a multiple myeloma cell. In certain embodiments, the cell is a benign neoplastic cell. In certain embodiments, the cell is an endothelial cell. In certain embodiments, the cell is an immune cell.

In another aspect, the present invention provides methods of down-regulating the expression of a CDK (e.g., CDK7, CDK1, CDK2, CDK5, CDK8, CDK9, CDK12, CDK13) in a biological sample or subject. In another aspect, the present invention provides methods of down-regulating the expression of IRAK1, JNK1, JNK2, or MLK3 in a biological sample or subject.

Another aspect of the invention relates to methods of inhibiting the activity of a kinase in a biological sample or subject. In certain embodiments, the kinase is CDK. In certain embodiments, the kinase is CDK7. In other embodiments, the kinase is CDK12 or CDK13. In certain embodiments, the activity of the kinase is aberrant activity of the kinase. In certain embodiments, the inhibition of the activity of the kinase is irreversible. In other embodiments, the inhibition of the activity of the kinase is reversible. In certain embodiments, the methods of inhibiting the activity of the kinase include attaching a compound of Formula (I) to the kinase.

Also provided in the present invention are methods of inhibiting transcription in a biological sample or subject.

The present invention also provides methods of inhibiting cell growth in a biological sample or subject.

In still another aspect, the present invention provides methods of inducing apoptosis of a cell in a biological sample or a subject.

In certain embodiments, the methods described herein include administering to a subject or contacting a biological sample with an effective amount of a compound of Formula (I), or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the methods described herein include administering to a subject or contacting a biological sample with an effective amount of a compound of Formula (I), or a pharmaceutically acceptable salt thereof, or a pharmaceutical composition thereof. In certain embodiments, the compound is contacted with a biological sample. In certain embodiments, the compound is administered to a subject. In certain embodiments, the compound is administered in combination with one or more additional pharmaceutical agents described herein. The additional pharmaceutical agent may be an anti-proliferative agent. In certain embodiments, the additional pharmaceutical agent is an anti-cancer agent. The additional pharmaceutical agent may also be a kinase inhibitor. In certain embodiments, the additional pharmaceutical agent is an inhibitor of a CDK. In certain embodiments, the additional pharmaceutical agent is an inhibitor of CDK7. In certain embodiments, the additional pharmaceutical agent is a selective inhibitor of CDK7. In certain embodiments, the additional pharmaceutical agent is a nonselective inhibitor of CDK7. In certain embodiments, the additional pharmaceutical agent is flavopiridol, triptolide, SNS-032 (BMS-387032), PHA-767491, PHA-793887, BS-181, (S)—CR8, (R)—CR8, or NU6140. In certain embodiments, the additional pharmaceutical agent is an inhibitor of a mitogen-activated protein kinase (MAPK). In certain embodiments, the additional pharmaceutical agent is an inhibitor of a glycogen synthase kinase 3 (GSK3). In certain embodiments, the additional pharmaceutical agent is an inhibitor of an AGC kinase. In certain embodiments, the additional pharmaceutical agent is an inhibitor of a CaM kinase. In certain embodiments, the additional pharmaceutical agent is an inhibitor of a casein kinase 1. In certain embodiments, the additional pharmaceutical agent is an inhibitor of a STE kinase. In certain embodiments, the additional pharmaceutical agent is an inhibitor of a tyrosine kinase.

In some embodiments, the additional pharmaceutical agent is a topoisomerase inhibitor, a MCL1 inhibitor, a BCL-2 inhibitor, a BCL-xL inhibitor, a BRD4 inhibitor, a CDK9 inhibitor, a Jumonji histone demethylase inhibitor, or a DNA damage inducer. In some embodiments, the additional pharmaceutical agent is etoposide, obatoclax, navitoclax, JQ1, 4-(((5'-chloro-2'-(((1R,4R)-4-(((R)-1-methoxypropan-2-yl)amino)cyclohexyl)amino)-[2,4'-bipyridin]-6-yl)amino)methyl)tetrahydro-2H-pyran-4-carbonitrile, JIB04, or cisplatin. In some embodiments, the additional pharmaceutical agent is etoposide, obatoclax, or navitoclax, and the disease to be treated is breast cancer, e.g., triple-negative breast cancer, HER2 positive breast cancer, ER-positive breast cancer, or ER/PR-positive breast cancer. In some embodiments, the additional pharmaceutical agent is etoposide, JIB04, or cisplatin, and the disease to be treated is Ewing's sarcoma. In some embodiments, the additional pharmaceutical agent is JQ1 or NVP2, and the disease to be treated is leukemia, e.g., acute myelogenous leukemia, myeloblastic leukemia, promyelocytic leukemia, myelomonocytic leukemia, monocytic leukemia, monoblastic leukemia, or megakaryoblastic leukemia. In certain embodiments, a pharmaceutical composition described herein further comprises a combination of the additional pharmaceutical agents described herein.

The inventive compounds or compositions may synergistically augment inhibition of CDK7 induced by the additional pharmaceutical agent(s) in the biological sample or subject. Thus, the combination of the inventive compounds or compositions and the additional pharmaceutical agent(s) may be useful in treating proliferative diseases resistant to a treatment using the additional pharmaceutical agent(s) without the inventive compounds or compositions.

Another aspect of the invention relates to methods of screening a library of compounds to identify one or more compounds that are useful in the treatment of a proliferative disease, in inhibiting a kinase (e.g., CDK, such as CDK7, CDK12, CDK13), in inhibiting cell growth, in inducing apoptosis of a cell, and/or in inhibiting transcription. In certain embodiments, the library of compounds is a library of compounds of Formula (I). The methods of screening a library include providing at least two different compounds of Formula (I), or pharmaceutically acceptable salts, solvates, hydrates, polymorphs, co-crystals, tautomers, stereoisomers, isotopically labeled derivatives, or prodrugs thereof, or pharmaceutical compositions thereof; and performing at least one assay using the different compounds of Formula (I), or pharmaceutically acceptable salts, solvates, hydrates, polymorphs, co-crystals, tautomers, stereoisomers, isotopically labeled derivatives, or prodrugs thereof, or pharmaceutical compositions thereof, to detect one or more characteristics associated with the proliferative disease. In certain embodiments, the methods of screening a library include providing at least two different compounds of Formula (I), or pharmaceutically acceptable salts thereof, or pharmaceutical compositions thereof; and performing at least one assay using the different compounds of Formula (I), or pharmaceutically acceptable salts thereof, or pharmaceutical compositions thereof, to detect one or more characteristics associated with the proliferative disease. The characteristic to be detected may be a desired characteristic associated with the proliferative disease. In certain embodiments, the desired characteristic is anti-proliferation. In certain embodiments, the desired characteristic is anti-cancer. In certain embodiments, the desired characteristic is inhibition of a kinase. In certain embodiments, the desired characteristic is inhibition of CDK. In certain embodiments, the desired characteristic is inhibition of CDK7. In certain embodiments, the desired characteristic is down-regulation of a kinase such as CDK (e.g., CDK7). In certain embodiments, the desired characteristic is induction of apoptosis of a cell. In certain embodiments, the desired characteristic is inhibition of transcription. The characteristic to be detected may also be an undesired characteristic associated with the proliferative disease, cell growth, apoptosis of a cell, and/or transcription. In certain embodiments, the undesired characteristic is induction of cell growth. In certain embodiments, the undesired characteristic is inhibition of apoptosis of a cell. In certain embodiments, the undesired characteristic is induction of transcription.

The different compounds of Formula (I) may be provided from natural sources (see, e.g., Sternberg et al., *Proc. Nat. Acad. Sci. USA*, (1995) 92:1609-1613) or generated by synthetic methods such as combinatorial chemistry (see, e.g., Ecker et al., *Bio/Technology*, (1995) 13:351-360 and U.S. Pat. No. 5,571,902). In certain embodiments, the different compounds are provided by liquid-phase or solution synthesis. In certain embodiments, the different compounds are provided by solid-phase synthesis. In certain embodiments, the different compounds are provided by a high-throughput, parallel, or combinatorial synthesis. In certain embodiments, the different compounds are provided by a low-throughput synthesis. In certain embodiments, the different compounds are provided by a one-pot synthesis. The different compounds may be provided robotically or manually. In certain embodiments, the step of providing at least two different compounds of the present invention include arraying into at least two vessels at least two different compounds of the present invention wherein the compounds are bound to solid supports, cleaving the compounds from the solid supports, and dissolving the cleaved compounds in a solvent. The solid supports include, but do not limit to, beads (e.g., resin beads and magnetic beads), hollow fibers, solid fibers, plates, dishes, flasks, meshes, screens, and membranes. In certain embodiments, the solid supports are beads. In certain embodiments, one solid support is capable of supporting at least 50 nmol of a compound. In certain embodiments, one solid support is capable of supporting at least 100 nmol of a compound. In certain embodiments, one solid support is capable of supporting at least 200 nmol of a compound. Each vessel may contain one or more support-bound compounds of the present invention. In certain embodiments, each vessel contains one support-bound compounds of the present invention. The solid supports and/or the compounds may be labeled with one or more labeling agents for the identification or detection of the compounds. The vessels may be wells of a microtiter plate. The solvent may be an inorganic solvent, organic solvent, or a mixture thereof. The steps of arraying, cleaving, and dissolving may be performed robotically or manually.

Typically, the methods of screening a library of compounds involve at least one assay. In certain embodiments, the assay is performed to detect one or more characteristics associated with the proliferative disease described herein. The assay may be an immunoassay, such as a sandwich-type assay, competitive binding assay, one-step direct test, two-step test, or blot assay. The step of performing at least one assay may be performed robotically or manually. In certain embodiments, the activity of a kinase is inhibited. In certain embodiments, the activity of CDK is inhibited. In certain embodiments, the activity of CDK7 is inhibited. In certain embodiments, the expression of a kinase such as CDK (e.g., CDK7) is down-regulated. In certain embodiments, apoptosis of a cell is induced. In certain embodiments, transcription is inhibited. In yet another aspect, the present invention provides the compounds of Formula (I), and pharmaceutically acceptable salts, solvates, hydrates, polymorphs, co-crystals, tautomers, stereoisomers, isotopically labeled derivatives, prodrugs, and compositions thereof, for use in the treatment of a proliferative disease in a subject. In certain embodiments, provided by the invention are the compounds described herein, and pharmaceutically acceptable salts and compositions thereof, for use in the treatment of a proliferative disease in a subject. In certain embodiments, provided by the invention are the compounds described herein, and pharmaceutically acceptable salts and compositions thereof, for use in inhibiting cell growth. In certain embodiments, provided by the invention are the compounds described herein, and pharmaceutically acceptable salts and compositions thereof, for use in inducing apoptosis in a cell. In certain embodiments, provided by the invention are the compounds described herein, and pharmaceutically acceptable salts and compositions thereof, for use in inhibiting transcription.

In another aspect, the present invention discloses a method for the design and/or identification of a potential binding compound for cyclin-dependent kinase 7 (CDK7) comprising the steps of:

(a) generating, on a computer, a three-dimensional representation of CDK7 having the coordinates of the solved X-ray structure, available publically as 1UA2 on PDB.org (b) identifying amino acid residues forming a binding pocket in the three-dimensional structure of CDK7 from step (a), in proximity to cysteine-312;

(c) generating a three-dimensional model of the active site;

(d) designing and/or selecting a compound that potentially binds to the active site using the three-dimensional model of the active site; and (e) synthesizing and/or choosing the potential binding compound.

In certain embodiments, the binding pocket comprises the CDK7 active site.

In certain embodiments, the binding pocket comprises the CDK7 amino acids phenylalanine-93, aspartic acid-92, aspartic acid-97, asparagine-142, and leucine-144, methionine-94, lysine-41, and phenylalanine-91.

In another aspect, the present invention discloses a method of identifying a compound that binds cyclin-dependent kinase 7 (CDK7), the method comprising computationally identifying a compound that binds to CDK7 using the atomic coordinates of cysteine-312, phenylalanine-93, aspartic acid-92, aspartic acid-97, asparagine-142, and leucine-144, methionine-94, lysine-41, and phenylalanine-91.

In another aspect, the present invention discloses a method of identifying a binding compound of cyclin-dependent kinase 7 (CDK7), the method comprising:
(a) providing a set of atomic coordinates for CDK7; and
(b) identifying in silico a binding compound that binds to CDK7 using the coordinates of step (a).

In another aspect, the present invention discloses a method of identifying a drug candidate for the treatment of a disease, the method comprising:
a) using the available atomic coordinates to form a three-dimensional structure of CDK7;
b) selecting a test compound having the best fit with the structure of CDK7; and
c) optionally, assaying the ability of the test compound to modulate CDK7 activity, wherein a test compound that modulates CDK7 activity is considered a drug candidate for treating a disease.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Synthesis of the Compounds

The compounds provided herein can be prepared from readily available starting materials using the following general methods and procedures. See, e.g., Scheme 1 below. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Scheme 1. Exemplary synthesis of exemplary compounds of the invention.

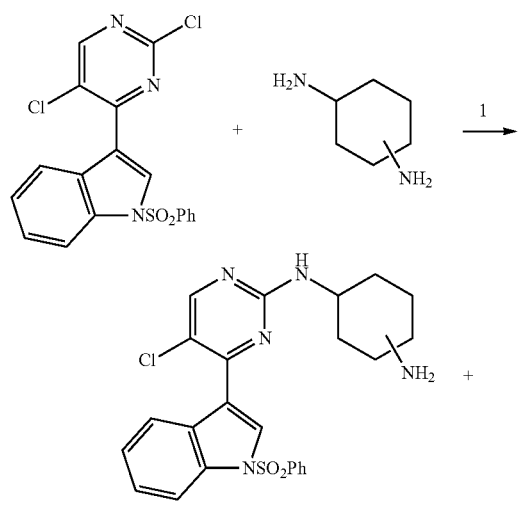

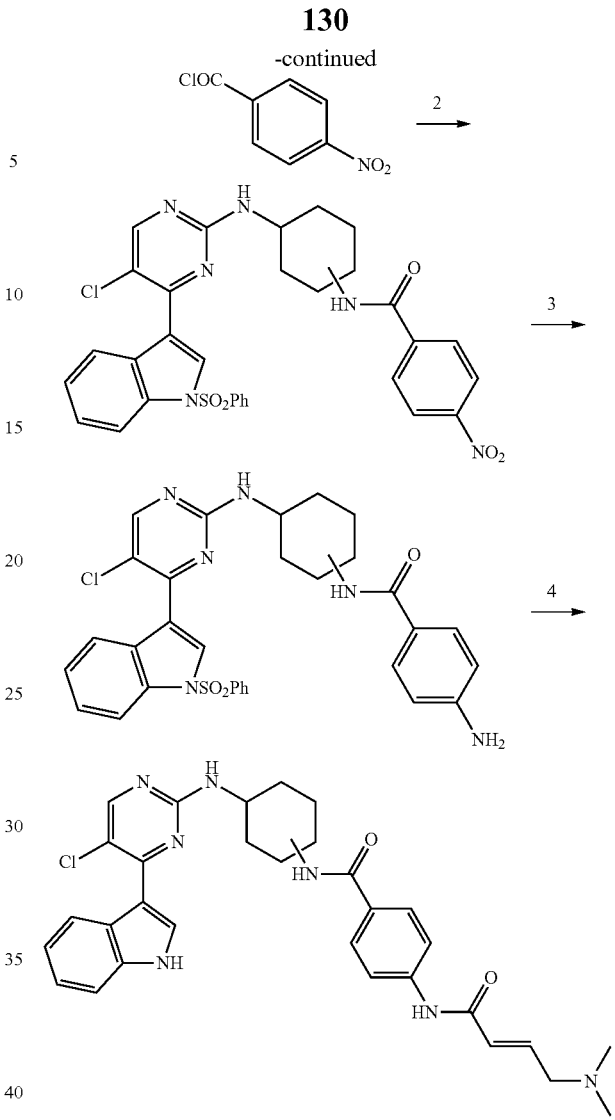

Reagents and conditions: (1) 1,2-dimethoxylmethanol, DIPEA, 120° C.; (2) pyridine, 80° C.; (3) SnCl$_2$, ethyl acetate, and methanol; (4) (a) 4-bromobut-2-enoyl chloride, CH$_3$CN, NHMe$_2$, 0° C. to room temperature; (b) 1M NaOH, 1,4-dioxane, room temperature.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

The compounds of the invention, such as those exemplified in FIGS. 1A-1I, may be synthesized according to the methods described herein or in U.S. Provisional Patent Application Ser. No. 61/561,078, filed Nov. 17, 2011, and international PCT Application, PCT/US2012/065618, filed Nov. 16, 2012, published on May 23, 2013 under Publication No. WO 2013/074986, each of which is incorporated herein in its entirety by reference. Detailed herein are exemplary syntheses of the compounds shown in FIGS. 1A-1I.

TABLE 1A

Abbreviations

| | |
|---|---|
| Ac | acetyl |
| ACN | acetonitrile |
| aq. | aqueous |
| atm | atmosphere(s) |
| Boc; BOC | tert-butoxy carbonyl |
| $Boc_2O$ | Di-t-butyl dicarbonate |
| CDI | 1,1'-Carbonyldiimidazole |
| DBU | 1-8-Diazabicyclo[5.4.0]undec-7-ene |
| DCC | N,N'-Dicyclohexylcarbodiimide |
| DCM | Dichloromethane |
| DIAD | Diisopropyl azodicarboxylate |
| DIPEA | N,N-Diisopropyl ethylamine |
| DMA | Dimethyl acetate |
| DMAP | 4-(Dimethylamino)pyridine |
| DMF | Dimethylformamide |
| DMSO | Dimethylsulfoxide |
| DPPA | Diphenoxyphosphoryl azide |
| EDTA | Ethylenediamine tetraacetic acid |
| eq(s). | equivalent(s) |
| EtOAc | Ethyl acetate |
| Et | Ethyl |
| EtOH | Ethanol |
| $Et_3N$ | Triethylamine |
| g | gram(s) |
| h | hour(s) |
| HATU | (Dimethylamino)-N,N-dimethyl(3H-[1,2,3]triazolo[4,5-b]pyridin-3-yloxy)methaniminium hexafluorophosphate |
| HBTU | O-Benzotriazole-N,N,N',N'-tetramethyl-uronium-hexafluoro-phosphate |
| Hex | Hexanes |
| HOBt | 1-Hydroxybenzotriazole |
| HPLC | High performance liquid chromatography |
| IPA | Isopropanol |
| LCMS; LC-MS | liquid chromatography mass spectrometry |
| MeOH | Methanol |
| mg | milligram(s) |
| min | Minute(s) |
| mL; ml | milliliter(s) |
| MS | mass spectrometry |
| MTBE | Methyl tert-butyl ether |
| mW | milliwatt |
| NMe | N-methyl |
| NMP | N-Methyl-2-pyrrolidone |
| NMR | Nuclear magnetic resonance |
| $Pd_2dba_3$ | Tris(dibenzylideneacetone) dipalladium(0) |
| Ph | phenyl |
| r.t.; rt; RT | Room temperature |
| S., sat. | saturated |
| TEA | Triethylamine |
| TFA | Trifluoroacetic acid |
| THF | Tetrahydrofuran |
| TLC | Thin layer chromatography |
| TMSI | Trimethylsilyl iodide |
| Tol | Toluene |
| X-Phos | 2-Dicyclohexylphosphino-2',4',6'-triisopropylbiphenyl |

Example 1. N-((1S,3R)-3-(5-chloro-4-(1H-indol-3-yl)pyrimidin-2-ylamino)cyclohexyl)-4-((E)-4-(dimethylamino)but-2-enamido)benzamide (Compound 102)

(1S,3R)-3-(Benzyloxycarbonylamino)cyclohexylamino 2,2-dimethylpropionate

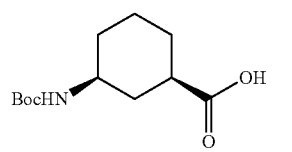

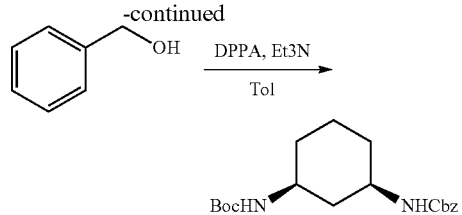

To a solution of (1R,3S)-3-(tert-butoxycarbonylamino) cyclohexane-carboxylic acid (8.77 g, 36.1 mmol) in toluene (Tol) was added $Et_3N$ (5.53 mL, 39.7 mmol) and DPPA (7.7 mL, 36.1 mmol). The resulting solution was stirred for 2 h at 110° C. and cooled down to 80° C. Benzyl alcohol (4.66 mL, 45.1 mmol) and triethylamine (5.53 mL, 39.7 mmol) were added, and the mixture was stirred for 20 h at 80° C. The cooled solution was diluted with EtOAc (100 mL) and water (50 mL). The layers were separated, and the aqueous layer was extracted with EtOAc (2×50 mL). The combined organic layers were dried over $MgSO_4$, filtered, and concentrated under reduced pressure. The residue was purified by $SiO_2$ chromatography (EtOAc in hexanes, 1 to 100% gradient) to afford the title compound (9.89 g, 28.4 mmol, 79% yield) as a white solid.

tert-butyl (1S,3R)-3-aminocyclohexylcarbamate

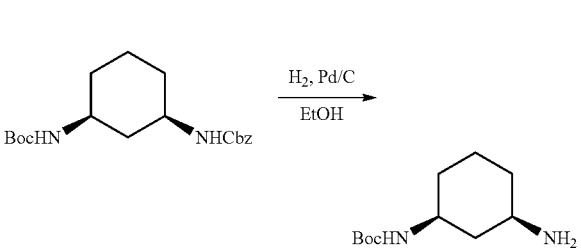

To a degassed solution of (1S,3R)-3-(benzyloxycarbonylamino) cyclohexylamino 2,2-dimethylpropionate (10 g, 28.4 mmol) in EtOH (473 mL) was added 10% w/w Pd/C (450 mg). The reaction mixture was stirred for 5 h under $H_2$ (1 atm.). The reaction mixture was filtered through a pad of Celite® (and washed with EtOH), and the filtrate was concentrated under reduced pressure to afford the title compound (6.08 g, 28.4 mmol, 100% yield) as a white solid.

tert-butyl (1S,3R)-3-(5-chloro-4-(1-(phenylsulfonyl)-1H-indol-3-yl)pyrimidin-2-ylamino)cyclohexylcarbamate

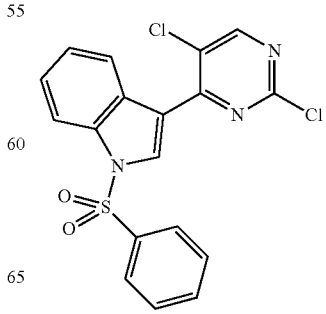

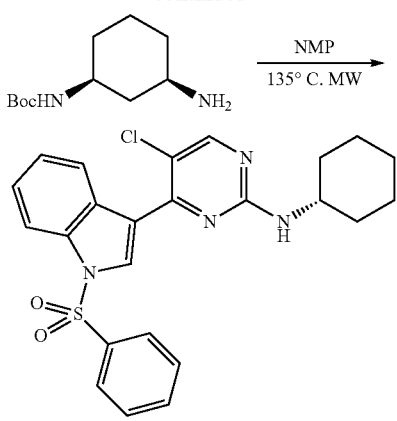

A solution of 3-(2,5-dichloropyrimidin-4-yl)-1-(phenylsulfonyl)-1H-indole (2.91 g, 7.20 mmol), tert-butyl (1S, 3R)-3-aminocyclohexylcarbamate (1.24 g, 5.76 mmol), and diisopropylethylamine (1.05 mL, 6.05 mmol) in NMP (14.5 mL) was heated for 1.5 h at 135° C. in a microwave (MW) reactor. The mixture was diluted with EtOAc (200 mL), washed with water (50 mL) and brine (50 mL), dried (MgSO₄), filtered, and concentrated under reduced pressure. The residue was purified by SiO₂ chromatography (EtOAc in DCM, 0 to 30% gradient) to afford the title compound (1.88 g, 3.23 mmol, 56% yield) as a light yellow foam.

(1R,3S)—N1-(5-chloro-4-(1-(phenylsulfonyl)-1H-indol-3-yl)pyrimidin-2-yl)cyclohexane-1,3-diamine.HCl

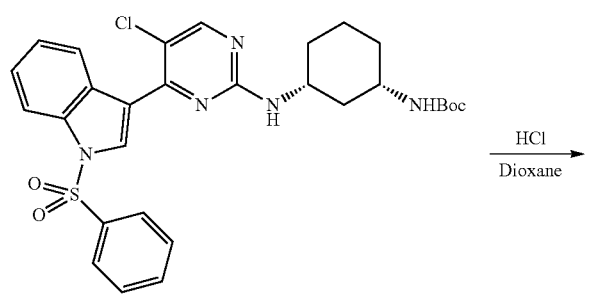

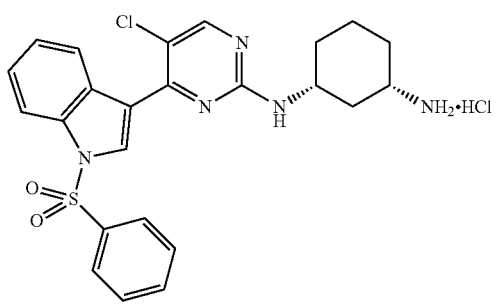

To a solution of tert-butyl (1S,3R)-3-(5-chloro-4-(1-(phenylsulfonyl)-1H-indol-3-yl)pyrimidin-2-ylamino)cyclohexylcarbamate (1.88 g, 3.23 mmol) in DCM (16.1 mL) was added a solution of HCl (4 N in dioxane, 12.11 mL, 48.44 mmol). The resulting mixture was stirred for 1.5 h at rt (room temperature) before being concentrated under reduced pressure to afford the title compound (1.72 g, 3.10 mmol, 96% yield) as a light yellow solid, which was used in the next step without further purification.

tert-butyl 4-((1S,3R)-3-(5-chloro-4-(1-(phenylsulfonyl)-1H-indol-3-yl)pyrimidin-2-ylamino)cyclohexylcarbamoyl)phenylcarbamate

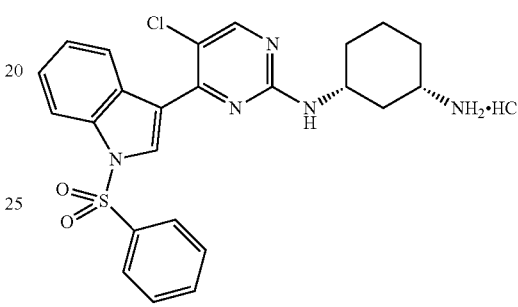

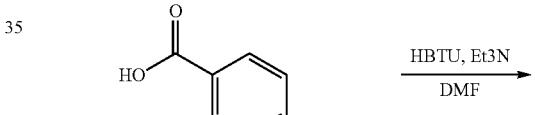

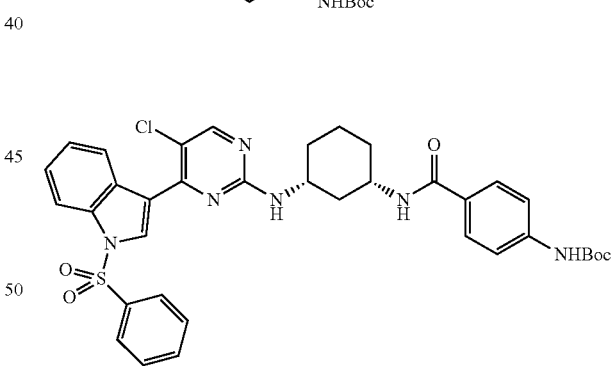

A solution of (1R,3S)—N1-(5-chloro-4-(1-(phenylsulfonyl)-1H-indol-3-yl)pyrimidin-2-yl)cyclohexane-1,3-diamine HCl salt (840 mg, 1.62 mmol), 4-(tert-butoxycarbonylamino)benzoic acid (462 mg, 1.95 mmol), HBTU (924 mg, 2.44 mmol), Et₃N (680 µL, 4.87 mmol) in DMF (8.0 mL) was stirred overnight at rt. The mixture was diluted with EtOAc (50 mL), washed with sat. (saturated) NaHCO₃ (10 mL), water (10 mL), and brine (10 mL). The organic layer was dried (over MgSO₄), filtered, and concentrated under reduced pressure to afford the title compound, which was used in the next step without further purification (1.14 g, 1.62 mmol, 100% yield).

tert-butyl 4-((1S,3R)-3-(5-chloro-4-(1H-indol-3-yl)pyrimidin-2-ylamino)cyclohexylcarbamoyl)-phenylcarbamate

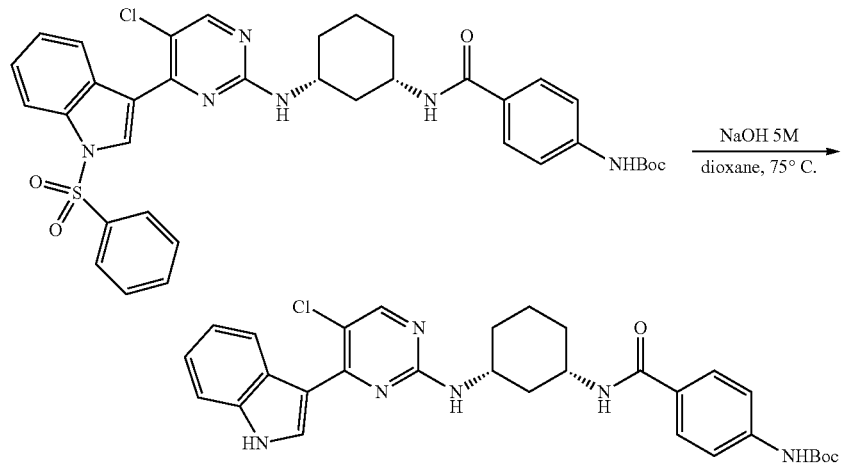

A solution of tert-butyl 4-((1S,3R)-3-(5-chloro-4-(1-(phenylsulfonyl)-1H-indol-3-yl)pyrimidin-2-ylamino)cyclohexylcarbamoyl)phenylcarbamate (2.84 g, 4.05 mmol) and 5 M NaOH (12 mL, 60.8 mmol) in dioxane (40 mL) and water (10 mL) was heated for 3 h at 75° C. The cooled mixture was concentrated under reduced pressure to remove the dioxane. Water (5 mL) was added, and the resulting mixture was sonicated for 5 min. A solid formed and was filtrated and washed with water (3×5 mL). The solid was dried under high vacuum and afforded the title compound (2.27 g, 2.27 mmol, 100% yield) as a white solid.

4-amino-N-((1S,3R)-3-(5-chloro-4-(1H-indol-3-yl)pyrimidin-2-ylamino)cyclohexyl)benzamide

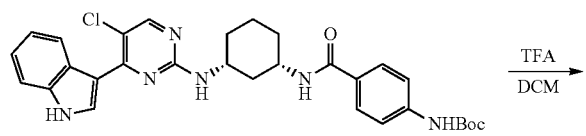

A solution of tert-butyl 4-((1S,3R)-3-(5-chloro-4-(1H-indol-3-yl)pyrimidin-2-ylamino)cyclohexylcarbamoyl)phenylcarbamate (2.27 g, 4.05 mmol) DCM (20 mL) was treated with TFA (3.10 mL, 40.53 mmol) and stirred overnight at rt. The mixture was concentrated under reduced pressure, diluted with DCM (1 mL), treated with sat. NaHCO₃ (2 mL) until basic pH (about 8), and sonicated for 5 min. A solid formed and was filtrated and washed with water (3×5 mL). The solid was dried under high vacuum and afforded the title compound (1.86 g, 4.05 mmol, 100% yield) as a yellow solid.

N-((1S,3R)-3-(5-chloro-4-(1H-indol-3-yl)pyrimidin-2-ylamino)cyclohexyl)-4-((E)-4-(dimethylamino)but-2-enamido)benzamide

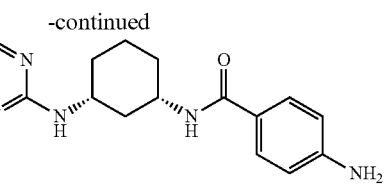

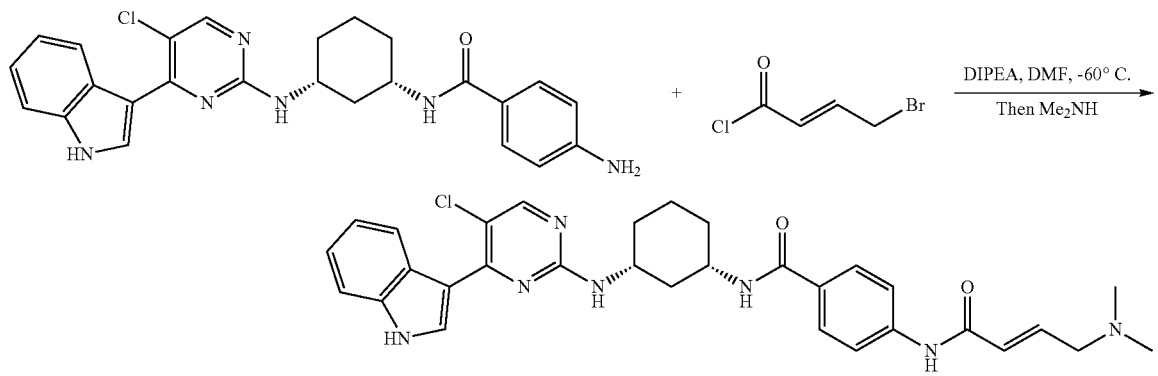

To a cold solution (−60° C.) of 4-amino-N-((1S,3R)-3-(5-chloro-4-(1H-indol-3-yl)pyrimidin-2-ylamino)cyclohexyl)benzamide (1.47 g, 3.19 mmol) and DIPEA (1.67 ml, 9.57 mmol) in THF (21 mL) and NMP (8 mL) was added a 54.2 mg/mL solution of (E)-4-bromobut-2-enoyl chloride (10.8 mL, 3.19 mmol) in THF. After 16 h at −60° C., SiO$_2$ (5 g) was added, and the mixture was evaporated under reduced pressure. The resulting bromide was purified by SiO$_2$ chromatography (THF in DCM, 0 to 70% gradient) and afforded the intermediate bromide (1.17 g) as a white solid. The bromide was dissolved in NMP (7.5 mL), cooled at −20° C., and a 2 M solution of dimethylamine in THF (6.38 mL, 12.76 mmol) was added. The mixture was stirred for 20 min at −20° C. and slowly warmed up to rt. THF was evaporated under reduced pressure, and the residue was purified by reverse phase chromatography (0.1% HCOOH, ACN in H$_2$O, 0 to 50% gradient) to afford the title compound (1.92 g, 1.31 mmol, 41% yield) as a white solid after lyophilization. $^1$H NMR (500 MHz, DMSO-d$_6$) δ 11.83 (s, 1H), 10.26 (s, 1H), 8.58 (s, 1H), 8.47 (s, 1H), 8.35-8.18 (m, 2H), 7.81 (d, J=8.7 Hz, 2H), 7.70 (d, J=8.7 Hz, 2H), 7.48 (d, J=8.4 Hz, 1H), 7.32 (d, J=7.9 Hz, 1H), 7.28-7.03 (m, 2H), 6.75 (dt, J=15.4, 5.8 Hz, 1H), 6.28 (d, J=15.5 Hz, 1H), 3.95 (s, 2H), 3.07 (d, J=5.4 Hz, 2H), 2.18 (s, 6H), 2.11-1.71 (m, 3H), 1.57-1.22 (m, 4H) ppm. MS (m/z): 572.4 [M+1]$^+$.

Example 2. (E)-N-(3-((5-chloro-4-(1H-indol-3-yl)pyrimidin-2-yl)amino)cyclohexyl)-4-(4-(dimethylamino)but-2-enamido)benzamide (Compound 100)

N$^1$-(5-chloro-4-(1-(phenylsulfonyl)-1H-indol-3-yl)pyrimidin-2-yl)cyclohexane-1,3-diamine

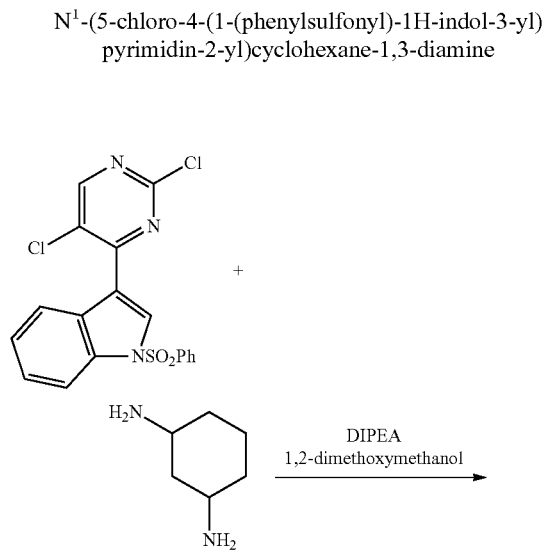

To a solution of 3-(2, 5-dichloropyrimidin-4-yl)-1-(phenylsulfonyl)-1H-indole (402 mg) in 1, 2-dimethoxylmethanol was added cyclohexane-1,3-diamine (114 mg, 1.0 equiv.) and diisopropylethylamine (129 mg, 1.0 equiv.). The solution was heated for 2 h at 120° C. The cooled solution was diluted with 100 mL of CHCl$_3$/i-PrOH (4:1) and then washed with water. The volatiles were removed, and the crude residue was separated by silica gel chromatography with CH$_2$Cl$_2$/methanol (10:1) to give the title product (300 mg, 62% yield).

N-(3-((5-chloro-4-(1-(phenylsulfonyl)-1H-indol-3-yl)pyrimidin-2-yl)amino)cyclohexyl)-4-nitrobenzamide

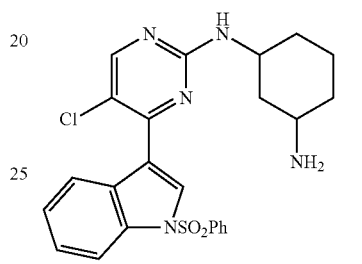

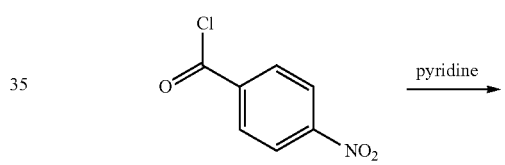

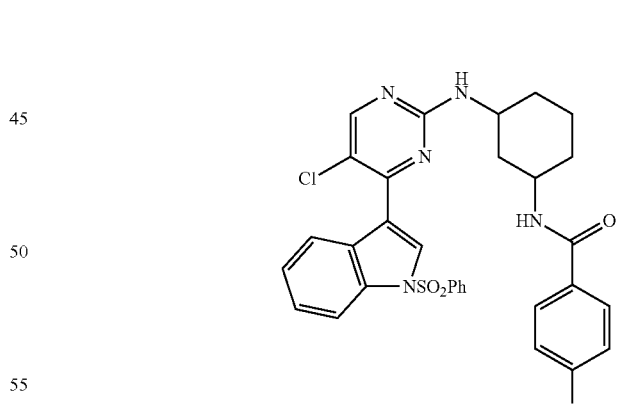

To a stirred solution of the product of the previous step (300 mg) in 10 mL of CH$_2$Cl$_2$ was added 4-nitrobenzoyl chloride (113 mg, 1.0 equiv.) at room temperature. The reaction mixture was heated to 80° C. for 2 h and then concentrated under reduced pressure. The resulting crude product was purified by flash column chromatography with CH$_2$Cl$_2$/methanol (10:1) to provide the title compound (310 mg, 80% yield).

139
4-amino-N-(3-((5-chloro-4-(1-(phenylsulfonyl)-1H-indol-3-yl)pyrimidin-2-yl)amino)cyclohexyl)benzamide

140
(E)-N-(3-((5-chloro-4-(1H-indol-3-yl)pyrimidin-2-yl)amino)cyclohexyl)-4-(4-(dimethylamino)but-2-enamido)benzamide

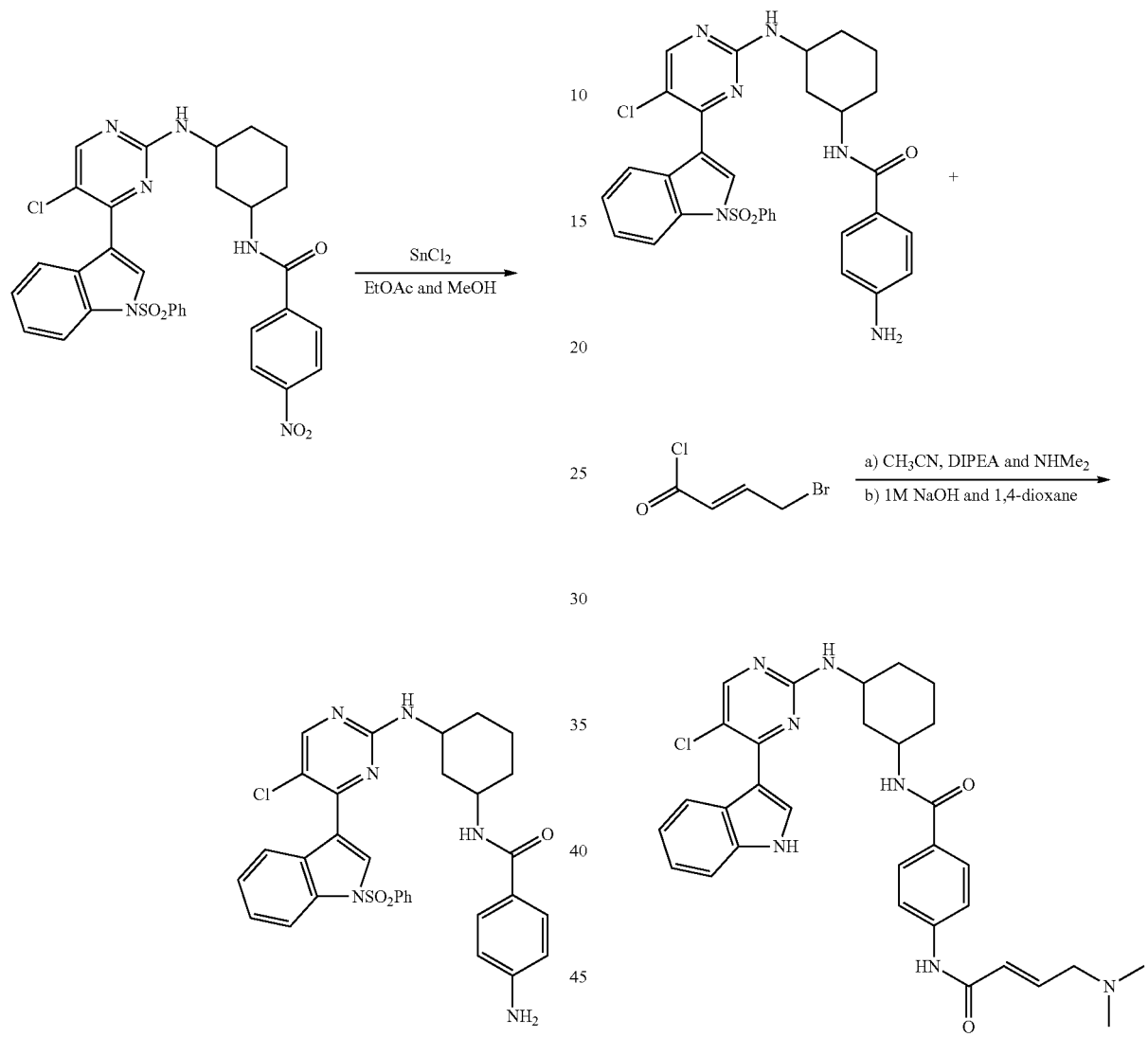

The nitro compound obtained from the previous step (310 mg) was suspended in 30 mL of ethyl acetate/methanol (5:1) and treated with SnCl$_2$ (232 mg, 2.5 equiv.). After stirring for 2 h at 80° C., the reaction mixture was cooled to room temperature and poured into saturated aqueous NaHCO$_3$. The mixture was stirred for 10 min, and the aqueous phase was then extracted with 100 mL of chloroform/2-propanol (4:1). The combined organic layers were washed with water and brine, dried over MgSO$_4$, filtered through a pad of Celite®, and concentrated under reduced pressure. The resulting crude product was purified by flash column chromatography with CH$_2$Cl$_2$/methanol (10:1) to provide the title compound (177 mg, 60% yield).

To the solution of the aniline product obtained from the previous step (60 mg) in 10 mL of acetonitrile was added diisopropylethylamine (13 mg, 1.0 equiv.). The reaction mixture was cooled to 0° C. and then treated with 4-chlorobut-2-enoyl chloride (54 mg, 3.0 equiv.) in CH$_2$Cl$_2$. The reaction mixture was stirred for 10 min at 0° C. and then treated with a solution of dimethylamine in THF. The reaction mixture was then warmed to room temperature, stirred for 1 h, and concentrated under reduced pressure. The resulting crude product was purified by preparative HPLC. The obtained product then was dissolved in 5 mL of 1,4-dioxane and 5 mL of 1 M NaOH. The solution was allowed to stir at room temperature for 2 h, and then 5 mL of 1 M HCl was added. The solution was then diluted with 30 mL of chloroform/2-propanol (4:1), and the organic layer was washed with water. The removal of solvent provides the crude product, which was purified by HPLC to give the final product (23 mg, 40% yield). MS 572 (M+1).

141

Example 3. (E)-N-(3-(5-chloro-4-(1H-indol-3-yl)pyrimidin-2-ylamino)tricyclo[3.3.1.1³,⁷]decanyl)-4-(4-(dimethylamino)but-2-enamido)benzamide (Compound 108)

Dibenzyl tricyclo[3.3.1.1³,⁷]decane-1,3-diyldicarbamate

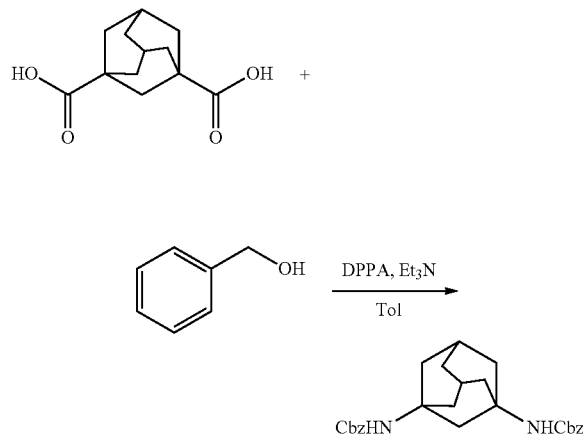

A solution of tricyclo[3.3.1.1³,⁷]decane-1,3-dicarboxylic acid (500 mg, 2.230 mmol) in toluene (9 mL) was treated with Et₃N (0.68 mL, 4.91 mmol) and DPPA (0.96 mL, 4.46 mmol) and heated at 110° C. for 1 h. The mixture was cooled down to 80° C., then treated with benzyl alcohol (0.580 mL, 5.574 mmol) and Et₃N (0.68 mL, 4.91 mmol). The resulting mixture was heated at 80° C. for 20 h, and after cooling, the mixture was diluted with EtOAc (50 mL) and H₂O (50 mL). The layers were separated and the aqueous layer was extracted with EtOAc (3×50 mL). The combined organics layers were washed with brine (50 mL), filtered and evaporated to dryness. The residue was purified by SiO₂ chromatography (Hex/EtOAc 0 to 70% gradient) and afforded the title compound (800 mg, 1.97 mmol, 88%) as a clear oil.

Tricyclo[3.3.1.1³,⁷]decane-1,3-diamine

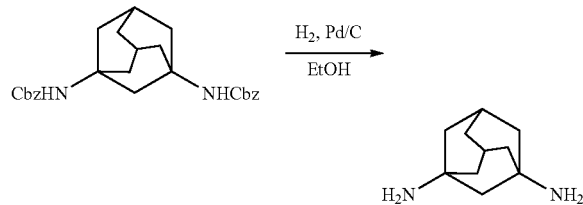

A degassed solution of dibenzyl tricyclo[3.3.1.1³,⁷]decane-1,3-diyldicarbamate (773 mg, 0.223 mmol) in EtOH (45 mL) was treated with 10% w/w Pd/C (356 mg). The mixture was stirred 18 h under hydrogen (1 atm) before filtration over a pad of Celite® (EtOH). The filtrate was evaporated under reduced pressure and afforded the title compound (348 mg, 2.10 mmol, 94%) as a colorless oil which was used in the next step without further purification.

142

N1-(5-chloro-4-(1-(phenylsulfonyl)-1H-indol-3-yl)pyrimidin-2-yl)tricyclo[3.3.1.1³,⁷]decane-1,3-diamine

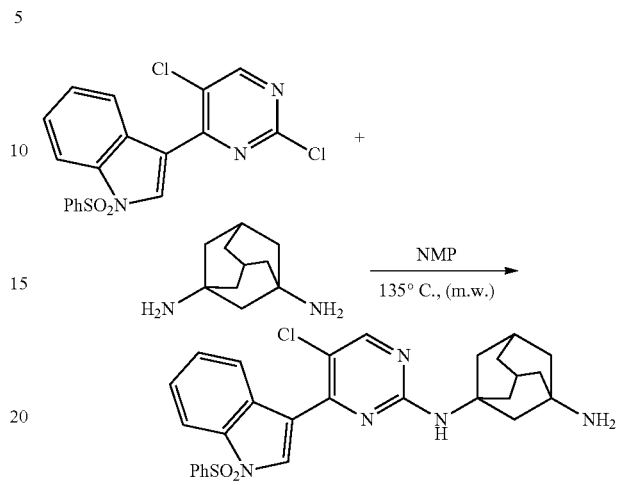

A solution of 3-(2,5-dichloropyrimidin-4-yl)-1-(phenylsulfonyl)-1H-indole (450 mg, 1.11 mmol), tricyclo[3.3.1.1³,⁷]decane-1,3-diamine (278 mg, 1.67 mmol) and DIPEA (0.29 mL, 1.67 mmol) in NMP (11 mL) was heated at 135° C. (microwave) for 75 min. The cooled mixture was diluted with EtOAc (50 mL), washed with H₂O (15 mL), brine (15 mL), dried over MgSO₄, filtered and evaporated to dryness. The residue was purified by C₁₈ chromatography (H₂O/ACN+0.1% HCO₂H 5 to 100% gradient) and afforded the title compound (168 mg, 0.315 mmol, 28%) as a light orange oil.

tert-butyl 4-(3-(5-chloro-4-(1-(phenylsulfonyl)-1H-indol-3-yl)pyrimidin-2-ylamino) tricyclo[3.3.1.1³,⁷]decanylcarbamoyl)phenylcarbamate

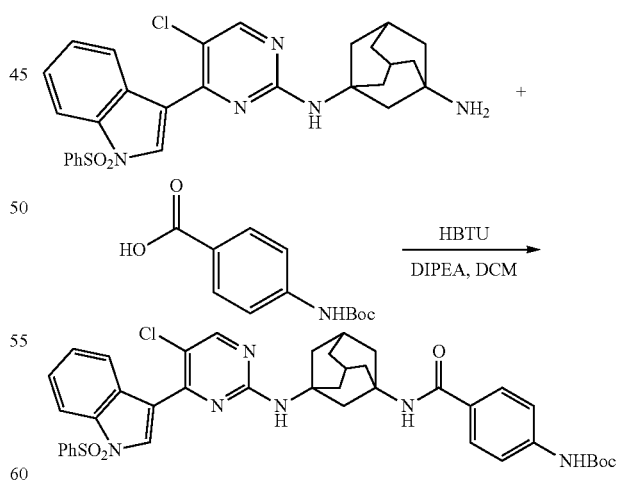

A solution of N1-(5-chloro-4-(1-(phenylsulfonyl)-1H-indol-3-yl)pyrimidin-2-yl)tricyclo [3.3.1.1³,⁷]decane-1,3-diamine (193 mg, 0.360 mmol) and 4-(tert-butoxycarbonylamino)benzoic acid (86 mg, 0.360 mmol) in 4:1 DCM/DMF (5 mL) was treated with HBTU (274 mg, 0.720 mmol) and DIPEA (0.19 mL, 1.08 mmol). The resulting mixture was stirred 18 h at rt and diluted with DCM (20 mL) and saturated NaHCO₃ (10 mL). The layers were separated and the organic layer was extracted with DCM (3×10 mL). The combined organic layers were washed with brine (10 mL), dried over MgSO₄, filtered and evaporated to dryness. The residue was purified by SiO₂ chromatography (DCM/EtOAc 0 to 50% gradient) and afforded the title compound (70 mg, 0.093 mmol, 26%) as a light yellow oil.

4-amino-N-(3-(5-chloro-4-(1-(phenylsulfonyl)-1H-indol-3-yl)pyrimidin-2-ylamino) tricyclo[3.3.1.1³,⁷]decanyl)benzamide.TFA

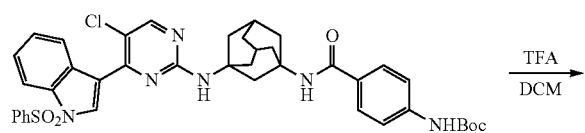

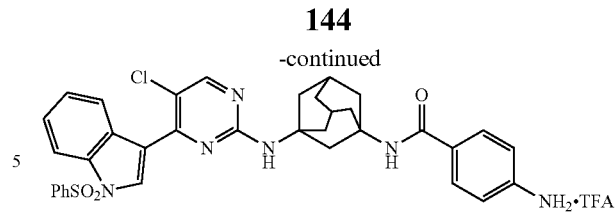

A solution of tert-butyl 4-(3-(5-chloro-4-(1-(phenylsulfonyl)-1H-indol-3-yl)pyrimidin-2-ylamino)tricyclo[3.3.1.1³,⁷]decanylcarbamoyl)phenylcarbamate (70 mg, 0.093 mmoL) in DCM (2 mL) was treated with TFA (1.1 mL, 13.94 mmol). The resulting mixture was stirred 1 h at rt before being evaporated to dryness. The residue was dried under high vacuum and afforded the title compound (71 mg, 0.093 mmol, 100%) as a light yellow oil which was used in the next step without further purification.

4-amino-N-(3-(5-chloro-4-(1H-indol-3-yl)pyrimidin-2-ylamino)tricyclo[3.3.1.1³,⁷]decanxyl)benzamide

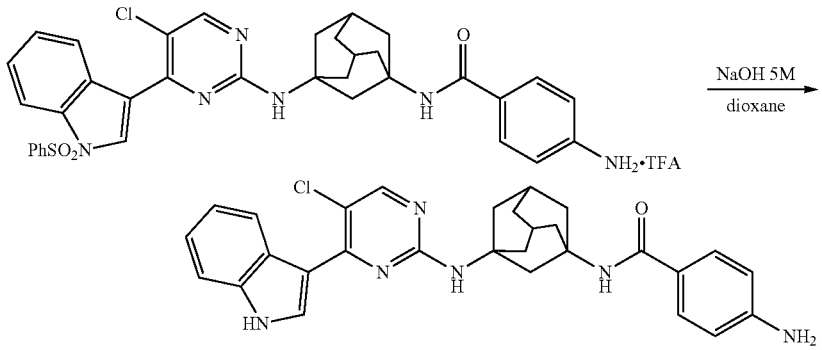

A solution of 4-amino-N-(3-(5-chloro-4-(1-(phenylsulfonyl)-1H-indol-3-yl)pyrimidin-2-ylamino)tricyclo[3.3.1.1³,⁷]decanyl)benzamide.TFA (47 mg, 0.072 mmol) in dioxane (1.5 mL) was treated with a 5M aqueous solution of NaOH (0.29 mL, 1.44 mmol) and heated 70° C. for 4 h. The cooled mixture was treated with a 1M aqueous solution of HCl until ph=7, extracted with EtOAc (3×10 mL), dried over MgSO₄, filtered and evaporated under reduced pressure. The residue was purified by C₁₈ chromatography (H₂O/ACN+0.1% HCO₂H 5 to 100% gradient) and afforded the title compound (9.5 mg, 0.019 mmol, 26%) as a white solid.

(E)-N-(3-(5-chloro-4-(1H-indol-3-yl)pyrimidin-2-ylamino)tricyclo[3.3.1.1³,⁷]decanyl)-4-(4-(dimethylamino)but-2-enamido)benzamide

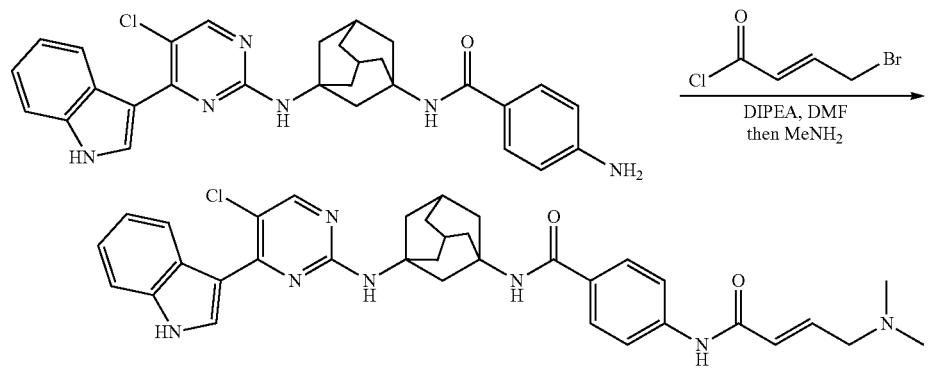

A −60° C. solution of 4-amino-N-(3-(5-chloro-4-(1H-indol-3-yl)pyrimidin-2-ylamino)tricyclo[3.3.1.1$^{3,7}$]decanxyl)benzamide and DIPEA (0.0403 mmol) in 1:1 NMP/THF (1.6 mL) was treated with a 54.2 mg/mL solution of (E)-4-bromobut-2-enoyl chloride in DCM (0.0141 mmol). The resulting mixture was stirred 1 h at −60° C. before addition of a 2M solution of dimethylamine in THF (0.0807 mmol). The resulting mixture was warmed to rt before being evaporated to dryness. The residue was purified by reverse phase chromatography (C$_{18}$, H$_2$O/ACN+0.1% HCO$_2$H 0 to 100% gradient) and afforded the title compounds (2.0 mg, 0.003 mmol, 24%) as a yellow solid after lyophilisation. $^1$H NMR (500 MHz, d$_6$-DMSO) δ 11.81 (s, 1H), 10.23 (s, 1H), 8.60 (br s, 1H), 8.38 (s, 1H), 8.26 (s, 1H), 7.76 (d, J=8.8 Hz, 2H), 7.67 (d, J=8.8 Hz, 2H), 7.61 (s, 1H), 7.47 (d, J=8.1 Hz, 1H), 7.19 (t, J=7.3 Hz, 1H), 7.15 (d, J=6.8 Hz, 1H), 6.82 (s, 1H), 6.75 (dt, J=15.5, 5.9 Hz, 1H), 6.27 (d, J=15.4 Hz, 1H), 3.06-3.01 (m, 2H), 2.20-2.14 (m, 2H), 2.17 (s, 6H), 2.07-2.03 (m, 4H), 1.61 (s, 2H), 0.97 (d, J=6.5 Hz, 6H); MS (m/z): 624.69 [M+1]$^+$.

Example 4. (+/−)-N-(-3-(5-chloro-4-(1H-indol-3-yl)pyrimidin-2-ylamino)-5-hydroxycyclohexyl)-4-((E)-4-(dimethylamino)but-2-enamido)benzamide (Compound 109)

(+/−)-5-(tert-butyldimethylsilyloxy)cyclohexane-1,3-diamine

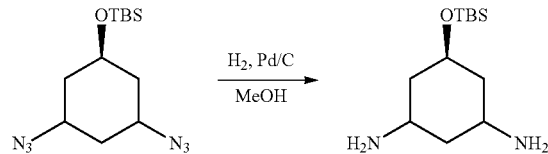

A degassed solution of tert-butyl((+/−)-3,5-diazidocyclohexyloxy)dimethylsilane (300 mg, 1.01 mmol) (prepared following New J. Chem., 2005, 29, 1152-1158) in MeOH (7 mL) was treated with 10% Pd/C (108 mg, 0.10 mmol) and stirred 2 h under hydrogen (1 atm). The resulting mixture was filtered over a pad of Celite® and the filtrate was evaporated to dryness leaving the title compound (227 mg, 0.930 mmol, 92%) as a beige solid which was used in the next step without further purification.

(+/−)-5-(tert-butyldimethylsilyloxy)-N$^1$-(5-chloro-4-(1-(phenylsulfonyl)-1H-indol-3-yl)pyrimidin-2-yl)cyclohexane-1,3-diamine

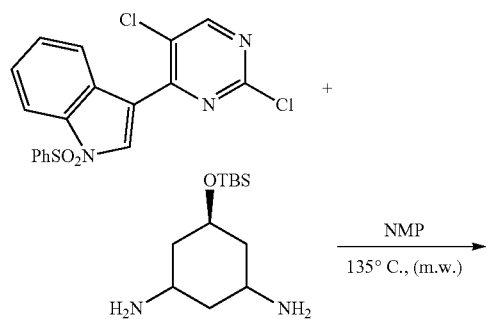

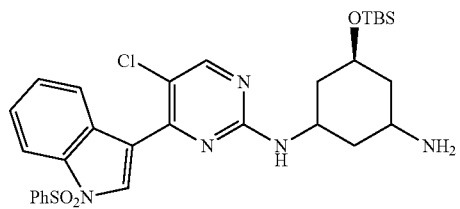

A solution of 3-(2,5-dichloropyrimidin-4-yl)-1-(phenylsulfonyl)-1H-indole (340 mg, 0.84 mmol), (+/−)-5-(tert-butyldimethylsilyloxy)cyclohexane-1,3-diamine (226 mg, 0.93 mmol) and DIPEA (0.93 mmol) in NMP (1.4 mL) was heated at 135° C. (microwave) for 25 min. The cooled mixture was diluted with EtOAc (30 mL), washed with H$_2$O (10 mL), brine (10 mL), dried over MgSO$_4$, filtered and evaporated to dryness. The residue was purified by C$_{18}$ chromatography (H$_2$O/ACN+0.1% HCO$_2$H 5 to 80% gradient) and afforded the title compound (97 mg, 0.158 mmol, 19%) as a pale yellow solid.

(+/−)-tert-butyl 4-(-3-(tert-butyldimethylsilyloxy)-5-(5-chloro-4-(1-(phenylsulfonyl)-1H-indol-3-yl)pyrimidin-2-ylamino)cyclohexylcarbamoyl)phenylcarbamate

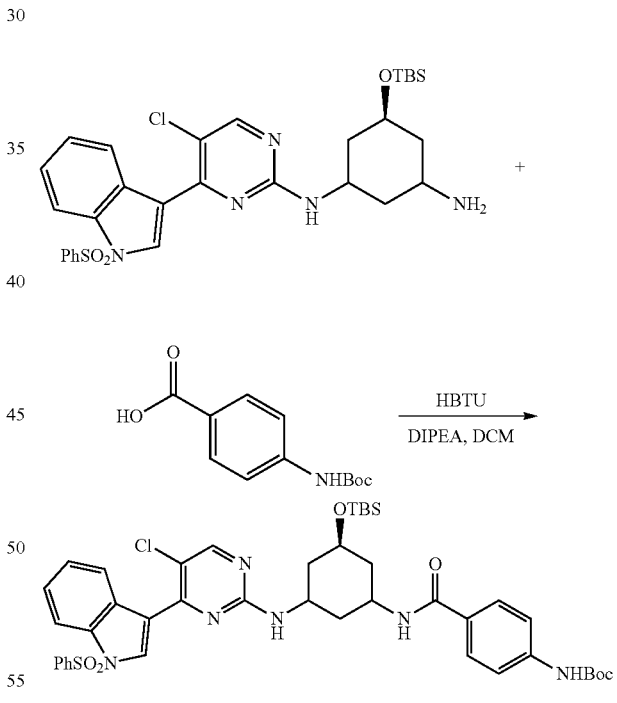

A solution of (+/−)-5-(tert-butyldimethylsilyloxy)-N$^1$-(5-chloro-4-(1-(phenylsulfonyl)-1H-indol-3-yl)pyrimidin-2-yl)cyclohexane-1,3-diamine (97 mg, 0.16 mmol) and 4-(tert-butoxycarbonylamino)benzoic acid (38 mg, 0.16 mmol) in DCM (1.1 mL) was treated with HBTU (120 mg, 0.32 mmol) and DIPEA (0.48 mmol). The resulting mixture was stirred 18 h at rt and evaporated to dryness. The residue was purified by SiO$_2$ chromatography (DCM/EtOAc 0 to 50% gradient) and afforded the title compound (93 mg, 0.111 mmol, 71%) as a light yellow oil.

(+/−)-4-amino-N-(3-(5-chloro-4-(1H-indol-3-yl) pyrimidin-2-ylamino)-5-hydroxycyclohexyl)benzamide

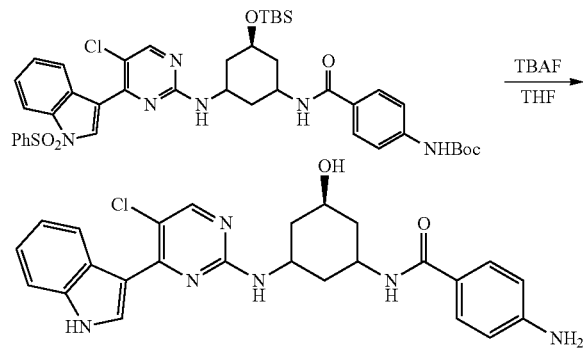

A solution of (+/−)-tert-butyl 4-(-3-(tert-butyldimethylsilyloxy)-5-(5-chloro-4-(1-(phenylsulfonyl)-1H-indol-3-yl) pyrimidin-2-ylamino)cyclohexylcarbamoyl)phenylcarbamate (93.0 mg, 0.112 mmol) in THF (4.5 mL) was treated with a 1M solution of TBAF in THF (0.168 mmol) and stirred for 2 days at rt. The resulting mixture was evaporated to dryness and the residue was purified by reverse phase chromatography ($C_{18}$, $H_2O$/ACN+0.1% $HCO_2H$ 10 to 100% gradient) and afforded the title compounds (32 mg, 0.067 mmol, 60%) as a yellow solid.

(+/−)-N-(-3-(5-chloro-4-(1H-indol-3-yl)pyrimidin-2-ylamino)-5-hydroxycyclohexyl)-4-((E)-4-(dimethylamino)but-2-enamido)benzamide

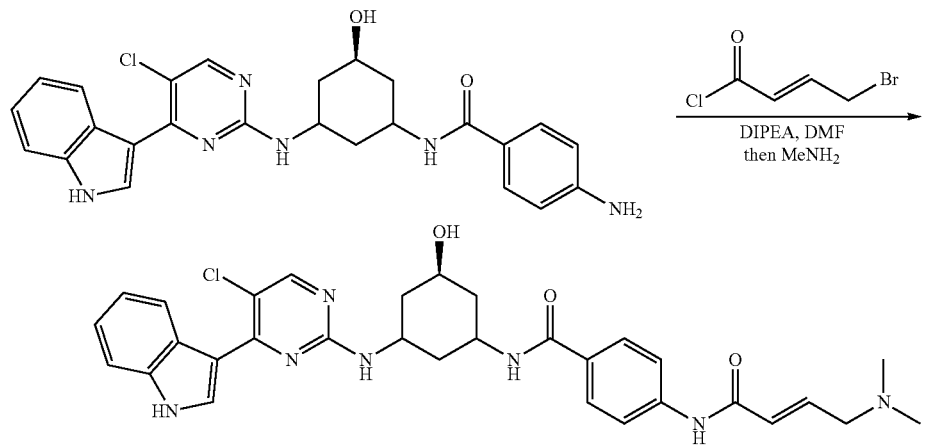

A −60° C. solution of (+/−)-4-amino-N-(3-(5-chloro-4-(1H-indol-3-yl)pyrimidin-2-ylamino)-5-hydroxycyclohexyl)benzamide (15.7 mg, 0.033 mmol) and DIPEA (0.099 mmol) in 1:1 NMP/THF (2.1 mL) was treated with a 54.2 mg/mL solution of (E)-4-bromobut-2-enoyl chloride in DCM (0.099 mmol). The resulting mixture was stirred 1 h 30 at −60° C. before addition of a 2M solution of dimethylamine in THF (0.099 mmol). The resulting mixture was warmed to rt before being evaporated to dryness. The residue was purified by reverse phase chromatography ($C_{18}$, $H_2O$/ACN+0.1% $HCO_2H$ 5 to 50% gradient) and afforded the title compounds (10.6 mg, 0.018 mmol, 55%) as a yellow solid after lyophilisation. $^1$H NMR (500 MHz, $d_6$-DMSO) δ 11.81 (d, J=2.6 Hz, 1H), 10.26 (s, 1H), 8.67 (d, J=8.2 Hz, 1H), 8.46 (d, J=2.8 Hz, 1H), 8.31-8.20 (m, 1H), 8.13 (d, J=8.4 Hz, 1H), 7.80 (d, J=8.8 Hz, 2H), 7.69 (d, J=8.8 Hz, 2H), 7.47 (d, J=8.5 Hz, 1H), 7.32-7.22 (m, 1H), 7.20 (t, J=7.2 Hz, 2H), 6.75 (dt, J=15.4, 5.9 Hz, 1H), 6.27 (dt, J=15.4, 1.1 Hz, 1H), 4.69 (s(br), 1H), 4.55-4.40 (m, 1H), 4.40-4.21 (m, 1H), 4.18-4.10 (m, 1H), 3.06 (dd, J=5.8, 1.1 Hz, 2H), 2.31-2.19 (m, 1H), 2.17 (s, 6H), 1.99-1.80 (m, 2H), 1.55-1.43 (m, 2H), 1.43-1.26 (m, 1H); MS (m/z): 588.65 [M+1]$^+$.

Example 5. N-((1S,3R)-3-(5-chloro-4-(1H-indol-3-yl)pyrimidin-2-ylamino)cyclohexyl)-4-((E)-4-morpholinobut-2-enamido)benzamide (Compound 110)

(1S,3R)-3-(Benzyloxycarbonylamino)cyclohexylamino 2,2-dimethylpropionate

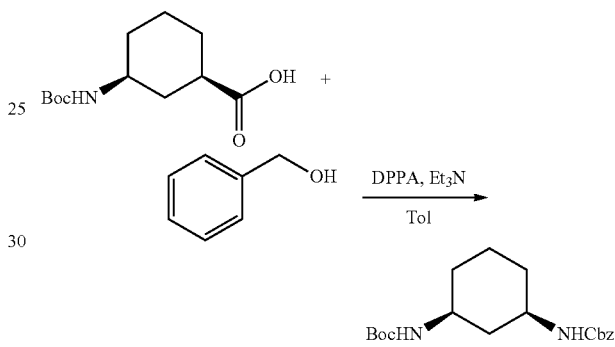

To a solution of (1R,3S)-3-(tert-butoxycarbonylamino) cyclohexanecarboxylic acid (prepared following *Tetrahedron: Asymmetry* 2010 (21), 864-866) (8.77 g, 36.1 mmol) was added $Et_3N$ (5.53 mL, 39.7 mmol) and DPPA (7.7 mL, 36.1 mmol). The resulting solution was stirred 2 h at 110° C. then cooled down to 80° C. Benzyl alcohol (4.66 mL, 45.1 mmol) and triethylamine (5.53 mL, 39.7 mmol) were added and the mixture was stirred 20 h at 80° C. The cooled solution was diluted with EtOAc (100 mL) and $H_2O$ (50 mL). The layers were separated and the aqueous layer was extracted with EtOAc (2×50 mL). The combined organics were dried (MgSO$_4$), filtered and evaporated to dryness. The residue was purified by SiO$_2$ chromatography (Hex/EtOAc 1 to 100% gradient), and afforded the title compound (9.89 g, 28.4 mmol, 79%) as a white solid.

tert-butyl (1S,3R)-3-aminocyclohexylcarbamate

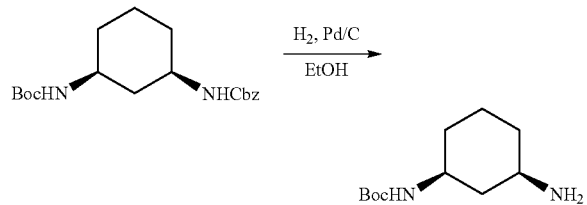

To a degassed solution of (1S,3R)-3-(benzyloxycarbonylamino)cyclohexylamino 2,2-dimethylpropionate (10 g, 28.4 mmol) in EtOH (473 mL) was added 10% w/w Pd/C (450 mg). The reaction mixture was stirred 5 h under H$_2$ (1 atm). The reaction mixture was filtered through a pad of Celite® (EtOH), then the filtrate was evaporated to dryness and afforded the title compound (6.08 g, 28.4 mmol, 100%) as a white solid.

tert-butyl (1S,3R)-3-(5-chloro-4-(1-(phenylsulfonyl)-1H-indol-3-yl)pyrimidin-2-ylamino) cyclohexylcarbamate

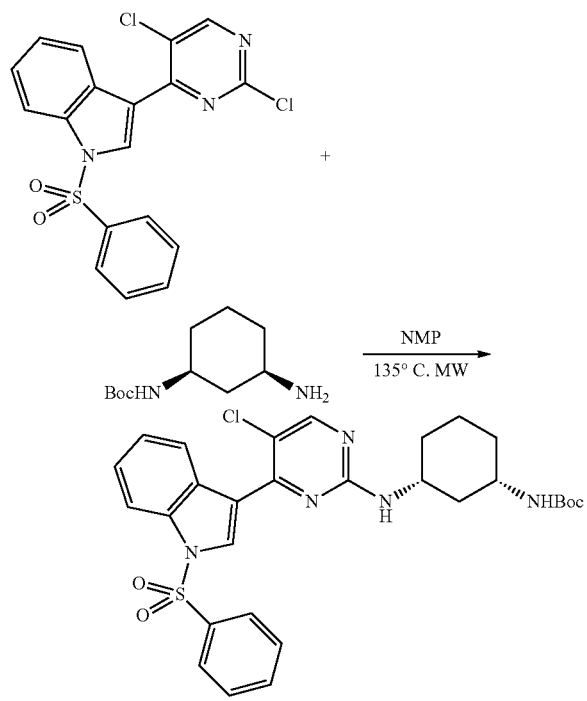

A solution of 3-(2,5-dichloropyrimidin-4-yl)-1-(phenylsulfonyl)-1H-indole (2.91 g, 7.20 mmol), tert-butyl (1S,3R)-3-aminocyclohexylcarbamate (1.24 g, 5.76 mmol) and diisopropylethylamine (1.05 mL, 6.05 mmol) in NMP (14.5 mL) was heated 1 h 30 at 135° C. (mW). The mixture was diluted with EtOAc (200 mL), washed with H$_2$O (50 mL), brine (50 mL), dried (MgSO$_4$), filtered and evaporated to dryness. The residue was purified by SiO$_2$ chromatography (DCM/EtOAc 0 to 30% gradient), and afforded the title compound (1.88 g, 3.23 mmol, 56%) as a light yellow foam.

(1R,3S)—N$^1$-(5-chloro-4-(1-(phenylsulfonyl)-1H-indol-3-yl)pyrimidin-2-yl)cyclohexane-1,3-diamine.HCl

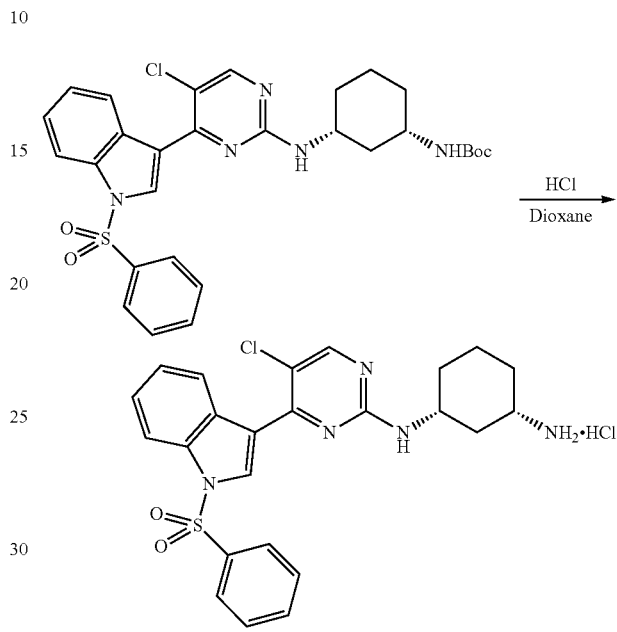

To a solution of tert-butyl (1S,3R)-3-(5-chloro-4-(1-(phenylsulfonyl)-1H-indol-3-yl)pyrimidin-2-ylamino)cyclohexylcarbamate (1.88 g, 3.23 mmol) in DCM (16.1 mL) was added a solution of HCl 4 N in dioxane (12.11 mL, 48.44 mmol). The resulting mixture was stirred 1.5 h at rt before being evaporated to dryness and afforded the title compound (1.72 g, 3.10 mmol, 96%) as a light yellow solid which was used in the next step without further purification.

tert-butyl 4-((1S,3R)-3-(5-chloro-4-(1-(phenylsulfonyl)-1H-indol-3-yl)pyrimidin-2-ylamino)cyclohexylcarbamoyl)phenylcarbamate

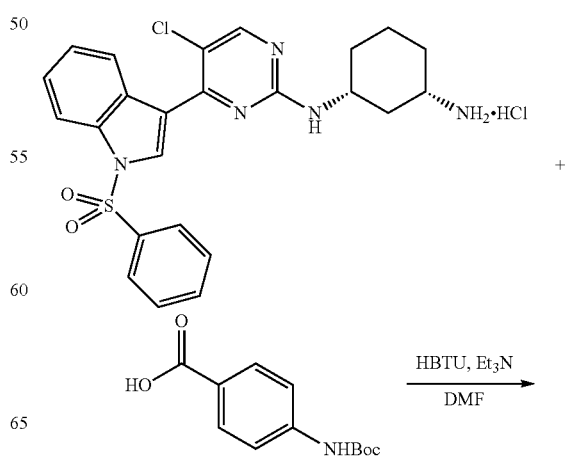

-continued

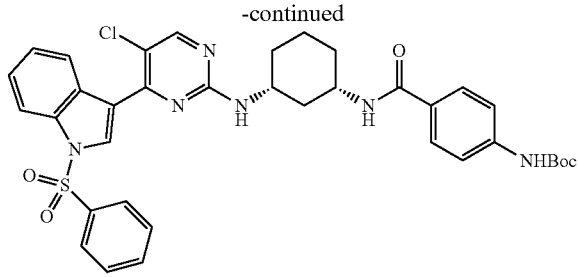

A solution of (1R,3S)—N¹-(5-chloro-4-(1-(phenylsulfonyl)-1H-indol-3-yl)pyrimidin-2-yl)cyclohexane-1,3-diamine.HCl (840 mg, 1.62 mmol), 4-(tert-butoxycarbonylamino)benzoic acid (462 mg, 1.95 mmol), HBTU (924 mg, 2.44 mmol), Et$_3$N (4.87 mmol) in DMF (8.0 mL) was stirred overnight at rt. The mixture was diluted with EtOAc (50 mL), washed with sat NaHCO$_3$ (10 mL), H$_2$O (10 mL) and brine (10 mL). The organic layer was dried over MgSO$_4$, filtered and concentrated under reduced pressure and afforded the title compound which was used in the next step without further purification (1.14 g, 1.62 mmol, 100%)

4-amino-N-((1S,3R)-3-(5-chloro-4-(1-(phenylsulfonyl)-1H-indol-3-yl)pyrimidin-2-ylamino)cyclohexyl) benzamide.HCl

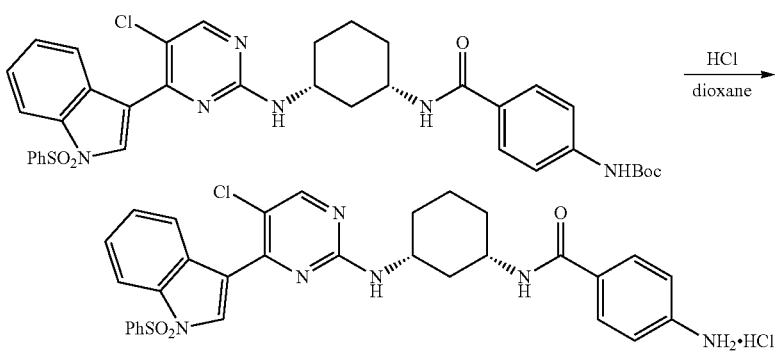

A solution of tert-butyl 4-((1S,3R)-3-(5-chloro-4-(1-(phenylsulfonyl)-1H-indol-3-yl)pyrimidin-2-ylamino)cyclohexylcarbamoyl)phenylcarbamate (1.14 g, 1.62 mmol) in DCM (10 mL) was treated with a 4M solution of HCl in dioxane (8.1 mL, 32.4 mmol) and stirred 3 h at rt. The resulting mixture was evaporated to dryness and afforded the title compound (948 mg, 1.62 mmol, 100%) as a pale yellow solid which was used in the next step without further purification.

4-amino-N-((1S,3R)-3-(5-chloro-4-(1H-indol-3-yl)pyrimidin-2-ylamino)cyclohexyl) benzamide

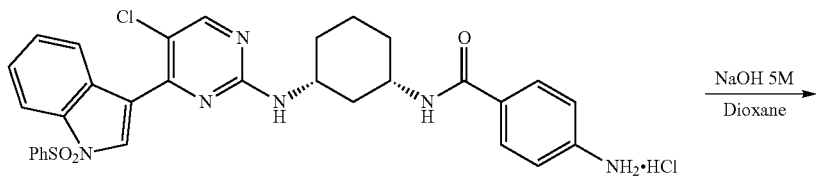

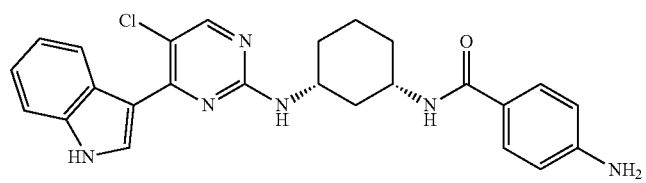

A solution of 4-amino-N-((1S,3R)-3-(5-chloro-4-(1-(phenylsulfonyl)-1H-indol-3-yl)pyrimidin-2-ylamino)cyclohexyl)benzamide.HCl (1.72 g, 3.10 mmol) and NaOH 5M (9.3 mL, 46.5 mmol) in dioxane (20 mL) was stirred 2.5 h at 75° C. The cooled mixture was concentrated, diluted with DCM (100 mL) and H₂O (20 mL). The layers were separated and the aqueous layer was extracted with DCM (3×20 mL), dried over MgSO₄, filtered, evaporated to dryness and afforded the title compound (1.20 g, 2.60 mmol, 84%) as a white solid which was used in the next step without further purification.

4-((E)-4-bromobut-2-enamido)-N-((1S,3R)-3-(5-chloro-4-(1H-indol-3-yl)pyrimidin-2-ylamino)cyclohexyl)benzamide

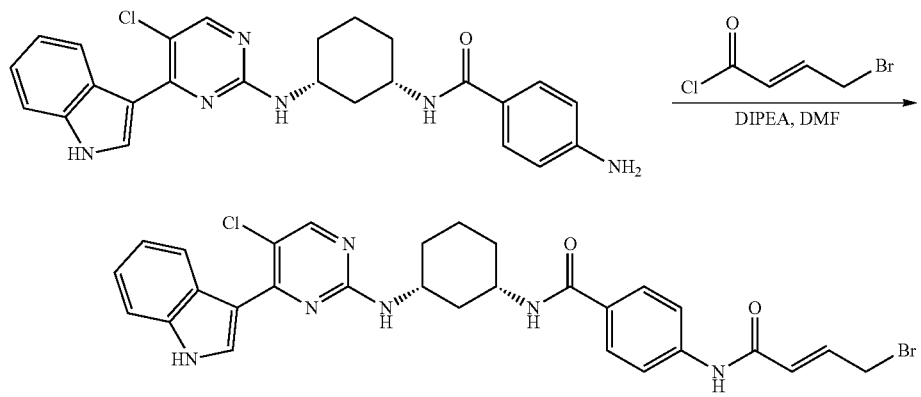

A cold solution (−60° C.) of 4-amino-N-((1S,3R)-3-(5-chloro-4-(1H-indol-3-yl)pyrimidin-2-ylamino)cyclohexyl)benzamide (1.47 g, 3.19 mmol) and DIPEA (1.67 ml, 9.57 mmol) in 3:1 THF/NMP (30 mL) was treated with a 54.2 mg/mL solution of (E)-4-bromobut-2-enoyl chloride (10.8 mL, 3.19 mmol) in THF. After 16 h at (−60° C.), SiO₂ (5 g) was added and the mixture was evaporated to dryness. The residue was purified by SiO₂ chromatography (DCM/THF 0 to 70% gradient) and afforded the title compound (1.17 g, 1.92 mmol, 60%) as a white solid.

N-((1S,3R)-3-(5-chloro-4-(1H-indol-3-yl)pyrimidin-2-ylamino)cyclohexyl)-4-((E)-4-morpholinobut-2-enamido)benzamide

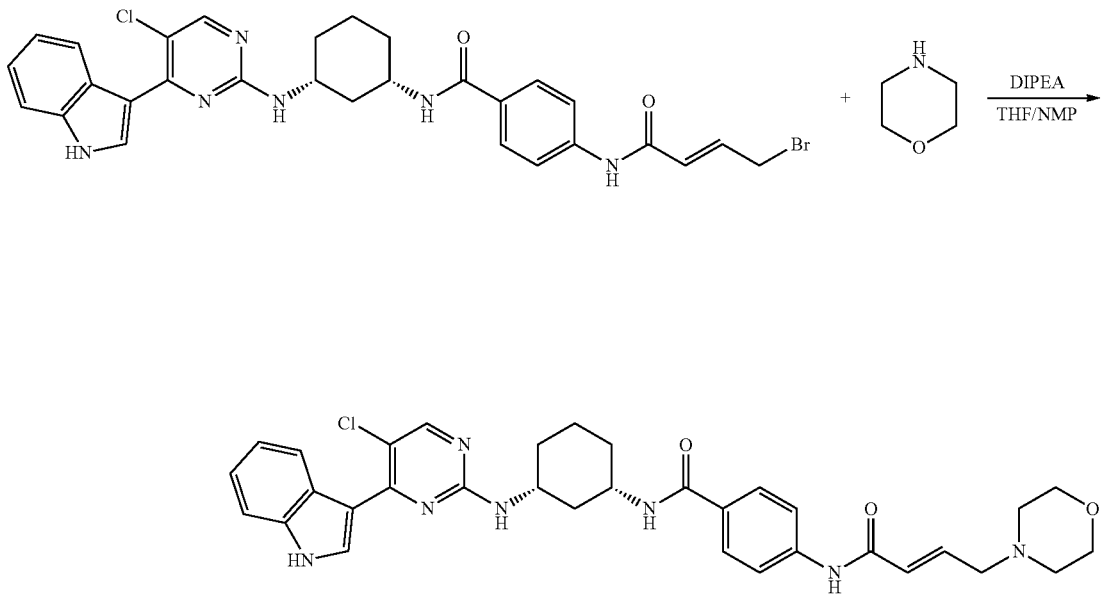

A cooled (−40° C.) solution of 4-((E)-4-bromobut-2-enamido)-N-((1S,3R)-3-(5-chloro-4-(1H-indol-3-yl)pyrimidin-2-ylamino)cyclohexyl)benzamide (102.05 mg, 0.1678 mmol) and DIPEA (0.1678 mmol) in 2:1 THF/NMP (2.5 mL) was treated with morpholine (0.5033 mmol) and stirred overnight at rt. The volatiles were removed by evaporation and the residue was purified by reverse phase chromatography (C$_{18}$, H$_2$O/ACN+0.1% HCO$_2$H 0 to 60% gradient) and afforded the title compound (53.0 mg, 0.086 mmol, 51%) as a creamy solid after lyophilisation. $^1$H NMR (500 MHz, d$_6$-DMSO) δ 11.82 (brs, 1H), 10.24 (s, 1H), 8.61 (brs, 1H), 8.47 (s, 1H), 8.26 (s, 1H), 8.21 (d, J=7.9 Hz, 1H), 7.82 (d, J=8.8 Hz, 2H), 7.70 (d, J=8.8 Hz, 2H), 7.49 (d, J=8.9 Hz, 1H), 7.30 (d, J=8.1 Hz, 1H), 7.23-7.11 (m, 2H), 6.74 (dt, J=13.6, 7.8 Hz, 1H), 6.29 (d, J=15.4 Hz, 1H), 3.96 (brs, 3H), 3.60 (t, 4H), 3.13 (dd, J=5.8, 1.3 Hz, 2H), 2.39 (brs, 4H), 2.20 (brs, 1H), 2.01 (brs, 1H), 1.88 (brs, 2H), 1.45 (brs, 2H), 1.36-1.20 (m, 2H); MS (m/z): 614.67 [M+1]$^+$.

Example 6. N-((1S,3R)-3-(5-chloro-4-(1H-indol-3-yl)pyrimidin-2-ylamino)cyclohexyl)-4-((E)-4-(4-methylpiperazin-1-yl)but-2-enamido)benzamide (Compound 111)

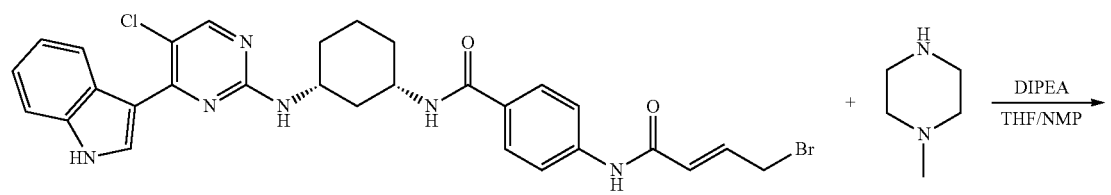

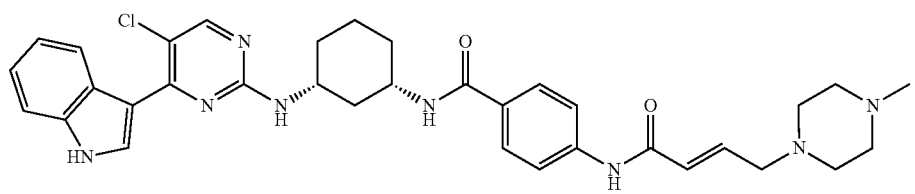

A cooled (−20° C.) solution of 4-((E)-4-bromobut-2-enamido)-N-((1S,3R)-3-(5-chloro-4-(1H-indol-3-yl)pyrimidin-2-ylamino)cyclohexyl)benzamide (105 mg, 0.173 mmol) and DIPEA (0.173 mmol) in 2:1 THF/NMP (2.5 mL) was treated with N-methylpiperazine (0.518 mmol) and stirred 2 h at rt. The volatiles were removed by evaporation and the residue was purified by reverse phase chromatography (C$_{18}$, H$_2$O/ACN+0.1% HCO$_2$H 0 to 60% gradient) and afforded the title compound (57.6 mg, 0.092 mmol, 53%) as a pale yellow solid after lyophilisation. $^1$H NMR (500 MHz, d$_6$-DMSO) δ 11.83 (s, 1H), 10.24 (s, 1H), 8.60 (s, 1H), 8.46 (s, 1H), 8.25 (s, 1H), 8.23-8.14 (m, 2H), 7.81 (d, J=8.8 Hz, 2H), 7.70 (d, J=8.8 Hz, 2H), 7.54-7.42 (m, 1H), 7.29 (d, J=8.0 Hz, 1H), 7.26-7.11 (m, 2H), 6.74 (dt, J=15.4, 5.9 Hz, 1H), 6.27 (d, J=15.4 Hz, 1H), 3.94 (s, 2H), 3.11 (d, J=4.8 Hz, 2H), 2.36 (d, J=1.8 Hz, 6H), 2.25-2.11 (m, 4H), 2.11-1.93 (m, 1H), 1.93-1.69 (m, 2H), 1.45 (s, 2H), 1.37-1.17 (m, 2H); MS (m/z): 627.71 [M+1]$^+$.

Example 7. 4-acrylamido-N-((1S,3R)-3-(5-chloro-4-(1H-indol-3-yl)pyrimidin-2-ylamino)cyclohexyl)benzamide (Compound 112)

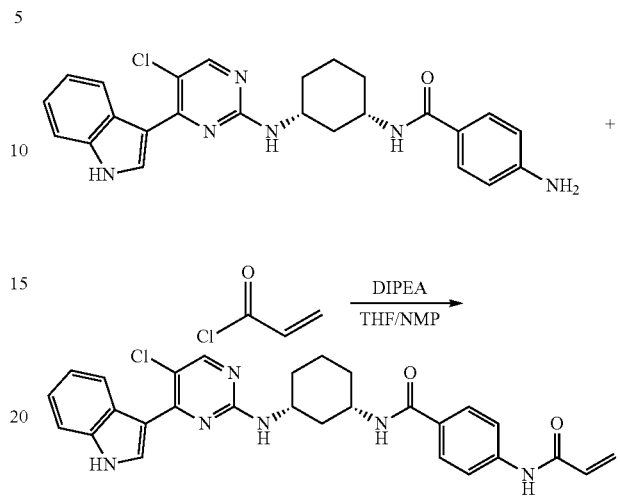

A cold (−60° C.) solution of 4-amino-N-((1S,3R)-3-(5-chloro-4-(1H-indol-3-yl)pyrimidin-2-ylamino)cyclohexyl)benzamide prepared as in Example 1 (100 mg, 0.2169 mmol) and DIPEA (0.651 mmol) in 7:1 THF/NMP (8 mL) was treated with acryloyl chloride (0.228 mmol). After 30 min at −60° C., the mixture was warmed to rt and evaporated to dryness. The residue was purified by reverse phase chromatography (C$_{18}$, H$_2$O/ACN+0.1% HCO$_2$H 70 to 100% gradient) and afforded the title compound (45.0 mg, 0.087 mmol, 40%) as a creamy solid after lyophilisation. $^1$H NMR (500 MHz, d$_6$-DMSO) δ 11.82 (s, 1H), 10.33 (s, 1H), 8.60 (s, 1H), 8.46 (s, 1H), 8.30-8.13 (m, 2H), 7.83 (d, J=8.8 Hz, 2H), 7.72 (d, J=8.8 Hz, 2H), 7.49 (d, J=9.1 Hz, 1H), 7.30 (d, J=8.1 Hz, 1H), 7.21 (s, 2H), 6.44 (dd, J=17.0, 10.2 Hz, 1H), 6.28 (dd, J=17.0, 1.9 Hz, 1H), 5.78 (dd, J=10.1, 1.9 Hz, 1H), 3.95 (s, 2H), 2.21 (s, 1H), 2.08 (d, J=6.4 Hz, 1H), 1.88 (d, J=27.3 Hz, 2H), 1.45 (s, 2H), 1.30 (d, J=11.3 Hz, 2H); MS (m/z): 515.57 [M+1]+.

Example 8. N-((1S,3R)-3-(5-chloro-4-(1H-indol-3-yl)pyrimidin-2-ylamino)cyclohexyl)-4-methacrylamidobenzamide (Compound 113)

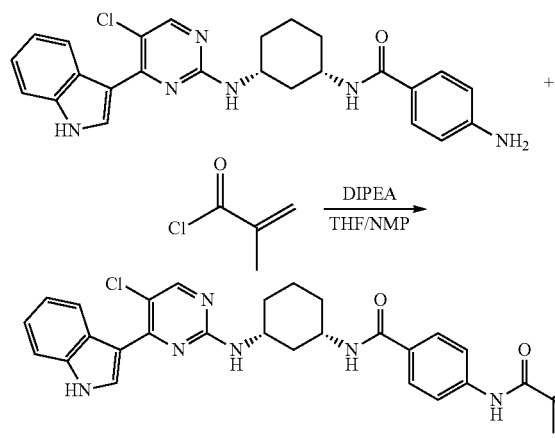

A cold (−60° C.) solution of 4-amino-N-((1S,3R)-3-(5-chloro-4-(1H-indol-3-yl)pyrimidin-2-ylamino)cyclohexyl)benzamide prepared as in Example 1 (100 mg, 0.217 mmol) and DIPEA (0.651 mmol) in 7:1 THF/NMP (8 mL) was treated with methacryloyl chloride (0.228 mmol). After 2 h at −60° C., the mixture was warmed to rt and evaporated to dryness. The residue was purified by reverse phase chromatography ($C_{18}$, $H_2O$/ACN+0.1% $HCO_2H$ 70 to 100% gradient) and afforded the title compound (38.0 mg, 0.072 mmol, 33%) as a light yellow solid after lyophilisation. $^1H$ NMR (500 MHz, $d_6$-DMSO) δ 11.83 (s, 1H), 9.95 (s, 1H), 8.58 (br s, 1H), 8.46 (s, 1H), 8.32-8.15 (m, 2H), 7.81 (d, J=8.8 Hz, 2H), 7.75 (d, J=8.8 Hz, 2H), 7.49 (d, J=8.8 Hz, 1H), 7.30 (d, J=8.1 Hz, 1H), 7.26-7.10 (m, 2H), 5.83 (s, 1H), 5.54 (s, 1H), 3.94 (br s, 2H), 2.21 (br s, 1H), 2.06-1.98 (m, 1H), 1.95 (s, 3H), 1.90-1.80 (m, 2H), 1.52-1.38 (m, 2H), 1.38-1.08 (m, 2H); MS (m/z): 529.62 $[M+1]^+$.

Example 9. (1S,3R,E)-3-(5-chloro-4-(1H-indol-3-yl)pyrimidin-2-ylamino)-N-(4-(4-(dimethylamino)but-2-enamido)phenyl)cyclohexanecarboxamide (Compound 114)

(1S,3R)-methyl 3-(tert-butoxycarbonylamino)cyclohexanecarboxylate

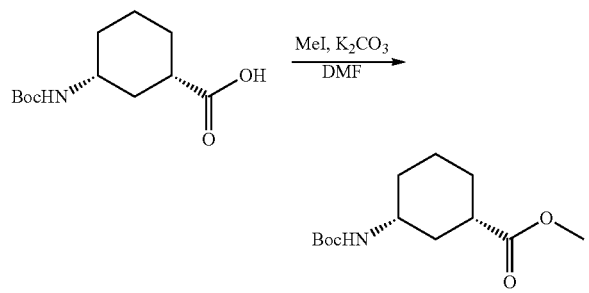

A solution of (1R,3S)-3-(tert-butoxycarbonylamino)cyclohexanecarboxylic acid (prepared following Tetrahedron: Asymmetry 2010 (21), 864-866) (1.0 g, 4.11 mmol), $K_2CO_3$ (474 mg, 3.43 mmol) and MeI (0.21 mL, 3.43 mmol) in DMF (8 mL) was stirred 72 h at rt. The resulting mixture was diluted with $H_2O$ (30 mL) and EtOAc (100 mL). The layers were separated and the aqueous layer was extracted with EtOAc (3×50 mL). The combined organic layers were dried over $MgSO_4$, filtered and evaporated to dryness leaving the title compound (1.35 g, 4.11 mmol, 100%) as a light orange solid which was used in the next step without further purification.

(1S,3R)-methyl 3-aminocyclohexanecarboxylate.HCl

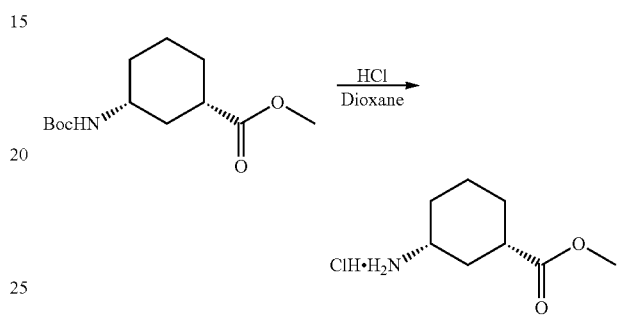

A solution of (1S,3R)-methyl 3-(tert-butoxycarbonylamino)cyclohexanecarboxylate (1.058 g, 4.111 mmol) in DCM (20.6 mL) was treated with a 4M solution of HCl in dioxane (10.3 mL, 10.3 mmol) and stirred for 16 h. The mixture was concentrated to dryness leaving the title compound (739 mg, 3.81 mmol, 93%) as a light yellow solid which was used in the next step without further purification.

(1S,3R)-methyl 3-(5-chloro-4-(1-(phenylsulfonyl)-1H-indol-3-yl)pyrimidin-2-ylamino)cyclohexanecarboxylate

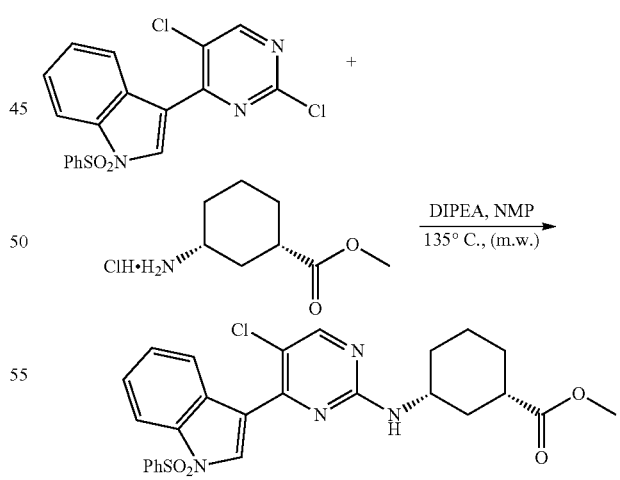

A solution of 3-(2,5-dichloropyrimidin-4-yl)-1-(phenylsulfonyl)-1H-indole (1.401 g, 3.464 mmol), (1S,3R)-methyl 3-aminocyclohexanecarboxylate.HCl (639 mg, 3.299 mmol) and DIPEA (1.7 mL, 9.90 mmol) in NMP (13 mL) was heated at 135° C. (microwave) for 25 min. The cooled mixture was diluted with EtOAc (50 mL), washed with $H_2O$ (15 mL), brine (15 mL), dried over $MgSO_4$, filtered and evaporated to dryness. The residue was purified by SiO₂ chromatography (DCM/EtOAc 0 to 10% gradient) and afforded the title compound (900 mg, 1.71 mmol, 52%) as a white foam.

(1S,3R)-3-(5-chloro-4-(1-(phenylsulfonyl)-1H-indol-3-yl)pyrimidin-2-ylamino)cyclohexanecarboxylic acid

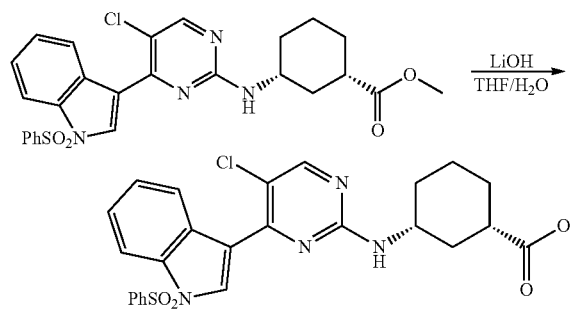

A solution of (1S,3R)-methyl 3-(5-chloro-4-(1-(phenylsulfonyl)-1H-indol-3-yl)pyrimidin-2-ylamino)cyclohexanecarboxylate (200 mg, 0.38 mmol) in THF was treated with a 0.55M solution of LiOH.H₂O in H₂O (0.8 mL, 0.4 mmol) and stirred over the weekend at rt. The mixture was diluted with EtOAc (20 mL) and acidified with 1M HCl until the pH reached 2-3. The layers were separated and the aqueous layer was extracted with EtOAc (3×10 mL), dried over MgSO₄, filtered and evaporated to dryness leaving the title compound (108 mg, 0.211 mmol, 56%) as a white solid which was used in the next step without further purification.

tert-butyl 4-((1S,3R)-3-(5-chloro-4-(1-(phenylsulfonyl)-1H-indol-3-yl)pyrimidin-2-ylamino)cyclohexanecarboxamido)phenylcarbamate

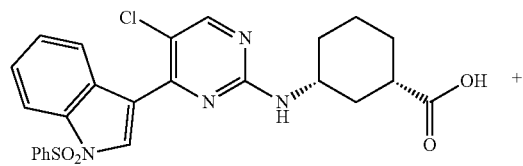

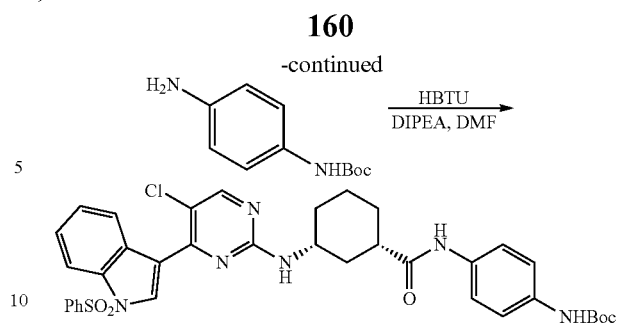

A solution of (1S,3R)-3-(5-chloro-4-(1-(phenylsulfonyl)-1H-indol-3-yl)pyrimidin-2-ylamino)cyclohexanecarboxylic acid (108 mg, 0.21 mmol) and tert-butyl 4-aminophenylcarbamate (44 mg, 0.21 mmol) in DCM (1.4 mL) was treated with HBTU (160 mg, 0.42 mmol) and DIPEA (0.11 mL, 0.63 mmol). The resulting mixture was stirred 18 h at rt and evaporated to dryness. The residue was purified by SiO₂ chromatography (Hex/EtOAc 15 to 100% gradient) and afforded the title compound (144 mg, 0.205 mmol, 97%) as a light yellow oil.

(1S,3R)—N-(4-aminophenyl)-3-(5-chloro-4-(1-(phenylsulfonyl)-1H-indol-3-yl)pyrimidin-2-ylamino)cyclohexanecarboxamide.TFA

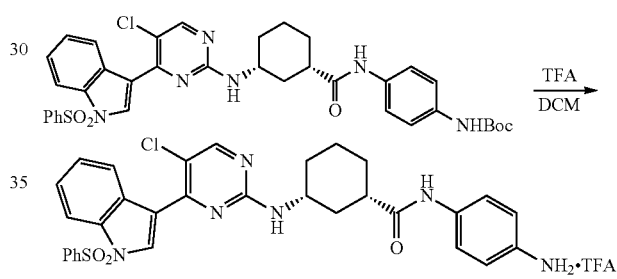

A solution of tert-butyl 4-((1S,3R)-3-(5-chloro-4-(1-(phenylsulfonyl)-1H-indol-3-yl)pyrimidin-2-ylamino)cyclohexanecarboxamido)phenylcarbamate (144 mg, 0.21 mmol) in DCM (1 mL) was treated with TFA (0.16 mL, 2.05 mmol) and stirred 1 h at rt. The mixture was evaporated to dryness and afforded the title compound (142 mg, 0.811 mmol, 97%) as a yellow solid.

(1S,3R)—N-(4-aminophenyl)-3-(5-chloro-4-(1H-indol-3-yl)pyrimidin-2-ylamino) cyclohexanecarboxamide

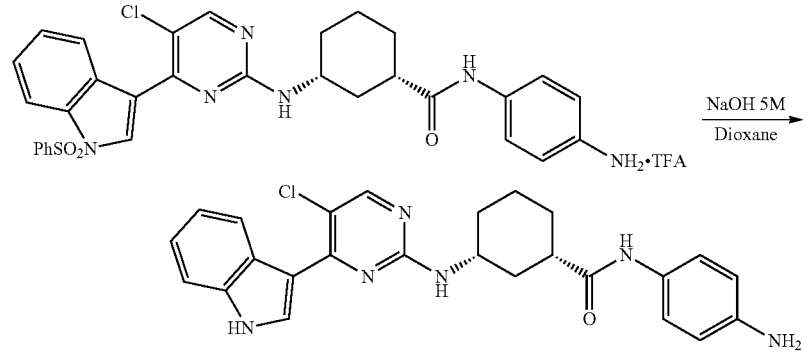

A solution of (1S,3R)—N-(4-aminophenyl)-3-(5-chloro-4-(1-(phenylsulfonyl)-1H-indol-3-yl)pyrimidin-2-ylamino)cyclohexanecarboxamide.TFA (142 mg, 0.20 mmol) in dioxane (1.4 mL) was treated with a 5M solution of NaOH in H$_2$O (0.81 mL, 4.07 mmol) and stirred at 75° C. for 3 h. The cooled mixture was evaporated to dryness and H$_2$O (2 mL) was added to the residue. The resulting solid was filtered, washed with H$_2$O (2×1 mL), dried under high vacuum leaving the title compound (90 mg, 0.195 mmol, 96%) as a white solid which was used in the next step without further purification.

(1S,3R,E)-3-(5-chloro-4-(1H-indol-3-yl)pyrimidin-2-ylamino)-N-(4-(4-(dimethylamino)but-2-enamido)phenyl)cyclohexanecarboxamide

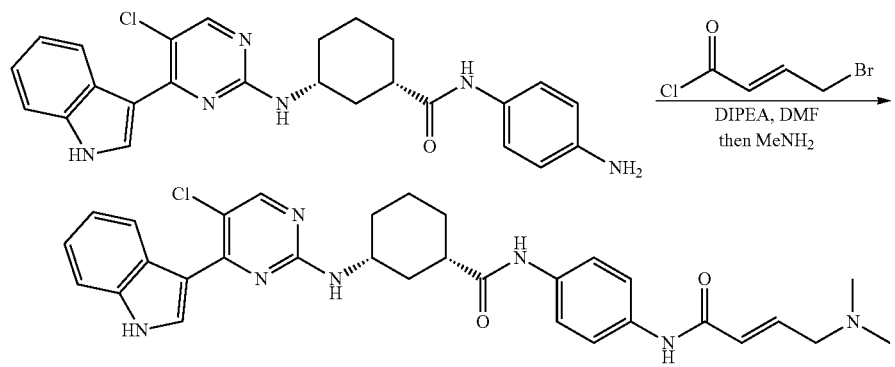

A cooled (−60° C.) solution of (1S,3R)—N-(4-aminophenyl)-3-(5-chloro-4-(1H-indol-3-yl)pyrimidin-2-ylamino)cyclohexanecarboxamide (79.0 mg, 0.171 mmol) and DIPEA (0.514 mmol) in 3:1 NMP/THF (7.0 mL) was treated with a 54.2 mg/mL solution of (E)-4-bromobut-2-enoyl chloride in DCM (0.180 mmol). The resulting mixture was stirred 1 h at −60° C. before addition of a 2M solution of dimethylamine in THF (0.514 mmol). The resulting mixture was warmed to rt before being evaporated to dryness. The residue was purified by reverse phase chromatography (C$_{18}$, H$_2$O/ACN+0.1% HCO$_2$H 5 to 60% gradient) and afforded the title compound (24.2 mg, 0.042 mmol, 25%) as a yellow solid after lyophilisation. $^1$H NMR (500 MHz, d$_6$-DMSO) δ 11.84 (s, 1H), 9.97 (s, 1H), 9.84 (s, 1H), 8.76-8.51 (m, 1H), 8.47 (s, 1H), 8.24 (s, J=14.8 Hz, 1H), 7.54 (q, J=9.2 Hz, 4H), 7.49 (d, J=7.5 Hz, 1H), 7.28 (d, J=7.7 Hz, 1H), 7.25-7.12 (m, 2H), 6.69 (dt, J=15.4, 5.9 Hz, 1H), 6.24 (d, J=15.4 Hz, 1H), 4.05-3.73 (m, 2H), 3.04 (d, J=4.9 Hz, 2H), 2.17 (s, 6H), 2.13-2.04 (m, 1H), 1.94-1.77 (m, 2H), 1.68-1.17 (m, 5H); MS (m/z): 572.59 [M+1]$^+$.

Example 10. N-((1S,3R)-3-(5-cyclopropyl-4-(1H-indol-3-yl)pyrimidin-2-ylamino) cyclohexyl)-4-((E)-4-(dimethylamino)but-2-enamido)benzamide (Compound 115)Benzyl (1S,3R)-3-aminocyclohexylcarbamate.HCl

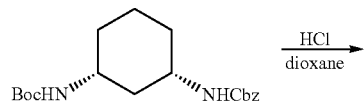

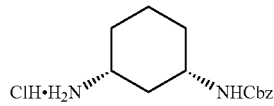

A solution of (1R,3S)-3-(Benzyloxycarbonylamino)cyclohexylamino 2,2-dimethylpropionate prepared similarly to Example 1 (1.50 g, 4.31 mmol) in DCM (43 mL) was treated with a 4M solution of HCl in dioxane (16 mL, 64.6 mmol) and stirred 2 h at rt. The resulting solution was evaporated to dryness and afforded the title compound (1.23 g, 4.31 mmol, 100%) as a white solid which was used in the next step without further purification.

Benzyl (1S,3R)-3-(5-chloro-4-(1-(phenylsulfonyl)-1H-indol-3-yl)pyrimidin-2-ylamino)cyclohexylcarbamate

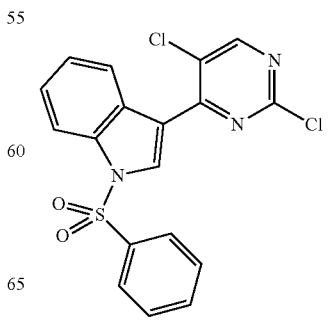

-continued

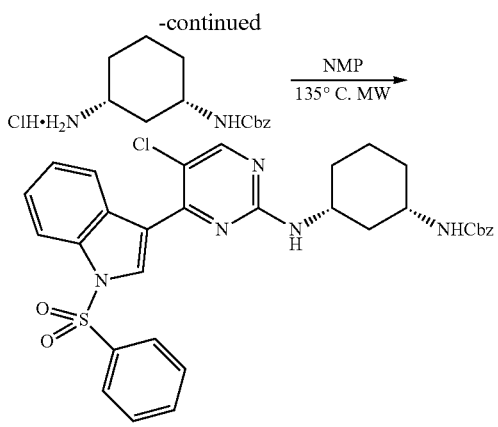

A solution of 3-(2,5-dichloropyrimidin-4-yl)-1-(phenylsulfonyl)-1H-indole (791 mg, 1.96 mmol), benzyl (1S,3R)-3-aminocyclohexylcarbamate (613 mg, 2.15 mmol) and diisopropylethylamine (0.75 mL, 4.31 mmol) in NMP (20.0 mL) was heated 30 min at 135° C. (mW). The mixture was diluted with EtOAc (100 mL), washed with H₂O (50 mL), brine (50 mL), dried (MgSO₄), filtered and evaporated to dryness. The residue was purified by SiO₂ chromatography (Hex/EtOAc 5 to 70% gradient), and afforded the title compound (1.04 g, 1.69 mmol, 40%) as a yellow solid.

Benzyl (1S,3R)-3-(5-cyclopropyl-4-(1-(phenylsulfonyl)-1H-indol-3-yl)pyrimidin-2-ylamino)cyclohexylcarbamate

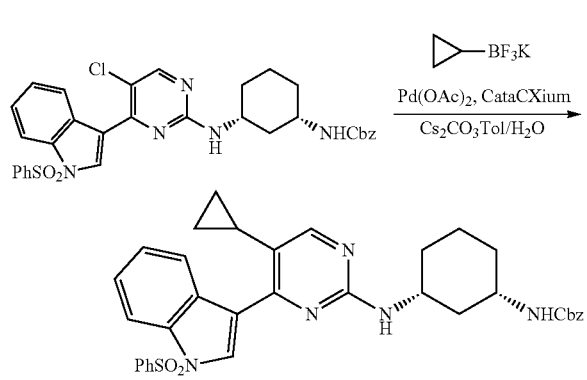

A degassed solution of benzyl (1S,3R)-3-(5-chloro-4-(1-(phenylsulfonyl)-1H-indol-3-yl)pyrimidin-2-ylamino)cyclohexylcarbamate (prepared similarly to Example 1) (500 mg, 0.812 mmol), Cs₂CO₃ (794 mg, 2.435 mmol) and potassium cyclopropyltrifluoroborate (360 mg, 2.435 mmol) in 2:1 tol/H₂O (15 mL) was treated with a premixed solution of Pd(OAc)₂ (9 mg, 0.04 mmol) and butyldi-1-adamantylphosphine (29 mg, 0.08 mmol) in degassed tol (2 mL) and heated at 140° C. (microwave) for 2 h. The cooled mixture was diluted with EtOAc (50 mL) and saturated NaHCO₃ (20 mL). The layers were separated and the aqueous layer was extracted with EtOAc (2×20 mL). The combined organic layers were dried over Na₂SO₄, filtered and evaporated to dryness. The residue was purified by SiO₂ chromatography (Hex/EtOAc 0 to 60% gradient) and afforded the title compound (324 mg, 0.521 mmol, 64%) as a pale yellow solid.

(1R,3S)—N¹-(5-cyclopropyl-4-(1-(phenylsulfonyl)-1H-indol-3-yl)pyrimidin-2-yl)cyclohexane-1,3-diamine

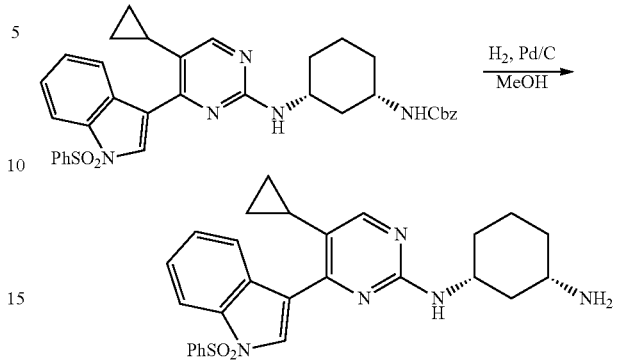

A degassed solution of Benzyl (1S,3R)-3-(5-cyclopropyl-4-(1-(phenylsulfonyl)-1H-indol-3-yl)pyrimidin-2-ylamino)cyclohexylcarbamate (778 mg, 1.250 mmol) in MeOH (60 mL) was treated with 10% wet Pd/C (150 mg) and stirred under H₂ (1 atm) for 6 h. The mixture was filtered on Celite® (MeOH) and the filtrate was evaporated to dryness affording the title compound (610 mg, 1.25 mmol, 75%) as a white foam which was used in the next step without further purification.

tert-butyl 4-((1S,3R)-3-(5-cyclopropyl-4-(1-(phenylsulfonyl)-1H-indol-3-yl)pyrimidin-2-ylamino)cyclohexylcarbamoyl)phenylcarbamate

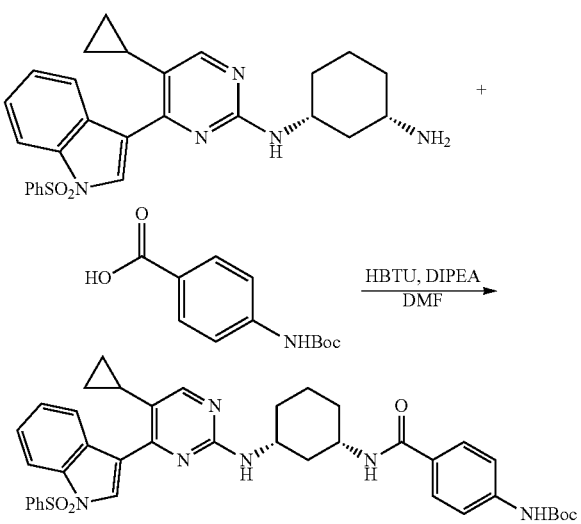

A solution of (1R,3S)—N¹-(5-cyclopropyl-4-(1-(phenylsulfonyl)-1H-indol-3-yl)pyrimidin-2-yl)cyclohexane-1,3-diamine (457 mg, 0.937 mmol) and 4-(tert-butoxycarbonylamino)benzoic acid (245 mg, 1.031 mmol) in DMF (10 mL) was treated with HBTU (533 mg, 1.406 mmol) and DIPEA (245 uL, 1.406 mmol). The resulting mixture was stirred overnight at rt and diluted with EtOAc (50 mL) and saturated NaHCO₃ (20 mL). The layers were separated and the aqueous layer was extracted with EtOAc (2×30 mL). The combined organic layers were dried over Na₂SO₄, filtered and evaporated to dryness leaving the title compound (662 mg, 0.936 mmol, 100%) as a yellow solid which was used in the next step without further purification.

tert-butyl 4-((1S,3R)-3-(5-cyclopropyl-4-(1H-indol-3-yl)pyrimidin-2-ylamino) cyclohexylcarbamoyl) phenylcarbamate

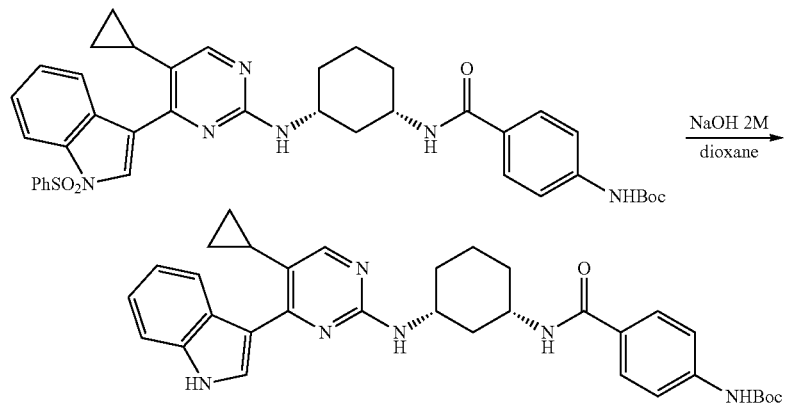

A solution of tert-butyl 4-((1S,3R)-3-(5-cyclopropyl-4-(1-(phenylsulfonyl)-1H-indol-3-yl)pyrimidin-2-ylamino)cyclohexylcarbamoyl)phenylcarbamate (663 mg, 0.938 mmol) in dioxane (10 mL) was treated with a 2M solution of NaOH (7 mL, 14 mmol) and heated at 70° C. for 1 h. The cooled mixture was diluted with MeTHF (20 mL) and the layers were separated. The aqueous layer was extracted with MeTHF (3×20 mL) and the combine organic layers were dried over Na$_2$SO$_4$, filtered and evaporated to dryness affording the title compound (531 mg, 0.937 mmol, 99.9%) as a pale yellow solid which was used in the next step without further purification.

4-amino-N-((1S,3R)-3-(5-cyclopropyl-4-(1H-indol-3-yl)pyrimidin-2-ylamino) cyclohexyl)benzamide-.HCl

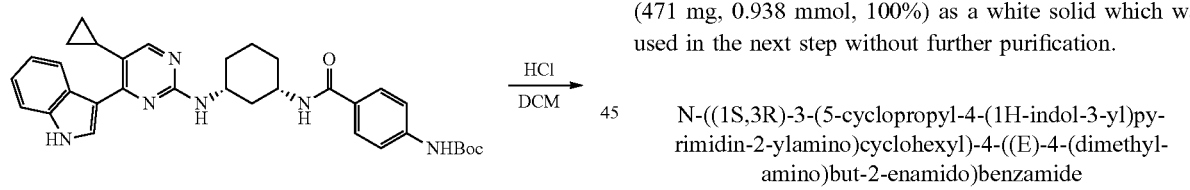

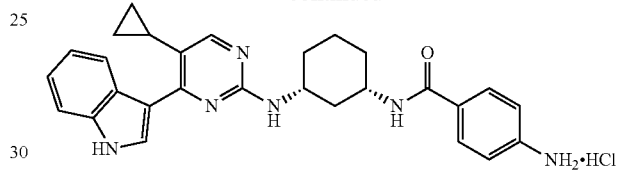

A solution of tert-butyl 4-((1S,3R)-3-(5-cyclopropyl-4-(1H-indol-3-yl)pyrimidin-2-ylamino) cyclohexylcarbamoyl)phenylcarbamate (531 mg, 0.938 mmol) in DCM (10 mL) was treated with a 4M solution of HCl in dioxane (3.50 mL, 14.0 mmol) and stirred 2 h at rt. The resulting mixture was evaporated to dryness and afforded the title compound (471 mg, 0.938 mmol, 100%) as a white solid which was used in the next step without further purification.

N-((1S,3R)-3-(5-cyclopropyl-4-(1H-indol-3-yl)pyrimidin-2-ylamino)cyclohexyl)-4-((E)-4-(dimethylamino)but-2-enamido)benzamide

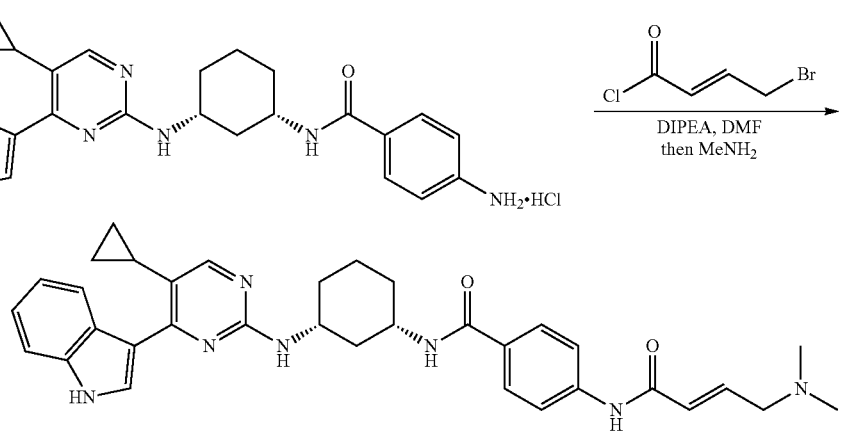

A cooled (−60° C.) solution of 4-amino-N-((1S,3R)-3-(5-cyclopropyl-4-(1H-indol-3-yl)pyrimidin-2-ylamino)cyclohexyl)benzamide.HCl (471 mg, 0.936 mmol) and DIPEA (4.68 mmol) in 4:1 NMP/THF (25 mL) was treated with a 54.2 mg/mL solution of (E)-4-bromobut-2-enoyl chloride in DCM (2.7 mL, 0.796 mmol). The resulting mixture was stirred 1 h at −60° C. before addition of a 2M solution of dimethylamine in THF (2.8 mL, 5.62 mmol). The resulting mixture was warmed to rt before being evaporated to dryness. The residue was purified by reverse phase chromatography (C$_{18}$, H$_2$O/ACN+0.1% HCO$_2$H 0 to 30% gradient) and afforded the title compounds (102 mg, 0.176 mmol, 19%) as a white solid after lyophilisation. $^1$H NMR (500 MHz, d$_6$-DMSO) δ 11.63 (s, 1H), 10.24 (s, 1H), 8.68 (brs, 1H), 8.29 (d, J=2.9 Hz, 1H), 8.19 (d, J=7.9 Hz, 1H), 8.05 (s, 1H), 7.81 (d, J=8.8 Hz, 2H), 7.70 (d, J=8.8 Hz, 2H), 7.47-7.45 (m, 1H), 7.17-7.15 (m, 2H), 6.81-6.72 (m, 2H), 6.29 (dt, 1H), 3.94 (brs, 2H), 3.05 (dd, J=5.9, 1.3 Hz, 2H), 2.21-2.17 (m, 7H), 2.05-1.77 (m, 4H), 1.49-1.41 (m, 2H), 1.30-1.24 (m, 2H), 0.97-0.95 (m, 2H), 0.59 (brs, 2H); MS (m/z): 578.76 [M+1]$^+$.

Example 11. N-((1S,3R)-3-(5-chloro-4-(pyridin-3-yl)pyrimidin-2-ylamino)cyclohexyl)-4-((E)-4-(dimethylamino)but-2-enamido)benzamide (Compound 116)

tert-butyl (1S,3R)-3-(5-chloro-4-(pyridin-3-yl)pyrimidin-2-ylamino)cyclohexylcarbamate

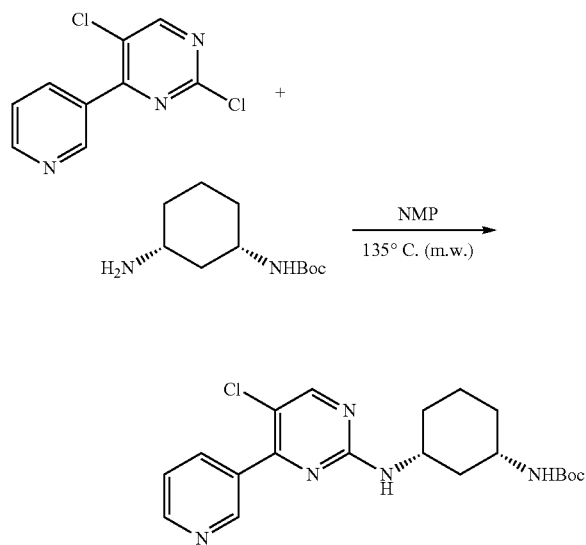

A solution of 2,5-dichloro-4-(pyridin-3-yl)pyrimidine (173 mg, 0.0.764 mmol), tert-butyl (1S,3R)-3-aminocyclohexylcarbamate (182 mg, 0.849 mmol) and DIPEA (0.16 mL, 0.892 mmol) in NMP 7.1 mL) was heated at 135° C. (microwave) for 60 min. The cooled mixture was diluted with EtOAc (30 mL), washed with H$_2$O (10 mL), brine (10 mL), dried over MgSO$_4$, filtered and evaporated to dryness. The residue was purified by SiO$_2$ chromatography (DCM/EtOAc 0 to 70% gradient) and afforded the title compound (185 mg, 0.458 mmol, 54%) as a light yellow foam.

(1R,3S)—N$^1$-(5-chloro-4-(pyridin-3-yl)pyrimidin-2-yl)cyclohexane-1,3-diamine.HCl

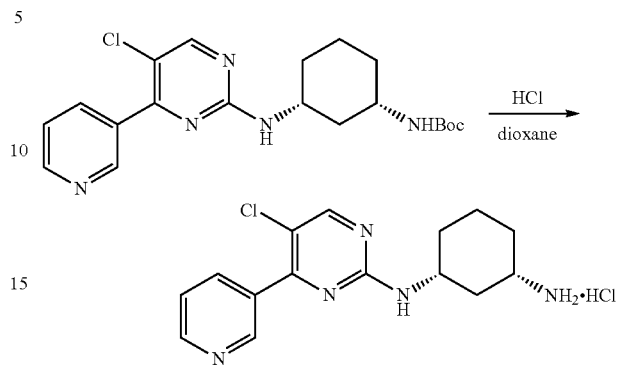

A solution of tert-butyl (1S,3R)-3-(5-chloro-4-(pyridin-3-yl)pyrimidin-2-ylamino) cyclohexylcarbamate (210 mg, 0.520 mmol) in DCM (2.6 mL) was treated with a 4M solution of HCl in dioxane (1.3 mL, 5.130 mmol) and stirred 2 h at rt. The resulting mixture was evaporated to dryness and afforded the title compound (177 mg, 0.520 mmol, 100%) as a light yellow solid which was used in the next step without further purification.

tert-butyl 4-((1S,3R)-3-(5-chloro-4-(pyridin-3-yl) pyrimidin-2-ylamino) cyclohexylcarbamoyl)phenylcarbamate

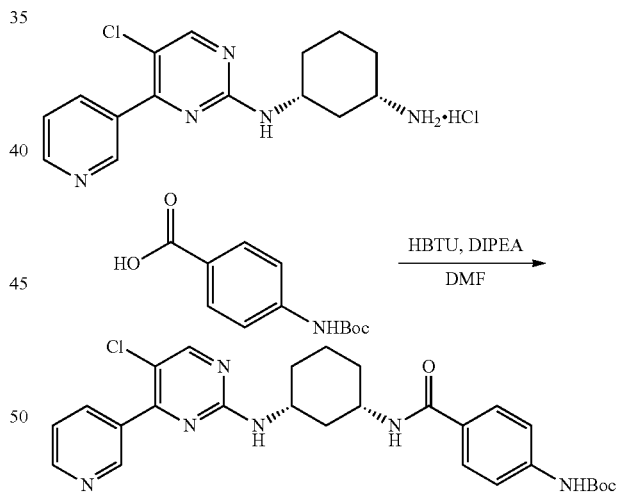

A solution of (1R,3S)—N$^1$-(5-chloro-4-(pyridin-3-yl)pyrimidin-2-yl)cyclohexane-1,3-diamine.HCl (297 mg, 0.783 mmol) and 4-(tert-butoxycarbonylamino)benzoic acid (149 mg, 0.626 mmol) in DMF (5.2 mL) was treated with HBTU (297 mg, 0.783 mmol) and DIPEA (2.087 mmol). The resulting mixture was stirred overnight at rt and diluted with EtOAc (30 mL) and saturated NaHCO$_3$ (15 mL). The layers were separated and the aqueous layer was extracted with EtOAc (2×30 mL). The combined organic layers were dried over MgSO$_4$, filtered and evaporated to dryness. The residue was purified by SiO$_2$ chromatography (DCM/EtOAc 0 to 100% gradient) and afforded the title compound (227 mg, 0.434 mmol, 83%) as a light yellow solid.

4-amino-N-((1S,3R)-3-(5-chloro-4-(pyridin-3-yl)
pyrimidin-2-ylamino) cyclohexyl)benzamide

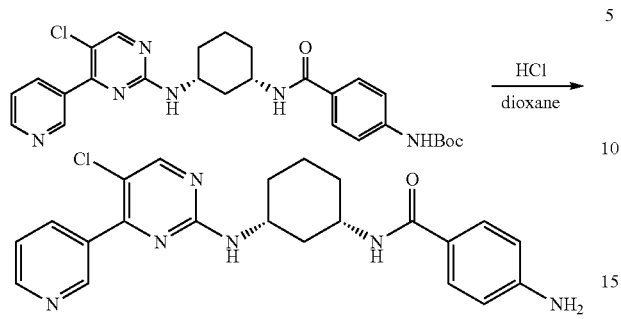

A solution of tert-butyl 4-((1S,3R)-3-(5-chloro-4-(pyridin-3-yl)pyrimidin-2-ylamino)cyclohexylcarbamoyl)phenylcarbamate (166 mg, 0.317 mmol) in DCM (3.2 mL) was treated with a 4M solution of HCl in dioxane (0.79 mL, 3.17 mmol) and stirred 16 h at rt. The resulting mixture was evaporated to dryness and diluted with EtOAc (20 mL) and saturated NaHCO$_3$ (10 mL). The layers were separated and the aqueous layer was extracted with EtOAc (3×15 mL). The combined organic layers were dried over MgSO$_4$, filtered and evaporated to dryness affording the title compound (134 mg, 0.317 mmol, 100%) as a white solid which was used in the next step without further purification.

N-((1S,3R)-3-(5-chloro-4-(pyridin-3-yl)pyrimidin-2-
ylamino)cyclohexyl)-4-((E)-4-(dimethylamino)but-
2-enamido)benzamide

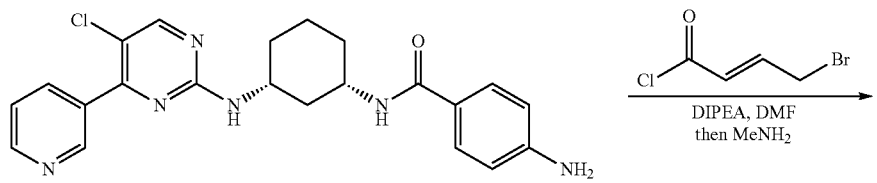

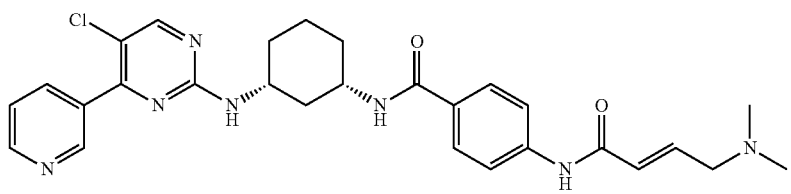

A cooled (−60° C.) solution of 4-amino-N-((1S,3R)-3-(5-chloro-4-(pyridin-3-yl)pyrimidin-2-ylamino)cyclohexyl)benzamide (125 mg, 0.296 mmol) and DIPEA (0.887 mmol) in 3:1 NMP/THF (9.0 mL) was treated with a 54.2 mg/mL solution of (E)-4-bromobut-2-enoyl chloride in DCM (1.04 mL, 0.310 mmol). The resulting mixture was stirred 30 min at −60° C. before addition of a 2M solution of dimethylamine in THF (1.8 mL, 3.55 mmol). The resulting mixture was warmed to rt before being evaporated to dryness. The residue was purified by reverse phase chromatography (C$_{18}$, H$_2$O/ACN+0.1% HCO$_2$H 0 to 100% gradient) and afforded the title compounds (40 mg, 0.075 mmol, 25%) as a white solid after lyophilisation. $^1$H NMR (500 MHz, d$_6$-DMSO) δ 10.25 (s, 1H), 8.88 (br s, 1H), 8.69 (d, J=3.6 Hz, 1H), 8.46 (s, 1H), 8.18 (d, J=7.6 Hz, 1H), 8.13 (br s, 1H), 7.80 (d, J=8.5 Hz, 2H), 7.70 (d, J=8.5 Hz, 2H), 7.68 (br s, 1H), 7.55 (br s, 1H), 6.75 (dt, J=15.2, 5.9 Hz, 1H), 6.28 (d, J=15.3 Hz, 1H), 3.83-3.80 (m, 2H), 3.06 (d, J=5.4 Hz, 2H), 2.17 (s, 6H), 2.14-2.11 (m, 1H), 1.91 (d, J=10.4 Hz, 1H), 1.79 (t, J=10.9 Hz, 2H), 1.37 (dd, J=23.7, 11.9 Hz, 2H), 1.24 (dt, J=41.9, 20.1 Hz, 2H); MS (m/z): 534.59 [M+1]$^+$.

Example 12. N-((1S,3R)-3-(5-cyano-4-(1H-indol-3-yl)pyrimidin-2-ylamino)cyclohexyl)-4-((E)-4-(dimethylamino)but-2-enamido)benzamide (Compound 117)

4-amino-N-((1S,3R)-3-(5-cyano-4-(1-(phenylsulfonyl)-1H-indol-3-yl)pyrimidin-2-ylamino) cyclohexyl)benzamide

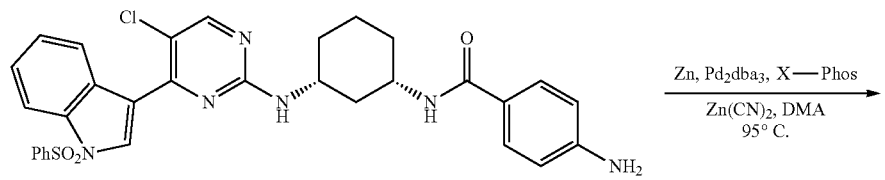

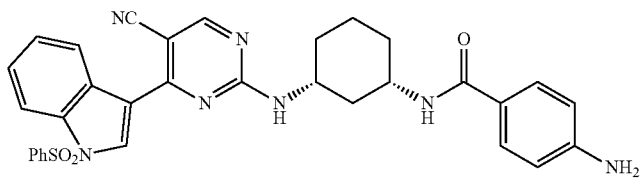

A degassed solution of 4-amino-N-((1S,3R)-3-(5-chloro-4-(1-(phenylsulfonyl)-1H-indol-3-yl)pyrimidin-2-ylamino) cyclohexyl)benzamide (prepared as in Example 1) (222 mg, 0.369 mmol) in DMA (4 mL) was treated with a premixed and degassed solution of Zn (2.4 mg, 0.04 mmol), Pd$_2$dba$_3$ (33.8 mg, 0.04 mmol), X-Phos (35.2 mg, 0.07 mmol) and Zn(CN)$_2$ (26.0 mg, 0.22 mmol) in DMA (3 mL) and heated at 95° C. for 18 h. The cooled mixture was diluted with EtOAc (40 mL), washed with H$_2$O (10 mL), brine (10 mL), dried over MgSO$_4$, filtered and evaporated to dryness. The residue was purified by SiO$_2$ chromatography (DCM/EtOAc 0 to 70% gradient) and afforded the title compound (113 mg, 0.191 mmol, 52%) as a light yellow solid.

4-amino-N-((1S,3R)-3-(5-cyano-4-(1H-indol-3-yl)pyrimidin-2-ylamino)cyclohexyl) benzamide

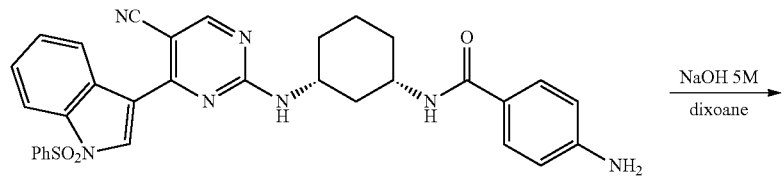

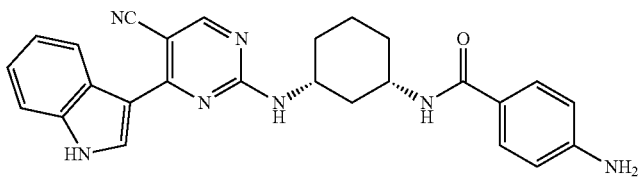

A solution of 4-amino-N-((1S,3R)-3-(5-cyano-4-(1-(phenylsulfonyl)-1H-indol-3-yl)pyrimidin-2-ylamino)cyclohexyl)benzamide (33 mg, 0.0549 mmol) in dioxane (3.8 mL) was treated with a 5M solution of NaOH (0.275 mmol) and heated at 50° C. for 43 h. The cooled mixture was treated with a 1M solution of HCl until a pH of 3 was reached and the mixture was evaporated to dryness. The residue was purified by reverse phase chromatography ($C_{18}$, $H_2O$/ACN+ 0.1% $HCO_2H$ 80 to 100% gradient) and afforded the title compound (48 mg, 0.106 mmol, 55%) as a white solid after lyophilisation.

N-((1S,3R)-3-(5-cyano-4-(1H-indol-3-yl)pyrimidin-2-ylamino)cyclohexyl)-4-((E)-4-(dimethylamino)but-2-enamido)benzamide

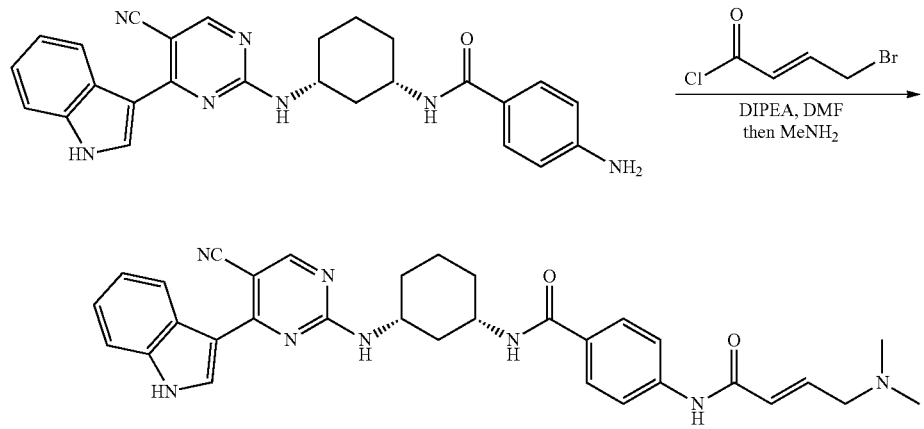

A cooled (−60° C.) solution of 4-amino-N-((1S,3R)-3-(5-cyano-4-(1H-indol-3-yl)pyrimidin-2-ylamino)cyclohexyl)benzamide (50.6 mg, 0.112 mmol) and DIPEA (0.336 mmol) in 3:1 NMP/THF (4.0 mL) was treated with a 54.2 mg/mL solution of (E)-4-bromobut-2-enoyl chloride in DCM (0.673 mmol). The resulting mixture was stirred 30 min at −60° C. before addition of a 2M solution of dimethylamine in THF (0.673 mmol). The resulting mixture was warmed to rt before being evaporated to dryness. The residue was purified by reverse phase chromatography ($C_{18}$, $H_2O$/ACN+0.1% $HCO_2H$ 0 to 100% gradient) and afforded the title compounds (47 mg, 0.083 mmol, 75%) as a white solid after lyophilisation. $^1H$ NMR (500 MHz, $d_6$-DMSO) rotamer 1 δ 12.00 (br s, 1H), 10.25 (d, J=3.4 Hz, 1H), 8.57 (s, 1H), 8.55-8.41 (m, 2H), 8.27-8.11 (m, 2H), 7.81 (d, J=8.6 Hz, 2H), 7.76-7.64 (m, 2H), 7.52 (dd, J=12.5, 8.1 Hz, 1H), 7.32-7.15 (m, 2H), 6.75 (dt, J=15.3, 5.8 Hz, 1H), 6.27 (d, J=15.3 Hz, 1H), 4.12-3.76 (m, 2H), 3.06 (d, J=5.7 Hz, 2H), 2.24 (d, J=10.0 Hz, 1H), 2.17 (s, 6H), 2.04 (d, J=7.0 Hz, 1H), 1.95-1.77 (m, 2H), 1.58-1.38 (m, 2H), 1.39-1.24 (m, 2H). Rotamer 2 δ 11.96 (br s, 1H), 10.25 (d, J=3.4 Hz, 1H), 8.71 (d, J=8.2 Hz, 1H), 8.65 (s, 1H), 8.55-8.41 (m, 1H), 8.27-8.11 (m, 2H), 7.81 (d, J=8.6 Hz, 2H), 7.76-7.64 (m, 2H), 7.52 (dd, J=12.5, 8.1 Hz, 1H), 7.32-7.15 (m, 2H), 6.75 (dt, J=15.3, 5.8 Hz, 1H), 6.27 (d, J=15.3 Hz, 1H), 4.12-3.76 (m, 2H), 3.06 (d, J=5.7 Hz, 2H), 2.24 (d, J=10.0 Hz, 1H), 2.17 (s, 6H), 2.04 (d, J=7.0 Hz, 1H), 1.95-1.77 (m, 2H), 1.58-1.38 (m, 2H), 1.39-1.24 (m, 2H); MS (m/z): 563.64 [M+1]+.

Example 13. N-((1S,3R)-3-(5-chloro-4-(1H-indol-3-yl)pyrimidin-2-ylamino)cyclohexyl)-4-(3-methylbut-2-enamido)benzamide (Compound 118)

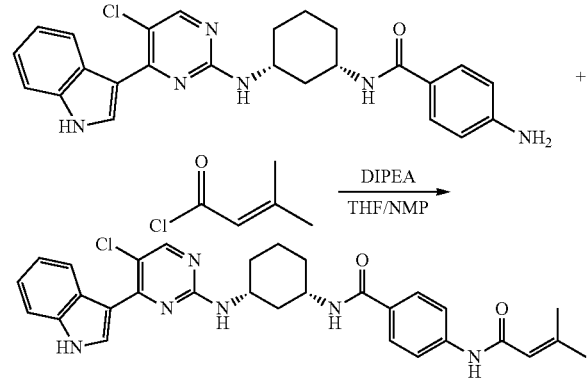

A cold (−60° C.) solution of 4-amino-N-((1S,3R)-3-(5-chloro-4-(1H-indol-3-yl)pyrimidin-2-ylamino)cyclohexyl)benzamide prepared as in Example 1 (50.0 mg, 0.1085 mmol) and DIPEA (0.325 mmol) in 7:1 THF/NMP (4 mL) was treated with 3,3-dimethyl acryloyl chloride (0.114 mmol). After 2 h at −60° C., the mixture was warmed up to rt and evaporated to dryness. The residue was purified by reverse phase chromatography ($C_{18}$, $H_2O$/ACN+0.1% $HCO_2H$ 70 to 100% gradient) and afforded the title compound (26.0 mg, 0.048 mmol, 44%) as a light yellow solid after lyophilisation. $^1H$ NMR (500 MHz, $d_6$-DMSO) δ 11.82 (s, 1H), 10.01 (s, 1H), 8.61 (s, 1H), 8.46 (s, 1H), 8.25 (s, 1H), 8.19 (d, J=7.9 Hz, 1H), 7.79 (d, J=8.7 Hz, 2H), 7.67 (d, J=8.7

Hz, 2H), 7.48 (d, J=8.6 Hz, 1H), 7.29 (d, J=8.0 Hz, 1H), 7.21 (s, 2H), 5.87 (s, 1H), 4.11 (d, J=4.7 Hz, 1H), 3.94 (br s, 1H), 3.17 (d, J=4.3 Hz, 2H), 2.21 (d, J=40.8 Hz, 1H), 2.16 (s, 3H), 2.04-1.97 (m, 1H), 1.87 (s, 3H), 1.50-1.37 (m, 2H), 1.37-1.20 (m, 2H); MS (m/z): 543.61 [M+1]$^+$.

Example 14. (+/−)-N-(3-(5-chloro-4-(1H-indol-3-yl) pyrimidin-2-ylamino)-5-fluorocyclohexyl)-4-((E)-4-(dimethylamino)but-2-enamido)benzamide (Compound 119)

(+/−)-1,3-diazido-5-fluorocyclohexane

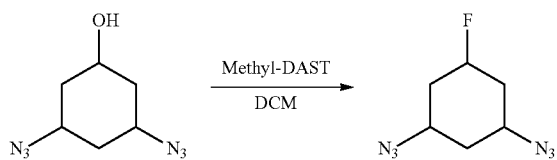

A cooled (−78° C.) solution of (+/−)-3,5-diazidocyclohexanol (prepared following New J. Chem., 2005, 29, 1152-1158) in DCM (30 mL) was treated dropwise with Me-DAST (2.74 mmol) and stirred 18 h at this temperature. A saturated solution of NaHCO$_3$ (10 mL) was added, the layers were separated and the aqueous layer was extracted with EtOAc (3×10 mL). The combined organic layers were dried over MgSO$_4$, filtered and evaporated to dryness. The residue was purified by SiO$_2$ chromatography (Hex/Et$_2$O 0 to 5% gradient) and afforded the title compound (141 mg, 0.349 mmol, 35%) as a colorless oil.

(+/−)-5-fluorocyclohexane-1,3-diamine

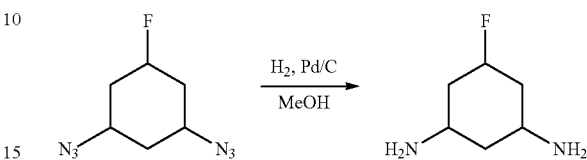

A degassed solution of (+/−)-1,3-diazido-5-fluorocyclohexane (141 mg, 0.77 mmol) in MeOH (5 mL) was treated with 10% Pd/C (81 mg, 0.08 mmol) and stirred under H$_2$ (1 atm) for 5 h. The resulting mixture was filtered over Celite® (MeOH) and the filtrate was evaporated to dryness affording the title compound (77 mg, 0.583 mmol, 76%) as a beige solid which was used in the next step without further purification.

(+/−)-tert-butyl 4-(-3-(5-chloro-4-(1-(phenylsulfonyl)-1H-indol-3-yl)pyrimidin-2-ylamino)-5-fluorocyclohexylcarbamoyl)phenylcarbamate

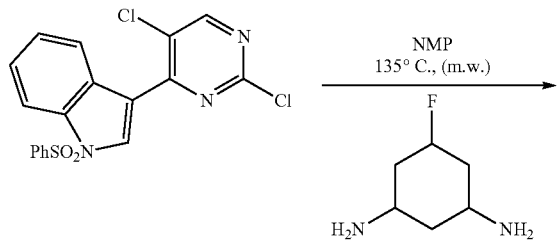

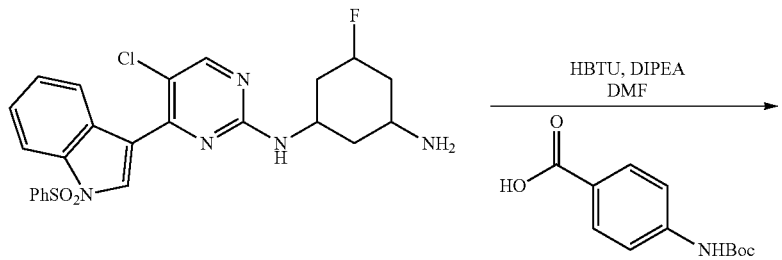

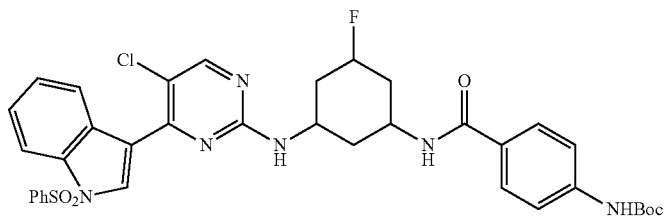

A solution of 3-(2,5-dichloropyrimidin-4-yl)-1-(phenylsulfonyl)-1H-indole (180 mg, 0.45 mmol), (+/−)-5-fluorocyclohexane-1,3-diamine (77 mg, 0.58 mmol) and DIPEA (3.54 mmol) in NMP (3 mL) was heated at 135° C. (microwave) for 25 min. The cooled mixture was then treated with 4-(tert-butoxycarbonylamino)benzoic acid (93 mg, 0.45 mmol), HBTU (338 mg, 0.89 mmol) and DIPEA (0.23 mL, 1.34 mmol). The resulting mixture was stirred overnight at rt and then diluted with EtOAc (30 mL) and saturated NaHCO₃ (10 mL). The layers were separated and the aqueous layer was extracted with EtOAc (3×10 mL). The combined organic layers were washed with brine (10 mL), dried over MgSO₄, filtered and evaporated to dryness. The residue was purified by SiO₂ chromatography (Hex/EtOAc 0 to 100% gradient) and afforded the title compound (198 mg, 0.275 mmol, 62%) as a brownish solid.

(+/−)-4-amino-N-(3-(5-chloro-4-(1-(phenylsulfonyl)-1H-indol-3-yl)pyrimidin-2-ylamino)-5-fluorocyclohexyl)benzamide.TFA

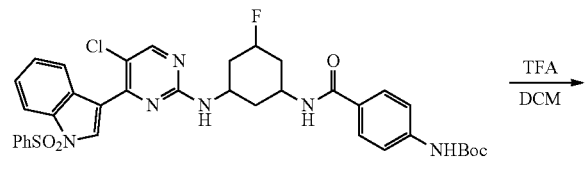

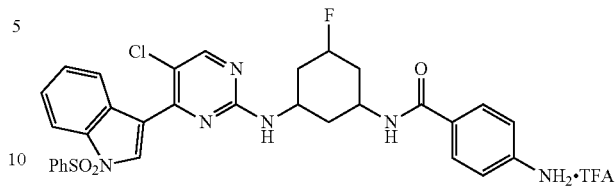

A solution of (+/−)-tert-butyl 4-(-3-(5-chloro-4-(1-(phenylsulfonyl)-1H-indol-3-yl)pyrimidin-2-ylamino)-5-fluorocyclohexylcarbamoyl)phenylcarbamate (198 mg, 0.28 mmol) in DCM (1.2 mL) was treated with TFA (2.75 mmol) and stirred 2 h at rt. The mixture was evaporated to dryness and afforded the title compound (205 mg, 0.28 mmol, 100%) as a pale yellow solid which was used in the next step without further purification.

(+/−)-4-amino-N-(3-(5-chloro-4-(1H-indol-3-yl)pyrimidin-2-ylamino)-5-fluorocyclohexyl) benzamide

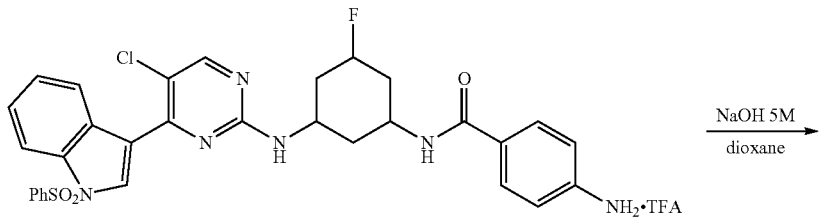

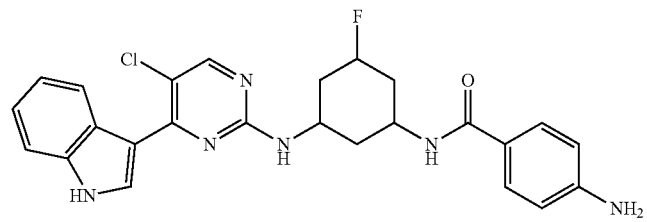

A solution of (+/−)-4-amino-N-(3-(5-chloro-4-(1-(phenylsulfonyl)-1H-indol-3-yl)pyrimidin-2-ylamino)-5-fluorocyclohexyl)benzamide.TFA (256 mg, 0.36 mmol) in dioxane (2.4 mL) was treated with a 5M solution of NaOH in H₂O (1.43 mL, 7.15 mmol) and heated at 75° C. overnight. The cooled mixture was evaporated to dryness and the resulting solid was suspended in H₂O (2 mL) and filtered. The solid was washed with H₂O (2×2 ml) and dried under high vacuum affording the title compound (96 mg, 0.208 mmol, 58%) as a white solid which was used in the next step without further purification.

4-amino-N-((1R,3S,5S)-3-(5-chloro-4-(1H-indol-3-yl)pyrimidin-2-ylamino)-5-fluorocyclohexyl)benzamide

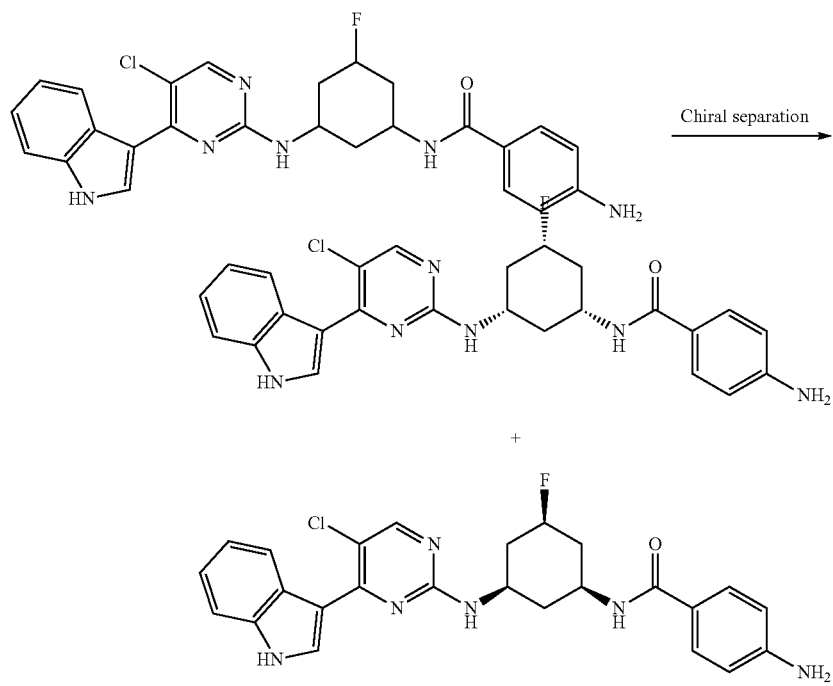

Both enantiomers of (+/−)-4-amino-N-(3-(5-chloro-4-(1H-indol-3-yl)pyrimidin-2-ylamino)-5-fluorocyclohexyl)benzamide (76 mg, 0.165 mmol) were separated using preparative chiral HPLC (ChiralPak IB, 5 μm, 20×250 mm; Hex/MeOH/DCM 70:15:15) and afforded the title compounds (21.9 mg, 0.047, 29%) as white solids.

(+/−)-N-((1R,3S,5S)-3-(5-chloro-4-(1H-indol-3-yl)pyrimidin-2-ylamino)-5-fluorocyclohexyl)-4-((E)-4-(dimethylamino)but-2-enamido)benzamide (Compound 119)

Compound 119 was prepared using the methods described herein in Example 15, except that 4-amino-N-((1S,3R,5R)-3-(5-chloro-4-(1H-indol-3-yl)pyrimidin-2-ylamino)-5-fluorocyclohexyl)benzamide was replaced with (+/−)-4-amino-N-(3-(5-chloro-4-(1H-indol-3-yl)pyrimidin-2-ylamino)-5-fluorocyclohexyl) benzamide.

Example 15. N-((1S,3R,5R)-3-(5-chloro-4-(1H-indol-3-yl)pyrimidin-2-ylamino)-5-fluorocyclohexyl)-4-((E)-4-(dimethylamino)but-2-enamido) benzamide (Compound 120)

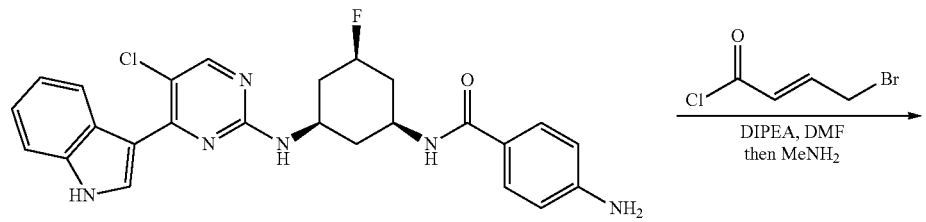

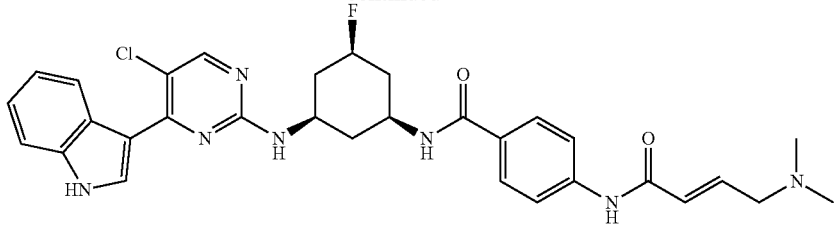

A cooled (−60° C.) solution of 4-amino-N-((1S,3R,5R)-3-(5-chloro-4-(1H-indol-3-yl)pyrimidin-2-ylamino)-5-fluorocyclohexyl)benzamide prepared as in Example 14 (51 mg, 0.106 mmol) and DIPEA (0.139 mmol) in 1:3 NMP/THF (4.3 mL) was treated with a 54.2 mg/mL solution of (E)-4-bromobut-2-enoyl chloride in DCM (0.032 mmol). The resulting mixture was stirred 40 min at −60° C. before addition of a 2M solution of dimethylamine in THF (0.319 mmol). The resulting mixture was warmed up to rt before being evaporated to dryness. The residue was purified by reverse phase chromatography ($C_{18}$, $H_2O$/ACN+0.1% $HCO_2H$ 5 to 60% gradient) and afforded the title compounds (4.6 mg, 0.0078 mmol, 24%) as white solid after lyophilisation. $^1$H NMR (500 MHz, $d_6$-DMSO) δ 11.91 (s, 1H), 10.32 (s, 1H), 8.47 (s, 1H), 8.44-8.37 (m, 1H), 8.34 (d, J=8.0 Hz, 1H), 8.28 (s, 1H), 7.82 (d, J=8.7 Hz, 2H), 7.72 (d, J=8.6 Hz, 2H), 7.49 (d, J=8.6 Hz, 1H), 7.42 (d, J=7.9 Hz, 1H), 7.30-7.12 (m, 2H), 6.75 (dt, J=15.3, 5.9 Hz, 1H), 6.29 (d, J=15.4 Hz, 1H), 4.80 (dm, J=48.2 Hz, 1H), 4.15-3.89 (m, 2H), 3.06 (d, J=5.4 Hz, 2H), 2.49-2.35 (m, 2H), 2.35-2.27 (m, 1H), 2.17 (s, 6H), 1.57 (dd, J=21.9, 10.9 Hz, 2H), 1.49-1.35 (m, 1H); MS (m/z): 590.64 [M+1]$^+$.

Example 16. N-((1R,3S,5S)-3-(5-chloro-4-(1H-indol-3-yl)pyrimidin-2-ylamino)-5-fluorocyclohexyl)-4-((E)-4-(dimethylamino)but-2-enamido)benzamide (Compound 173)

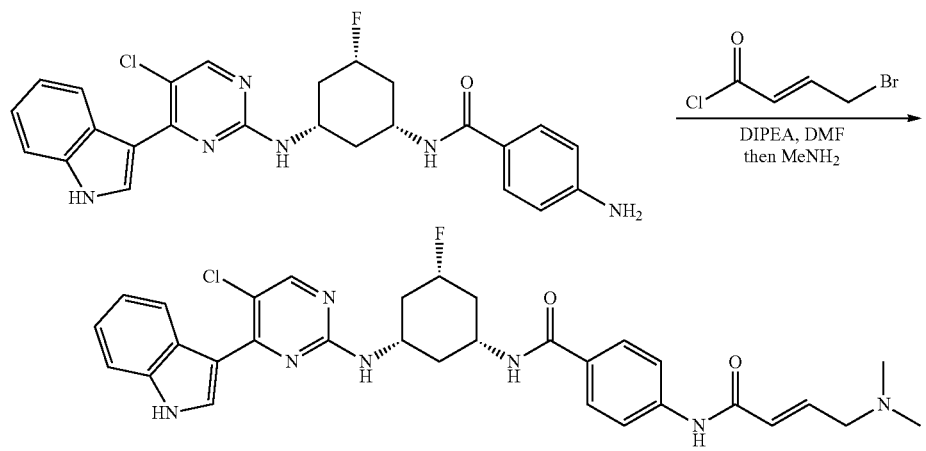

A cooled (−60° C.) solution of 4-amino-N-((1R,3S,5S)-3-(5-chloro-4-(1H-indol-3-yl)pyrimidin-2-ylamino)-5-fluorocyclohexyl)benzamide (20.0 mg, 0.042 mmol) prepared as in Example 14 and DIPEA (0.125 mmol) in 1:3 NMP/THF (1.6 mL) was treated with a 54.2 mg/mL solution of (E)-4-bromobut-2-enoyl chloride in DCM (0.044 mmol). The resulting mixture was stirred 40 min at −60° C. before addition of a 2M solution of dimethylamine in THF (0.125 mmol). The resulting mixture was warmed to rt before being evaporated to dryness. The residue was purified by reverse phase chromatography ($C_{18}$, $H_2O$/ACN+0.1% $HCO_2H$ 5 to 60% gradient) and afforded the title compounds (3.6 mg, 0.006 mmol, 55%) as a white solid after lyophilisation. $^1$H NMR (500 MHz, $d_6$-DMSO) δ 11.91 (s, 1H), 10.32 (s, 1H), 8.47 (s, 1H), 8.44-8.37 (m, 1H), 8.34 (d, J=8.0 Hz, 1H), 8.28 (s, 1H), 7.82 (d, J=8.7 Hz, 2H), 7.72 (d, J=8.6 Hz, 2H), 7.49

(d, J=8.6 Hz, 1H), 7.42 (d, J=7.9 Hz, 1H), 7.30-7.12 (m, 2H), 6.75 (dt, J=15.3, 5.9 Hz, 1H), 6.29 (d, J=15.4 Hz, 1H), 4.80 (dm, J=48.2 Hz, 1H), 4.15-3.89 (m, 2H), 3.06 (d, J=5.4 Hz, 2H), 2.49-2.35 (m, 2H), 2.35-2.27 (m, 1H), 2.17 (s, 6H), 1.57 (dd, J=21.9, 10.9 Hz, 2H), 1.49-1.35 (m, 1H); MS (m/z): 590.61 [M+1]$^+$.

Example 17. (E)-N-(5-(5-chloro-4-(1H-indol-3-yl)pyrimidin-2-ylamino)bicyclo[3.1.1]heptan-1-yl)-4-(4-(dimethylamino)but-2-enamido)benzamide (Compound 121)

N-(5-chloro-4-(1-(phenylsulfonyl)-1H-indol-3-yl)pyrimidin-2-yl)bicyclo[3.1.1]heptane-1,5-diamine

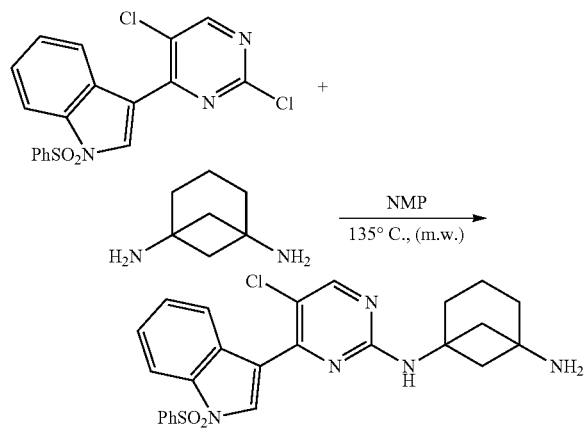

A solution of 3-(2,5-dichloropyrimidin-4-yl)-1-(phenylsulfonyl)-1H-indole (300 mg, 0.742 mmol), bicyclo[3.1.1]heptane-1,5-diamine (prepared as in WO2006012395) (120 mg, 0.951 mmol) and DIPEA (0.816 mmol) in NMP (5 mL) was heated at 135° C. (microwave) for 2 h. The cooled mixture was diluted with EtOAc (30 mL), washed with H$_2$O (10 mL), brine (10 mL), dried over MgSO$_4$, filtered and evaporated to dryness. The residue was purified by SiO$_2$ chromatography (DCM/MeOH 0 to 20% gradient) and afforded the title compound (202 mg, 0.409 mmol, 55%) as a yellow foam.

tert-butyl 4-(5-(5-chloro-4-(1-(phenylsulfonyl)-1H-indol-3-yl)pyrimidin-2-ylamino)bicyclo [3.1.1]heptan-1-ylcarbamoyl)phenylcarbamate

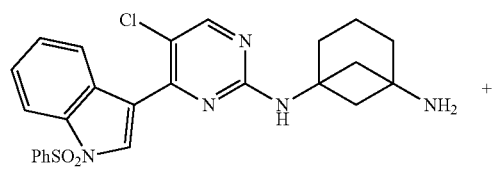

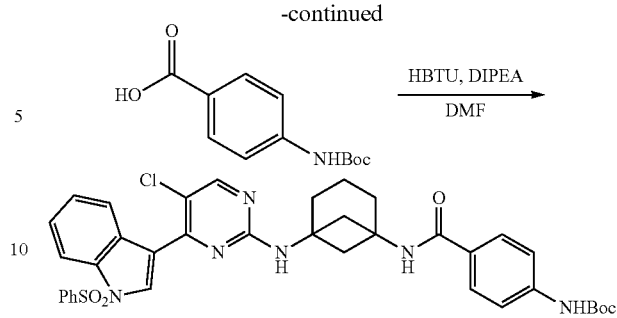

A solution of N$^1$-(5-chloro-4-(1-(phenylsulfonyl)-1H-indol-3-yl)pyrimidin-2-yl)bicyclo[3.1.1]heptane-1,5-diamine (202 mg, 0.409 mmol) and 4-(tert-butoxycarbonylamino)benzoic acid (116 mg, 0.491 mmol) in DMF (5.0 mL) was treated with HBTU (233 mg, 0.613 mmol) and DIPEA (0.818 mmol). The resulting mixture was stirred overnight at rt and diluted with EtOAc (30 mL) and saturated NaHCO$_3$ (15 mL). The layers were separated and the aqueous layer was extracted with EtOAc (2×30 mL). The combined organic layers were dried over MgSO$_4$, filtered and evaporated to dryness affording the title compound (291 mg, 0.408 mmol, 100%) as a brown oil which was used in the next step without further purification.

4-amino-N-(5-(5-chloro-4-(1-(phenylsulfonyl)-1H-indol-3-yl)pyrimidin-2-ylamino)bicyclo [3.1.1]heptan-1-yl)benzamide.TFA

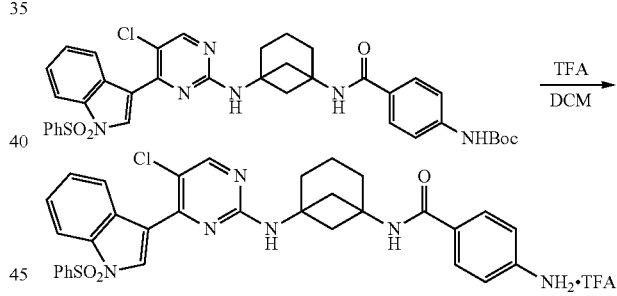

A solution of tert-butyl 4-(5-(5-chloro-4-(1-(phenylsulfonyl)-1H-indol-3-yl)pyrimidin-2-ylamino)bicyclo[3.1.1]heptan-1-ylcarbamoyl)phenylcarbamate (291 mg, 0.408 mmol) in DCM (4 mL) was treated with TFA (1.56 mL, 20.4 mmol) and stirred 1 h at rt. The mixture was evaporated to dryness and afforded the title compound (250 mg, 0.408 mmol, 100%) as a yellowish oil.

4-amino-N-(5-(5-chloro-4-(1H-indol-3-yl)pyrimidin-2-ylamino)bicyclo[3.1.1]heptan-1-yl)benzamide

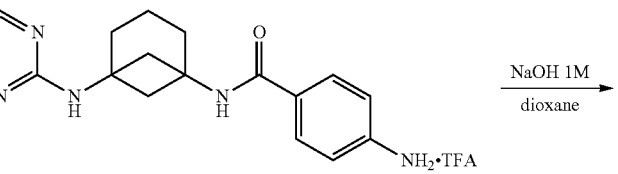

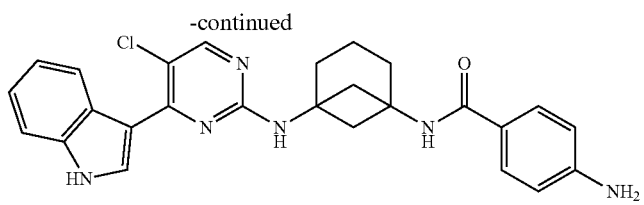

A solution of 4-amino-N-(5-(5-chloro-4-(1-(phenylsulfonyl)-1H-indol-3-yl)pyrimidin-2-ylamino)bicyclo[3.1.1]heptan-1-yl)benzamide.TFA (250 mg, 0.408 mmol) in dioxane (10 mL) was treated with a 1M solution of NaOH (6.0 mL, 6.0 mmol) and heated at 75° C. for 1 h. The cooled mixture was diluted with Me-THF (30 mL) and the organic layer was washed with H₂O (10 mL), dried over MgSO₄, filtered and evaporated to dryness affording the title compound (193 mg, 0.408 mmol, 100%) as a creamy solid which was used in the next step without further purification.

(E)-N-(5-(5-chloro-4-(1H-indol-3-yl)pyrimidin-2-ylamino)bicyclo[3.1.1]heptan-1-yl)-4-(4-(dimethylamino)but-2-enamido)benzamide

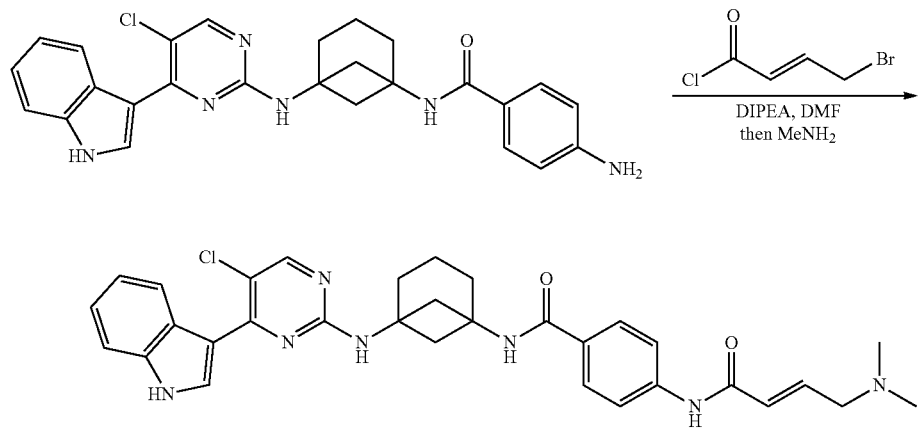

A cooled (−60° C.) solution of 4-amino-N-(5-(5-chloro-4-(1H-indol-3-yl)pyrimidin-2-ylamino)bicyclo[3.1.1]heptan-1-yl)benzamide (75 mg, 0.1586 mmol) and DIPEA (0.476 mmol) in 1:5 NMP/THF (10 mL) was treated with a 54.2 mg/mL solution of (E)-4-bromobut-2-enoyl chloride in DCM (0.143 mmol). The resulting mixture was stirred 2 h at −60° C. before addition of a 2M solution of dimethylamine in THF (0.951 mmol). The resulting mixture was warmed to rt before being evaporated to dryness. The residue was purified by reverse phase chromatography (C₁₈, H₂O/ACN+0.1% HCO₂H 5 to 60% gradient) and afforded the title compound (41 mg, 0.070 mmol, 44%) as a yellow solid after lyophilisation. ¹H NMR (500 MHz, d₆-DMSO) δ 11.81 (d, J=2.7 Hz, 1H), 10.24 (s, 1H), 8.58 (brs, 1H), 8.45-8.31 (m, 2H), 8.25 (s, 1H), 7.77 (d, J=8.7 Hz, 2H), 7.68 (d, J=8.8 Hz, 2H), 7.58 (s, 1H), 7.48 (d, J=8.0 Hz, 1H), 7.23-7.10 (m, 2H), 6.75 (dt, J=15.4, 5.9 Hz, 1H), 6.27 (dt, J=15.3, 1.6 Hz, 1H), 3.05 (dd, J=5.9, 1.4 Hz, 2H), 2.41 (d, J=7.7 Hz, 2H), 2.17 (s, 6H), 2.06 (brs, 2H), 1.95 (brs, 2H), 1.87 (brs, 2H); MS (m/z): 584.67 [M+1]+.

Example 18. (+/−)-N-(5-(5-chloro-4-(1H-indol-3-yl)pyrimidin-2-ylamino)-3,3-difluorocyclohexyl)-4-((E)-4-(dimethylamino)but-2-enamido)benzamide (Compound 122) and stereoisomers Compounds 139 and 174 (+/−)-dibenzyl-5,5-difluorocyclohexane-1,3-diyldicarbamate

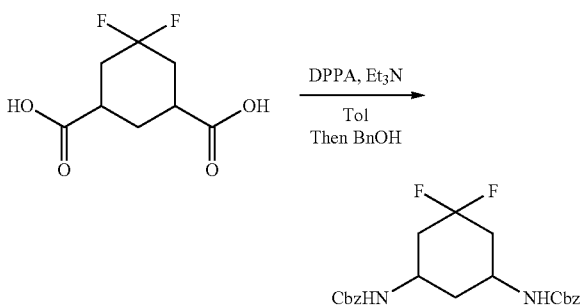

A solution of (+/−)-5,5-difluorocyclohexane-1,3-dicarboxylic acid (prepared as in WO2011005608) (454 mg, 2.18 mmol) in toluene (10 mL) was treated with Et₃N (4.80 mmol) and DPPA (4.36 mmol) and heated at 110° C. for 1 h. The solution was cooled down to 80° C. and treated with Et₃N (4.80 mmol) and BnOH (4.80 mmol) and stirred overnight at this temperature. The cooled mixture as diluted with EtOAc (50 mL) and H₂O (20 mL). The layers were separated and the aqueous layer was extracted with EtOAc (3×20 mL). The combined organic layers were dried over MgSO₄, filtered, and evaporated to dryness. The residue was triturated with Hex (10 mL) followed by Et₂O (5 mL) and the solid was filtered and washed with Hex affording the title compound (694 mg, 1.66 mmol, 76%) as a creamy solid which was used in the next step without further purification.

(+/−)-5,5-difluorocyclohexane-1,3-diamine

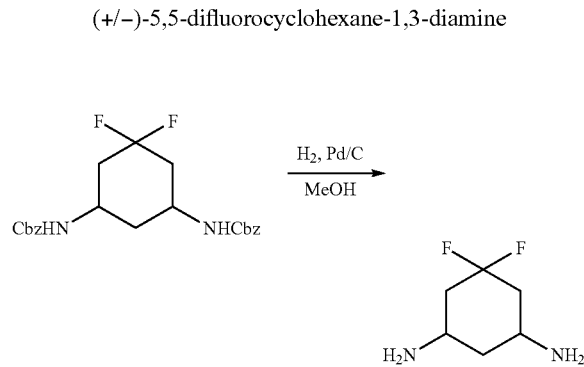

A degassed solution of (+/−)-dibenzyl-5,5-difluorocyclohexane-1,3-diyldicarbamate (694 mg, 1.66 mmol) in MeOH (100 mL) was treated with 10% Pd/C (100 mg) and stirred 5 h under H₂ (1 atm). The resulting mixture was filtrated over Celite® (MeOH) and the filtrate was evaporated to dryness affording the title compound (249 mg, 1.66 mmol, 100%) as a colorless oil which was used in the next step without further purification.

(+/−)-N-(5-chloro-4-(1-(phenylsulfonyl)-1H-indol-3-yl)pyrimidin-2-yl)-5,5-difluorocyclohexane-1,3-diamine

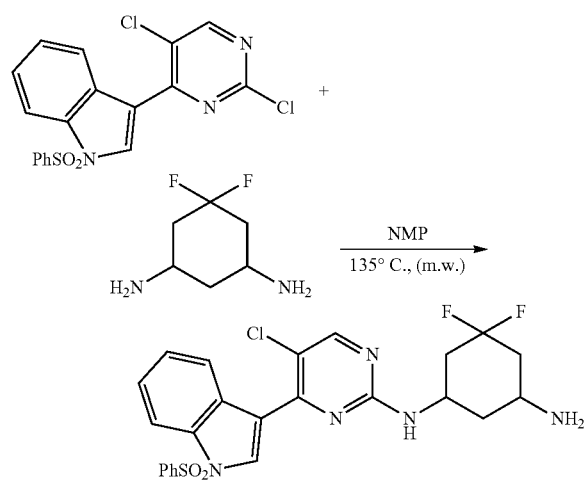

A solution of 3-(2,5-dichloropyrimidin-4-yl)-1-(phenylsulfonyl)-1H-indole (560 mg, 1.380 mmol), (+/−)-5,5-difluorocyclohexane-1,3-diamine (249 mg, 1.658 mmol) and DIPEA (1.518 mmol) in NMP (15 mL) was heated at 135° C. (microwave) for 40 min. The cooled mixture was diluted with EtOAc (50 mL), washed with H₂O (10 mL), brine (10 mL), dried over MgSO₄, filtered and evaporated to dryness. The residue was purified by SiO₂ chromatography (DCM/MeOH 0 to 20% gradient) and afforded the title compound (192 mg, 0.371 mmol, 27%) as a yellow foam.

(+/−)-tert-butyl 4-(5-(5-chloro-4-(1-(phenylsulfonyl)-1H-indol-3-yl)pyrimidin-2-ylamino)-3,3-difluorocyclohexylcarbamoyl)phenylcarbamate

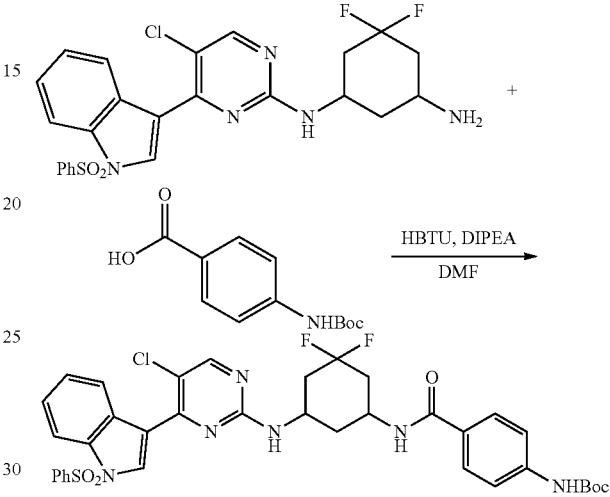

A solution of (+/−)-N¹-(5-chloro-4-(1-(phenylsulfonyl)-1H-indol-3-yl)pyrimidin-2-yl)-5,5-difluorocyclohexane-1,3-diamine (192 mg, 0.370 mmol) and 4-(tert-butoxycarbonylamino) benzoic acid (105 mg, 0.444 mmol) in DMF (6.0 mL) was treated with HBTU (211 mg, 0.555 mmol) and DIPEA (0.740 mmol). The resulting mixture was stirred overnight at rt and diluted with EtOAc (30 mL) and saturated NaHCO₃ (15 mL). The layers were separated and the aqueous layer was extracted with EtOAc (2×30 mL). The combined organic layers were dried over MgSO₄, filtered, and evaporated to dryness affording the title compound (272 mg, 0.370 mmol, 100%) as a brown oil which was used in the next step without further purification.

(+/−)-4-amino-N-(5-(5-chloro-4-(1-(phenylsulfonyl)-1H-indol-3-yl)pyrimidin-2-ylamino)-3,3-difluorocyclohexyl)benzamide.TFA

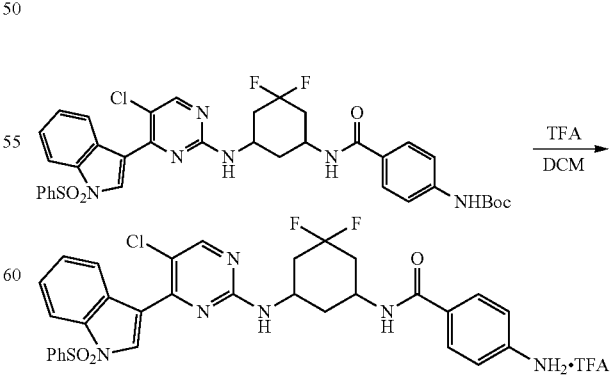

A solution of (+/−)-tert-butyl 4-(5-(5-chloro-4-(1-(phenylsulfonyl)-1H-indol-3-yl)pyrimidin-2-ylamino)-3,3-difluorocyclohexylcarbamoyl)phenylcarbamate (272 mg, 0.370 mmol) in DCM (4 mL) was treated with TFA (1.45 mL, 19.0 mmol) and stirred 2 h at rt. The resulting mixture was evaporated to dryness and afforded the title compound (235 mg, 0.370 mmol, 100%) as a brownish oil which was used in the next step without further purification.

(+/−)-4-amino-N-(5-(5-chloro-4-(1H-indol-3-yl) pyrimidin-2-ylamino)-3,3-difluorocyclohexyl) benzamide

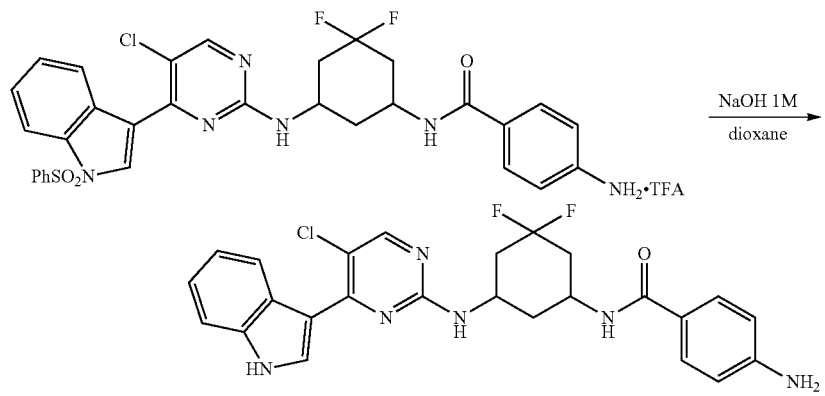

A solution of (+/−)-4-amino-N-(5-(5-chloro-4-(1-(phenylsulfonyl)-1H-indol-3-yl)pyrimidin-2-ylamino)-3,3-difluorocyclohexyl)benzamide.TFA (235 mg, 0.370 mmol) in dioxane (10 mL) was treated with a 1M solution of NaOH in H₂O (6.0 mL, 6.0 mmol) and heated at 75° C. for 2 h. The volatiles were removed by evaporation and the aqueous layer was extracted with MeTHF (30 mL). The organic layer was washed with H₂O (10 mL), dried over Na₂SO₄, filtered and evaporated to dryness affording the title compound (157 mg, 0.316 mmol, 85%) as a yellow solid which was used in the next step without further purification.

4-amino-N-((1R,5S)-5-(5-chloro-4-(1H-indol-3-yl) pyrimidin-2-ylamino)-3,3-difluorocyclohexyl)benzamide

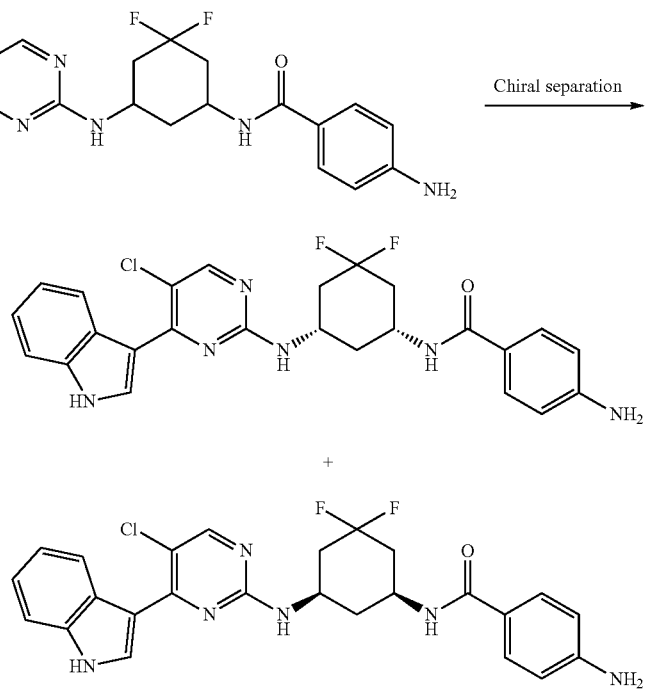

Both enantiomers of (+/−)-4-amino-N-(5-(5-chloro-4-(1H-indol-3-yl)pyrimidin-2-ylamino)-3,3-difluorocyclohexyl)benzamide (62 mg, 0.125 mmol) were separated using preparative chiral HPLC (ChiralPak IB, 5 μm, 20×250 mm; Hex/MeOH/DCM 64:18:18) and afforded the title compounds (19.1 mg, 0.038, 31%) as white solids.

N-((1R,5S)-5-(5-chloro-4-(1H-indol-3-yl)pyrimidin-2-ylamino)-3,3-difluorocyclohexyl)-4-((E)-4-(dimethylamino)but-2-enamido)benzamide (Compound 174)

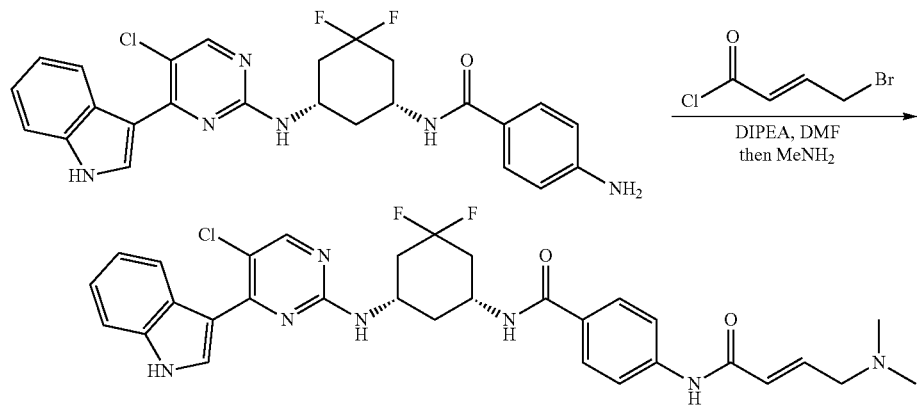

A cooled (−60° C.) solution of 4-amino-N-((1R,5S)-5-(5-chloro-4-(1H-indol-3-yl)pyrimidin-2-ylamino)-3,3-difluorocyclohexyl)benzamide (19.1 mg, 0.038 mmol) and DIPEA (0.124 mmol) in 1:5 NMP/THF (4 mL) was treated with a 54.2 mg/mL solution of (E)-4-bromobut-2-enoyl chloride in DCM (0.0370 mmol). The resulting mixture was stirred 2 h at −60° C. before addition of a 2M solution of dimethylamine in THF (0.247 mmol). The resulting mixture was warmed to rt before being evaporated to dryness. The residue was purified by reverse phase chromatography ($C_{18}$, $H_2O$/ACN+0.1% $HCO_2H$ 5 to 60% gradient) and afforded the title compound (12 mg, 0.020 mmol, 53%) as a white solid after lyophilisation. $^1$H NMR (500 MHz, $d_6$-DMSO) δ 11.86 (brs, 1H), 10.27 (s, 1H), 8.56 (brs, 1H), 8.48 (d, J=2.7 Hz, 1H), 8.40 (d, J=8.0 Hz, 1H), 8.29 (brs, 1H), 7.84-7.77 (m, 2H), 7.72 (d, J=8.9 Hz, 2H), 7.47 (dd, J=19.2, 8.2 Hz, 2H), 7.22-7.17 (m, 2H), 6.75 (dt, J=15.4, 5.9 Hz, 1H), 6.27 (dt, J=15.4, 1.6 Hz, 1H), 4.20 (brs, 3H), 3.05 (dd, J=5.9, 1.5 Hz, 2H), 2.35 (brs, 1H), 2.25 (brs, 1H), 2.17 (s, 6H), 2.03-1.88 (m, 2H), 1.63 (brs, 1H); MS (m/z): 608.32 [M+1]$^+$. Compound 139 was prepared in the same manner.

Example 19. (E)-N-(4-(N-((1S,3R)-3-(5-chloro-4-(1H-indol-3-yl)pyrimidin-2-ylamino)cyclohexyl)sulfamoyl)phenyl)-4-(dimethylamino)but-2-enamide (Compound 123)

N-((1S,3R)-3-(5-chloro-4-(1-(phenylsulfonyl)-1H-indol-3-yl)pyrimidin-2-ylamino)cyclohexyl)-4-nitrobenzenesulfonamide

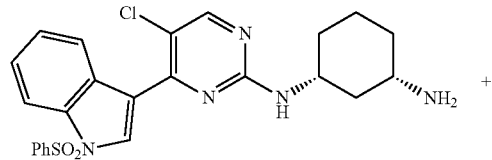

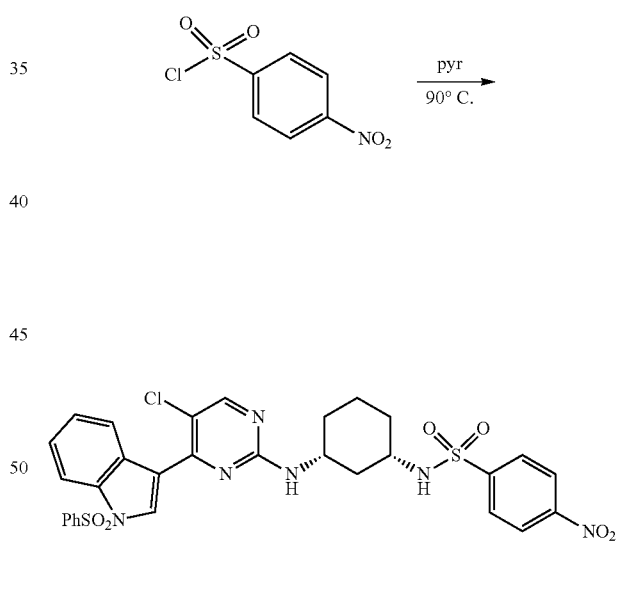

A solution of (1R,3S)—N1-(5-chloro-4-(1-(phenylsulfonyl)-1H-indol-3-yl)pyrimidin-2-yl)cyclohexane-1,3-diamine prepared as in Example 1 (150 mg, 0.289 mmol) in pyr (2.2 mL) was treated with 4-nitrobenzene-1-sulfonyl chloride (64 mg, 0.289 mmol) and heated at 90° C. for 16 h. The cooled mixture was evaporated to dryness and the residue was purified by $SiO_2$ chromatography (DCM/EtOAc 0 to 100% gradient) and afforded the title compound (147 mg, 0.220 mmol, 76%) as a yellow foam.

4-amino-N-((1S,3R)-3-(5-chloro-4-(1-(phenylsulfo-nyl)-1H-indol-3-yl)pyrimidin-2-ylamino)cyclohexyl) benzenesulfonamide

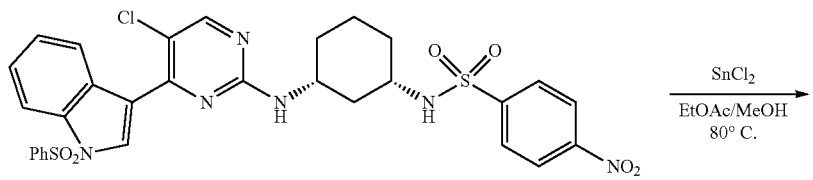

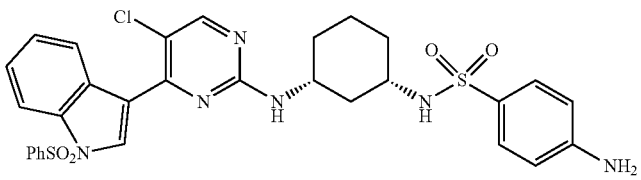

A solution of N-((1S,3R)-3-(5-chloro-4-(1-(phenylsulfo-nyl)-1H-indol-3-yl)pyrimidin-2-ylamino)cyclohexyl)-4-nitrobenzenesulfonamide (147 mg, 0.223 mmol) in 5:1 EtOAc/MeOH (4 mL) was treated with SnCl$_2$.10H$_2$O (126 mg, 0.557 mmol) and heated at 90° C. in a sealed tube for 4 h. The cooled mixture was diluted with saturated NaHCO$_3$ (10 mL), then stirred 20 min at rt and the aqueous layer was extracted with 4:1 CHCl$_3$/IPA (3×30 mL). The combined organic layers were washed with H$_2$O (10 mL), brine (10 mL), dried over MgSO$_4$, filtered through a pad of Celite® (4:1 CHCl$_3$/IPA) and evaporated to dryness. The residue was purified by SiO$_2$ chromatography (DCM/EtOAc 0 to 80% gradient) and afforded the title compound (109 mg, 0.171 mmol, 77%) as a colorless oil.

4-amino-N-((1S,3R)-3-(5-chloro-4-(1H-indol-3-yl) pyrimidin-2-ylamino)cyclohexyl) benzenesulfona-mide

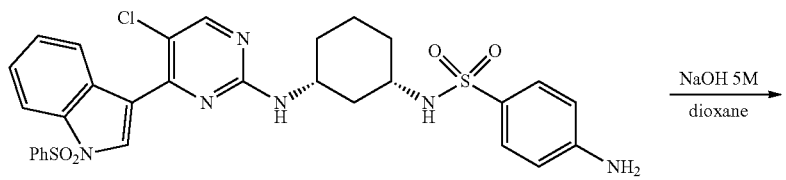

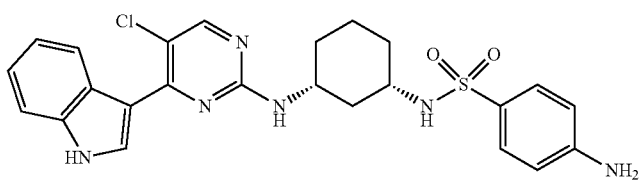

A solution of 4-amino-N-((1S,3R)-3-(5-chloro-4-(1-(phenylsulfonyl)-1H-indol-3-yl)pyrimidin-2-ylamino)cyclohexyl)benzenesulfonamide (109 mg, 0.171 mmol) in dioxane (3.4 mL) was treated with a 5M solution of NaOH in $H_2O$ (0.855 mmol) and heated at 50° C. overnight. The cooled mixture was treated with a 1M solution of HCl in $H_2O$ until the pH reached 7, then the mixture was evaporated to dryness. The residue was purified by $SiO_2$ chromatography (DCM/MeOH 0 to 20% gradient) and afforded the title compound (50 mg, 0.101 mmol, 59%) as a light yellow solid.

(E)-N-(4-(N-((1S,3R)-3-(5-chloro-4-(1H-indol-3-yl)pyrimidin-2-ylamino)cyclohexyl) sulfamoyl)phenyl)-4-(dimethylamino)but-2-enamide

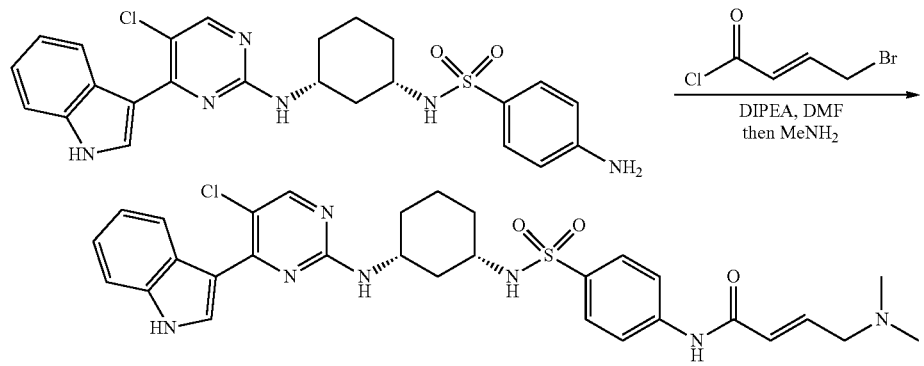

A cooled (−60° C.) solution of 4-amino-N-((1S,3R)-3-(5-chloro-4-(1H-indol-3-yl)pyrimidin-2-ylamino)cyclohexyl)benzenesulfonamide (43 mg, 0.0865 mmol) and DIPEA (0.260 mmol) in 1:3 NMP/THF (4 mL) was treated with a 54.2 mg/mL solution of (E)-4-bromobut-2-enoyl chloride in DCM (0.0908 mmol). The resulting mixture was stirred 2 h at −60° C. before addition of a 2M solution of dimethylamine in THF (0.519 mmol). The resulting mixture was warmed to rt before being evaporated to dryness. The residue was purified by reverse phase chromatography ($C_{18}$, $H_2O$/ACN+0.1% $HCO_2H$ 0 to 100% gradient) and afforded the title compound (11 mg, 0.018 mmol, 21%) as a light yellow solid after lyophilisation. $^1H$ NMR (500 MHz, $d_6$-DMSO) δ 11.82 (s, 1H), 10.38 (s, 1H), 8.69-8.52 (m, 1H), 8.44 (s, 1H), 8.35 (s, 1H), 8.19 (s, 1H), 7.79 (ddt, J=44.8, 36.5, 18.1 Hz, 4H), 7.64 (s, 1H), 7.48 (d, J=8.2 Hz, 1H), 7.23-7.14 (m, 2H), 7.12 (d, J=7.6 Hz, 1H), 6.77 (dt, J=15.3, 5.8 Hz, 1H), 6.28 (d, J=15.2 Hz, 1H), 3.87-3.64 (m, 2H), 3.06 (d, J=4.4 Hz, 2H), 2.49 (s, 5H), 2.18 (s, 5H), 2.03-1.78 (m, 3H), 1.65 (ddd, J=26.9, 8.9, 3.4 Hz, 2H), 1.29-0.99 (m, 4H); MS (m/z): 608.60 $[M+1]^+$.

Example 20. N-((1S,3R)-3-(5-chloro-4-(1H-indol-3-yl)pyrimidin-2-ylamino)cyclohexyl)-4-((E)-4-hydroxybut-2-enamido)benzamide (Compound 124)

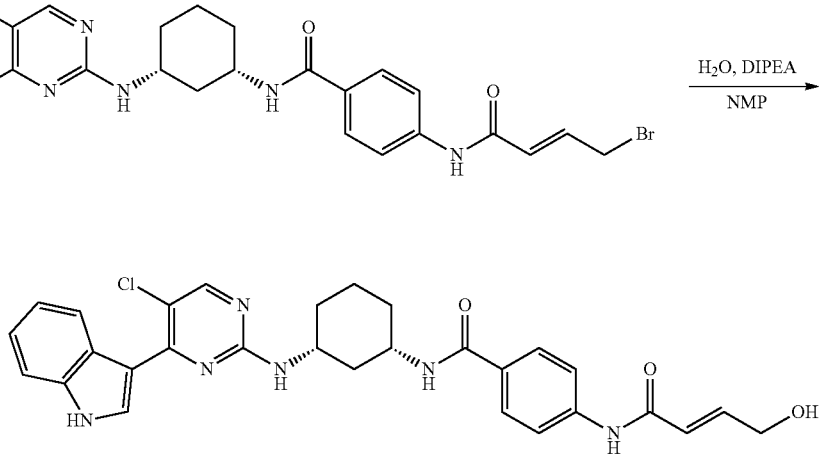

A solution of 4-((E)-4-bromobut-2-enamido)-N-((1S,3R)-3-(5-chloro-4-(1H-indol-3-yl)pyrimidin-2-ylamino)cyclohexyl)benzamide prepared as in Example 1 (45 mg, 0.074 mmol) and DIPEA (0.273 mmol) in 2:1 NMP/H$_2$O (3 mL) was heated at 80° C. for 4 h. The cooled mixture was evaporated to dryness and the residue was purified by reverse phase chromatography (C$_{18}$, H$_2$O/ACN+0.1% HCO$_2$H 0 to 100% gradient) and afforded the title compounds (7.5 mg, 0.014 mmol, 18%) as a light yellow solid after lyophilisation. $^1$H NMR (500 MHz, d$_6$-DMSO) δ 11.83 (s, 1H), 10.25 (s, 1H), 8.60 (br s, 1H), 8.46 (s, 1H), 8.27-8.17 (m, 2H), 7.81 (d, J=8.8 Hz, 2H), 7.71 (d, J=8.8 Hz, 2H), 7.49 (d, J=9.1 Hz, 1H), 7.30 (d, J=8.0 Hz, 1H), 7.24-7.15 (m, 2H), 6.90 (dt, J=15.3, 3.6 Hz, 1H), 6.35 (dt, J=15.2, 2.1 Hz, 1H), 5.13 (s, 1H), 4.18 (s, 2H), 3.94 (br s, 2H), 2.25-2.17 (m, 1H), 2.07-1.95 (m, 1H), 1.92-1.80 (m, 2H), 1.50-1.37 (m, 2H), 1.36-1.23 (m, 2H); MS (m/z): 545.62 [M+1]$^+$.

Example 21. N-((1S,3R)-3-(5-chloro-4-(1H-indol-3-yl)pyrimidin-2-ylamino)cyclohexyl)-4-((E)-4-(dimethylamino)but-2-enamido)-2-fluorobenzamide (Compound 164)

N-((1S,3R)-3-(5-chloro-4-(1-(phenylsulfonyl)-1H-indol-3-yl)pyrimidin-2-ylamino)cyclohexyl)-2-fluoro-4-nitrobenzamide

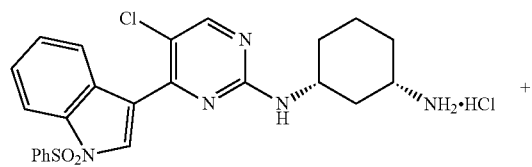

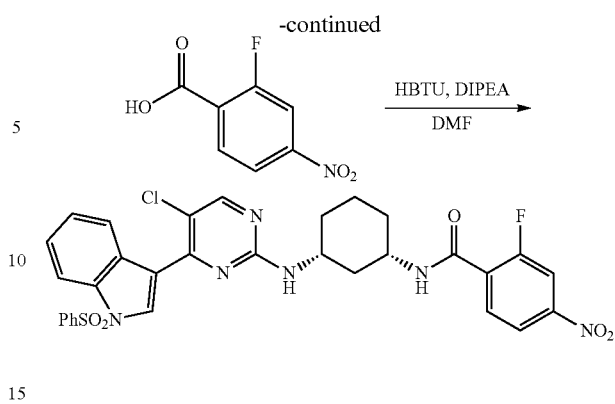

A solution of (1R,3S)—N1-(5-chloro-4-(1-(phenylsulfonyl)-1H-indol-3-yl)pyrimidin-2-yl)cyclohexane-1,3-diamine.HCl prepared as in Example 1 (150 mg, 0.29 mmol) and 2-fluoro-4-nitrobenzoic acid (54 mg, 0.29 mmol) in DCM (1.9 mL) was treated with HBTU (219 mg, 0.58 mmol) and DIPEA (0.870 mmol). The resulting mixture was stirred overnight at rt and diluted with EtOAc (30 mL) and saturated NaHCO$_3$ (15 mL). The layers were separated and the aqueous layer was extracted with EtOAc (2×30 mL). The combined organic layers were dried over MgSO$_4$, filtered and evaporated to dryness. The residue was purified by SiO$_2$ chromatography (DCM/EtOAc 0 to 50% gradient) and afforded the title compound (174 mg, 0.268 mmol, 93%) as a beige solid.

4-amino-N-((1S,3R)-3-(5-chloro-4-(1-(phenylsulfonyl)-1H-indol-3-yl)pyrimidin-2-ylamino)cyclohexyl)-2-fluorobenzamide

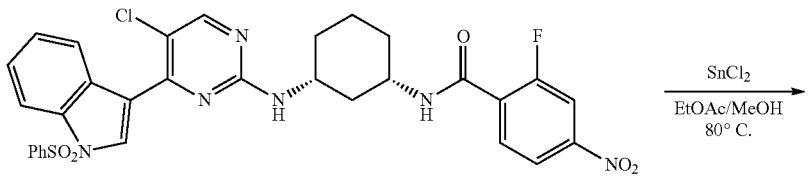

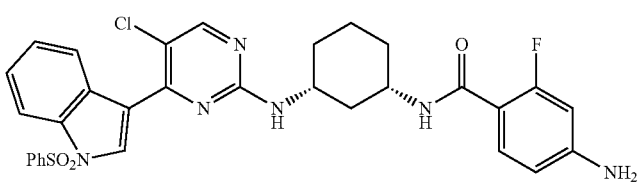

A solution of N-((1S,3R)-3-(5-chloro-4-(1-(phenylsulfonyl)-1H-indol-3-yl)pyrimidin-2-ylamino)cyclohexyl)-2-fluoro-4-nitrobenzamide (174 mg, 0.27 mmol) in 5:1 EtOAc/MeOH (5 mL) was treated with SnCl$_2$.10H$_2$O (151 mg, 0.67 mmol) and heated at 80° C. in a sealed tube for 5 h. The cooled mixture was diluted with saturated NaHCO$_3$ (10 mL), then stirred 20 min at rt, followed by extraction of the aqueous layer with EtOAc (3×30 mL). The combined organic layers were washed with H$_2$O (10 mL), brine (10 mL), dried over MgSO$_4$, filtered, and evaporated to dryness affording the title compound (147 mg, 0.237 mmol, 88%) as a pale yellow solid which was used in the next step without further modification.

4-amino-N-((1S,3R)-3-(5-chloro-4-(1H-indol-3-yl)pyrimidin-2-ylamino)cyclohexyl)-2-fluorobenzamide

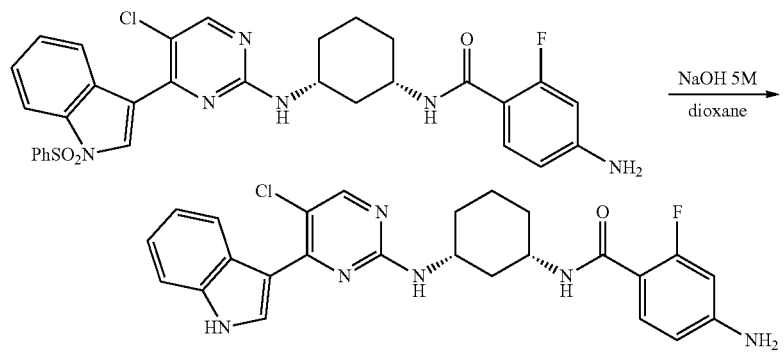

A solution of 4-amino-N-((1S,3R)-3-(5-chloro-4-(1-(phenylsulfonyl)-1H-indol-3-yl)pyrimidin-2-ylamino)cyclohexyl)-2-fluorobenzamide (146 mg, 0.24 mmol) in dioxane (1.6 mL) was treated with a 5M solution of NaOH in H$_2$O (4.72 mmol) and heated at 75° C. overnight. The cooled mixture was diluted with MeTHF (20 mL) and H$_2$O (10 mL). The layers were separated and the aqueous layer was extracted with MeTHF (3×15 mL). The combined organic layers were dried over MgSO$_4$, filtered and evaporated to dryness. The residue was purified by SiO$_2$ chromatography (DCM/THF 0 to 60% gradient) and afforded the title compound (98 mg, 0.205 mmol, 67%) as a white solid.

N-((1S,3R)-3-(5-chloro-4-(1H-indol-3-yl)pyrimidin-2-ylamino)cyclohexyl)-4-((E)-4-(dimethylamino)but-2-enamido)-2-fluorobenzamide

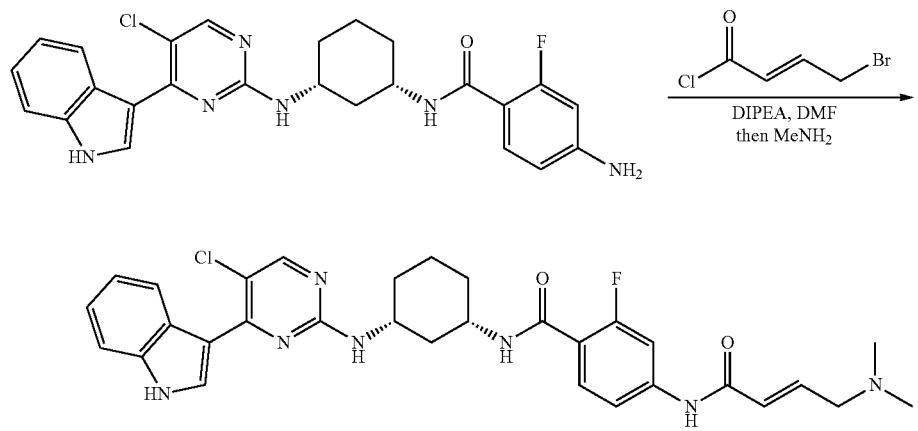

A cooled (−60° C.) solution of 4-amino-N-((1S,3R)-3-(5-chloro-4-(1H-indol-3-yl)pyrimidin-2-ylamino)cyclohexyl)-2-fluorobenzamide (98 mg, 0.205 mmol) and DIPEA (0.614 mmol) in 1:2 NMP/THF (8 mL) was treated with a 54.2 mg/mL solution of (E)-4-bromobut-2-enoyl chloride in DCM (0.215 mmol). The resulting mixture was stirred 2 h at −60° C. before addition of a 2M solution of dimethylamine in THF (0.614 mmol). The resulting mixture was warmed to rt before being evaporated to dryness. The residue was purified by reverse phase chromatography ($C_{18}$, $H_2O$/ACN+0.1% $HCO_2H$ 0 to 60% gradient) and afforded the title compound (17 mg, 0.029 mmol, 14%) as a light white solid after lyophilisation. $^1H$ NMR (500 MHz, $d_6$-DMSO) δ 11.83 (s, 1H), 10.41 (s, 1H), 8.73-8.52 (m, 1H), 8.47 (d, J=2.8 Hz, 1H), 8.25 (s, J=14.8 Hz, 1H), 8.10 (d, J=7.2 Hz, 1H), 7.72 (dd, J=13.1, 1.8 Hz, 1H), 7.54 (t, J=8.4 Hz, 1H), 7.51-7.45 (m, 1H), 7.34 (dd, J=8.5, 1.9 Hz, 1H), 7.28 (d, J=8.0 Hz, 1H), 7.24-7.15 (m, 2H), 6.77 (dt, J=15.4, 5.8 Hz, 1H), 6.26 (dt, J=15.3, 1.5 Hz, 1H), 3.99-3.81 (m, 2H), 3.06 (dd, J=5.8, 1.3 Hz, 2H), 2.29-2.20 (m, 1H), 2.17 (s, 6H), 2.05-1.94 (m, 1H), 1.93-1.86 (m, 1H), 1.82 (d, J=13.2 Hz, 1H), 1.48-1.34 (m, 2H), 1.32-1.21 (m, 2H); MS (m/z): 590.60 [M+1]+.

Example 22. N-((1S,3R)-3-(5-chloro-4-(1H-indol-3-yl)pyrimidin-2-ylamino)cyclohexyl)-4-((E)-4-(dimethylamino)but-2-enamido)-3-fluorobenzamide (Compound 126)

4-amino-N-((1S,3R)-3-(5-chloro-4-(1-(phenylsulfonyl)-1H-indol-3-yl)pyrimidin-2-ylamino)cyclohexyl)-3-fluorobenzamide

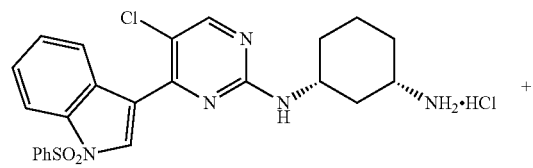
+

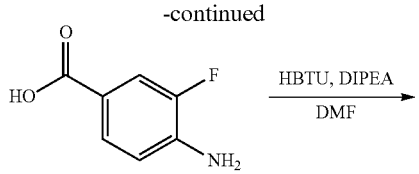

A solution of (1R,3S)—N1-(5-chloro-4-(1-(phenylsulfonyl)-1H-indol-3-yl)pyrimidin-2-yl)cyclohexane-1,3-diamine.HCl prepared as in Example 1 (150 mg, 0.29 mmol) and 4-amino-3-fluorobenzoic acid (45 mg, 0.29 mmol) in DMF (1.9 mL) was treated with HBTU (219 mg, 0.58 mmol) and DIPEA (0.870 mmol). The resulting mixture was stirred overnight at rt and diluted with MeTHF (30 mL) and saturated $NaHCO_3$ (15 mL). The layers were separated and the aqueous layer was extracted with MeTHF (2×30 mL). The combined organic layers were dried over $MgSO_4$, filtered and evaporated to dryness. The residue was purified by $SiO_2$ chromatography (DCM/EtOAc 0 to 100% gradient) and afforded the title compound (178 mg, 0.287 mmol, 99%) as a pale yellow solid.

4-amino-N-((1S,3R)-3-(5-chloro-4-(1H-indol-3-yl)pyrimidin-2-ylamino)cyclohexyl)-3-fluorobenzamide

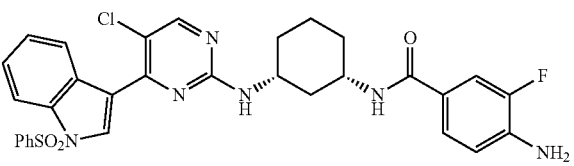

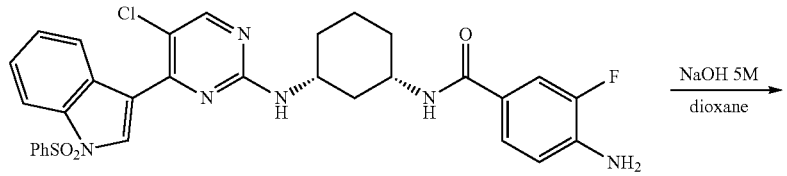

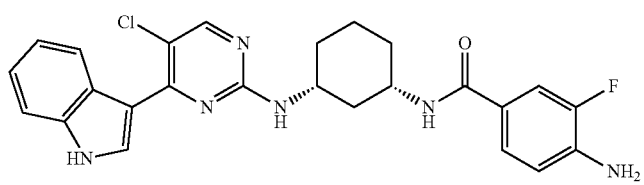

A solution of 4-amino-N-((1S,3R)-3-(5-chloro-4-(1-(phenylsulfonyl)-1H-indol-3-yl)pyrimidin-2-ylamino)cyclohexyl)-3-fluorobenzamide (179 mg, 0.29 mmol) in dioxane (1.9 mL) was treated with a 5M solution of NaOH in H₂O (1.16 mL, 5.78 mmol) and heated at 75° C. overnight. The cooled mixture was diluted with MeTHF (20 mL) and H₂O (10 mL). The layers were separated and the aqueous layer was extracted with MeTHF (3×15 mL). The combined organic layers were dried over MgSO₄, filtered, and evaporated to dryness. The residue was purified by SiO₂ chromatography (DCM/THF 0 to 60% gradient) and afforded the title compound (89 mg, 0.185 mmol, 64%) as a white solid.

N-((1S,3R)-3-(5-chloro-4-(1H-indol-3-yl)pyrimidin-2-ylamino)cyclohexyl)-4-((E)-4-(dimethylamino)but-2-enamido)-3-fluorobenzamide

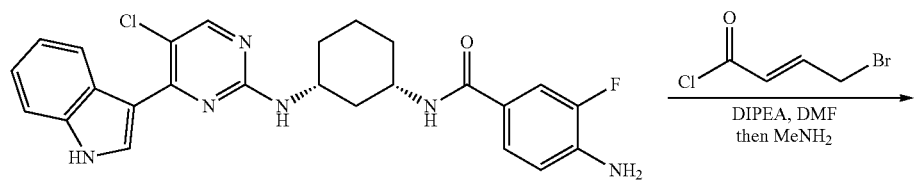

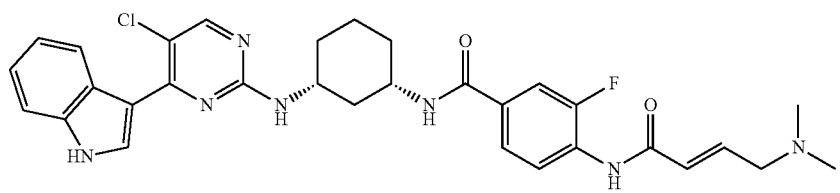

A cooled (−60° C.) solution of 4-amino-N-((1S,3R)-3-(5-chloro-4-(1H-indol-3-yl)pyrimidin-2-ylamino)cyclohexyl)-3-fluorobenzamide (83.8 mg, 0.175 mmol) and DIPEA (0.525 mmol) in 1:2 NMP/THF (7 mL) was treated with a 54.2 mg/mL solution of (E)-4-bromobut-2-enoyl chloride in DCM (0.184 mmol). The resulting mixture was stirred 2 h at −60° C. before addition of a 2M solution of dimethylamine in THF (0.614 mmol). The resulting mixture was warmed to rt before being evaporated to dryness. The residue was purified by reverse phase chromatography (C₁₈, H₂O/ACN+0.1% HCO₂H 0 to 60% gradient) and afforded the title compound (23 mg, 0.039 mmol, 22%) as a pale yellow solid after lyophilisation. ¹H NMR (500 MHz, d₆-DMSO) δ 11.85 (s, 1H), 10.01 (s, 1H), 8.72-8.53 (m, 1H), 8.47 (d, J=1.8 Hz, 1H), 8.35 (d, J=7.9 Hz, 1H), 8.25 (s, 1H), 8.16 (t, J=8.2 Hz, 1H), 7.73 (dd, J=11.9, 1.9 Hz, 1H), 7.69 (dd, J=8.5, 1.7 Hz, 1H), 7.51-7.45 (m, 1H), 7.30 (d, J=8.0 Hz, 1H), 7.24-7.17 (m, 2H), 6.77 (dt, J=15.4, 5.9 Hz, 1H), 6.49 (d, J=15.4 Hz, 1H), 4.05-3.83 (m, 2H), 3.05 (dd, J=5.9, 1.2 Hz, 2H), 2.28-2.18 (m, 1H), 2.17 (s, 6H), 2.08-1.93 (m, 1H), 1.93-1.78 (m, 2H), 1.51-1.37 (m, 2H), 1.35-1.23 (m, 2H); MS (m/z): 590.67 [M+1]⁺.

Example 23. tert-butyl (1S,3R)-3-(5-chloro-4-(1H-indol-3-yl)pyrimidin-2-ylamino) cyclohexyl(4-((E)-4-(dimethylamino)but-2-enamido)benzyl)carbamate (Compound 127)

(1R,3S)—N1-(5-chloro-4-(1-(phenylsulfonyl)-H-indol-3-yl)pyrimidin-2-yl)-N3-(4-nitrobenzyl)cyclohexane-1,3-diamine

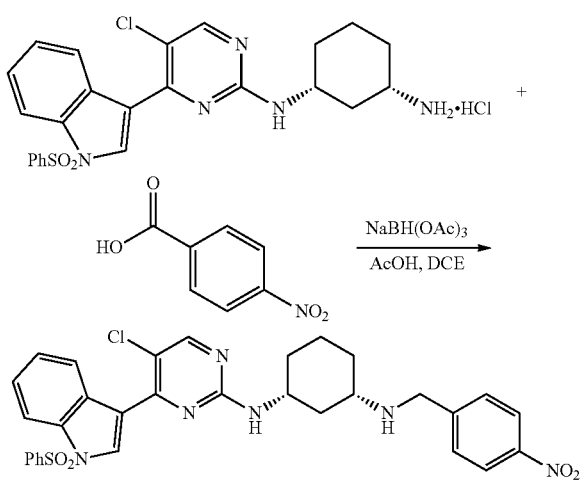

A suspension of (1R,3S)—N1-(5-chloro-4-(1-(phenylsulfonyl)-1H-indol-3-yl)pyrimidin-2-yl)cyclohexane-1,3-diamine.HCl (295 mg, 0.57 mmol) in DCE (5.7 mL) was sequentially treated with DIPEA (0.57 mmol), AcOH (0.28 mmol), 4-nitrobenzaldehyde (86 mg, 0.57 mmol) and NaBH(OAc)₃ (181 mg, 0.85 mmol). The resulting mixture was stirred 48 h at rt before dilution with DCM (30 mL), saturated NaHCO₃ (5 ML) and brine (5 mL). The layers were separated and the organic layer was dried over MgSO₄, filtered and evaporated to dryness affording the title compound (302 mg, 0.489 mmol, 86%) as a yellow solid which was used in the next step without further purification.

tert-butyl (1S,3R)-3-(5-chloro-4-(1-(phenylsulfonyl)-1H-indol-3-yl)pyrimidin-2-ylamino)cyclohexyl(4-nitrobenzyl)carbamate

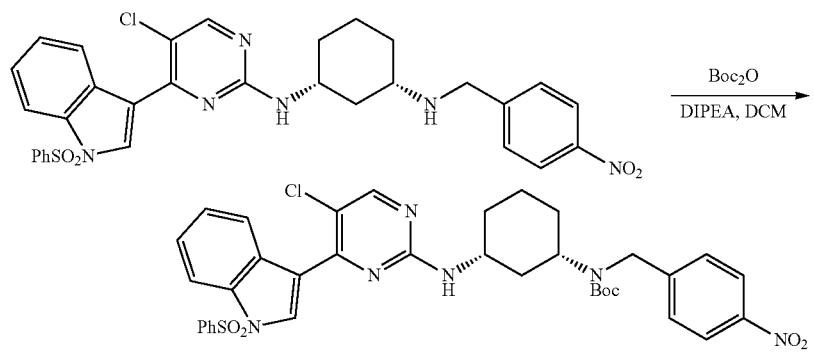

A solution of (1R,3S)—N1-(5-chloro-4-(1-(phenylsulfonyl)-1H-indol-3-yl)pyrimidin-2-yl)-N3-(4-nitrobenzyl)cyclohexane-1,3-diamine (302 mg, 0.489 mmol) and DIPEA (0.61 mmol) was treated with Boc₂O (134 mg, 0.61 mmol) and stirred overnight at rt. The resulting mixture was diluted with DCM (30 mL) and saturated NaHCO₃ (5 mL) and brine (5 mL). The layers were separated and the organic layer was dried over MgSO₄, filtered and evaporated to dryness. The residue was purified by SiO₂ chromatography (DCM/EtOAc 0 to 25% gradient) and afforded the title compound (343 mg, 0.478 mmol, 98%) as a pale yellow solid.

tert-butyl 4-aminobenzyl(((1S,3R)-3-(5-chloro-4-(1-(phenylsulfonyl)-1H-indol-3-yl)pyrimidin-2-ylamino)cyclohexyl)carbamate

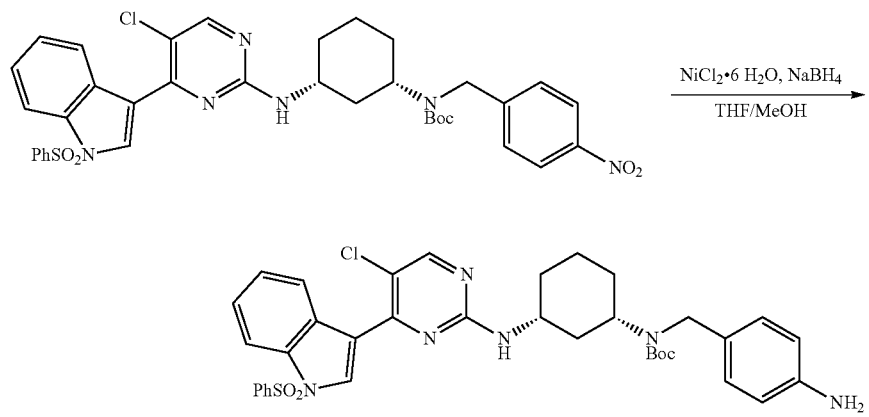

A solution of tert-butyl (1S,3R)-3-(5-chloro-4-(1-(phenylsulfonyl)-1H-indol-3-yl)pyrimidin-2-ylamino)cyclohexyl(4-nitrobenzyl)carbamate (212 mg, 0.30 mmol) in 2:1 MeOH/THF (3.0 mL) was sequentially treated with NiCl$_2$.6H$_2$O (35 mg, 0.15 mmol) and NaBH$_4$ (45 mg, 1.18 mmol). The resulting mixture was stirred 15 min at rt before being diluted with EtOAc (15 mL) and H$_2$O (10 mL). The layers were separated and the aqueous layer was extracted with EtOAc (3×10 mL). The combined organic layers were washed with brine (10 mL), dried over MgSO$_4$, filtered and evaporated to dryness. The residue was purified by SiO$_2$ chromatography (DCM/EtOAc 0 to 50% gradient) and afforded the title compound (106 mg, 0.154 mmol, 52%) as a pale yellow solid.

tert-butyl 4-aminobenzyl((1S,3R)-3-(5-chloro-4-(1H-indol-3-yl)pyrimidin-2-ylamino) cyclohexyl)carbamate

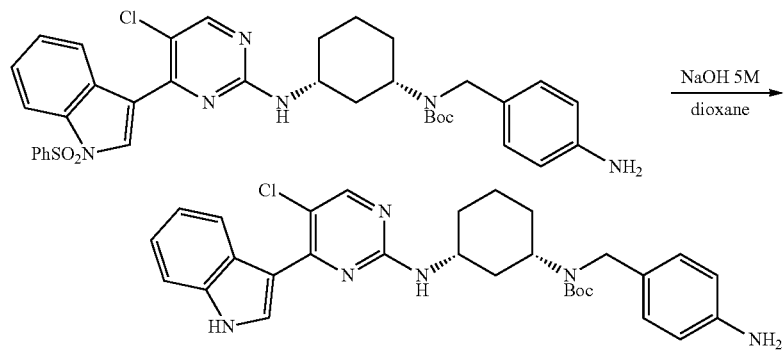

A solution of tert-butyl 4-aminobenzyl((1S,3R)-3-(5-chloro-4-(1-(phenylsulfonyl)-1H-indol-3-yl)pyrimidin-2-ylamino)cyclohexyl)carbamate (136 mg, 0.20 mmol) in dioxane (1.3 mL) was treated with a 5M solution of NaOH in H$_2$O (0.40 mL, 1.98 mmol) and heated at 65° C. for 5 h. The cooled mixture was concentrated to dryness and the residue was purified by reverse phase chromatography (C$_{18}$, H$_2$O/ACN+0.1% HCO$_2$H 0 to 60% gradient) and afforded the title compounds (100 mg, 0.183 mmol, 92%) as a beige solid.

tert-butyl (1S,3R)-3-(5-chloro-4-(1H-indol-3-yl)pyrimidin-2-ylamino)cyclohexyl(4-((E)-4-(dimethylamino)but-2-enamido)benzyl)carbamate

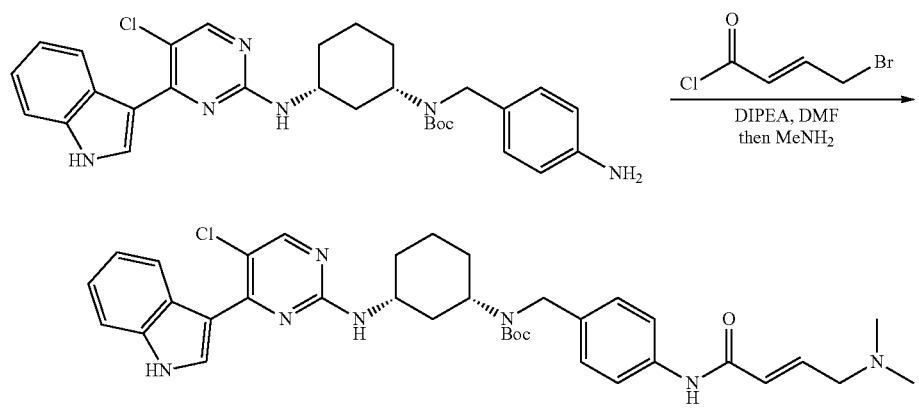

A cooled (−60° C.) solution of tert-butyl 4-aminobenzyl (((1S,3R)-3-(5-chloro-4-(1H-indol-3-yl)pyrimidin-2-ylamino)cyclohexyl)carbamate (99.5 mg, 0.182 mmol) and DIPEA (0.546 mmol) in 1:2 NMP/THF (7 mL) was treated with a 54.2 mg/mL solution of (E)-4-bromobut-2-enoyl chloride in DCM (0.191 mmol). The resulting mixture was stirred 30 min at −60° C. before addition of a 2M solution of dimethylamine in THF (0.546 mmol). The resulting mixture was warmed to rt and stirred 3 h at this temperature before being evaporated to dryness. The residue was purified by reverse phase chromatography ($C_{18}$, $H_2O$/ACN+0.1% $HCO_2H$ 0 to 60% gradient) and afforded the title compounds (68 mg, 0.103 mmol, 57%) as a white solid after lyophilisation. $^1H$ NMR (500 MHz, $d_6$-DMSO) δ 11.83 (s, 1H), 9.99 (s, 1H), 8.73-8.49 (m, 1H), 8.45 (d, J=2.6 Hz, 1H), 8.26-8.17 (m, 1H), 7.56 (d, J=4.2 Hz, 2H), 7.49 (d, J=6.0 Hz, 1H), 7.24-7.11 (m, 5H), 6.69 (dt, J=15.4, 5.9 Hz, 1H), 6.23 (d, J=15.4 Hz, 1H), 4.41-4.21 (m, 2H), 4.08-3.69 (m, 2H), 3.03 (dd, J=5.9, 1.3 Hz, 2H), 2.16 (s, 6H), 1.98-1.84 (m, 2H), 1.81-1.68 (m, 1H), 1.68-1.52 (m, 2H), 1.50-1.40 (m, 2H), 1.31 (s, 9H), 1.20-1.09 (m, 1H); MS (m/z): 658.69 $[M+1]^+$.

Example 24. (E)-N-(4-((((1S,3R)-3-(5-chloro-4-(1H-indol-3-yl)pyrimidin-2-ylamino) cyclohexylamino) methyl)phenyl)-4-(dimethylamino)but-2-enamide (Compound 129)

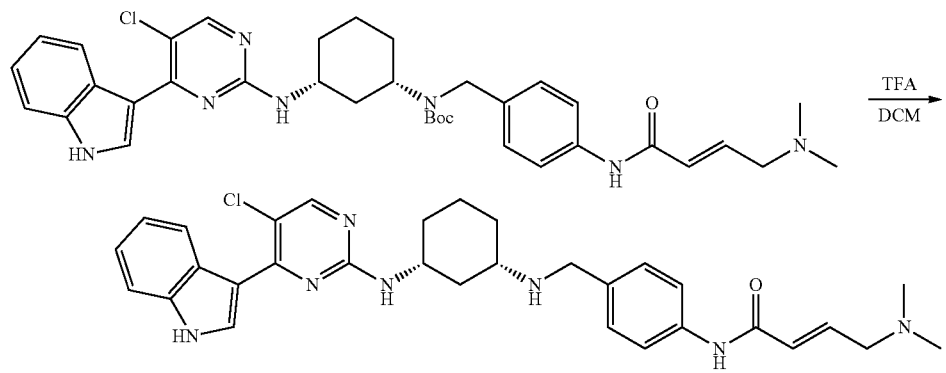

A solution of tert-butyl (1S,3R)-3-(5-chloro-4-(1H-indol-3-yl)pyrimidin-2-ylamino) cyclohexyl(4-((E)-4-(dimethylamino)but-2-enamido)benzyl)carbamate prepared as in Example 23 (9.8 mg, 0.02 mmol) in DCM (3 mL) was treated with TFA (0.15 mmol) and stirred 3 h at rt. The resulting mixture was evaporated to dryness and the residue was diluted with MeTHF (20 mL) and saturated $NaHCO_3$ (5 mL). The layers were separated and the organic layer was washed with saturated $NaHCO_3$ (2×5 mL), brine (5 mL), dried over $MgSO_4$, filtered and evaporated to dryness. The residue was purified by reverse phase chromatography ($C_{18}$, $H_2O$/ACN+0.1% $HCO_2H$ 0 to 60% gradient) and afforded the title compound (4.8 mg, 0.0086 mmol, 58%) as a white solid after lyophilisation. $^1H$ NMR (500 MHz, $d_6$-DMSO) δ 11.83 (s, 1H), 10.09 (s, 1H), 8.75-8.48 (m, 1H), 8.47 (d, J=2.9 Hz, 1H), 8.25 (s, 1H), 8.17 (s, 1H), 7.63 (d, J=7.6 Hz, 2H), 7.48 (d, J=8.2 Hz, 1H), 7.36-7.30 (m, 2H), 7.20 (t, J=7.6 Hz, 1H), 7.16-7.00 (m, 1H), 6.73 (dt, J=15.4, 5.9 Hz, 1H), 6.54 (s, 1H), 6.27 (d, J=15.4 Hz, 1H), 3.91 (s, 2H), 3.06 (d, J=4.7 Hz, 2H), 2.92-2.81 (m, 2H), 2.18 (s, J=5.9 Hz, 6H), 2.08-2.02 (m, 1H), 1.98 (t, J=3.4 Hz, 1H), 1.88-1.77 (m, 2H), 1.37-1.21 (m, 4H); MS (m/z): 558.66 [M+1]+.

Example 25. N-(5-(5-chloro-4-(1H-indol-3-yl)pyrimidin-2-ylamino)bicyclo[3.1.1]heptan-1-yl)-4-(3-(trimethylsilyl)propiolamido)benzamide (Compound 130)

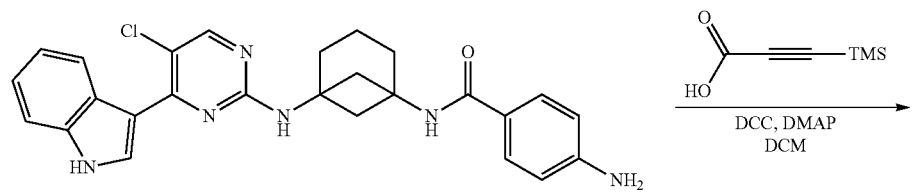

-continued

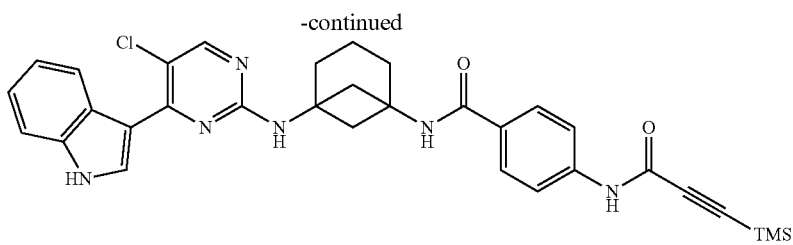

A solution of TMS-propynoic acid (10 mg, 0.07 mmol) and DCC (14 mg, 0.07 mmol) in DCM (1 mL) was treated with 4-amino-N-(5-(5-chloro-4-(1H-indol-3-yl)pyrimidin-2-ylamino)bicyclo[3.1.1]heptan-1-yl)benzamide prepared as in Example 17 (29 mg, 0.06 mmol) and DMAP (catalytic amount). The mixture was stirred overnight at rt and evaporated to dryness. The residue was purified by reverse phase chromatography ($C_{18}$, $H_2O$/ACN+0.1% $HCO_2H$ 5 to 60% gradient) and afforded the title compound (2.0 mg, 0.0034 mmol, 5.5%) as a white solid after lyophilisation. $^1$H NMR (500 MHz, $d_6$-DMSO) δ 11.83 (s, 1H), 10.93 (s, 1H), 8.58 (s, 1H), 8.51 (s, 1H), 8.46 (s, 1H), 8.38 (s, 1H), 7.81-7.74 (m, 2H), 7.66-7.57 (m, 3H), 7.49 (d, J=8.0 Hz, 1H), 7.21 (t, J=7.0 Hz, 1H), 7.15 (t, J=7.5 Hz, 1H), 6.84 (s, 2H), 2.45-2.35 (m, 2H), 2.17 (brs, 2H), 2.07 (brs, 2H), 1.95 (d, J=6.6 Hz, 2H), 1.88 (brs, 2H), 0.26 (s, 9H); MS (m/z): 597.63 [M+1]$^+$.

Example 26 2-(((E)-4-(4-((1S,3R)-3-(5-chloro-4-(1H-indol-3-yl)pyrimidin-2-ylamino) cyclohexylcarbamoyl)phenylamino)-4-oxobut-2-enyl)(methyl)amino)acetic acid (Compound 131)

Methyl 2-(((E)-4-(4-((1S,3R)-3-(5-chloro-4-(1H-indol-3-yl)pyrimidin-2-ylamino)cyclohexylcarbamoyl)phenylamino)-4-oxobut-2-enyl)(methyl)amino) acetate

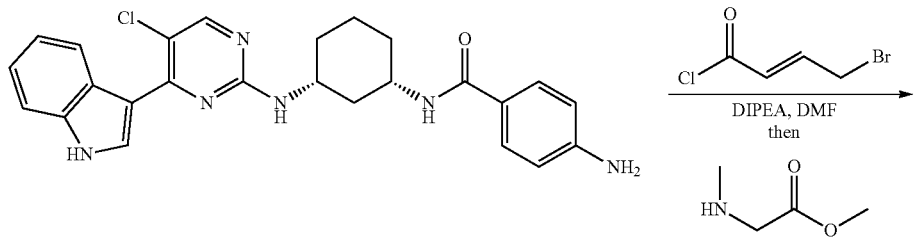

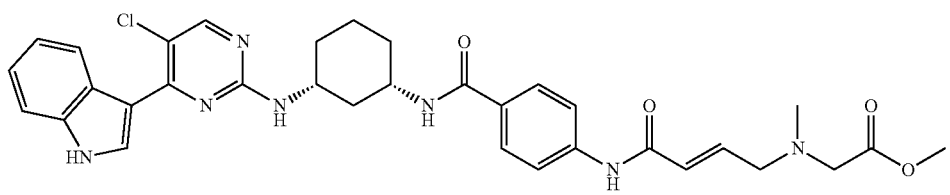

A cooled (−60° C.) solution of 4-amino-N-((1S,3R)-3-(5-chloro-4-(1H-indol-3-yl)pyrimidin-2-ylamino)cyclohexyl)benzamide prepared as in Example 1 (40 mg, 0.067 mmol) and DIPEA (0.200 mmol) in 1:6 NMP/THF (6.8 mL) was treated with a 54.2 mg/mL solution of (E)-4-bromobut-2-enoyl chloride in DCM (0.067 mmol). The resulting mixture was stirred 1 h at −60° C. before addition of methyl 2-(methylamino)acetate.HCl (18.7 mg, 0.134 mmol). The resulting mixture was warmed to rt and stirred overnight at this temperature before evaporation to dryness. The residue was purified by $SiO_2$ chromatography (DCM/MeOH 0 to 20% gradient) and afforded the title compound (25 mg, 0.032 mmol, 49%) as a white solid.

2-(((E)-4-(4-(((1S,3R)-3-(5-chloro-4-(1H-indol-3-yl) pyrimidin-2-ylamino) cyclohexylcarbamoyl)phenylamino)-4-oxobut-2-enyl)(methyl)amino)acetic acid

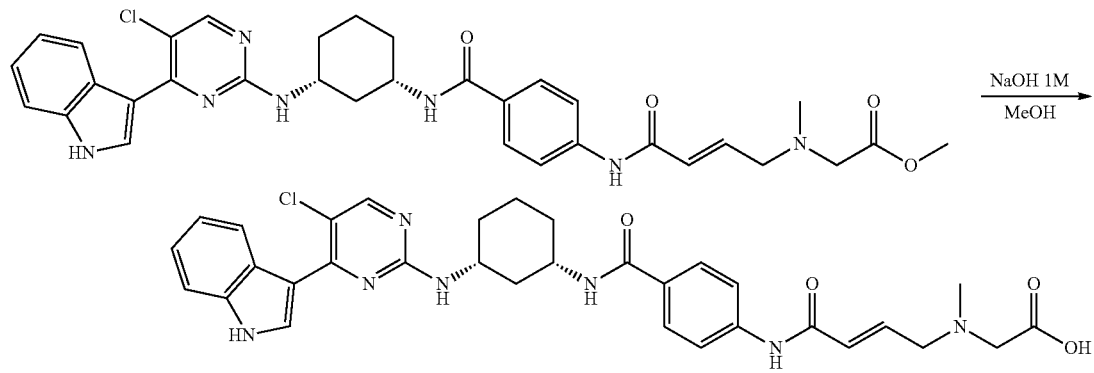

A solution of methyl 2-(((E)-4-(4-(((1S,3R)-3-(5-chloro-4-(1H-indol-3-yl)pyrimidin-2-ylamino)cyclohexylcarbamoyl)phenylamino)-4-oxobut-2-enyl)(methyl)amino)acetate (25 mg, 0.032 mmol) in MeOH (1 mL) was treated with a 1M solution of NaOH in H$_2$O (0.096 mmol) and stirred overnight at rt. The resulting mixture was evaporated to dryness and the residue was purified by reverse phase chromatography (C$_{18}$, H$_2$O/ACN+0.1% HCO$_2$H 5 to 60% gradient) and afforded the title compound (5.0 mg, 0.0081 mmol, 25%) as a white solid after lyophilisation. $^1$H NMR (500 MHz, d$_6$-DMSO) δ 11.82 (brs, 1H), 10.27 (s, 1H), 8.61 (brs, 1H), 8.46 (s, 1H), 8.29-8.14 (m, 2H), 7.80 (t, J=9.8 Hz, 2H), 7.70 (d, J=8.7 Hz, 1H), 7.65 (d, J=8.5 Hz, 1H), 7.47 (d, J=9.1 Hz, 1H), 7.29 (d, J=8.0 Hz, 1H), 7.24-7.17 (m, 2H), 6.75 (dt, J=15.3 Hz, J=5.9 Hz, 1H), 6.29 (d, J=15.4 Hz, 1H), 3.94 (brs, 4H), 2.60 (brs, 1H), 2.34 (d, 3H), 2.20 (brs, 1H), 2.00 (brs, 1H), 1.85 (brs, 2H), 1.53-1.20 (m, 5H); MS (m/z): 616.32 [M+1]$^+$.

Example 27 N-((1S,3R)-3-(4-(1H-indol-3-yl)pyrimidin-2-ylamino)cyclohexyl)-4-((E)-4-(dimethylamino)but-2-enamido)benzamide (Compound 132)

tert-butyl 4-((1S,3R)-3-(4-(1H-indol-3-yl)pyrimidin-2-ylamino)cyclohexylcarbamoyl) phenylcarbamate

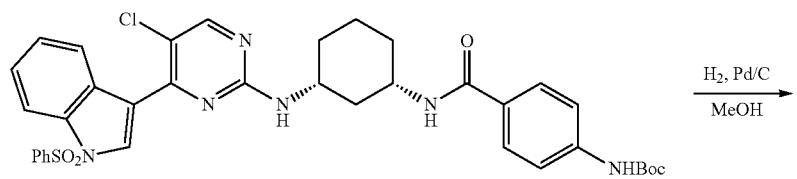

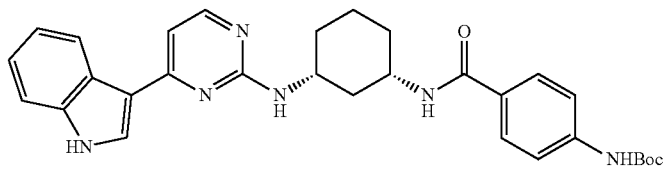

+

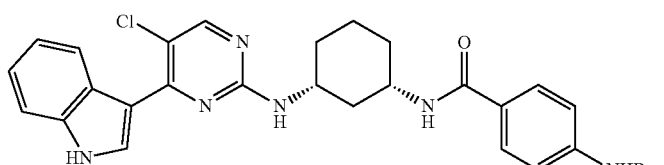

A degassed solution of tert-butyl 4-((1S,3R)-3-(5-chloro-4-(1-(phenylsulfonyl)-1H-indol-3-yl)pyrimidin-2-ylamino)cyclohexylcarbamoyl)phenylcarbamate prepared as in Example 1 (148 mg, 0.211 mmol) in MeOH (10 mL) was treated with 10% Pd/C (25 mg) and stirred overnight under $H_2$ (50 psi). The resulting mixture was filtered over Celite® (MeOH) and the filtrate was evaporated to dryness affording an inseparable mixture of the title compound and chlorinated pyrimidine which was used in the next step without purification.

N-((1S,3R)-3-(4-(1H-indol-3-yl)pyrimidin-2-ylamino)cyclohexyl)-4-aminobenzamide

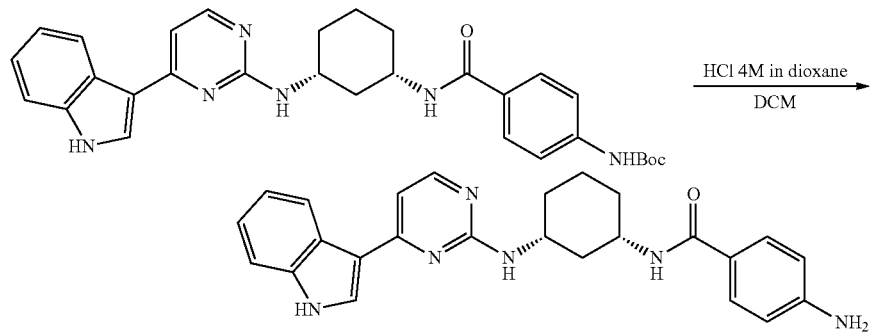

A solution of tert-butyl 4-((1S,3R)-3-(4-(1H-indol-3-yl)pyrimidin-2-ylamino) cyclohexylcarbamoyl)phenylcarbamate (100 mg, as a mixture with chlorinated pyrimidine from previous step) in DCM (2.0 mL) was treated with a 4M solution of HCl in dioxane (750 mL, 3.0 mmol) and stirred 4 h at rt. The mixture was evaporated to dryness and the residue was purified by reverse phase chromatography ($C_{18}$, $H_2O$/ACN+0.1% $HCO_2H$ 5 to 60% gradient) and afforded the title compound (12.5 mg, 0.0081 mmol, 25%) as a white solid.

N-((1S,3R)-3-(4-(1H-indol-3-yl)pyrimidin-2-ylamino)cyclohexyl)-4-((E)-4-(dimethylamino)but-2-enamido)benzamide

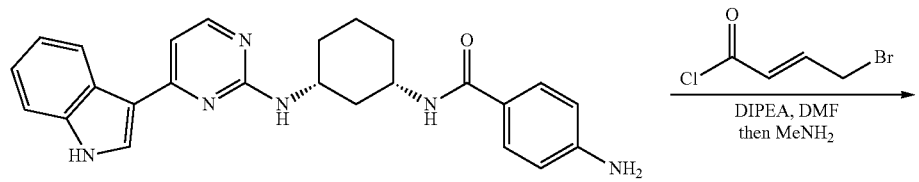

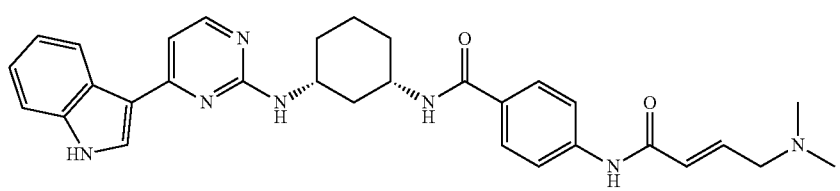

A cooled (−60° C.) solution of N-((1S,3R)-3-(4-(1H-indol-3-yl)pyrimidin-2-ylamino)cyclohexyl)-4-aminobenzamide (12.5 mg, 0.0293 mmol) and DIPEA (0.088 mmol) in 1:3 NMP/THF (3.0 mL) was treated with a 54.2 mg/mL solution of (E)-4-bromobut-2-enoyl chloride in DCM (0.029 mmol). The resulting mixture was stirred 1 h at −60° C. before addition of a 2M solution of dimethylamine in THF (0.176 mmol). The resulting mixture was warmed to rt before being evaporated to dryness. The residue was purified by reverse phase chromatography ($C_{18}$, $H_2O$/ACN+0.1% $HCO_2H$ 5 to 70% gradient) and afforded the title compound (2.0 mg, 0.0037 mmol, 13%) as a white solid after lyophilisation. $^1H$ NMR (500 MHz, $d_6$-DMSO) δ 11.68 (s, 1H), 10.26 (s, 1H), 8.46 (brs, 1H), 8.24-8.19 (s, 1H), 8.13 (d, J=5.4 Hz, 1H), 7.82 (d, J=8.8 Hz, 2H), 7.70 (d, J=8.8 Hz, 2H), 7.45-7.43 (m, 1H), 7.17 (brs, 2H), 7.00 (d, J=5.3 Hz, 1H), 6.93 (d, J=7.7 Hz, 1H), 6.78-6.73 (dt, 1H), 6.31-6.26 (m, 2H), 3.97 (brs, 3H), 3.06 (d, J=4.5 Hz, 2H), 2.17 (s, 6H), 2.09-1.96 (brs, 1H), 1.93-1.78 (m, 2H), 1.50-1.25 (m, 4H); MS (m/z): 538.71 $[M+1]^+$.

Example 28 4-acrylamido-N-((1S,3R)-3-(5-chloro-4-(1H-indol-3-yl)pyrimidin-2-ylamino)cyclohexyl)-2-morpholinobenzamide (Compound 133)

2-morpholino-4-nitrobenzoic acid

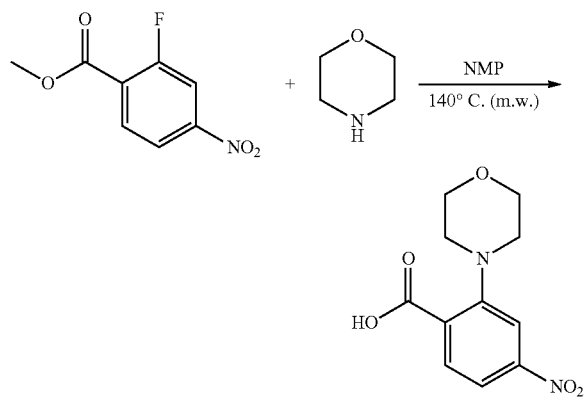

A solution of methyl 2-fluoro-4-nitrobenzoate (200 mg, 1.00 mmol) and morpholine (8.04 mmol) in NMP (2.1 mL) was heated at 140° C. (microwave) for 35 min. The cooled mixture was diluted with EtOAc (20 mL) and washed with $H_2O$ (10 mL) and brine (10 ml). The combined aqueous layers were acidified to pH=2 with a 1M solution of HCl in $H_2O$ and extracted with DCM (3×20 mL). The combined organic layers were dried by passing through a phase cartridge separator and evaporated to dryness affording the title compound as a mixture with morpholine which was used in the next step without further purification.

N-((1S,3R)-3-(5-chloro-4-(1-(phenylsulfonyl)-1H-indol-3-yl)pyrimidin-2-ylamino)cyclohexyl)-2-morpholino-4-nitrobenzamide

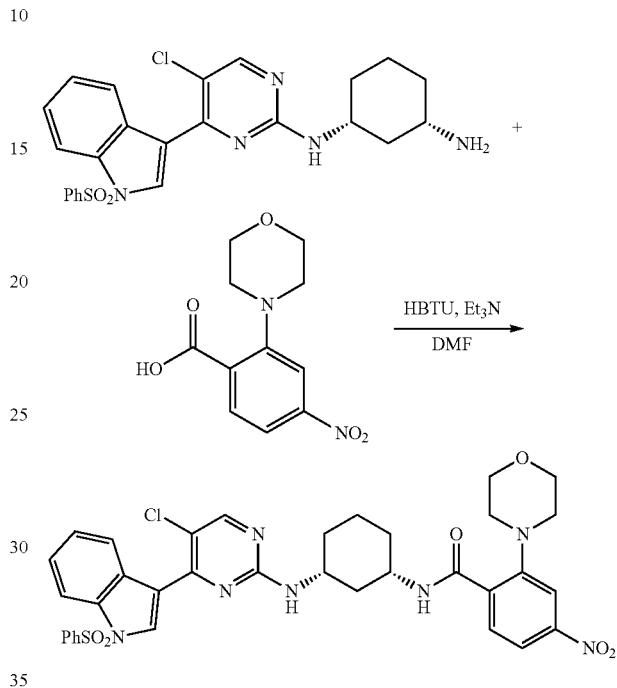

A solution of (1R,3S)—N1-(5-chloro-4-(1-(phenylsulfonyl)-1H-indol-3-yl)pyrimidin-2-yl)cyclohexane-1,3-diamine prepared as in Example 1 (50 mg, 0.104 mmol) and 2-morpholino-4-nitrobenzoic acid (29 mg, 0.114 mmol) in DMF (5.0 mL) was treated with $Et_3N$ (0.311 mmol) and HBTU (59 mg, 0.156 mmol). The resulting mixture was stirred overnight at rt, diluted with EtOAc (20 mL) and saturated $NaHCO_3$ (10 mL). The layers were separated and the organic layer was washed with brine (10 mL), dried over $MgSO_4$, filtered and evaporated to dryness. The residue was purified by $SiO_2$ chromatography (DCM/EtOAc 0 to 70% gradient) and afforded the title compound (48 mg, 0.067 mmol, 65%) as a pale yellow solid.

4-amino-N-((1S,3R)-3-(5-chloro-4-(1-(phenylsulfonyl)-1H-indol-3-yl)pyrimidin-2-ylamino)cyclohexyl)-2-morpholinobenzamide

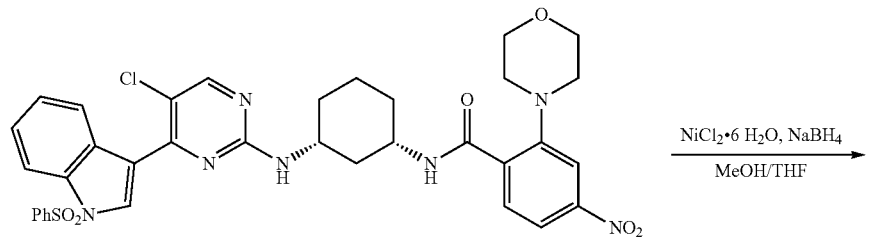

-continued

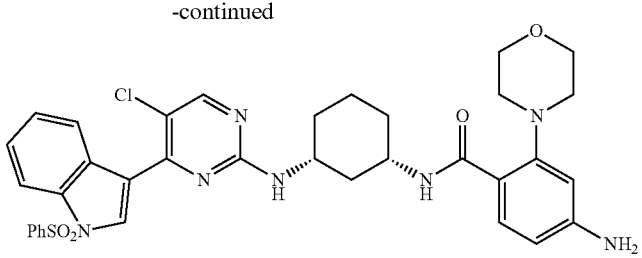

A cooled (0° C.) solution of N-((1S,3R)-3-(5-chloro-4-(1-(phenylsulfonyl)-1H-indol-3-yl)pyrimidin-2-ylamino)cyclohexyl)-2-morpholino-4-nitrobenzamide (76 mg, 0.106 mmol) in 2:1 MeOH/THF (1 mL) was sequentially treated with NiCl$_2$.6H$_2$O (12.6 mg, 0.053 mmol) and NaBH$_4$ (16.1 mg, 0.425 mmol). The resulting black mixture was stirred 15 min at rt before dilution with EtOAc (20 mL) and H$_2$O (10 mL). The layers were separated and the aqueous layer was extracted with EtOAc (3×10 mL). The combined organic layers were washed with brine (10 mL), dried over MgSO$_4$, filtered and evaporated to dryness. The residue was purified by SiO$_2$ chromatography (DCM/EtOAc 0 to 70% gradient) and afforded the title compound (26 mg, 0.038 mmol, 36%) as a pale yellow solid.

4-amino-N-((1S,3R)-3-(5-chloro-4-(1H-indol-3-yl)pyrimidin-2-ylamino)cyclohexyl)-2-morpholinobenzamide

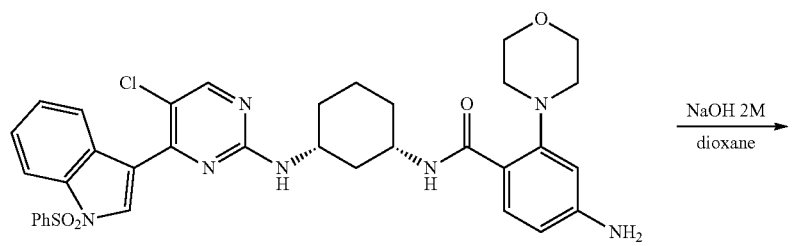

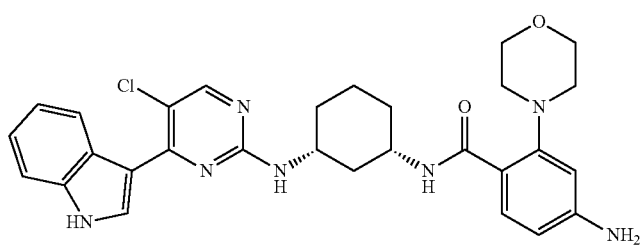

A solution of 4-amino-N-((1S,3R)-3-(5-chloro-4-(1-(phenylsulfonyl)-1H-indol-3-yl)pyrimidin-2-ylamino)cyclohexyl)-2-morpholinobenzamide (24 mg, 0.035 mmol) in dioxane (0.35 mL) was treated with a 2M solution of NaOH in H₂O (0.525 mmol) and stirred overnight at rt and 2 h at 60° C. The cooled mixture was concentrated to remove volatiles and the resulting was diluted with MeTHF (15 mL) and H₂O (10 mL). The layers were separated and the aqueous layer was extracted with MeTHF (3×10 mL). The combined organic layers were dried over Na₂SO₄, filtered and evaporated to dryness affording the title compound (19 mg, 0.0248 mmol, 71%) as a pale yellow solid which was used in the next step without further purification.

4-acrylamido-N-((1S,3R)-3-(5-chloro-4-(1H-indol-3-yl)pyrimidin-2-ylamino)cyclohexyl)-2-morpholinobenzamide

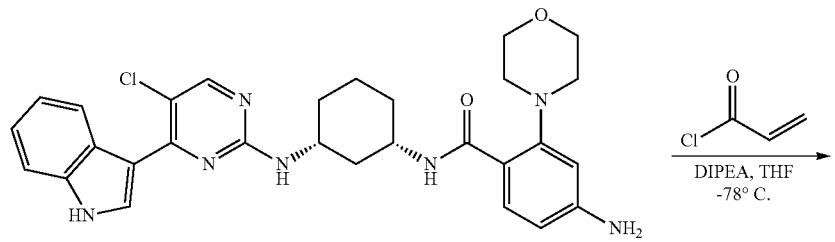

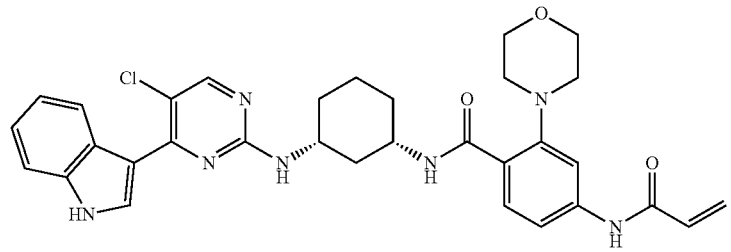

A cooled (−60° C.) solution of 4-amino-N-((1S,3R)-3-(5-chloro-4-(1H-indol-3-yl)pyrimidin-2-ylamino)cyclohexyl)-2-morpholinobenzamide (19 mg, 0.0348 mmol) and DIPEA (0.104 mmol) in 1:6 NMP/THF (0.8 mL) was treated with acryloyl chloride (0.0365 mmol). The resulting mixture was stirred overnight at −20° C. and then warmed to rt before being evaporated to dryness. The residue was purified by reverse phase chromatography (C₁₈, H₂O/ACN+0.1% HCO₂H 0 to 70% gradient) and afforded the title compound (11 mg, 0.018 mmol, 51%) as a pale yellow solid after lyophilisation. ¹H NMR (500 MHz, d₆-DMSO) δ 11.85 (s, 1H), 10.35 (s, 1H), 9.20 (s, 1H), 8.60 (bs, 1H), 8.49 (d, J=12.2 Hz, 1H), 8.25 (s, 1H), 7.72 (d, J=8.6 Hz, 1H), 7.63 (s, 1H), 7.52-7.46 (m, 1H), 7.43 (dd, J=8.5, 1.8 Hz, 1H), 7.29 (d, J=8.0 Hz, 1H), 7.20 (t, J=5.8 Hz, 2H), 6.43 (dd, J=16.9, 10.1 Hz, 1H), 6.27 (dd, J=17.0, 1.9 Hz, 1H), 5.78 (dd, J=10.1, 1.9 Hz, 1H), 4.06 (s, 1H), 3.95 (s, 2H), 3.80-3.53 (m, 3H), 2.87 (s, 4H), 2.02 (s, 2H), 1.83 (s, 1H), 1.60-1.35 (m, 2H), 1.35-1.09 (m, 2H); MS (m/z): 600.34 [M+1]+.

Example 29. 3-acrylamido-N-((trans)-4-(5-chloro-4-(1H-indol-3-yl)pyrimidin-2-ylamino)cyclohexyl)benzamide (Compound 135)

(trans)-N1-(5-chloro-4-(1-(phenylsulfonyl)-H-indol-3-yl)pyrimidin-2-yl)cyclohexane-1,4-diamine

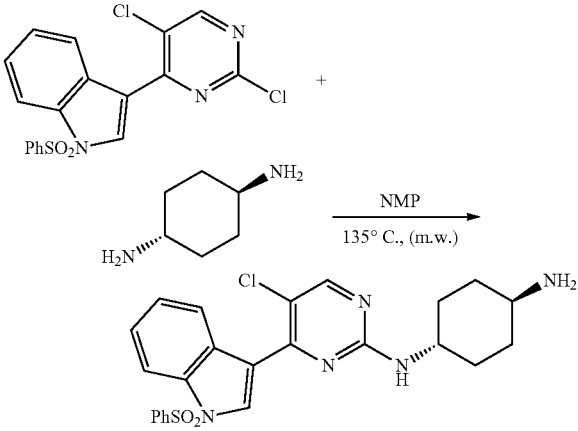

A solution of 3-(2,5-dichloropyrimidin-4-yl)-1-(phenylsulfonyl)-1H-indole (500 mg, 1.24 mmol), trans-1,4-diaminocyclohexane (170 mg, 1.49 mmol) and DIPEA (1.49 mmol) in NMP (15 mL) was heated at 135° C. (microwave) for 40 min. The cooled mixture was diluted with EtOAc (30 mL), washed with H₂O (60 mL), brine (60 mL), dried over Na₂SO₄, filtered and evaporated to dryness. The residue was purified by SiO₂ chromatography (DCM/MeOH 5 to 30% gradient) and afforded the title compound (298 mg, 0.618 mmol, 50%) as a white solid.

tert-butyl 3-(trans-4-(5-chloro-4-(1-(phenylsulfonyl)-1H-indol-3-yl)pyrimidin-2-ylamino)cyclohexylcarbamoyl)phenylcarbamate

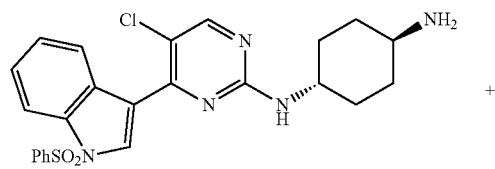
+
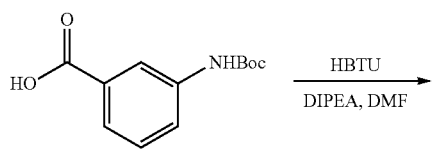
HBTU
―――――→
DIPEA, DMF

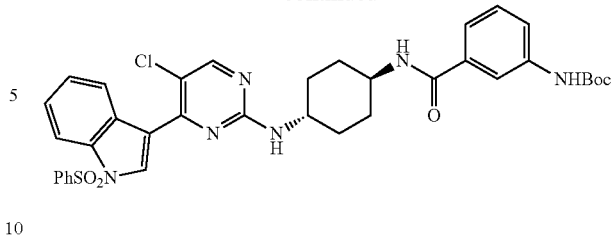

A solution of (trans)-N1-(5-chloro-4-(1-(phenylsulfonyl)-1H-indol-3-yl)pyrimidin-2-yl)cyclohexane-1,4-diamine (125 mg, 0.260 mmol) and 3-(tert-butoxycarbonylamino)benzoic acid (69 mg, 0.290 mmol) in DMF (2.5 mL) was treated with DIPEA (0.390 mmol) and HBTU (148 mg, 0.390 mmol). The resulting mixture was stirred overnight at rt, diluted with EtOAc (20 mL) and saturated NaHCO₃ (10 mL). The layers were separated and the aqueous layer was extracted with EtOAc (2×20 mL). The combined organic layers were washed with brine (10 mL), dried over Na₂SO₄, filtered and evaporated to dryness affording the title compound (182 mg, 0.290 mmol, 100%) as a yellow solid which was used in the next step without further purification.

tert-butyl 3-(trans-4-(5-chloro-4-(1H-indol-3-yl)pyrimidin-2-ylamino)cyclohexylcarbamoyl) phenylcarbamate

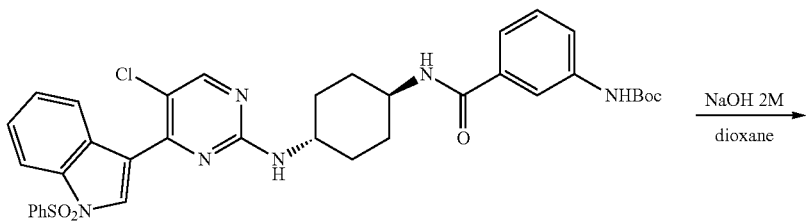 NaOH 2M
―――――→
dioxane

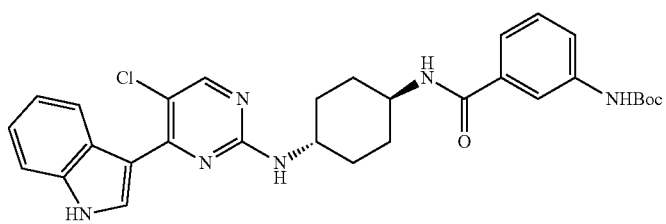

A solution of tert-butyl 3-(trans-4-(5-chloro-4-(1-(phenylsulfonyl)-1H-indol-3-yl)pyrimidin-2-ylamino)cyclohexylcarbamoyl)phenylcarbamate (182 mg, 0.290 mmol) in dioxane (3.0 mL) was treated with a 2M solution of NaOH in H₂O (2.5 mL, 5.00 mmol) and stirred at 70° C. for 1 h. The cooled mixture was evaporated to dryness and the residue was dissolved in MeTHF (20 mL) and H₂O (10 mL). The layers were separated and the aqueous layer was extracted with MeTHF (3×10 mL). The combined organic layers were dried over Na₂SO₄, filtered and evaporated to dryness affording the title compound (163 mg, 0.290 mmol, 100%) as a yellow solid which was used in the next step without further purification.

3-amino-N-(trans-4-(5-chloro-4-(1H-indol-3-yl)pyrimidin-2-ylamino)cyclohexyl)benzamide.HCl

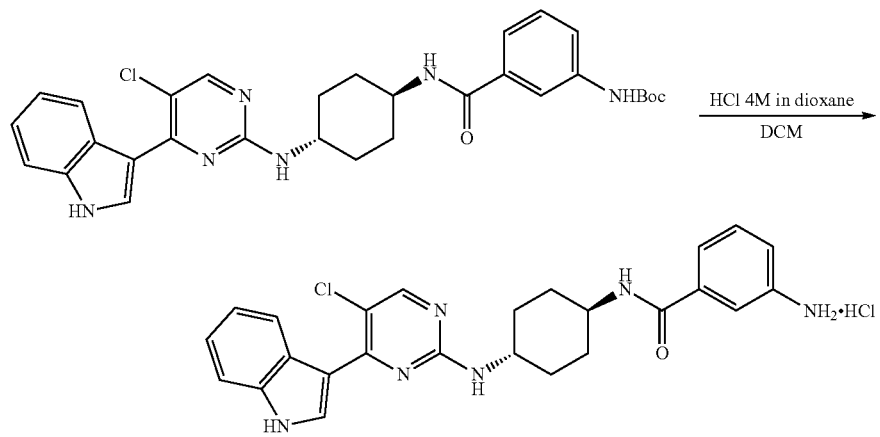

A solution of tert-butyl 3-(trans-4-(5-chloro-4-(1H-indol-3-yl)pyrimidin-2-ylamino)cyclohexylcarbamoyl)phenylcarbamate (163 mg, 0.290 mmol) in DCM (3.0 mL) was treated with a 4M solution of HCl in dioxane (1.10 mL, 4.54 mmol) and stirred 30 min at rt. The resulting mixture was evaporated to dryness and afforded the title compound (144 mg, 0.290 mmol, 100%) as a yellow solid which was used in the next step without further purification.

3-acrylamido-N-((trans)-4-(5-chloro-4-(1H-indol-3-yl)pyrimidin-2-ylamino) cyclohexyl)benzamide

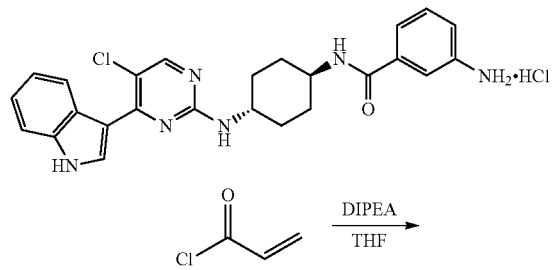

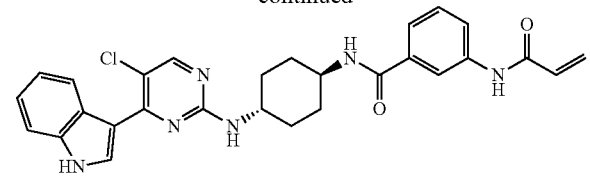

A cooled (−78° C.) solution of 3-amino-N-(trans-4-(5-chloro-4-(1H-indol-3-yl)pyrimidin-2-ylamino)cyclohexyl)benzamide.HCl (67 mg, 0.135 mmol) and DIPEA (0.54 mmol) in 3:1 THF/NMP (4.0 mL) was treated with acryloyl chloride (0.1283 mmol) and stirred 30 min at this temperature. The resulting mixture was warmed up to rt and evaporated to dryness. The residue was purified by reverse phase chromatography (C₁₈, H₂O/ACN+0.1% HCO₂H 0 to 60% gradient) and afforded the title compound (40 mg, 0.078 mmol, 58%) as a white solid after lyophilisation. ¹H NMR (500 MHz, d₆-DMSO) δ 11.84 (brs, 1H), 10.30 (s, 1H), 8.63 (brs, 1H), 8.48 (s, 1H), 8.31 (brs, 1H), 8.22 (d, 1H), 8.02 (s, 1H), 7.90 (d, J=7.9 Hz, 1H), 7.55 (d, J=7.7 Hz, 1H), 7.50 (d, J=6.5 Hz, 1H), 7.41 (t, J=7.9 Hz, 1H), 7.23-7.19 (m, 3H), 6.45 (dd, J=17.0, 10.1 Hz, 1H), 6.28 (dd, J=17.0, 1.9 Hz, 1H), 5.78 (dd, J=10.1, 1.9 Hz, 3H), 4.06 (brs, 1H), 3.82 (brs, 2H), 2.11-1.91 (m, 3H), 1.56-1.42 (m, 3H); MS (m/z): 515.33 [M+1]+.

Example 30. N-(4-((R)-1-((1S,3R)-3-(5-chloro-4-(1H-indol-3-yl)pyrimidin-2-ylamino) cyclohexylamino)-2,2,2-trifluoroethyl)phenyl)acrylamide (Compound 136)

tert-butyl (1R,3S)-3-(hydroxymethyl)cyclohexylcarbamate

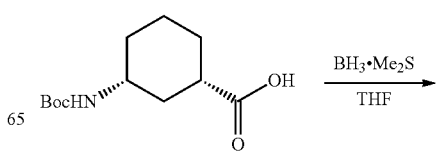

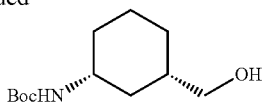

A cooled (0° C.) solution of (1S,3R)-3-(tert-butoxycarbonylamino)cyclohexanecarboxylic acid (prepared following Tetrahedron: *Asymmetry* 2010 (21), 864-866) (1.24 g, 5.09 mmol) in THF (34 mL) was treated with a 2M solution of BH₃.Me₂S in THF (3.7 mL, 7.38 mmol) and stirred overnight at rt. The resulting solution was treated with a 1M solution of HCl in H₂O (20 mL) and extracted with EtOAc (3×20 mL). The combined organic layers were dried over MgSO₄, filtered and evaporated to dryness affording the title compound (1.17 g, 5.09 mmol, 100%) as a colorless oil which was used in the next step without further purification.

(R)-tert-butyl 3-methylenecyclohexylcarbamate

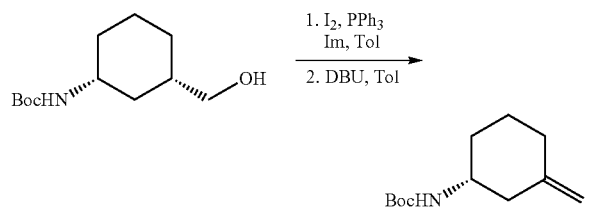

A cooled (0° C.) solution of tert-butyl (1R,3S)-3-(hydroxymethyl)cyclohexylcarbamate (200 mg, 0.87 mmol) in Tol (6 mL) was sequentially treated with imidazole (148 mg, 2.18 mmol), PPh₃ (572 mg, 2.18 mmol) and I₂ (288 mg, 1.13 mmol). The resulting mixture was stirred overnight at rt before being diluted with a saturated solution of NaHCO₃ (10 mL), a 5% solution of Na₂S₂O₃ (10 mL) and DCM (30 mL). The layers were separated and the aqueous layer was extracted with DCM (2×30 mL). The combined organic layers were dried over MgSO₄, filtered and evaporated to dryness. The residue was dissolved in Tol (10 mL), treated with DBU (1.74 mmol) and heated overnight at 80° C. The cooled mixture was diluted with a saturated solution of NH₄Cl (10 mL) and EtOAc (20 mL). The layers were separated and the aqueous layer was extracted with EtOAc (3×20 mL). The combined organic layers were dried over MgSO₄, filtered and evaporated to dryness. The residue was purified by SiO₂ chromatography (Hex/EtOAc 5 to 30% gradient) and afforded the title compound (72 mg, 0.341 mmol, 39%) as a white solid.

(R)-tert-butyl 3-oxocyclohexylcarbamate

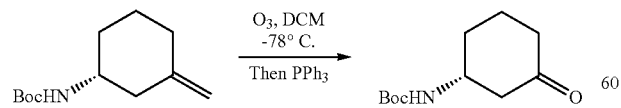

O₃ was bubbled into a cooled (−78° C.) solution of (R)-tert-butyl 3-methylenecyclohexylcarbamate (424 mg, 2.01 mmol) in DCM (40 mL) for 30 min, at which point PPh₃ (917 mg, 6.02 mmol) was added. The resulting mixture was warmed to rt and evaporated to dryness. The residue was purified by SiO₂ chromatography (Hex/EtOAc 0 to 60% gradient) and afforded the title compound (415 mg, 1.95 mmol, 97%) as a white solid.

tert-butyl (1R,3S)-3-((R)-1-(4-bromophenyl)-2,2,2trifluoroethylamino)cyclohexylcarbamate

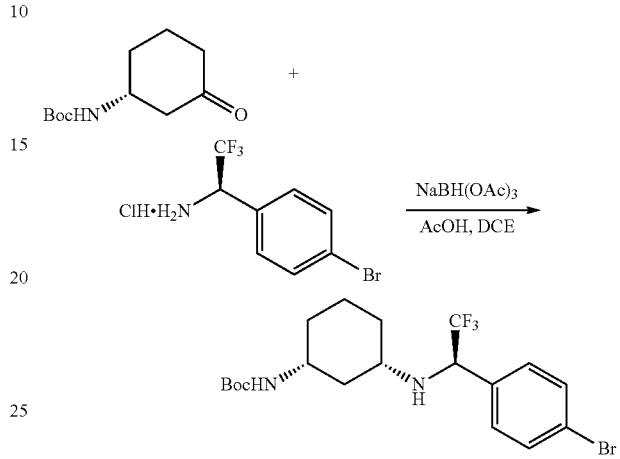

A solution of (R)-1-(4-bromophenyl)-2,2,2-trifluoroethanamine.HCl (prepared following *Org. Lett.* 2005, 7, 2, 355-358) (501 mg, 1.72 mmol) in DCE (16.4 mL) was sequentially treated with DIPEA (1.81 mmol), AcOH (0.82 mmol), (R)-tert-butyl 3-oxocyclohexylcarbamate (350 mg, 1.64 mmol) and NaBH(OAc)₃ (522 mg, 2.46 mmol). The resulting mixture was stirred 16 at rt and then diluted with DCM (20 mL) and a saturated solution of NaHCO₃ (10 mL). The layers were separated and the organic layer was washed with brine (10 mL), dried over MgSO₄, filtered and evaporated to dryness. The residue was purified by SiO₂ chromatography (Hex/EtOAc 5 to 50% gradient) and afforded the title compound (356 mg, 0.789 mmol, 48%) as a white solid together with the trans isomer (0.123 mg, 0.273, 17%) as white solid.

(1S,3R)—N1-((R)-1-(4-bromophenyl)-2,2,2-trifluoroethyl)cyclohexane-1,3-diamine.HCl

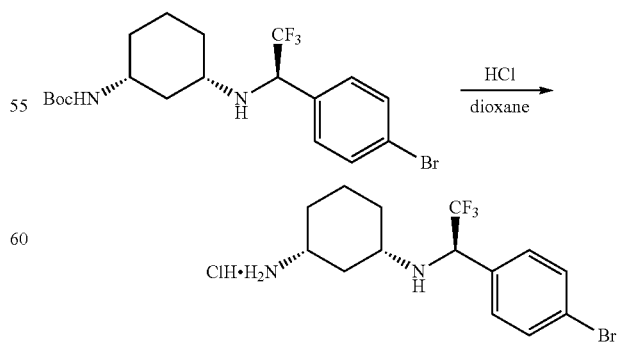

229

A solution of tert-butyl (1R,3S)-3-((R)-1-(4-bromophenyl)-2,2,2-trifluoroethylamino)cyclohexylcarbamate (144 mg, 0.32 mmol) in DCM (0.65 mL) was treated with a 4M solution of HCl in dioxane (1.60 mL, 6.38 mmol) and stirred 1 h at rt. The resulting mixture was evaporated to dryness and afforded the title compound (121 mg, 0.312 mmol, 98%) as a beige solid which was used in the next step without further purification.

(1S,3R)—N1-((R)-1-(4-bromophenyl)-2,2,2-trifluoroethyl)-N3-(5-chloro-4-(1-(phenylsulfonyl)-1H-indol-3-yl)pyrimidin-2-yl)cyclohexane-1,3-diamine

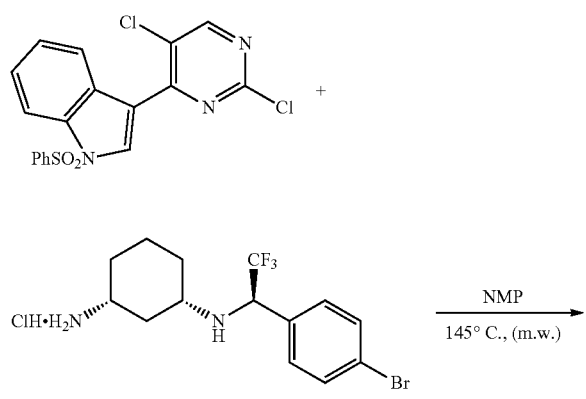

230

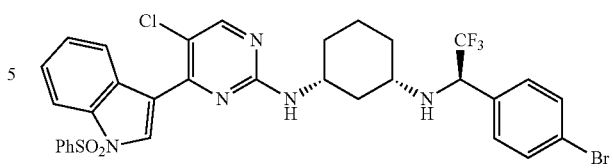

A solution of 3-(2,5-dichloropyrimidin-4-yl)-1-(phenylsulfonyl)-1H-indole (155 mg, 0.380 mmol), (1S,3R)—N1-((R)-1-(4-bromophenyl)-2,2,2-trifluoroethyl)cyclohexane-1,3-diamine.HCl (126 mg, 0.325 mmol) and DIPEA (1.15 mmol) in NMP (2.6 mL) was heated at 145° C. (microwave) for 90 min. The cooled mixture was diluted with MeTHF (20 mL), washed with H₂O (10 mL), brine (10 mL), dried over MgSO₄, filtered and evaporated to dryness. The residue was purified by SiO₂ chromatography (Hex/EtOAc 0 to 100% gradient) and afforded the title compound (141 mg, 0.196 mmol, 60%) as a pale yellow foam.

tert-butyl 4-((R)-1-((1S,3R)-3-(5-chloro-4-(1-(phenylsulfonyl)-1H-indol-3-yl)pyrimidin-2-ylamino)cyclohexylamino)-2,2,2-trifluoroethyl)phenylcarbamate

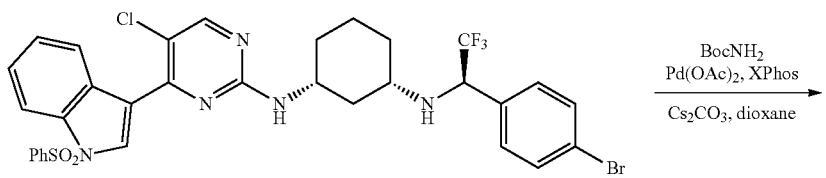

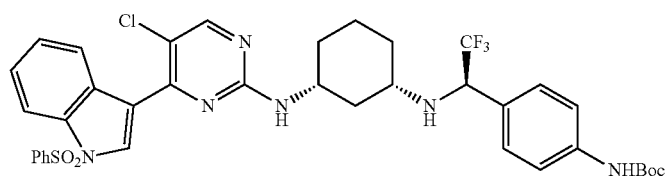

A degassed solution of (1S,3R)—N1-((R)-1-(4-bromophenyl)-2,2,2-trifluoroethyl)-N3-(5-chloro-4-(1-(phenylsulfonyl)-1H-indol-3-yl)pyrimidin-2-yl)cyclohexane-1,3-diamine (141 mg, 0.196 mmol), t-butylcarbamate (28 mg, 0.24 mmol), Pd(OAc)$_2$ (1.3 mg, 0.01 mmol), Xphos (8.4 mg, 0.02 mmol) and Cs$_2$CO$_3$ (90 mg, 0.27 mmol) in dioxane (2.0 mL) was heated at 90° C. for 12 h. The cooled mixture was filtered over Celite® (EtOAc) and the filtrate was evaporated to dryness. The residue was purified by SiO$_2$ chromatography (Hex/EtOAc 0 to 100% gradient) and afforded the title compound (191 mg as a mixture with an unknown impurity) as a pale yellow foam.

(1S,3R)—N1-((R)-1-(4-aminophenyl)-2,2,2-trifluoroethyl)-N3-(5-chloro-4-(1H-indol-3-yl)pyrimidin-2-yl)cyclohexane-1,3-diamine

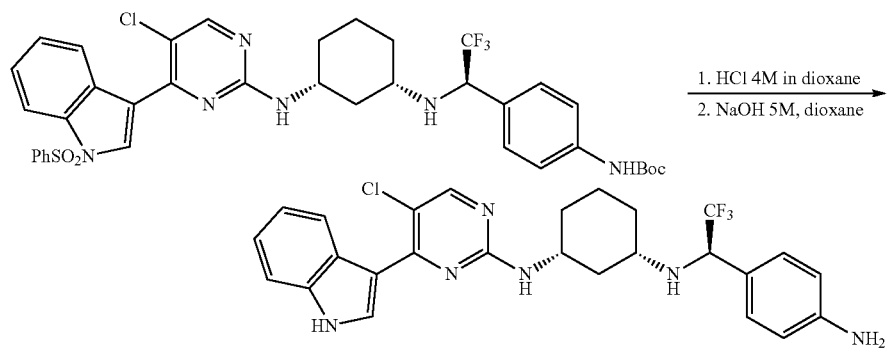

A solution of tert-butyl 4-((R)-1-((1S,3R)-3-(5-chloro-4-(1-(phenylsulfonyl)-1H-indol-3-yl)pyrimidin-2-ylamino)cyclohexylamino)-2,2,2-trifluoroethyl)phenylcarbamate (191 mg as a mixture with unknown impurity) in DCM (0.4 mL) was treated with a 4M solution of HCl in dioxane (2.94 mmol) and stirred 30 min at rt. The resulting mixture was evaporated to dryness, suspended in dioxane (1.3 mL) and treated with a 5M solution of NaOH in H$_2$O (2.94 mmol). The resulting mixture was stirred 5 h at rt and diluted with MeTHF (20 mL) and H$_2$O (10 mL). The layers were separated and the aqueous layer was extracted with MeTHF (2×10 mL). The combined organic layers were dried over MgSO$_4$, filtered and evaporated to dryness. The residue was purified by SiO$_2$ chromatography (DCM/THF 0 to 50% gradient) and afforded the title compound (59 mg, 0.115 mmol, 58% over 2 steps) as a pale yellow solid.

N-(4-((R)-1-((1S,3R)-3-(5-chloro-4-(1H-indol-3-yl)pyrimidin-2-ylamino)cyclohexylamino)-2,2,2-trifluoroethyl)phenyl)acrylamide

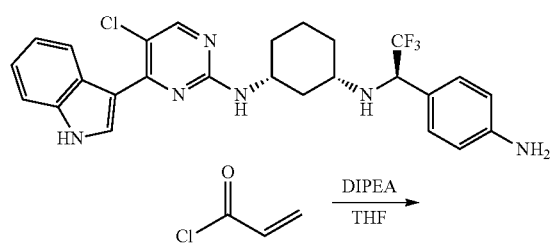

-continued

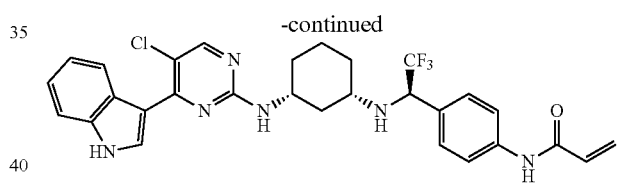

A cooled (−78° C.) solution of (1S,3R)—N1-((R)-1-(4-aminophenyl)-2,2,2-trifluoroethyl)-N3-(5-chloro-4-(1H-indol-3-yl)pyrimidin-2-yl)cyclohexane-1,3-diamine (59 mg, 0.114 mmol) and DIPEA (0.341 mmol) in 3:1 THF/NMP (2.0 mL) was treated with acryloyl chloride (0.116 mmol) and stirred 60 min at this temperature. The resulting mixture was warmed to rt and evaporated to dryness. The residue was purified by reverse phase chromatography (C$_{18}$, H$_2$O/ACN+0.1% HCO$_2$H 0 to 60% gradient) and afforded the title compound (21.8 mg, 0.038 mmol, 34%) as a yellow solid after lyophilisation. $^1$H NMR (500 MHz, d$_6$-DMSO) δ 11.81 (s, 1H), 10.20 (s, 1H), 8.69 (br s, 1H), 8.45 (d, J=3.0 Hz, 1H), 8.44-8.36 (m, 1H), 8.22 (s, 1H), 7.65 (d, J=7.4 Hz, 2H), 7.47 (d, J=8.2 Hz, 2H), 7.46-7.41 (m, 1H), 7.28-7.20 (m, 1H), 7.20-7.11 (m, 1H), 7.02-6.86 (m, 1H), 6.44 (dd, J=17.0, 10.1 Hz, 1H), 6.26 (dd, J=17.0, 1.9 Hz, 1H), 5.76 (dd, J=10.1, 1.9 Hz, 1H), 4.54-4.41 (m, 1H), 3.87-3.72 (m, 1H), 3.72-3.56 (m, 1H), 2.64 (dd, J=5.8, 4.0 Hz, 1H), 2.30-2.19 (m, 1H), 1.83-1.74 (m, 1H), 1.73-1.64 (m, 1H), 1.27-1.12 (m, 3H), 1.01 (dd, J=21.6, 10.5 Hz, 1H); MS (m/z): 569.55 [M+1]$^+$.

Example 31 4-acrylamido-N-((1S,3R)-3-(5-fluoro-4-(1H-indol-3-yl)pyrimidin-2-ylamino)cyclohexyl)benzamide (Compound 137)

3-(2-chloro-5-fluoropyrimidin-4-yl)-1-(phenylsulfonyl)-1H-indole

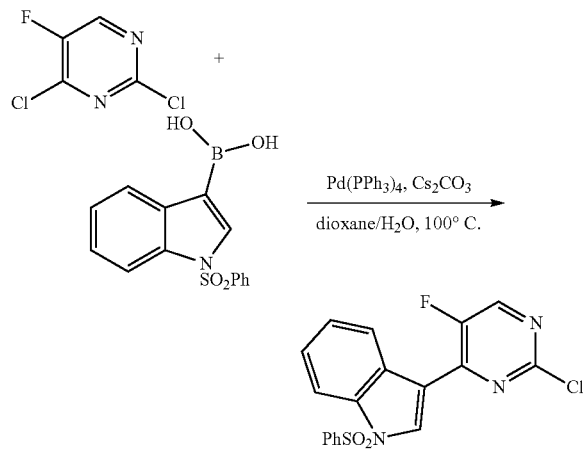

A degassed solution of 2,4-dichloro-5-fluoropyrimidine (500 mg, 2.99 mmol), 1-(phenylsulfonyl)-1H-indol-3-ylboronic acid (947 mg g, 3.14 mmol), Cs₂CO₃ (1.95 g, 5.99 mmol) and Pd(PPh₃)₄ (346 mg, 0.30 mmol) in 2:1 dioxane/H₂O (30 ml) was heated overnight at 100° C. The cooled mixture was diluted with EtOAc (50 mL) and saturated NaHCO₃ (20 ml). The layers were separated and the aqueous layer was extracted with EtOAc (3×20 mL). The combined organic layers were washed with brine (20 mL), dried over MgSO₄ and evaporated to dryness. The residue was purified by SiO₂ chromatography (DCM) and afforded the title compound (599 mg, 1.55 mmol, 52%) as a pale orange oil.

tert-butyl (1S,3R)-3-(5-fluoro-4-(1-(phenylsulfonyl)-1H-indol-3-yl)pyrimidin-2-ylamino) cyclohexylcarbamate

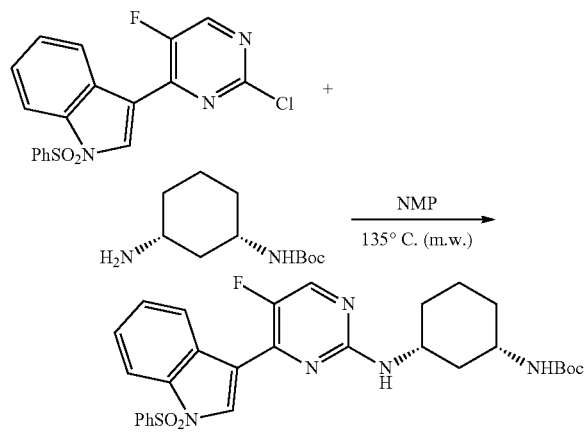

A solution of 3-(2-chloro-5-fluoropyrimidin-4-yl)-1-(phenylsulfonyl)-1H-indole (250 mg, 0.64 mmol), tert-butyl (1S,3R)-3-aminocyclohexylcarbamate prepared as in Example 1 (138 mg, 0.64 mmol) and DIPEA (1.93 mmol) in NMP (4.3 mL) was heated at 140° C. (microwave) for 60 min. The cooled mixture was diluted with MeTHF (30 mL), washed with H₂O (10 mL), brine (10 mL), dried over MgSO₄, filtered and evaporated to dryness. The residue was purified by SiO₂ chromatography (DCM/EtOAc 0 to 30% gradient) and afforded the title compound (76 mg, 0.134 mmol, 21%) as a pale yellow solid.

(1R,3S)—N1-(5-fluoro-4-(1-(phenylsulfonyl)-1H-indol-3-yl)pyrimidin-2-yl)cyclohexane-1,3-diamine.HCl

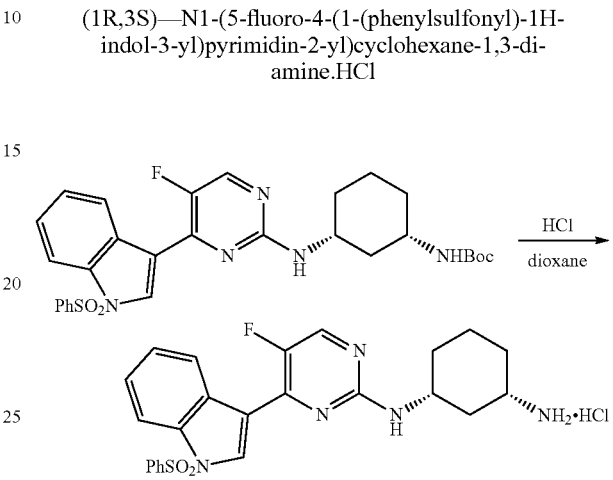

A solution of tert-butyl (1S,3R)-3-(5-fluoro-4-(1-(phenylsulfonyl)-1H-indol-3-yl)pyrimidin-2-ylamino)cyclohexylcarbamate (76 mg, 0.134 mmol) in dioxane (0.3 mL) was treated with a 4M solution of HCl in dioxane (1.34 mmol) and stirred 1 h at rt. The resulting mixture was evaporated to dryness and afforded the title compound (64 mg, 0.127 mmol, 95%) as a white solid which was used in the next step without further purification.

tert-butyl 4-((1S,3R)-3-(5-fluoro-4-(1-(phenylsulfonyl)-1H-indol-3-yl)pyrimidin-2-ylamino) cyclohexylcarbamoyl)phenylcarbamate

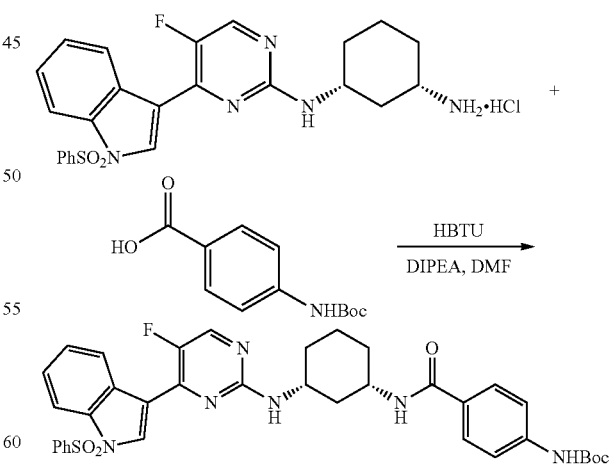

A solution of (1R,3S)—N1-(5-fluoro-4-(1-(phenylsulfonyl)-1H-indol-3-yl)pyrimidin-2-yl)cyclohexane-1,3-diamine.HCl (64 mg, 0.127 mmol) and 4-(tert-butoxycarbonylamino)benzoic acid (27 mg, 0.130 mmol) in DMF (0.85 mL) was treated with DIPEA (0.51 mmol) and HBTU (97 mg, 0.256 mmol). The resulting mixture was stirred overnight at rt, diluted with EtOAc (20 mL) and saturated NaHCO₃ (10 mL). The layers were separated and the aqueous layer was extracted with EtOAc (2×20 mL). The combined organic layers were washed with brine (10 mL), dried over Na₂SO₄, filtered and evaporated to dryness. The residue was purified by SiO₂ chromatography (DCM/EtOAc 0 to 100% gradient) and afforded the title compound (87 mg, 0.127 mmol, 100%) as a pale yellow solid.

tert-butyl 4-((1S,3R)-3-(5-fluoro-4-(1H-indol-3-yl)
pyrimidin-2-ylamino) cyclohexylcarbamoyl)phenyl-
carbamate

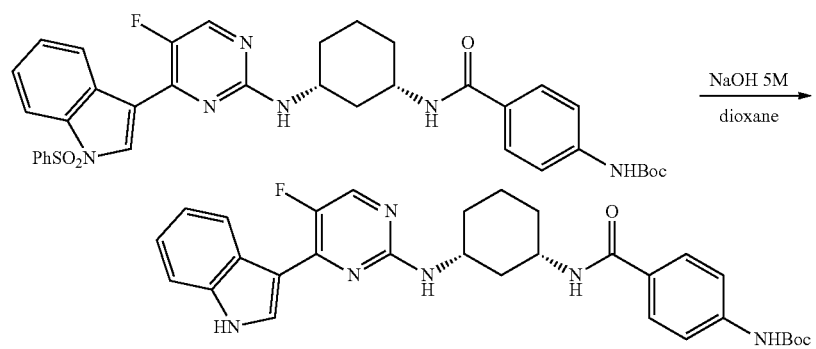

A solution of tert-butyl 4-((1S,3R)-3-(5-fluoro-4-(1-(phenylsulfonyl)-1H-indol-3-yl)pyrimidin-2-ylamino)cyclohexylcarbamoyl)phenylcarbamate (87 mg, 0.127 mmol) in dioxane (0.85 ml) was treated with a 5M solution of NaOH in H₂O (1.91 mmol) and heated at 65° C. for 5 h. The cooled mixture was evaporated to dryness and the residue was purified by SiO₂ chromatography (DCM/THF 0 to 50% gradient) and afforded the title compound (59 mg, 0.108 mmol, 85%) as a pale yellow solid.

4-amino-N-((1S,3R)-3-(5-fluoro-4-(1H-indol-3-yl)
pyrimidin-2-ylamino) cyclohexyl) benzamide.HCl

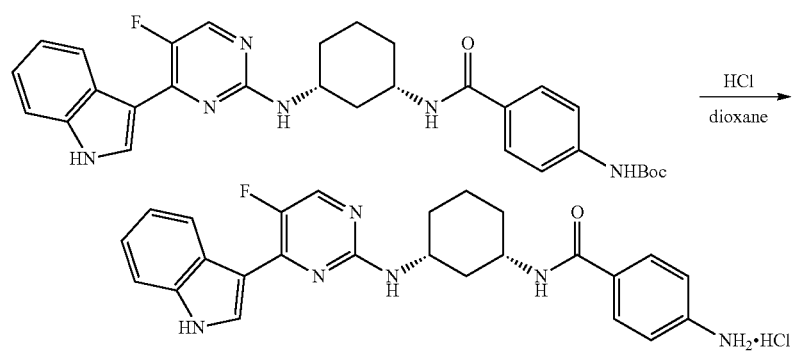

A solution of tert-butyl 4-((1S,3R)-3-(5-fluoro-4-(1H-indol-3-yl)pyrimidin-2-ylamino)cyclohexylcarbamoyl)phenylcarbamate (59 mg, 0.108 mmol) in dioxane was treated with a 4M solution of HCl in dioxane (1.62 mmol) and stirred overnight at rt. The resulting mixture was evaporated to dryness and afforded the title compound (52 mg, 0.108 mmol, 100%) as a white solid which was used in the next step without further purification.

4-acrylamido-N-((1S,3R)-3-(5-fluoro-4-(1H-indol-3-
yl)pyrimidin-2-ylamino) cyclohexyl)benzamide

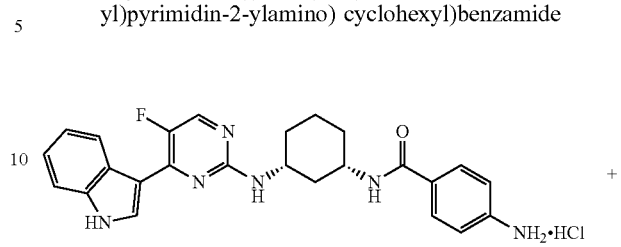

-continued

A cooled (−78° C.) solution of 4-amino-N-((1S,3R)-3-(5-fluoro-4-(1H-indol-3-yl)pyrimidin-2-ylamino)cyclohexyl) benzamide.HCl (52 mg, 0.108 mmol) and DIPEA (0.324 mmol) in 5:2 THF/NMP (2.1 mL) was treated with acryloyl chloride (0.110 mmol) and stirred 90 min at this temperature. The resulting mixture was warmed to rt and evaporated to dryness. The residue was purified by reverse phase chromatography (C$_{18}$, H$_2$O/ACN+0.1% HCO$_2$H 0 to 70% gradient) and afforded the title compound (24.3 mg, 0.049 mmol, 45%) as a pale yellow solid after lyophilisation. $^1$H NMR (500 MHz, d$_6$-DMSO) δ 11.78 (d, J=2.4 Hz, 1H), 10.27 (s, 1H), 8.63 (br s, 1H), 8.19-8.13 (m, 2H), 8.03 (t, J=3.0 Hz, 1H), 7.76 (d, J=8.8 Hz, 2H), 7.65 (d, J=8.8 Hz, 2H), 7.45-7.39 (m, 1H), 7.15 (dd, J=6.1, 3.0 Hz, 2H), 6.97 (d, J=7.8 Hz, 1H), 6.37 (dd, J=17.0, 10.1 Hz, 1H), 6.21 (dd, J=17.0, 1.9 Hz, 1H), 5.72 (dd, J=10.1, 1.9 Hz, 1H), 3.99-3.85 (m, 1H), 3.85-3.72 (m, 1H), 2.23-2.13 (m, 1H), 2.00-1.90 (m, 1H), 1.85-1.72 (m, 2H), 1.45-1.29 (m, 2H), 1.30-1.12 (m, 2H); MS (m/z): 499.58 [M+1]$^+$.

Example 32 4-acrylamido-N-((1S,3R)-3-(5-chloro-4-(pyrazolo[1,5-a]pyridin-3-yl)pyrimidin-2-ylamino)cyclohexyl)benzamide (Compound 138)

tert-butyl (1S,3R)-3-(5-chloro-4-(pyrazolo[1,5-a]pyridin-3-yl)pyrimidin-2-ylamino) cyclohexylcarbamate

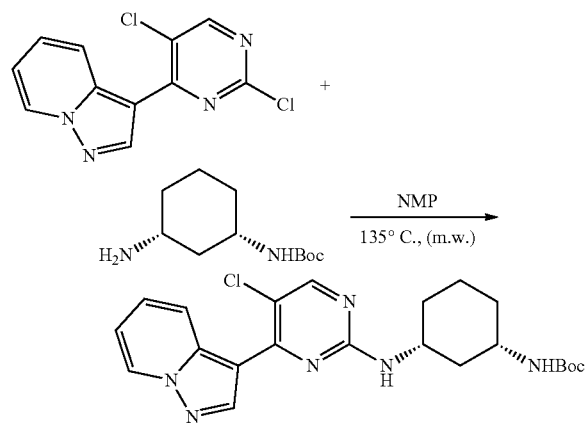

A solution of 3-(2,5-dichloropyrimidin-4-yl)pyrazolo[1,5-a]pyridine (prepared following *J. Med. Chem*, 2013, 56(17), 7025-7048) (223 mg, 0.84 mmol), tert-butyl (1S,3R)-3-aminocyclohexylcarbamate prepared as in Example 1 (200 mg, 0.933 mmol) and DIPEA (0.980 mmol) in NMP (7.8 mL) was heated at 135° C. (microwave) for 30 min. The cooled mixture was diluted with EtOAc (30 mL), washed with H$_2$O (10 mL), brine (10 mL), dried over MgSO$_4$, filtered and evaporated to dryness. The residue was purified by SiO$_2$ chromatography (DCM/MeOH 0 to 12% gradient) and afforded the title compound (280 mg, 0.632 mmol, 68%) as an orange foam.

(1R,3S)—N1-(5-chloro-4-(pyrazolo[1,5-a]pyridin-3-yl)pyrimidin-2-yl)cyclohexane-1,3-diamine.HCl

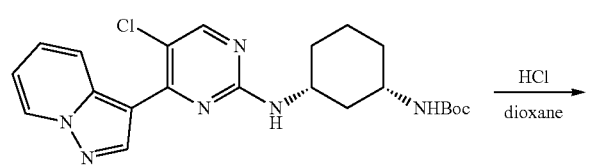

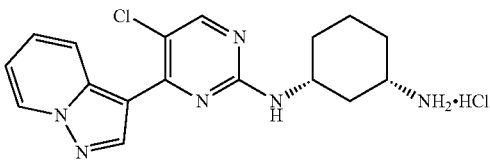

A solution of tert-butyl (1S,3R)-3-(5-chloro-4-(pyrazolo[1,5-a]pyridin-3-yl)pyrimidin-2-ylamino)cyclohexylcarbamate (280 mg, 0.632 mmol) in DCM (4.1 mL) was treated with a 4M solution of HCl in dioxane (2.04 mL, 8.165 mmol) and stirred 5 h at rt. The mixture was diluted with EtOAc (5 mL) and H$_2$O (5 mL) and the formed precipitate was filtrated and washed with EtOAc, affording the title compound (142 mg, 0.415 mmol, 66%) as a white solid which was used in the next step without further purification.

tert-butyl 4-((1S,3R)-3-(5-chloro-4-(pyrazolo[1,5-a]pyridin-3-yl)pyrimidin-2-ylamino)cyclohexylcarbamoyl)phenylcarbamate

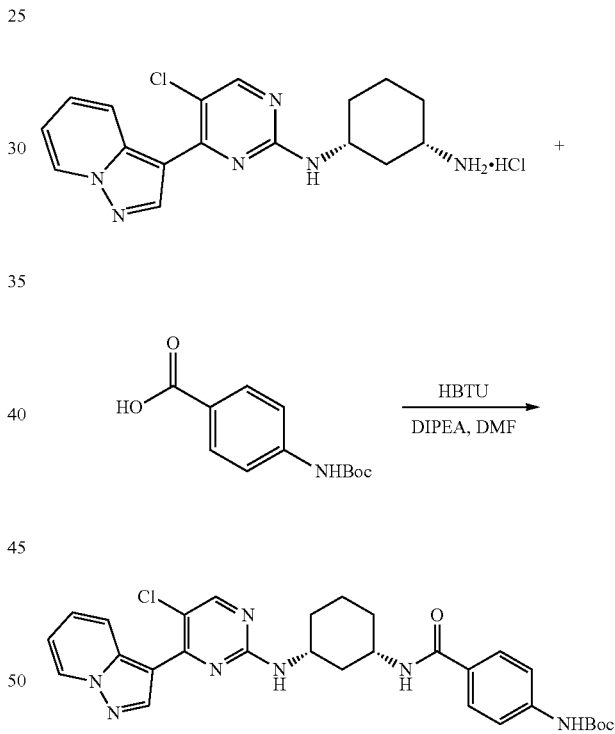

A solution of (1R,3S)—N1-(5-chloro-4-(pyrazolo[1,5-a]pyridin-3-yl)pyrimidin-2-yl)cyclohexane-1,3-diamine.HCl (140 mg, 0.408 mmol) and 4-(tert-butoxycarbonylamino)benzoic acid (116 mg, 0.49 mmol) in DMF (4.1 mL) was treated with DIPEA (1.63 mmol) and HBTU (232 mg, 0.613 mmol). The resulting mixture was stirred overnight at rt, diluted with EtOAc (30 mL) and saturated NaHCO$_3$ (10 mL). The layers were separated and the organic layer was washed with brine (10 mL), dried over MgSO$_4$, filtered and evaporated to dryness. The residue was purified by SiO$_2$ chromatography (Hex/EtOAc 0 to 100% gradient) and afforded the title compound (229 mg, 0.408 mmol, 100%) as an orange oil.

4-amino-N-((1S,3R)-3-(5-chloro-4-(pyrazolo[1,5-a]pyridin-3-yl)pyrimidin-2-ylamino)cyclohexyl)benzamide.HCl

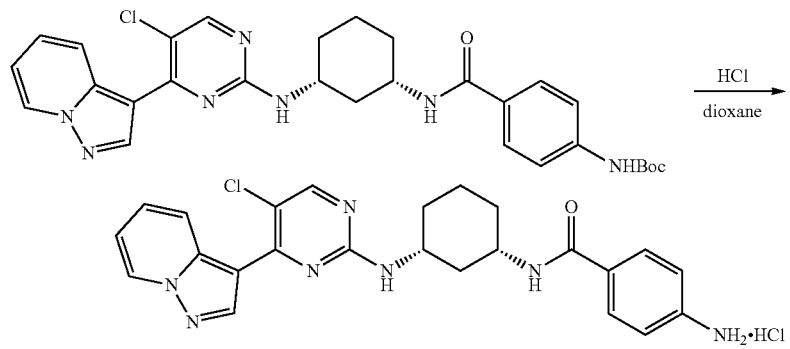

A solution of tert-butyl 4-((1S,3R)-3-(5-chloro-4-(pyrazolo[1,5-a]pyridin-3-yl)pyrimidin-2-ylamino)cyclohexylcarbamoyl)phenylcarbamate (229 mg, 0.408 mmol) in DCM (1.0 mL) was treated with a 4M solution of HCl in dioxane (2.0 mL, 8.0 mmol) and stirred 1 h at rt. The resulting mixture was evaporated to dryness and the residue was triturated in EtOAc. The solid was filtered and washed with EtOAc affording the title compound (28 mg, 0.061 mmol, 15%) as a beige solid which was used in the next step without further purification.

4-acrylamido-N-((1S,3R)-3-(5-chloro-4-(pyrazolo[1,5-a]pyridin-3-yl)pyrimidin-2-ylamino) cyclohexyl)benzamide

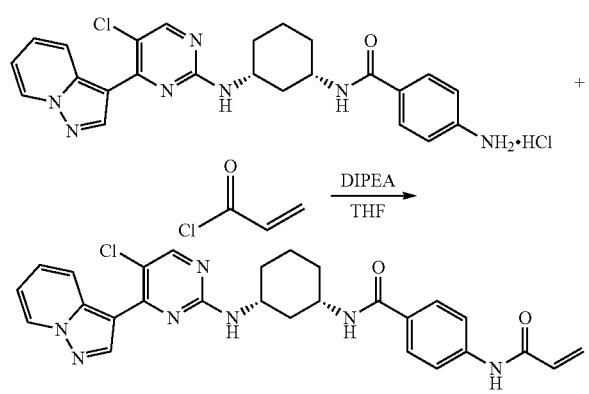

A cooled (−78° C.) solution of 4-amino-N-((1S,3R)-3-(5-chloro-4-(pyrazolo[1,5-a]pyridin-3-yl)pyrimidin-2-ylamino)cyclohexyl)benzamide.HCl (28 mg, 0.0606 mmol) and DIPEA (0.303 mmol) in 5:2 THF/NMP (2.5 mL) was treated with acryloyl chloride (0.0636 mmol) and stirred 2 h at this temperature. The resulting mixture was warmed to rt and evaporated to dryness. The residue was purified by reverse phase chromatography ($C_{18}$, $H_2O$/ACN+0.1% $HCO_2H$ 0 to 65% gradient) and afforded the title compound (3.4 mg, 0.007 mmol, 11%) as a pale yellow solid after lyophilisation. $^1$H NMR (500 MHz, $d_6$-DMSO) δ 10.34 (s, 1H), 8.93 (s, 1H), 8.86 (d, J=6.9 Hz, 1H), 8.66-8.57 (m, 1H), 8.50-8.42 (m, 1H), 8.31 (s, 1H), 8.23 (d, J=9.5 Hz, 1H), 7.82 (d, J=8.8 Hz, 2H), 7.72 (d, J=8.8 Hz, 2H), 7.70-7.48 (m, 1H), 7.44 (d, J=7.8 Hz, 1H), 7.16 (t, J=6.8 Hz, 1H), 6.44 (dd, J=17.0, 10.1 Hz, 1H), 6.28 (dd, J=17.0, 1.9 Hz, 1H), 5.78 (dd, J=10.1, 1.9 Hz, 1H), 4.10-3.94 (m, 1H), 3.90-3.80 (m, 2H), 2.25-2.01 (m, 1H), 2.00-1.90 (m, 1H), 1.87-1.80 (m, 2H), 1.45-1.39 (m, 2H), 1.38-1.20 (m, 2H); MS (m/z): 516.61 [M+1]$^+$.

Example 33. 4-acrylamido-N-((1S,3R)-3-((5-chloro-4-(1H-indazol-3-yl)pyrimidin-2-yl)amino)cyclohexyl)benzamide (Compound 151)

3-iodo-1H-indazole

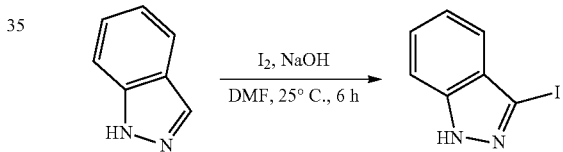

To a mixture of 1H-indazole (5 g, 42.32 mmol) and NaOH (3.4 g, 84.6 mmol) in DMF (50 mL) was added $I_2$ (16.1 g, 63.4 mmol) in one portion at 25° C. and the mixture was stirred for 6 h. The mixture was concentrated, diluted with water (150 mL) extracted with EA (100 mL×3), and the combined organic phase was washed with saturated brine (200 mL×2), dried with anhydrous $Na_2SO_4$ and concentrated under vacuum. The residue was purified by silica gel chromatography to afford the title compound (8 g, 77.5%) as a white solid.

tert-butyl 3-iodo-1H-indazole-1-carboxylate

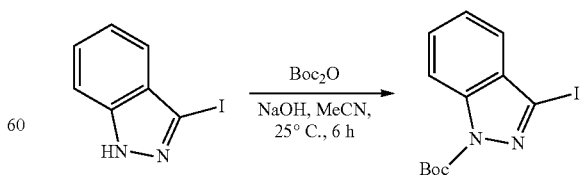

To a mixture of 3-iodo-1H-indazole (8 g, 32.7 mmol) and $Boc_2O$ (8.6 g, 39.2 mmol) in MeCN (100 mL) was added NaOH (2.0 g, 49.1 mmol) at 25° C. and the mixture was stirred for 12 h. The mixture was poured into water (150 mL), extracted with EA (50 mL×2), and the combined organic phase was washed with saturated brine (200 mL×2), dried with anhydrous Na$_2$SO$_4$ and concentrated under vacuum. The residue was purified by silica gel chromatography to afford the title compound (11.2 g, 97.5%) as a white solid. MS (m/z): 477.2 [M+1]$^+$.

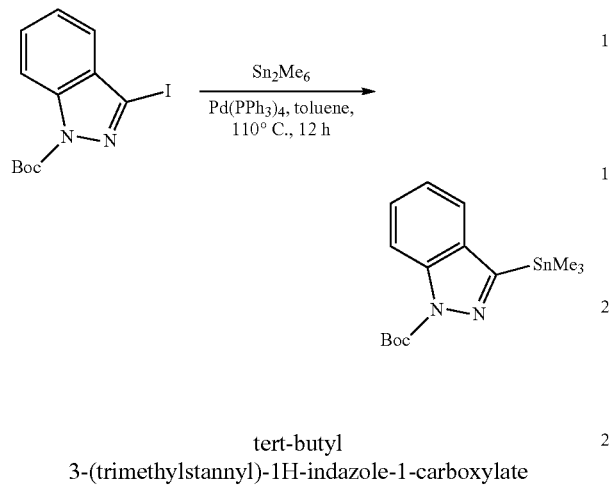

tert-butyl 3-(trimethylstannyl)-1H-indazole-1-carboxylate

A mixture of tert-butyl 3-iodoindazole-1-carboxylate (4.0 g, 11.6 mmol), Sn$_2$Me$_6$ (5.7 g, 17.4 mmol) and Pd(PPh$_3$)$_4$ (1.3 g, 1.2 mmol) in toluene (20 mL) was heated to 110° C. and stirred for 12 h. The mixture was concentrated under vacuum to give the title compound (4.43 g, crude), which was used directly in the next step. MS (m/z): 327.0 [M+1]$^+$.

tert-butyl 3-(2,5-dichloropyrimidin-4-yl)-1H-indazole-1-carboxylate

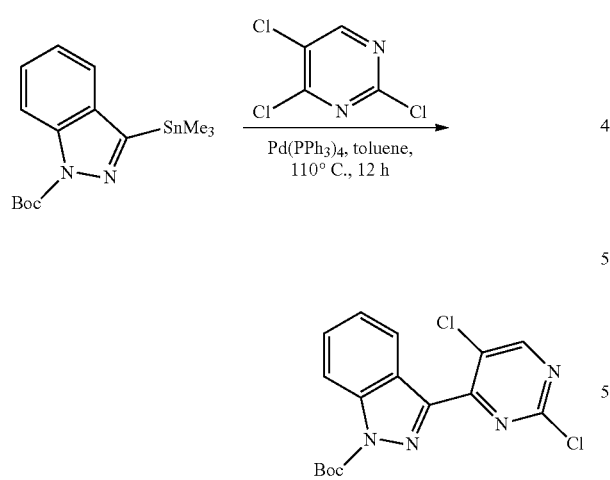

A mixture of tert-butyl 3-trimethylstannylindazole-1-carboxylate (5.0 g, 13.1 mmol), 2,4,5-trichloropyrimidine (2.4 g, 13.1 mmol) and Pd(PPh$_3$)$_4$ (1.5 g, 1.3 mmol) in toluene (100 mL) was heated to 110° C. and stirred for 12 h. The mixture was concentrated under vacuum and the residue was purified by silica gel chromatography to afford the title compound (1.5 g, 31.3% for two steps).

Benzyl((1S,3R)-3-((5-chloro-4-(1H-indazol-3-yl)pyrimidin-2-yl)amino)cyclohexyl)carbamate

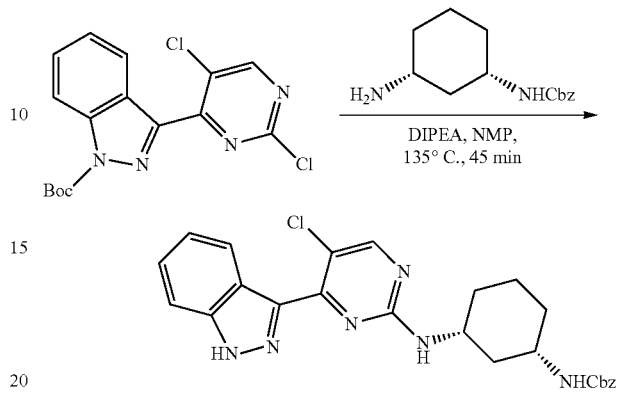

A mixture of tert-butyl 3-(2,5-dichloropyrimidin-4-yl)indazole-1-carboxylate (1 g, 2.74 mmol), benzyl N-[(1S,3R)-3-aminocyclohexyl]carbamate (0.816 g, 3.3 mmol), and DIPEA (2.1 g, 16.2 mmol) in NMP (20 mL) was stirred at 135° C. for 45 min by microwave. The mixture was poured into water (20 mL), extracted with ethyl acetate (20 mL×2), and the combined organic phase was washed with saturated brine (20 mL×3), dried with anhydrous Na$_2$SO$_4$, and concentrated under vacuum. The residue was purified by prep-HPLC to afford the title compound (0.75 g, 57.3%) as a yellow solid. MS (m/z): 477.2 [M+1]$^+$.

5-chloro-N-((1R,3S)-3-(piperazin-1-yl)cyclohexyl)-4-(pyrazolo[1,5-a]pyridin-3-yl)pyrimidin-2-amine

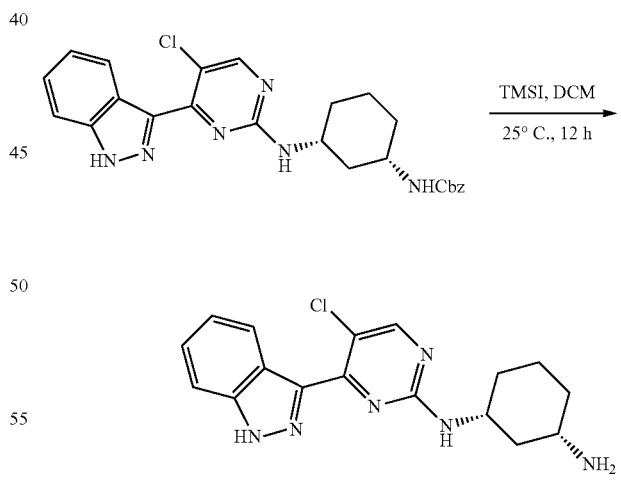

To a mixture of benzyl N-[(1 S,3R)-3-[[5-chloro-4-(1H-indazol-3-yl)pyrimidin-2-yl] amino]cyclohexyl]carbamate (0.7 g, 1.5 mmol) in DCM (10 mL) was added TMSI (1.47 g, 7.3 mmol) at 25° C. and the mixture was stirred for 12 h. The mixture was poured into water (20 mL), extracted with ethyl acetate (10 mL×2), and the aqueous phase was concentrated under vacuum to afford the title compound (0.32 g, crude).

tert-butyl (4-(((1S,3R)-3-((5-chloro-4-(1H-indazol-3-yl)pyrimidin-2-yl)amino)cyclohexyl) carbamoyl) phenyl)carbamate

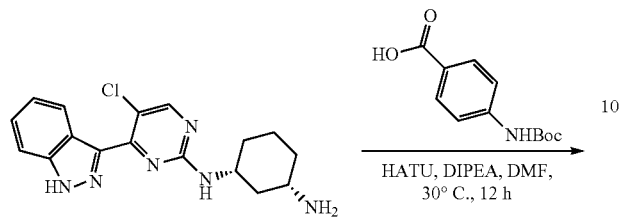

To a mixture of (1R,3S)—N1-[5-chloro-4-(1H-indazol-3-yl)pyrimidin-2-yl]cyclohexane-1,3-diamine (300 mg, 0.9 mmol) and 4-(tert-butoxycarbonylamino)benzoic acid (249.1 mg, 1.1 mmol) in DMF (10 mL) was added HATU (499.1 mg, 1.3 mmol) and DIPEA (226.2 mg, 1.8 mmol) at 30° C. and the mixture was stirred for 12 h. The mixture was poured into water (50 mL), extracted with EA (20 mL×2), and the combined organic phase was washed with saturated brine (50 mL×2), dried with anhydrous Na$_2$SO$_4$, and concentrated under vacuum. The residue was purified by silica gel chromatography to afford the title compound (200 mg, 25.8% for two steps). MS (m/z): 562.1 [M+1]$^+$.

4-amino-N-((1S,3R)-3-((5-chloro-4-(1H-indazol-3-yl)pyrimidin-2-yl)amino)cyclohexyl)benzamide

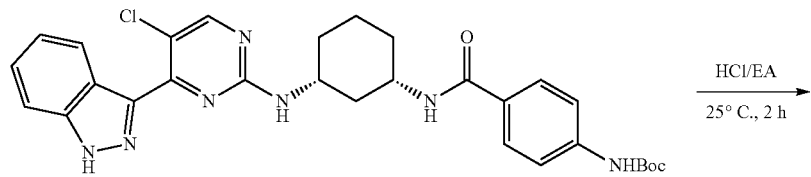

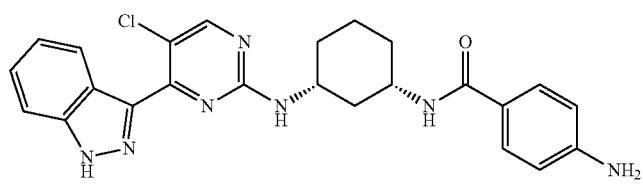

A mixture of tert-butyl N-[4-[[(1S,3R)-3-[[5-chloro-4-(1H-indazol-3-yl)pyrimidin-2-yl]amino] cyclohexyl]carbamoyl]phenyl]carbamate (200 mg, 0.35 mmol) in HCl/MeOH (20 mL) was stirred at 25° C. for 2 h. The mixture was concentrated under vacuum to afford the title compound (150 mg, crude). MS (m/z): 462.2 [M+1]$^+$.

4-acrylamido-N-((1S,3R)-3-((5-chloro-4-(1H-indazol-3-yl)pyrimidin-2-yl)amino)cyclohexyl)benzamide

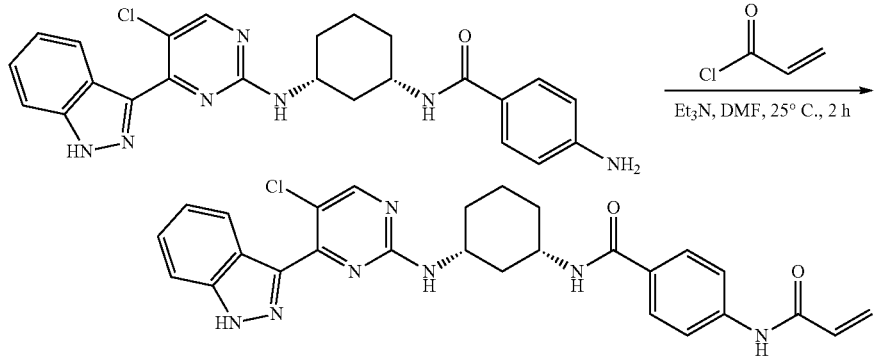

To a mixture of 4-amino-N-[(1S,3R)-3-[[5-chloro-4-(1H-indazol-3-yl)pyrimidin-2-yl]amino] cyclohexyl]benzamide (150.0 mg, 0.32 mmol) and Et$_3$N (65.7 mg, 0.65 mmol) in DMF (5 mL) was added acryloyl chloride (44.1 mg, 0.49 mmol) at 25° C. and the mixture was stirred for 2 h. The mixture was added MeOH (2 mL) and evaporated, and the residue was purified by prep-HPLC to afford the title compound (10 mg, 5.4% for two steps) as a yellow solid. $^1$H NMR: (MeOD-d$_6$, 400 MHz) δ 8.49 (d, J=8.38 Hz, 1H), 8.44 (s, 1H), 7.78-7.84 (m, 2H), 7.71-7.77 (m, 2H), 7.67 (d, J=8.38 Hz, 1H), 7.50 (t, J=7.50 Hz, 1H), 7.40 (t, J=7.50 Hz, 1H), 6.34-6.49 (m, 2H), 5.79 (dd, J=9.48, 2.43 Hz, 1H), 4.10 (br. s., 2H), 2.46 (d, J=11.03 Hz, 1H), 2.18 (d, J=10.58 Hz, 1H), 1.94-2.10 (m, 2H), 1.52-1.68 (m, 2H), 1.33-1.51 (m, 2H). MS (m/z): 516.2 [M+1]$^+$.

Example 34. N-((1S,3R)-3-((5-chloro-4-(2-methyl-1H-indol-3-yl)pyrimidin-2-yl)amino) cyclohexyl)-4-((E)-4-(dimethylamino)but-2-enamido)benzamide (Compound 154)

3-iodo-2-methyl-1H-indole

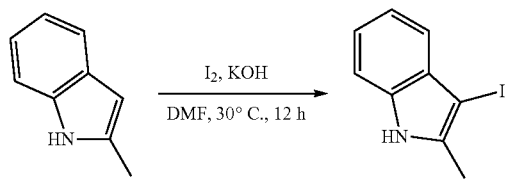

To a mixture of 2-methyl-1H-indole (20 g, 152.47 mmol) and KOH (21.39 g, 381.18 mmol) in DMF (200 mL) was added I$_2$ (38.7 g, 152.47 mmol) at 30° C. and the mixture was stirred for 12 h. The mixture was poured into water, extracted with EA, and the organic layer was dried over Na$_2$SO$_4$ and concentrated. The residue was purified by column (PE:EA=15:1) to afford the title compound (25 g, 63.8%).

3-iodo-2-methyl-1-(phenylsulfonyl)-1H-indole

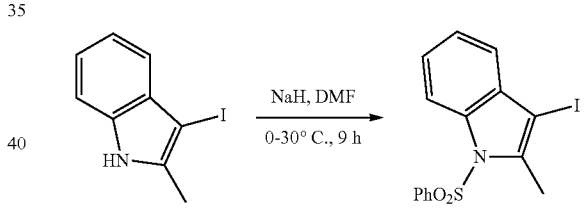

To a solution of 3-iodo-2-methyl-1H-indole (25 g, 97.25 mmol) in DMF (320 mL) was added NaH (4.67 g, 116.70 mmol) at 0° C. and the mixture was stirred at 30° C. for 1 h. Then benzenesulfonyl chloride (18.04 g, 102.11 mmol) was added and the mixture was stirred at 30° C. for 8 h. The mixture was poured into water, extracted with EA, and the organic layer was dried over Na$_2$SO$_4$ and concentrated. The residue was purified by column (PE:EA=20:1) to afford the title compound (28 g, 72.8%).

3-(2,5-dichloropyrimidin-4-yl)-2-methyl-1-(phenylsulfonyl)-1H-indole

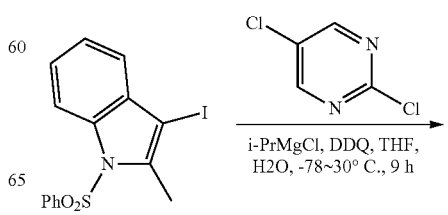

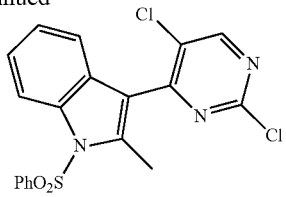

To a solution of 3-iodo-2-methyl-1-(phenylsulfonyl)-1H-indole (20 g, 50.35 mmol) in THF (400 mL) was added i-PrMgCl.LiCl (14.63 g, 100.70 mmol) at −78° C. and the mixture was stirred under N₂ for 1 h. Then 2,5-dichloropyrimidine (15 g, 100.70 mmol) was added at −78° C. and the reaction was stirred at 30° C. for 3 h, at which point H₂O (115.80 mmol) in THF (10 mL) was added at 0° C. Finally DDQ (22.86 g, 100.70 mmol) was added and the final mixture was stirred at 30° C. for 6 h. The mixture concentrated, diluted with water, extracted with EA, and the organic layer was concentrated. The residue was purified by column (PE:EA=10:1) to afford the title compound (6 g, 28.5%).

Benzyl ((1S,3R)-3-((5-chloro-4-(2-methyl-1-(phenylsulfonyl)-H-indol-3-yl) pyrimidin-2-yl)amino)cyclohexyl)carbamate

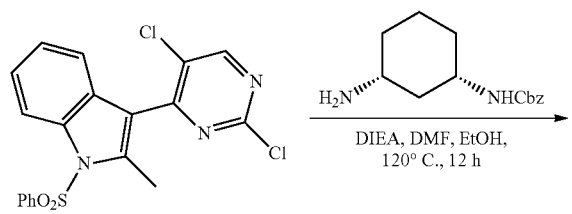

A mixture of 3-(2,5-dichloropyrimidin-4-yl)-2-methyl-1-(phenylsulfonyl)-1H-indole (5.0 g, 11.95 mmol), benzyl ((1S,3R)-3-aminocyclohexyl)carbamate (3.4 g, 11.95 mmol) and DIEA (5.41 g, 41.83 mmol) in DMF (30 mL) and EtOH (30 mL) was stirred at 120° C. for 12 h. The mixture was concentrated and the residue was purified by column (PE:EA=4:1) to afford the title compound (5.1 g, 67.7%).

(1R,3S)—N1-(5-chloro-4-(2-methyl-1-(phenylsulfonyl)-1H-indol-3-yl)pyrimidin-2-yl)cyclohexane-1,3-diamine

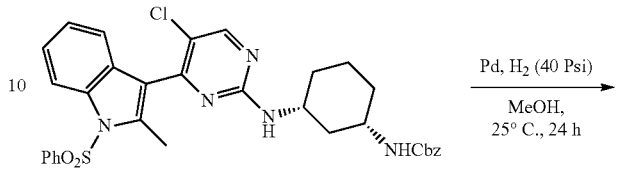

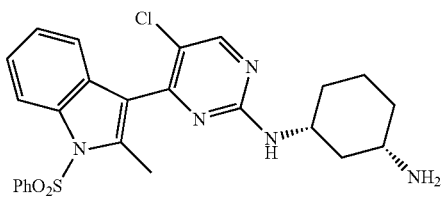

A mixture of benzyl ((1S,3R)-3-((5-chloro-4-(2-methyl-1-(phenylsulfonyl)-1H-indol-3-yl)pyrimidin-2-yl)amino)cyclohexyl)carbamate (5.0 g, 7.93 mmol) and Pd/C (0.80 g) in MeOH (100 mL) was stirred at 25° C. for 24 h under H₂ (40 psi). The mixture was filtered and the filtrate was concentrated to afford the title compound (2.7 g, crude).

tert-butyl (4-(((1S,3R)-3-((5-chloro-4-(2-methyl-1-(phenylsulfonyl)-1H-indol-3-yl)pyrimidin-2-yl)amino)cyclohexyl)carbamoyl)phenyl)carbamate

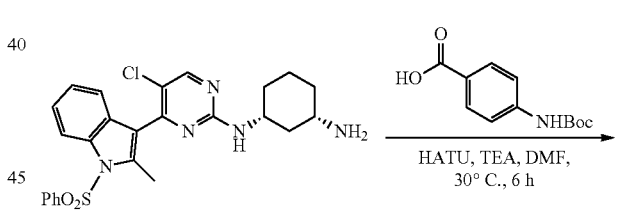

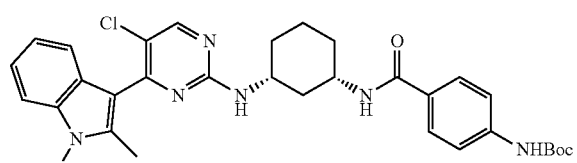

A mixture of (1R,3S)—N1-(5-chloro-4-(2-methyl-1-(phenylsulfonyl)-1H-indol-3-yl) pyrimidin-2-yl)cyclohexane-1,3-diaminetrifluoromethanesulfonate (1.5 g, 3.02 mmol), 4-((tert-butoxycarbonyl)amino)benzoic acid (0.72 g, 3.02 mol), HATU (1.21 g, 3.18 mmol), and DIEA (0.47 g, 3.63 mmol) in DMF (30 mL) was stirred at 30° C. for 6 h. The reaction solution was poured into water, extracted with EA, and the organic layer was dried and concentrated to afford the title compound (2.0 g, crude).

tert-butyl (4-(((1S,3R)-3-((5-chloro-4-(2-methyl-1H-indol-3-yl)pyrimidin-2-yl)amino)cyclohexyl)carbamoyl)phenyl)carbamate

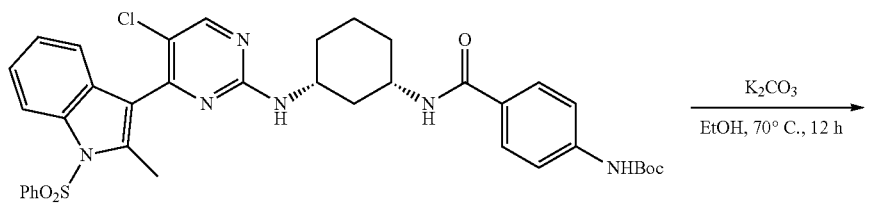

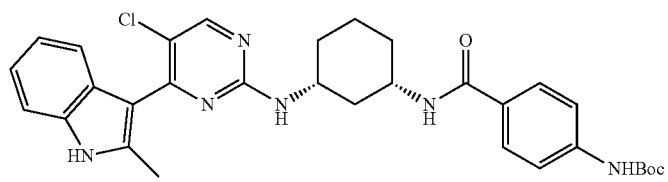

A mixture of tert-butyl (4-(((1S,3R)-3-((5-chloro-4-(2-methyl-1-(phenylsulfonyl)-1H-indol-3-yl)pyrimidin-2-yl)amino)cyclohexyl)carbamoyl)phenyl)carbamate (1.8 g, 2.52 mmol), $K_2CO_3$ (6.97 g, 0.44 mmol), and morpholine (0.44 g, 5.04 mmol) in EtOH (50 mL) was stirred at 70° C. for 12 h. The mixture was filtered and concentrated. The residue was purified by prep-HPLC (acidic conditions) to afford the title compound (0.63 g, 43.6%).

4-amino-N-((1S,3R)-3-((5-chloro-4-(2-methyl-1H-indol-3-yl)pyrimidin-2-yl)amino)cyclohexyl)benzamide

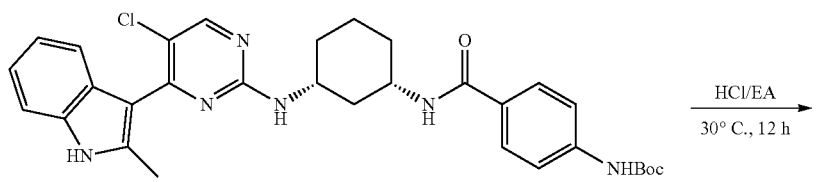

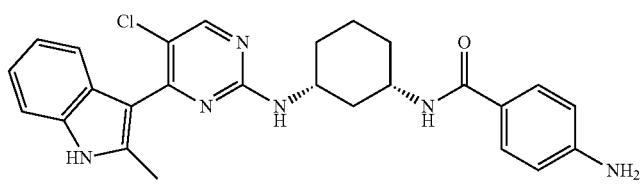

To a solution of tert-butyl (4-(((1S,3R)-3-((5-chloro-4-(2-methyl-1H-indol-3-yl) pyrimidin-2-yl)amino)cyclohexyl)carbamoyl)phenyl)carbamate (700 mg, 1.22 mmol) in EA (5 mL) was added into a solution of HCl/EA (25 mL) and the mixture was stirred at 30° C. for 12 h. The mixture was concentrated to afford the title compound (500 mg, 80.1%).

N-((1S,3R)-3-((5-chloro-4-(2-methyl-1H-indol-3-yl)pyrimidin-2-yl)amino)cyclohexyl)-4-((E)-4-(dimethylamino)but-2-enamido)benzamide

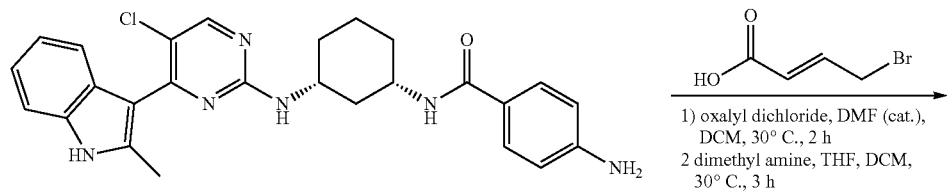

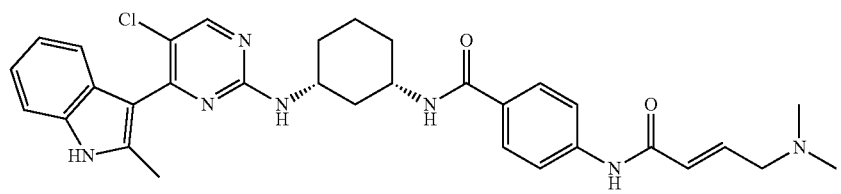

To a solution of (E)-4-bromobut-2-enoic acid (28 mg, 0.168 mmol) in DCM (2 mL) was added oxalyl dichloride (22.45 mg, 0.176 mmol) and a drop of DMF at 0° C. The mixture was stirred at 30° C. for 1 h, and then added into a solution of 4-amino-N-((1S,3R)-3-((5-chloro-4-(2-methyl-1H-indol-3-yl)pyrimidin-2-yl)amino)cyclohexyl)benzamide hydrochloride (80 mg, 168.43 mmol) and DIEA (174.14 mg, 1.35 mmol) in DCM (2 mL) and THF (2 mL) at 30° C. and the mixture was stirred for 2 h. Dimethyl amine (7.59 mg, 168.43 umol) was added and the mixture was stirred at 30° C. for 3 h, after which the mixture was concentrated and the residue was purified by prep-HPLC (neutral conditions) to afford the title compound (15 mg, 13.1%). $^1$H NMR (DMSO, 400 MHz) δ 8.34 (s, 1H), 8.17 (d, J=8.0 Hz, 1H), 7.82 (d, J=8.0 Hz, 2H), 7.75 (d, J=8.8 Hz, 2H), 7.41 (d, J=8.0 Hz, 2H), 7.35-7.31 (m, 2H), 7.07-7.05 (m, 2H), 6.77-6.74 (m, 1H), 6.28 (d, J=16.4 Hz, 1H), 3.82 (br, 2H), 3.06 (d, J=4.8 Hz, 1H), 2.45 (s, 3H), 2.18 (s., 6H), 1.93-1.91 (m, 1H), 1.79 (br, 2H), 1.39-1.27 (m, 7H). MS (m/z): 586.3 [M+1]$^+$.

Example 35. 4-acrylamido-N-((1S,3R)-3-((5-chloro-4-(2-methyl-1H-indol-3-yl)pyrimidin-2-yl)amino)cyclohexyl)benzamide (Compound 153)

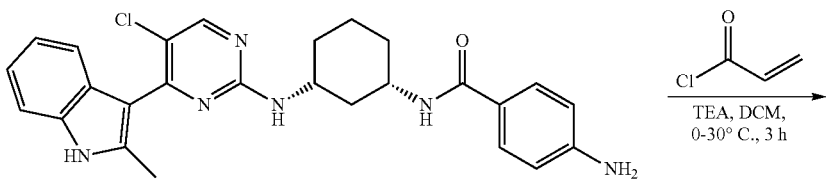

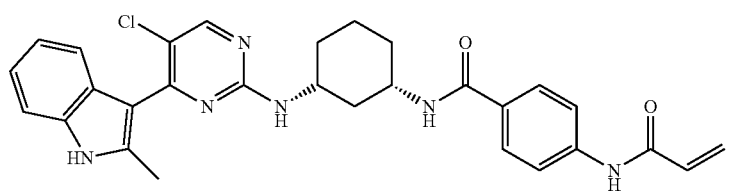

To a mixture of 4-amino-N-((1S,3R)-3-((5-chloro-4-(2-methyl-1H-indol-3-yl) pyrimidin-2-yl)amino)cyclohexyl)benzamide (200 mg, 0.42 mmol) and TEA (340.8 mg, 0.42 mmol) in DCM (7 mL) was added a solution of acryloyl chloride (38.1 mg, 0.42 mmol) in DCM (3 mL) at 0° C. and the mixture was stirred at 30° C. for 3 h. The mixture was concentrated, and the residue was purified by prep-HPLC (neutral conditions) to afford the title compound (32 mg, 14.3%) as a white solid. $^1$H NMR (DMSO-d$_6$, 400 MHz) δ 11.46 (br, 1H), 10.34 (s, 1H), 8.35 (s, 1H), 8.19 (d, J=8 Hz, 1H), 7.83 (d, J=8 Hz, 1H), 7.73 (d, J=8 Hz, 1H), 7.42-7.32 (m, 3H), 7.06-7.01 (m, 2H), 6.45-6.42 (m, 1H), 6.29 (d, J=16 Hz, 1H), 5.79 (d, J=9.2 Hz, 1H), 3.82 (br. s., 3H), 2.46 (s, 3H), 2.15 (d, J=8.4 Hz, 1H), 1.93 (d, J=8.4 Hz, 1H), 1.80 (br. s., 2H), 1.41-1.26 (m, 4H). MS (m/z): 529.2 [M+1]$^+$.

Example 36. N-(3-((((1R,4R)-4-((5-chloro-4-(1H-indol-3-yl)pyrimidin-2-yl)amino) cyclohexyl)oxy) methyl)phenyl)acrylamide (Compound 155)

2-((1R,4R)-4-hydroxycyclohexyl)isoindoline-1,3-dione

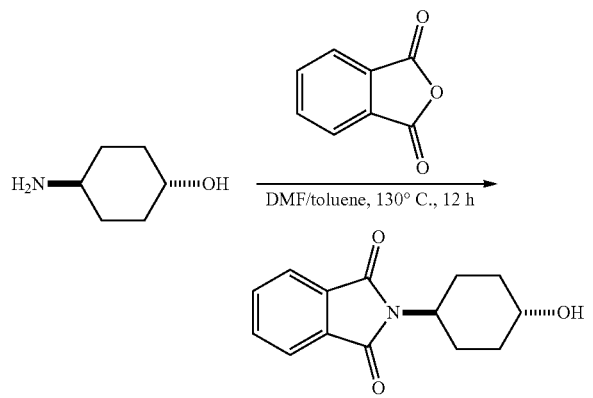

To a solution of isobenzofuran-1,3-dione (25.0 g, 168 mmol) in DMF (160 mL) and toluene (160 mL) at 25° C. was added (1R,4R)-4-aminocyclohexanol (19.4 g, 168 mmol). The reaction was heated to 130° C. stirred at for 12 h. The reaction was diluted with H$_2$O (200 mL), the mixture was filtered, and the filter cake was dried and evaporated under pressure to give the title compound (30.0 g, 72.5%).

3-nitrobenzyl 2,2,2-trichloroacetimidate

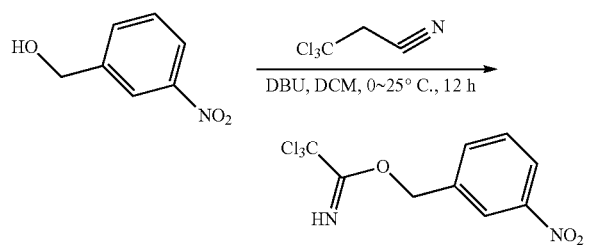

To a solution of (3-nitrophenyl)methanol (12.0 g, 78.4 mmol) and DBU (2.4 g, 15.7 mmol) in DCM (200 mL) was added 3,3,3-trichloropropanenitrile (18.6 g, 117.5 mmol) at 0° C. The mixture was stirred at 25° C. for 12 h, after which the reaction was concentrated in vacuo and purified by silica gel column chromatography (PE/EA=20:1) to afford the title compound (20.0 g, 85.8%).

2-((1R,4R)-4-((3-nitrobenzyl)oxy)cyclohexyl)isoindoline-1,3-dione

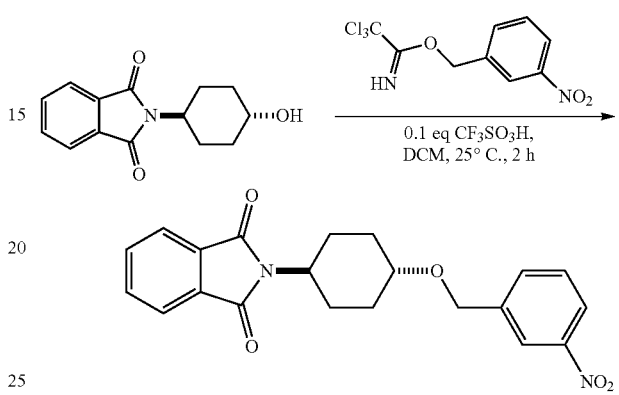

To a solution of 2-((1R,4R)-4-hydroxycyclohexyl)isoindoline-1,3-dione (20.0 g, 81.5 mmol) and 3-nitrobenzyl 2,2,2-trichloroacetimidate (36.4 g, 122.3 mmol) in DCM (200 mL) was added CF$_3$SO$_3$H (271.8 mg, 1.2 mmol) at 25° C. After 2 h, the reaction was quenched with NaHCO$_3$ solution (100 mL) and the aqueous was exacted with DCM (50 mL×4). The organic phase was dried over Na$_2$SO$_4$, concentrated and purified by silica gel column chromatography (PE/EA=10:1) to afford the title compound (8.0 g, 25.8%).

(1R,4R)-4-((3-nitrobenzyl)oxy)cyclohexanamine

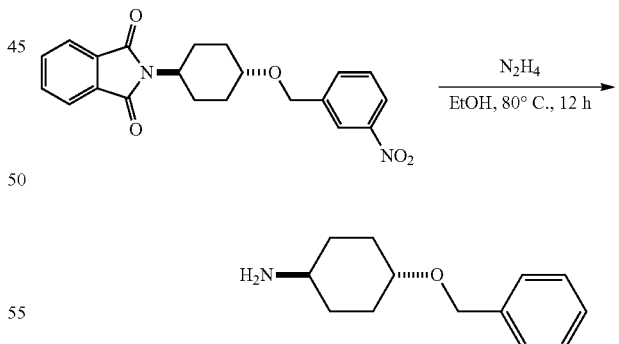

2-((1R,4R)-4-((3-nitrobenzyl)oxy)cyclohexyl)isoindoline-1,3-dione (8.0 g, 21 mmol) was dissolved in EtOH (100 mL), and then N$_2$H$_4$ (1.35 g, 42 mmol) was added. The resulting mixture was heated at 80° C. for 12 h. The mixture then was filtered, and the filtrate was concentrated and purified by prep-HPLC (TFA condition) to give the title compound (0.3 g, 5.7%). MS (m/z): 251.3 [M+1]$^+$.

5-chloro-N-((1R,4R)-4-((3-nitrobenzyl)oxy)cyclohexyl)-4-(1-(phenylsulfonyl)-1H-indol-3-yl)pyrimidin-2-amine

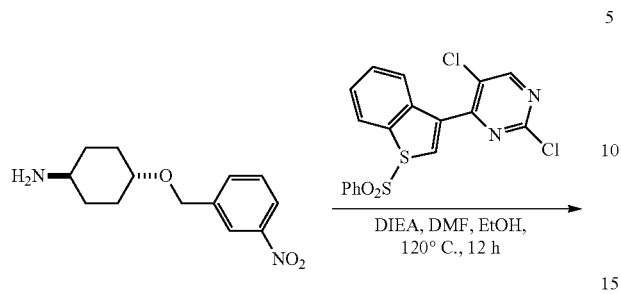

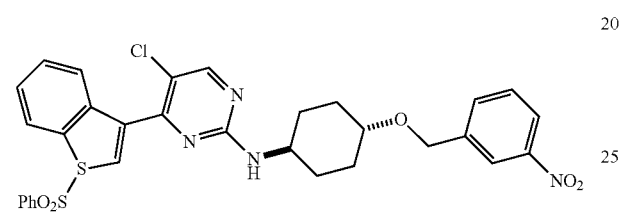

To a solution of 3-(2,5-dichloropyrimidin-4-yl)-1-(phenylsulfonyl)-1H-indole (250 mg, 0.62 mmol) and (1R,4R)-4-((3-nitrobenzyl)oxy)cyclohexanamine (154.8 mg, 0.62 mmol) in EtOH (10 mL) and DMF (10 mL) was added DIPEA (0.4 mg, 3.09 mmol). The reaction was stirred at 25° C. for 10 min, then heated to 120° C. and stirred for 12 h. The reaction was concentrated, diluted with H₂O (20 mL), and extracted with DCM (20 mL×3). The organic was concentrated, and the residue was purified by column (PE/EA=5:1) to afford the title compound (180 mg, 47.1%).

N-((1R,4R)-4-((3-aminobenzyl)oxy)cyclohexyl)-5-chloro-4-(1-(phenylsulfonyl)-1H-indol-3-yl)pyrimidin-2-amine

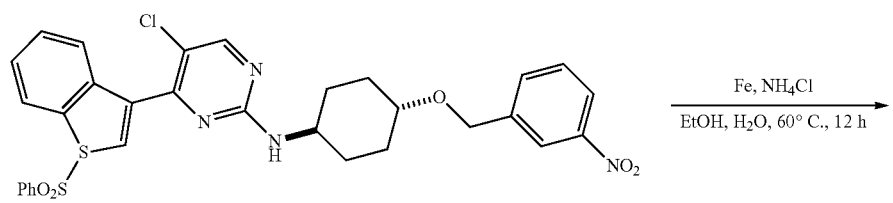

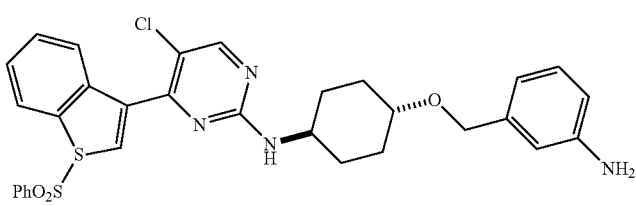

To a solution of 5-chloro-N-((1R,4R)-4-((3-nitrobenzyl)oxy)cyclohexyl)-4-(1-(phenylsulfonyl)-1H-indol-3-yl)pyrimidin-2-amine (200 mg, 0.32 mmol) in EtOH (5 mL) and H$_2$O (5 mL) were added Fe (90.4 mg, 1.60 mmol) and NH$_4$Cl (17.3 mg, 0.32 mmol). The reaction was heated to 60° C. and stirred for 12 h. The mixture was filtered and the filtrate concentrated to give the title compound (150 mg, crude) as a yellow solid. MS (m/z): 588 [M+1]$^+$.

N-((1R,4R)-4-((3-aminobenzyl)oxy)cyclohexyl)-5-chloro-4-(1H-indol-3-yl)pyrimidin-2-amine

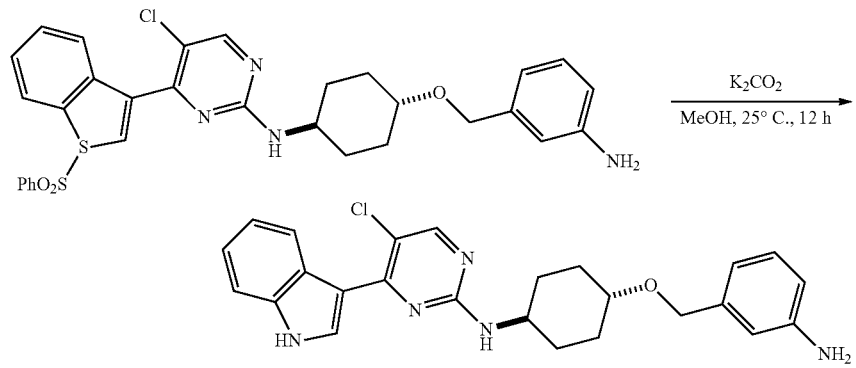

To a solution of N-((1R,4R)-4-((3-aminobenzyl)oxy)cyclohexyl)-5-chloro-4-(1-(phenyl sulfonyl)-1H-indol-3-yl) pyrimidin-2-amine (150 mg, 0.25 mmol) in MeOH (5 mL) was added K$_2$CO$_3$ (105.7 mg, 0.76 mmol). The mixture was stirred at 25° C. for 12 h. The reaction was concentrated, then the residue was diluted with H$_2$O (20 mL), extracted with DCM (20 mL×3), and the organic was dried, filtered, and concentrated to give the title compound (120 mg, crude) as a light yellow solid. MS (m/z): 448 [M+1]$^+$.

N-(3-(((((1R,4R)-4-((5-chloro-4-(1H-indol-3-yl)pyrimidin-2-yl)amino)cyclohexyl)oxy) methyl)phenyl) acrylamide

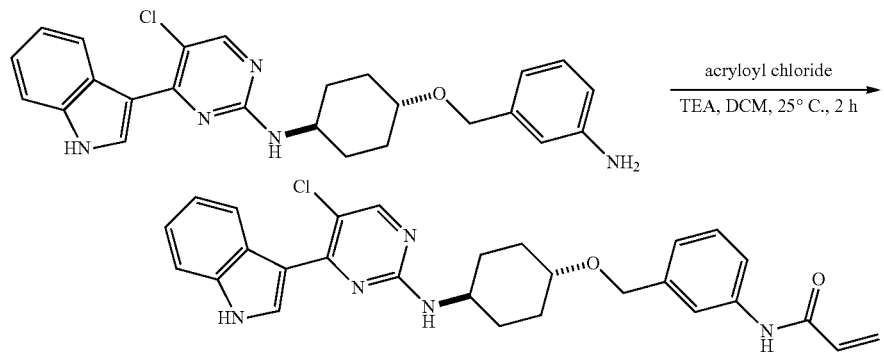

To a solution of N-((1R,4R)-4-((3-aminobenzyl)oxy)cyclohexyl)-5-chloro-4-(1H-indol-3-yl)pyrimidin-2-amine (80 mg, 0.18 mmol) and TEA (54.2 mg, 0.54 mmol) in DCM (5 mL) was added acryloyl chloride (24.5 mg, 0.27 mmol) at 0° C. and the reaction was stirred at 25° C. for 2 h. The reaction was diluted with NH$_4$Cl solution (50 mL), extracted with DCM (20 mL×3), dried over Na$_2$SO$_4$, and concentrated. The residue was purified by prep-HPLC (neutral conditions) to afford the title compound (13 mg, 14.5%) as a light yellow solid. $^1$H NMR: (MeOD, 400 MHz) δ 8.64 (d, J=7.94 Hz, 1H), 8.48 (s, 1H), 8.14 (s, 1H), 7.69 (s, 1H), 7.59 (d, J=7.94 Hz, 1H), 7.46 (d, J=7.94 Hz, 1H), 7.32 (t, J=7.94 Hz, 1H), 7.07-7.29 (m, 3H), 6.32-6.51 (m, 2H), 5.77 (dd, J=9.70, 2.21 Hz, 1H), 4.60 (s, 4H), 3.94 (br. s., 1H), 3.48 (d, J=10.14 Hz, 1H), 2.21 (d, J=9.26 Hz, 2H), 1.27-1.59 (m, 4H). MS (m/z): 502 [M+1]+.

Example 37. N-(4-((((1S,3R)-3-((5-chloro-4-(1H-indazol-3-yl)pyrimidin-2-yl)amino)cyclohexyl)amino)methyl)phenyl)acrylamide (Compound 162)

(1R,3S)—N1-(5-chloro-4-(H-indazol-3-yl)pyrimidin-2-yl)-N3-(4-nitrobenzyl)cyclohexane-1,3-diamine

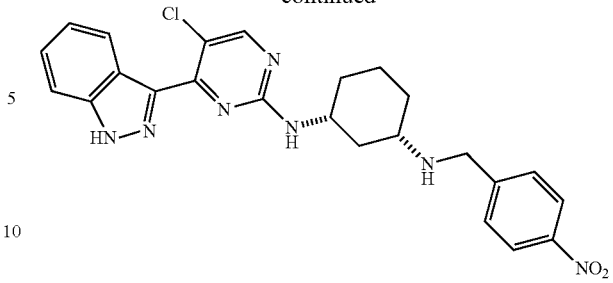

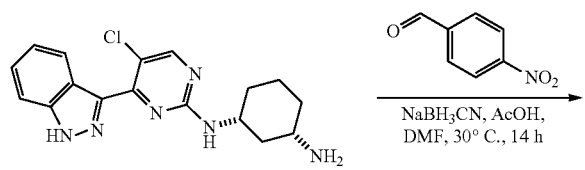

A mixture of (1R,3S)—N1-(5-chloro-4-(1H-indazol-3-yl)pyrimidin-2-yl)cyclohexane-1,3-diamine (500 mg, 1.3 mmol) and 4-nitrobenzaldehyde (294 mg, 1.9 mmol) in DMF (10 mL) and AcOH (0.5 mL) was stirred at 30° C. for 12 h. Then NaBH$_3$CN (163 mg, 2.6 mmol) was added, and the mixture was stirred at 30° C. for 2 h. The mixture was poured into water (100 mL), extracted with EA (50 mL×3), and the organic layer was concentrated. The residue was directly purified by prep-HPLC (TFA conditions) to afford the title compound (200 mg, 31.7%). MS (m/z): 478.2 [M+1]$^+$.

tert-benzyl((1S,3R)-3-((5-chloro-4-(1H-indol-4-yl)pyrimidin-2-yl)amino)cyclohexyl)carbamate

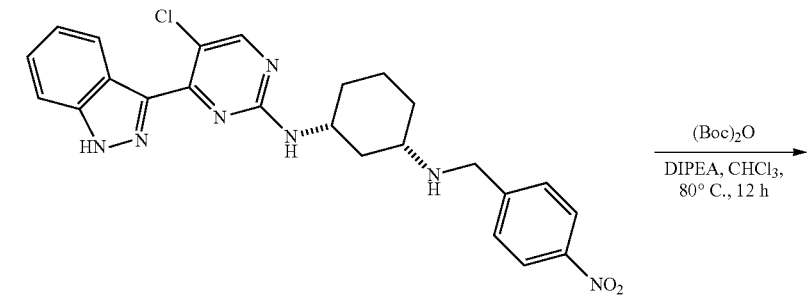

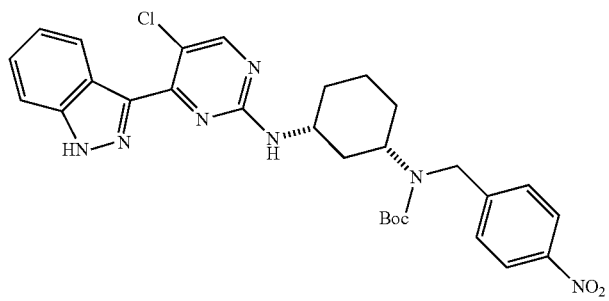

To a mixture of (1R,3S)—N1-(5-chloro-4-(1H-indazol-3-yl)pyrimidin-2-yl)-N3-(4-nitrobenzyl)cyclohexane-1,3-diamine (200 mg, 0.42 mmol) and (Boc)$_2$O (137 mg, 0.63 mmol) in CH$_3$Cl (20 mL) was added DIPEA (108 mg, 0.84 mmol) under N$_2$. The mixture was heated to 80° C. and stirred for 12 h, then concentrated under reduced pressure. The residue was purified by prep-HPLC (TFA condition) to afford the title compound (180 mg, 74.4%). MS (m/z): 578.2 [M+1]$^+$.

tert-butyl4-aminobenzyl((1S,3R)-3-((5-chloro-4-(1H-indazol-3-yl)pyrimidin-2-yl)amino)cyclohexyl)carbamate

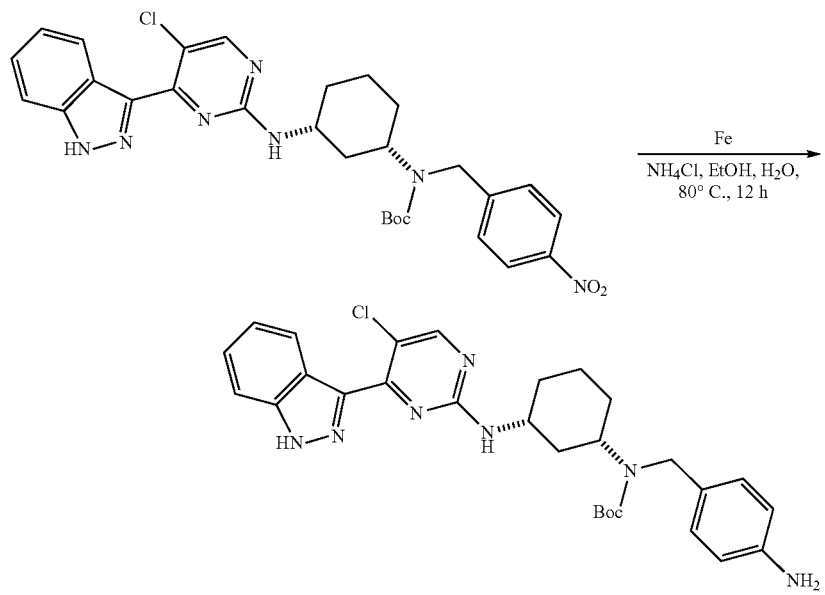

To a mixture of tert-butyl ((1S,3R)-3-((5-chloro-4-(1H-indazol-3-yl)pyrimidin-2-yl) amino)cyclohexyl)(4-nitrobenzyl)carbamate (400 mg, 0.7 mmol) and NH$_4$Cl (74 mg, 1.4 mmol) in EtOH (10 mL) and H$_2$O (1 mL) was added Fe (193 mg, 3.5 mmol) at 25° C. The mixture was heated to 80° C. and stirred for 12 h. The mixture was poured into water (20 mL), extracted with EA (10 mL×2), and the organic layer was concentrated in vacuum and purified by flash column to give the title compound (230 mg, 60.6%) as a brown solid.

tert-butyl4-acrylamidobenzyl((1S,3R)-3-((5-chloro-4-(1H-indazol-3-yl)pyrimidin-2-yl)amino)cyclohexyl)carbamate

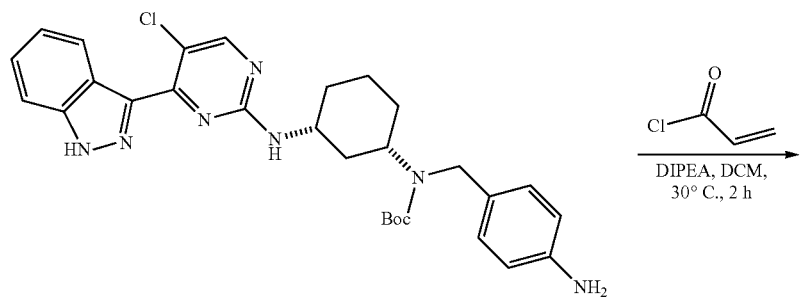

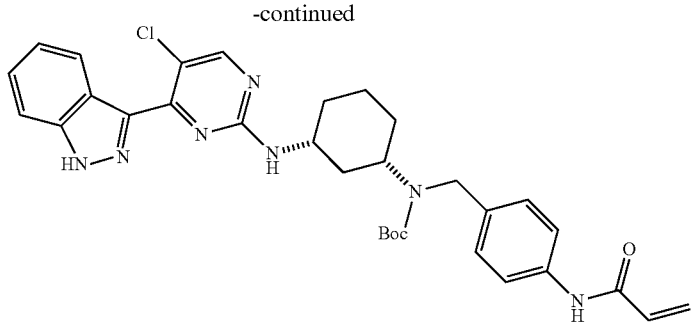

To a mixture of tert-butyl4-aminobenzyl((1S,3R)-3-((5-chloro-4-(1H-indazol-3-yl) pyrimidin-2-yl)amino)cyclohexyl)carbamate (200 mg, 0.36 mmol) and DIPEA (47.2 g, 0.36 mmol) in DCM (10 mL) was added acryloyl chloride (29.7 mg, 0.32 mmol) at 30° C. under $N_2$ and the mixture was stirred for 2 h. The mixture was poured into water (20 mL), extracted with DCM (10 mL×2), and the organic layer was concentrated to give the title compound (200 mg, crude), which was used directly in next step.

N-(4-(((((1S,3R)-3-((5-chloro-4-(1H-indazol-3-yl) pyrimidin-2-yl)amino)cyclohexyl)amino) methyl) phenyl)acrylamide

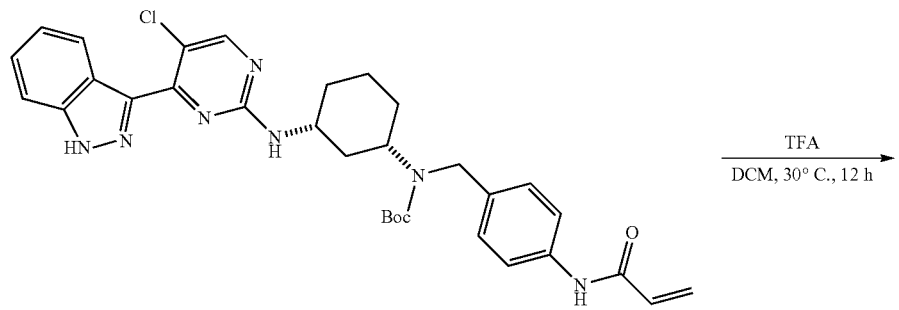

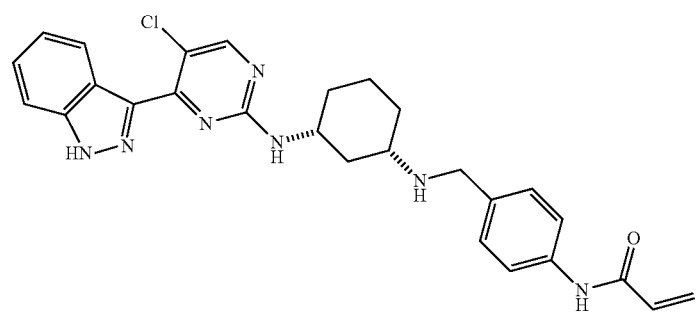

A mixture of tert-butyl4-acrylamidobenzyl((1S,3R)-3-((5-chloro-4-(1H-indazol-3-yl)pyrimidin-2-yl)amino)cyclohexyl)carbamate (150 mg, 0.32 mmol) in DCM (10 mL) and TFA (0.5 mL) was stirred at 30° C. for 12 h under $N_2$. The mixture was concentrated, and the residue was purified by prep-HPLC (HCl conditions) to afford Compound 162 (50 mg, 29.9%). $^1$H NMR: (MeOH, 400 MHz) δ 8.50 (br. s., 1H), 8.32 (d, J=8.38 Hz, 1H), 7.72 (d, J=8.38 Hz, 2H), 7.64 (d, J=7.94 Hz, 1H), 7.51 (br.s., 1H), 7.44 (d, J=8.38 Hz, 2H), 7.30 (t, J=7.28 Hz, 1H), 6.34-6.48 (m, 2H), 5.79 (dd, J=9.48, 2.43 Hz, 1H), 4.21 (s, 2H), 4.06 (br. s., 2H), 2.67 (d, J=9.70 Hz, 1H), 2.28 (d, J=11.03 Hz, 1H), 2.18 (d, J=7.94 Hz, 1H), 2.06 (d, J=12.79 Hz, 1H), 1.36-1.65 (m, 4H). MS (m/z): 502.3 [M+1]$^+$.

Example 38. (+/−)-N-(3-(5-chloro-4-(1H-indol-3-yl)pyrimidin-2-ylamino)-1-methylcyclohexyl)-4-((E)-4-(dimethylamino)but-2-enamido)benzamide (Compound 175)

tert-butyl (1R,3S)-3-(Benzyloxycarbonylamino)-3-methylcyclohexylcarbamate

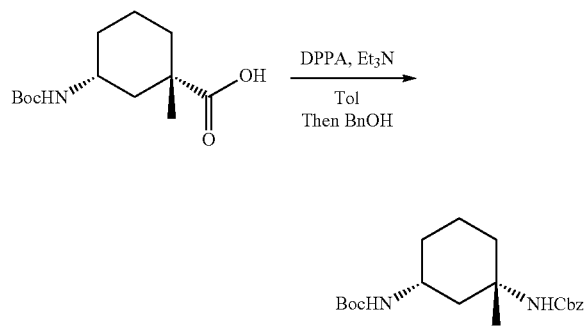

A solution of (1S,3R)-3-(tert-butoxycarbonylamino)-1-methylcyclohexanecarboxylic acid prepared as in WO2010/148197 (100 mg, 0.389 mmol) in toluene (1.5 mL) was treated with Et₃N (0.43 mmol) and DPPA (0.39 mmol) and heated at 110° C. for 1 h. The mixture was cooled down to 80° C., treated with benzyl alcohol (0.41 mmol) and Et₃N (0.43 mmol). The resulting mixture was heated at 80° C. for 20 h. The cooled mixture was then diluted with EtOAc (20 mL) and H₂O (10 mL). The layers were separated and the aqueous layer was extracted with EtOAc (3×10 mL). The combined organics layers were washed with brine (10 mL), filtered and evaporated to dryness. The residue was purified by SiO₂ chromatography (Hex/EtOAc 0 to 50% gradient) and afforded the title compound (59 mg, 0.180 mmol, 46%) as a colorless oil.

(+/−)-benzyl-3-amino-1-methylcyclohexylcarbamate.HCl

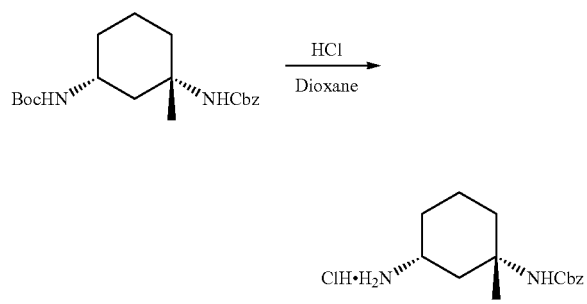

A solution of tert-butyl (1R,3S)-3-(Benzyloxycarbonylamino)-3-methylcyclohexylcarbamate (45 mg, 0.124 mmol) in DCM (0.6 mL) was treated with a 4M solution of HCl in dioxane (2.48 mmol) and stirred 1 h at rt. The mixture was evaporated to dryness and afforded the title compound (37 mg, 0.124 mmol, 100%) as a white solid that was used in the next step without further purification.

(+/−)-benzyl-3-(5-chloro-4-(1-(phenylsulfonyl)-1H-indol-3-yl)pyrimidin-2-ylamino)-1-methylcyclohexylcarbamate

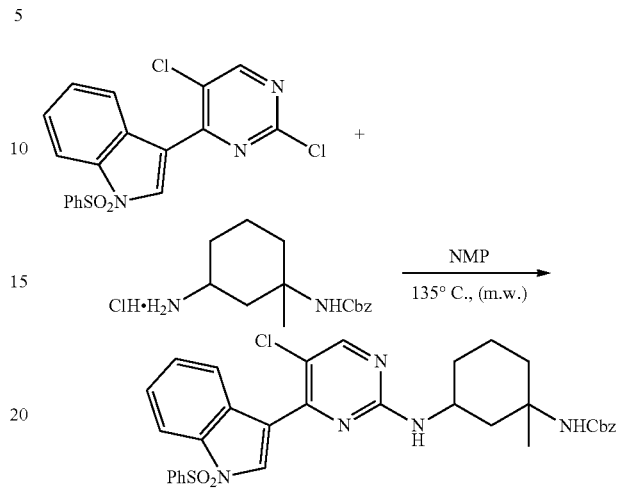

A solution of 3-(2,5-dichloropyrimidin-4-yl)-1-(phenylsulfonyl)-1H-indole (63 mg, 0.155 mmol), (+/−)-benzyl-3-amino-1-methylcyclohexylcarbamate.HCl (37 mg, 0.124 mmol) and DIPEA (0.254 mmol) in NMP (0.5 mL) was heated at 135° C. (microwave) for 25 min. The cooled mixture was diluted with EtOAc (20 mL), washed with H₂O (5 mL), brine (5 mL), dried over MgSO₄, filtered and evaporated to dryness. The residue was purified by SiO₂ chromatography (DCM/EtOAc 0 to 30% gradient) and afforded the title compound (52 mg, 0.083 mmol, 66%) as a yellow foam.

(+/−)-N1-(5-chloro-4-(1-(phenylsulfonyl)-1H-indol-3-yl)pyrimidin-2-yl)-3-methylcyclohexane-1,3-diamine

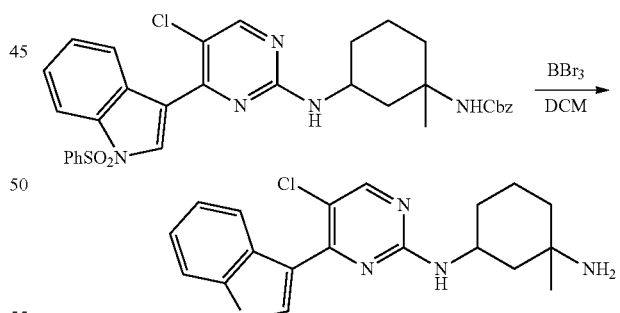

A cooled (−78° C.) solution of (+/−)-benzyl-3-(5-chloro-4-(1-(phenylsulfonyl)-1H-indol-3-yl)pyrimidin-2-ylamino)-1-methylcyclohexylcarbamate (51 mg, 0.081 mmol) in DCM (0.32 mL) was treated with a 1M solution of BBr₃ in DCM (0.097 mmol) and was slowly warmed to rt. MeOH (1 ML) was added to the mixture was the resulting solution was stirred 1 h at rt. The resulting mixture was evaporated to dryness and afforded the title compound (40 mg, 0.081 mmol, 100%) as a yellow solid which was used in the next step without further purification.

267

(+/−)-tert-butyl 4-(3-(5-chloro-4-(1-(phenylsulfo-nyl)-1H-indol-3-yl)pyrimidin-2-ylamino)-1-methyl-cyclohexylcarbamoyl)phenylcarbamate

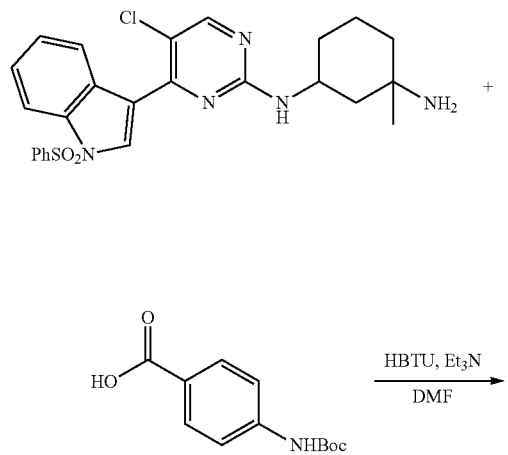

268

-continued

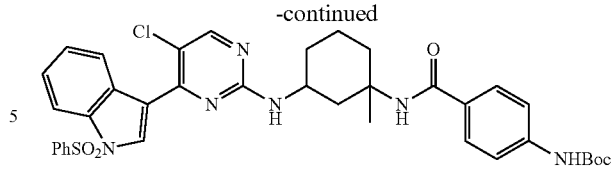

A solution of (+/−)-benzyl-3-(5-chloro-4-(1-(phenylsulfonyl)-1H-indol-3-yl)pyrimidin-2-ylamino)-1-methylcyclohexylcarbamate (40 mg, 0.81 mmol) and 4-(tert-butoxycarbonylamino) benzoic acid (23 mg, 0.97 mmol) in DMF (0.4 mL) was treated with HBTU (46 mg, 0.121 mmol) and $Et_3N$ (0.242 mmol). The resulting mixture was stirred overnight at rt and diluted with EtOAc (10 mL) and saturated $NaHCO_3$ (10 mL). The layers were separated and the aqueous layer was extracted with AtOAc (2×10 mL). The combined organic layers were dried over $MgSO_4$, filtered and evaporated to dryness. The residue was purified by $SiO_2$ chromatography (DCM/EtOAc 0 to 100% gradient) and afforded the title compound (48 mg, 0.067 mmol, 83%) as a beige solid.

(+/−)-tert-butyl 4-(3-(5-chloro-4-(1H-indol-3-yl)pyrimidin-2-ylamino)-1-methylcyclohexylcarbamoyl)phenylcarbamate

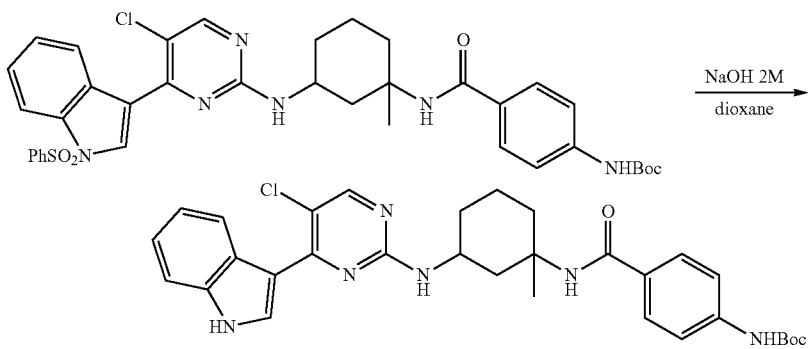

A solution of (+/−)-tert-butyl 4-(3-(5-chloro-4-(1-(phenylsulfonyl)-1H-indol-3-yl)pyrimidin-2-ylamino)-1-methylcyclohexylcarbamoyl)phenylcarbamate (45 mg, 0.063 mmol) in dioxane (0.6 mL) was treated with a 2M solution of NaOH in $H_2O$ (0.944 mmol) and heated at 60° C. for 1 h. The cooled mixture was diluted with MeTHF (20 mL) and $H_2O$ (10 mL). The layers were separated and the aqueous layer was extracted with MeTHF (3×10 mL). The combined organic layers were dried over $MgSO_4$, filtered and evaporated to dryness affording the title compound (36 mg, 0.063 mmol, 100%) as a yellow solid which was used in the next step without further purification.

(+/−)-4-amino-N-(3-(5-chloro-4-(1H-indol-3-yl)pyrimidin-2-ylamino)-1-methylcyclohexyl)benzamide

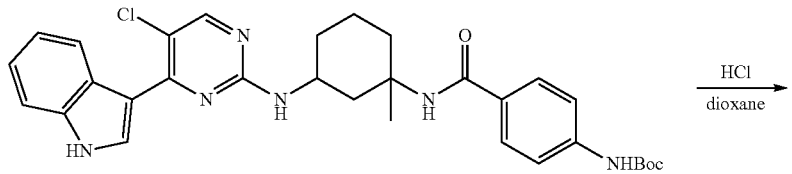

-continued

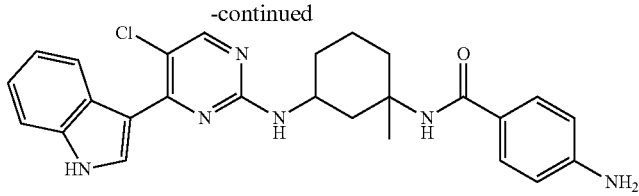

A solution of (+/−)-tert-butyl 4-(3-(5-chloro-4-(1H-indol-3-yl)pyrimidin-2-ylamino)-1-methylcyclohexylcarbamoyl)phenylcarbamate (36 mg, 0.063 mmol) in DCM was treated with a 4M solution of HCl in dioxane (0.939 mmol) and stirred overnight at rt. The resulting mixture was diluted with MeTHF (10 mL) and saturated NaHCO₃ (5 mL). The layers were separated and the aqueous layer was extracted with MeTHF (3×10 mL). The combined organic layers were dried over MgSO₄, filtered and evaporated to dryness affording the title compound (30 mg, 0.063 mmol, 100%) as a pale yellow solid which was used in the next step without further purification.

(+/−)-N-(3-(5-chloro-4-(1H-indol-3-yl)pyrimidin-2-ylamino)-1-methylcyclohexyl)-4-((E)-4-(dimethylamino)but-2-enamido)benzamide

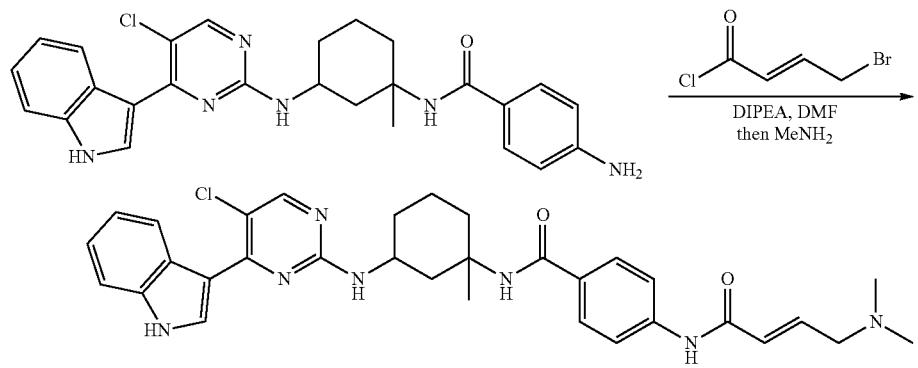

A cooled (−60° C.) solution of (+/−)-4-amino-N-(3-(5-chloro-4-(1H-indol-3-yl)pyrimidin-2-ylamino)-1-methylcyclohexyl)benzamide (29 mg, 0.0611 mmol) and DIPEA (0.183 mmol) in THF (0.4 mL) was treated with a 54.2 mg/mL solution of (E)-4-bromobut-2-enoyl chloride in DCM (0.055 mmol). The resulting mixture was stirred 2 h at −60° C. before addition of a 2M solution of dimethylamine in THF (0.244 mmol). The resulting mixture was warmed to rt and stirred 45 min at this temperature before being evaporated to dryness. The residue was purified by reverse phase chromatography (C₁₈, H₂O/ACN+0.1% HCO₂H 0 to 60% gradient) and afforded the title compound (15 mg, 0.026 mmol, 41%) as a white solid after lyophilisation.

Example 39. N-((1S,3R)-3-(5-chloro-4-(1H-indol-3-yl)pyrimidin-2-ylamino)-1-methylcyclohexyl)-4-((E)-4-(dimethylamino)but-2-enamido)benzamide (Compound 176)

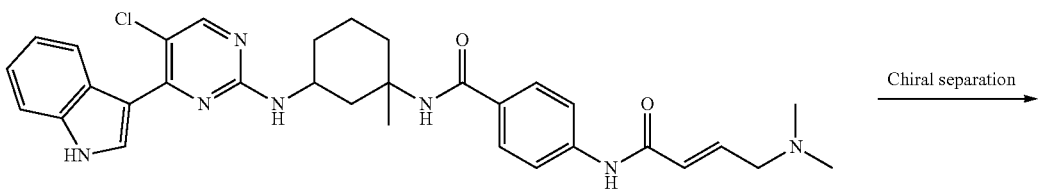

Chiral separation

-continued

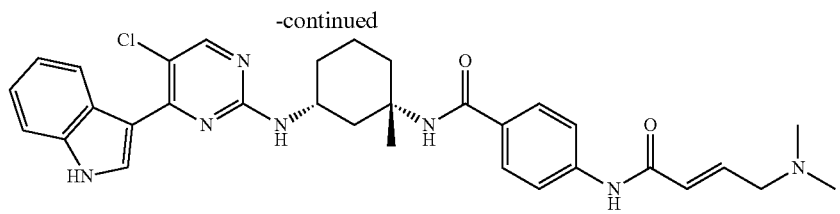

Both enantiomers of (+/−)-N-(3-(5-chloro-4-(1H-indol-3-yl)pyrimidin-2-ylamino)-1-methylcyclohexyl)-4-((E)-4-(dimethylamino)but-2-enamido)benzamide (12 mg, 0.020 mmol) were separated using preparative chiral HPLC (ChiralPak IB, 5 μm, 20×250 mm; Hex/MeOH/DCM 64/18/18) and afforded the title compound (2.1 mg, 0.0036, 18%) as a white solid after lyophilisation. $^1$H NMR (500 MHz, $d_6$-DMSO) δ 11.84 (s, 1H), 10.34 (s, 1H), 8.66 (bs, 1H), 8.47 (d, J=2.9 Hz, 1H), 8.25 (s, 2H), 7.77 (d, J=8.8 Hz, 2H), 7.69 (d, J=8.8 Hz, 2H), 7.63 (s, 1H), 7.49 (d, J=8.0 Hz, 1H), 7.17 (ddd, J=30.1, 15.1, 7.2 Hz, 3H), 6.76 (dt, J=15.4, 6.4 Hz, 1H), 6.35 (d, J=15.2 Hz, 1H), 4.06 (bs, 1H), 2.40 (s, 6H), 1.96 (bs, 2H), 1.86-1.63 (m, 3H), 1.63-1.43 (m, 4H), 1.38 (s, 3H); MS (m/z): 586.64 [M+1]$^+$.

Example 40 N-(4-((((1S,3R)-3-(5-chloro-4-(1H-indol-3-yl)pyrimidin-2-ylamino)cyclohexyl)(methyl)amino)methyl)phenyl)acrylamide (Compound 178)

tert-butyl 4-(((1S,3R)-3-(5-chloro-4-(1-(phenylsulfonyl)-1H-indol-3-yl)pyrimidin-2-ylamino)cyclohexylamino)methyl)phenylcarbamate

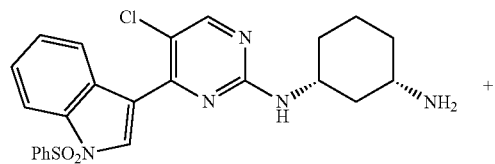

-continued

A solution of (1R,3S)—N1-(5-chloro-4-(1-(phenylsulfonyl)-1H-indol-3-yl)pyrimidin-2-yl)cyclohexane-1,3-diamine prepared as in Example 1 (180 mg, 0.373 mmol), tert-butyl 4-formylphenylcarbamate (124 mg, 0.822 mmol) and AcOH (0.221 mmol) in DCM (3.7 mL) was treated with NaBH(OAc)$_3$ (198 mg, 0.934 mmol) and stirred overnight at rt. The resulting mixture was diluted with DCM (20 mL) and saturated NaHCO$_3$ (10 mL). The layers were separated and the aqueous layer was extracted with DCM (2×10 mL). The combined organic layers were dried over MgSO$_4$, filtered and evaporated to dryness. The residue was purified by SiO$_2$ chromatography (DCM/MeOH 0 to 12% gradient) and afforded the title compound (178 mg, 0.259 mmol, 69%) as a white foam.

tert-butyl 4-(((((1S,3R)-3-(5-chloro-4-(1-(phenylsulfonyl)-1H-indol-3-yl)pyrimidin-2-ylamino)cyclohexyl)(methyl)amino)methyl)phenylcarbamate

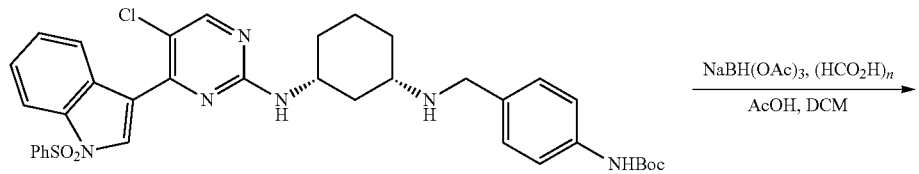

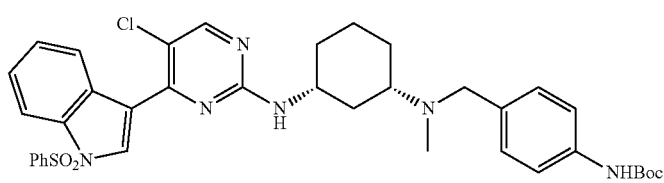

A solution of tert-butyl 4-((((1S,3R)-3-(5-chloro-4-(1-(phenylsulfonyl)-1H-indol-3-yl)pyrimidin-2-ylamino)cyclohexylamino)methyl)phenylcarbamate (178 mg, 0.259 mmol), paraformaldehyde (14 mg, 0.466 mmol) and AcOH (0.259 mmol) in DCM (4.3 mL) was treated with NaBH(OAc)₃ (132 mg, 0.622 mmol) and stirred 40 h at rt. The resulting mixture was diluted with DCM (20 mL) and saturated NaHCO₃ (10 mL). The layers were separated and the aqueous layer was extracted with DCM (2×10 mL). The combined organic layers were dried over MgSO₄, filtered and evaporated to dryness. The residue was purified by SiO₂ chromatography (DCM/MeOH 0 to 12% gradient) and afforded the title compound (96 mg, 0.137 mmol, 53%) as a white foam.

tert-butyl 4-(((((1S,3R)-3-(5-chloro-4-(1H-indol-3-yl)pyrimidin-2-ylamino)cyclohexyl)(methyl)amino)methyl)phenylcarbamate

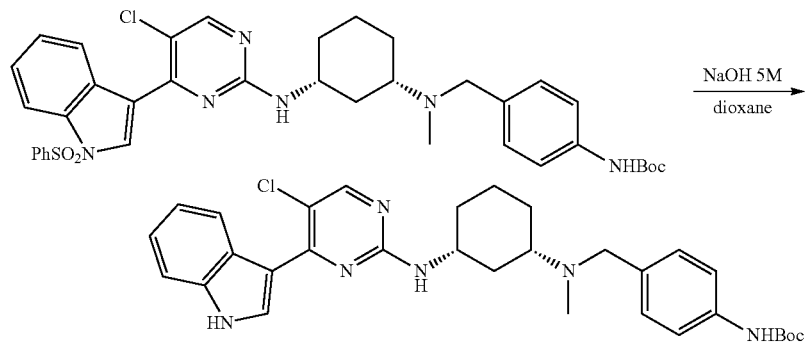

A solution of tert-butyl 4-(((((1S,3R)-3-(5-chloro-4-(1-(phenylsulfonyl)-1H-indol-3-yl)pyrimidin-2-ylamino)cyclohexyl)(methyl)amino)methyl)phenylcarbamate (96 mg, 0.137 mmol) in dioxane (2.7 mL) was treated with a 5M solution of NaOH in H₂O (0.55 mL, 2.74 mmol) and heated at 65° C. for 2 h. The cooled mixture was diluted with H₂O (5 mL) and MeTHF (10 mL). The layers were separated and the aqueous layer was extracted with MeTHF (3×10 mL). The combined organic layers were dried over MgSO4, filtered and evaporated to dryness. The residue was purified by SiO₂ chromatography (DCM/MeOH 0 to 12% gradient) and afforded the title compound (57 mg, 0.102 mmol, 74%) as a pale yellow foam.

(1S,3R)—N1-(4-aminobenzyl)-N3-(5-chloro-4-(1H-indol-3-yl)pyrimidin-2-yl)-N1-methylcyclohexane-1,3-diamine.HCl

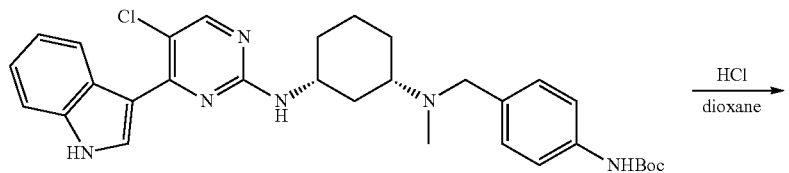

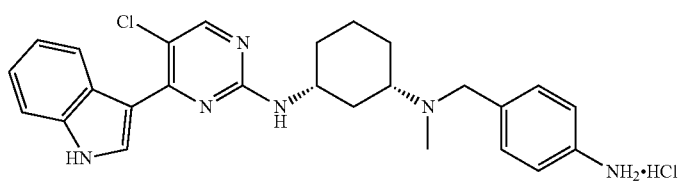

A solution of tert-butyl 4-((((1S,3R)-3-(5-chloro-4-(1H-indol-3-yl)pyrimidin-2-ylamino)cyclohexyl)(methyl)amino)methyl)phenylcarbamate (57 mg, 0.101 mmol) in DCM (2.0 mL) was treated with a 4M solution of HCl in dioxane (1.0 mL, 4.06 mmol) and stirred 18 h at rt. The resulting mixture was evaporated to dryness and afforded the title compound (50 mg, 0.101 mmol, 100%) as a bright yellow solid which was used in the next step without further purification.

N-(4-((((1S,3R)-3-(5-chloro-4-(1H-indol-3-yl)pyrimidin-2-ylamino)cyclohexyl) (methyl)amino)methyl)phenyl)acrylamide

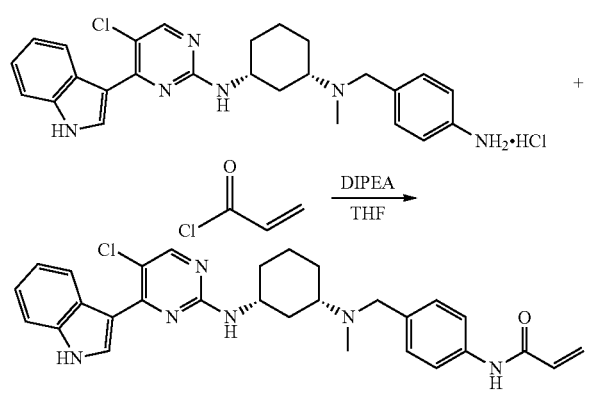

A cooled (−78° C.) solution of (1S,3R)—N1-(4-aminobenzyl)-N3-(5-chloro-4-(1H-indol-3-yl)pyrimidin-2-yl)-N1-methylcyclohexane-1,3-diamine.HCl (50 mg, 0.101 mmol) and DIPEA (0.408 mmol) in 5/2 THF:NMP (4.0 mL) was treated with acryloyl chloride (0.107 mmol) and stirred 1 h at this temperature. The resulting mixture was warmed up to rt and evaporated to dryness. The residue was purified by reverse phase chromatography (Cis, $H_2O$/ACN+0.1% $HCO_2H$ 0 to 100% gradient) and afforded the title compounds (26.3 mg, 0.051 mmol, 50%) as a pale yellow solid after lyophilisation. $^1$H NMR (500 MHz, $d_6$-DMSO) δ 11.82 (s, 1H), 10.09 (s, 1H), 8.56 (br s, 1H), 8.55 (s, 1H), 8.47 (s, 1H), 8.24 (s, 1H), 7.61 (d, J=8.2 Hz, 2H), 7.48 (d, J=8.2 Hz, 1H), 7.27-7.13 (m, 4H), 7.08 (br s, 1H), 6.42 (dd, J=17.0, 10.1 Hz, 1H), 6.24 (dd, J=17.0, 2.0 Hz, 1H), 5.73 (dd, J=10.2, 1.9 Hz, 1H), 3.89 (br s, 1H), 3.52-3.48 (m, 2H), 3.03 (br s, 1H), 2.10 (s, 3H), 2.02-1.76 (m, 3H), 1.40-1.22 (m, 5H); MS (m/z): 515.29 [M+1]$^+$.

Example 41. Synthesis of Other Exemplary Compounds of the Invention

Other exemplary compounds of the invention were synthesized using modification to or one or more of the foregoing examples. In Table 1B, the specific examples and modifications are indicated for each compound, as well as the 1H NMR (δ (ppm)) and MS (m/z [M+1]$^+$) characterization data. Compound numbers ("Compound No.") correspond to the compound numbers ("Compound No.") shown in FIGS. 1A-1I.

TABLE 1B

Exemplary synthesis and analytical data of other exemplary compounds of the invention

| Compound No. | Synthetic Protocol | $^1$H NMR δ (ppm) | m/z [M + 1]$^+$ |
|---|---|---|---|
| 105 | Starting from cyclohexane-1,4-diamine using the same synthetic sequence as Example 2 | $^1$H NMR (600 MHz, DMSO-$d_6$) δ 11.83 (s, 1H), 10.53 (s, 1H), 9.90 (br, 1H), 8.48 (s, 1H), 8.24 (s, 1H), 8.18 (br, 1H), 7.85 (d, J = 8.7 Hz, 2H), 7.73 (d, J = 8.7 Hz, 2H), 7.49 (d, J = 8.4 Hz, 1H), 7.22 (m, 3H), 6.76 (dt, J = 15.4, 5.8 Hz, 1H), 6.28 (d, J = 15.5 Hz, 1H), 3.95 (s, 2H), 3.82 (m, 1H), 2.82 (m, 1H), 2.78 (s, 6H), 2.10 (m, 2H), 1.89 (m, 2H), 1.55 (m, 2H), 1.41(m, 2H) | 572 |
| 106 | Following the same synthetic sequence for Compound 105, followed by resolution with chiral HPLC | $^1$H NMR (600 MHz, DMSO-d6) δ 11.83 (s, 1H), 10.53 (s, 1H), 9.90 (br, 1H), 8.48 (s, 1H), 8.24 (s, 1H), 8.18 (br, 1H), 7.85 (d, J = 8.7 Hz, 2H), 7.73 (d, J = 8.7 Hz, 2H), 7.49 (d, J = 8.4 Hz, 1H), 7.22 (m, 3H), 6.76 (dt, J = 15.4, 5.8 Hz, 1H), 6.28 (d, J = 15.5 Hz, 1H), 3.95 (s, 2H), 3.82 (m, 1H), 2.82 (m, 1H), 2.78 (s, 6H), 2.10 (m, 2H), 1.89 (m, 2H), 1.55 (m, 2H), 1.41(m, 2H) | 572 |
| 141 | Starting from 5-(2,5-dichloropyrimidin-4-yl)-2,4-dimethylthiazole using the same synthetic sequence as Example 1 | $^1$H NMR (500 MHz, DMSO) δ 10.25 (s, 1H), 8.46-8.34 (m, 1H), 8.18 (d, J = 8.0 Hz, 1H), 7.80 (d, J = 8.8 Hz, 2H), 7.70 (d, J = 8.8 Hz, 2H), 7.59 (d, J = 8.0 Hz, 1H), 6.75 (dt, J = 15.4, 5.9 Hz, 1H), 6.27 (dt, J = 15.3, 1.6 Hz, 1H), 3.91-3.80 (m, 1H), 3.80-3.71 (m, 1H), 3.06 (dd, J = 5.9, 1.5 Hz, 2H), 2.66 (s, J = 8.7 Hz, 3H), 2.17 (s, 6H), 2.13-2.06 (m, 1H), 1.94-1.85 (m, 1H), 1.84-1.73 (m, 2H), 1.37 (dd, J = 23.8, 11.8 Hz, 2H), 1.31-1.15 (m, 2H) | 568.62 |
| 142 | Starting from 5-(2,5-dichloropyrimidin-4-yl)-2,4-dimethylthiazole using the same synthetic sequences as | $^1$H NMR (500 MHz, DMSO) δ 10.34 (s, 1H), 8.48-8.35 (m, 1H), 8.19 (d, J = 8.0 Hz, 1H), 7.81 (d, J = 8.8 Hz, 2H), 7.71 (d, J = 8.8 Hz, 2H), 7.59 (d, J = 8.0 Hz, 1H), 6.44 (dd, J = 16.9, 10.1 Hz, 1H), 6.28 (dd, J = 17.0, 1.9 Hz, 1H), 5.79 (dd, J = 10.1, 1.9 Hz, 1H), | 511.54 |

… TABLE 1B-continued

Exemplary synthesis and analytical data of other exemplary compounds of the invention

| Compound No. | Synthetic Protocol | $^1$H NMR δ (ppm) | m/z [M + 1]$^+$ |
|---|---|---|---|
|  | Examples 1 and 7 | 3.90-3.81 (m, 1H), 3.80-3.71 (m, 1H), 2.66 (s, J = 7.0 Hz, 3H), 2.09 (dd, J = 11.6, 7.8 Hz, 1H), 1.90 (br d, J = 12.3 Hz, 1H), 1.83-1.74 (m, 2H), 1.37 (dd, J = 23.5, 11.7 Hz, 2H), 1.31-1.18 (m, 2H) |  |
| 143 | Following the same synthetic sequence as Example 1, using 1-(2-methoxyethyl)piperazine in the final step | $^1$H NMR (500 MHz, DMSO) δ 11.83 (brs, 1H), 10.24 (s, 1H), 8.60 (brs, 1H), 8.47 (d, J = 2.3 Hz, 1H), 8.31-8.15 (m, 2H), 7.81 (d, J = 8.8 Hz, 2H), 7.70 (d, J = 8.8 Hz, 2H), 7.53-7.44 (m, 1H), 7.30 (d, J = 8.0 Hz, 1H), 7.25-7.16 (m, 2H), 6.74 (dt, J = 15.4, 5.8 Hz, 1H), 6.27 (d, J = 15.4 Hz, 1H), 3.94 (brs, 2H), 3.41 (t, J = 5.9 Hz, 1H), 3.22 (s, 3H), 3.13-3.07 (m, 2H), 2.47-1.84 (m, 15H), 1.52-1.21 (m, 4H) | 671.69 |
| 144 | Starting from 4-(2,5-dichloropyrimidin-4-yl)-3,5-dimethylisoxazole and benzyl (1S,3R)-3-aminocyclohexyl-carbamate hydrochloride using the same synthetic sequence as Example 1 | $^1$H NMR (500 MHz, DMSO) δ 10.25 (s, 1H), 8.43 (brs, 1H), 8.17 (d, J = 8.0 Hz, 1H), 7.80 (d, J = 8.8 Hz, 2H), 7.70 (d, J = 8.8 Hz, 2H), 7.62 (d, J = 8.0 Hz, 1H), 6.76 (dt, J = 15.4, 5.9 Hz, 1H), 6.28 (dt, J = 15.4, 1.6 Hz, 1H), 3.85 (brs, 1H), 3.75 (brs, 1H), 3.06 (dd, J = 5.9, 1.4 Hz, 2H), 2.39 (s, 3H), 2.23 (s, 3H), 2.18 (s, 6H), 2.14-2.07 (m, 1H), 1.90-1.76 (m, 3H), 1.42-1.15 (m, 4H) | 552.67 |
| 145 | Starting from 4-(2,5-dichloropyrimidin-4-yl)-3,5-dimethylisoxazole and benzyl (1S,3R)-3-aminocyclohexyl-carbamate hydrochloride using the same synthetic sequence as Examples 1 and 7 | $^1$H NMR (500 MHz, DMSO) δ 10.34 (s, 1H), 8.43 (brs, 1H), 8.19 (d, J = 7.9 Hz, 1H), 7.82 (d, J = 8.8 Hz, 2H), 7.72 (d, J = 8.8 Hz, 2H), 7.62 (d, J = 8.0 Hz, 1H), 6.45 (dd, J = 17.0, 10.1 Hz, 1H), 6.28 (dd, J = 17.0, 1.9 Hz, 1H), 5.79 (dd, J = 10.1, 1.9 Hz, 1H), 3.85 (brs, 1H), 3.76 (brs, 1H), 2.39 (s, 3H), 2.23 (s, 3H), 2.11 (d, J = 11.0 Hz, 1H), 1.88 (brs, 1H), 1.79 (brs, 2H), 1.42-1.12 (m, 4H) | 495.62 |
| 146 | Starting from 4 tert-butyl 4-((1S,3R)-3-(5-cyclopropyl-4-(1-(phenylsulfonyl)-1H-indol-3-yl)pyrimidin-2-ylamino)-cyclohexyl-carbamoyl)phenyl carbamate in Example 10, using the same synthetic sequence as Example 7 | $^1$H NMR (500 MHz, DMSO) δ 11.57 (s, 1H), 10.27 (s, 1H), 8.61 (brs, 1H), 8.22 (d, J = 2.9 Hz, 1H), 8.14 (d, J = 7.9 Hz, 1H), 7.99 (s, 1H), 7.76 (d, J = 8.8 Hz, 2H), 7.65 (d, J = 8.8 Hz, 2H), 7.39 (d, J = 9.0 Hz, 1H), 7.16-7.04 (m, 2H), 6.74 (d, J = 7.7 Hz, 1H), 6.38 (dd, J = 17.0, 10.2 Hz, 1H), 6.21 (dd, J = 17.0, 1.9 Hz, 1H), 5.71 (dd, J = 10.1, 1.9 Hz, 1H), 3.87 (brs, 2H), 2.13 (brs, 1H), 1.98-1.71 (m, 4H), 1.45-1.17 (m, 4H), 0.88 (brs, 2H), 0.52 (s, 2H) | 521.68 |
| 147 | Starting from cis-1,4-diaminocyclohexane using the same synthetic sequence as Example 29 | $^1$H NMR (500 MHz, DMSO) δ 11.83 (s, 1H), 10.35 (s, 1H), 8.64 (br s, 1H), 8.48 (d, J = 3.0 Hz, 1H), 8.27 (s, 1H), 8.01 (d, J = 6.7 Hz, 1H), 7.85 (d, J = 8.8 Hz, 2H), 7.73 (d, J = 8.8 Hz, 2H), 7.49 (d, J = 7.9 Hz, 1H), 7.26-7.12 (m, 2H), 6.99 (d, J = 6.7 Hz, 1H), 6.45 (dd, J = 17.0, 10.1 Hz, 1H), 6.29 (dd, J = 17.0, 1.9 Hz, 1H), 5.79 (dd, J = 10.1, 1.9 Hz, 1H), 3.94 (br s, 2H), 1.99-1.82 (m, 4H), 1.81-1.71 (m, 2H), 1.70-1.60 (m, 2H) | 515.58 |
| 148 | Starting from 3-(2,5-dichloropyrimidin-4-yl)pyrazolo[1,5-a]pyridine using the same synthetic sequence as Example 5 | $^1$H NMR (500 MHz, DMSO) δ 10.26 (s, 1H), 9.04-8.75 (m, 2H), 8.73-8.55 (m, 1H), 8.38-8.10 (m, 2H), 7.88-7.30 (m, 6H), 7.16 (t, J = 6.7 Hz, 1H), 6.75 (dt, J = 15.4, 5.9 Hz, 1H), 6.29 (d, J = 15.4 Hz, 1H), 3.85 (s, 2H), 3.67-3.54 (m, 4H), 3.12 (dd, J = 5.9, 1.4 Hz, 2H), 2.37 (d, J = 12.6 Hz, 4H), 2.30-2.11 (m, 1H), 1.97 (s, 1H), 1.84 (s, 2H), 1.56-1.18 (m, 4H), 0.97 (d, J = 6.5 Hz, 1H) | 615.32 |
| 149 | Starting from 3-(2,5-dichloropyrimidin-4-yl)pyrazolo[1,5-a]pyridine using the same synthetic | $^1$H NMR (500 MHz, DMSO) δ 10.24 (s, 1H), 8.98-8.79 (m, 2H), 8.76-8.54 (m, 1H), 8.41-8.09 (m, 2H), 7.89-7.76 (m, 2H), 7.70 (d, J = 8.8 Hz, 3H), 7.43 (d, J = 7.9 Hz, 1H), 7.16 (t, J = 6.8 Hz, 1H), 6.74 (dt, J = | 654.38 |

TABLE 1B-continued

Exemplary synthesis and analytical data of other exemplary compounds of the invention

| Compound No. | Synthetic Protocol | $^1$H NMR δ (ppm) | m/z [M + 1]$^+$ |
|---|---|---|---|
| | sequence as Example 5 using cyclopropylpiperazine in the final step | 15.4, 5.9 Hz, 1H), 6.27 (d, J = 15.4 Hz, 1H), 4.17-3.77 (m, 2H), 3.09 (dd, J = 5.8, 1.3 Hz, 2H), 2.55 (s, 3H), 2.36 (d, J = 1.9 Hz, 4H), 1.84 (s, 3H), 1.65-1.55 (m, 1H), 1.35 (dd, J = 58.2, 12.5 Hz, 4H), 0.44-0.34 (m, 2H), 0.31-0.20 (m, 2H) | |
| 150 | Starting from 3-(2,5-dichloropyrimidin-4-yl)-1-methyl-1H-indole from example 43 using the same synthetic sequence as Example 1 | $^1$H NMR (500 MHz, DMSO) δ 10.26 (s, 1H), 8.51 (s, 2H), 8.23 (dd, J = 12.8, 7.5 Hz, 2H), 7.82 (d, J = 8.6 Hz, 2H), 7.71 (d, J = 8.6 Hz, 2H), 7.53 (d, J = 8.2 Hz, 1H), 7.29 (dd, J = 15.0, 7.8 Hz, 3H), 6.75 (dt, J = 15.3, 5.8 Hz, 1H), 6.28 (d, J = 15.4 Hz, 1H), 3.93 (d, J = 24.7 Hz, 5H), 3.06 (d, J = 5.4 Hz, 2H), 2.29-2.08 (m, 6H), 2.07-1.74 (m, 3H), 1.55-1.16 (m, 5H) | 586.33 |
| 152 | Starting from 3-(2,5-dichloropyrimidin-4-yl)-1-methyl-1H-indole from using the same synthetic sequence as Examples 1 and 7 | $^1$H NMR (500 MHz, DMSO) δ 10.34 (s, 1H), 8.63 (brs, 1H), 8.52 (s, 1H), 8.29-8.18 (m, 2H), 7.83 (d, J = 8.7 Hz, 2H), 7.72 (d, J = 8.7 Hz, 2H), 7.54 (d, J = 8.5 Hz, 1H), 7.33-7.20 (m, 3H), 6.44 (dd, J = 16.9, 10.1 Hz, 1H), 6.28 (dd, J = 17.0, 1.8 Hz, 1H), 5.79 (dd, J = 10.1, 1.9 Hz, 1H), 3.91 (brs, 5H), 2.21 (brs, 1H), 2.01 (brs, 1H), 1.85 (brs, 2H), 1.41 (brs, 2H), 1.36-1.18 (m, 2H) | 529.27 |
| 156 | Starting from (R)-benzyl-3-(5-chloro-4-(1-(phenylsulfonyl)-1H-indol-3-yl)pyrimidin-2-ylamino)-1-methylcyclohexyl-carbamante and 4-fluorobenzoic acid using the same synthetic sequence outlined in Example 33 | $^1$H NMR (500 MHz, DMSO) δ 11.77 (s, 1H), 10.03 (s, 1H), 8.58 (d, J = 6.5 Hz, 1H), 8.40 (d, J = 2.9 Hz, 1H), 8.18 (s, 1H), 8.07 (t, J = 8.2 Hz, 1H), 7.71 (s, 1H), 7.64 (dd, J = 11.9, 1.9 Hz, 1H), 7.58 (d, J = 8.7 Hz, 1H), 7.19-7.09 (m, 2H), 7.06 (t, J = 7.1 Hz, 1H), 6.58 (dd, J = 17.0, 10.2 Hz, 1H), 6.23 (dd, J = 17.0, 1.9 Hz, 1H), 5.73 (dd, J = 10.2, 1.9 Hz, 1H), 4.18-3.95 (m, 1H), 2.42-2.31 (m, 1H), 1.96-1.81 (m, 2H), 1.73-1.65 (m, 3H), 1.58-1.36 (m, 4H), 1.25 (dd, J = 22.3, 9.3 Hz, 1H) | |
| 157 | Starting from (R)-benzyl-3-(5-chloro-4-(1-(phenylsulfonyl)-1H-indol-3-yl)pyrimidin-2-ylamino)-1-methylcyclohexyl-carbamante and 4-amino-2-fluorobenzoic acid using the same synthetic sequence outlined in Example 33 | $^1$H NMR (500 MHz, DMSO) δ 11.83 (s, 1H), 10.38 (s, 1H), 8.64 (s, 1H), 8.47 (d, J = 2.9 Hz, 1H), 8.24 (s, 1H), 7.70 (dd, J = 13.1, 1.7 Hz, 1H), 7.66 (d, J = 2.6 Hz, 2H), 7.51 (dd, J = 16.6, 8.2 Hz, 1H), 7.33 (dd, J = 8.5, 1.8 Hz, 1H), 7.25-7.08 (m, 3H), 6.77 (dt, J = 15.4, 5.8 Hz, 1H), 6.26 (d, J = 15.5 Hz, 1H), 4.20-4.10 (m, 1H), 3.06 (d, J = 5.4 Hz, 2H), 2.41 (s, 1H), 2.17 (s, 6H), 2.01-1.86 (m, 2H), 1.85-1.67 (m, 3H), 1.53 (s, 4H), 1.35-1.23 (m, 1H) | 604.41 |
| 159 | Starting from tert-butyl (1S,3R)-3-amino-3-methylcyclohexyl-carbamate and following Example 33 | $^1$H NMR (500 MHz, DMSO) δ 11.81 (s, 1H), 10.25 (s, 1H), 8.56 (brs, 1H), 8.38 (s, 1H), 8.26 (s, 1H), 8.10 (d, J = 8.1 Hz, 1H), 7.79 (d, J = 8.8 Hz, 2H), 7.69 (d, J = 8.8 Hz, 2H), 7.46 (d, J = 8.1 Hz, 1H), 7.15 (dt, J = 26.8, 6.9 Hz, 2H), 6.85 (s, 1H), 6.75 (dt, J = 15.5, 5.9 Hz, 1H), 6.28 (d, J = 15.4 Hz, 1H), 4.03 (s, 1H), 3.06 (d, J = 4.4 Hz, 2H), 2.46-2.40 (m, 1H), 2.17 (s, 6H), 2.05-1.95 (m, 1H), 1.85-1.65 (m, 4H), 1.53 (brs, 4H), 1.38-1.30 (m, 1H). | 586.40 |
| 160 | Following the same synthetic sequence as Example 5 using N,O-dimethylhydroxylamine hydrochloride in the final step | $^1$H NMR (500 MHz, DMSO) δ 11.82 (brs, 1H), 10.26 (s, 1H), 8.64 (brs, 2H), 8.46 (s, 1H), 8.26-8.19 (m, 2H), 7.82 (d, J = 8.8 Hz, 2H), 7.70 (d, J = 8.8 Hz, 2H), 7.52-7.48 (m, 1H), 7.29 (d, J = 7.8 Hz, 1H), 7.25-7.19 (m, 1H), 6.82 (dt, J = 15.5, 6.1 Hz, 1H), 6.27 (d, J = 15.4 Hz, 1H), 3.99-3.90 (brs, 2H), 3.46-3.40 (m, 5H), 2.54 (s, 3H), 2.22 (brs, 1H), 2.05-1.96 (m, 1H), 1.90-1.80 (m, 2H), 1.50-1.36 (m, 2H), 1.33-1.23 (m, 2H). | 588.28 |

Biological Assays of the Compounds

Example 42. Inhibition of Kinase Activity

Compounds of the invention were assayed for activity against a variety of different kinases at Life Technologies™ (Grand Island, N.Y.) using their commercially available Adapta® (for CDK7, CDK9/cyclin T1, and IRAK1 kinases), Z'-Lyte® (for CDK1, CDK2, CDK5/p25, CDK5/p35, JNK1 and JNK2 kinases), and LanthaScreen Eu® (for CDK8, CDK9/cyclin K and MLK3) kinase assay services. Test compounds were tested at 100 nM and 1 µM final concentrations in 1% DMSO against all kinases except CDK7. For CDK7, test compounds were tested at concentrations ranging from 10 µM to 0.514 nM in a series of 3-fold serial dilutions. Detailed protocols of these assays, including substrates used for each kinase, are known in the art, such as on the Life Technologies web site (www.lifetechnologies.com/us/en/homellife-science/drug-discovery/target-and-lead-identification-and-validation/kinasebiology/kinase-activity-assays.html). Exemplary results are presented as calculated $IC_{50}$ values (Tables 1C and 2) or as percent inhibitions of activity (Tables 3A to 3C). In Tables 1C and 2, "A" represents a calculated $IC_{50}$ value of less than 100 nM; "B" represents a calculated $IC_{50}$ value of greater than or equal to 100 nM and less than 1 µM; and "C" represents a calculated $IC_{50}$ value of 1 µM or greater. In Tables 3A to 3C, "A" represents greater than 70% inhibition of a kinase by the test compound, "B" represents between 50% and 70% inhibition, inclusive; and "C" represents less than 50% inhibition. The co-factors used for each kinase in the assays were as follows: CDK1: cyclin B; CDK2: cyclin A; CDK5: p25 or p35 as indicated; CDK7: cyclin H and MNAT1; CDK8: cyclin C; CDK9: cyclin K or cyclin T1 as indicated; IRAK1: Histone $H_3$ (1-20) peptide; JNK1: none required; JNK2: none required; MLK3: none required.

TABLE 1C

Calculated $IC_{50}$ values of exemplary compounds of the invention against CDK7

| Compound No. | CDK7 $IC_{50}$ |
| --- | --- |
| 100 | A |
| 101 | B |
| 102 | A |
| 103 | B |
| 104 | A |
| 105 | A |

TABLE 1C-continued

Calculated $IC_{50}$ values of exemplary compounds of the invention against CDK7

| Compound No. | CDK7 $IC_{50}$ |
| --- | --- |
| 106 | A |
| 108 | B |
| 109 | A |
| 110 | A |
| 111 | A |
| 112 | A |
| 113 | B |
| 114 | A |
| 115 | A |
| 116 | B |
| 117 | A |
| 118 | B |
| 119 | A |
| 120 | B |
| 121 | A |
| 122 | A |
| 123 | B |
| 124 | A |
| 125 | A |
| 126 | A |
| 127 | B |
| 128 | A |
| 129 | A |
| 130 | A |
| 131 | A |
| 132 | C |
| 133 | B |
| 134 | C |
| 135 | A |
| 136 | C |
| 137 | B |
| 138 | A |
| 139 | C |
| 140 | A |
| 141 | A |
| 142 | B |
| 143 | A |
| 144 | B |
| 145 | AB |
| 146 | B |
| 147 | AB |
| 148 | A |
| 149 | A |
| 150 | A |
| 151 | A |
| 152 | B |
| 153 | A |
| 154 | A |
| 155 | C |
| 160 | B |

TABLE 2

Calculated $IC_{50}$ values of exemplary compounds of the invention against various kinases

| Compound No. | CDK7 | CDK2 | CDK5$^e$ | CDK8 | CDK9$^e$ | CDK9$^f$ | MLK3 |
| --- | --- | --- | --- | --- | --- | --- | --- |
| 100 | A | C | C | B | B | B | |
| 101 | B | | C | | | | C |
| 102 | A | | C | | | | C |
| 103 | B | | C | | | | C |
| 104 | A | | C | | | | C |
| 105 | A | | | | | | |

TABLE 3A

Percent inhibition of various kinases by exemplary compounds of the invention

| Compound No. | CDK1[a] | CDK1[b] | CDK2[a] | CDK2[b] | CDK5[a,c] | CDK5[b,c] |
|---|---|---|---|---|---|---|
| 102 | C | C | C | C | C | C |
| 103 | C | C | C | C | C | C |

TABLE 3B

Percent inhibition of various kinases by exemplary compounds of the invention

| Compound No. | CDK5[a,d] | CDK5[b,d] | CDK8[a] | CDK8[b] | CDK9[a,e] | CDK9[b,e] |
|---|---|---|---|---|---|---|
| 102 | C | C | C | C | C | C |
| 103 | C | C | C | C | C | B |

TABLE 3C

Percent inhibition of various kinases by exemplary compounds of the invention

| Compound No. | IRAK1[a] | IRAK1[b] | JNK1[a] | JNK1[b] | JNK2[a] | JNK2[b] | MLK3[a] |
|---|---|---|---|---|---|---|---|
| 102 | C | C | C | B | C | B | C |
| 103 | C | C | C | B | C | A | C |

Exemplary compounds of the invention were further tested for inhibitory activity against CDK7 using an assay developed using a Caliper/LabChip EZ Reader (Perkin Elmer, Waltham, Mass.). In this protocol, the concentration of phosphorylated peptide substrate produced as a fraction of total peptide activity is monitored following an incubation period (30 minutes), which was selected such that the total fraction of phosphorylated peptide produced was less than 20% for the uninhibited kinase. Compounds of the invention were assayed at concentrations ranging from 10 µM to 0.514 nM in a series of 3-fold serial dilutions, and were incubated with CDK7/Cyclin H/MAT1 trimeric complex (10 nM), ATP (2 mM), and "FAM-CDK7tide" peptide substrate (2 µM, synthesized fluorophore-labeled peptide with the following sequence: 5-FAM-YSPTSPSYSPTSPSYSPTSPSKKKK) in a buffer comprising 20 mM MES, pH 6.75; 6 mM $MgCl_2$; 0.01% Tween 20; and 0.05 mg/mL BSA. $IC_{50}$ values were recorded for selected test compounds and are reported in Table 4, wherein "A" represents a calculated $IC_{50}$ of less than 100 nM, "B" represents a calculated $IC_{50}$ of between 100 nM and 1 µM, inclusive and "C" represents a calculated $IC_{50}$ of greater than 1 µM.

[a] Compound tested at 100 nM.
[b] Compound tested at 1 µM.
[c] CDK5 tested using p25 co-factor.
[d] CDK5 tested using p35 co-factor.
[e] CDK9 tested using cyclin T1 co-factor.
[f] CDK9 tested using cyclin K co-factor.

TABLE 4

Calculated $IC_{50}$ values of exemplary compounds of the invention against CDK7

| Compound No. | CDK7 $IC_{50}$ |
|---|---|
| 135 | B |
| 155 | C |
| 156 | C |
| 157 | B |
| 158 | A |
| 159 | C |

Example 43. Inhibition of Cell Proliferation

Exemplary compounds of the invention were tested at different concentrations (from 10 µM to 316 µM; 0.5 log serial dilutions) for their ability to inhibit the proliferation of various cancer cell lines. Known CDK inhibitors flavopiridol and triptolide were used as positive controls. Cells were grown in the indicated media below. All cell lines were supplemented with FBS (Life Technologies) and 100 $U·mL^{-1}$ penicillin, 100 $µg·mL^{-1}$ streptomycin (Invitrogen) and cultured at 37° C. in a humidified chamber in the presence of 5% $CO_2$. Proliferation assays were conducted over a 72 hour time period. CellTiter-Glo® (Promega Corporation, Madison, Wis. USA) was used to assess the anti-proliferative effects of the compounds following manufacturer's directions and utilizing the reagents supplied with the CellTiter-Glo® kit.

The following cancer cell lines were tested with the media conditions indicated:

Blood Cancer Cell Lines
  Jurkat—RPMI 1640+10% FBS+1% Glutamax
  HL60—RPMI 1640+10% FBS+1% Glutamax
  THP-1—RPMI 1640+10% FBS+1% Glutamax+0.05 mM 2-Mercaptoethanol
  MV4-11—RPMI 1640+10% FBS+1% Glutamax
  RS4-11—RPMI 1640+10% FBS+1% Glutamax Breast Cancer Cell Lines
  hTERT-HME1—Mammary Epithelial Cell Basal Medium (500 mL; Lonza CC-3151)+2 mL BPE+0.5 mL hEGF+0.5 mL Hydrocortisone+0.5 mL GA-1000+0.5 mL insulin (Lonza CC-4136)+100 ng/mL cholera toxin.
  MDA-MB231—Leibovitz's L-15 Medium+10% FBS+1% Glutamax
  MCF7—RPMI 1640+10% FBS+1% Glutamax
  MCF10A—Mammary Epithelial Cell Basal Medium (500 mL; Lonza CC-3151)+2 mL BPE+0.5 mL hEGF+0.5 mL Hydrocortisone+0.5 mL GA-1000+0.5 mL insulin (Lonza CC-4136)+100 ng/mL cholera toxin.
  SKBR3—McCoy's 5a Medium Modified+10% FBS
  T47D—RPMI 1640+10% FBS+1% Glutamax+0.2 Units/ml bovine insulin Osteosarcoma Cell Lines
  143B—EMEM+10% FBS+15 ug/ml Bromo-deoxy Uridine (BUdR)+2 mM Glutamine+1% Non Essential Amino Acids (NEAA)
  MNNG-HOS Cl #5—EMEM+10% FBS
  SAOS—McCoy's 5a Medium Modified+10% FBS+2 mM L-Glut
  MG-63—EMEM+10% FBS Ewing's Sarcoma Cell Lines
  Hs863T—DMEM (4 mM L-Glut, 4.5 g/L Glucose, 1 mM pyruvate, 1.5 g/l bicarb)+10% FBS
  Hs822T—DMEM (4 mM L-Glut, 4.5 g/L Glucose, 1 mM pyruvate, 1.5 g/l bicarb)+10% FBS
  A673—DMEM (4 mM L-Glut, 4.5 g/L Glucose, 1 mM pyruvate, 1.5 g/l bicarb)+10% FBS
  SK-ES-1—McCoy's 5a Medium Modified (modified—1.5 mM L-glut, 2.2 g/L bicarb)+15% FBS
  RD-ES—RPMI 1640+15% FBS.

Exemplary results of these assays are set forth in Tables 5A to 5D, where "A" represents an $IC_{50}$ value of less than 500 nM; "B" represents an $IC_{50}$ value of between 500 nM and 5 μM, inclusive; and "C" represents an $IC_{50}$ value of greater than 5 μM.

TABLE 5A

Inhibition of proliferation of various blood cancer cell lines by exemplary compounds of the invention

| Compound No. | HL60 | THP-1 | MV4-11 | RS4-11 |
| --- | --- | --- | --- | --- |
| 102 | A | A | A | A |
| 103 | B | B | A | B |
| Flavopiridol | A | A | A | A |
| Triptolide | A | A | A | A |

TABLE 5B

Inhibition of proliferation of various breast cancer cell lines by exemplary compounds of the invention

| Compound No. | hTERT-HME1 | MDA-MB231 | MCF7 | MCF10A | T47D | SKBR3 |
| --- | --- | --- | --- | --- | --- | --- |
| 102 | A | A | C | A | C | C |
| 103 | B | B | B | A | C | C |
| Flavopiridol | A | A | B | A | C | A |
| Triptolide | A | A | A | A | C | A |

TABLE 5C

Inhibition of proliferation of various cancer cell lines by exemplary compounds of the invention

| Compound No. | Ewing's Sarcoma | | | | | Osteosarcoma | | |
| --- | --- | --- | --- | --- | --- | --- | --- | --- |
| | A673 | Hs822T | Hs863T | RD-ES | SK-ES-1 | SAOS | MNNG-HOS Cl#5 | 143B |
| 102 | A | C | C | A | A | A | C | C |
| 103 | A | C | C | B | B | B | C | C |
| Flavopiridol | A | C | C | A | A | A | B | B |
| Triptolide | A | B | C | A | A | A | A | A |

TABLE 5D

Inhibition of proliferation of Jurkat cells by exemplary compounds of the invention

| Compound No. | Jurkat $IC_{50}$ |
| --- | --- |
| 101 | B |
| 102 | A |
| 103 | B |
| 104 | A |
| 108 | B |
| 109 | A |
| 110 | A |
| 111 | A |
| 112 | A |
| 113 | B |
| 114 | A |
| 115 | A |
| 116 | A |
| 117 | A |
| 118 | B |
| 119 | A |
| 120 | B |
| 121 | A |
| 122 | A |

TABLE 5D-continued

Inhibition of proliferation of Jurkat cells by exemplary compounds of the invention

| Compound No. | Jurkat IC$_{50}$ |
|---|---|
| 123 | A |
| 124 | A |
| 125 | A |
| 126 | A |
| 127 | B |
| 128 | A |
| 129 | A |
| 130 | A |
| 131 | A |
| 133 | A |
| 134 | C |
| 135 | A |
| 137 | A |
| 138 | A |
| 139 | B |
| 140 | A |
| 141 | A |
| 142 | A |
| 143 | A |
| 144 | A |
| 145 | A |
| 146 | B |
| 147 | A |
| 152 | A |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating a proliferative disease in a subject in need thereof, the method comprising administering to the subject a therapeutically effective amount of a pharmaceutical composition comprising a compound having Formula (Ia):

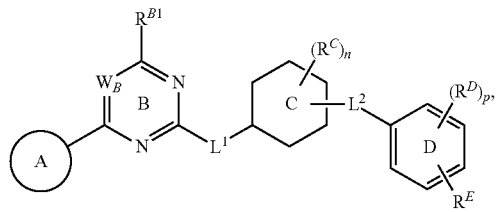

or a pharmaceutically acceptable salt thereof, wherein:
the proliferative disease is leukemia, breast cancer, or bone cancer;
Ring A is selected from the group consisting of

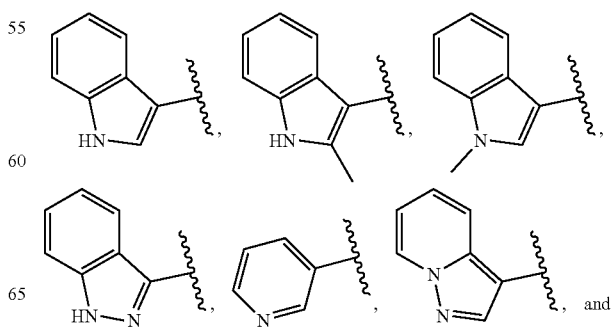

-continued

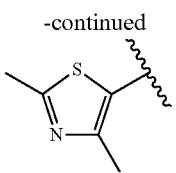

wherein Ring A may be substituted with a substituent selected from the group consisting of halogen, optionally substituted $C_1$-$C_3$ alkyl, optionally substituted $C_3$-$C_{10}$ carbocyclyl, optionally substituted 3- to 10-membered heterocyclyl, optionally substituted $C_6$, $C_{10}$, or $C_{14}$ aryl, and optionally substituted 5- to 10-membered monocyclic or bicyclic heteroaryl;

$W_B$ is $CR^{B2}$, wherein $R^{B2}$ is selected from the group consisting of halogen, substituted or unsubstituted $C_3$-$C_{10}$ carbocyclyl, unsubstituted $C_{1-6}$ alkyl, $C_{1-6}$alkyl substituted with one or more halogen, and —CN;

$R^{B1}$ is hydrogen or halogen;

$L^1$ is —N($R^{L1}$)—, wherein $R^{L1}$ is hydrogen or unsubstituted $C_{1-6}$ alkyl;

each instance of $R^C$ is independently selected from the group consisting of halogen, —$OR^{C1}$, and substituted or unsubstituted $C_{1-6}$ alkyl, wherein each instance of $R^{C1}$ is independently hydrogen or substituted or unsubstituted $C_{1-6}$ alkyl, or two $R^C$ are taken together to form an optionally substituted 3- to 10-membered heterocyclyl or $C_3$-$C_8$ carbocyclyl fused to the ring to which the RC are bound;

$L^2$ is selected from the group consisting of —N($R^{L2}$)C(=O)—, —C(=O)N($R^{L2}$)—, —N($R^{L2}$)—($C_{1-2}$ alkylene)-, —N($R^{L2}$)—, —NH—S(O)$_2$—, and —S(O)$_2$—NH—, wherein each instance of $R^{L2}$ is independently hydrogen, or substituted or unsubstituted $C_{1-6}$ alkyl;

each instance of $R^D$ is independently halogen or optionally substituted $C_1$-$C_4$ alkyl;

$R^E$ is selected from:

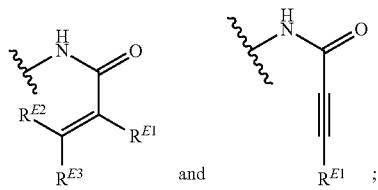

$R^{E1}$ is selected from the group consisting of hydrogen, halogen, optionally substituted $C_{1-6}$ alkyl, optionally substituted $C_{2-6}$ alkenyl, optionally substituted $C_{2-6}$alkynyl, optionally substituted $C_3$-$C_{10}$ carbocyclyl, optionally substituted 3- to 10-membered heterocyclyl, optionally substituted $C_6$, $C_{10}$, or $C_{14}$ aryl, optionally substituted 3- to 10-membered heteroaryl, —CN, —CH$_2$OR$^{E1a}$, —CH$_2$N(R$^{E1a}$)$_2$, —CH$_2$SR$^{E1a}$, —OR$^{E1a}$, —N(R$^{E1a}$)$_2$, —Si(R$^{E1a}$)$_3$, and —SR$^{E1a}$, wherein each occurrence of $R^{E1a}$ is independently selected from the group consisting of hydrogen, optionally substituted $C_{1-6}$ alkyl, optionally substituted $C_{2-6}$ alkenyl, optionally substituted $C_{2-6}$alkynyl, optionally substituted $C_3$-$C_{10}$ carbocyclyl, optionally substituted 3- to 10-membered heterocyclyl, optionally substituted $C_6$, $C_{10}$, or $C_{14}$ aryl, and optionally substituted 3- to 10-membered heteroaryl, or two $R^{E1a}$ groups are joined to form an optionally substituted 3- to 10-membered heterocyclic ring;

$R^{E2}$ is selected from the group consisting of hydrogen, halogen, optionally substituted $C_{1-6}$ alkyl, optionally substituted $C_{2-6}$ alkenyl, optionally substituted $C_{2-6}$ alkynyl, optionally substituted $C_3$-$C_{10}$ carbocyclyl, optionally substituted 3- to 10-membered heterocyclyl, optionally substituted $C_6$, $C_{10}$, or $C_{14}$ aryl, optionally substituted 3- to 10-membered heteroaryl, —CN, —CH$_2$OR$^{E2a}$, —CH$_2$N(R$^{E2a}$)$_2$, —CH$_2$SR$^{E2a}$, —OR$^{E2a}$, —N(R$^{E2a}$)$_2$, and —SR$^{E2a}$, wherein each occurrence of $R^{E2a}$ is independently selected from the group consisting of hydrogen, optionally substituted $C_{1-6}$ alkyl, optionally substituted $C_{2-6}$ alkenyl, optionally substituted $C_{2-6}$ alkynyl, optionally substituted $C_3$-$C_{10}$ carbocyclyl, optionally substituted 3- to 10-membered heterocyclyl, optionally substituted $C_6$, $C_{10}$, or $C_{14}$ aryl, and optionally substituted 3- to 10-membered heteroaryl, or two $R^{E2a}$ groups are joined to form an optionally substituted 3- to 10-membered heterocyclic ring;

$R^{E3}$ is selected from the group consisting of hydrogen, halogen, optionally substituted $C_{1-6}$ alkyl, optionally substituted $C_{2-6}$ alkenyl, optionally substituted $C_{2-6}$ alkynyl, optionally substituted $C_3$-$C_{10}$ carbocyclyl, optionally substituted 3- to 10-membered heterocyclyl, optionally substituted $C_6$, $C_{10}$, or $C_{14}$ aryl, optionally substituted 3- to 10-membered heteroaryl, —CN, —CH$_2$OR$^{E3a}$, —CH$_2$N(R$^{E3a}$)$_2$, —CH$_2$SR$^{E3a}$, —OR$^{E3a}$, —N(R$^{E3a}$)$_2$, and —SR$^{E3a}$, wherein each occurrence of $R^{E3a}$ is independently selected from the group consisting of hydrogen, optionally substituted $C_{1-6}$ alkyl, optionally substituted $C_{2-6}$ alkenyl, optionally substituted $C_{2-6}$ alkynyl, optionally substituted $C_3$-$C_{10}$ carbocyclyl, optionally substituted 3- to 10-membered heterocyclyl, optionally substituted $C_6$, $C_{10}$, or $C_{14}$ aryl, and optionally substituted 3- to 10-membered heteroaryl, or two $R^{E3a}$ groups are joined to form an optionally substituted 3- to 10-membered heterocyclic ring;

optionally $R^{E1}$ and $R^{E3}$, or $R^{E2}$ and $R^{E3}$, or $R^{E1}$ and $R^{E2}$ are joined to form an optionally substituted $C_3$-$C_{10}$ carbocyclic or optionally substituted 3- to 10-membered heterocyclic ring;

n is 0, 1, or 2; and p is 0 or 1.

2. The method of claim 1, wherein $R^{B2}$ is chloro, cyclopropyl, or —CN.

3. The method of claim 1, wherein $L^1$ is —NH—.

4. The method of claim 1, wherein each instance of $R^C$ is independently fluoro, —OH, or methyl, or Ring C and all instances of $R^C$ are taken together to form a ring:

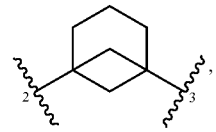 [SMILES: *C12CCCC(*)(C1)C2]

wherein "2" represents a portion of the ring bound to $L^1$, and "3" represents a portion of the ring bound to $L^2$.

5. The method of claim 1, wherein n is 1.

6. The method of claim 1, wherein $L^2$ is —NHC(=O)—, —C(=O)NH—, —NH—($C_{1-2}$alkylene)-, or —NH—.

7. The method of claim 1, wherein p is 0.

8. The method of claim 1, wherein $R^E$ is selected from:

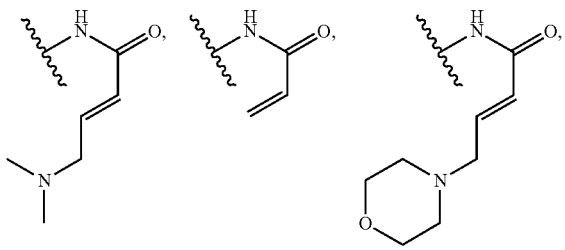

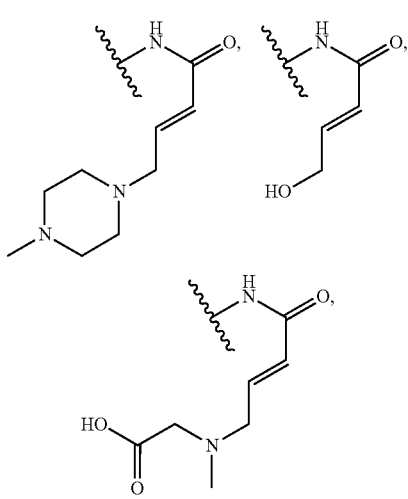

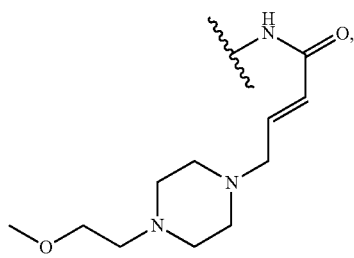

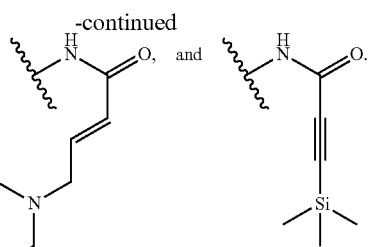

9. The method of claim 1, wherein ring A is

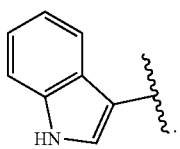 [SMILES: *c1c[nH]c2ccccc12]

10. The method of claim 1, wherein ring C is

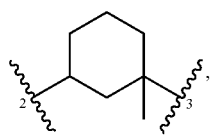 [SMILES: *C1CCCC(*)(C)C1]

wherein "2" represents a portion of ring C bound to $L^1$, and "3" represents a portion of ring C bound to $L^2$.

11. The method of claim 1, wherein $L^2$ is *—NH—C(O)—, "*" represents a point of attachment to ring C, and $L^1$ and $L^2$ are positioned 1,3 relative to one another on ring C.

12. The method of claim 1, wherein $R^E$ is

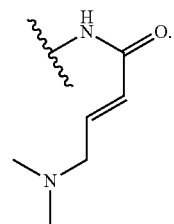 [SMILES: *NC(=O)/C=C/CN(C)C]

13. The method of claim 1, wherein the compound is (Compound 176)

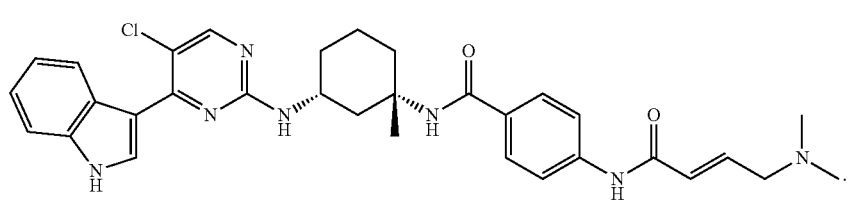

14. The method of claim 1, wherein the compound is
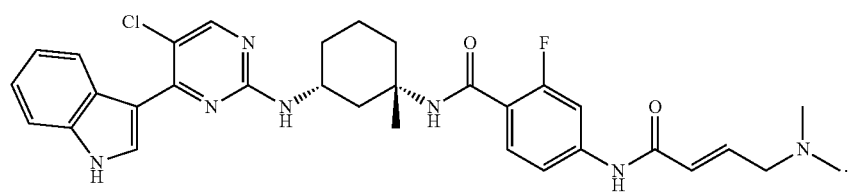
(Compound 157)
15. The method of claim 1, wherein the compound is
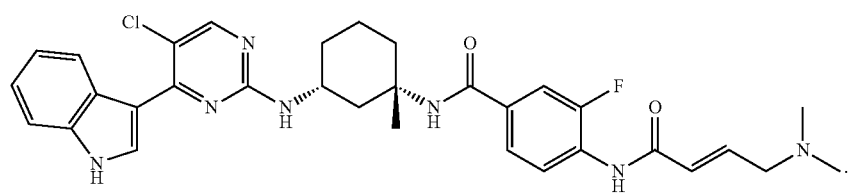
(Compound 158)
16. The method of claim 1, wherein the compound is
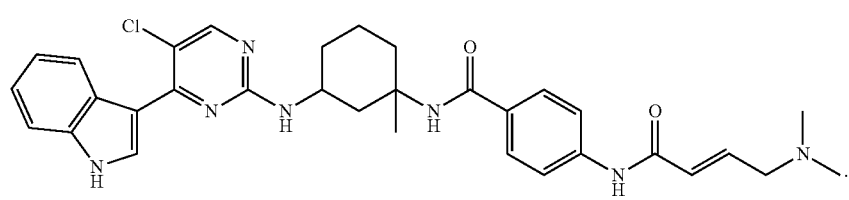
(Compound 175)
17. The method of claim 1, wherein the compound is
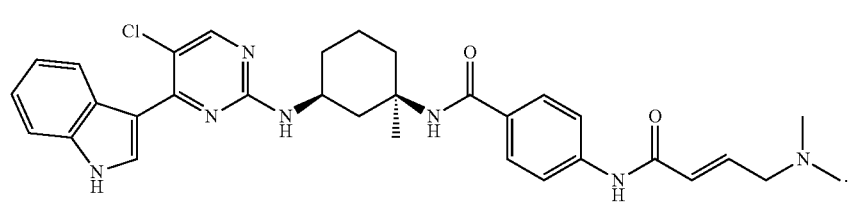
(Compound 177)

18. The method of claim 1, wherein Ring C is of the formula:

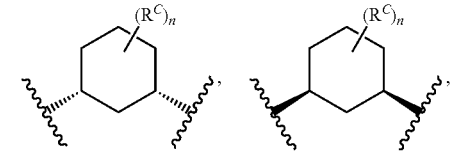

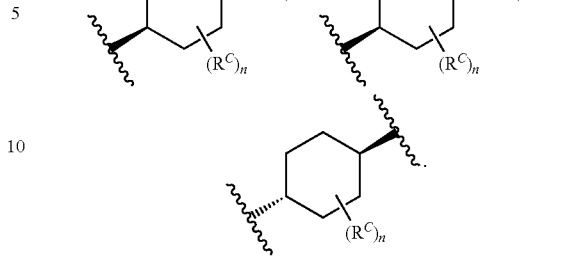

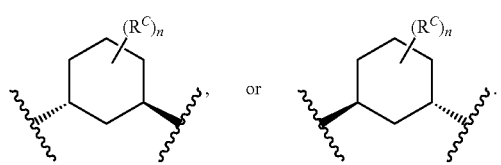

19. The method of claim 1, wherein Ring C is of the formula:

20. The method of claim 1, wherein $R^E$ and $L^2$ are para to each other.

21. The method of claim 1, wherein $R^E$ and $L^2$ are meta to each other.

22. A method of treating a proliferative disease in a subject in need thereof, the method comprising administering to the subject a therapeutically effective amount of a pharmaceutical composition comprising a compound, wherein the proliferative disease is leukemia, breast cancer, or bone cancer, and wherein the compound is:

| Compound No. | Structure |
|---|---|
| 100 | 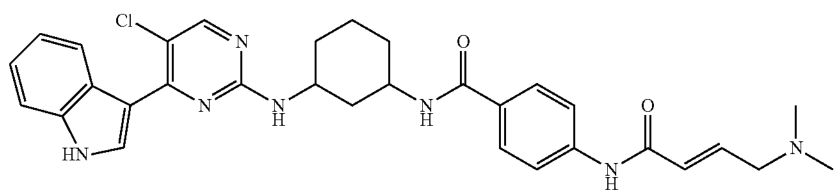 [SMILES: CN(C)C/C=C/C(=O)Nc1ccc(C(=O)NC2CCCC(Nc3ncc(Cl)c(-c4c[nH]c5ccccc45)n3)C2)cc1] |
| 101 | 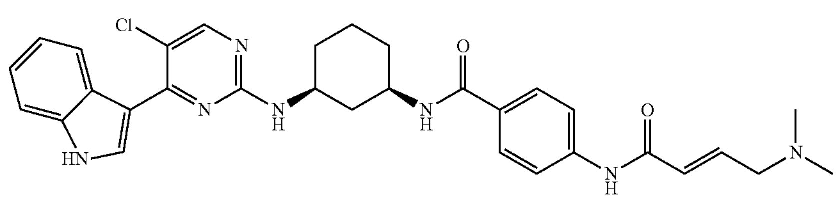 [SMILES: CN(C)C/C=C/C(=O)Nc1ccc(C(=O)N[C@@H]2CCC[C@H](Nc3ncc(Cl)c(-c4c[nH]c5ccccc45)n3)C2)cc1] |
| 102 | 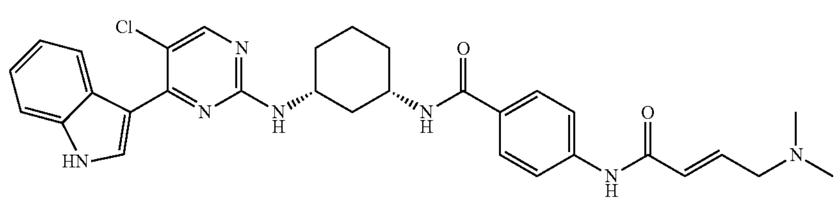 [SMILES: CN(C)C/C=C/C(=O)Nc1ccc(C(=O)N[C@H]2CCC[C@@H](Nc3ncc(Cl)c(-c4c[nH]c5ccccc45)n3)C2)cc1] |
| 103 | 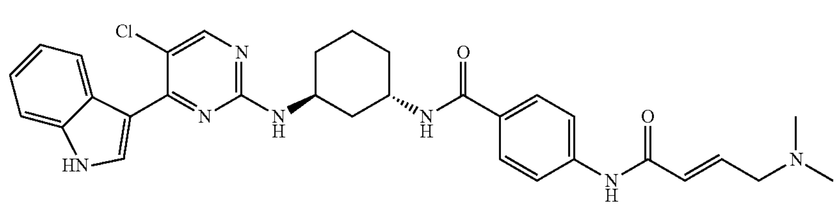 [SMILES: CN(C)C/C=C/C(=O)Nc1ccc(C(=O)N[C@H]2CCC[C@H](Nc3ncc(Cl)c(-c4c[nH]c5ccccc45)n3)C2)cc1] |

| Compound No. | Structure |
|---|---|
| 104 | 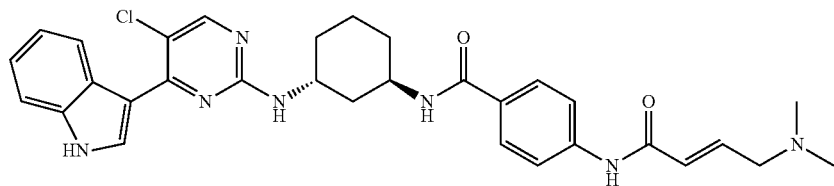 [SMILES: CN(C)C/C=C/C(=O)Nc1ccc(C(=O)N[C@@H]2CCC[C@@H](Nc3ncc(Cl)c(-c4c[nH]c5ccccc45)n3)C2)cc1] |
| 105 | 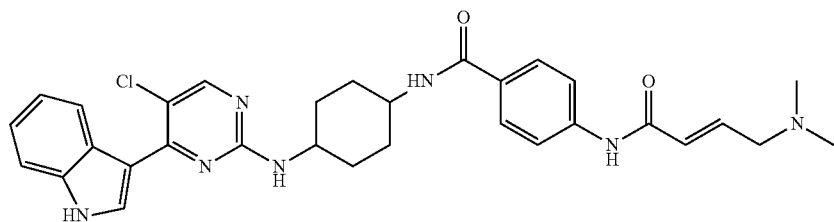 [SMILES: CN(C)C/C=C/C(=O)Nc1ccc(C(=O)NC2CCC(Nc3ncc(Cl)c(-c4c[nH]c5ccccc45)n3)CC2)cc1] |
| 106 | 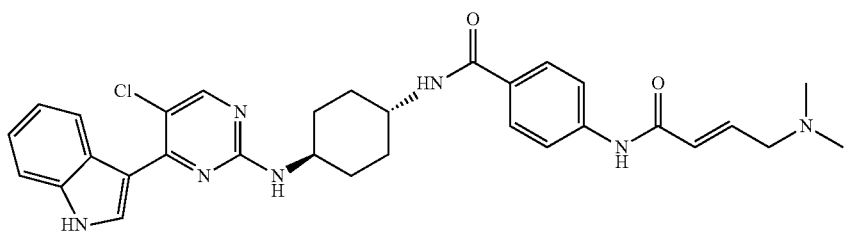 [SMILES: CN(C)C/C=C/C(=O)Nc1ccc(C(=O)N[C@H]2CC[C@H](Nc3ncc(Cl)c(-c4c[nH]c5ccccc45)n3)CC2)cc1] |
| 108 | 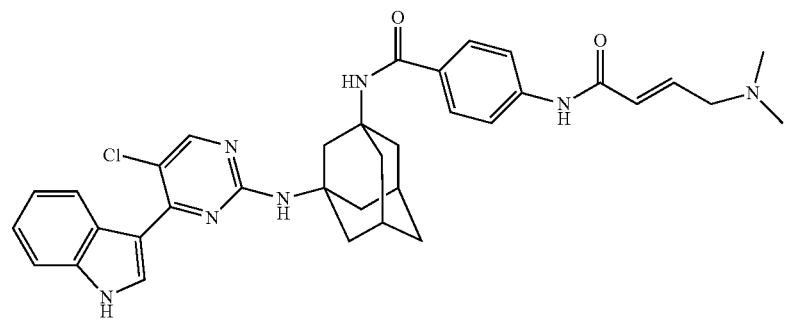 [SMILES: CN(C)C/C=C/C(=O)Nc1ccc(C(=O)NC23CC4CC(C2)CC(Nc2ncc(Cl)c(-c5c[nH]c6ccccc56)n2)(C4)C3)cc1] |
| 109 | 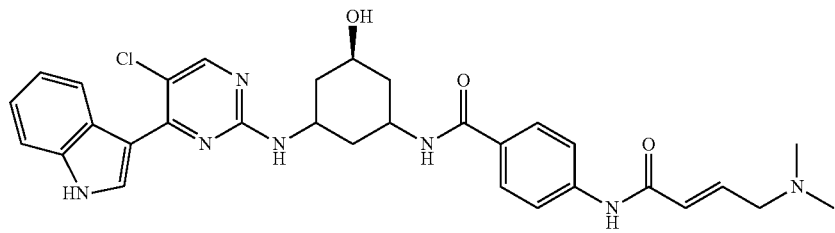 [SMILES: CN(C)C/C=C/C(=O)Nc1ccc(C(=O)NC2CC(Nc3ncc(Cl)c(-c4c[nH]c5ccccc45)n3)C[C@@H](O)C2)cc1] |
| 112 | 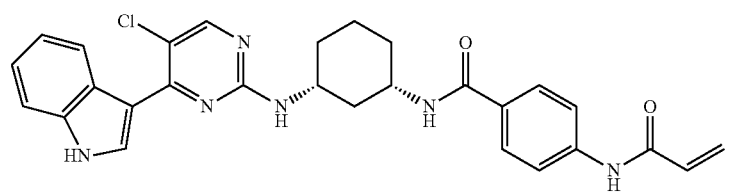 [SMILES: C=CC(=O)Nc1ccc(C(=O)N[C@H]2CCC[C@@H](Nc3ncc(Cl)c(-c4c[nH]c5ccccc45)n3)C2)cc1] |

| Compound No. | Structure |
|---|---|
| 113 | 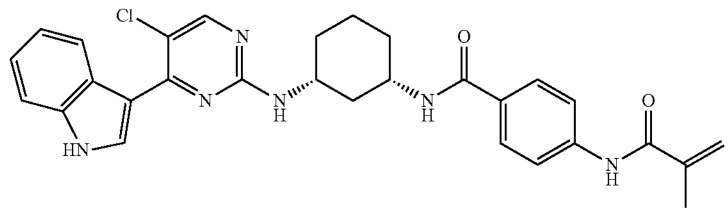 [SMILES: C=C(C)C(=O)Nc1ccc(C(=O)N[C@H]2CCC[C@@H](Nc3ncc(Cl)c(-c4c[nH]c5ccccc45)n3)C2)cc1] |
| 114 | 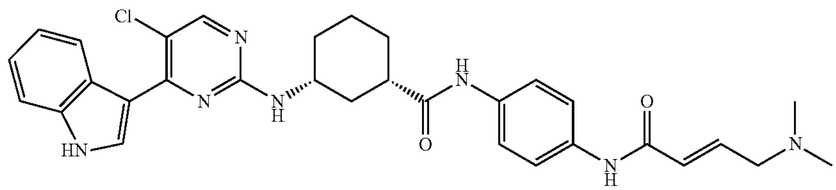 [SMILES: CN(C)C/C=C/C(=O)Nc1ccc(NC(=O)[C@H]2CCC[C@@H](Nc3ncc(Cl)c(-c4c[nH]c5ccccc45)n3)C2)cc1] |
| 115 | 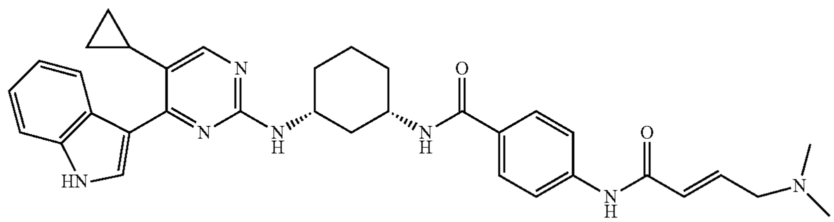 [SMILES: CN(C)C/C=C/C(=O)Nc1ccc(C(=O)N[C@H]2CCC[C@@H](Nc3ncc(C4CC4)c(-c4c[nH]c5ccccc45)n3)C2)cc1] |
| 116 | 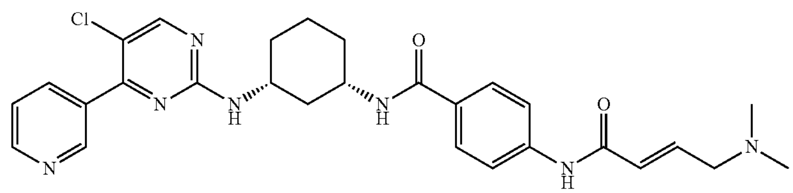 [SMILES: CN(C)C/C=C/C(=O)Nc1ccc(C(=O)N[C@H]2CCC[C@@H](Nc3ncc(Cl)c(-c4cccnc4)n3)C2)cc1] |
| 117 | 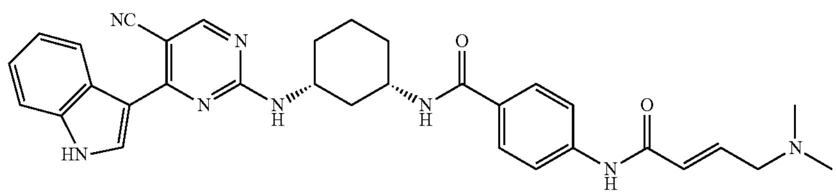 [SMILES: CN(C)C/C=C/C(=O)Nc1ccc(C(=O)N[C@H]2CCC[C@@H](Nc3ncc(C#N)c(-c4c[nH]c5ccccc45)n3)C2)cc1] |
| 118 | 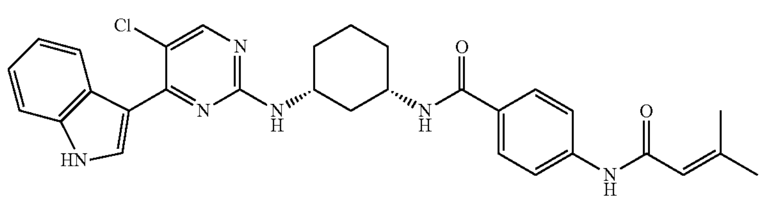 [SMILES: CC(C)=CC(=O)Nc1ccc(C(=O)N[C@H]2CCC[C@@H](Nc3ncc(Cl)c(-c4c[nH]c5ccccc45)n3)C2)cc1] |
| 119 | 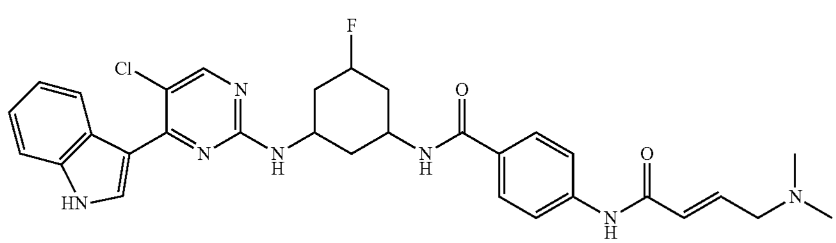 [SMILES: CN(C)C/C=C/C(=O)Nc1ccc(C(=O)NC2CC(F)CC(Nc3ncc(Cl)c(-c4c[nH]c5ccccc45)n3)C2)cc1] |

-continued
| Compound No. | Structure |
|---|---|
| 120 | 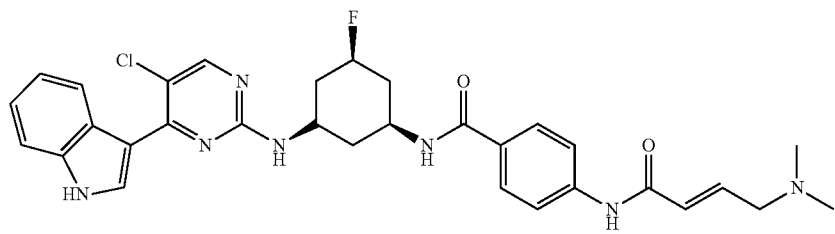 |
| 121 | 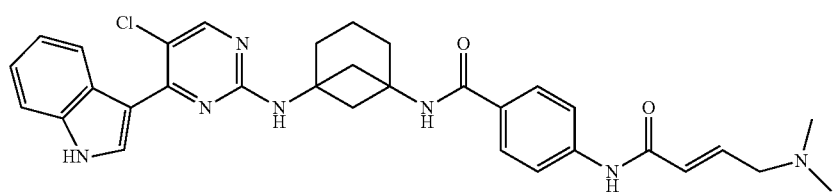 [SMILES: CN(C)C/C=C/C(=O)Nc1ccc(C(=O)NC23CCCC(Nc4ncc(Cl)c(-c5c[nH]c6ccccc56)n4)(C2)C3)cc1] |
| 122 | 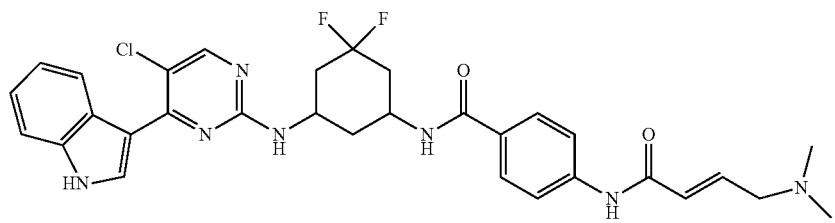 [SMILES: CN(C)C/C=C/C(=O)Nc1ccc(C(=O)NC2CC(Nc3ncc(Cl)c(-c4c[nH]c5ccccc45)n3)CC(F)(F)C2)cc1] |
| 123 | 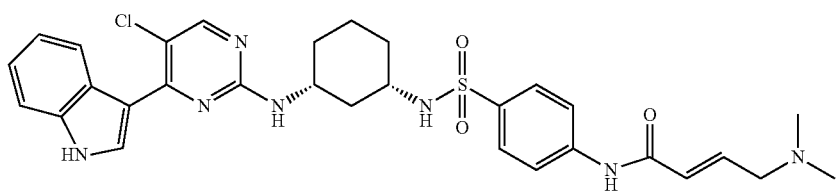 [SMILES: CN(C)C/C=C/C(=O)Nc1ccc(S(=O)(=O)N[C@H]2CCC[C@@H](Nc3ncc(Cl)c(-c4c[nH]c5ccccc45)n3)C2)cc1] |
| 124 | 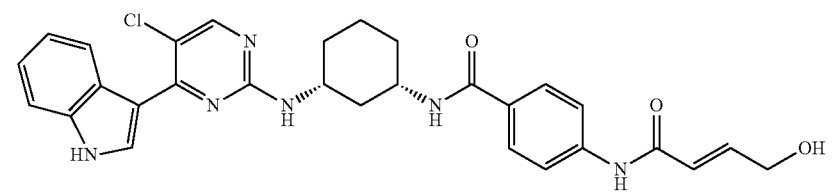 [SMILES: O=C(/C=C/CO)Nc1ccc(C(=O)N[C@H]2CCC[C@@H](Nc3ncc(Cl)c(-c4c[nH]c5ccccc45)n3)C2)cc1] |
| 125 | 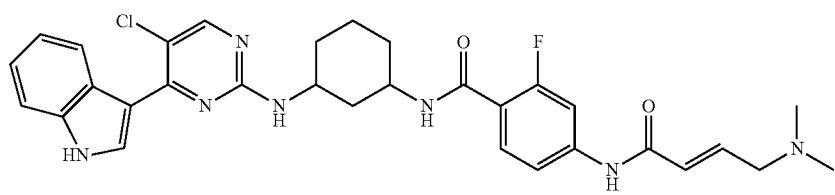 [SMILES: CN(C)C/C=C/C(=O)Nc1ccc(C(=O)NC2CCCC(Nc3ncc(Cl)c(-c4c[nH]c5ccccc45)n3)C2)c(F)c1] |
| 126 | 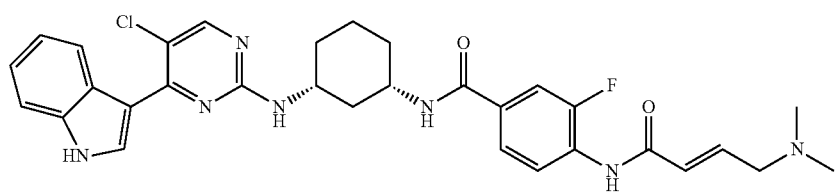 [SMILES: CN(C)C/C=C/C(=O)Nc1ccc(C(=O)N[C@H]2CCC[C@@H](Nc3ncc(Cl)c(-c4c[nH]c5ccccc45)n3)C2)cc1F] |

| Compound No. | Structure |
|---|---|
| 128 | 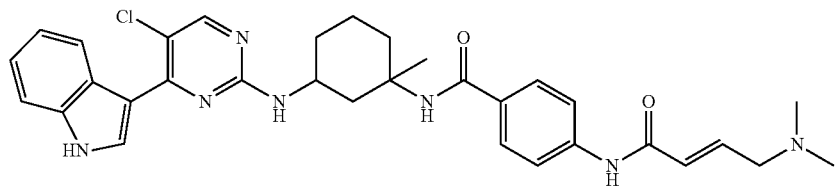 [SMILES: CN(C)C/C=C/C(=O)Nc1ccc(C(=O)NC2(C)CCCC(Nc3ncc(Cl)c(-c4c[nH]c5ccccc45)n3)C2)cc1] |
| 129 | 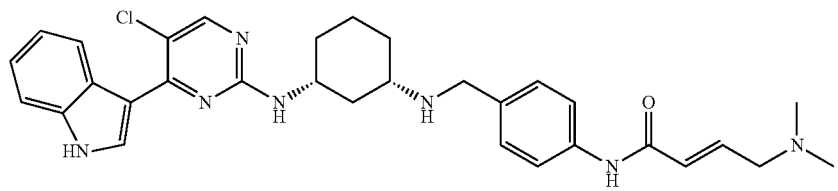 [SMILES: CN(C)C/C=C/C(=O)Nc1ccc(CN[C@H]2CCC[C@@H](Nc3ncc(Cl)c(-c4c[nH]c5ccccc45)n3)C2)cc1] |
| 130 | 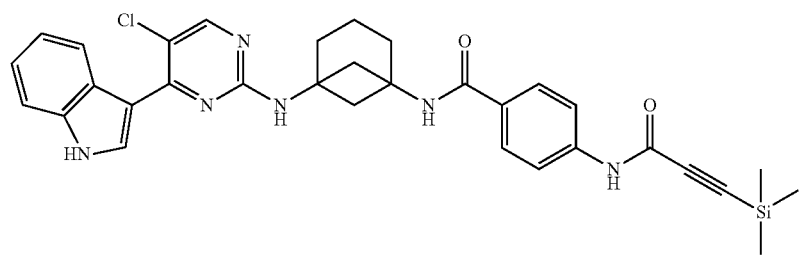 [SMILES: C[Si](C)(C)C#CC(=O)Nc1ccc(C(=O)NC23CCCC(Nc4ncc(Cl)c(-c5c[nH]c6ccccc56)n4)(C2)C3)cc1] |
| 131 | 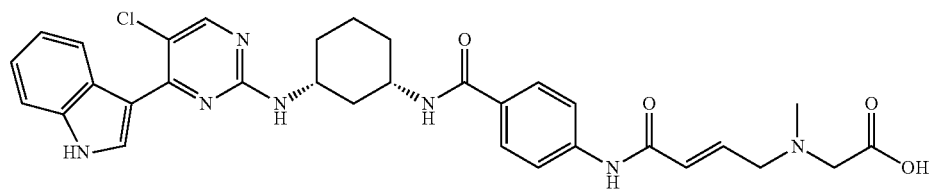 [SMILES: CN(C/C=C/C(=O)Nc1ccc(C(=O)N[C@H]2CCC[C@@H](Nc3ncc(Cl)c(-c4c[nH]c5ccccc45)n3)C2)cc1)CC(=O)O] |
| 132 | 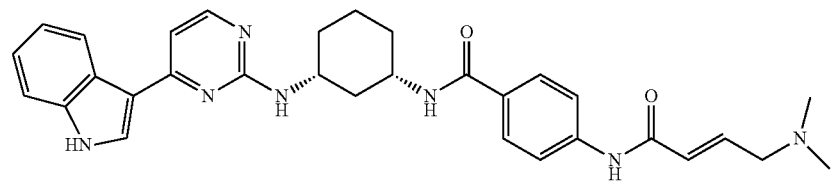 [SMILES: CN(C)C/C=C/C(=O)Nc1ccc(C(=O)N[C@H]2CCC[C@@H](Nc3nccc(-c4c[nH]c5ccccc45)n3)C2)cc1] |
| 135 | 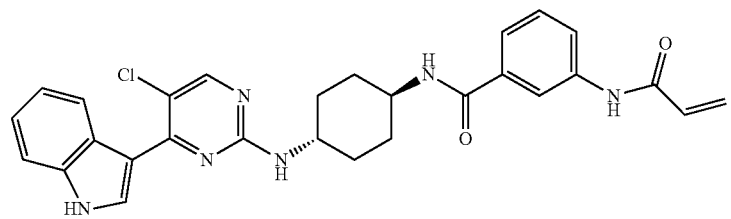 [SMILES: C=CC(=O)Nc1cccc(C(=O)N[C@H]2CC[C@H](Nc3ncc(Cl)c(-c4c[nH]c5ccccc45)n3)CC2)c1] |
| 136 | 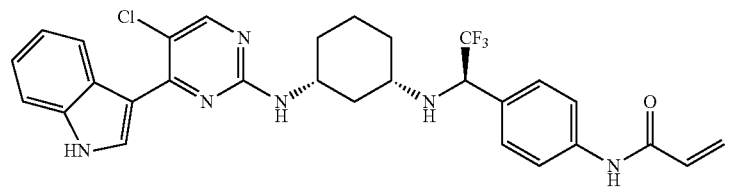 [SMILES: C=CC(=O)Nc1ccc([C@@H](N[C@H]2CCC[C@@H](Nc3ncc(Cl)c(-c4c[nH]c5ccccc45)n3)C2)C(F)(F)F)cc1] |

| Compound No. | Structure |
|---|---|
| 137 | 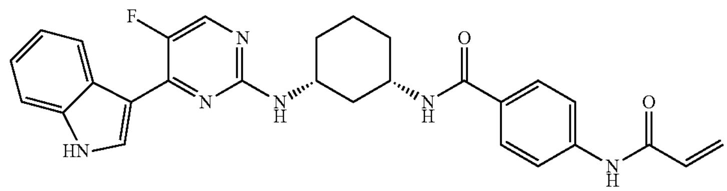 [SMILES: C=CC(=O)Nc1ccc(C(=O)N[C@H]2CCC[C@@H](Nc3ncc(F)c(-c4c[nH]c5ccccc45)n3)C2)cc1] |
| 138 | 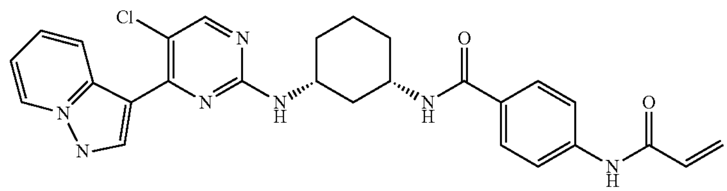 |
| 139 | 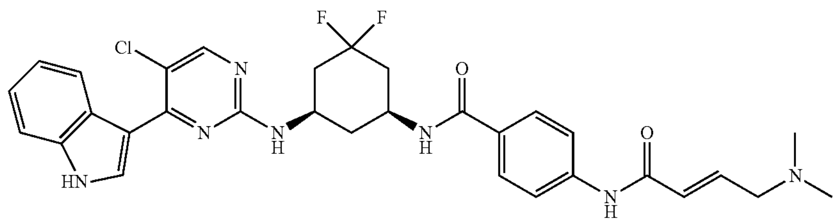 [SMILES: CN(C)C/C=C/C(=O)Nc1ccc(C(=O)N[C@H]2C[C@@H](Nc3ncc(Cl)c(-c4c[nH]c5ccccc45)n3)CC(F)(F)C2)cc1] |
| 140 | 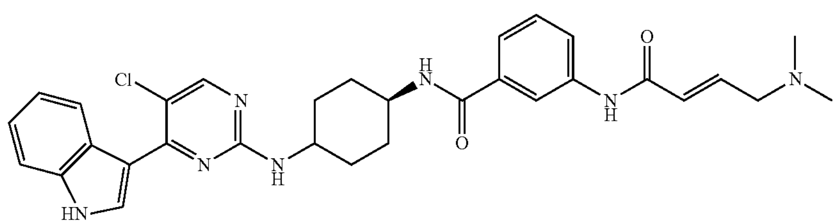 |
| 141 | 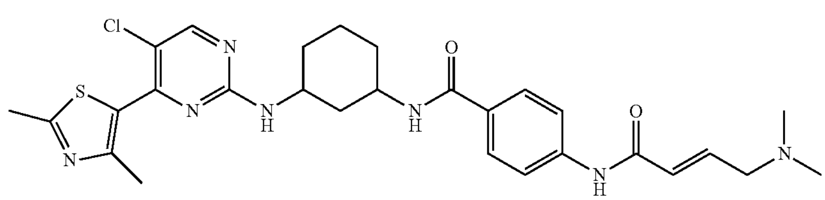 |
| 142 | 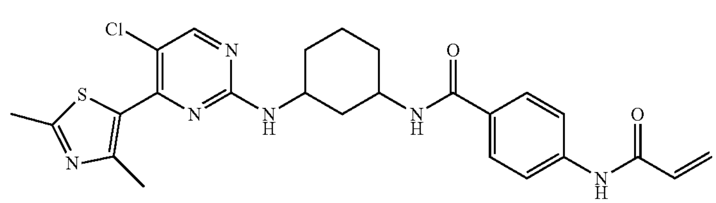 [SMILES: C=CC(=O)Nc1ccc(C(=O)NC2CCCC(Nc3ncc(Cl)c(-c4sc(C)nc4C)n3)C2)cc1] |
| 146 | 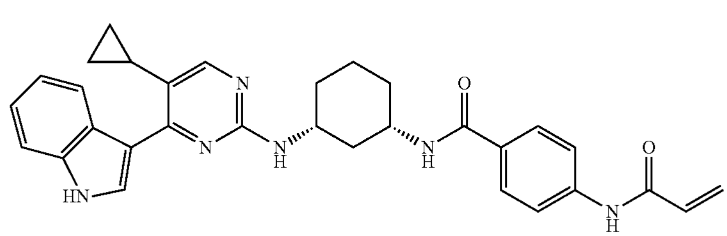 [SMILES: C=CC(=O)Nc1ccc(C(=O)N[C@H]2CCC[C@@H](Nc3ncc(C4CC4)c(-c4c[nH]c5ccccc45)n3)C2)cc1] |

| Compound No. | Structure |
|---|---|
| 147 | 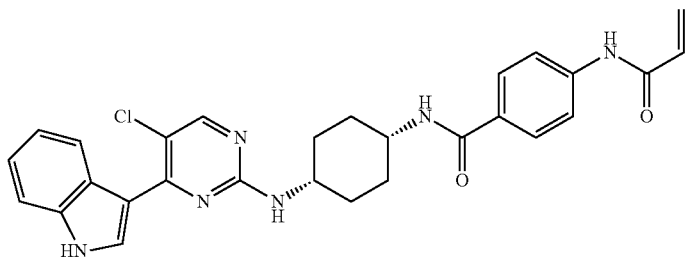 [SMILES: C=CC(=O)Nc1ccc(C(=O)N[C@H]2CC[C@@H](Nc3ncc(Cl)c(-c4c[nH]c5ccccc45)n3)CC2)cc1] |
| 150 | 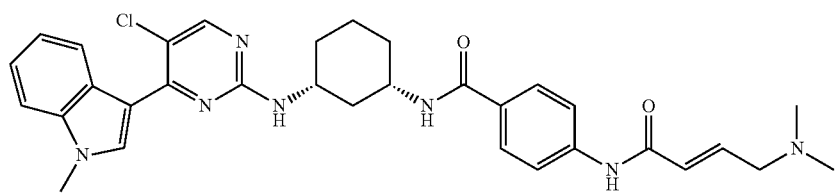 [SMILES: CN(C)C/C=C/C(=O)Nc1ccc(C(=O)N[C@H]2CCC[C@@H](Nc3ncc(Cl)c(-c4cn(C)c5ccccc45)n3)C2)cc1] |
| 151 | 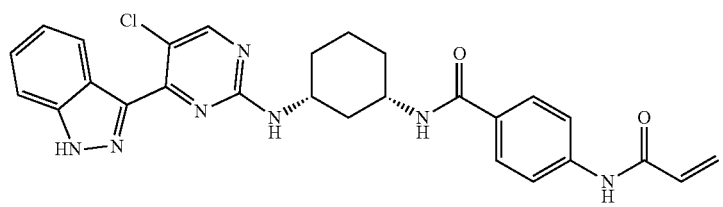 [SMILES: C=CC(=O)Nc1ccc(C(=O)N[C@H]2CCC[C@@H](Nc3ncc(Cl)c(-c4n[nH]c5ccccc45)n3)C2)cc1] |
| 152 | 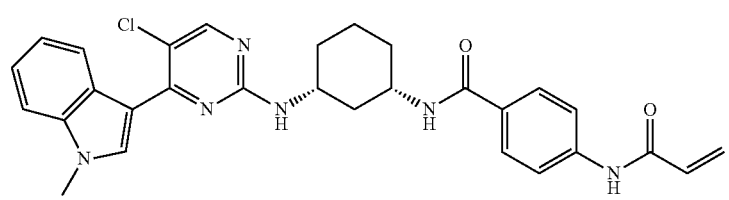 [SMILES: C=CC(=O)Nc1ccc(C(=O)N[C@H]2CCC[C@@H](Nc3ncc(Cl)c(-c4cn(C)c5ccccc45)n3)C2)cc1] |
| 153 | 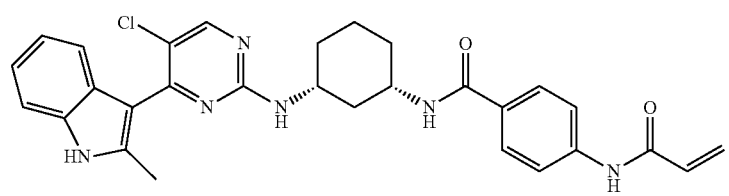 [SMILES: C=CC(=O)Nc1ccc(C(=O)N[C@H]2CCC[C@@H](Nc3ncc(Cl)c(-c4c(C)[nH]c5ccccc45)n3)C2)cc1] |
| 154 | 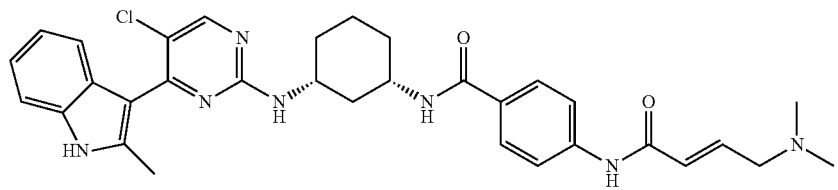 [SMILES: Cc1[nH]c2ccccc2c1-c1nc(N[C@@H]2CCC[C@H](NC(=O)c3ccc(NC(=O)/C=C/CN(C)C)cc3)C2)ncc1Cl] |
| 156 | 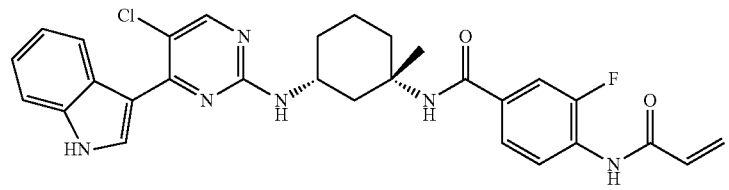 [SMILES: C=CC(=O)Nc1ccc(C(=O)N[C@@]2(C)CCC[C@@H](Nc3ncc(Cl)c(-c4c[nH]c5ccccc45)n3)C2)cc1F] |

| Compound No. | Structure |
|---|---|
| 157 | 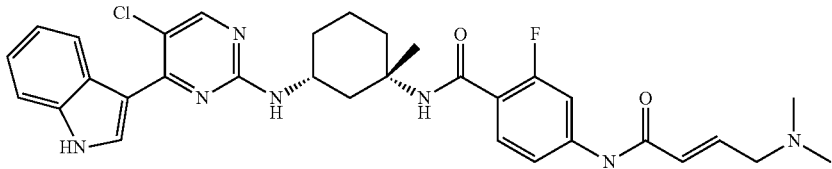 |
| 158 | 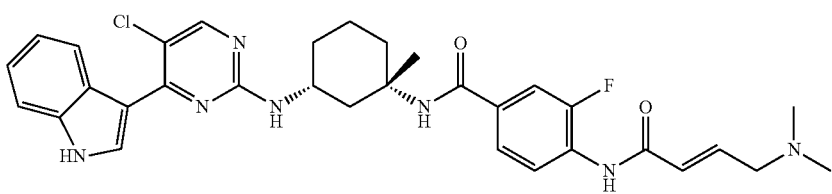 [SMILES: CN(C)C/C=C/C(=O)Nc1ccc(C(=O)N[C@@]2(C)CCC[C@@H](Nc3ncc(Cl)c(-c4c[nH]c5ccccc45)n3)C2)cc1F] |
| 159 | 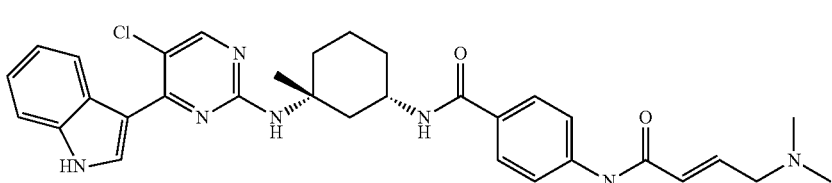 |
| 160 | 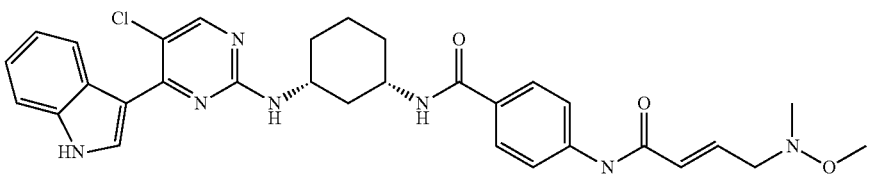 |
| 161 | 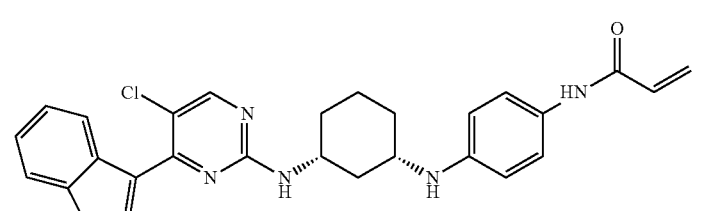 |
| 162 | 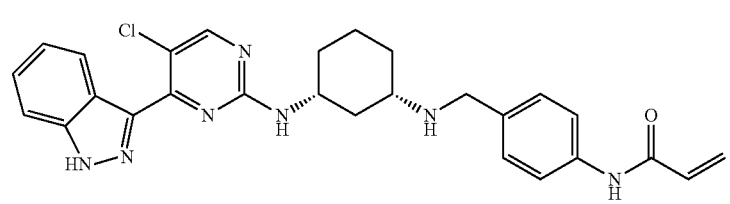 [SMILES: C=CC(=O)Nc1ccc(CN[C@H]2CCC[C@@H](Nc3ncc(Cl)c(-c4n[nH]c5ccccc45)n3)C2)cc1] |
| 164 | 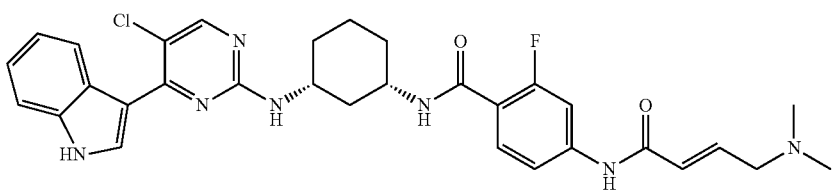 [SMILES: CN(C)C/C=C/C(=O)Nc1ccc(C(=O)N[C@H]2CCC[C@@H](Nc3ncc(Cl)c(-c4c[nH]c5ccccc45)n3)C2)c(F)c1] |

| Compound No. | Structure |
|---|---|
| 173 | 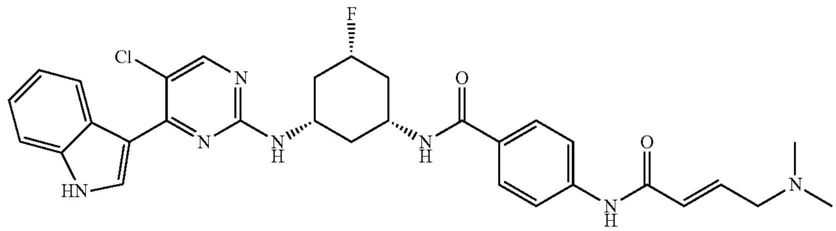 [SMILES: CN(C)C/C=C/C(=O)Nc1ccc(C(=O)N[C@H]2C[C@@H](F)C[C@@H](Nc3ncc(Cl)c(-c4c[nH]c5ccccc45)n3)C2)cc1] |
| 174 | 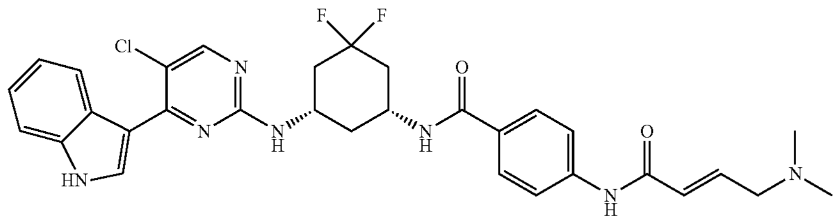 [SMILES: CN(C)C/C=C/C(=O)Nc1ccc(C(=O)N[C@@H]2C[C@H](Nc3ncc(Cl)c(-c4c[nH]c5ccccc45)n3)CC(F)(F)C2)cc1] |
| 175 | 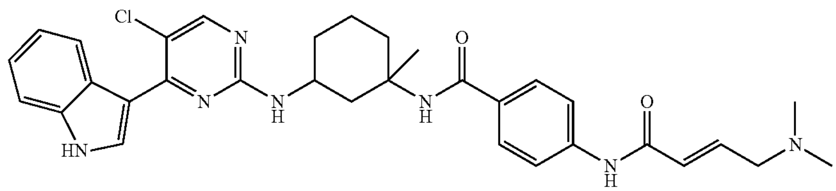 [SMILES: CN(C)C/C=C/C(=O)Nc1ccc(C(=O)NC2(C)CCCC(Nc3ncc(Cl)c(-c4c[nH]c5ccccc45)n3)C2)cc1] |
| 176 | 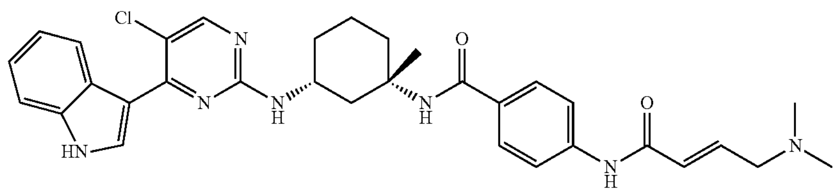 [SMILES: CN(C)C/C=C/C(=O)Nc1ccc(C(=O)N[C@@]2(C)CCC[C@@H](Nc3ncc(Cl)c(-c4c[nH]c5ccccc45)n3)C2)cc1] |
| 177 | 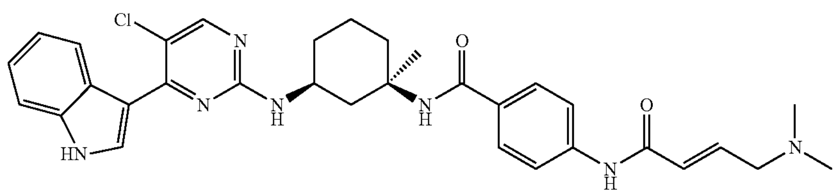 |
| 178 | | or a pharmaceutically acceptable salt thereof.

23. The method of claim 1, wherein the proliferative disease is leukemia.

24. The method of claim 1, wherein the proliferative disease is breast cancer.

25. The method of claim 1, wherein the proliferative disease is bone cancer.

26. The method of claim 25, wherein the bone cancer is Ewing's sarcoma.

27. The method of claim 25, wherein the bone cancer is osteosarcoma.

28. The method of claim 22, wherein the proliferative disease is leukemia.

29. The method of claim 22, wherein the proliferative disease is breast cancer.

30. The method of claim 22, wherein the proliferative disease is bone cancer.

31. The method of claim 30, wherein the bone cancer is Ewing's sarcoma.

32. The method of claim 30, wherein the bone cancer is osteosarcoma.

* * * * *

UNITED STATES PATENT AND TRADEMARK OFFICE
CERTIFICATE OF CORRECTION

PATENT NO. : 10,906,889 B2
APPLICATION NO. : 16/051896
DATED : February 2, 2021
INVENTOR(S) : Gray et al.

Page 1 of 1

It is certified that error appears in the above-identified patent and that said Letters Patent is hereby corrected as shown below:

In Claim 22, at Columns 305 and 306, compound number 138, the formula:

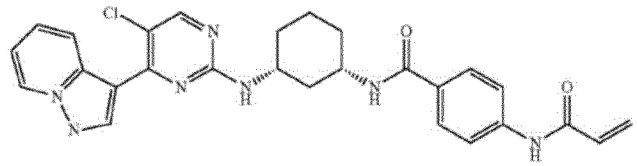

should be replaced with the formula:

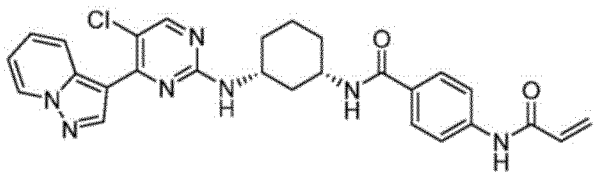

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*